United States Patent

Fujita et al.

[11] Patent Number: 6,013,663
[45] Date of Patent: Jan. 11, 2000

[54] DITHIOLAN DERIVATIVES, THEIR PREPARATION AND THEIR THERAPEUTIC EFFECT

[75] Inventors: Takashi Fujita, Kashiwa; Tomihisa Yokoyama, Urawa, both of Japan

[73] Assignee: Sankyo Company, Limited, Tokyo, Japan

[21] Appl. No.: 09/052,095

[22] Filed: Mar. 31, 1998

[30] Foreign Application Priority Data

Apr. 2, 1997 [JP] Japan ................................ 9-083749
Jan. 20, 1998 [JP] Japan ................................ 10-008837

[51] Int. Cl.[7] .................... A61K 31/385; C07D 339/04
[52] U.S. Cl. .................. 514/440; 514/227.8; 514/231.5; 514/255; 514/336; 514/360; 514/365; 514/369; 514/397; 544/60; 544/145; 544/379; 546/207; 546/280.7; 548/123; 548/183; 548/200; 548/315.1; 548/467; 548/527; 549/39
[58] Field of Search ................................ 549/39; 514/440; 548/315.1, 123, 467, 527, 200, 183; 546/207, 280.7; 544/145, 60, 379; 574/397, 360, 231.5, 414, 422, 336, 227.8, 255, 365, 369

[56] References Cited

U.S. PATENT DOCUMENTS

| 5,508,275 | 4/1996 | Weithmann et al. ............. 514/182 |
| 5,693,664 | 12/1997 | Wessel et al ....................... 574/440 |

FOREIGN PATENT DOCUMENTS

| 424282 | 4/1991 | European Pat. Off. . |
| 550006 | 6/1993 | European Pat. Off. . |
| 1 294 134 | 10/1962 | France . |
| 2 707 983 | 1/1995 | France . |
| 43 27 462 | 2/1995 | Germany . |
| 1 210 892 | 2/1996 | Germany . |
| 1 210 893 | 2/1996 | Germany . |
| 42-001286 | 1/1967 | Japan . |
| 45-003378 | 2/1970 | Japan . |
| 61-170733 | 8/1986 | Japan . |
| 62-050330 | 3/1987 | Japan . |
| 2 148 296 | 5/1985 | United Kingdom . |
| WO 97/21444 | 6/1997 | WIPO . |

OTHER PUBLICATIONS

Oizumi J & Hayakawa K. Biochem. J. 266(2), 427–34, 1990.
Fujiwara K et al. J. Biol. Chem. 261(19), 8836–41, 1986.
Vesa V et al. Proizvod. Primen. Mikrobn. Fermentn. Prep. 2, 86–92, 1975.
Goedde HW et al. S. Naturforsch., B: Anorg. Chem., Org. Chem., Biochem., Biophys., Biol. 22 (12), 1300–3, 1967.
Casolaro M & Busi E. Polymer. 35(2), 360–6, 1994.
Maitra et al, "α–Lipoic Acid Prevents Buthionine Sulfoximine–Induced Cataract Formation in Newborn Rats", Free Radical Biology & Medicine, vol. 18, No. 4, pp. 823–829, 1995.
File Caplus, File Covers vol. 128 Iss 24, American Chemical Society, Chemical Abstracts, AN 1995:494643 of FR 2707993, filed 1–1995.
File WPIDS, 1998 Derwent Information Ltd., AN 95:068752 of FR 2707993, filed 1–1995.
Chemical Abstracts, vol. 106, No. 74, p. 633, col. 2, Columbus, Ohio, Abstract No. 129241r of JP 61 170 733 A, 1987.
Szajewski et al, "Rate Constants and Equilibrium Constants for Thiol–Disulfide Interchange Reactions Involving Oxidized Glutathione", Journal of the American Chemical Society, vol. 102, No. 6, pp. 2011–2026, Mar. 1980.
Bustamante et al, "Antioxidant Inhibition of Thymocyte Apoptosis by Dihydrolipoic Acid", Free Radical Biology & Medicine, vol. 19, No. 3, pp. 339–347, 1995.
Biewenga et al, "Lipoic Acid Favors Thiosulfinate Formation After Hypochlorous Acid Scavenging: A Study With Lipoic Acid Derivatives", Archives of Biochemistry and Biophysics, vol. 312, No. 1, pp. 114–120, 1994.
Sen et al, "Regulation of Cellular Thiols in Human Lymphocytes by α–Lipoic Acid: A Flow Cytometric Analysis", Free Radical Biology & Medicine, vol. 22, No. 7, pp. 1241–1257, 1997.
Kliukiene et al, "The Protective Effects of Dehydrolipoamide and Glutathione Against Photodynamic Damage by A1–Phtalocyanine Tetrasulfonate", Biochemistry and Molecular Biology International, vol. 41, No. 4, pp. 707–713, Apr. 1997.

*Primary Examiner*—Evelyn Mei Huang
*Attorney, Agent, or Firm*—Frishauf, Holtz, Goodman, Langer & Chick, P.C.

[57] ABSTRACT

A compound of formula (I):

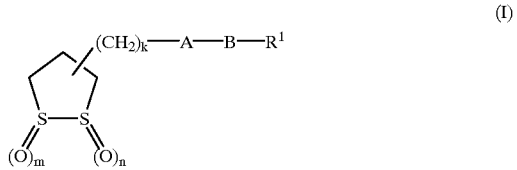

wherein one of m and n represents 0, and the other represents 0, 1 or 2; k represents 0 or 1 to 12; $R^1$ is hydrogen, an aryl, a heterocyclic, an alkyl, a hydroxy or $-OR^7$, wherein $R^7$ is an alkyl, an alkenyl or an aralkyl; A is $-CON(R^2)SO_2-$, wherein $R^2$ is hydrogen, an alkyl or an aralkyl; B is a single bond; and pharmaceutically acceptable salts thereof. The compounds have the ability to enhance the activity of glutathione reductase and can therefore be used for the treatment and prevention of a variety of diseases including cataracts.

47 Claims, No Drawings

DITHIOLAN DERIVATIVES, THEIR PREPARATION AND THEIR THERAPEUTIC EFFECT

BACKGROUND OF THE INVENTION

The present invention relates to a series of new dithiolan derivatives having an excellent ability to enhance the activity of glutathione reductase. The invention also provides a process for preparing these compounds and methods and compositions using them.

Glutathione is found throughout the tissues of the living body, is a major reducing agent in cells, and plays a very important role in the oxidation-reduction metabolic processes. In particular, reduced glutathione (GSH), thanks to the presence of a thiol group, plays a key role in various cellular defence and repair mechanisms. Glutathione peroxidase catalyses the reactions involved in these mechanisms, and is an important enzyme in the antioxidant system, wherein perocides (e.g. hydrogen peroxide, lipid peroxides and so on) are reduced by GSH. On the other hand, glutathione reductase is an enzyme which reduces oxidized glutathione (oxidized-type glutathione; GSSG) in the presence of NADPH to regenerate GSH.

The antioxidant system comprising these materials and enzymes protects cells from the harmful effects of oxidising materials (e.g. above described peroxides, free radicals and so on). Oxidative stress occurs when the balance between oxidising materials and the antioxidant mechanisms is shifted in favor of the former [J. Appl. Physiol. 1996 November, 81(5), 2199–2202]. It has been reported that oxidative stress is associated with various diseases, such as coronary heart disease, cataracts, pulmonary diseases (e.g., idiopathic pulmonary fibrosis, adult respiratory distress syndrome, emphysema, asthma, bronchopulmonary dysplasia and interstitial pulmonary fibrosis), chronic renal failure, disorders of the nervous system including the peripheral nervous system and the central nervous system (e.g. Parkinson's disease, schizophrenia, Alzheimer's disease, epilepsy, amyotrophic lateral sclerosis and cerebral ischemia), gastric ulcers, diabetes, hepatocyte necrosis and apoptosis including ethanol-induced hepatopathy, viral disease (including influenza, hepatitis B and HIV), and colorectal cancer [J. Appl. Physiol. 1996 November, 81(5), 2199–2202; Free Radical Biology & Medicine, Vol. 21 No. 6, 845–853 (1996); Free Radical Biology & Medicine, Vol. 20 No. 7, 925–931 (1996); Gastroenterology, 112, 855–863 (1997); Free Radical Biology & Medicine, Vol. 34, 161–165 (1996); Lancet, 338, 215–216 (1991); Diabetologia, 39, 357–363 (1996); Eur. J. Cancer., 1996 January, 32A(1), 30–38; Am. J. Med., 1991 September 30. 91(3c), 95s–105s; Alcohol. Clin. Exp. Res., 1996 December 20(9 Suppl), 340A–346A; Free Radical Biology & Medicine, Vol. 21 No. 5, 641–649 (1996); Pharmacol. Toxicol., 1997 April, 80(4), 159–166; Cell. Mol. Biol. (Noisy-le-grand) 1996 February, 42(1), 17–26; Prostaglandins. Leukot. Essent. Fatty Acids, 1996 August, 55(1–2), 33–43; FASEB J., 1995 September, 9(12), 1173–1182].

In addition to the above, oxidative stress is thought to be a factor in Down's syndrome, nephritis, pancreatitis, dermatitis, fatigue, rheumatism, various malformations (e.g. Duchenne muscular dystrophy, Becker dystrophy, Dubin-Johnson-Spring syndrome, favism and so on), Fanconi's anemia, canceration and metastases, septicemia, enhanced permeability of the blood vessels, leukocyte adherence, retinopathy of prematurity, siderosis, toxic effects of medicines (e.g. carcinostatics including platinum chelate, antibiotics, antiparasitics, paraquat, carbon tetrachloride and halothane) and radiogenic damages [Yoshihiko Oyanagi, Superoxide dismutase and agents controlling active oxygen species].

In WO94/12527, it is disclosed that compounds which enhance the synthesis of endogenous GSH are suitable for human therapy, in particular for the treatment of various diseases induced by glutathione deficiency, such as the pathological states related to oxidative tissue damage, in particular when resulting from an excess of free radicals. Some examples of such diseases are: intracellular oxidative state disequilibrium following alcohol abuse, exposure to xenobiotic agents, damage caused by radiation, hepatic diseases, intoxication from drugs and chemical agents, poisoning by heavy metals, physiological brain ageing (e.g. Parkinson's disease), brain degeneration due to decreased glutathione levels caused by altered antioxidant defence mechanisms, such as acute and chronic neurodegenerative diseases (e.g., acute pathologies such as: acute ischemic states, in particular cerebral ictus, hypoglycemia, and epileptic attacks; chronic pathologies such as: amyotrophic lateral sclerosis, Alzheimer's disease, Huntington's chorea), diseases related to altered functionality of the immune system, in particular resulting from tumour immunotherapy, and infertility, in particular male infertility. It is also disclosed that the compounds are suitable for organ reperfusion following ischemic events mainly imputable to free radicals.

Furthermore, in Japanese patent publication Kokai Showa 64-26516, it is disclosed that a compound which increases glutathione levels is useful for the treatment and prevention of various diseases including cataracts, hepatic disorders, nephritic disorders.

At this time, lipoic acid (thioctic acid), which has dithiolan ring in its molecule, is known to influence the biosynthesis and regeneration of reduced glutathione [I. Maitra et al., Free Radical Biology & Medicine, Vol. 18 No. 4, 823–829 (1995)]. In this literature, it is reported that the total glutathhione (oxidized and reduced glutathione) level is decreased by administering buthionine sulfoximine (BSO), which is an inhibitor of glutathione synthetase, to newborn rats, that the decrease is prevented by administering lipoic acid together with BSO, and that cataract formation is suppressed. In addition, the literature describes a test on the effects on glutathione reductase achieved by administering only BSO or by administering both BSO and lipoic acid. Considering these results, it is understood that the activity of glutathione reductase does not change when BSO is simply administered by itself, and that the activity of glutathione reductase also does not increase when lipoic acid is administered in addition to BSO.

It can, therefore, be deduced from this literature that the total glutathione level will be increased and that disorders can be treated when lipoic acid is administered to a patient who is suffering from a disease caused by a deficiency of glutathione synthesis, but lipoic acid is not thought to provide sufficient effect against diseases which occur in spite of enough glutathione synthesis since it is understood not to increase glutathione reductase activity.

On the contrary, if the activity of glutathione reductase can be increased, then whether glutathione synthesis is or is not adequate, diseases which occur in spite of enough glutathione synthesis and which are caused by oxidative stress can be prevented or treated since the supply of reduced glutathione is increased.

Furthermore, in general, in the case of ophthalmologic diseases, such as cataracts, topical application to the eyes is preferred to oral administration. However, since lipoic acid is a powerful stimulant, it is impossible to administer it to the eyes.

We have now discovered a series of dithiolan derivatives, which have the ability to cause a significant increase in the activity of glutathione reductase and which also remove peroxides. Moreover, the compounds of the present invention are less stimulating to the eyes than lipoic acid and similar known compounds are thus especially suitable for topical application.

For the avoidance of doubt, the compounds of the present invention are named following the IUPAC Rules, using, as appropriate, lipoic acid (also known as thioctic acid) as the parent compound. This compound has the formula:

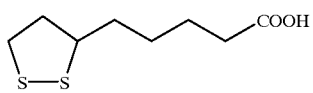

It is an object of the present invention to provide a series of new dithiolan derivatives.

It is a further and more specific object of the present invention to provide such compounds which increase the activity of glutathione reductase.

BRIEF SUMMARY OF INVENTION

The compounds of the present invention are those compounds of formula (I):

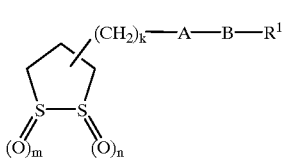

(I)

wherein:
one of m and n represents 0, and the other represents 0, 1 and 2;

k represents 0 or an integer of from 1 to 12;

$R^1$ represents:
a hydrogen atom,
a group selected from substituents α, defined below, or
an alkyl group having from 1 to 12 carbon atoms which is unsubstituted or is substituted by from 1 to 3 substituents selected from the group consisting of substitutents α and the substituents γ or such a substituted or unsubstituted alkyl group in which the carbon chain is interrupted by an oxygen atom and/or a sulfur atom;

A represents a single bond, an oxygen atom, a carbonyl group or a group of formula —N($R^2$)CO—, —N($R^2$)CS—, —N($R^2$)SO$_2$—, —CON($R^2$)N($R^3$)CO—, —CON($R^2$)CO—, —CON($R^2$)CS—, —CON($R^2$)SO$_2$—, —O—CO—, —ON($R^2$)CO—, —ON($R^2$)SO$_2$—, —O—CON($R^2$)N($R^3$)CO—, —O—CON($R^2$)CO—, —O—CON($R^2$)SO$_2$—, —CO—O—, —CO—CO—, —CO—CON($R^2$)N($R^3$)CO—, —CO—CON($R^2$)CO—, —CO—CON($R^2$)SO$_2$—, —N($R^2$)O—, —N($R^2$)COCO—, —N($R^2$)N($R^3$)CO—, —N($R^2$)N($R^3$)SO$_2$—, —N($R^2$)CON($R^3$)N($R^4$)CO—, —N($R^2$)CON($R^3$)CO—, —N($R^2$)CON($R^3$)SO$_2$—, or —N($R^2$)CON($R^3$)SO$_2$N($R^4$)CO— wherein $R^2$, $R^3$ and $R^4$ are the same or different and each represents a hydrogen atom, an alkyl group having from 1 to 12 carbon atoms, an aralkyl group, an aralkyl group of which the aryl moiety is substituted with from 1 to 3 groups selected from the group consisting of substituents β, an acyl group or a group selected from the group consisting of substituents α;

B represents a single bond, or a group of formula —N($R^5$)— or —N($R^6$)N($R^5$)—
wherein $R^5$ and $R^6$ are the same or different and each represents a hydrogen atom, an alkyl group having from 1 to 12 carbon atoms, an aralkyl group, an aralkyl group of which the aryl moiety is substituted with from 1 to 3 groups selected from the group consisting of substituents β, an acyl group or a group selected from the group consisting of substituents α, or $R^5$, together with $R^1$ and the nitrogen atom to which they are bonded, may form a heterocyclic ring having from 5 to 7 ring atoms;

or, where A represents a group of formula —N($R^2$)CO—, —N($R^2$)CS—, —CON($R^2$)N($R^3$)CO—, —CON($R^2$)CO—, —CON($R^2$)CS—, —O—CO—, —ON($R^2$)CO—, —O—CON($R^2$)N($R^3$)CO—, —O—CON($R^2$)CO—, —CO—CON($R^2$)N($R^3$)CO—, —CO—CON($R^2$)CO—, —N($R^2$)N($R^3$)CO—, —N($R^2$)CON($R^3$)N($R^4$)CO— or —N($R^2$)CON($R^3$)CO— [wherein $R^2$, $R^3$ and $R^4$ are as defined above] and B represents a single bond, $R^1$ may represent a group of formula —$OR^7$ (wherein $R^7$ represents a lower alkyl group, a lower alkenyl group, an aralkyl group, an aralkyl group of which the aryl moiety is substituted with 1 to 3 groups selected from the group consisting of substituents β or a group selected from the consisting of substituents α);

or, where A represents a group of formula —CON($R^2$)SO$_2$—, —ON($R^2$)SO$_2$—, —O—CON($R^2$)SO$_2$—, —CO—CO—, —CO—CON($R^2$)SO$_2$—, —N($R^2$)COCO—, —N($R^2$)N($R^3$)SO$_2$—, or —N($R^2$)CON($R^3$)SO$_2$— [wherein $R^2$ and $R^3$ are as defined above ] and B represents a single bond, or, where A does not represent an oxygen atom, a group of formula —CO—O— or —N($R^6$)O— and B represents —N($R^5$)— [wherein $R^5$ is as defined above], $R^1$ may represent a hydroxy group or a group of formula —$OR^7$ (wherein $R^7$ is as defined above);

Substituents α are selected from the group consisting of aryl groups, heterocyclic groups, aryl groups substituted with from 1 to 3 of substituents β, and heterocyclic groups substituted with from 1 to 3 of substituents β;

Substituents β are selected from the group consisting of lower alkyl groups, halogenated lower alkyl groups, lower alkoxy groups, lower alkylthio groups, hydroxy groups, carboxy groups, carbamoyl groups of which the nitrogen atom may be substituted, lower alkoxycarbonyl groups, halogen atoms, nitro groups, amine residues, sulfo groups, sulfamoyl groups, cyano groups, hydroxy-substituted lower alkyl groups;

Substituents γ are selected from the group consisting of lower alkoxy groups, lower alkylthio groups, hydroxy groups, nitrooxy groups, carboxy groups, lower alkoxycarbonyl groups, halogen atoms, sulfo groups, sulfamoyl groups, amine residues, carbamoyl groups of which the nitrogen atom may be substituted;

PROVIDED THAT:
where A represents an oxygen atom, B represents a single bond or a group of formula —N($R^5$)— [wherein $R^5$ is as defined above], where A represents a group of formula —CO—O— or —N($R^2$)O— [wherein $R^2$ is as defined above], B represents a single bond, and where k represents 4, the group of formula —A—B—R$^1$ does not represent a carboxyl group
and pharmaceutically acceptable salts thereof.

The present invention also provides a method of enhancing the activity of glutathione reductase in a mammal, which may be human, by administering to said mammal an effective amount of a compounds of formula (I) or a pharmaceutically acceptable salt thereof.

The present invention also provides a method for the treatment or prevention of cataract in a mammal, which may be human, by administering to said mammal an effective amount of a compounds of formula (I) or a pharmaceutically acceptable salt thereof.

DETAILED DESCRIPTION OF INVENTION

In the compounds of the present invention, one of m and n represents 0, and the other represents 0, 1 or 2. Preferably, either both of m and n represent 0, or one of m and n represents 0 and the other represents 1. More preferably, both of m and n represent 0.

We prefer those compounds of formula (I) wherein k represents 0 or an integer of from 1 to 6, more preferably an integer of from 2 to 6, and most preferably an integer of from 4 to 6.

Where R$^1$ or substituent α represents an aryl group, this is a carbocyclic aromatic hydrocarbon group having from 6 to 14 ring carbon atoms in one or more aromatic carbocyclic rings or is such a group which is fused to a cycloalkyl group having from 3 to 10 ring carbon atoms, Examples of carbocyclic aromatic hydrocarbon groups having from 6 to 14 ring carbon atoms in one or more aromatic carbocyclic rings include the phenyl, naphthyl (1- or 2-naphthyl), phenanthrenyl and anthracenyl groups. An example of a group in which an aromatic carbocyclic ring is fused to a cycloalkyl group is the 2-indanyl group.

Where R$^1$ or substituent α represents a heterocyclic group, this has from 5 to 7 ring atoms of which from 1 to 3 are hetero-atoms selected from the group consisting of sulfur, oxygen and nitrogen hetero-atoms. The group may be saturated or it may be unsaturated and preferably aromatic.

Where the heterocyclic groups referred to herein have 3 hetero-atoms, we prefer that all three, two or one of these atoms are nitrogen atoms, and, correspondingly, none, one or two are sulfur and/or oxygen atoms.

Examples of such saturated heterocyclic groups include, for example, the pyrrolidinyl, imidazolidinyl, pyrazolidinyl, oxazolidinyl, isoxazolidinyl, thiazolidinyl, isothiazolidinyl, dithiolanyl, thiadiazolidinyl, oxadiazolidinyl, dithiazolidinyl, piperidyl, piperazinyl, morpholinyl, thiomorpholinyl dioxanyl and homopiperazinyl groups. Of these groups, we particularly prefer those 5- to 7-membered saturated heterocyclic groups which have one or two nitrogen atoms or have one nitrogen atom and one sulfur atom or one oxygen atom, such as the pyrrolidinyl, thiazolidinyl, imidazolidinyl, piperidyl, morpholinyl, thiomorpholinyl and piperazinyl groups.

If desired, the above-described saturated heterocyclic groups may be substituted by one or two atoms selected from the group consisting of sulfur atoms and oxygen atoms to form an oxo group and/or a thioxo group. Examples of such groups include the piperidonyl, pyrrolidonyl, thiazolidonyl, dioxothiazolidinyl, thioxodithiazolidinyl, dioxomidazolidinyl and dioxooxazolidinyl groups.

Also, the above-described saturated heterocyclic group may be fused with another cyclic group, preferably having 3, 4, 5 or 6 ring atoms, and which may be carboxyxlic or heterocyclic, most preferably a benzene ring. Examples of such fused ring groups include the benzodioxanyl, indolinyl, isoindolinyl, benzooxazinyl, benzothiazolidinyl, benzothiazinyl, chromanyl, 6-acetoxy-2,5,7,8-tetramethylchroman-2-yl, and isoindol-1,3-dion-2-yl groups.

Examples of such aromatic heterocyclic groups include the furyl, thienyl, pyrrolyl, azepinyl, pyazolyl, imidazolyl, oxazolyl, isoxazolyl, thiazolyl, isothiazolyl, oxadiazolyl, triazolyl, tetrazolyl, thiadiazolyl, pyranyl, pyridyl, pyridazinyl, pyrimidinyl and pyrazinyl groups. Of these, those 5- to 7-membered aromatic heterocyclic groups which have at least one nitrogen atom and may have an oxygen atom or a sulfur atom are preferred. Examples of such groups include the pyrrolyl, azepinyl, pyrazolyl, imidazolyl, oxazolyl, isoxazolyl, thiazolyl, isothiazolyl, oxadiazolyl, triazolyl, tetrazolyl, thiadiazolyl, pyridyl, pyridazinyl, pyrimidinyl and pyrazinyl groups. The pyridyl, imidazolyl, oxazolyl, pyrazinyl and thiazolyl groups are most preferred.

Also, if desired, the above-described aromatic heterocyclic group may be fused with another cyclic group, preferably having 3, 4, 5 or 6 ring atoms, and which may be carbocyclic or heterocyclic, most preferably a benzene ring. Examples of such fused ring groups include the indolyl, benzofuryl, benzothienyl, benzooxazolyl, benzoimidazolyl, quinolyl, isoquinolyl, quinoxalyl groups.

Also, the above-described aromatic heterocyclic groups may be substituted by one or two atoms selected from the group consisting of sulfur atoms and oxygen atoms to form an oxo group and/or a thioxo group, and examples of such groups include the pyridonyl, oxazilonyl, pyrazolonyl, isoxazolonyl and thioxodithiazolyl groups.

If desired, any of the above aryl and heterocyclic groups may be substituted by one of more, preferably from 1 to 3, substituent selected from the group consisting of substituents β, defined above and exemplified below.

Where R$^1$ represents an alkyl group having from 1 to 12 carbon atoms, this may be a straight or branched chain group which may be unsubstituted or may be substituted by from 1 to 3 substituents selected from the group consisting of substituents γ, defined above and exemplified below. Examples of such unsubstituted alkyl groups include the methyl, ethyl, propyl, isopropyl, butyl, isobutyl, sec-butly, t-butyl, pentyl, 2-pentyl, 3-pentyl, 2-methylbutyl, 3-methylbutyl, 1,1-dimethylpropyl, 1,2-dimethylpropyl, 2,2-dimethylpropyl, hexyl, 2-hexyl, 3-hexyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, heptyl, 2-heptyl, 3-heptyl, 4-heptyl, 3,3-dimethylpentyl, octyl, 2-methylhepty, 2-ethylhexyl, 1,1,3,3-tetramethylbutyl, nonyl, 2-nonyl, 3-nonyl, 4-nonyl, 5-nonyl, 2-methyloctyl, 3-methyloctyl, 4-methyloctyl, 5-methyloctyl, 6-methyloctyl, 7-methyloctyl, 8-methyloctyl, 6,6-dimethylheptyl, decyl, 2-decyl, 3-decyl, 4-decyl, 5-decyl, 2-methylnonyl, 3-methylnonyl, 4-methylnonyl, 6,6-dimethyloctyl, undecyl, 2-undecyl, 3-undecyl, 4-undecyl, 5-undecyl, 6-undecyl, 2-methyldecyl, 3-methyldecyl, 4-methyldecyl, 5-methyldecyl, 6-methyldecyl, 7-methyldecyl, 8-methyldecyl, 9-methyldecyl, 7-ethynonyl, dodecyl, 2-dodecyl, 3-dodecyl, 4-dodecyl, 5-dodecyl, 6-dodecyl, 2-methylundecyl, 3-methylundecyl, 4-methylundecyl, 5-methylundecyl, 6-methylundecyl, 7-methylundecyl, 8-methylundecyl, 9-methylundecyl and 10-methylundecyl groups. Of these, straight or branched alkyl groups having from 1 to 6 carbon atoms are preferred, straight or branched alkyl groups having from 1 to 4 carbon atoms are more preferred, and the methyl, ethyl, propyl, isopropyl, butyl, isobutyl, and t-butyl groups are most preferred.

Alternatively, $R^1$ may represent such an alkyl group in which the carbon chain is interrupted by one or more oxygen atoms and/or sulfur atoms. Examples of such groups include any of the above alkyl groups which are substituted by a single alkoxy or alkylthio group, which itself may be further substituted by an alkoxy or alkylthio group, the alkoxy and alkylthio groups being as exemplified below in relation to substituents β and γ. Specific examples of such groups include alkoxyalkyl groups having from 2 to 10 carbon atoms, alkylthioalkyl groups having from 2 to 10 carbon atoms, benzyloxyalkyl groups of which the alkyl part has from 1 to 5 carbon atoms and benzylthioalkyl groups of which the alkyl part has from 1 to 5 carbon atoms (the benzyl part of the benzyloxyalkyl and benzylthoalkyl groups may be unsubstituted or substituted with from 1 to 3 substituents selected from the group consisting of substituents β) groups. Of these, the methoxymethyl, methoxyethyl, ethoxymethyl, methylthiomethyl, methylthioethyl, ethylthiomethyl, benzyloxymethyl, benzyloxyethyl, benzylthiomethyl and 4-methoxybenxylthiomethyl groups are preferred.

Where $R^2$, $R^3$, $R^4$, $R^5$ and $R^6$ represents an alkyl group having from 1 to 12 carbon atoms, this may be straight or branched chain group, as defined and exemplified above in relation to $R^1$, Where $R^2$, $R^3$, $R^4$, $R^5$ and $R^6$ represents an aralkyl group, this is a lower alkyl group (preferably having from 1 to 6 carbon atoms, more preferably from 1 to 4 carbon atoms, still more preferably from 1 to 3 carbon atoms and most preferably 1 or 2 carbon atoms) which is substituted by from 1 to 3 aryl groups as defined and exemplified above in relation to $R^1$. Specific examples of such aralkyl groups include the benzyl, 1-phenylethyl, 2-phenylethyl, α-naphthylmethyl, β-naphthylmethyl, diphenylmethyl, triphenylmethyl, α-naphthyldiphenylmethyl and 9-anthrylmethyl groups. Of these, the benzyl, 1-phenylethyl and 2-phenylethyl groups are preferred. Any of the above groups may be unsubstituted or it may be substituted by from 1 to 3 substituents selected from the group consisting of substituents γ defined and exemplified below.

Where $R^2$, $R^3$, $R^4$, $R^5$ and $R^6$ represents an acyl group, this may be an aliphatic, aromatic or heterocyclic acyl group, for example:

an alkylcarbonyl group having from 1 to 30, preferably from 1 to 21 and more preferably from 1 to 8 carbon atoms, such as the formyl, acetyl, propionyl, butyryl, isobutyryl, pivaloyl, valeryl, isovaleryl, octanoyl, nonylcarbonyl, decylcarbonyl, 3-methylnonylcarbonyl, 8-methylnonylcarbonyl, 3-ethyloctylcarbonyl, 3,7-dimethyloctylcarbonyl, undecylcarbonyl, dodecylcarbonyl, tridecylcarbonyl, tetradecylcarbonyl, pentadecylcarbonyl, hexadecylcarbonyl, 1-methylpentadecylcarbonyl, 14-methylpentadecylcarbonyl, 13,13-dimethyltetradecylcarbonyl, heptadecylcarbonyl, 15-methylhexadecylcarbonyl, octadecylcarbonyl, 1-methylheptadecylcarbonyl, nonadecylcarbonyl, eicosylcarbonyl and heneicosylcarbonyl groups; of these, the groups having from 1 to 5 carbon atoms are most preferred;

a halogenated alkylcarbonyl group having from 2 to 6 carbon atoms, preferably 2 or 3 carbon atoms, such as the chloroacetyl, dichloroacetyl, trichloroacetyl and trifluoroacetyl groups;

a lower alkoxyalkylcarbonyl group in which the alkyl and alkoxy parts each preferably has from 1 to 4 carbon atoms, such as the methoxyacetyl group;

an unsaturated alkylcarbonyl group having from 3 to 6 carbon atoms, such as the acryloyl, propioloyl, methacryloyl, crotonoyl, allylcarbonyl, isocrotonoyl and (E)-2-methyl-2-butenoyl groups;

an arylcarbonyl group, such as the benzoyl, α-naphthoyl and β-naphthoyl groups;

a halogenated arylcarbonyl group, such as the 2-bromobenzoyl and 4-chlorobenzoyl groups;

a lower alkyl-substituted arylcarbonyl group, such as the 2,4,6-trimethylbenzoyl and 4-toluoyl groups;

a hydroxy-substituted arylcarbonyl group, such as the 3,5-dimethyl-4-hydroxybenzoyl and 3,5-di-t-butyl-4-hydroxybenzoyl groups;

a lower alkoxy-substituted arylcarbonyl group, such as the 4-anisoyl group;

a nitro-substituted arylcarbonyl group such as the 4-nitrobenzoyl and 2nitrobenzoyl groups;

a lower alkoxycarbonyl-substituted arylcarbonyl group, such as the 2-(methoxycarbonyl)benzoyl group;

an aryl-substituted arylcarbonyl group, such as the 4-phenylbenzoyl group;

a lower alkoxycarbonyl group preferably having from 2 to 7 carbon atoms, such as the methoxycarbonyl, ethoxycarbonyl, propoxycarbonyl, butoxycarbonyl, sec-butoxycarbonyl, t-butoxycarbonyl and isobutoxycarbonyl groups;

a lower alkoxycarbonyl group, preferably having from 2 to 7 carbon atoms, which is substituted with a halogen atom or a tri-lower alkylsilyl group, such as the 2,2,2-trichloroethoxycarbonyl and 2 - trimethylsilylethoxycarbonyl groups;

an aralkylcarbonyl group, of which the aryl ring may be unsubstituted or may be substituted with 1 or 2 lower alkoxy or nitro groups, such as the benzylcarbonyl, 4-methoxybenzylcarbonyl, 3,4-dimethoxybenzylcarbonyl, 2-nitrobenzylcarbonyl and 4-nitrobenzylcarbonyl groups;

a lower alkanesulfonyl group, preferably having from 1 to 6 carbon atoms, such as the methanesulfonyl, ethanesulfonyl and propanesulfonyl groups;

a halogenated lower alkanesulfonyl group, preferably having from 1 to 6 carbon atoms, such as the chloromethanesulfonyl, trifluoromethanesulfonyl and pentafluoroethanesulfonyl groups; and an arylsulfonyl group, in which the aryl part is as defined and exemplified above in relation to $R^1$, such as the benzenesulfonyl and p-toluenesulfonyl group.

Of the above groups, we prefer the aliphatic acyl groups, the aromatic acyl groups, the alkoxycarbonyl groups and the lower alkanesulfonyl groups, more preferably the alkylcarbonyl groups and the lower alkoxycarbonyl groups.

Where $R^5$, together with $R^1$ and the nitrogen atom to which they are attached forms a heterocyclic group, this has from 5 to7, more preferably 5 or 6, ring atoms of which from 1 to 3 are hetero-atoms selected from the group consisting of nitrogen, oxygen and sulfur atoms, at least one being a nitrogen atom. Preferably there are one or two nitrogen atoms and no or one oxygen atoms or sulfur atoms. Examples of such groups include the pyrrolidino, 3-thiazolidinyl, piperidino, piperazino, morpholino, thiomorpholino, homopiperazino, imidazolidinyl and imidazolyl groups. Such groups may be substituted or unsubstituted, preferably with one or two oxygen atoms and/or with 1 to 3 substituents selected from the group consisting of substituents β, as defined above, and may be fused with another cyclic group, preferably having 3, 4, 5 or 6 ring atoms, and which may be carbocyclic or heterocyclic, most preferably a benzene ring. Examples of such groups are the N-methylpiperazino, N-t-butoxycarbonylpiperazino, 1-indolinyl, 2-carboxy-1-indolinyl, 2-methoxycarbonyl-1-indolinyl, 3,4-dimethylindolin-2,5-dione-1-yl and isoindol-1,3-dion-2-yl groups.

Where $R^7$ or substituent β represents lower alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. Of these, we prefer those alkyl groups having from 1 to 4 carbon atoms, particularly the methyl, ethyl, propyl, isopropyl, butyl, isobutyl and t-butyl groups, and most preferably the methyl group.

Where $R^7$ represents a lower alkenyl group, this may be a straight or branched chain group having from 2 to 6, preferably 3 or 4, carbon atoms, and examples include the vinyl, allyl, methallyl, 1-propenyl, isoprepenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl and 4-hexenyl groups, of which the vinyl, allyl, methallyl, 1-propenyl, isopropenyl and butenyl groups are preferred, the allyl and 2-butenyl groups being most preferred.

Where $R^7$ represents an aralkyl group, this may be any of the aralkyl groups defined and exemplified above in relation to $R^2$.

Where substituent β represents a halogenated lower alkyl group, this may be any of the above alkyl groups which is substituted by at least one halogen atom. Although there is no critical limitation on the number of halogen substituents, and the group may, if desired, be perhalogenated, in general, from 1 to 3 halogen atoms, selected from the group consisting of fluorine, chlorine, bromine and iodine atoms are preferred. Examples of such haloalkyl groups include the chloromethyl, dichloromethyl, trichloromethyl, trifluoromethyl, 2-chloroethyl, 2-fluoroethyl, 2-bromoethyl, 2-iodoethyl, 2,2,2-trichloroethyl, 2,2,2-trifluoroethyl, 3-chloropropyl, 3-fluoropropyl, 3-bromopropyl, 3-iodopropyl, 3,3,3-trichloropropyl, 3,3,3-trifluoropropyl, 4-chlorobutyl, 4-fluorobutyl, 4-bromobutyl and 4-iodobutyl groups.

Where substituent β or substituent γ represents a lower alkoxy group, this may be a straight or branched chain group having from 1 to 6, preferably from 1 to 4, carbon atoms, and examples include the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, hexyloxy, isohexyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups. Of these, we prefer those alkoxy groups having from 1 to 4 carbon atoms, particularly the methoxy, ethoxy, propoxy, isopropoxy, butoxy and t-butoxy groups, and most preferably the methoxy group.

Where substituent β or substituent γ represents a lower alkylthio group, this may be a straight or branched chain group having from 1 to 6, preferably from 1 to 4, carbon atoms, and examples include the methylthio, ethylthio, propylthio isopropylthio, butylthio, isobutylthio, sec-butylthio, t-butylthio, pentylthio, isopentylthio, neopentylthio, 2-methylbutylthio, 1-ethylpropylthio, hexylthio, isohexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio and 2-ethylbutylthio groups. Of these, we prefer those alkylthio groups having from 1 to 4 carbon atoms, particularly the methylthio, ehtylthio, propylthio, isopropylthio, butylthio and isobutylthio groups, and most preferably the methylthio group.

Where substituent β or substituent γ represents an amine residue, this is a group of formula —$NR^aR^b$, where $R^a$ and $R^b$ are the same or different and each represents a hydrogen atom, a lower alkyl group (as defined and exemplified above in relation to $R^7$ or substituent β), a cycloalkyl group having from 3 to 8, preferably 5 or 6, ring carbon atoms, an aryl group (as defined and exemplified above in relation to $R^1$), an aralkyl group (as defined and exemplified above in relation to $R^2$), a heterocyclic group (as defined and exemplified above in relation to $R^1$), or $R^a$ and $R^b$ together with the nitrogen atom to which they are attached represent a nitrogen-containing heterocyclic group (as defined and exemplified above in relation to $R^5$ and $R^1$). Examples of such groups include:

the amino group;

alkylamino and dialkylamino groups, such as the methylamino, ethylamino, isopropylamino, butylamino, dimethylamino, diethylamino, diisopropylamino and ditubylamino groups;

cycloalkylamino and dicycloalkylamino groups, such as the cyclopentylamino, cyclohexylamino, dicyclopentylamino and dicyclohexylamino groups;

saturated cyclic amino groups, that is heterocyclic groups having a nitrogen atom in the ring, such as the pyrrolidino, piperidino, piperazino, N-methylpiperazino, morpholino and thiomorpholino groups;

aryl- and aralkylamino groups of which the nitrogen atom may be substituted with a lower alkyl group, such as the anilino, benzylamino, N-methylanilino and N-methylbenzylamino groups; and a heterocyclic-substituted amino group, in which the nitrogen atom may be substituted with a lower alkyl group, such as the pyridylamino, N-methylpyridylamino and N-ethylpyridylamino groups.

Of these, we prefer the amino group, mono- and di-alkylamino groups, saturated cyclic amino groups (such as the pyrrolidino, piperidino, piperazino, N-methylpiperazino, morpholino and thiomorpholino groups) and aryl- and aralkylamino groups of which the nitrogen atom may be substituted with a lower alkyl group (such as the anilino, benzylamino, N-methylanilino and N-methylbenzylamino groups).

Where substituent β or substituent γ represents a carbamoyl group of which the nitrogen atom may be substituted, this is a group of formula —$CONR^{a'}R^{b'}$, where $R^{a'}$ and $R^{b'}$ are the same or different and each represents any of the atoms or groups represented by $R^a$ and $R^b$ or a one of $R^a$ and $R^b$ represents a hydrogen atom and the other represents an acyl group (which may be any of the acyl groups defined and exemplified above in relation to $R^2$) or an aminosulfonyl group. Examples of such carbamoyl groups include:

- the carbamoyl group;
- alkylcarbamoyl and dialkylcarbamoyl groups, such as the methylcarbamoyl, ethylcarbamoyl, isopropylcarbamoyl, butylcarbamoyl, dimethylcarbamoyl, diethylcarbamoyl, diisopropylcarbamoyl and dibutylcarbamoyl groups;
- cycloalkylcarbamoyl and dicycloalkylcarbamoyl groups, such as the cyclopentylcarbamoyl, cyclohexylcarbamoyl, dicyclopentylcarbamoyl and dicyclohexylcarbamoyl groups;
- saturated cyclic aminocarbonyl groups, that is carbonyl groups attached to a heterocyclic group having a nitrogen atom in the ring, such as the pyrrolidinocarbonyl, piperidinocarbonyl, piperazinocarbonyl, N-methylpiperazinocarbonyl, morpholinocarbonyl and thiomorpholinocarbonyl groups;
- aryl- and aralkylcarbamoyl groups of which the nitrogen atom may be substituted with a lower alkyl group, such as the phenylcarbamoyl, benzylcarbamoyl, N-methylphenylcarbamoyl and N-methylbenzylcarbamoyl groups;
- a heterocyclic-substituted carbamoyl group, in which the nitrogen atom may be substituted with a lower alkyl group, such as the pyridylcarbamoyl, N-methylpyridylcarbamoyl and N-ethylpyridylcarbamoyl groups; and
- acylcarbamoyl groups, especially alkanesulfonylaminocarbonyl groups, such as the methanesulfonylaminocarbonyl group and the aminosulfonylaminocarbonyl group.

Of these, we prefer the carbamoyl group, mono- and di-alkylcarbamoyl groups, saturated cyclic carbamoyl groups (such as the pyrrolidinocarbonyl, piperidinocarbonyl, piperazinocarbonyl, N-methylpiperazinocarbonyl, morpholinocarbonyl and thiomorpholinocarbonyl groups), aryl- and aralkylcarbamoyl groups of which the nitrogen atom may be substituted with a lower alkyl group (such as the phenylcarbamoyl, benzylcarbamoyl, N-methylphenylcarbamoyl and N-methylbenzylcarbamoyl groups) or an alkanesulfonylaminocarbonyl group (such as the methanesulfonylaminocarbonyl group).

Where substituent β or substituent γ represents a lower alkoxycarbonyl group, this may be a straight or branched chain group having from 1 to 6, preferably from 1 to 4, carbon atoms in the alkoxy part (i.e. from 2 to 7 carbon atoms in the alkoxycarbonyl part), and examples include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, hexyloxycarbonyl, isohexyloxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl and 2-ethylbutoxycarbonyl groups. Of these, we prefer those alkoxycarbonyl groups having from 1 to 4 carbon atoms, particularly the methoxycarbonyl, ethoxycarbonyl, propoxycarbonyl, isopropoxycarbonyl, butoxycarbonyl and t-butoxycarbonyl groups, and most preferably the methoxycarbonyl group.

Where substitutent β or substitutent γ represents a halogen atom, this may be a fluorine, chlorine, bromine or iodine atom, preferably a fluorine or chlorine atom.

Where substituent β represents a hydroxy-substituted lower alkyl group, this may be any of the lower alkyl groups defined and exemplified above in relation to $R^2$ which is substituted by one or more hydroxy groups. Examples of such groups include the hydroxymethyl, hydroxyethyl, hydroxypropyl and hydroxybutyl groups.

Of the compounds of the present invention, those compounds of formula (I) in which the group of formula —(CH$_2$)$_k$—ABR$^1$ is bonded to the 3-positin of the dithiolan ring are preferred. Such compounds may be represented by the formula (I'):

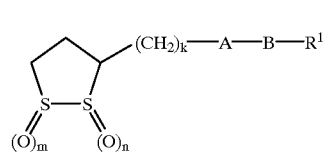

(I')

in which A, B, $R^1$, k, m and n are as defined above).

Where the compounds of the present invention possess a basic group, such as an amino or imino group, the compounds can form salts with acids. On the other hand, where the compounds of the present invention possess an acidic group, such as a carboxy group or an imido group, they can form salts with bases. There is no particular restriction on the nature of such salts, provided that, where they are intended for pharmaceutical use, they are pharmaceutically acceptable, that is they are not less active (or unacceptably less active) than the compound of formula (I), and are not more toxic (or unacceptably more toxic) than the compound of formula (I).

Examples of such salts formed between a basic group in the compound of the present invention and an acid include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glycine, lysine, arginine, ornithine, glutamic acid or aspartic acid.

Examples of such salts formed between an acidic group in the compound of the present invention and a base include: salts with an alkali metal, such as sodium, potassium or lithium; salts with an alkaline earth metal, such as barium or calcium; salts with another metal, such as magnesium, aluminum or ion; ammonium salts; organic base salts, such as a salt with t-octylamine, dibenzylamine, morpholine, glucosamine, a phenylglycine alkyl ester, ethylenediamine, N-methylglucamine, guanidine, methylamine, dimethylamine, diethylamine, triethylamine, diisopropylamine, cyclohexylamine, dicyclohexylamine, N,N-dibenzylethylenediamine, chloroprocaine, procaine, diethanolamine, N-benzylphenethylamine, piperazine, tetramethylammonium, and tris(hydroxymethyl) aminomethane; and salts with an amino acid, such as glycine, lysine, arginine, ornithine, glutamic acid or aspartic acid.

Also, when a compound of the present invention is allowed to stand in the air, it may absorb water to form a hydrate. Such hydrates also form a part of the present invention.

Where a compound of the present invention contains an asymmetric carbon atom in its molecule, it can form optical isomers which are in the R- or S-configuration. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Of the compounds of the present invention, we prefer those compounds of formula (I) and salts thereof in which:

(A) one of m and n is 0, and the other is 0 or 1;

(B) k is 0 or an integer of from 1 to 8;

(C) $R^1$ represents a hydroxy group, an alkoxy group having from 1 to 5 carbon atoms, a heterocyclic group, an alkyl group having from 1 to 12 carbon atoms which is unsubstituted or is substituted by from 1 to 3 substitutents selected from the group consisting of substituents α and substitutents γ or such a substituted or unsubstituted alkyl group in which the carbon chain is interrupted by an oxygen atom and/or a sulfur atom;

(D) A is a group of formula —CO—, —CON($R^2$)SO$_2$—, —N($R^2$)CO—, —N($R^2$)CS—, —CON($R^2$)CO—, —N($R^2$)COCO— or —N($R^2$)SO$_2$— [wherein, $R^2$ is a hydrogen atom, an alkyl group having from 1 to 12 carbon atoms or a benzyl group], in particular a group of formula —CON($R^2$)SO$_2$—, —N($R^2$)CS—, —CON($R^2$)CO—, —N($R^2$)COCO—, or —N($R^2$)SO$_2$—;

(E) B represents a single bond, or a group of formula —N($R^5$)— or —N($R^5$)N($R^6$)— [wherein $R^5$ and $R^6$ are the same or different and each represents a hydrogen atom, an alkyl group having from 1 to 12 carbon atoms or a benzyl group];

Of the above, we particularly prefer those compounds of formula (I) in which m and n are as defined in (A) above, k is as defined in (B) above, $R^1$ is as defined in (C) above, A is as defined in (D) above, and B is as defined in (E) above.

More preferred compounds of the present invention are those compounds of formula (I) and salts thereof in which:

(F) both of m and n are 0;

(G) k is an integer of from 2 to 6;

(H) $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group, an alkoxy group having from 1 to 5 carbon atoms or hydroxy group;

(I) A represents a group of formula —CO—, —CON($R^2$)SO$_2$—, —N($R^2$)CO—, —N($R^2$)CS—, —CON($R^2$)CO—, —N($R^2$)COCO— or —N($R^2$)SO$_2$— [wherein $R^2$ represents a hydrogen atom or an alkyl group having from 1 to 12 carbon atoms], in particular a group of formula —CON($R^2$)SO$_2$—, —N($R^2$)CS—, —CON($R^2$)CO—, —N($R^2$)COCO—, or —N($R^2$)SO$_2$—;

(J) B represents a single bond, or a group of formula —N($R^5$)— or —N($R^5$)N($R^6$)— [wherein $R^5$ and $R^6$ are the same or different and each represents a hydrogen atom or an alkyl group having from 1 to 12 carbon atoms];

Of the above, we particularly prefer those compounds of formula (I) in which m and n are as defined in (F) above, k is as defined in (G) above, $R^1$ is as defined in (H) above, A is as defined in (I) above, and B is as defined in (J) above.

The most preferred compounds of the present invention are those compounds of formula (I) and salts thereof in which:

(K) both of m and n are 0;

(L) k is 4 or 5;

(M) $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group or an alkoxy group having from 1 to 5 carbon atoms;

(N) A represents a group of formula —CONHSO$_2$—, —CONCH$_3$SO$_2$—, —NHCO—, —NHCS—, —CONHCO—, —NHCOCO—, —NHSO$_2$— or —CO—, in particular a group of formula —CONHSO$_2$—, —CONCH$_3$SO$_2$—, —NHCS—, —CONHCO—, —NHCOCO—, or —NHSO$_2$—;

(O) B represents a single bond, or a group of formula —NH—, —NCH$_3$— or —NHNCH$_3$—;

Of the above, we particularly prefer those compounds of formula (I) in which m and n are as defined in (K) above, k is as defined in (L) above, $R^1$ is as defined in (M) above, A is as defined in (N) above, and B is as defined in (O) above.

Specific examples of individual compounds of the present invention are shown in the following formulae (I-1), (I-2) and (I-3), in which the substituent groups are as shown in the corresponding one of Tables 1 to 3. In the Tables, the following abbreviations are used:

| | |
|---|---|
| Ac | acetyl; |
| Bu | butyl; |
| iBu | isobutyl; |
| sBu | sec-butyl; |
| tBu | t-butyl; |
| Bz | benzyl; |
| 1,3-diox-IInd | isoindol-1,3-dione-2-yl; |
| 3,4-diMe-2,5-diox-1-Imdd | 3,4-dimethyl-imidazolidin-2,5-dione-lyl, |
| Et | ethyl; |
| Hx | hexyl; |
| Indn | indolinyl; |
| Me | methyl; |
| Mor | morpholino; |
| Ph | phenyl; |
| Pipra | piperazino; |
| Pipri | piperidino; |
| Pn | pentyl; |
| ipn | isopentyl; |
| Pr | propyl; |
| iPr | isopropyl; |
| Py | pyridyl; |
| Pyr | pyrrolidinyl; |
| Thiad | 3-thiazolidinyl; |
| Thmor | thiomorpholino. |

Also, in the Tables, the groups represented by Z-1 to Z-12 have the following formulae:

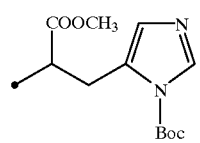

Z-1

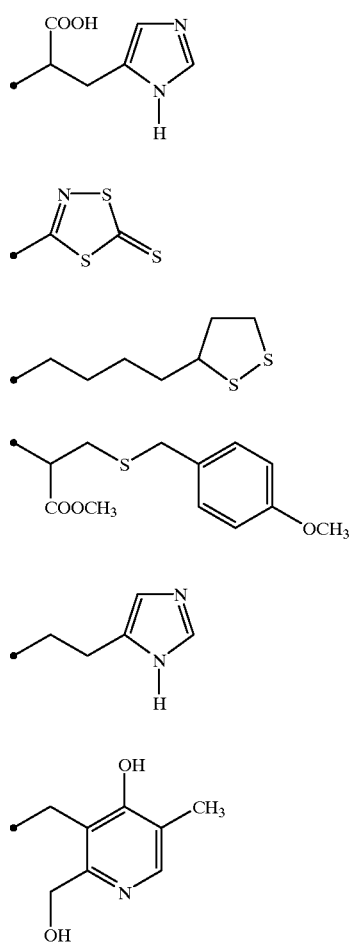
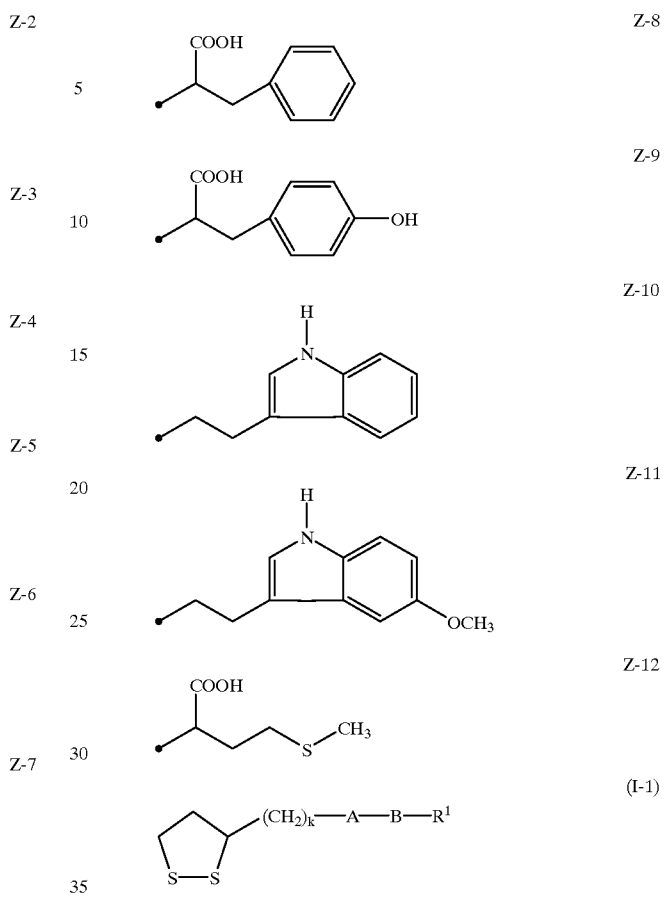
TABLE 1
| Cpd. No. | k | A | B | R¹ |
|---|---|---|---|---|
| 1-1 | 4 | CO | NH | H |
| 1-2 | 4 | CO | NH | Ph |
| 1-3 | 4 | CO | NH | 2-Me—Ph |
| 1-4 | 4 | CO | NH | 4-Me—Ph |
| 1-5 | 4 | CO | NH | 2,4-diMe—Ph |
| 1-6 | 4 | CO | NH | 3,4-diMe—Ph |
| 1-7 | 4 | CO | NH | 2-(CF$_3$)Ph |
| 1-8 | 4 | CO | NH | 4-(CF$_3$)Ph |
| 1-9 | 4 | CO | NH | 2-MeOPh |
| 1-10 | 4 | CO | NH | 4-MeOPh |
| 1-11 | 4 | CO | NH | 2-EtOPh |
| 1-12 | 4 | CO | NH | 4-EtOPh |
| 1-13 | 4 | CO | NH | 2-HOPh |
| 1-14 | 4 | CO | NH | 4-HOPh |
| 1-15 | 4 | CO | NH | 2-(HOOC)Ph |
| 1-16 | 4 | CO | NH | 4-(HOOC)Ph |
| 1-17 | 4 | CO | NH | 2-(MeOOC)Ph |
| 1-18 | 4 | CO | NH | 4-(MeOOC)Ph |
| 1-19 | 4 | CO | NH | 2-(EtOOC)Ph |
| 1-20 | 4 | CO | NH | 4-(EtOOC)Ph |
| 1-21 | 4 | CO | NH | 2-(tBuOOC)Ph |
| 1-22 | 4 | CO | NH | 4-(tBuOOC)Ph |
| 1-23 | 4 | CO | NH | 2-Cl—Ph |
| 1-24 | 4 | CO | NH | 4-Cl—Ph |
| 1-25 | 4 | CO | NH | 2-Br—Ph |
| 1-26 | 4 | CO | NH | 4-Br—Ph |
| 1-27 | 4 | CO | NH | 2-I—Ph |

TABLE 1-continued

| Cpd. No. | k | A | B | R[1] |
|---|---|---|---|---|
| 1-28 | 4 | CO | NH | 4-I—Ph |
| 1-29 | 4 | CO | NH | 2-NO$_2$—Ph |
| 1-30 | 4 | CO | NH | 4-NO$_2$—Ph |
| 1-31 | 4 | CO | NH | 2-NH$_2$—Ph |
| 1-32 | 4 | CO | NH | 4-NH$_2$—Ph |
| 1-33 | 4 | CO | NH | 2-(HO$_3$S)Ph |
| 1-34 | 4 | CO | NH | 4-(HO$_3$S)Ph |
| 1-35 | 4 | CO | NH | 2-(NH$_2$O$_2$S)Ph |
| 1-36 | 4 | CO | NH | 4-(NH$_2$O$_2$S)Ph |
| 1-37 | 4 | CO | NH | 2-CN—Ph |
| 1-38 | 4 | CO | NH | 4-CN—Ph |
| 1-39 | 4 | CO | NH | 2-(HOCH$_2$)Ph |
| 1-40 | 4 | CO | NH | 4-(HOCH$_2$)Ph |
| 1-41 | 4 | CO | NH | Me |
| 1-42 | 4 | CO | NH | Et |
| 1-43 | 4 | CO | NH | Pr |
| 1-44 | 4 | CO | NH | iPr |
| 1-45 | 4 | CO | NH | Bu |
| 1-46 | 4 | CO | NH | HOOCCH$_2$— |
| 1-47 | 4 | CO | NH | MeOOCCH$_2$— |
| 1-48 | 4 | CO | NH | MeCH(COOH)— |
| 1-49 | 4 | CO | NH | HOOC—(CH$_2$)$_2$— |
| 1-50 | 4 | CO | NH | MeCH(COOMe)— |
| 1-51 | 4 | CO | NH | 1-HOOC-iBu |
| 1-52 | 4 | CO | NH | 1-MeOOC-iBu |
| 1-53 | 4 | CO | NH | 1-HOOC-iPn |
| 1-54 | 4 | CO | NH | 1-MeOOC-iPn |
| 1-55 | 4 | CO | NH | 1-HOOC-2-Me—Bu |
| 1-56 | 4 | CO | NH | 1-MeOOC-2-Me—Bu |
| 1-57 | 4 | CO | NH | CH$_2$CH$_2$SO$_3$H |
| 1-58 | 4 | CO | NH | OH |
| 1-59 | 4 | CO | NH | MeO |
| 1-60 | 4 | CO | NH | EtO |
| 1-61 | 4 | CO | NH | PrO |
| 1-62 | 4 | CO | NH | iPrO |
| 1-63 | 4 | CO | NH | BuO |
| 1-64 | 4 | CO | NH | iBuO |
| 1-65 | 4 | CO | NH | sBuO |
| 1-66 | 4 | CO | NH | tBuO |
| 1-67 | 4 | CO | NH | HxO |
| 1-68 | 4 | CO | NH | PhO |
| 1-69 | 4 | CO | NH | BzO |
| 1-70 | 4 | CO | NH | Z-1 |
| 1-71 | 4 | CO | NH | Z-2 |
| 1-72 | 4 | CO | NH | Z-3 |
| 1-73 | 4 | CO | NH | Z-4 |
| 1-74 | 4 | CO | NH | Z-5 |
| 1-75 | 4 | CO | NH | Z-6 |
| 1-76 | 4 | CO | NH | Z-7 |
| 1-77 | 4 | CO | NH | Z-8 |
| 1-78 | 4 | CO | NH | Z-9 |
| 1-79 | 4 | CO | NH | Z-10 |
| 1-80 | 4 | CO | NH | Z-11 |
| 1-81 | 4 | CO | NH | Z-12 |
| 1-82 | 4 | CO | NH | 3-Py |
| 1-83 | 4 | CO | NH | 4-Py |
| 1-84 | 4 | CO | N(Ac) | H |
| 1-85 | 4 | CO | N(Ac) | Ph |
| 1-86 | 4 | CO | N(Ac) | 2-Me—Ph |
| 1-87 | 4 | CO | N(Ac) | 4-Me—Ph |
| 1-88 | 4 | CO | N(Ac) | 2,4-diMe—Ph |
| 1-89 | 4 | CO | N(Ac) | 3,4-diMe—Ph |
| 1-90 | 4 | CO | N(Ac) | 2-(CF$_3$)Ph |
| 1-91 | 4 | CO | N(Ac) | 4-(CF$_3$)Ph |
| 1-92 | 4 | CO | N(Ac) | 2-MeOPh |
| 1-93 | 4 | CO | N(Ac) | 4-MeOPh |
| 1-94 | 4 | CO | N(Ac) | 2-EtOPh |
| 1-95 | 4 | CO | N(Ac) | 4-EtOPh |
| 1-96 | 4 | CO | N(Ac) | 2-HOPh |
| 1-97 | 4 | CO | N(Ac) | 4-HOPh |
| 1-98 | 4 | CO | N(Ac) | 2-(HOOC)Ph |
| 1-99 | 4 | CO | N(Ac) | 4-(HOOC)Ph |
| 1-100 | 4 | CO | N(Ac) | 2-(MeOOC)Ph |
| 1-101 | 4 | CO | N(Ac) | 4-(MeOOC)Ph |
| 1-102 | 4 | CO | N(Ac) | 2-(EtOOC)Ph |
| 1-103 | 4 | CO | N(Ac) | 4-(EtOOC)Ph |

TABLE 1-continued

| Cpd. No. | k | A | B | R¹ |
|---|---|---|---|---|
| 1-104 | 4 | CO | N(Ac) | 2-(tBuOOC)Ph |
| 1-105 | 4 | CO | N(Ac) | 4-(tBuOOC)Ph |
| 1-106 | 4 | CO | N(Ac) | 2-Cl—Ph |
| 1-107 | 4 | CO | N(Ac) | 4-Cl—Ph |
| 1-108 | 4 | CO | N(Ac) | 2-Br—Ph |
| 1-109 | 4 | CO | N(Ac) | 4-Br—Ph |
| 1-110 | 4 | CO | N(Ac) | 2-I—Ph |
| 1-111 | 4 | CO | N(Ac) | 4-I—Ph |
| 1-112 | 4 | CO | N(Ac) | 2-NO$_2$—Ph |
| 1-113 | 4 | CO | N(Ac) | 4-NO$_2$—Ph |
| 1-114 | 4 | CO | N(Ac) | 2-NH$_2$—Ph |
| 1-115 | 4 | CO | N(Ac) | 4-NH$_2$—Ph |
| 1-116 | 4 | CO | N(Ac) | 2-(HO$_3$S)Ph |
| 1-117 | 4 | CO | N(Ac) | 4-(HO$_3$S)Ph |
| 1-118 | 4 | CO | N(Ac) | 2-(NH$_2$O$_2$S)Ph |
| 1-119 | 4 | CO | N(Ac) | 4-(NH$_2$O$_2$S)Ph |
| 1-120 | 4 | CO | N(Ac) | 2-CN—Ph |
| 1-121 | 4 | CO | N(Ac) | 4-CN—Ph |
| 1-122 | 4 | CO | N(Ac) | 2-(HOCH$_2$)Ph |
| 1-123 | 4 | CO | N(Ac) | 4-(HOCH$_2$)Ph |
| 1-124 | 4 | CO | N(Ac) | Me |
| 1-125 | 4 | CO | N(Ac) | Et |
| 1-126 | 4 | CO | N(Ac) | Pr |
| 1-127 | 4 | CO | N(Ac) | iPr |
| 1-128 | 4 | CO | N(Ac) | Bu |
| 1-129 | 4 | CO | N(Ac) | HOOCCH$_2$— |
| 1-130 | 4 | CO | N(Ac) | MeOOCCH$_2$— |
| 1-131 | 4 | CO | N(Ac) | MeCH(COOH) |
| 1-132 | 4 | CO | N(Ac) | HOOC—(CH$_2$)$_2$— |
| 1-133 | 4 | CO | N(Ac) | MeCH(COOMe) |
| 1-134 | 4 | CO | N(Ac) | 1-HOOC-iBu |
| 1-135 | 4 | CO | N(Ac) | 1-MeOOC-iBu |
| 1-136 | 4 | CO | N(Ac) | 1-HOOC-iPn |
| 1-137 | 4 | CO | N(Ac) | 1-MeOOC-iPn |
| 1-138 | 4 | CO | N(Ac) | 1-HOOC-2-Me—Bu |
| 1-139 | 4 | CO | N(Ac) | 1-MeOOC-2-Me—Bu |
| 1-140 | 4 | CO | N(Ac) | CH$_2$CH$_2$SO$_3$H |
| 1-141 | 4 | CO | N(Ac) | OH |
| 1-142 | 4 | CO | N(Ac) | MeO |
| 1-143 | 4 | CO | N(Ac) | EtO |
| 1-144 | 4 | CO | N(Ac) | PrO |
| 1-145 | 4 | CO | N(Ac) | iPrO |
| 1-146 | 4 | CO | N(Ac) | BuO |
| 1-147 | 4 | CO | N(Ac) | iBuO |
| 1-148 | 4 | CO | N(Ac) | sBuO |
| 1-149 | 4 | CO | N(Ac) | tBuO |
| 1-150 | 4 | CO | N(Ac) | HxO |
| 1-151 | 4 | CO | N(Ac) | PhO |
| 1-152 | 4 | CO | N(Ac) | BzO |
| 1-153 | 4 | CO | N(Ac) | Z-1 |
| 1-154 | 4 | CO | N(Ac) | Z-2 |
| 1-155 | 4 | CO | N(Ac) | Z-3 |
| 1-156 | 4 | CO | N(Ac) | Z-4 |
| 1-157 | 4 | CO | N(Ac) | Z-5 |
| 1-158 | 4 | CO | N(Ac) | Z-6 |
| 1-159 | 4 | CO | N(Ac) | Z-7 |
| 1-160 | 4 | CO | N(Ac) | Z-8 |
| 1-161 | 4 | CO | N(Ac) | Z-9 |
| 1-162 | 4 | CO | N(Ac) | Z-10 |
| 1-163 | 4 | CO | N(Ac) | Z-11 |
| 1-164 | 4 | CO | N(Ac) | Z-12 |
| 1-165 | 4 | CO | N(Ac) | 3-Py |
| 1-166 | 4 | CO | N(Ac) | 4-Py |
| 1-167 | 4 | COO | — | H |
| 1-168 | 4 | COO | — | Ph |
| 1-169 | 4 | COO | — | 2-Me—Ph |
| 1-170 | 4 | COO | — | 4-Me—Ph |
| 1-171 | 4 | COO | — | 2,4-diMe—Ph |
| 1-172 | 4 | COO | — | 3,4-diMe—Ph |
| 1-173 | 4 | COO | — | 2-(CF$_3$)Ph |
| 1-174 | 4 | COO | — | 4-(CF$_3$)Ph |
| 1-175 | 4 | COO | — | 2-MeOPh |
| 1-176 | 4 | COO | — | 4-MeOPh |
| 1-177 | 4 | COO | — | 2-EtOPh |
| 1-178 | 4 | COO | — | 4-EtOPh |
| 1-179 | 4 | COO | — | 2-HOPh |

TABLE 1-continued

| Cpd. No. | k | A | B | R$^1$ |
|---|---|---|---|---|
| 1-180 | 4 | COO | — | 4-HOPh |
| 1-181 | 4 | COO | — | 2-(HOOC)Ph |
| 1-182 | 4 | COO | — | 4-(HOOC)Ph |
| 1-183 | 4 | COO | — | 2-(MeOOC)Ph |
| 1-184 | 4 | COO | — | 4-(MeOOC)Ph |
| 1-185 | 4 | COO | — | 2-(EtOOC)Ph |
| 1-186 | 4 | COO | — | 4-(EtOOC)Ph |
| 1-187 | 4 | COO | — | 2-(tBuOOC)Ph |
| 1-188 | 4 | COO | — | 4-(tBuOOC)Ph |
| 1-189 | 4 | COO | — | 2-Cl—Ph |
| 1-190 | 4 | COO | — | 4-Cl—Ph |
| 1-191 | 4 | COO | — | 2-Br—Ph |
| 1-192 | 4 | COO | — | 4-Br—Ph |
| 1-193 | 4 | COO | — | 2-I—Ph |
| 1-194 | 4 | COO | — | 4-I—Ph |
| 1-195 | 4 | COO | — | 2-NO$_2$—Ph |
| 1-196 | 4 | COO | — | 4-NO$_2$—Ph |
| 1-197 | 4 | COO | — | 2-NH$_2$—Ph |
| 1-198 | 4 | COO | — | 4-NH$_2$—Ph |
| 1-199 | 4 | COO | — | 2-(HO$_3$S)Ph |
| 1-200 | 4 | COO | — | 4-(HO$_3$S)Ph |
| 1-201 | 4 | COO | — | 2-(NH$_2$O$_2$S)Ph |
| 1-202 | 4 | COO | — | 4-(NH$_2$O$_2$S)Ph |
| 1-203 | 4 | COO | — | 2-CN—Ph |
| 1-204 | 4 | COO | — | 4-CN—Ph |
| 1-205 | 4 | COO | — | 2-(HOCH$_2$)Ph |
| 1-206 | 4 | COO | — | 4-(HOCH$_2$)Ph |
| 1-207 | 4 | COO | — | Me |
| 1-208 | 4 | COO | — | Et |
| 1-209 | 4 | COO | — | Pr |
| 1-210 | 4 | COO | — | iPr |
| 1-211 | 4 | COO | — | Bu |
| 1-212 | 4 | COO | — | HOOCCH$_2$— |
| 1-213 | 4 | COO | — | HOOC—(CH$_2$)$_2$— |
| 1-214 | 4 | COO | — | MeCH(COOMe) |
| 1-215 | 4 | COO | — | 1-HOOC-iBu |
| 1-216 | 4 | COO | — | 1-HOOC-iPn |
| 1-217 | 4 | COO | — | Z-1 |
| 1-218 | 4 | COO | — | Z-2 |
| 1-219 | 4 | COO | — | Z-3 |
| 1-220 | 4 | COO | — | Z-4 |
| 1-221 | 4 | COO | — | Z-5 |
| 1-222 | 4 | COO | — | Z-6 |
| 1-223 | 4 | COO | — | Z-7 |
| 1-224 | 4 | COO | — | Z-8 |
| 1-225 | 4 | COO | — | Z-9 |
| 1-226 | 4 | COO | — | Z-10 |
| 1-227 | 4 | COO | — | Z-11 |
| 1-228 | 4 | COO | — | Z-12 |
| 1-229 | 4 | COO | — | 3-Py |
| 1-230 | 4 | COO | — | 4-Py |
| 1-231 | 4 | CONHCO | — | H |
| 1-232 | 4 | CONHCO | — | Ph |
| 1-233 | 4 | CONHCO | — | 2-Me—Ph |
| 1-234 | 4 | CONHCO | — | 4-Me—Ph |
| 1-235 | 4 | CONHCO | — | 2,4-diMe—Ph |
| 1-236 | 4 | CONHCO | — | 3,4-diMe—Ph |
| 1-237 | 4 | CONHCO | — | 2-(CF$_3$)Ph |
| 1-238 | 4 | CONHCO | — | 4-(CF$_3$)Ph |
| 1-239 | 4 | CONHCO | — | 2-MeOPh |
| 1-240 | 4 | CONHCO | — | 4-MeOPh |
| 1-241 | 4 | CONHCO | — | 2-EtOPh |
| 1-242 | 4 | CONHCO | — | 4-EtOPh |
| 1-243 | 4 | CONHCO | — | 2-HOPh |
| 1-244 | 4 | CONHCO | — | 4-HOPh |
| 1-245 | 4 | CONHCO | — | 2-(HOOC)Ph |
| 1-246 | 4 | CONHCO | — | 4-(HOOC)Ph |
| 1-247 | 4 | CONHCO | — | 2-(MeOOC)Ph |
| 1-248 | 4 | CONHCO | — | 4-(MeOOC)Ph |
| 1-249 | 4 | CONHCO | — | 2-(EtOOC)Ph |
| 1-250 | 4 | CONHCO | — | 4-(EtOOC)Ph |
| 1-251 | 4 | CONHCO | — | 2-(tBuOOC)Ph |
| 1-252 | 4 | CONHCO | — | 4-(tBuOOC)Ph |
| 1-253 | 4 | CONHCO | — | 2-Cl—Ph |
| 1-254 | 4 | CONHCO | — | 4-Cl—Ph |
| 1-255 | 4 | CONHCO | — | 2-Br—Ph |

TABLE 1-continued

| Cpd. No. | k | A | B | R¹ |
|---|---|---|---|---|
| 1-256 | 4 | CONHCO | — | 4-Br—Ph |
| 1-257 | 4 | CONHCO | — | 2-I—Ph |
| 1-258 | 4 | CONHCO | — | 4-I—Ph |
| 1-259 | 4 | CONHCO | — | 2-$NO_2$—Ph |
| 1-260 | 4 | CONHCO | — | 4-$NO_2$—Ph |
| 1-261 | 4 | CONHCO | — | 2-$NH_2$—Ph |
| 1-262 | 4 | CONHCO | — | 4-$NH_2$—Ph |
| 1-263 | 4 | CONHCO | — | 2-($HO_3S$)Ph |
| 1-264 | 4 | CONHCO | — | 4-($HO_3S$)Ph |
| 1-265 | 4 | CONHCO | — | 2-($NH_2O_2S$)Ph |
| 1-266 | 4 | CONHCO | — | 4-($NH_2O_2S$)Ph |
| 1-267 | 4 | CONHCO | — | 2-CN—Ph |
| 1-268 | 4 | CONHCO | — | 4-CN—Ph |
| 1-269 | 4 | CONHCO | — | 2-($HOCH_2$)Ph |
| 1-270 | 4 | CONHCO | — | 4-($HOCH_2$)Ph |
| 1-271 | 4 | CONHCO | — | Me |
| 1-272 | 4 | CONHCO | — | Et |
| 1-273 | 4 | CONHCO | — | Pr |
| 1-274 | 4 | CONHCO | — | iPr |
| 1-275 | 4 | CONHCO | — | Bu |
| 1-276 | 4 | CONHCO | — | $HOOCCH_2$— |
| 1-277 | 4 | CONHCO | — | $MeOOCCH_2$— |
| 1-278 | 4 | CONHCO | — | MeCH(COOH) |
| 1-279 | 4 | CONHCO | — | HOOC—$(CH_2)_2$— |
| 1-280 | 4 | CONHCO | — | MeCH(COOMe) |
| 1-281 | 4 | CONHCO | — | 1-HOOC-iBu |
| 1-282 | 4 | CONHCO | — | 1-MeOOC-iBu |
| 1-283 | 4 | CONHCO | — | 1-HOOC-iPn |
| 1-284 | 4 | CONHCO | — | 1-MeOOC-iPn |
| 1-285 | 4 | CONHCO | — | 1-HOOC-2-Me—Bu |
| 1-286 | 4 | CONHCO | — | 1-MeOOC-2-Me—Bu |
| 1-287 | 4 | CONHCO | — | $CH_2CH_2SO_3H$ |
| 1-288 | 4 | CONHCO | — | Z-1 |
| 1-289 | 4 | CONHCO | — | Z-2 |
| 1-290 | 4 | CONHCO | — | Z-3 |
| 1-291 | 4 | CONHCO | — | Z-4 |
| 1-292 | 4 | CONHCO | — | Z-5 |
| 1-293 | 4 | CONHCO | — | Z-6 |
| 1-294 | 4 | CONHCO | — | Z-7 |
| 1-295 | 4 | CONHCO | — | Z-8 |
| 1-296 | 4 | CONHCO | — | Z-9 |
| 1-297 | 4 | CONHCO | — | Z-10 |
| 1-298 | 4 | CONHCO | — | Z-11 |
| 1-299 | 4 | CONHCO | — | Z-12 |
| 1-300 | 4 | CONHCO | — | 3-Py |
| 1-301 | 4 | CONHCO | — | 4-Py |
| 1-302 | 4 | CON(Ac)CO | — | H |
| 1-303 | 4 | CON(Ac)CO | — | Ph |
| 1-304 | 4 | CON(Ac)CO | — | 2-Me—Ph |
| 1-305 | 4 | CON(Ac)CO | — | 4-Me—Ph |
| 1-306 | 4 | CON(Ac)CO | — | 2,4-diMe—Ph |
| 1-307 | 4 | CON(Ac)CO | — | 3,4-diMe—Ph |
| 1-308 | 4 | CON(Ac)CO | — | 2-($CF_3$)Ph |
| 1-309 | 4 | CON(Ac)CO | — | 4-($CF_3$)Ph |
| 1-310 | 4 | CON(Ac)CO | — | 2-MeOPh |
| 1-311 | 4 | CON(Ac)CO | — | 4-MeOPh |
| 1-312 | 4 | CON(Ac)CO | — | 2-EtOPh |
| 1-313 | 4 | CON(Ac)CO | — | 4-EtOPh |
| 1-314 | 4 | CON(Ac)CO | — | 2-HOPh |
| 1-315 | 4 | CON(Ac)CO | — | 4-HOPh |
| 1-316 | 4 | CON(Ac)CO | — | 2-(HOOC)Ph |
| 1-317 | 4 | CON(Ac)CO | — | 4-(HOOC)Ph |
| 1-318 | 4 | CON(Ac)CO | — | 2-(MeOOC)Ph |
| 1-319 | 4 | CON(Ac)CO | — | 4-(MeOOC)Ph |
| 1-320 | 4 | CON(Ac)CO | — | 2-(EtOOC)Ph |
| 1-321 | 4 | CON(Ac)CO | — | 4-(EtOOC)Ph |
| 1-322 | 4 | CON(Ac)CO | — | 2-(tBuOOC)Ph |
| 1-323 | 4 | CON(Ac)CO | — | 4-(tBuOOC)Ph |
| 1-324 | 4 | CON(Ac)CO | — | 2-Cl—Ph |
| 1-325 | 4 | CON(Ac)CO | — | 4-Cl—Ph |
| 1-326 | 4 | CON(Ac)CO | — | 2-Br—Ph |
| 1-327 | 4 | CON(Ac)CO | — | 4-Br—Ph |
| 1-328 | 4 | CON(Ac)CO | — | 2-I—Ph |
| 1-329 | 4 | CON(Ac)CO | — | 4-I—Ph |
| 1-330 | 4 | CON(Ac)CO | — | 2-$NO_2$—Ph |
| 1-331 | 4 | CON(Ac)CO | — | 4-$NO_2$—Ph |

TABLE 1-continued

| Cpd. No. | k | A | B | R$^1$ |
|---|---|---|---|---|
| 1-332 | 4 | CON(Ac)CO | — | 2-NH$_2$—Ph |
| 1-333 | 4 | CON(Ac)CO | — | 4-NH$_2$—Ph |
| 1-334 | 4 | CON(Ac)CO | — | 2-(HO$_3$S)Ph |
| 1-335 | 4 | CON(Ac)CO | — | 4-(HO$_3$S)Ph |
| 1-336 | 4 | CON(Ac)CO | — | 2-(NH$_2$O$_2$S)Ph |
| 1-337 | 4 | CON(Ac)CO | — | 4-(NH$_2$O$_2$S)Ph |
| 1-338 | 4 | CON(Ac)CO | — | 2-CN—Ph |
| 1-339 | 4 | CON(Ac)CO | — | 4-CN—Ph |
| 1-340 | 4 | CON(Ac)CO | — | 2-(HOCH$_2$)Ph |
| 1-341 | 4 | CON(Ac)CO | — | 4-(HOCH$_2$)Ph |
| 1-342 | 4 | CON(Ac)CO | — | Me |
| 1-343 | 4 | CON(Ac)CO | — | Et |
| 1-344 | 4 | CON(Ac)CO | — | Pr |
| 1-345 | 4 | CON(Ac)CO | — | iPr |
| 1-346 | 4 | CON(Ac)CO | — | Bu |
| 1-347 | 4 | CON(Ac)CO | — | HOOCCH$_2$— |
| 1-348 | 4 | CON(Ac)CO | — | MeOOCCH$_2$— |
| 1-349 | 4 | CON(Ac)CO | — | MeCH(COOH) |
| 1-350 | 4 | CON(Ac)CO | — | HOOC—(CH$_2$)$_2$— |
| 1-351 | 4 | CON(Ac)CO | — | MeCH(COOMe) |
| 1-352 | 4 | CON(Ac)CO | — | 1-HOOC-iBu |
| 1-353 | 4 | CON(Ac)CO | — | 1-MeOOC-iBu |
| 1-354 | 4 | CON(Ac)CO | — | 1-HOOC-iPn |
| 1-355 | 4 | CON(Ac)CO | — | 1-MeOOC-iPn |
| 1-356 | 4 | CON(Ac)CO | — | 1-HOOC-2-Me—Bu |
| 1-357 | 4 | CON(Ac)CO | — | 1-MeOOC-2-Me—Bu |
| 1-358 | 4 | CON(Ac)CO | — | CH$_2$CH$_2$SO$_3$H |
| 1-359 | 4 | CON(Ac)CO | — | Z-1 |
| 1-360 | 4 | CON(Ac)CO | — | Z-2 |
| 1-361 | 4 | CON(Ac)CO | — | Z-3 |
| 1-362 | 4 | CON(Ac)CO | — | Z-4 |
| 1-363 | 4 | CON(Ac)CO | — | Z-5 |
| 1-364 | 4 | CON(Ac)CO | — | Z-6 |
| 1-365 | 4 | CON(Ac)CO | — | Z-7 |
| 1-366 | 4 | CON(Ac)CO | — | Z-8 |
| 1-367 | 4 | CON(Ac)CO | — | Z-9 |
| 1-368 | 4 | CON(Ac)CO | — | Z-10 |
| 1-369 | 4 | CON(Ac)CO | — | Z-11 |
| 1-370 | 4 | CON(Ac)CO | — | Z-12 |
| 1-371 | 4 | CON(Ac)CO | — | 3-Py |
| 1-372 | 4 | CON(Ac)CO | — | 4-Py |
| 1-373 | 4 | CONHCO | NH | H |
| 1-374 | 4 | CONHCO | NH | Ph |
| 1-375 | 4 | CONHCO | NH | 2-Me—Ph |
| 1-376 | 4 | CONHCO | NH | 4-Me—Ph |
| 1-377 | 4 | CONHCO | NH | 2,4-diMe—Ph |
| 1-378 | 4 | CONHCO | NH | 3,4-diMe—Ph |
| 1-379 | 4 | CONHCO | NH | 2-(CF$_3$)Ph |
| 1-380 | 4 | CONHCO | NH | 4-(CF$_3$)Ph |
| 1-381 | 4 | CONHCO | NH | 2-MeOPh |
| 1-382 | 4 | CONHCO | NH | 4-MeOPh |
| 1-383 | 4 | CONHCO | NH | 2-EtOPh |
| 1-384 | 4 | CONHCO | NH | 4-EtOPh |
| 1-385 | 4 | CONHCO | NH | 2-HOPh |
| 1-386 | 4 | CONHCO | NH | 4-HOPh |
| 1-387 | 4 | CONHCO | NH | 2-(HOOC)Ph |
| 1-388 | 4 | CONHCO | NH | 4-(HOOC)Ph |
| 1-389 | 4 | CONHCO | NH | 2-(MeOOC)Ph |
| 1-390 | 4 | CONHCO | NH | 4-(MeOOC)Ph |
| 1-391 | 4 | CONHCO | NH | 2-(EtOOC)Ph |
| 1-392 | 4 | CONHCO | NH | 4-(EtOOC)Ph |
| 1-393 | 4 | CONHCO | NH | 2-(tBuOOC)Ph |
| 1-394 | 4 | CONHCO | NH | 4-(tBuOOC)Ph |
| 1-395 | 4 | CONHCO | NH | 2-Cl—Ph |
| 1-396 | 4 | CONHCO | NH | 4-Cl—Ph |
| 1-397 | 4 | CONHCO | NH | 2-Br—Ph |
| 1-398 | 4 | CONHCO | NH | 4-Br—Ph |
| 1-399 | 4 | CONHCO | NH | 2-I—Ph |
| 1-400 | 4 | CONHCO | NH | 4-I—Ph |
| 1-401 | 4 | CONHCO | NH | 2-NO$_2$—Ph |
| 1-402 | 4 | CONHCO | NH | 4-NO$_2$—Ph |
| 1-403 | 4 | CONHCO | NH | 2-NH$_2$—Ph |
| 1-404 | 4 | CONHCO | NH | 4-NH$_2$—Ph |
| 1-405 | 4 | CONHCO | NH | 2-(HO$_3$S)Ph |
| 1-406 | 4 | CONHCO | NH | 4-(HO$_3$S)Ph |
| 1-407 | 4 | CONHCO | NH | 2-(NH$_2$O$_2$S)Ph |

TABLE 1-continued

| Cpd. No. | k | A | B | R¹ |
|---|---|---|---|---|
| 1-408 | 4 | CONHCO | NH | 4-($NH_2O_2S$)Ph |
| 1-409 | 4 | CONHCO | NH | 2-CN—Ph |
| 1-410 | 4 | CONHCO | NH | 4-CN—Ph |
| 1-411 | 4 | CONHCO | NH | 2-($HOCH_2$)Ph |
| 1-412 | 4 | CONHCO | NH | 4-($HOCH_2$)Ph |
| 1-413 | 4 | CONHCO | NH | Me |
| 1-414 | 4 | CONHCO | NH | Et |
| 1-415 | 4 | CONHCO | NH | Pr |
| 1-416 | 4 | CONHCO | NH | iPr |
| 1-417 | 4 | CONHCO | NH | Bu |
| 1-418 | 4 | CONHCO | NH | $HOOCCH_2$— |
| 1-419 | 4 | CONHCO | NH | $MeOOCCH_2$— |
| 1-420 | 4 | CONHCO | NH | MeCH(COOH) |
| 1-421 | 4 | CONHCO | NH | HOOC-$(CH_2)_2$— |
| 1-422 | 4 | CONHCO | NH | MeCH(COOMe) |
| 1-423 | 4 | CONHCO | NH | 1-HOOC-iBu |
| 1-424 | 4 | CONHCO | NH | 1-MeOOC-iBu |
| 1-425 | 4 | CONHCO | NH | 1-HOOC-iPn |
| 1-426 | 4 | CONHCO | NH | 1-MeOOC-iPn |
| 1-427 | 4 | CONHCO | NH | 1-HOOC-2-Me—Bu |
| 1-428 | 4 | CONHCO | NH | 1-MeOOC-2-Me—Bu |
| 1-429 | 4 | CONHCO | NH | $CH_2CH_2SO_3H$ |
| 1-430 | 4 | CONHCO | NH | HO |
| 1-431 | 4 | CONHCO | NH | MeO |
| 1-432 | 4 | CONHCO | NH | EtO |
| 1-433 | 4 | CONHCO | NH | PrO |
| 1-434 | 4 | CONHCO | NH | iPrO |
| 1-435 | 4 | CONHCO | NH | BuO |
| 1-436 | 4 | CONHCO | NH | iBuO |
| 1-437 | 4 | CONHCO | NH | sBuO |
| 1-438 | 4 | CONHCO | NH | tBuO |
| 1-439 | 4 | CONHCO | NH | HxO |
| 1-440 | 4 | CONHCO | NH | PhO |
| 1-441 | 4 | CONHCO | NH | BzO |
| 1-442 | 4 | CONHCO | NH | Z-1 |
| 1-443 | 4 | CONHCO | NH | Z-2 |
| 1-444 | 4 | CONHCO | NH | Z-3 |
| 1-445 | 4 | CONHCO | NH | Z-4 |
| 1-446 | 4 | CONHCO | NH | Z-5 |
| 1-447 | 4 | CONHCO | NH | Z-6 |
| 1-448 | 4 | CONHCO | NH | Z-7 |
| 1-449 | 4 | CONHCO | NH | Z-8 |
| 1-450 | 4 | CONHCO | NH | Z-9 |
| 1-451 | 4 | CONHCO | NH | Z-10 |
| 1-452 | 4 | CONHCO | NH | Z-11 |
| 1-453 | 4 | CONHCO | NH | Z-12 |
| 1-454 | 4 | CONHCO | NH | 3-Py |
| 1-455 | 4 | CONHCO | NH | 4-Py |
| 1-456 | 4 | $CONHSO_2$ | — | H |
| 1-457 | 4 | $CONHSO_2$ | — | Ph |
| 1-458 | 4 | $CONHSO_2$ | — | 2-Me—Ph |
| 1-459 | 4 | $CONHSO_2$ | — | 4-Me—Ph |
| 1-460 | 4 | $CONHSO_2$ | — | 2,4-diMe—Ph |
| 1-461 | 4 | $CONHSO_2$ | — | 3,4-diMe—Ph |
| 1-462 | 4 | $CONHSO_2$ | — | 2-($CF_3$)Ph |
| 1-463 | 4 | $CONHSO_2$ | — | 4-($CF_3$)Ph |
| 1-464 | 4 | $CONHSO_2$ | — | 2-MeOPh |
| 1-465 | 4 | $CONHSO_2$ | — | 4-MeOPh |
| 1-466 | 4 | $CONHSO_2$ | — | 2-EtOPh |
| 1-467 | 4 | $CONHSO_2$ | — | 4-EtOPh |
| 1-468 | 4 | $CONHSO_2$ | — | 2-HOPh |
| 1-469 | 4 | $CONHSO_2$ | — | 4-HOPh |
| 1-470 | 4 | $CONHSO_2$ | — | 2-(HOOC)Ph |
| 1-471 | 4 | $CONHSO_2$ | — | 4-(HOOC)Ph |
| 1-472 | 4 | $CONHSO_2$ | — | 2-(MeOOC)Ph |
| 1-473 | 4 | $CONHSO_2$ | — | 4-(MeOOC)Ph |
| 1-474 | 4 | $CONHSO_2$ | — | 2-(EtOOC)Ph |
| 1-475 | 4 | $CONHSO_2$ | — | 4-(EtOOC)Ph |
| 1-476 | 4 | $CONHSO_2$ | — | 2-(tBuOOC)Ph |
| 1-477 | 4 | $CONHSO_2$ | — | 4-(tBuOOC)Ph |
| 1-478 | 4 | $CONHSO_2$ | — | 2-Cl—Ph |
| 1-479 | 4 | $CONHSO_2$ | — | 4-Cl—Ph |
| 1-480 | 4 | $CONHSO_2$ | — | 2-Br—Ph |
| 1-481 | 4 | $CONHSO_2$ | — | 4-Br—Ph |
| 1-482 | 4 | $CONHSO_2$ | — | 2-I—Ph |
| 1-483 | 4 | $CONHSO_2$ | — | 4-I—Ph |

TABLE 1-continued

| Cpd. No. | k | A | B | R$^1$ |
|---|---|---|---|---|
| 1-484 | 4 | CONHSO$_2$ | — | 2-NO$_2$—Ph |
| 1-485 | 4 | CONHSO$_2$ | — | 4-NO$_2$—Ph |
| 1-486 | 4 | CONHSO$_2$ | — | 2-NH$_2$—Ph |
| 1-487 | 4 | CONHSO$_2$ | — | 4-NH$_2$—Ph |
| 1-488 | 4 | CONHSO$_2$ | — | 2-(HO$_3$S)Ph |
| 1-489 | 4 | CONHSO$_2$ | — | 4-(HO$_3$S)Ph |
| 1-490 | 4 | CONHSO$_2$ | — | 2-(NH$_2$O$_2$S)Ph |
| 1-491 | 4 | CONHSO$_2$ | — | 4-(NH$_2$O$_2$S)Ph |
| 1-492 | 4 | CONHSO$_2$ | — | 2-CN—Ph |
| 1-493 | 4 | CONHSO$_2$ | — | 4-CN—Ph |
| 1-494 | 4 | CONHSO$_2$ | — | 2-(HOCH$_2$)Ph |
| 1-495 | 4 | CONHSO$_2$ | — | 4-(HOCH$_2$)Ph |
| 1-496 | 4 | CONHSO$_2$ | — | Me |
| 1-497 | 4 | CONHSO$_2$ | — | Et |
| 1-498 | 4 | CONHSO$_2$ | — | Pr |
| 1-499 | 4 | CONHSO$_2$ | — | iPr |
| 1-500 | 4 | CONHSO$_2$ | — | Bu |
| 1-501 | 4 | CONHSO$_2$ | — | HOOCCH$_2$— |
| 1-502 | 4 | CONHSO$_2$ | — | MeOOCCH$_2$— |
| 1-503 | 4 | CONHSO$_2$ | — | MeCH(COOH) |
| 1-504 | 4 | CONHSO$_2$ | — | HOOC—(CH$_2$)$_2$— |
| 1-505 | 4 | CONHSO$_2$ | — | MeCH(COOMe) |
| 1-506 | 4 | CONHSO$_2$ | — | 1-HOOC-iBu |
| 1-507 | 4 | CONHSO$_2$ | — | 1-MeOOC-iBu |
| 1-508 | 4 | CONHSO$_2$ | — | 1-HOOC-iPn |
| 1-509 | 4 | CONHSO$_2$ | — | 1-MeOOC-iPn |
| 1-510 | 4 | CONHSO$_2$ | — | 1-HOOC-2-Me—Bu |
| 1-511 | 4 | CONHSO$_2$ | — | 1-MeOOC-2-Me—Bu |
| 1-512 | 4 | CONHSO$_2$ | — | CH$_2$CH$_2$SO$_3$H |
| 1-513 | 4 | CONHSO$_2$ | — | OH |
| 1-514 | 4 | CONHSO$_2$ | — | MeO |
| 1-515 | 4 | CONHSO$_2$ | — | EtO |
| 1-516 | 4 | CONHSO$_2$ | — | PrO |
| 1-517 | 4 | CONHSO$_2$ | — | iPrO |
| 1-518 | 4 | CONHSO$_2$ | — | BuO |
| 1-519 | 4 | CONHSO$_2$ | — | iBuO |
| 1-520 | 4 | CONHSO$_2$ | — | sBuO |
| 1-521 | 4 | CONHSO$_2$ | — | tBuO |
| 1-522 | 4 | CONHSO$_2$ | — | HxO |
| 1-523 | 4 | CONHSO$_2$ | — | PhO |
| 1-524 | 4 | CONHSO$_2$ | — | BzO |
| 1-525 | 4 | CONHSO$_2$ | — | Z-1 |
| 1-526 | 4 | CONHSO$_2$ | — | Z-2 |
| 1-527 | 4 | CONHSO$_2$ | — | Z-3 |
| 1-528 | 4 | CONHSO$_2$ | — | Z-4 |
| 1-529 | 4 | CONHSO$_2$ | — | Z-5 |
| 1-530 | 4 | CONHSO$_2$ | — | Z-6 |
| 1-531 | 4 | CONHSO$_2$ | — | Z-7 |
| 1-532 | 4 | CONHSO$_2$ | — | Z-8 |
| 1-533 | 4 | CONHSO$_2$ | — | Z-9 |
| 1-534 | 4 | CONHSO$_2$ | — | Z-10 |
| 1-535 | 4 | CONHSO$_2$ | — | Z-11 |
| 1-536 | 4 | CONHSO$_2$ | — | Z-12 |
| 1-537 | 4 | CONHSO$_2$ | — | 3-Py |
| 1-538 | 4 | CONHSO$_2$ | — | 4-Py |
| 1-539 | 4 | CONHSO$_2$ | NH | H |
| 1-540 | 4 | CONHSO$_2$ | NH | Ph |
| 1-541 | 4 | CONHSO$_2$ | NH | 2-Me—Ph |
| 1-542 | 4 | CONHSO$_2$ | NH | 4-Me—Ph |
| 1-543 | 4 | CONHSO$_2$ | NH | 2,4-diMe—Ph |
| 1-544 | 4 | CONHSO$_2$ | NH | 3,4-diMe—Ph |
| 1-545 | 4 | CONHSO$_2$ | NH | 2-(CF$_3$)Ph |
| 1-546 | 4 | CONHSO$_2$ | NH | 4-(CF$_3$)Ph |
| 1-547 | 4 | CONHSO$_2$ | NH | 2-MeOPh |
| 1-548 | 4 | CONHSO$_2$ | NH | 4-MeOPh |
| 1-549 | 4 | CONHSO$_2$ | NH | 2-EtOPh |
| 1-550 | 4 | CONHSO$_2$ | NH | 4-EtOPh |
| 1-551 | 4 | CONHSO$_2$ | NH | 2-HOPh |
| 1-552 | 4 | CONHSO$_2$ | NH | 4-HOPh |
| 1-553 | 4 | CONHSO$_2$ | NH | 2-(HOOC)Ph |
| 1-554 | 4 | CONHSO$_2$ | NH | 4-(HOOC)Ph |
| 1-555 | 4 | CONHSO$_2$ | NH | 2-(MeOOC)Ph |
| 1-556 | 4 | CONHSO$_2$ | NH | 4-(MeOOC)Ph |
| 1-557 | 4 | CONHSO$_2$ | NH | 2-(EtOOC)Ph |
| 1-558 | 4 | CONHSO$_2$ | NH | 4-(EtOOC)Ph |
| 1-559 | 4 | CONHSO$_2$ | NH | 2-(tBuOOC)Ph |

TABLE 1-continued

| Cpd. No. | k | A | B | R¹ |
|---|---|---|---|---|
| 1-560 | 4 | CONHSO$_2$ | NH | 4-(tBuOOC)Ph |
| 1-561 | 4 | CONHSO$_2$ | NH | 2-Cl—Ph |
| 1-562 | 4 | CONHSO$_2$ | NH | 4-Cl—Ph |
| 1-563 | 4 | CONHSO$_2$ | NH | 2-Br—Ph |
| 1-564 | 4 | CONHSO$_2$ | NH | 4-Br—Ph |
| 1-565 | 4 | CONHSO$_2$ | NH | 2-I—Ph |
| 1-566 | 4 | CONHSO$_2$ | NH | 4-I—Ph |
| 1-567 | 4 | CONHSO$_2$ | NH | 2-NO$_2$—Ph |
| 1-568 | 4 | CONHSO$_2$ | NH | 4-NO$_2$—Ph |
| 1-569 | 4 | CONHSO$_2$ | NH | 2-NH$_2$—Ph |
| 1-570 | 4 | CONHSO$_2$ | NH | 4-NH$_2$—Ph |
| 1-571 | 4 | CONHSO$_2$ | NH | 2-(HO$_3$S)Ph |
| 1-572 | 4 | CONHSO$_2$ | NH | 4-(HO$_3$S)Ph |
| 1-573 | 4 | CONHSO$_2$ | NH | 2-(NH$_2$O$_2$S)Ph |
| 1-574 | 4 | CONHSO$_2$ | NH | 4-(NH$_2$O$_2$S)Ph |
| 1-575 | 4 | CONHSO$_2$ | NH | 2-CN—Ph |
| 1-576 | 4 | CONHSO$_2$ | NH | 4-CN—Ph |
| 1-577 | 4 | CONHSO$_2$ | NH | 2-(HOCH$_2$)Ph |
| 1-578 | 4 | CONHSO$_2$ | NH | 4-(HOCH$_2$)Ph |
| 1-579 | 4 | CONHSO$_2$ | NH | Me |
| 1-580 | 4 | CONHSO$_2$ | NH | Et |
| 1-581 | 4 | CONHSO$_2$ | NH | Pr |
| 1-582 | 4 | CONHSO$_2$ | NH | iPr |
| 1-583 | 4 | CONHSO$_2$ | NH | Bu |
| 1-584 | 4 | CONHSO$_2$ | NH | HOOCCH$_2$— |
| 1-555 | 4 | CONHSO$_2$ | NH | MeOOCCH$_2$— |
| 1-586 | 4 | CONHSO$_2$ | NH | MeCH(COOH) |
| 1-587 | 4 | CONHSO$_2$ | NH | HOOC—(CH$_2$)$_2$— |
| 1-588 | 4 | CONHSO$_2$ | NH | MeCH(COOMe) |
| 1-589 | 4 | CONHSO$_2$ | NH | 1-HOOC-iBu |
| 1-590 | 4 | CONHSO$_2$ | NH | 1-MeOOC-iBu |
| 1-591 | 4 | CONHSO$_2$ | NH | 1-HOOC-iPn |
| 1-592 | 4 | CONHSO$_2$ | NH | 1-MeOOC-iPn |
| 1-593 | 4 | CONHSO$_2$ | NH | 1-HOOC-2-Me—Bu |
| 1-594 | 4 | CONHSO$_2$ | NH | 1-MeOOC-2-Me—Bu |
| 1-595 | 4 | C0NHSO$_2$ | NH | CH$_2$CH$_2$SO$_3$H |
| 1-596 | 4 | CONHSO$_2$ | NH | OH |
| 1-597 | 4 | CONHSO$_2$ | NH | MeO |
| 1-598 | 4 | CONHSO$_2$ | NH | EtO |
| 1-599 | 4 | CONHSO$_2$ | NH | PrO |
| 1-600 | 4 | CONHSO$_2$ | NH | iPrO |
| 1-601 | 4 | CONHSO$_2$ | NH | BuO |
| 1-602 | 4 | CONHSO$_2$ | NH | iBuO |
| 1-603 | 4 | CONHSO$_2$ | NH | sBuO |
| 1-604 | 4 | CONHSO$_2$ | NH | tBuO |
| 1-605 | 4 | CONHSO$_2$ | NH | HxO |
| 1-606 | 4 | CONHSO$_2$ | NH | PhO |
| 1-607 | 4 | CONHSO$_2$ | NH | BzO |
| 1-608 | 4 | CONHSO$_2$ | NH | Z-1 |
| 1-609 | 4 | CONHSO$_2$ | NH | Z-2 |
| 1-610 | 4 | CONHSO$_2$ | NH | Z-3 |
| 1-611 | 4 | CONHSO$_2$ | NH | Z-4 |
| 1-612 | 4 | CONHSO$_2$ | NH | Z-5 |
| 1-613 | 4 | CONHSO$_2$ | NH | Z-6 |
| 1-614 | 4 | CONHSO$_2$ | NH | Z-7 |
| 1-615 | 4 | CONHSO$_2$ | NH | Z-8 |
| 1-616 | 4 | CONHSO$_2$ | NH | Z-9 |
| 1-617 | 4 | CONHSO$_2$ | NH | Z-10 |
| 1-618 | 4 | CONHSO$_2$ | NH | Z-11 |
| 1-619 | 4 | CONHSO$_2$ | NH | Z-12 |
| 1-620 | 4 | CONHSO$_2$ | NH | 3-Py |
| 1-621 | 4 | CONHSO$_2$ | NH | 4-Py |
| 1-622 | 4 | NHCO | — | H |
| 1-623 | 4 | NHCO | — | Ph |
| 1-624 | 4 | NHCO | — | 2-Me—Ph |
| 1-625 | 4 | NHCO | — | 4-Me—Ph |
| 1-626 | 4 | NHCO | — | 2,4-diMe—Ph |
| 1-627 | 4 | NHCO | — | 3,4-diMe—Ph |
| 1-628 | 4 | NHCO | — | 2-(CF$_3$)Ph |
| 1-629 | 4 | NHCO | — | 4-(CF$_3$)Ph |
| 1-630 | 4 | NHCO | — | 2-MeOPh |
| 1-631 | 4 | NHCO | — | 4-MeOPh |
| 1-632 | 4 | NHCO | — | 2-EtOPh |
| 1-633 | 4 | NHCO | — | 4-EtOPh |
| 1-634 | 4 | NHCO | — | 2-HOPh |
| 1-635 | 4 | NHCO | — | 4-HOPh |

TABLE 1-continued

| Cpd. No. | k | A | B | R¹ |
|---|---|---|---|---|
| 1-636 | 4 | NHCO | — | 2-(HOOC)Ph |
| 1-637 | 4 | NHCO | — | 4-(HOOC)Ph |
| 1-638 | 4 | NHCO | — | 2-(MeOOC)Ph |
| 1-639 | 4 | NHCO | — | 4-(MeOOC)Ph |
| 1-640 | 4 | NHCO | — | 2-(EtOOC)Ph |
| 1-641 | 4 | NHCO | — | 4-(EtOOC)Ph |
| 1-642 | 4 | NHCO | — | 2-(tBuOOC)Ph |
| 1-643 | 4 | NHCO | — | 4-(tBuOOC)Ph |
| 1-644 | 4 | NHCO | — | 2-Cl—Ph |
| 1-645 | 4 | NHCO | — | 4-Cl—Ph |
| 1-646 | 4 | NHCO | — | 2-Br—Ph |
| 1-647 | 4 | NHCO | — | 4-Br—Ph |
| 1-648 | 4 | NHCO | — | 2-I—Ph |
| 1-649 | 4 | NHCO | — | 4-I—Ph |
| 1-650 | 4 | NHCO | — | 2-$NO_2$—Ph |
| 1-651 | 4 | NHCO | — | 4-$NO_2$—Ph |
| 1-652 | 4 | NHCO | — | 2-$NH_2$—Ph |
| 1-653 | 4 | NHCO | — | 4-$NH_2$—Ph |
| 1-654 | 4 | NHCO | — | 2-($HO_3S$)Ph |
| 1-655 | 4 | NHCO | — | 4-($HO_3S$)Ph |
| 1-656 | 4 | NHCO | — | 2-($NH_2O_2S$)Ph |
| 1-657 | 4 | NHCO | — | 4-($NH_2O_2S$)Ph |
| 1-658 | 4 | NHCO | — | 2-CN—Ph |
| 1-659 | 4 | NHCO | — | 4-CN—Ph |
| 1-660 | 4 | NHCO | — | 2-($HOCH_2$)Ph |
| 1-661 | 4 | NHCO | — | 4-($HOCH_2$)Ph |
| 1-662 | 4 | NHCO | — | Me |
| 1-663 | 4 | NHCO | — | Et |
| 1-664 | 4 | NHCO | — | Pr |
| 1-665 | 4 | NHCO | — | iPr |
| 1-666 | 4 | NHCO | — | Bu |
| 1-667 | 4 | NHCO | — | HOOC$CH_2$— |
| 1-668 | 4 | NHCO | — | MeOOC$CH_2$— |
| 1-669 | 4 | NHCO | — | MeCH(COOH) |
| 1-670 | 4 | NHCO | — | HOOC—($CH_2)_2$— |
| 1-671 | 4 | NHCO | — | MeCH(COOMe) |
| 1-672 | 4 | NHCO | — | 1-HOOC-iBu |
| 1-673 | 4 | NHCO | — | 1-HOOC-iPn |
| 1-674 | 4 | NHCO | — | 1-HOOC-2-Me—Bu |
| 1-675 | 4 | NHCO | — | $CH_2CH_2SO_3H$ |
| 1-676 | 4 | NHCO | — | MeO |
| 1-677 | 4 | NHCO | — | EtO |
| 1-678 | 4 | NHCO | — | PrO |
| 1-679 | 4 | NHCO | — | Z-1 |
| 1-680 | 4 | NHCO | — | Z-2 |
| 1-681 | 4 | NHCO | — | Z-3 |
| 1-682 | 4 | NHCO | — | Z-4 |
| 1-683 | 4 | NHCO | — | Z-5 |
| 1-684 | 4 | NHCO | — | Z-6 |
| 1-685 | 4 | NHCO | — | Z-7 |
| 1-686 | 4 | NHCO | — | Z-8 |
| 1-687 | 4 | NHCO | — | Z-9 |
| 1-688 | 4 | NHCO | — | Z-10 |
| 1-689 | 4 | NHCO | — | Z-11 |
| 1-690 | 4 | NHCO | — | Z-12 |
| 1-691 | 4 | NHCO | — | 3-Py |
| 1-692 | 4 | NHCO | — | 4-Py |
| 1-693 | 4 | NHCO | NH | H |
| 1-694 | 4 | NHCO | NH | Ph |
| 1-695 | 4 | NHCO | NH | 2-Me—Ph |
| 1-696 | 4 | NHCO | NH | 4-Me—Ph |
| 1-697 | 4 | NHCO | NH | 2,4-diMe—Ph |
| 1-698 | 4 | NHCO | NH | 3,4-diMe—Ph |
| 1-699 | 4 | NHCO | NH | 2-($CF_3$)Ph |
| 1-700 | 4 | NHCO | NH | 4-($CF_3$)Ph |
| 1-701 | 4 | NHCO | NH | 2-MeOPh |
| 1-702 | 4 | NHCO | NH | 4-MeOPh |
| 1-703 | 4 | NHCO | NH | 2-EtOPh |
| 1-704 | 4 | NHCO | NH | 4-EtOPh |
| 1-705 | 4 | NHCO | NH | 2-HOPh |
| 1-706 | 4 | NHCO | NH | 4-HOPh |
| 1-707 | 4 | NHCO | NH | 2-(HOOC)Ph |
| 1-708 | 4 | NHCO | NH | 4-(HOOC)Ph |
| 1-709 | 4 | NHCO | NH | 2-(MeOOC)Ph |
| 1-710 | 4 | NHCO | NH | 4-(MeOOC)Ph |
| 1-711 | 4 | NHCO | NH | 2-(EtOOC)Ph |

TABLE 1-continued

| Cpd. No. | k | A | B | R¹ |
|---|---|---|---|---|
| 1-712 | 4 | NHCO | NH | 4-(EtOOC)Ph |
| 1-713 | 4 | NHCO | NH | 2-(tBuOOC)Ph |
| 1-714 | 4 | NHCO | NH | 4-(tBuOOC)Ph |
| 1-715 | 4 | NHCO | NH | 2-Cl—Ph |
| 1-716 | 4 | NHCO | NH | 4-Cl—Ph |
| 1-717 | 4 | NHCO | NH | 2-Br—Ph |
| 1-718 | 4 | NHCO | NH | 4-Br—Ph |
| 1-719 | 4 | NHCO | NH | 2-I—Ph |
| 1-720 | 4 | NHCO | NH | 4-I—Ph |
| 1-721 | 4 | NHCO | NH | 2-$NO_2$—Ph |
| 1-722 | 4 | NHCO | NH | 4-$NO_2$—Ph |
| 1-723 | 4 | NHCO | NH | 2-$NH_2$—Ph |
| 1-724 | 4 | NHCO | NH | 4-$NH_2$—Ph |
| 1-725 | 4 | NHCO | NH | 2-($HO_3S$)Ph |
| 1-726 | 4 | NHCO | NH | 4-($HO_3S$)Ph |
| 1-727 | 4 | NHCO | NH | 2-($NH_2O_2S$)Ph |
| 1-728 | 4 | NHCO | NH | 4-($NH_2O_2S$)Ph |
| 1-729 | 4 | NHCO | NH | 2-CN—Ph |
| 1-730 | 4 | NHCO | NH | 4-CN—Ph |
| 1-731 | 4 | NHCO | NH | 2-($HOCH_2$)Ph |
| 1-732 | 4 | NHCO | NH | 4-($HOCH_2$)Ph |
| 1-733 | 4 | NHCO | NH | Me |
| 1-734 | 4 | NHCO | NH | Et |
| 1-735 | 4 | NHCO | NH | Pr |
| 1-736 | 4 | NHCO | NH | iPr |
| 1-737 | 4 | NHCO | NH | Bu |
| 1-738 | 4 | NHCO | NH | HOOCCH$_2$— |
| 1-739 | 4 | NHCO | NH | MeOOCCH$_2$— |
| 1-740 | 4 | NHCO | NH | MeCH(COOH) |
| 1-741 | 4 | NHCO | NH | HOOC—(CH$_2$)$_2$— |
| 1-742 | 4 | NHCO | NH | MeCH(COOMe) |
| 1-743 | 4 | NHCO | NH | 1-HOOC-iBu |
| 1-744 | 4 | NHCO | NH | 1-MeOOC-iBu |
| 1-745 | 4 | NHCO | NH | 1-HOOC-iPn |
| 1-746 | 4 | NHCO | NH | 1-MeOOC-iPn |
| 1-747 | 4 | NHCO | NH | 1-HOOC-2-Me—Bu |
| 1-748 | 4 | NHCO | NH | 1-MeOOC-2-Me—Bu |
| 1-749 | 4 | NHCO | NH | CH$_2$CH$_2$SO$_3$H |
| 1-750 | 4 | NHCO | NH | OH |
| 1-751 | 4 | NHCO | NH | MeO |
| 1-752 | 4 | NHCO | NH | EtO |
| 1-753 | 4 | NHCO | NH | PrO |
| 1-754 | 4 | NHCO | NH | iPrO |
| 1-755 | 4 | NHCO | NH | BuO |
| 1-756 | 4 | NHCO | NH | iBuO |
| 1-757 | 4 | NHCO | NH | sBuO |
| 1-758 | 4 | NHCO | NH | tBuO |
| 1-759 | 4 | NHCO | NH | HxO |
| 1-760 | 4 | NHCO | NH | PhO |
| 1-761 | 4 | NHCO | NH | BzO |
| 1-762 | 4 | NHCO | NH | Z-1 |
| 1-763 | 4 | NHCO | NH | Z-2 |
| 1-764 | 4 | NHCO | NH | Z-3 |
| 1-765 | 4 | NHCO | NH | Z-4 |
| 1-766 | 4 | NHCO | NH | Z-5 |
| 1-767 | 4 | NHCO | NH | Z-6 |
| 1-768 | 4 | NHCO | NH | Z-7 |
| 1-769 | 4 | NHCO | NH | Z-8 |
| 1-770 | 4 | NHCO | NH | Z-9 |
| 1-771 | 4 | NHCO | NH | Z-10 |
| 1-772 | 4 | NHCO | NH | Z-11 |
| 1-773 | 4 | NHCO | NH | Z-12 |
| 1-774 | 4 | NHCO | NH | 3-Py |
| 1-775 | 4 | NHCO | NH | 4-Py |
| 1-776 | 4 | NHCO | NMe | Ph |
| 1-777 | 4 | NHCO | NMe | 2-Me—Ph |
| 1-778 | 4 | NHCO | NMe | 4-Me—Ph |
| 1-779 | 4 | NHCO | NMe | 2,4-diMe—Ph |
| 1-780 | 4 | NHCO | NMe | 3,4-diMe—Ph |
| 1-781 | 4 | NHCO | NMe | 2-(CF$_3$)Ph |
| 1-782 | 4 | NHCO | NMe | 4-(CF$_3$)Ph |
| 1-783 | 4 | NHCO | NMe | 2-MeOPh |
| 1-784 | 4 | NHCO | NMe | 4-MeOPh |
| 1-785 | 4 | NHCO | NMe | 2-EtOPh |
| 1-786 | 4 | NHCO | NMe | 4-EtOPh |
| 1-787 | 4 | NHCO | NMe | 2-HOPh |

TABLE 1-continued

| Cpd. No. | k | A | B | R¹ |
|---|---|---|---|---|
| 1-788 | 4 | NHCO | NMe | 4-HOPh |
| 1-789 | 4 | NHCO | NMe | 2-(HOOC)Ph |
| 1-790 | 4 | NHCO | NMe | 4-(HOOC)Ph |
| 1-791 | 4 | NHCO | NMe | 2-(MeOOC)Ph |
| 1-792 | 4 | NHCO | NMe | 4-(MeOOC)Ph |
| 1-793 | 4 | NHCO | NMe | 2-(EtOOC)Ph |
| 1-794 | 4 | NHCO | NMe | 4-(EtOOC)Ph |
| 1-795 | 4 | NHCO | NMe | 2-(tBuOOC)Ph |
| 1-796 | 4 | NHCO | NMe | 4-(tBuOOC)Ph |
| 1-797 | 4 | NHCO | NMe | 2-Cl—Ph |
| 1-798 | 4 | NHCO | NMe | 4-Cl—Ph |
| 1-799 | 4 | NHCO | NMe | 2-Br—Ph |
| 1-800 | 4 | NHCO | NMe | 4-Br—Ph |
| 1-801 | 4 | NHCO | NMe | 2-I—Ph |
| 1-802 | 4 | NHCO | NMe | 4-I—Ph |
| 1-803 | 4 | NHCO | NMe | 2-$NO_2$—Ph |
| 1-804 | 4 | NHCO | NMe | 4-$NO_2$—Ph |
| 1-805 | 4 | NHCO | NMe | 2-$NH_2$—Ph |
| 1-806 | 4 | NHCO | NMe | 4-$NH_2$—Ph |
| 1-807 | 4 | NHCO | NMe | 2-($HO_3S$)Ph |
| 1-808 | 4 | NHCO | NMe | 4-($HO_3S$)Ph |
| 1-809 | 4 | NHCO | NMe | 2-($NH_2O_2S$)Ph |
| 1-810 | 4 | NHCO | NMe | 4-($NH_2O_2S$)Ph |
| 1-811 | 4 | NHCO | NMe | 2-CN—Ph |
| 1-812 | 4 | NHCO | NMe | 4-CN—Ph |
| 1-813 | 4 | NHCO | NMe | 2-($HOCH_2$)Ph |
| 1-814 | 4 | NHCO | NMe | 4-($HOCH_2$)Ph |
| 1-815 | 4 | NHCO | NMe | Me |
| 1-816 | 4 | NHCO | NMe | Et |
| 1-817 | 4 | NHCO | NMe | Pr |
| 1-818 | 4 | NHCO | NMe | iPr |
| 1-819 | 4 | NHCO | NMe | Bu |
| 1-820 | 4 | NHCO | NMe | HOOCCH$_2$— |
| 1-821 | 4 | NHCO | NMe | MeOOCCH$_2$— |
| 1-822 | 4 | NHCO | NMe | MeCH(COOH) |
| 1-823 | 4 | NHCO | NMe | HOOC—(CH$_2$)$_2$— |
| 1-824 | 4 | NHCO | NMe | MeCH(COOMe) |
| 1-825 | 4 | NHCO | NMe | 1-HOOC-iBu |
| 1-826 | 4 | NHCO | NMe | 1-MeOOC-iBu |
| 1-827 | 4 | NHCO | NMe | 1-HOOC-iPn |
| 1-828 | 4 | NHCO | NMe | 1-MeOOC-iPn |
| 1-829 | 4 | NHCO | NMe | 1-HOOC-2-Me—Bu |
| 1-830 | 4 | NHCO | NMe | 1-MeOOC-2-Me—Bu |
| 1-831 | 4 | NHCO | NMe | CH$_2$CH$_2$SO$_3$H |
| 1-832 | 4 | NHCO | NMe | OH |
| 1-833 | 4 | NHCO | NMe | MeO |
| 1-834 | 4 | NHCO | NMe | EtO |
| 1-835 | 4 | NHCO | NMe | PrO |
| 1-836 | 4 | NHCO | NMe | iPrO |
| 1-837 | 4 | NHCO | NMe | BuO |
| 1-838 | 4 | NHCO | NMe | iBuO |
| 1-839 | 4 | NHCO | NMe | sBuO |
| 1-840 | 4 | NHCO | NMe | tBuO |
| 1-841 | 4 | NHCO | NMe | HxO |
| 1-842 | 4 | NHCO | NMe | PhO |
| 1-843 | 4 | NHCO | NMe | BzO |
| 1-844 | 4 | NHCO | NMe | Z-1 |
| 1-845 | 4 | NHCO | NMe | Z-2 |
| 1-846 | 4 | NHCO | NMe | Z-3 |
| 1-847 | 4 | NHCO | NMe | Z-4 |
| 1-848 | 4 | NHCO | NMe | Z-5 |
| 1-849 | 4 | NHCO | NMe | Z-6 |
| 1-850 | 4 | NHCO | NMe | Z-7 |
| 1-851 | 4 | NHCO | NMe | Z-8 |
| 1-852 | 4 | NHCO | NMe | Z-9 |
| 1-853 | 4 | NHCO | NMe | Z-10 |
| 1-854 | 4 | NHCO | NMe | Z-11 |
| 1-855 | 4 | NHCO | NMe | Z-12 |
| 1-856 | 4 | NHCO | NMe | 3-Py |
| 1-857 | 4 | NHCO | NMe | 4-Py |
| 1-858 | 4 | NHCO | NHNH | H |
| 1-859 | 4 | NHCO | NHNH | Me |
| 1-860 | 4 | NHCO | NHNH | Et |
| 1-861 | 4 | NHCO | NHNMe | Me |
| 1-862 | 4 | NHCO | NHNMe | Et |
| 1-863 | 4 | NHCO | NNNMe | Pr |

TABLE 1-continued

| Cpd. No. | k | A | B | R¹ |
|---|---|---|---|---|
| 1-864 | 4 | NHCONHNHCO | NH | H |
| 1-865 | 4 | NHCONHNHCO | NH | Ph |
| 1-866 | 4 | NHCONHNHCO | NH | 2-Me—Ph |
| 1-867 | 4 | NHCONHNHCO | NH | 4-Me—Ph |
| 1-868 | 4 | NHCONHNHCO | NH | 2,4-diMe—Ph |
| 1-869 | 4 | NHCONHNHCO | NH | 3,4-diMe—Ph |
| 1-870 | 4 | NHCONHNHCO | NH | 2-(CF$_3$)Ph |
| 1-871 | 4 | NHCONHNHCO | NH | 4-(CF$_3$)Ph |
| 1-872 | 4 | NHCONHNHCO | NH | 2-MeOPh |
| 1-873 | 4 | NHCONHNHCO | NH | 4-MeOPh |
| 1-874 | 4 | NHCONHNHCO | NH | 2-EtOPh |
| 1-875 | 4 | NHCONHNHCO | NH | 4-EtOPh |
| 1-876 | 4 | NHCONHNHCO | NH | 2-HOPh |
| 1-877 | 4 | NHCONHNHCO | NH | 4-HOPh |
| 1-878 | 4 | NHCONHNHCO | NH | 2-(HOOC)Ph |
| 1-879 | 4 | NHCONHNHCO | NH | 4-(HOOC)Ph |
| 1-880 | 4 | NHCONMNHCO | NH | 2-(MeOOC)Ph |
| 1-881 | 4 | NHCONHNHCO | NH | 4-(MeOOC)Ph |
| 1-882 | 4 | NHCONHNHCO | NH | 2-(EtOOC)Ph |
| 1-883 | 4 | NHCONHNHCO | NH | 4-(EtOOC)Ph |
| 1-884 | 4 | NHCONHNHCO | NH | 2-(tBuOOC)Ph |
| 1-885 | 4 | NHCONHNHCO | NH | 4-(tBuOOC)Ph |
| 1-886 | 4 | NHCONHNHCO | NH | 2-Cl—Ph |
| 1-887 | 4 | NHCONHNHCO | NH | 4-Cl—Ph |
| 1-888 | 4 | NHCONHNHCO | NH | 2-Br—Ph |
| 1-889 | 4 | NHCONHNHCO | NH | 4-Br—Ph |
| 1-890 | 4 | NHCONHNHCO | NH | 2-I—Ph |
| 1-891 | 4 | NHCONHNHCO | NH | 4-I—Ph |
| 1-892 | 4 | NHCONHNHCO | NH | 2-NO$_2$—Ph |
| 1-893 | 4 | NHCONHNHCO | NH | 4-NO$_2$—Ph |
| 1-894 | 4 | NHCONHNHCO | NH | 2-NH$_2$—Ph |
| 1-895 | 4 | NHCONHNHCO | NH | 4-NH$_2$—Ph |
| 1-896 | 4 | NHCONHNHCO | NH | 2-(HO$_3$S)Ph |
| 1-897 | 4 | NHCONHNHCO | NH | 4-(HO$_3$S)Ph |
| 1-898 | 4 | NHCONHNHCO | NH | 2-(NH$_2$O$_2$S)Ph |
| 1-899 | 4 | NHCONHNHCO | NH | 4-(NH$_2$O$_2$S)Ph |
| 1-900 | 4 | NHCONHNHCO | NH | 2-CN—Ph |
| 1-901 | 4 | NHCONHNHCO | NH | 4-CN—Ph |
| 1-902 | 4 | NHCONHNHCO | NH | 2-(HOCH$_2$)Ph |
| 1-903 | 4 | NHCONHNHCO | NH | 4-(HOCH$_2$)Ph |
| 1-904 | 4 | NHCONHNHCO | NH | Me |
| 1-905 | 4 | NHCONHNHCO | NH | Et |
| 1-906 | 4 | NHCONHNHCO | NH | Pr |
| 1-907 | 4 | NHCONHNHCO | NH | iPr |
| 1-908 | 4 | NHCONHNHCO | NH | Bu |
| 1-909 | 4 | NHCONHNHCO | NH | HOOCCH$_2$— |
| 1-910 | 4 | NHCONHNHCO | NH | MeOOCCH$_2$— |
| 1-911 | 4 | NHCONHNHCO | NH | MeCH(COOH) |
| 1-912 | 4 | NHCONHNHCO | NH | HOOC—(CH$_2$)$_2$— |
| 1-913 | 4 | NHCONHNHCO | NH | MeCH(COOMe) |
| 1-914 | 4 | NHCONHNHCO | NH | 1-HOOC-iBu |
| 1-915 | 4 | NHCONHNHCO | NH | 1-MeOOC-iBu |
| 1-916 | 4 | NHCONHNHCO | NH | 1-HOOC-iPn |
| 1-917 | 4 | NHCONHNHCO | NH | 1-MeOOC-iPn |
| 1-918 | 4 | NHCONHNHCO | NH | 1-HOOC-2-Me—Bu |
| 1-919 | 4 | NHCONHNHCO | NH | 1-MeOOC-2-Me—Bu |
| 1-920 | 4 | NHCONHNHCO | NH | CH$_2$CH$_2$SO$_3$H |
| 1-921 | 4 | NHCONHNHCO | NH | OH |
| 1-922 | 4 | NHCONHNHCO | NH | MeO |
| 1-923 | 4 | NHCONHNHCO | NH | EtO |
| 1-924 | 4 | NHCONHNHCO | NH | PrO |
| 1-925 | 4 | NHCONHNHCO | NH | iPrO |
| 1-926 | 4 | NHCONHNHCO | NH | BuO |
| 1-927 | 4 | NHCONHNHCO | NH | iBuO |
| 1-928 | 4 | NHCONHNHCO | NH | sBuO |
| 1-929 | 4 | NHCONHNHCO | NH | tBuO |
| 1-930 | 4 | NHCONHNHCO | NH | HxO |
| 1-931 | 4 | NHCONHNHCO | NH | PhO |
| 1-932 | 4 | NHCONHNHCO | NH | BzO |
| 1-933 | 4 | NHCONHNHCO | NH | Z-1 |
| 1-934 | 4 | NHCONHNHCO | NH | Z-2 |
| 1-935 | 4 | NHCONHNHCO | NH | Z-3 |
| 1-936 | 4 | NHCONHNHCO | NH | Z-4 |
| 1-937 | 4 | NHCONHNHCO | NH | Z-5 |
| 1-938 | 4 | NHCONHNHCO | NH | Z-6 |
| 1-939 | 4 | NHCONHNHCO | NH | Z-7 |

TABLE 1-continued

| Cpd. No. | k | A | B | R¹ |
|---|---|---|---|---|
| 1-940 | 4 | NHCONHNHCO | NH | Z-8 |
| 1-941 | 4 | NHCONHNHCO | NH | Z-9 |
| 1-942 | 4 | NHCONHNHCO | NH | Z-10 |
| 1-943 | 4 | NHCONHNHCO | NH | Z-11 |
| 1-944 | 4 | NHCONHNHCO | NH | Z-12 |
| 1-945 | 4 | NHCONHNHCO | NH | 3-Py |
| 1-946 | 4 | NHCONHNHCO | NH | 4-Py |
| 1-947 | 4 | NHCONHCO | — | H |
| 1-948 | 4 | NHCONHCO | — | Ph |
| 1-949 | 4 | NHCONHCO | — | 2-Me—Ph |
| 1-950 | 4 | NHCONHCO | — | 4-Me—Ph |
| 1-951 | 4 | NHCONHCO | — | 2,4-diMe—Ph |
| 1-952 | 4 | NHCONHCO | — | 3,4-diMe—Ph |
| 1-953 | 4 | NHCONHCO | — | 2-($CF_3$)Ph |
| 1-954 | 4 | NHCONHCO | — | 4-($CF_3$)Ph |
| 1-955 | 4 | NHCONHCO | — | 2-MeOPh |
| 1-956 | 4 | NHCONHCO | — | 4-MeOPh |
| 1-957 | 4 | NHCONHCO | — | 2-EtOPh |
| 1-958 | 4 | NHCONHCO | — | 4-EtOPh |
| 1-959 | 4 | NHCONHCO | — | 2-HOPh |
| 1-960 | 4 | NHCONHCO | — | 4-HOPh |
| 1-961 | 4 | NHCONHCO | — | 2-(HOOC)Ph |
| 1-962 | 4 | NHCONHCO | — | 4-(HOOC)Ph |
| 1-963 | 4 | NHCONHCO | — | 2-(MeOOC)Ph |
| 1-964 | 4 | NHCONHCO | — | 4-(MeOOC)Ph |
| 1-965 | 4 | NHCONHCO | — | 2-(EtOOC)Ph |
| 1-966 | 4 | NHCONHCO | — | 4-(EtOOC)Ph |
| 1-967 | 4 | NHCONHCO | — | 2-(tBuOOC)Ph |
| 1-968 | 4 | NHCONHCO | — | 4-(tBuOOC)Ph |
| 1-969 | 4 | NHCONHCO | — | 2-Cl—Ph |
| 1-970 | 4 | NHCONHCO | — | 4-Cl—Ph |
| 1-971 | 4 | NHCONHCO | — | 2-Br—Ph |
| 1-972 | 4 | NHCONHCO | — | 4-Br—Ph |
| 1-973 | 4 | NHCONHCO | — | 2-I—Ph |
| 1-974 | 4 | NHCONHCO | — | 4-I—Ph |
| 1-975 | 4 | NHCONHCO | — | 2-$NO_2$—Ph |
| 1-976 | 4 | NHCONHCO | — | 4-$NO_2$—Ph |
| 1-977 | 4 | NHCONHCO | — | 2-$NH_2$—Ph |
| 1-978 | 4 | NHCONHCO | — | 4-$NH_2$—Ph |
| 1-979 | 4 | NHCONHCO | — | 2-($HO_3S$)Ph |
| 1-980 | 4 | NHCONHCO | — | 4-($HO_3S$)Ph |
| 1-981 | 4 | NHCONHCO | — | 2-($NH_2O_2S$)Ph |
| 1-982 | 4 | NHCONHCO | — | 4-($NH_2O_2S$)Ph |
| 1-983 | 4 | NHCONHCO | — | 2-CN—Ph |
| 1-984 | 4 | NHCONHCO | — | 4-CN—Ph |
| 1-985 | 4 | NHCONHCO | — | 2-($HOCH_2$)Ph |
| 1-986 | 4 | NHCONHCO | — | 4-($HOCH_2$)Ph |
| 1-987 | 4 | NHCONHCO | — | Me |
| 1-988 | 4 | NHCONHCO | — | Et |
| 1-989 | 4 | NHCONHCO | — | Pr |
| 1-990 | 4 | NHCONHCO | — | iPr |
| 1-991 | 4 | NHCONHCO | — | Bu |
| 1-992 | 4 | NHCONHCO | — | HOOC$CH_2$— |
| 1-993 | 4 | NHCONHCO | — | MeOOC$CH_2$— |
| 1-994 | 4 | NHCONHCO | — | MeCH(COOH) |
| 1-995 | 4 | NHCONHCO | — | HOOC—$(CH_2)_2$— |
| 1-996 | 4 | NHCONHCO | — | MeCH(COOMe) |
| 1-997 | 4 | NHCONHCO | — | 1-HOOC-iBu |
| 1-998 | 4 | NHCONHCO | — | 1-MeOOC-iBu |
| 1-999 | 4 | NHCONHCO | — | 1-HOOC-iPn |
| 1-1000 | 4 | NHCONHCO | — | 1-MeOOC-iPn |
| 1-1001 | 4 | NHCONHCO | — | 1-HOOC-2-Me—Bu |
| 1-1002 | 4 | NHCONHCO | — | 1-MeOOC-2-Me—Bu |
| 1-1003 | 4 | NHCONHCO | — | $CH_2CH_2SO_3H$ |
| 1-1004 | 4 | NHCONHCO | — | MeO |
| 1-1005 | 4 | NHCONHCO | — | EtO |
| 1-1006 | 4 | NHCONHCO | — | PrO |
| 1-1007 | 4 | NHCONHCO | — | iPrO |
| 1-1008 | 4 | NHCONHCO | — | BuO |
| 1-1009 | 4 | NHCONHCO | — | iBuO |
| 1-1010 | 4 | NHCONHCO | — | sBuO |
| 1-1011 | 4 | NHCONHCO | — | tBuO |
| 1-1012 | 4 | NHCONHCO | — | HxO |
| 1-1013 | 4 | NHCONHCO | — | PhO |
| 1-1014 | 4 | NHCONHCO | — | BzO |
| 1-1015 | 4 | NHCONHCO | — | Z-1 |

TABLE 1-continued

| Cpd. No. | k | A | B | R$^1$ |
|---|---|---|---|---|
| 1-1016 | 4 | NHCONHCO | — | Z-2 |
| 1-1017 | 4 | NHCONHCO | — | Z-3 |
| 1-1018 | 4 | NHCONHCO | — | Z-4 |
| 1-1019 | 4 | NHCONHCO | — | Z-5 |
| 1-1020 | 4 | NHCONHCO | — | Z-6 |
| 1-1021 | 4 | NHCONHCO | — | Z-7 |
| 1-1022 | 4 | NHCONHCO | — | Z-8 |
| 1-1023 | 4 | NHCONHCO | — | Z-9 |
| 1-1024 | 4 | NHCONHCO | — | Z-10 |
| 1-1025 | 4 | NHCONHCO | — | Z-11 |
| 1-1026 | 4 | NHCONHCO | — | Z-12 |
| 1-1027 | 4 | NHCONHCO | — | 3-Py |
| 1-1028 | 4 | NHCONHCO | — | 4-Py |
| 1-1029 | 4 | NHCONHSO$_2$ | — | H |
| 1-1030 | 4 | NHCONHSO$_2$ | — | Ph |
| 1-1031 | 4 | NHCONHSO$_2$ | — | 2-Me—Ph |
| 1-1032 | 4 | NHCONHSO$_2$ | — | 4-Me—Ph |
| 1-1033 | 4 | NHCONHSO$_2$ | — | 2,4-diMe—Ph |
| 1-1034 | 4 | NHCONHSO$_2$ | — | 3,4-diMe—Ph |
| 1-1035 | 4 | NHCONHSO$_2$ | — | 2-(CF$_3$)Ph |
| 1-1036 | 4 | NHCONHSO$_2$ | — | 4-(CF$_3$)Ph |
| 1-1037 | 4 | NHCONHSO$_2$ | — | 2-MeOPh |
| 1-1038 | 4 | NHCONHSO$_2$ | — | 4-MeOPh |
| 1-1039 | 4 | NHCONHSO$_2$ | — | 2-EtOPh |
| 1-1040 | 4 | NHCONHSO$_2$ | — | 4-EtOPh |
| 1-1041 | 4 | NHCONHSO$_2$ | — | 2-HOPh |
| 1-1042 | 4 | NHCONHSO$_2$ | — | 4-HOPh |
| 1-1043 | 4 | NHCONHSO$_2$ | — | 2-(HOOC)Ph |
| 1-1044 | 4 | NHCONHSO$_2$ | — | 4-(HOOC)Ph |
| 1-1045 | 4 | NHCONHSO$_2$ | — | 2-(MeOOC)Ph |
| 1-1046 | 4 | NHCONHSO$_2$ | — | 4-(MeOOC)Ph |
| 1-1047 | 4 | NHCONHSO$_2$ | — | 2-(EtOOC)Ph |
| 1-1048 | 4 | NHCONHSO$_2$ | — | 4-(EtOOC)Ph |
| 1-1049 | 4 | NHCONHSO$_2$ | — | 2-(tBuOOC)Ph |
| 1-1050 | 4 | NHCONHSO$_2$ | — | 4-(tBuOOC)Ph |
| 1-1051 | 4 | NHCONHSO$_2$ | — | 2-Cl—Ph |
| 1-1052 | 4 | NHCONHSO$_2$ | — | 4-Cl—Ph |
| 1-1053 | 4 | NHCONHSO$_2$ | — | 2-Br—Ph |
| 1-1054 | 4 | NHCONHSO$_2$ | — | 4-Br—Ph |
| 1-1055 | 4 | NHCONHSO$_2$ | — | 2-I—Ph |
| 1-1056 | 4 | NHCONHSO$_2$ | — | 4-I—Ph |
| 1-1057 | 4 | NHCONHSO$_2$ | — | 2-NO$_2$—Ph |
| 1-1058 | 4 | NHCONHSO$_2$ | — | 4-NO$_2$—Ph |
| 1-1059 | 4 | NHCONHSO$_2$ | — | 2-NH$_2$—Ph |
| 1-1060 | 4 | NHCONHSO$_2$ | — | 4-NH$_2$—Ph |
| 1-1061 | 4 | NHCONHSO$_2$ | — | 2-(HO$_3$S)Ph |
| 1-1062 | 4 | NHCONHSO$_2$ | — | 4-(HO$_3$S)Ph |
| 1-1063 | 4 | NHCONHSO$_2$ | — | 2-(NH$_2$O$_2$S)Ph |
| 1-1064 | 4 | NHCONHSO$_2$ | — | 4-(NH$_2$O$_2$S)Ph |
| 1-1065 | 4 | NHCONHSO$_2$ | — | 2-CN—Ph |
| 1-1066 | 4 | NHCONHSO$_2$ | — | 4-CN—Ph |
| 1-1067 | 4 | NHCONHSO$_2$ | — | 2-(HOCH$_2$)Ph |
| 1-1068 | 4 | NHCONHSO$_2$ | — | 4-(HOCH$_2$)Ph |
| 1-1069 | 4 | NHCONHSO$_2$ | — | Me |
| 1-1070 | 4 | NHCONHSO$_2$ | — | Et |
| 1-1071 | 4 | NHCONHSO$_2$ | — | Pr |
| 1-1072 | 4 | NHCONHSO$_2$ | — | iPr |
| 1-1073 | 4 | NHCONHSO$_2$ | — | Bu |
| 1-1074 | 4 | NHCONHSO$_2$ | — | HOOCCH$_2$— |
| 1-1075 | 4 | NHCONHSO$_2$ | — | MeOOCCH$_2$— |
| 1-1076 | 4 | NHCONHSO$_2$ | — | MeCH(COOH) |
| 1-1077 | 4 | NHCONHSO$_2$ | — | HOOC—(CH$_2$)$_2$— |
| 1-1078 | 4 | NHCONHSO$_2$ | — | MeCH(COOMe) |
| 1-1079 | 4 | NHCONHSO$_2$ | — | 1-HOOC-iBu |
| 1-1080 | 4 | NHCONHSO$_2$ | — | 1-MeOOC-iBu |
| 1-1081 | 4 | NHCONHSO$_2$ | — | 1-HOOC-iPn |
| 1-1082 | 4 | NHCONHSO$_2$ | — | 1-MeOOC-iPn |
| 1-1083 | 4 | NHCONHSO$_2$ | — | 1-HOOC-2-Me—Bu |
| 1-1084 | 4 | NHCONHSO$_2$ | — | 1-MeOOC-2-Me—Bu |
| 1-1085 | 4 | NHCONHSO$_2$ | — | CH$_2$CH$_2$SO$_3$H |
| 1-1086 | 4 | NHCONHSO$_2$ | — | OH |
| 1-1087 | 4 | NHCONHSO$_2$ | — | MeO |
| 1-1088 | 4 | NHCONHSO$_2$ | — | EtO |
| 1-1089 | 4 | NHCONHSO$_2$ | — | PrO |
| 1-1090 | 4 | NHCONHSO$_2$ | — | iPrO |
| 1-1091 | 4 | NHCONHSO$_2$ | — | BuO |

TABLE 1-continued

| Cpd. No. | k | A | B | R¹ |
|---|---|---|---|---|
| 1-1092 | 4 | NHCONHSO$_2$ | — | iBuO |
| 1-1093 | 4 | NHCONHSO$_2$ | — | sBuO |
| 1-1094 | 4 | NHCONHSO$_2$ | — | tBuO |
| 1-1095 | 4 | NHCONHSO$_2$ | — | HxO |
| 1-1096 | 4 | NHCONHSO$_2$ | — | PhO |
| 1-1097 | 4 | NHCONHSO$_2$ | — | BzO |
| 1-1098 | 4 | NHCONHSO$_2$ | — | Z-1 |
| 1-1099 | 4 | NHCONHSO$_2$ | — | Z-2 |
| 1-1100 | 4 | NHCONHSO$_2$ | — | Z-3 |
| 1-1101 | 4 | NHCONHSO$_2$ | — | Z-4 |
| 1-1102 | 4 | NHCONHSO$_2$ | — | Z-5 |
| 1-1103 | 4 | NHCONHSO$_2$ | — | Z-6 |
| 1-1104 | 4 | NHCONHSO$_2$ | — | Z-7 |
| 1-1105 | 4 | NHCONHSO$_2$ | — | Z-8 |
| 1-1106 | 4 | NHCONHSO$_2$ | — | Z-9 |
| 1-1107 | 4 | NHCONHSO$_2$ | — | Z-10 |
| 1-1108 | 4 | NHCONHSO$_2$ | — | Z-11 |
| 1-1109 | 4 | NHCONHSO$_2$ | — | Z-12 |
| 1-1110 | 4 | NHCONHSO$_2$ | — | 3-Py |
| 1-1111 | 4 | NHCONHSO$_2$ | — | 4-Py |
| 1-1112 | 4 | NHCONHSO$_2$ | NH | H |
| 1-1113 | 4 | NHCONHSO$_2$ | NH | Me |
| 1-1114 | 4 | NHCONHSO$_2$ | NH | Et |
| 1-1115 | 4 | NHCONHSO$_2$ | NH | Pr |
| 1-1116 | 4 | NHCONHSO$_2$ | NH | iPr |
| 1-1117 | 4 | NHCONHSO$_2$ | NH | Bu |
| 1-1118 | 4 | NHCONHSO$_2$ | NMe | Me |
| 1-1119 | 4 | NHCONHSO$_2$ | NMe | Et |
| 1-1120 | 4 | NHCONHSO$_2$ | NMe | Pr |
| 1-1121 | 4 | NHCONHSO$_2$ | NMe | iPr |
| 1-1122 | 4 | NHCONHSO$_2$ | NMe | Bu |
| 1-1123 | 4 | — | NH | H |
| 1-1124 | 4 | — | NH | Me |
| 1-1125 | 4 | — | NH | Et |
| 1-1126 | 4 | — | NH | Pr |
| 1-1127 | 4 | — | NH | iPr |
| 1-1128 | 4 | — | NH | Bu |
| 1-1129 | 4 | CO | | Pyr |
| 1-1130 | 4 | CO | | Pipri |
| 1-1131 | 4 | CO | | Pipra |
| 1-1132 | 4 | CO | | Mor |
| 1-1133 | 4 | CO | | Thmor |
| 1-1134 | 4 | CO | | NHPyr |
| 1-1135 | 4 | CO | | NHPipri |
| 1-1136 | 4 | CO | | NHPipra |
| 1-1137 | 4 | CO | | NHMor |
| 1-1138 | 4 | CO | | NHThmor |
| 1-1139 | 4 | NHCO | | Pyr |
| 1-1140 | 4 | NHCO | | Pipri |
| 1-1141 | 4 | NHCO | | Pipra |
| 1-1142 | 4 | NHCO | | Mor |
| 1-1143 | 4 | NHCO | | Thmor |
| 1-1144 | 4 | NHCO | | NHPyr |
| 1-1145 | 4 | NHCO | | NHPipri |
| 1-1146 | 4 | NHCO | | NHPipra |
| 1-1147 | 4 | NHCO | | NHMor |
| 1-1148 | 4 | NHCO | | NHThmor |
| 1-1149 | 4 | CONHCO | | Pyr |
| 1-1150 | 4 | CONHCO | | Pipri |
| 1-1151 | 4 | CONHCO | | Pipra |
| 1-1152 | 4 | CONHCO | | Mor |
| 1-1153 | 4 | CONHCO | | Thmor |
| 1-1154 | 4 | CONHCO | | NHPyr |
| 1-1155 | 4 | CONHCO | | NHPipri |
| 1-1156 | 4 | CONHCO | | NHPipra |
| 1-1157 | 4 | CONHCO | | NHMor |
| 1-1158 | 4 | CONHCO | | NHThmor |
| 1-1159 | 4 | CONHSO$_2$ | | Pyr |
| 1-1160 | 4 | CONHSO$_2$ | | Pipri |
| 1-1161 | 4 | CONHSO$_2$ | | Pipra |
| 1-1162 | 4 | CONHSO$_2$ | | Mor |
| 1-1163 | 4 | CONHSO$_2$ | | Thmor |
| 1-1164 | 4 | CONHSO$_2$ | | NHPyr |
| 1-1165 | 4 | CONHSO$_2$ | | NHPipri |
| 1-1166 | 4 | CONHSO$_2$ | | NHPipra |
| 1-1167 | 4 | CONHSO$_2$ | | NHMor |

TABLE 1-continued

| Cpd. No. | k | A | B | R¹ |
|---|---|---|---|---|
| 1-1168 | 4 | CONHSO₂ | | NHThmor |
| 1-1169 | 4 | NHSO₂ | NH | Z-4 |
| 1-1170 | 4 | NHSO₂ | — | Me |
| 1-1171 | 4 | NHSO₂ | — | Et |
| 1-1172 | 4 | NHSO₂ | — | Pr |
| 1-1173 | 4 | NHSO₂ | — | CH₂Cl |
| 1-1174 | 4 | NHSO₂ | — | Ph |
| 1-1175 | 4 | NHSO₂ | — | 4-Me—Ph |
| 1-1176 | 4 | CO | NMe | Ph |
| 1-1177 | 4 | CO | NMe | 2-Me—Ph |
| 1-1178 | 4 | CO | NMe | 4-Me—Ph |
| 1-1179 | 4 | CO | NMe | 2,4-diMe—Ph |
| 1-1180 | 4 | CO | NMe | 3,4-diMe—Ph |
| 1-1181 | 4 | CO | NMe | 2-(CF₃)Ph |
| 1-1182 | 4 | CO | NMe | 4-(CF₃)Ph |
| 1-1183 | 4 | CO | NMe | 2-MeOPh |
| 1-1184 | 4 | CO | NMe | 4-MeOPh |
| 1-1185 | 4 | CO | NMe | 2-EtOPh |
| 1-1186 | 4 | CO | NMe | 4-EtOPh |
| 1-1187 | 4 | CO | NMe | 2-HOPh |
| 1-1188 | 4 | CO | NMe | 4-HOPh |
| 1-1189 | 4 | CO | NMe | 2-(HOOC)Ph |
| 1-1190 | 4 | CO | NMe | 4-(HOOC)Ph |
| 1-1191 | 4 | CO | NMe | 2-(MeOOC)Ph |
| 1-1192 | 4 | CO | NMe | 4-(MeOOC)Ph |
| 1-1193 | 4 | CO | NMe | 2-(EtOOC)Ph |
| 1-1194 | 4 | CO | NMe | 4-(EtOOC)Ph |
| 1-1195 | 4 | CO | NMe | 2-(tBuOOC)Ph |
| 1-1196 | 4 | CO | NMe | 4-(tBuOOC)Ph |
| 1-1197 | 4 | CO | NMe | 2-Cl—Ph |
| 1-1198 | 4 | CO | NMe | 4-Cl—Ph |
| 1-1199 | 4 | CO | NMe | 2-Br—Ph |
| 1-1200 | 4 | CO | NMe | 4-Br—Ph |
| 1-1201 | 4 | CO | NMe | 2-I—Ph |
| 1-1202 | 4 | CO | NMe | 4-I—Ph |
| 1-1203 | 4 | CO | NMe | 2-NO₂—Ph |
| 1-1204 | 4 | CO | NMe | 4-NO₂—Ph |
| 1-1205 | 4 | CO | NMe | 2-NH₂—Ph |
| 1-1206 | 4 | CO | NMe | 4-NH₂—Ph |
| 1-1207 | 4 | CO | NMe | 2-(HO₃S)Ph |
| 1-1208 | 4 | CO | NMe | 4-(HO₃S)Ph |
| 1-1209 | 4 | CO | NMe | 2-(NH₂O₂S)Ph |
| 1-1210 | 4 | CO | NMe | 4-(NH₂O₂S)Ph |
| 1-1211 | 4 | CO | NMe | 2-CN—Ph |
| 1-1212 | 4 | CO | NMe | 4-CN—Ph |
| 1-1213 | 4 | CO | NMe | 2-(HOCH₂)Ph |
| 1-1214 | 4 | CO | NMe | 4-(HOCH₂)Ph |
| 1-1215 | 4 | CO | NMe | Me |
| 1-1216 | 4 | CO | NMe | Et |
| 1-1217 | 4 | CO | NMe | Pr |
| 1-1218 | 4 | CO | NMe | iPr |
| 1-1219 | 4 | CO | NMe | Bu |
| 1-1220 | 4 | CO | NMe | HOOCCH₂— |
| 1-1221 | 4 | CO | NMe | MeOOCCH₂— |
| 1-1222 | 4 | CO | NMe | MeCH(COOH) |
| 1-1223 | 4 | CO | NMe | HOOC—(CH₂)₂— |
| 1-1224 | 4 | CO | NMe | MeCH(COOMe) |
| 1-1225 | 4 | CO | NMe | 1-HOOC-iBu |
| 1-1226 | 4 | CO | NMe | 1-MeOOC-iBu |
| 1-1227 | 4 | CO | NMe | 1-HOOC-iPn |
| 1-1228 | 4 | CO | NMe | 1-MeOOC-iPn |
| 1-1229 | 4 | CO | NMe | 1-HOOC-2-Me—Bu |
| 1-1230 | 4 | CO | NMe | 1-MeOOC-2-Me—Bu |
| 1-1231 | 4 | CO | NMe | CH₂CH₂SO₃H |
| 1-1232 | 4 | CO | NMe | OH |
| 1-1233 | 4 | CO | NMe | MeO |
| 1-1234 | 4 | CO | NMe | EtO |
| 1-1235 | 4 | CO | NMe | PrO |
| 1-1236 | 4 | CO | NMe | iPrO |
| 1-1237 | 4 | CO | NMe | BuO |
| 1-1238 | 4 | CO | NMe | iBuO |
| 1-1239 | 4 | CO | NMe | sBuO |
| 1-1240 | 4 | CO | NMe | tBuO |
| 1-1241 | 4 | CO | NMe | HxO |
| 1-1242 | 4 | CO | NMe | PhO |
| 1-1243 | 4 | CO | NMe | BzO |

TABLE 1-continued

| Cpd. No. | k | A | B | R¹ |
|---|---|---|---|---|
| 1-1244 | 4 | CO | NMe | Z-1 |
| 1-1245 | 4 | CO | NMe | Z-2 |
| 1-1246 | 4 | CO | NMe | Z-3 |
| 1-1247 | 4 | CO | NMe | Z-4 |
| 1-1248 | 4 | CO | NMe | Z-5 |
| 1-1249 | 4 | CO | NMe | Z-6 |
| 1-1250 | 4 | CO | NMe | Z-7 |
| 1-1251 | 4 | CO | NMe | Z-8 |
| 1-1252 | 4 | CO | NMe | Z-9 |
| 1-1253 | 4 | CO | NMe | Z-10 |
| 1-1254 | 4 | CO | NMe | Z-11 |
| 1-1255 | 4 | CO | NMe | Z-12 |
| 1-1256 | 4 | CO | NMe | 3-Py |
| 1-1257 | 4 | CO | NMe | 4-Py |
| 1-1258 | 4 | CO | | Thiad |
| 1-1259 | 4 | CO | | NHThiad |
| 1-1260 | 4 | NHCO | | Thiad |
| 1-1261 | 4 | NHCO | | NHThiad |
| 1-1262 | 4 | CONHCO | | Thiad |
| 1-1263 | 4 | CONHCO | | NHThiad |
| 1-1264 | 4 | CONHSO₂ | | Thiad |
| 1-1265 | 4 | CONHSO₂ | | NHThiad |
| 1-1266 | 4 | NHCS | NH | H |
| 1-1267 | 4 | NHCS | NH | Me |
| 1-1268 | 4 | NHCS | NH | Et |
| 1-1269 | 4 | NHCS | NH | Ph |
| 1-1270 | 4 | NHCS | NH | HOOCCH₂— |
| 1-1271 | 4 | NHCS | NH | MeOOCCH₂— |
| 1-1272 | 4 | NHCS | NH | MeCH(COOH) |
| 1-1273 | 4 | NHCS | NH | HOOC—(CH₂)₂— |
| 1-1274 | 4 | NHCS | NH | MeCH(COOMe) |
| 1-1275 | 4 | CO | NH | HOOC—(CH₂)₃— |
| 1-1276 | 4 | NHCO | NH | HOOC—(CH₂)₃— |
| 1-1277 | 4 | NHCO | — | HOOC—(CH₂)₃— |
| 1-1278 | 4 | NHCS | NH | HOOC—(CH₂)₃— |
| 1-1279 | 4 | CO | NH | MeSO₂NHCOCH(Me) |
| 1-1280 | 4 | NHCO | NH | MeSO₂NHCOCH(Me) |
| 1-1281 | 4 | NHCO | — | MeSO₂NHCOCH(Me) |
| 1-1282 | 4 | NHCS | NH | MeSO₂NHCOCH(Me) |
| 1-1283 | 4 | — | NH | HOOCCH₂— |
| 1-1284 | 4 | — | NH | MeOOCCH₂— |
| 1-1285 | 4 | — | NH | MeCH(COOH) |
| 1-1286 | 4 | — | NH | HOOC—(CH₂)₂— |
| 1-1287 | 4 | — | NH | MeCH(COOMe) |
| 1-1288 | 4 | — | NH | HOOC—(CH₂)₃— |
| 1-1289 | 4 | NHCOCO | — | OH |
| 1-1290 | 4 | NHCOCO | — | MeO |
| 1-1291 | 4 | NHCOCO | — | EtO |
| 1-1292 | 4 | NHCOCO | — | PrO |
| 1-1293 | 4 | NHCOCO | — | iPrO |
| 1-1294 | 4 | NHCOCO | — | BuO |
| 1-1295 | 4 | NHCOCO | — | iBuO |
| 1-1296 | 4 | NHCOCO | — | sBuO |
| 1-1297 | 4 | NHCOCO | — | tBuO |
| 1-1298 | 4 | NHCOCO | — | HxO |
| 1-1299 | 4 | NHCOCO | — | PhO |
| 1-1300 | 4 | NHCOCO | — | BzO |
| 1-1301 | 5 | CO | NH | H |
| 1-1302 | 5 | CO | NH | Ph |
| 1-1303 | 5 | CO | NH | 2-Me—Ph |
| 1-1304 | 5 | CO | NH | 4-Me—Ph |
| 1-1305 | 5 | CO | NH | 2,4-diMe—Ph |
| 1-1306 | 5 | CO | NH | 3,4-diMe—Ph |
| 1-1307 | 5 | CO | NH | 2-(CF₃)Ph |
| 1-1308 | 5 | CO | NH | 4-(CF₃)Ph |
| 1-1309 | 5 | CO | NH | 2-MeOPh |
| 1-1310 | 5 | CO | NH | 4-MeOPh |
| 1-1311 | 5 | CO | NH | 2-EtOPh |
| 1-1312 | 5 | CO | NH | 4-EtOPh |
| 1-1313 | 5 | CO | NH | 2-HOPh |
| 1-1314 | 5 | CO | NH | 4-HOPh |
| 1-1315 | 5 | CO | NH | 2-(HOOC)Ph |
| 1-1316 | 5 | CO | NH | 4-(HOOC)Ph |
| 1-1317 | 5 | CO | NH | 2-(MeOOC)Ph |
| 1-1318 | 5 | CO | NH | 4-(MeOOC)Ph |
| 1-1319 | 5 | CO | NH | 2-(EtOOC)Ph |

TABLE 1-continued

| Cpd. No. | k | A | B | R¹ |
|---|---|---|---|---|
| 1-1320 | 5 | CO | NH | 4-(EtOOC)Ph |
| 1-1321 | 5 | CO | NH | 2-(tBuOOC)Ph |
| 1-1322 | 5 | CO | NH | 4-(tBuOOC)Ph |
| 1-1323 | 5 | CO | NH | 2-Cl—Ph |
| 1-1324 | 5 | CO | NH | 4-Cl—Ph |
| 1-1325 | 5 | CO | NH | 2-Br—Ph |
| 1-1326 | 5 | CO | NH | 4-Br—Ph |
| 1-1327 | 5 | CO | NH | 2-I—Ph |
| 1-1328 | 5 | CO | NH | 4-I—Ph |
| 1-1329 | 5 | CO | NH | 2-$NO_2$—Ph |
| 1-1330 | 5 | CO | NH | 4-$NO_2$—Ph |
| 1-1331 | 5 | CO | NH | 2-$NH_2$—Ph |
| 1-1332 | 5 | CO | NH | 4-$NH_2$—Ph |
| 1-1333 | 5 | CO | NH | 2-($HO_3S$)Ph |
| 1-1334 | 5 | CO | NH | 4-($HO_3S$)Ph |
| 1-1335 | 5 | CO | NH | 2-($NH_2O_2S$)Ph |
| 1-1336 | 5 | CO | NH | 4-($NH_2O_2S$)Ph |
| 1-1337 | 5 | CO | NH | 2-CN—Ph |
| 1-1338 | 5 | CO | NH | 4-CN—Ph |
| 1-1339 | 5 | CO | NH | 2-($HOCH_2$)Ph |
| 1-1340 | 5 | CO | NH | 4-($HOCH_2$)Ph |
| 1-1341 | 5 | CO | NH | Me |
| 1-1342 | 5 | CO | NH | Et |
| 1-1343 | 5 | CO | NH | Pr |
| 1-1344 | 5 | CO | NH | iPr |
| 1-1345 | 5 | CO | NH | Bu |
| 1-1346 | 5 | CO | NH | $HOOCCH_2$— |
| 1-1347 | 5 | CO | NH | $MeOOCCH_2$— |
| 1-1348 | 5 | CO | NH | MeCH(COOH) |
| 1-1349 | 5 | CO | NH | HOOC—$(CH_2)_2$— |
| 1-1350 | 5 | CO | NH | MeCH(COOMe) |
| 1-1351 | 5 | CO | NH | 1-HOOC-iBu |
| 1-1352 | 5 | CO | NH | 1-MeOOC-iBu |
| 1-1353 | 5 | CO | NH | 1-HOOC-iPn |
| 1-1354 | 5 | CO | NH | 1-MeOOC-iPn |
| 1-1355 | 5 | CO | NH | 1-HOOC-2-Me—Bu |
| 1-1356 | 5 | CO | NH | 1-MeOOC-2-Me—Bu |
| 1-1357 | 5 | CO | NH | $CH_2CH_2SO_3H$ |
| 1-1358 | 5 | CO | NH | OH |
| 1-1359 | 5 | CO | NH | MeO |
| 1-1360 | 5 | CO | NH | EtO |
| 1-1361 | 5 | CO | NH | PrO |
| 1-1362 | 5 | CO | NH | iPrO |
| 1-1363 | 5 | CO | NH | BuO |
| 1-1364 | 5 | CO | NH | iBuO |
| 1-1365 | 5 | CO | NH | sBuO |
| 1-1366 | 5 | CO | NH | tBuO |
| 1-1367 | 5 | CO | NH | HxO |
| 1-1368 | 5 | CO | NH | PhO |
| 1-1369 | 5 | CO | NH | BzO |
| 1-1370 | 5 | CO | NH | Z-1 |
| 1-1371 | 5 | CO | NH | Z-2 |
| 1-1372 | 5 | CO | NH | Z-3 |
| 1-1373 | 5 | CO | NH | Z-4 |
| 1-1374 | 5 | CO | NH | Z-5 |
| 1-1375 | 5 | CO | NH | Z-6 |
| 1-1376 | 5 | CO | NH | Z-7 |
| 1-1377 | 5 | CO | NH | Z-8 |
| 1-1378 | 5 | CO | NH | Z-9 |
| 1-1379 | 5 | CO | NH | Z-10 |
| 1-1380 | 5 | CO | NH | Z-11 |
| 1-1381 | 5 | CO | NH | Z-12 |
| 1-1382 | 5 | CO | NH | 3-Py |
| 1-1383 | 5 | CO | NH | 4-Py |
| 1-1384 | 5 | CO | N(Ac) | H |
| 1-1385 | 5 | CO | N(Ac) | Ph |
| 1-1386 | 5 | CO | N(Ac) | 2-Me—Ph |
| 1-1387 | 5 | CO | N(Ac) | 4-Me—Ph |
| 1-1388 | 5 | CO | N(Ac) | 2,4-diMe—Ph |
| 1-1389 | 5 | CO | N(Ac) | 3,4-diMe—Ph |
| 1-1390 | 5 | CO | N(Ac) | 2-($CF_3$)Ph |
| 1-1391 | 5 | CO | N(Ac) | 4-($CF_3$)Ph |
| 1-1392 | 5 | CO | N(Ac) | 2-MeOPh |
| 1-1393 | 5 | CO | N(Ac) | 4-MeOPh |
| 1-1394 | 5 | CO | N(Ac) | 2-EtOPh |
| 1-1395 | 5 | CO | N(Ac) | 4-EtOPh |

TABLE 1-continued

| Cpd. No. | k | A | B | R¹ |
|---|---|---|---|---|
| 1-1396 | 5 | CO | N(Ac) | 2-HOPh |
| 1-1397 | 5 | CO | N(Ac) | 4-HOPh |
| 1-1398 | 5 | CO | N(Ac) | 2-(HOOC)Ph |
| 1-1399 | 5 | CO | N(Ac) | 4-(HOOC)Ph |
| 1-1400 | 5 | CO | N(Ac) | 2-(MeOOC)Ph |
| 1-1401 | 5 | CO | N(Ac) | 4-(MeOOC)Ph |
| 1-1402 | 5 | CO | N(Ac) | 2-(EtOOC)Ph |
| 1-1403 | 5 | CO | N(Ac) | 4-(EtOOC)Ph |
| 1-1404 | 5 | CO | N(Ac) | 2-(tBuOOC)Ph |
| 1-1405 | 5 | CO | N(Ac) | 4-(tBuOOC)Ph |
| 1-1406 | 5 | CO | N(Ac) | 2-Cl—Ph |
| 1-1407 | 5 | CO | N(Ac) | 4-Cl—Ph |
| 1-1408 | 5 | CO | N(Ac) | 2-Br—Ph |
| 1-1409 | 5 | CO | N(Ac) | 4-Br—Ph |
| 1-1410 | 5 | CO | N(Ac) | 2-I—Ph |
| 1-1411 | 5 | CO | N(Ac) | 4-I—Ph |
| 1-1412 | 5 | CO | N(Ac) | 2-NO$_2$—Ph |
| 1-1413 | 5 | CO | N(Ac) | 4-NO$_2$—Ph |
| 1-1414 | 5 | CO | N(Ac) | 2-NH$_2$—Ph |
| 1-1415 | 5 | CO | N(Ac) | 4-NH$_2$—Ph |
| 1-1416 | 5 | CO | N(Ac) | 2-(HO$_3$S)Ph |
| 1-1417 | 5 | CO | N(Ac) | 4-(HO$_3$S)Ph |
| 1-1418 | 5 | CO | N(Ac) | 2-(NH$_2$O$_2$S)Ph |
| 1-1419 | 5 | CO | N(Ac) | 4-(NH$_2$O$_2$S)Ph |
| 1-1420 | 5 | CO | N(Ac) | 2-CN—Ph |
| 1-1421 | 5 | CO | N(Ac) | 4-CN—Ph |
| 1-1422 | 5 | CO | N(Ac) | 2-(HOCH$_2$)Ph |
| 1-1423 | 5 | CO | N(Ac) | 4-(HOCH$_2$)Ph |
| 1-1424 | 5 | CO | N(Ac) | Me |
| 1-1425 | 5 | CO | N(Ac) | Et |
| 1-1426 | 5 | CO | N(Ac) | Pr |
| 1-1427 | 5 | CO | N(Ac) | iPr |
| 1-1428 | 5 | CO | N(Ac) | Bu |
| 1-1429 | 5 | CO | N(Ac) | HOOCCH$_2$— |
| 1-1430 | 5 | CO | N(Ac) | MeOOCCH$_2$— |
| 1-1431 | 5 | CO | N(Ac) | MeCH(COOH) |
| 1-1432 | 5 | CO | N(Ac) | HOOC—(CH$_2$)$_2$— |
| 1-1433 | 5 | CO | N(Ac) | MeCH(COOMe) |
| 1-1434 | 5 | CO | N(Ac) | 1-HOOC-iBu |
| 1-1435 | 5 | CO | N(Ac) | 1-MeOOC-iBu |
| 1-1436 | 5 | CO | N(Ac) | 1-HOOC-iPn |
| 1-1437 | 5 | CO | N(Ac) | 1-MeOOC-iPn |
| 1-1438 | 5 | CO | N(Ac) | 1-HOOC-2-Me—Bu |
| 1-1439 | 5 | CO | N(Ac) | 1-MeOOC-2-Me—Bu |
| 1-1440 | 5 | CO | N(Ac) | CH$_2$CH$_2$SO$_3$H |
| 1-1441 | 5 | CO | N(Ac) | OH |
| 1-1442 | 5 | CO | N(Ac) | MeO |
| 1-1443 | 5 | CO | N(Ac) | EtO |
| 1-1444 | 5 | CO | N(Ac) | PrO |
| 1-4445 | 5 | CO | N(Ac) | iPrO |
| 1-1446 | 5 | CO | N(Ac) | BuO |
| 1-1447 | 5 | CO | N(Ac) | iBuO |
| 1-1448 | 5 | CO | N(Ac) | sBuO |
| 1-1449 | 5 | CO | N(Ac) | tBuO |
| 1-1450 | 5 | CO | N(Ac) | HxO |
| 1-1451 | 5 | CO | N(Ac) | PhO |
| 1-1452 | 5 | CO | N(Ac) | BzO |
| 1-1453 | 5 | CO | N(Ac) | Z-1 |
| 1-1454 | 5 | CO | N(Ac) | Z-2 |
| 1-1455 | 5 | CO | N(Ac) | Z-3 |
| 1-1456 | 5 | CO | N(Ac) | Z-4 |
| 1-1457 | 5 | CO | N(Ac) | Z-5 |
| 1-1458 | 5 | CO | N(Ac) | Z-6 |
| 1-1459 | 5 | CO | N(Ac) | Z-7 |
| 1-1460 | 5 | CO | N(Ac) | Z-8 |
| 1-1461 | 5 | CO | N(Ac) | Z-9 |
| 1-1462 | 5 | CO | N(Ac) | Z-10 |
| 1-1463 | 5 | CO | N(Ac) | Z-11 |
| 1-1464 | 5 | CO | N(Ac) | Z-12 |
| 1-1465 | 5 | CO | N(Ac) | 3-Py |
| 1-1466 | 5 | CO | N(Ac) | 4-Py |
| 1-1467 | 5 | COO | — | H |
| 1-1468 | 5 | COO | — | Ph |
| 1-1469 | 5 | COO | — | 2-Me—Ph |
| 1-1470 | 5 | COO | — | 4-Me—Ph |
| 1-1471 | 5 | COO | — | 2,4-diMe—Ph |

TABLE 1-continued

| Cpd. No. | k | A | B | R¹ |
|---|---|---|---|---|
| 1-1472 | 5 | COO | — | 3,4-diMe—Ph |
| 1-1473 | 5 | COO | — | 2-(CF$_3$)Ph |
| 1-1474 | 5 | COO | — | 4-(CF$_3$)Ph |
| 1-1475 | 5 | COO | — | 2-MeOPh |
| 1-1476 | 5 | COO | — | 4-MeOPh |
| 1-1477 | 5 | COO | — | 2-EtOPh |
| 1-1478 | 5 | COO | — | 4-EtOPh |
| 1-1479 | 5 | COO | — | 2-HOPh |
| 1-1480 | 5 | COO | — | 4-HOPh |
| 1-1481 | 5 | COO | — | 2-(HOOC)Ph |
| 1-1482 | 5 | COO | — | 4-(HOOC)Ph |
| 1-1483 | 5 | COO | — | 2-(MeOOC)Ph |
| 1-1484 | 5 | COO | — | 4-(MeOOC)Ph |
| 1-1485 | 5 | COO | — | 2-(EtOOC)Ph |
| 1-1486 | 5 | COO | — | 4-(EtOOC)Ph |
| 1-1487 | 5 | COO | — | 2-(tBuOOC)Ph |
| 1-1488 | 5 | COO | — | 4-(tBuOOC)Ph |
| 1-1489 | 5 | COO | — | 2-Cl—Ph |
| 1-1490 | 5 | COO | — | 4-Cl—Ph |
| 1-1491 | 5 | COO | — | 2-Br—Ph |
| 1-1492 | 5 | COO | — | 4-Br—Ph |
| 1-1493 | 5 | COO | — | 2-I—Ph |
| 1-1494 | 5 | COO | — | 4-I—Ph |
| 1-1495 | 5 | COO | — | 2-NO$_2$—Ph |
| 1-1496 | 5 | COO | — | 4-NO$_2$—Ph |
| 1-1497 | 5 | COO | — | 2-NH$_2$—Ph |
| 1-1498 | 5 | COO | — | 4-NH$_2$—Ph |
| 1-1499 | 5 | COO | — | 2-(HO$_3$S)Ph |
| 1-1500 | 5 | COO | — | 4-(HO$_3$S)Ph |
| 1-1501 | 5 | COO | — | 2-(NH$_2$O$_2$S)Ph |
| 1-1502 | 5 | COO | — | 4-(NH$_2$O$_2$S)Ph |
| 1-1503 | 5 | COO | — | 2-CN—Ph |
| 1-1504 | 5 | COO | — | 4-CN—Ph |
| 1-1505 | 5 | COO | — | 2-(HOCH$_2$)Ph |
| 1-1506 | 5 | COO | — | 4-(HOCH$_2$)Ph |
| 1-1507 | 5 | COO | — | Me |
| 1-1508 | 5 | COO | — | Et |
| 1-1509 | 5 | COO | — | Pr |
| 1-1510 | 5 | COO | — | iPr |
| 1-1511 | 5 | COO | — | Bu |
| 1-1512 | 5 | COO | — | HOOCCH$_2$— |
| 1-1513 | 5 | COO | — | HOOC—(CH$_2$)$_2$— |
| 1-1514 | 5 | COO | — | MeCH(COOMe) |
| 1-1515 | 5 | COO | — | 1-HOOC-iBu |
| 1-1516 | 5 | COO | — | 1-HOOC-iPn |
| 1-1517 | 5 | COO | — | Z-1 |
| 1-1518 | 5 | COO | — | Z-2 |
| 1-1519 | 5 | COO | — | Z-3 |
| 1-1520 | 5 | COO | — | Z-4 |
| 1-1521 | 5 | COO | — | Z-5 |
| 1-1522 | 5 | COO | — | Z-6 |
| 1-1523 | 5 | COO | — | Z-7 |
| 1-1524 | 5 | COO | — | Z-8 |
| 1-1525 | 5 | COO | — | Z-9 |
| 1-1526 | 5 | COO | — | Z-10 |
| 1-1527 | 5 | COO | — | Z-11 |
| 1-1528 | 5 | COO | — | Z-12 |
| 1-1529 | 5 | COO | — | 3-Py |
| 1-1530 | 5 | COO | — | 4-Py |
| 1-1531 | 5 | CONHCO | — | H |
| 1-1532 | 5 | CONHCO | — | Ph |
| 1-1533 | 5 | CONHCO | — | 2-Me—Ph |
| 1-1534 | 5 | CONHCO | — | 4-Me—Ph |
| 1-1535 | 5 | CONHCO | — | 2,4-diMe—Ph |
| 1-1536 | 5 | CONHCO | — | 3,4-diMe—Ph |
| 1-1537 | 5 | CONHCO | — | 2-(CF$_3$)Ph |
| 1-1538 | 5 | CONHCO | — | 4-(CF$_3$)Ph |
| 1-1539 | 5 | CONHCO | — | 2-MeOPh |
| 1-1540 | 5 | CONHCO | — | 4-MeOPh |
| 1-1541 | 5 | CONHCO | — | 2-EtOPh |
| 1-1542 | 5 | CONHCO | — | 4-EtOPh |
| 1-1543 | 5 | CONHCO | — | 2-HOPh |
| 1-1544 | 5 | CONHCO | — | 4-HOPh |
| 1-1545 | 5 | CONHCO | — | 2-(HOOC)Ph |
| 1-1546 | 5 | CONHCO | — | 4-(HOOC)Ph |
| 1-1547 | 5 | CONHCO | — | 2-(MeOOC)Ph |

TABLE 1-continued

| Cpd. No. | k | A | B | R¹ |
|---|---|---|---|---|
| 1-1548 | 5 | CONHCO | — | 4-(MeOOC)Ph |
| 1-1549 | 5 | CONHCO | — | 2-(EtOOC)Ph |
| 1-1550 | 5 | CONHCO | — | 4-(EtOOC)Ph |
| 1-1551 | 5 | CONHCO | — | 2-(tBuOOC)Ph |
| 1-1552 | 5 | CONHCO | — | 4-(tBuOOC)Ph |
| 1-1553 | 5 | CONHCO | — | 2-Cl—Ph |
| 1-1554 | 5 | CONHCO | — | 4-Cl—Ph |
| 1-1555 | 5 | CONHCO | — | 2-Br—Ph |
| 1-1556 | 5 | CONHCO | — | 4-Br—Ph |
| 1-1557 | 5 | CONHCO | — | 2-I—Ph |
| 1-1558 | 5 | CONHCO | — | 4-I—Ph |
| 1-1559 | 5 | CONHCO | — | 2-$NO_2$—Ph |
| 1-1560 | 5 | CONHCO | — | 4-$NO_2$—Ph |
| 1-1561 | 5 | CONHCO | — | 2-$NH_2$—Ph |
| 1-1562 | 5 | CONHCO | — | 4-$NH_2$—Ph |
| 1-1563 | 5 | CONHCO | — | 2-($HO_3S$)Ph |
| 1-1564 | 5 | CONHCO | — | 4-($HO_3S$)Ph |
| 1-1565 | 5 | CONHCO | — | 2-($NH_2O_2S$)Ph |
| 1-1566 | 5 | CONHCO | — | 4-($NH_2O_2S$)Ph |
| 1-1567 | 5 | CONHCO | — | 2-CN—Ph |
| 1-1568 | 5 | CONHCO | — | 4-CN—Ph |
| 1-1569 | 5 | CONHCO | — | 2-($HOCH_2$)Ph |
| 1-1570 | 5 | CONHCO | — | 4-($HOCH_2$)Ph |
| 1-1571 | 5 | CONHCO | — | Me |
| 1-1572 | 5 | CONHCO | — | Et |
| 1-1573 | 5 | CONHCO | — | Pr |
| 1-1574 | 5 | CONHCO | — | iPr |
| 1-1575 | 5 | CONHCO | — | Bu |
| 1-1576 | 5 | CONHCO | — | $HOOCCH_2$— |
| 1-1577 | 5 | CONHCO | — | $MeOOCCH_2$— |
| 1-1578 | 5 | CONHCO | — | MeCH(COOH) |
| 1-1579 | 5 | CONHCO | — | HOOC—$(CH_2)_2$— |
| 1-1580 | 5 | CONHCO | — | MeCH(COOMe) |
| 1-1581 | 5 | CONHCO | — | 1-HOOC-iBu |
| 1-1582 | 5 | CONHCO | — | 1-MeOOC-iBu |
| 1-1583 | 5 | CONHCO | — | 1-HOOC-iPn |
| 1-1584 | 5 | CONHCO | — | 1-MeOOC-iPn |
| 1-1585 | 5 | CONHCO | — | 1-HOOC-2-Me—Bu |
| 1-1586 | 5 | CONHCO | — | 1-MeOOC-2-Me—Bu |
| 1-1587 | 5 | CONHCO | — | $CH_2CH_2SO_3H$ |
| 1-1588 | 5 | CONHCO | — | Z-1 |
| 1-1589 | 5 | CONHCO | — | Z-2 |
| 1-1590 | 5 | CONHCO | — | Z-3 |
| 1-1591 | 5 | CONHCO | — | Z-4 |
| 1-1592 | 5 | CONHCO | — | Z-5 |
| 1-1593 | 5 | CONHCO | — | Z-6 |
| 1-1594 | 5 | CONHCO | — | Z-7 |
| 1-1595 | 5 | CONHCO | — | Z-8 |
| 1-1596 | 5 | CONHCO | — | Z-9 |
| 1-1597 | 5 | CONHCO | — | Z-10 |
| 1-1598 | 5 | CONHCO | — | Z-11 |
| 1-1599 | 5 | CONHCO | — | Z-12 |
| 1-1600 | 5 | CONHCO | — | 3-Py |
| 1-1601 | 5 | CONHCO | — | 4-Py |
| 1-1602 | 5 | CON(Ac)CO | — | H |
| 1-1603 | 5 | CON(Ac)CO | — | Ph |
| 1-1604 | 5 | CON(Ac)CO | — | 2-Me—Ph |
| 1-1605 | 5 | CON(Ac)CO | — | 4-Me—Ph |
| 1-1606 | 5 | CON(Ac)CO | — | 2,4-diMe—Ph |
| 1-1607 | 5 | CON(Ac)CO | — | 3,4-diMe—Ph |
| 1-1608 | 5 | CON(Ac)CO | — | 2-($CF_3$)Ph |
| 1-1609 | 5 | CON(Ac)CO | — | 4-($CF_3$)Ph |
| 1-1610 | 5 | CON(Ac)CO | — | 2-MeOPh |
| 1-1611 | 5 | CON(Ac)CO | — | 4-MeOPh |
| 1-1612 | 5 | CON(Ac)CO | — | 2-EtOPh |
| 1-1613 | 5 | CON(Ac)CO | — | 4-EtOPh |
| 1-1614 | 5 | CON(Ac)CO | — | 2-HOPh |
| 1-1615 | 5 | CON(Ac)CO | — | 4-HOPh |
| 1-1616 | 5 | CON(Ac)CO | — | 2-(HOOC)Ph |
| 1-1617 | 5 | CON(Ac)CO | — | 4-(HOOC)Ph |
| 1-1618 | 5 | CON(Ac)CO | — | 2-(MeOOC)Ph |
| 1-1619 | 5 | CON(Ac)CO | — | 4-(MeOOC)Ph |
| 1-1620 | 5 | CON(Ac)CO | — | 2-(EtOOC)Ph |
| 1-1621 | 5 | CON(Ac)CO | — | 4-(EtOOC)Ph |
| 1-1622 | 5 | CON(Ac)CO | — | 2-(tBuOOC)Ph |
| 1-1623 | 5 | CON(Ac)CO | — | 4-(tBuOOC)Ph |

TABLE 1-continued

| Cpd. No. | k | A | B | R¹ |
|---|---|---|---|---|
| 1-1624 | 5 | CON(Ac)CO | — | 2-Cl—Ph |
| 1-1625 | 5 | CON(Ac)CO | — | 4-Cl—Ph |
| 1-1626 | 5 | CON(Ac)CO | — | 2-Br—Ph |
| 1-1627 | 5 | CON(Ac)CO | — | 4-Br—Ph |
| 1-1628 | 5 | CON(Ac)CO | — | 2-I—Ph |
| 1-1629 | 5 | CON(Ac)CO | — | 4-I—Ph |
| 1-1630 | 5 | CON(Ac)CO | — | 2-$NO_2$—Ph |
| 1-1631 | 5 | CON(Ac)CO | — | 4-$NO_2$—Ph |
| 1-1632 | 5 | CON(Ac)CO | — | 2-$NH_2$—Ph |
| 1-1633 | 5 | CON(Ac)CO | — | 4-$NH_2$—Ph |
| 1-1634 | 5 | CON(Ac)CO | — | 2-($HO_3S$)Ph |
| 1-1635 | 5 | CON(Ac)CO | — | 4-($HO_3S$)Ph |
| 1-1636 | 5 | CON(Ac)CO | — | 2-($NH_2O_2S$)Ph |
| 1-1637 | 5 | CON(Ac)CO | — | 4-($NH_2O_2S$)Ph |
| 1-1638 | 5 | CON(Ac)CO | — | 2-CN—Ph |
| 1-1639 | 5 | CON(Ac)CO | — | 4-CN—Ph |
| 1-1640 | 5 | CON(Ac)CO | — | 2-($HOCH_2$)Ph |
| 1-1641 | 5 | CON(Ac)CO | — | 4-($HOCH_2$)Ph |
| 1-1642 | 5 | CON(Ac)CO | — | Me |
| 1-1643 | 5 | CON(Ac)CO | — | Et |
| 1-1644 | 5 | CON(Ac)CO | — | Pr |
| 1-1645 | 5 | CON(Ac)CO | — | iPr |
| 1-1646 | 5 | CON(Ac)CO | — | Bu |
| 1-1647 | 5 | CON(Ac)CO | — | $HOOCCH_2$— |
| 1-1648 | 5 | CON(Ac)CO | — | $MeOOCCH_2$— |
| 1-1649 | 5 | CON(Ac)CO | — | MeCH(COOH) |
| 1-1650 | 5 | CON(Ac)CO | — | HOOC—$(CH_2)_2$— |
| 1-1651 | 5 | CON(Ac)CO | — | MeCH(COOMe) |
| 1-1652 | 5 | CON(Ac)CO | — | 1-HOOC-iBu |
| 1-1653 | 5 | CON(Ac)CO | — | 1-MeOOC-iBu |
| 1-1654 | 5 | CON(Ac)CO | — | 1-HOOC-iPn |
| 1-1655 | 5 | CON(Ac)CO | — | 1-MeOOC-iPn |
| 1-1656 | 5 | CON(Ac)CO | — | 1-HOOC-2-Me—Bu |
| 1-1657 | 5 | CON(Ac)CO | — | 1-MeOOC-2-Me—Bu |
| 1-1658 | 5 | CON(Ac)CO | — | $CH_2CH_2SO_3H$ |
| 1-1659 | 5 | CON(Ac)CO | — | Z-1 |
| 1-1660 | 5 | CON(Ac)CO | — | Z-2 |
| 1-1661 | 5 | CON(Ac)CO | — | Z-3 |
| 1-1662 | 5 | CON(Ac)CO | — | Z-4 |
| 1-1663 | 5 | CON(Ac)CO | — | Z-5 |
| 1-1664 | 5 | CON(Ac)CO | — | Z-6 |
| 1-1665 | 5 | CON(Ac)CO | — | Z-7 |
| 1-1666 | 5 | CON(Ac)CO | — | Z-8 |
| 1-1667 | 5 | CON(Ac)CO | — | Z-9 |
| 1-1668 | 5 | CON(Ac)CO | — | Z-10 |
| 1-1669 | 5 | CON(Ac)CO | — | Z-11 |
| 1-1670 | 5 | CON(Ac)CO | — | Z-12 |
| 1-1671 | 5 | CON(Ac)CO | — | 3-Py |
| 1-1672 | 5 | CON(Ac)CO | — | 4-Py |
| 1-1673 | 5 | CONHCO | NH | H |
| 1-1674 | 5 | CONHCO | NH | Ph |
| 1-1675 | 5 | CONHCO | NH | 2-Me—Ph |
| 1-1676 | 5 | CONHCO | NH | 4-Me—Ph |
| 1-1677 | 5 | CONHCO | NH | 2,4-diMe—Ph |
| 1-1678 | 5 | CONHCO | NH | 3,4-diMe—Ph |
| 1-1679 | 5 | CONHCO | NH | 2-($CF_3$)Ph |
| 1-1680 | 5 | CONHCO | NH | 4-($CF_3$)Ph |
| 1-1681 | 5 | CONHCO | NH | 2-MeOPh |
| 1-1682 | 5 | CONHCO | NH | 4-MeOPh |
| 1-1683 | 5 | CONHCO | NH | 2-EtOPh |
| 1-1684 | 5 | CONHCO | NH | 4-EtOPh |
| 1-1685 | 5 | CONHCO | NH | 2-HOPh |
| 1-1686 | 5 | CONHCO | NH | 4-HOPh |
| 1-1687 | 5 | CONHCO | NH | 2-(HOOC)Ph |
| 1-1688 | 5 | CONHCO | NH | 4-(HOOC)Ph |
| 1-1689 | 5 | CONHCO | NH | 2-(MeOOC)Ph |
| 1-1690 | 5 | CONHCO | NH | 4-(MeOOC)Ph |
| 1-1691 | 5 | CONHCO | NH | 2-(EtOOC)Ph |
| 1-1692 | 5 | CONHCO | NH | 4-(EtOOC)Ph |
| 1-1693 | 5 | CONHCO | NH | 2-(tBuOOC)Ph |
| 1-1694 | 5 | CONHCO | NH | 4-(tBuOOC)Ph |
| 1-1695 | 5 | CONHCO | NH | 2-Cl—Ph |
| 1-1696 | 5 | CONHCO | NH | 4-Cl—Ph |
| 1-1697 | 5 | CONHCO | NH | 2-Br—Ph |
| 1-1698 | 5 | CONHCO | NH | 4-Br—Ph |
| 1-1699 | 5 | CONHCO | NH | 2-I—Ph |

TABLE 1-continued

| Cpd. No. | k | A | B | R$^1$ |
|---|---|---|---|---|
| 1-1700 | 5 | CONHCO | NH | 4-I—Ph |
| 1-1701 | 5 | CONHCO | NH | 2-NO$_2$—Ph |
| 1-1702 | 5 | CONHCO | NH | 4-NO$_2$—Ph |
| 1-1703 | 5 | CONHCO | NH | 2-NH$_2$—Ph |
| 1-1704 | 5 | CONHCO | NH | 4-NH$_2$—Ph |
| 1-1705 | 5 | CONHCO | NH | 2-(HO$_3$S)Ph |
| 1-1706 | 5 | CONHCO | NH | 4-(HO$_3$S)Ph |
| 1-1707 | 5 | CONHCO | NH | 2-(NH$_2$O$_2$S)Ph |
| 1-1708 | 5 | CONHCO | NH | 4-(NH$_2$O$_2$S)Ph |
| 1-1709 | 5 | CONHCO | NH | 2-CN—Ph |
| 1-1710 | 5 | CONHCO | NH | 4-CN—Ph |
| 1-1711 | 5 | CONHCO | NH | 2-(HOCH$_2$)Ph |
| 1-1712 | 5 | CONHCO | NH | 4-(HOCH$_2$)Ph |
| 1-1713 | 5 | CONHCO | NH | Me |
| 1-1714 | 5 | CONHCO | NH | Et |
| 1-1715 | 5 | CONHCO | NH | Pr |
| 1-1716 | 5 | CONHCO | NH | iPr |
| 1-1717 | 5 | CONHCO | NH | Bu |
| 1-1718 | 5 | CONHCO | NH | HOOCCH$_2$— |
| 1-1719 | 5 | CONHCO | NH | MeOOCCH$_2$— |
| 1-1720 | 5 | CONHCO | NH | MeCH(COOH) |
| 1-1721 | 5 | CONHCO | NH | HOOC—(CH$_2$)$_2$— |
| 1-1722 | 5 | CONHCO | NH | MeCH(COOMe) |
| 1-1723 | 5 | CONHCO | NH | 1-HOOC-iBu |
| 1-1724 | 5 | CONHCO | NH | 1-MeOOC-iBu |
| 1-1725 | 5 | CONHCO | NH | 1-HOOC-iPn |
| 1-1726 | 5 | CONHCO | NH | 1-MeOOC-iPn |
| 1-1727 | 5 | CONHCO | NH | 1-HOOC-2-Me—Bu |
| 1-1728 | 5 | CONHCO | NH | 1-MeOOC-2-Me—Bu |
| 1-1729 | 5 | CONHCO | NH | CH$_2$CH$_2$SO$_3$H |
| 1-1730 | 5 | CONHCO | NH | HO |
| 1-1731 | 5 | CONHCO | NH | MeO |
| 1-1732 | 5 | CONHCO | NH | EtO |
| 1-1733 | 5 | CONHCO | NH | PrO |
| 1-1734 | 5 | CONHCO | NH | iPrO |
| 1-1735 | 5 | CONHCO | NH | BuO |
| 1-1736 | 5 | CONHCO | NH | iBuO |
| 1-1737 | 5 | CONHCO | NH | sBuO |
| 1-1738 | 5 | CONHCO | NH | tBuO |
| 1-1739 | 5 | CONHCO | NH | HxO |
| 1-1740 | 5 | CONHCO | NH | PhO |
| 1-1741 | 5 | CONHCO | NH | BzO |
| 1-1742 | 5 | CONHCO | NH | Z-1 |
| 1-1743 | 5 | CONHCO | NH | Z-2 |
| 1-1744 | 5 | CONHCO | NH | Z-3 |
| 1-1745 | 5 | CONHCO | NH | Z-4 |
| 1-1746 | 5 | CONHCO | NH | Z-5 |
| 1-1747 | 5 | CONHCO | NH | Z-6 |
| 1-1748 | 5 | CONHCO | NH | Z-7 |
| 1-1749 | 5 | CONHCO | NH | Z-8 |
| 1-1750 | 5 | CONHCO | NH | Z-9 |
| 1-1751 | 5 | CONHCO | NH | Z-10 |
| 1-1752 | 5 | CONHCO | NH | Z-11 |
| 1-1753 | 5 | CONHCO | NH | Z-12 |
| 1-1754 | 5 | CONHCO | NH | 3-Py |
| 1-1755 | 5 | CONHCO | NH | 4-Py |
| 1-1756 | 5 | CONHSO$_2$ | — | H |
| 1-1757 | 5 | CONHSO$_2$ | — | Ph |
| 1-1758 | 5 | CONHSO$_2$ | — | 2-Me—Ph |
| 1-1759 | 5 | CONHSO$_2$ | — | 4-Me—Ph |
| 1-1760 | 5 | CONHSO$_2$ | — | 2,4-diMe—Ph |
| 1-1761 | 5 | CONHSO$_2$ | — | 3,4-diMe—Ph |
| 1-1762 | 5 | CONHSO$_2$ | — | 2-(CF$_3$)Ph |
| 1-1763 | 5 | CONHSO$_2$ | — | 4-(CF$_3$)Ph |
| 1-1764 | 5 | CONHSO$_2$ | — | 2-MeOPh |
| 1-1765 | 5 | CONHSO$_2$ | — | 4-MeOPh |
| 1-1766 | 5 | CONHSO$_2$ | — | 2-EtOPh |
| 1-1767 | 5 | CONHSO$_2$ | — | 4-EtOPh |
| 1-1768 | 5 | CONHSO$_2$ | — | 2-HOPh |
| 1-1769 | 5 | CONHSO$_2$ | — | 4-HOPh |
| 1-1770 | 5 | CONHSO$_2$ | — | 2-(HOOC)Ph |
| 1-1771 | 5 | CONHSO$_2$ | — | 4-(HOOC)Ph |
| 1-1772 | 5 | CONHSO$_2$ | — | 2-(MeOOC)Ph |
| 1-1773 | 5 | CONHSO$_2$ | — | 4-(MeOOC)Ph |
| 1-1774 | 5 | CONHSO$_2$ | — | 2-(EtOOC)Ph |
| 1-1775 | 5 | CONHSO$_2$ | — | 4-(EtOOC)Ph |

TABLE 1-continued

| Cpd. No. | k | A | B | R¹ |
|---|---|---|---|---|
| 1-1776 | 5 | CONHSO$_2$ | — | 2-(tBuOOC)Ph |
| 1-1777 | 5 | CONHSO$_2$ | — | 4-(tBuOOC)Ph |
| 1-1778 | 5 | CONHSO$_2$ | — | 2-Cl—Ph |
| 1-1779 | 5 | CONHSO$_2$ | — | 4-Cl—Ph |
| 1-1780 | 5 | CONHSO$_2$ | — | 2-Br—Ph |
| 1-1781 | 5 | CONHSO$_2$ | — | 4-Br—Ph |
| 1-1782 | 5 | CONHSO$_2$ | — | 2-I—Ph |
| 1-1783 | 5 | CONHSO$_2$ | — | 4-I—Ph |
| 1-1784 | 5 | CONHSO$_2$ | — | 2-NO$_2$—Ph |
| 1-1785 | 5 | CONHSO$_2$ | — | 4-NO$_2$—Ph |
| 1-1786 | 5 | CONHSO$_2$ | — | 2-NH$_2$—Ph |
| 1-1787 | 5 | CONHSO$_2$ | — | 4-NH$_2$—Ph |
| 1-1788 | 5 | CONHSO$_2$ | — | 2-(HO$_3$S)Ph |
| 1-1789 | 5 | CONHSO$_2$ | — | 4-(HO$_3$S)Ph |
| 1-1790 | 5 | CONHSO$_2$ | — | 2-(NH$_2$O$_2$S)Ph |
| 1-1791 | 5 | CONHSO$_2$ | — | 4-(NH$_2$O$_2$S)Ph |
| 1-1792 | 5 | CONHSO$_2$ | — | 2-CN—Ph |
| 1-1793 | 5 | CONHSO$_2$ | — | 4-CN—Ph |
| 1-1794 | 5 | CONHSO$_2$ | — | 2-(HOCH$_2$)Ph |
| 1-1795 | 5 | CONHSO$_2$ | — | 4-(HOCH$_2$)Ph |
| 1-1796 | 5 | CONHSO$_2$ | — | Me |
| 1-1797 | 5 | CONHSO$_2$ | — | Et |
| 1-1798 | 5 | CONHSO$_2$ | — | Pr |
| 1-1799 | 5 | CONHSO$_2$ | — | iPr |
| 1-1800 | 5 | CONHSO$_2$ | — | Bu |
| 1-1801 | 5 | CONHSO$_2$ | — | HOOCCH$_2$— |
| 1-1802 | 5 | CONHSO$_2$ | — | MeOOCCH$_2$— |
| 1-1803 | 5 | CONHSO$_2$ | — | MeCH(COOH) |
| 1-1804 | 5 | CONHSO$_2$ | — | HOOC—(CH$_2$)$_2$— |
| 1-1805 | 5 | CONHSO$_2$ | — | MeCH(COOMe) |
| 1-1806 | 5 | CONHSO$_2$ | — | 1-HOOC-iBu |
| 1-1807 | 5 | CONHSO$_2$ | — | 1-MeOOC-iBu |
| 1-1808 | 5 | CONHSO$_2$ | — | 1-HOOC-iPn |
| 1-1809 | 5 | CONHSO$_2$ | — | 1-MeOOC-iPn |
| 1-1810 | 5 | CONHSO$_2$ | — | 1-HOOC-2-Me—Bu |
| 1-1811 | 5 | CONHSO$_2$ | — | 1-MeOOC-2-Me—Bu |
| 1-1812 | 5 | CONHSO$_2$ | — | CH$_2$CH$_2$SO$_3$H |
| 1-1813 | 5 | CONHSO$_2$ | — | OH |
| 1-1814 | 5 | CONHSO$_2$ | — | MeO |
| 1-1815 | 5 | CONHSO$_2$ | — | EtO |
| 1-1816 | 5 | CONHSO$_2$ | — | PrO |
| 1-1817 | 5 | CONHSO$_2$ | — | iPrO |
| 1-1818 | 5 | CONHSO$_2$ | — | BuO |
| 1-1819 | 5 | CONHSO$_2$ | — | iBuO |
| 1-1820 | 5 | CONHSO$_2$ | — | sBuO |
| 1-1821 | 5 | CONHSO$_2$ | — | tBuO |
| 1-1822 | 5 | CONHSO$_2$ | — | HxO |
| 1-1823 | 5 | CONHSO$_2$ | — | PhO |
| 1-1824 | 5 | CONHSO$_2$ | — | BzO |
| 1-1825 | 5 | CONHSO$_2$ | — | Z-1 |
| 1-1826 | 5 | CONHSO$_2$ | — | Z-2 |
| 1-1827 | 5 | CONHSO$_2$ | — | Z-3 |
| 1-1828 | 5 | CONHSO$_2$ | — | Z-4 |
| 1-1829 | 5 | CONHSO$_2$ | — | Z-5 |
| 1-1830 | 5 | CONHSO$_2$ | — | Z-6 |
| 1-1831 | 5 | CONHSO$_2$ | — | Z-7 |
| 1-1832 | 5 | CONHSO$_2$ | — | Z-8 |
| 1-1833 | 5 | CONHSO$_2$ | — | Z-9 |
| 1-1834 | 5 | CONHSO$_2$ | — | Z-10 |
| 1-1835 | 5 | CONHSO$_2$ | — | Z-11 |
| 1-1836 | 5 | CONHSO$_2$ | — | Z-12 |
| 1-1837 | 5 | CONHSO$_2$ | — | 3-Py |
| 1-1838 | 5 | CONHSO$_2$ | — | 4-Py |
| 1-1839 | 5 | CONHSO$_2$ | NH | H |
| 1-1840 | 5 | CONHSO$_2$ | NH | Ph |
| 1-1841 | 5 | CONHSO$_2$ | NH | 2-Me—Ph |
| 1-1842 | 5 | CONHSO$_2$ | NH | 4-Me—Ph |
| 1-1843 | 5 | CONHSO$_2$ | NH | 2,4-diMe—Ph |
| 1-1844 | 5 | CONHSO$_2$ | NH | 3,4-diMe—Ph |
| 1-1845 | 5 | CONHSO$_2$ | NH | 2-(CF$_3$)Ph |
| 1-1846 | 5 | CONHSO$_2$ | NH | 4-(CF$_3$)Ph |
| 1-1847 | 5 | CONHSO$_2$ | NH | 2-MeOPh |
| 1-1848 | 5 | CONHSO$_2$ | NH | 4-MeOPh |
| 1-1849 | 5 | CONHSO$_2$ | NH | 2-EtOPh |
| 1-1850 | 5 | CONHSO$_2$ | NH | 4-EtOPh |
| 1-1851 | 5 | CONHSO$_2$ | NH | 2-HOPh |

TABLE 1-continued

| Cpd. No. | k | A | B | R¹ |
|---|---|---|---|---|
| 1-1852 | 5 | CONHSO$_2$ | NH | 4-HOPh |
| 1-1853 | 5 | CONHSO$_2$ | NH | 2-(HOOC)Ph |
| 1-1854 | 5 | CONHSO$_2$ | NH | 4-(HOOC)Ph |
| 1-1855 | 5 | CONHSO$_2$ | NH | 2-(MeOOC)Ph |
| 1-1856 | 5 | CONHSO$_2$ | NH | 4-(MeOOC)Ph |
| 1-1857 | 5 | CONHSO$_2$ | NH | 2-(EtOOC)Ph |
| 1-1858 | 5 | CONHSO$_2$ | NH | 4-(EtOOC)Ph |
| 1-1859 | 5 | CONHSO$_2$ | NH | 2-(tBuOOC)Ph |
| 1-1860 | 5 | CONHSO$_2$ | NH | 4-(tBuOOC)Ph |
| 1-1861 | 5 | CONHSO$_2$ | NH | 2-Cl—Ph |
| 1-1862 | 5 | CONHSO$_2$ | NH | 4-Cl—Ph |
| 1-1863 | 5 | CONHSO$_2$ | NH | 2-Br—Ph |
| 1-1864 | 5 | CONHSO$_2$ | NH | 4-Br—Ph |
| 1-1865 | 5 | CONHSO$_2$ | NH | 2-I—Ph |
| 1-1866 | 5 | CONHSO$_2$ | NH | 4-I—Ph |
| 1-1867 | 5 | CONHSO$_2$ | NH | 2-NO$_2$—Ph |
| 1-1868 | 5 | CONHSO$_2$ | NH | 4-NO$_2$—Ph |
| 1-1869 | 5 | CONHSO$_2$ | NH | 2-NH$_2$—Ph |
| 1-1870 | 5 | CONHSO$_2$ | NH | 4-NH$_2$—Ph |
| 1-1871 | 5 | CONHSO$_2$ | NH | 2-(HO$_3$S)Ph |
| 1-1872 | 5 | CONHSO$_2$ | NH | 4-(HO$_3$S)Ph |
| 1-1873 | 5 | CONHSO$_2$ | NH | 2-(NH$_2$O$_2$S)Ph |
| 1-1874 | 5 | CONHSO$_2$ | NH | 4-(NH$_2$O$_2$S)Ph |
| 1-1875 | 5 | CONHSO$_2$ | NH | 2-CN—Ph |
| 1-1876 | 5 | CONHSO$_2$ | NH | 4-CN—Ph |
| 1-1877 | 5 | CONHSO$_2$ | NH | 2-(HOCH$_2$)Ph |
| 1-1878 | 5 | CONHSO$_2$ | NH | 4-(HOCH$_2$)Ph |
| 1-1879 | 5 | CONHSO$_2$ | NH | Me |
| 1-1880 | 5 | CONHSO$_2$ | NH | Et |
| 1-1881 | 5 | CONHSO$_2$ | NH | Pr |
| 1-1882 | 5 | CONHSO$_2$ | NH | iPr |
| 1-1883 | 5 | CONHSO$_2$ | NH | Bu |
| 1-1884 | 5 | CONHSO$_2$ | NH | HOOCCH$_2$— |
| 1-1885 | 5 | CONHSO$_2$ | NH | MeOOCCH$_2$— |
| 1-1886 | 5 | CONHSO$_2$ | NH | MeCH(COOH) |
| 1-1887 | 5 | CONHSO$_2$ | NH | HOOC—(CH$_2$)$_2$— |
| 1-1888 | 5 | CONHSO$_2$ | NH | MeCH(COOMe) |
| 1-1889 | 5 | CONHSO$_2$ | NH | 1-HOOC-iBu |
| 1-1890 | 5 | CONHSO$_2$ | NH | 1-MeOOC-iBu |
| 1-1891 | 5 | CONHSO$_2$ | NH | 1-HOOC-iPn |
| 1-1892 | 5 | CONHSO$_2$ | NH | 1-MeOOC-iPn |
| 1-1893 | 5 | CONHSO$_2$ | NH | 1-HOOC-2-Me—Bu |
| 1-1894 | 5 | CONHSO$_2$ | NH | 1-MeOOC-2-Me—Bu |
| 1-1895 | 5 | CONHSO$_2$ | NH | CH$_2$CH$_2$SO$_3$H |
| 1-1896 | 5 | CONHSO$_2$ | NH | OH |
| 1-1897 | 5 | CONHSO$_2$ | NH | MeO |
| 1-1898 | 5 | CONHSO$_2$ | NH | EtO |
| 1-1899 | 5 | CONHSO$_2$ | NH | PrO |
| 1-1900 | 5 | CONHSO$_2$ | NH | iPrO |
| 1-1901 | 5 | CONHSO$_2$ | NH | BuO |
| 1-1902 | 5 | CONHSO$_2$ | NH | iBuO |
| 1-1903 | 5 | CONHSO$_2$ | NH | sBuO |
| 1-1904 | 5 | CONHSO$_2$ | NH | tBuO |
| 1-1905 | 5 | CONHSO$_2$ | NH | HxO |
| 1-1906 | 5 | CONHSO$_2$ | NH | PhO |
| 1-1907 | 5 | CONHSO$_2$ | NH | BzO |
| 1-1908 | 5 | CONHSO$_2$ | NH | Z-1 |
| 1-1909 | 5 | CONHSO$_2$ | NH | Z-2 |
| 1-1910 | 5 | CONHSO$_2$ | NH | Z-3 |
| 1-1911 | 5 | CONHSO$_2$ | NH | Z-4 |
| 1-1912 | 5 | CONHSO$_2$ | NH | Z-5 |
| 1-1913 | 5 | CONHSO$_2$ | NH | Z-6 |
| 1-1914 | 5 | CONHSO$_2$ | NH | Z-7 |
| 1-1915 | 5 | CONHSO$_2$ | NH | Z-8 |
| 1-1916 | 5 | CONHSO$_2$ | NH | Z-9 |
| 1-1917 | 5 | CONHSO$_2$ | NH | Z-10 |
| 1-1918 | 5 | CONHSO$_2$ | NH | Z-11 |
| 1-1919 | 5 | CONHSO$_2$ | NH | Z-12 |
| 1-1920 | 5 | CONHSO$_2$ | NH | 3-Py |
| 1-1921 | 5 | CONHSO$_2$ | NH | 4-Py |
| 1-1922 | 5 | NHCO | — | H |
| 1-1923 | 5 | NHCO | — | Ph |
| 1-1924 | 5 | NHCO | — | 2-Me—Ph |
| 1-1925 | 5 | NHCO | — | 4-Me—Ph |
| 1-1926 | 5 | NHCO | — | 2,4-diMe—Ph |
| 1-1927 | 5 | NHCO | — | 3,4-diMe—Ph |

TABLE 1-continued

| Cpd. No. | k | A | B | R¹ |
|---|---|---|---|---|
| 1-1928 | 5 | NHCO | — | 2-(CF$_3$)Ph |
| 1-1929 | 5 | NHCO | — | 4-(CF$_3$)Ph |
| 1-1930 | 5 | NHCO | — | 2-MeOPh |
| 1-1931 | 5 | NHCO | — | 4-MeOPh |
| 1-1932 | 5 | NHCO | — | 2-EtOPh |
| 1-1933 | 5 | NHCO | — | 4-EtOPh |
| 1-1934 | 5 | NHCO | — | 2-HOPh |
| 1-1935 | 5 | NHCO | — | 4-HOPh |
| 1-1936 | 5 | NHCO | — | 2-(HOOC)Ph |
| 1-1937 | 5 | NHCO | — | 4-(HOOC)Ph |
| 1-1938 | 5 | NHCO | — | 2-(MeOOC)Ph |
| 1-1939 | 5 | NHCO | — | 4-(MeOOC)Ph |
| 1-1940 | 5 | NHCO | — | 2-(EtOOC)Ph |
| 1-1941 | 5 | NHCO | — | 4-(EtOOC)Ph |
| 1-1942 | 5 | NHCO | — | 2-(tBuOOC)Ph |
| 1-1943 | 5 | NHCO | — | 4-(tBuOOC)Ph |
| 1-1944 | 5 | NHCO | — | 2-Cl—Ph |
| 1-1945 | 5 | NHCO | — | 4-Cl—Ph |
| 1-1946 | 5 | NHCO | — | 2-Br—Ph |
| 1-1947 | 5 | NHCO | — | 4-Br—Ph |
| 1-1948 | 5 | NHCO | — | 2-I—Ph |
| 1-1949 | 5 | NHCO | — | 4-I—Ph |
| 1-1950 | 5 | NHCO | — | 2-NO$_2$—Ph |
| 1-1951 | 5 | NHCO | — | 4-NO$_2$—Ph |
| 1-1952 | 5 | NHCO | — | 2-NH$_2$—Ph |
| 1-1953 | 5 | NHCO | — | 4-NH$_2$—Ph |
| 1-1954 | 5 | NHCO | — | 2-(HO$_3$S)Ph |
| 1-1955 | 5 | NHCO | — | 4-(HO$_3$S)Ph |
| 1-1956 | 5 | NHCO | — | 2-(NH$_2$O$_2$S)Ph |
| 1-1957 | 5 | NHCO | — | 4-(NH$_2$O$_2$S)Ph |
| 1-1958 | 5 | NHCO | — | 2-CN—Ph |
| 1-1959 | 5 | NHCO | — | 4-CN—Ph |
| 1-1960 | 5 | NHCO | — | 2-(HOCH$_2$)Ph |
| 1-1961 | 5 | NHCO | — | 4-(HOCH$_2$)Ph |
| 1-1962 | 5 | NHCO | — | Me |
| 1-1963 | 5 | NHCO | — | Et |
| 1-1964 | 5 | NHCO | — | Pr |
| 1-1965 | 5 | NHCO | — | iPr |
| 1-1966 | 5 | NHCO | — | Bu |
| 1-1967 | 5 | NHCO | — | HOOC—(CH$_2$)$_2$— |
| 1-1968 | 5 | NHCO | — | MeOOCCH$_2$— |
| 1-1969 | 5 | NHCO | — | MeCH(COOH) |
| 1-1970 | 5 | NHCO | — | HOOC—(CH$_2$)$_2$— |
| 1-1971 | 5 | NHCO | — | MeCH(COOMe) |
| 1-1972 | 5 | NHCO | — | 1-HOOC-iBu |
| 1-1973 | 5 | NHCO | — | 1-HOOC-iPn |
| 1-1974 | 5 | NHCO | — | 1-HOOC-2-Me—Bu |
| 1-1975 | 5 | NHCO | — | CH$_2$CH$_2$SO$_3$H |
| 1-1976 | 5 | NHCO | — | MeO |
| 1-1977 | 5 | NHCO | — | EtO |
| 1-1978 | 5 | NHCO | — | PrO |
| 1-1979 | 5 | NHCO | — | Z-1 |
| 1-1980 | 5 | NHCO | — | Z-2 |
| 1-1981 | 5 | NHCO | — | Z-3 |
| 1-1982 | 5 | NHCO | — | Z-4 |
| 1-1983 | 5 | NHCO | — | Z-5 |
| 1-1984 | 5 | NHCO | — | Z-6 |
| 1-1985 | 5 | NHCO | — | Z-7 |
| 1-1986 | 5 | NHCO | — | Z-8 |
| 1-1987 | 5 | NHCO | — | Z-9 |
| 1-1988 | 5 | NHCO | — | Z-10 |
| 1-1989 | 5 | NHCO | — | Z-11 |
| 1-1990 | 5 | NHCO | — | Z-12 |
| 1-1991 | 5 | NHCO | — | 3-Py |
| 1-1992 | 5 | NHCO | — | 4-Py |
| 1-1993 | 5 | NHCO | NH | H |
| 1-1994 | 5 | NHCO | NH | Ph |
| 1-1995 | 5 | NHCO | NH | 2-Me—Ph |
| 1-1996 | 5 | NHCO | NH | 4-Me—Ph |
| 1-1997 | 5 | NHCO | NH | 2,4-diMe—Ph |
| 1-1998 | 5 | NHCO | NH | 3,4-diMe—Ph |
| 1-1999 | 5 | NHCO | NH | 2-(CF$_3$)Ph |
| 1-2000 | 5 | NHCO | NH | 4-(CF$_3$)Ph |
| 1-2001 | 5 | NHCO | NH | 2-MeOPh |
| 1-2002 | 5 | NHCO | NH | 4-MeOPh |
| 1-2003 | 5 | NHCO | NH | 2-EtOPh |

TABLE 1-continued

| Cpd. No. | k | A | B | R¹ |
|---|---|---|---|---|
| 1-2004 | 5 | NHCO | NH | 4-EtOPh |
| 1-2005 | 5 | NHCO | NH | 2-HOPh |
| 1-2006 | 5 | NHCO | NH | 4-HOPh |
| 1-2007 | 5 | NHCO | NH | 2-(HOOC)Ph |
| 1-2008 | 5 | NHCO | NH | 4-(HOOC)Ph |
| 1-2009 | 5 | NHCO | NH | 2-(MeOOC)Ph |
| 1-2010 | 5 | NHCO | NH | 4-(MeOOC)Ph |
| 1-2011 | 5 | NHCO | NH | 2-(EtOOC)Ph |
| 1-2012 | 5 | NHCO | NH | 4-(EtOOC)Ph |
| 1-2013 | 5 | NHCO | NH | 2-(tBuOOC)Ph |
| 1-2014 | 5 | NHCO | NH | 4-(tBuOOC)Ph |
| 1-2015 | 5 | NHCO | NH | 2-Cl—Ph |
| 1-2016 | 5 | NHCO | NH | 4-Cl—Ph |
| 1-2017 | 5 | NHCO | NH | 2-Br—Ph |
| 1-2018 | 5 | NHCO | NH | 4-Br—Ph |
| 1-2019 | 5 | NHCO | NH | 2-I—Ph |
| 1-2020 | 5 | NHCO | NH | 4-I—Ph |
| 1-2021 | 5 | NHCO | NH | 2-$NO_2$—Ph |
| 1-2022 | 5 | NHCO | NH | 4-$NO_2$—Ph |
| 1-2023 | 5 | NHCO | NH | 2-$NH_2$—Ph |
| 1-2024 | 5 | NHCO | NH | 4-$NH_2$—Ph |
| 1-2025 | 5 | NHCO | NH | 2-($HO_3S$)Ph |
| 1-2026 | 5 | NHCO | NH | 4-($HO_3S$)Ph |
| 1-2027 | 5 | NHCO | NH | 2-($NH_2O_2S$)Ph |
| 1-2028 | 5 | NHCO | NH | 4-($NH_2O_2S$)Ph |
| 1-2029 | 5 | NHCO | NH | 2-CN—Ph |
| 1-2030 | 5 | NHCO | NH | 4-CN—Ph |
| 1-2031 | 5 | NHCO | NH | 2-($HOCH_2$)Ph |
| 1-2032 | 5 | NHCO | NH | 4-($HOCH_2$)Ph |
| 1-2033 | 5 | NHCO | NH | Me |
| 1-2034 | 5 | NHCO | NH | Et |
| 1-2035 | 5 | NHCO | NH | Pr |
| 1-2036 | 5 | NHCO | NH | iPr |
| 1-2037 | 5 | NHCO | NH | Bu |
| 1-2038 | 5 | NHCO | NH | $HOOCCH_2$— |
| 1-2039 | 5 | NHCO | NH | $MeOOCCH_2$— |
| 1-2040 | 5 | NHCO | NH | MeCH(COOH) |
| 1-2041 | 5 | NHCO | NH | HOOC—$(CH_2)_2$— |
| 1-2042 | 5 | NHCO | NH | MeCH(COOMe) |
| 1-2043 | 5 | NHCO | NH | 1-HOOC-iBu |
| 1-2044 | 5 | NHCO | NH | 1-MeOOC-iBu |
| 1-2045 | 5 | NHCO | NH | 1-HOOC-iPn |
| 1-2046 | 5 | NHCO | NH | 1-MeOOC-iPn |
| 1-2047 | 5 | NHCO | NH | 1-HOOC-2-Me—Bu |
| 1-2048 | 5 | NHCO | NH | 1-MeOOC-2-Me—Bu |
| 1-2049 | 5 | NHCO | NH | $CH_2CH_2SO_3H$ |
| 1-2050 | 5 | NHCO | NH | OH |
| 1-2051 | 5 | NHCO | NH | MeO |
| 1-2052 | 5 | NHCO | NH | EtO |
| 1-2053 | 5 | NHCO | NH | PrO |
| 1-2054 | 5 | NHCO | NH | iPrO |
| 1-2055 | 5 | NHCO | NH | BuO |
| 1-2056 | 5 | NHCO | NH | iBuO |
| 1-2057 | 5 | NHCO | NH | sBuO |
| 1-2058 | 5 | NHCO | NH | tBuO |
| 1-2059 | 5 | NHCO | NH | HxO |
| 1-2060 | 5 | NHCO | NH | PhO |
| 1-2061 | 5 | NHCO | NH | BzO |
| 1-2062 | 5 | NHCO | NH | Z-1 |
| 1-2063 | 5 | NHCO | NH | Z-2 |
| 1-2064 | 5 | NHCO | NH | Z-3 |
| 1-2065 | 5 | NHCO | NH | Z-4 |
| 1-2066 | 5 | NHCO | NH | Z-5 |
| 1-2067 | 5 | NHCO | NH | Z-6 |
| 1-2068 | 5 | NHCO | NH | Z-7 |
| 1-2069 | 5 | NHCO | NH | Z-8 |
| 1-2070 | 5 | NHCO | NH | Z-9 |
| 1-2071 | 5 | NHCO | NH | Z-10 |
| 1-2072 | 5 | NHCO | NH | Z-11 |
| 1-2073 | 5 | NHCO | NH | Z-12 |
| 1-2074 | 5 | NHCO | NH | 3-Py |
| 1-2075 | 5 | NHCO | NH | 4-Py |
| 1-2076 | 5 | NHCO | NMe | Ph |
| 1-2077 | 5 | NHCO | NMe | 2-Me—Ph |
| 1-2078 | 5 | NHCO | NMe | 4-Me—Ph |
| 1-2079 | 5 | NHCO | NMe | 2,4-diMe—Ph |

TABLE 1-continued

| Cpd. No. | k | A | B | R¹ |
|---|---|---|---|---|
| 1-2080 | 5 | NHCO | NMe | 3,4-diMe—Ph |
| 1-2081 | 5 | NHCO | NMe | 2-(CF$_3$)Ph |
| 1-2082 | 5 | NHCO | NMe | 4-(CF$_3$)Ph |
| 1-2083 | 5 | NHCO | NMe | 2-MeOPh |
| 1-2084 | 5 | NHCO | NMe | 4-MeOPh |
| 1-2085 | 5 | NHCO | NMe | 2-EtOPh |
| 1-2086 | 5 | NHCO | NMe | 4-EtOPh |
| 1-2087 | 5 | NHCO | NMe | 2-HOPh |
| 1-2088 | 5 | NHCO | NMe | 4-HOPh |
| 1-2089 | 5 | NHCO | NMe | 2-(HOOC)Ph |
| 1-2090 | 5 | NHCO | NMe | 4-(HOOC)Ph |
| 1-2091 | 5 | NHCO | NMe | 2-(MeOOC)Ph |
| 1-2092 | 5 | NHCO | NMe | 4-(MeOOC)Ph |
| 1-2093 | 5 | NHCO | NMe | 2-(EtOOC)Ph |
| 1-2094 | 5 | NHCO | NMe | 4-(EtOOC)Ph |
| 1-2095 | 5 | NHCO | NMe | 2-(tBuOOC)Ph |
| 1-2096 | 5 | NHCO | NMe | 4-(tBuOOC)Ph |
| 1-2097 | 5 | NHCO | NMe | 2-Cl—Ph |
| 1-2098 | 5 | NHCO | NMe | 4-Cl—Ph |
| 1-2099 | 5 | NHCO | NMe | 2-Br—Ph |
| 1-2100 | 5 | NHCO | NMe | 4-Br—Ph |
| 1-2101 | 5 | NHCO | NMe | 2-I—Ph |
| 1-2102 | 5 | NHCO | NMe | 4-I—Ph |
| 1-2103 | 5 | NHCO | NMe | 2-NO$_2$—Ph |
| 1-2104 | 5 | NHCO | NMe | 4-NO$_2$—Ph |
| 1-2105 | 5 | NHCO | NMe | 2-NH$_2$—Ph |
| 1-2106 | 5 | NHCO | NMe | 4-NH$_2$—Ph |
| 1-2107 | 5 | NHCO | NMe | 2-(HO$_3$S)Ph |
| 1-2108 | 5 | NHCO | NMe | 4-(HO$_3$S)Ph |
| 1-2109 | 5 | NHCO | NMe | 2-(NH$_2$O$_2$S)Ph |
| 1-2110 | 5 | NHCO | NMe | 4-(NH$_2$O$_2$S)Ph |
| 1-2111 | 5 | NHCO | NMe | 2-CN—Ph |
| 1-2112 | 5 | NHCO | NMe | 4-CN—Ph |
| 1-2113 | 5 | NHCO | NMe | 2-(HOCH$_2$)Ph |
| 1-2114 | 5 | NHCO | NMe | 4-(HOCH$_2$)Ph |
| 1-2115 | 5 | NHCO | NMe | Me |
| 1-2116 | 5 | NHCO | NMe | Et |
| 1-2117 | 5 | NHCO | NMe | Pr |
| 1-2118 | 5 | NHCO | NMe | iPr |
| 1-2119 | 5 | NHCO | NMe | Bu |
| 1-2120 | 5 | NHCO | NMe | HOOCCH$_2$— |
| 1-2121 | 5 | NHCO | NMe | MeOOCCH$_2$— |
| 1-2122 | 5 | NHCO | NMe | MeCH(COOH) |
| 1-2123 | 5 | NHCO | NMe | HOOC—(CH$_2$)$_2$— |
| 1-2124 | 5 | NHCO | NMe | MeCH(COOMe) |
| 1-2125 | 5 | NHCO | NMe | 1-HOOC-iBu |
| 1-2126 | 5 | NHCO | NMe | 1-MeOOC-iBu |
| 1-2127 | 5 | NHCO | NMe | 1-HOOC-iPn |
| 1-2128 | 5 | NHCO | NMe | 1-MeOOC-iPn |
| 1-2129 | 5 | NHCO | NMe | 1-HOOC-2-Me—Bu |
| 1-2130 | 5 | NHCO | NMe | 1-MeOOC-2-Me—Bu |
| 1-2131 | 5 | NHCO | NMe | CH$_2$CH$_2$SO$_3$H |
| 1-2132 | 5 | NHCO | NMe | OH |
| 1-2133 | 5 | NHCO | NMe | MeO |
| 1-2134 | 5 | NHCO | NMe | EtO |
| 1-2135 | 5 | NHCO | NMe | PrO |
| 1-2136 | 5 | NHCO | NMe | iPrO |
| 1-2137 | 5 | NHCO | NMe | BuO |
| 1-2138 | 5 | NHCO | NMe | iBuO |
| 1-2139 | 5 | NHCO | NMe | sBuO |
| 1-2140 | 5 | NHCO | NMe | tBuO |
| 1-2141 | 5 | NHCO | NMe | HxO |
| 1-2142 | 5 | NHCO | NMe | PhO |
| 1-2143 | 5 | NHCO | NMe | BzO |
| 1-2144 | 5 | NHCO | NMe | Z-1 |
| 1-2145 | 5 | NHCO | NMe | Z-2 |
| 1-2146 | 5 | NHCO | NMe | Z-3 |
| 1-2147 | 5 | NHCO | NMe | Z-4 |
| 1-2148 | 5 | NHCO | NMe | Z-5 |
| 1-2149 | 5 | NHCO | NMe | Z-6 |
| 1-2150 | 5 | NHCO | NMe | Z-7 |
| 1-2151 | 5 | NHCO | NMe | Z-8 |
| 1-2152 | 5 | NHCO | NMe | Z-9 |
| 1-2153 | 5 | NHCO | NMe | Z-10 |
| 1-2154 | 5 | NHCO | NMe | Z-11 |
| 1-2155 | 5 | NHCO | NMe | Z-12 |

TABLE 1-continued

| Cpd. No. | k | A | B | R¹ |
|---|---|---|---|---|
| 1-2156 | 5 | NHCO | NMe | 3-Py |
| 1-2157 | 5 | NHCO | NMe | 4-Py |
| 1-2158 | 5 | NHCO | NHNH | H |
| 1-2159 | 5 | NHCO | NHNH | Me |
| 1-2160 | 5 | NHCO | NHNH | Et |
| 1-2161 | 5 | NHCO | NHNMe | Me |
| 1-2162 | 5 | NHCO | NHNMe | Et |
| 1-2163 | 5 | NHCO | NHNMe | Pr |
| 1-2164 | 5 | NHCONHNHCO | NH | H |
| 1-2165 | 5 | NHCONHNHCO | NH | Ph |
| 1-2166 | 5 | NHCONHNHCO | NH | 2-Me—Ph |
| 1-2167 | 5 | NHCONHNHCO | NH | 4-Me—Ph |
| 1-2168 | 5 | NHCONHNHCO | NH | 2,4-diMe—Ph |
| 1-2169 | 5 | NHCONHNHCO | NH | 3,4-diMe—Ph |
| 1-2170 | 5 | NHCONHNHCO | NH | 2-($CF_3$)Ph |
| 1-2171 | 5 | NHCONHNHCO | NH | 4-($CF_3$)Ph |
| 1-2172 | 5 | NHCONHNHCO | NH | 2-MeOPh |
| 1-2173 | 5 | NHCONHNHCO | NH | 4-MeOPh |
| 1-2174 | 5 | NHCONHNHCO | NH | 2-EtOPh |
| 1-2175 | 5 | NHCONHNHCO | NH | 4-EtOPh |
| 1-2176 | 5 | NHCONHNHCO | NH | 2-HOPh |
| 1-2177 | 5 | NHCONHNHCO | NH | 4-HOPh |
| 1-2178 | 5 | NHCONHNHCO | NH | 2-(HOOC)Ph |
| 1-2179 | 5 | NHCONHNHCO | NH | 4-(HOOC)Ph |
| 1-2180 | 5 | NHCONHNHCO | NH | 2-(MeOOC)Ph |
| 1-2181 | 5 | NHCONHNHCO | NH | 4-(MeOOC)Ph |
| 1-2182 | 5 | NHCONHNHCO | NH | 2-(EtOOC)Ph |
| 1-2183 | 5 | NHCONHNHCO | NH | 4-(EtOOC)Ph |
| 1-2184 | 5 | NHCONHNHCO | NH | 2-(tBuOOC)Ph |
| 1-2185 | 5 | NHCONHNHCO | NH | 4-(tBuOOC)Ph |
| 1-2186 | 5 | NHCONHNHCO | NH | 2-Cl—Ph |
| 1-2187 | 5 | NHCONHNHCO | NH | 4-Cl—Ph |
| 1-2188 | 5 | NHCONHNHCO | NH | 2-Br—Ph |
| 1-2189 | 5 | NHCONHNHCO | NH | 4-Br—Ph |
| 1-2190 | 5 | NHCONHNHCO | NH | 2-I—Ph |
| 1-2191 | 5 | NHCONHNHCO | NH | 4-I—Ph |
| 1-2192 | 5 | NHCONHNHCO | NH | 2-$NO_2$—Ph |
| 1-2193 | 5 | NHCONHNHCO | NH | 4-$NO_2$—Ph |
| 1-2194 | 5 | NHCONHNHCO | NH | 2-$NH_2$—Ph |
| 1-2195 | 5 | NHCONHNHCO | NH | 4-$NH_2$—Ph |
| 1-2196 | 5 | NHCONHNHCO | NH | 2-($HO_3S$)Ph |
| 1-2197 | 5 | NHCONHNHCO | NH | 4-($HO_3S$)Ph |
| 1-2198 | 5 | NHCONHNHCO | NH | 2-($NH_2O_2S$)Ph |
| 1-2199 | 5 | NHCONHNHCO | NH | 4-($NH_2O_2S$)Ph |
| 1-2200 | 5 | NHCONHNHCO | NH | 2-CN—Ph |
| 1-2201 | 5 | NHCONHNHCO | NH | 4-CN—Ph |
| 1-2202 | 5 | NHCONHNHCO | NH | 2-($HOCH_2$)Ph |
| 1-2203 | 5 | NHCONHNHCO | NH | 4-($HOCH_2$)Ph |
| 1-2204 | 5 | NHCONHNHCO | NH | Me |
| 1-2205 | 5 | NHCONHNHCO | NH | Et |
| 1-2206 | 5 | NHCONHNHCO | NH | Pr |
| 1-2207 | 5 | NHCONHNHCO | NH | iPr |
| 1-2208 | 5 | NHCONHNHCO | NH | Bu |
| 1-2209 | 5 | NHCONHNHCO | NH | HOOC$CH_2$— |
| 1-2210 | 5 | NHCONHNHCO | NH | MeOOC$CH_2$— |
| 1-2211 | 5 | NHCONHNHCO | NH | MeCH(COOH) |
| 1-2212 | 5 | NHCONHNHCO | NH | HOOC—($CH_2$)$_2$— |
| 1-2213 | 5 | NHCONHNHCO | NH | MeCH(COOMe) |
| 1-2214 | 5 | NHCONHNHCO | NH | 1-HOOC-iBu |
| 1-2215 | 5 | NHCONHNHCO | NH | 1-MeOOC-iBu |
| 1-2216 | 5 | NHCONHNHCO | NH | 1-HOOC-iPn |
| 1-2217 | 5 | NHCONHNHCO | NH | 1-MeOOC-iPn |
| 1-2218 | 5 | NHCONHNHCO | NH | 1-HOOC-2-Me—Bu |
| 1-2219 | 5 | NHCONHNHCO | NH | 1-MeOOC-2-Me—Bu |
| 1-2220 | 5 | NHCONHNHCO | NH | $CH_2CH_2SO_3H$ |
| 1-2221 | 5 | NHCONHNHCO | NH | OH |
| 1-2222 | 5 | NHCONHNHCO | NH | MeO |
| 1-2223 | 5 | NHCONHNHCO | NH | EtO |
| 1-2224 | 5 | NHCONHNHCO | NH | PrO |
| 1-2225 | 5 | NHCONHNHCO | NH | iPrO |
| 1-2226 | 5 | NHCONHNHCO | NH | BuO |
| 1-2227 | 5 | NHCONHNHCO | NH | iBuO |
| 1-2228 | 5 | NHCONHNHCO | NH | sBuO |
| 1-2229 | 5 | NHCONHNHCO | NH | tBuO |
| 1-2230 | 5 | NHCONHNHCO | NH | HxO |
| 1-2231 | 5 | NHCONHNHCO | NH | PhO |

TABLE 1-continued

| Cpd. No. | k | A | B | R¹ |
|---|---|---|---|---|
| 1-2232 | 5 | NHCONHNHCO | NH | BzO |
| 1-2233 | 5 | NHCONHNHCO | NH | Z-1 |
| 1-2234 | 5 | NHCONHNHCO | NH | Z-2 |
| 1-2235 | 5 | NHCONHNHCO | NH | Z-3 |
| 1-2236 | 5 | NHCONHNHCO | NH | Z-4 |
| 1-2237 | 5 | NHCONHNHCO | NH | Z-5 |
| 1-2238 | 5 | NHCONHNHCO | NH | Z-6 |
| 1-2239 | 5 | NHCONHNHCO | NH | Z-7 |
| 1-2240 | 5 | NHCONHNHCO | NH | Z-8 |
| 1-2241 | 5 | NHCONHNHCO | NH | Z-9 |
| 1-2242 | 5 | NHCONHNHCO | NH | Z-10 |
| 1-2243 | 5 | NHCONHNHCO | NH | Z-11 |
| 1-2244 | 5 | NHCONHNHCO | NH | Z-12 |
| 1-2245 | 5 | NHCONHNHCO | NH | 3-Py |
| 1-2246 | 5 | NHCONHNHCO | NH | 4-Py |
| 1-2247 | 5 | NHCONHCO | — | H |
| 1-2248 | 5 | NHCONHCO | — | Ph |
| 1-2249 | 5 | NHCONHCO | — | 2-Me—Ph |
| 1-2250 | 5 | NHCONHCO | — | 4-Me—Ph |
| 1-2251 | 5 | NHCONHCO | — | 2,4-diMe—Ph |
| 1-2252 | 5 | NHCONHCO | — | 3,4-diMe—Ph |
| 1-2253 | 5 | NHCONHCO | — | 2-(CF$_3$)Ph |
| 1-2254 | 5 | NHCONHCO | — | 4-(CF$_3$)Ph |
| 1-2255 | 5 | NHCONHCO | — | 2-MeOPh |
| 1-2256 | 5 | NHCONHCO | — | 4-MeOPh |
| 1-2257 | 5 | NHCONHCO | — | 2-EtOPh |
| 1-2258 | 5 | NHCONHCO | — | 4-EtOPh |
| 1-2259 | 5 | NHCONHCO | — | 2-HOPh |
| 1-2260 | 5 | NHCONHCO | — | 4-HOPh |
| 1-2261 | 5 | NHCONHCO | — | 2-(HOOC)Ph |
| 1-2262 | 5 | NHCONHCO | — | 4-(HOOC)Ph |
| 1-2263 | 5 | NHCONHCO | — | 2-(MeOOC)Ph |
| 1-2264 | 5 | NHCONHCO | — | 4-(MeOOC)Ph |
| 1-2265 | 5 | NHCONHCO | — | 2-(EtOOC)Ph |
| 1-2266 | 5 | NHCONHCO | — | 4-(EtOOC)Ph |
| 1-2267 | 5 | NHCONHCO | — | 2-(tBuOOC)Ph |
| 1-2268 | 5 | NHCONHCO | — | 4-(tBuOOC)Ph |
| 1-2269 | 5 | NHCONHCO | — | 2-Cl—Ph |
| 1-2270 | 5 | NHCONHCO | — | 4-Cl—Ph |
| 1-2271 | 5 | NHCONHCO | — | 2-Br—Ph |
| 1-2272 | 5 | NHCONHCO | — | 4-Br—Ph |
| 1-2273 | 5 | NHCONHCO | — | 2-I—Ph |
| 1-2274 | 5 | NHCONHCO | — | 4-I—Ph |
| 1-2275 | 5 | NHCONHCO | — | 2-NO$_2$—Ph |
| 1-2276 | 5 | NHCONHCO | — | 4-NO$_2$—Ph |
| 1-2277 | 5 | NHCONHCO | — | 2-NH$_2$—Ph |
| 1-2278 | 5 | NHCONHCO | — | 4-NH$_2$—Ph |
| 1-2279 | 5 | NHCONHCO | — | 2-(HO$_3$S)Ph |
| 1-2280 | 5 | NHCONHCO | — | 4-(HO$_3$S)Ph |
| 1-2281 | 5 | NHCONHCO | — | 2-(NH$_2$O$_2$S)Ph |
| 1-2282 | 5 | NHCONHCO | — | 4-(NH$_2$O$_2$S)Ph |
| 1-2283 | 5 | NHCONHCO | — | 2-CN—Ph |
| 1-2284 | 5 | NHCONHCO | — | 4-CN—Ph |
| 1-2285 | 5 | NHCONHCO | — | 2-(HOCH$_2$)Ph |
| 1-2286 | 5 | NHCONHCO | — | 4-(HOCH$_2$)Ph |
| 1-2287 | 5 | NHCONHCO | — | Me |
| 1-2288 | 5 | NHCONHCO | — | Et |
| 1-2289 | 5 | NHCONHCO | — | Pr |
| 1-2290 | 5 | NHCONHCO | — | iPr |
| 1-2291 | 5 | NHCONHCO | — | Bu |
| 1-2292 | 5 | NHCONHCO | — | HOOCCH$_2$— |
| 1-2293 | 5 | NHCONHCO | — | MeOOCCH$_2$— |
| 1-2294 | 5 | NHCONHCO | — | MeCH(COOH) |
| 1-2295 | 5 | NHCONHCO | — | HOOC—(CH$_2$)$_2$— |
| 1-2296 | 5 | NHCONHCO | — | MeCH(COOMe) |
| 1-2297 | 5 | NHCONHCO | — | 1-HOOC-iBu |
| 1-2298 | 5 | NHCONHCO | — | 1-MeOOC-iBu |
| 1-2299 | 5 | NHCONHCO | — | 1-HOOC-iPn |
| 1-2300 | 5 | NHCONHCO | — | 1-MeOOC-iPn |
| 1-2301 | 5 | NHCONHCO | — | 1-HOOC-2-Me—Bu |
| 1-2302 | 5 | NHCONHCO | — | 1-MeOOC-2-Me—Bu |
| 1-2303 | 5 | NHCONHCO | — | CH$_2$CH$_2$SO$_3$H |
| 1-2304 | 5 | NHCONHCO | — | MeO |
| 1-2305 | 5 | NHCONHCO | — | EtO |
| 1-2306 | 5 | NHCONHCO | — | PrO |
| 1-2307 | 5 | NHCONHCO | — | iPrO |

TABLE 1-continued

| Cpd. No. | k | A | B | R¹ |
|---|---|---|---|---|
| 1-2308 | 5 | NHCONHCO | — | BuO |
| 1-2309 | 5 | NHCONHCO | — | iBuO |
| 1-2310 | 5 | NHCONHCO | — | sBuO |
| 1-2311 | 5 | NHCONHCO | — | tBuO |
| 1-2312 | 5 | NHCONHCO | — | HxO |
| 1-2313 | 5 | NHCONHCO | — | PhO |
| 1-2314 | 5 | NHCONHCO | — | BzO |
| 1-2315 | 5 | NHCONHCO | — | Z-1 |
| 1-2316 | 5 | NHCONHCO | — | Z-2 |
| 1-2317 | 5 | NHCONHCO | — | Z-3 |
| 1-2318 | 5 | NHCONHCO | — | Z-4 |
| 1-2319 | 5 | NHCONHCO | — | Z-5 |
| 1-2320 | 5 | NHCONHCO | — | Z-6 |
| 1-2321 | 5 | NHCONHCO | — | Z-7 |
| 1-2322 | 5 | NHCONHCO | — | Z-8 |
| 1-2323 | 5 | NHCONHCO | — | Z-9 |
| 1-2324 | 5 | NHCONHCO | — | Z-10 |
| 1-2325 | 5 | NHCONHCO | — | Z-11 |
| 1-2326 | 5 | NHCONHCO | — | Z-12 |
| 1-2327 | 5 | NHCONHCO | — | 3-Py |
| 1-2328 | 5 | NHCONHCO | — | 4-Py |
| 1-2329 | 5 | NHCONHSO$_2$ | — | H |
| 1-2330 | 5 | NHCONHSO$_2$ | — | Ph |
| 1-2331 | 5 | NHCONHSO$_2$ | — | 2-Me—Ph |
| 1-2332 | 5 | NHCONHSO$_2$ | — | 4-Me—Ph |
| 1-2333 | 5 | NHCONHSO$_2$ | — | 2,4-diMe—Ph |
| 1-2334 | 5 | NHCONHSO$_2$ | — | 3,4-diMe—Ph |
| 1-2335 | 5 | NHCONHSO$_2$ | — | 2-(CF$_3$)Ph |
| 1-2336 | 5 | NHCONHSO$_2$ | — | 4-(CF$_3$)Ph |
| 1-2337 | 5 | NHCONHSO$_2$ | — | 2-MeOPh |
| 1-2338 | 5 | NHCONHSO$_2$ | — | 4-MeOPh |
| 1-2339 | 5 | NHCONHSO$_2$ | — | 2-EtOPh |
| 1-2340 | 5 | NHCONHSO$_2$ | — | 4-EtOPh |
| 1-2341 | 5 | NHCONHSO$_2$ | — | 2-HOPh |
| 1-2342 | 5 | NHCONHSO$_2$ | — | 4-HOPh |
| 1-2343 | 5 | NHCONHSO$_2$ | — | 2-(HOOC)Ph |
| 1-2344 | 5 | NHCONHSO$_2$ | — | 4-(HOOC)Ph |
| 1-2345 | 5 | NHCONHSO$_2$ | — | 2-(MeOOC)Ph |
| 1-2346 | 5 | NHCONHSO$_2$ | — | 4-(MeOOC)Ph |
| 1-2347 | 5 | NHCONHSO$_2$ | — | 2-(EtOOC)Ph |
| 1-2348 | 5 | NHCONHSO$_2$ | — | 4-(EtOOC)Ph |
| 1-2349 | 5 | NHCONHSO$_2$ | — | 2-(tBuOOC)Ph |
| 1-2350 | 5 | NHCONHSO$_2$ | — | 4-(tBuOOC)Ph |
| 1-2351 | 5 | NHCONHSO$_2$ | — | 2-Cl—Ph |
| 1-2352 | 5 | NHCONHSO$_2$ | — | 4-Cl—Ph |
| 1-2353 | 5 | NHCONHSO$_2$ | — | 2-Br—Ph |
| 1-2354 | 5 | NHCONHSO$_2$ | — | 4-Br—Ph |
| 1-2355 | 5 | NHCONHSO$_2$ | — | 2-I—Ph |
| 1-2356 | 5 | NHCONHSO$_2$ | — | 4-I—Ph |
| 1-2357 | 5 | NHCONHSO$_2$ | — | 2-NO$_2$—Ph |
| 1-2358 | 5 | NHCONHSO$_2$ | — | 4-NO$_2$—Ph |
| 1-2359 | 5 | NHCONHSO$_2$ | — | 2-NH$_2$—Ph |
| 1-2360 | 5 | NHCONHSO$_2$ | — | 4-NH$_2$—Ph |
| 1-2361 | 5 | NHCONHSO$_2$ | — | 2-(HO$_3$S)Ph |
| 1-2362 | 5 | NHCONHSO$_2$ | — | 4-(HO$_3$S)Ph |
| 1-2363 | 5 | NHCONHSO$_2$ | — | 2-(NH$_2$O$_2$S)Ph |
| 1-2364 | 5 | NHCONHSO$_2$ | — | 4-(NH$_2$O$_2$S)Ph |
| 1-2365 | 5 | NHCONHSO$_2$ | — | 2-CN—Ph |
| 1-2366 | 5 | NHCONHSO$_2$ | — | 4-CN—Ph |
| 1-2367 | 5 | NHCONHSO$_2$ | — | 2-(HOCH$_2$)Ph |
| 1-2368 | 5 | NHCONHSO$_2$ | — | 4-(HOCH$_2$)Ph |
| 1-2369 | 5 | NHCONHSO$_2$ | — | Me |
| 1-2370 | 5 | NHCONHSO$_2$ | — | Et |
| 1-2371 | 5 | NHCONHSO$_2$ | — | Pr |
| 1-2372 | 5 | NHCONHSO$_2$ | — | iPr |
| 1-2373 | 5 | NHCONHSO$_2$ | — | Bu |
| 1-2374 | 5 | NHCONHSO$_2$ | — | HOOCCH$_2$ |
| 1-2375 | 5 | NHCONHSO$_2$ | — | MeOOCCH$_2$ |
| 1-2376 | 5 | NHCONHSO$_2$ | — | MeCH(COOH) |
| 1-2377 | 5 | NHCONHSO$_2$ | — | HOOC—(CH$_2$)$_2$ |
| 1-2378 | 5 | NHCONHSO$_2$ | — | MeCH(COOMe) |
| 1-2379 | 5 | NHCONHSO$_2$ | — | 1-HOOC-iBu |
| 1-2380 | 5 | NHCONHSO$_2$ | — | 1-MeOOC-iBu |
| 1-2381 | 5 | NHCONHSO$_2$ | — | 1-HOOC-iPn |
| 1-2382 | 5 | NHCONHSO$_2$ | — | 1-MeOOC-iPn |
| 1-2383 | 5 | NHCONHSO$_2$ | — | 1-HOOC-2-Me—Bu |

TABLE 1-continued

| Cpd. No. | k | A | B | R[1] |
|---|---|---|---|---|
| 1-2384 | 5 | NHCONHSO$_2$ | — | 1-MeOOC-2-Me—Bu |
| 1-2385 | 5 | NHCONHSO$_2$ | — | CH$_2$CH$_2$SO$_3$H |
| 1-2386 | 5 | NHCONHSO$_2$ | — | OH |
| 1-2387 | 5 | NHCONHSO$_2$ | — | MeO |
| 1-2388 | 5 | NHCONHSO$_2$ | — | EtO |
| 1-2389 | 5 | NHCONHSO$_2$ | — | PrO |
| 1-2390 | 5 | NHCONHSO$_2$ | — | iPrO |
| 1-2391 | 5 | NHCONHSO$_2$ | — | BuO |
| 1-2392 | 5 | NHCONHSO$_2$ | — | iBuO |
| 1-2393 | 5 | NHCONHSO$_2$ | — | sBuO |
| 1-2394 | 5 | NHCONHSO$_2$ | — | tBuO |
| 1-2395 | 5 | NHCONHSO$_2$ | — | HxO |
| 1-2396 | 5 | NHCONHSO$_2$ | — | PhO |
| 1-2397 | 5 | NHCONHSO$_2$ | — | BzO |
| 1-2398 | 5 | NHCONHSO$_2$ | — | Z-1 |
| 1-2399 | 5 | NHCONHSO$_2$ | — | Z-2 |
| 1-2400 | 5 | NHCONHSO$_2$ | — | Z-3 |
| 1-2401 | 5 | NHCONHSO$_2$ | — | Z-4 |
| 1-2402 | 5 | NHCONHSO$_2$ | — | Z-5 |
| 1-2403 | 5 | NHCONHSO$_2$ | — | Z-6 |
| 1-2404 | 5 | NHCONHSO$_2$ | — | Z-7 |
| 1-2405 | 5 | NHCONHSO$_2$ | — | Z-8 |
| 1-2406 | 5 | NHCONHSO$_2$ | — | Z-9 |
| 1-2407 | 5 | NHCONHSO$_2$ | — | Z-10 |
| 1-2408 | 5 | NHCONHSO$_2$ | — | Z-11 |
| 1-2409 | 5 | NHCONHSO$_2$ | — | Z-12 |
| 1-2410 | 5 | NHCONHSO$_2$ | — | 3-Py |
| 1-2411 | 5 | NHCONHSO$_2$ | — | 4-Py |
| 1-2412 | 5 | NHCONHSO$_2$ | NH | H |
| 1-2413 | 5 | NHCONHSO$_2$ | NH | Me |
| 1-2414 | 5 | NHCONHSO$_2$ | NH | Et |
| 1-2415 | 5 | NHCONHSO$_2$ | NH | Pr |
| 1-2416 | 5 | NHCONHSO$_2$ | NH | iPr |
| 1-2417 | 5 | NHCONHSO$_2$ | NH | Bu |
| 1-2418 | 5 | NHCONHSO$_2$ | NMe | Me |
| 1-2419 | 5 | NHCONHSO$_2$ | NMe | Et |
| 1-2420 | 5 | NHCONHSO$_2$ | NMe | Pr |
| 1-2421 | 5 | NHCONHSO$_2$ | NMe | iPr |
| 1-2422 | 5 | NHCONHSO$_2$ | NMe | Bu |
| 1-2423 | 5 | — | NH | H |
| 1-2424 | 5 | — | NH | Me |
| 1-2425 | 5 | — | NH | Et |
| 1-2426 | 5 | — | NH | Pr |
| 1-2427 | 5 | — | NH | iPr |
| 1-2428 | 5 | — | NH | Bu |
| 1-2429 | 5 | CO | | Pyr |
| 1-2430 | 5 | CO | | Pipri |
| 1-2431 | 5 | CO | | Pipra |
| 1-2432 | 5 | CO | | Mor |
| 1-2433 | 5 | CO | | Thmor |
| 1-2434 | 5 | CO | | NHPyr |
| 1-2435 | 5 | CO | | NHPipri |
| 1-2436 | 5 | CO | | NHPipra |
| 1-2437 | 5 | CO | | NHMor |
| 1-2438 | 5 | CO | | NHThmor |
| 1-2439 | 5 | NHCO | | Pyr |
| 1-2440 | 5 | NHCO | | Pipri |
| 1-2441 | 5 | NHCO | | Pipra |
| 1-2442 | 5 | NHCO | | Mor |
| 1-2443 | 5 | NHCO | | Thmor |
| 1-2444 | 5 | NHCO | | NHPyr |
| 1-2445 | 5 | NHCO | | NHPipri |
| 1-2446 | 5 | NHCO | | NHPipra |
| 1-2447 | 5 | NHCO | | NHMor |
| 1-2448 | 5 | NHCO | | NHThmor |
| 1-2449 | 5 | CONHCO | | Pyr |
| 1-2450 | 5 | CONHCO | | Pipri |
| 1-2451 | 5 | CONHCO | | Pipra |
| 1-2452 | 5 | CONHCO | | Mor |
| 1-2453 | 5 | CONHCO | | Thmor |
| 1-2454 | 5 | CONHCO | | NHPyr |
| 1-2455 | 5 | CONHCO | | NHPipri |
| 1-2456 | 5 | CONHCO | | NHPipra |
| 1-2457 | 5 | CONHCO | | NHMor |
| 1-2458 | 5 | CONHCO | | NHThmor |
| 1-2459 | 5 | CONHSO$_2$ | | Pyr |

TABLE 1-continued

| Cpd. No. | k | A | B | R¹ |
|---|---|---|---|---|
| 1-2460 | 5 | CONHSO$_2$ | | Pipri |
| 1-2461 | 5 | CONHSO$_2$ | | Pipra |
| 1-2462 | 5 | CONHSO$_2$ | | Mor |
| 1-2463 | 5 | CONHSO$_2$ | | Thmor |
| 1-2464 | 5 | CONHSO$_2$ | | NHPyr |
| 1-2465 | 5 | CONHSO$_2$ | | NHPipri |
| 1-2466 | 5 | CONHSO$_2$ | | NHPipra |
| 1-2467 | 5 | CONHSO$_2$ | | NHMor |
| 1-2468 | 5 | CONHSO$_2$ | | NHThmor |
| 1-2469 | 5 | NHSO$_2$ | NH | Z-4 |
| 1-2470 | 5 | NHSO$_2$ | — | Me |
| 1-2471 | 5 | NHSO$_2$ | — | Et |
| 1-2472 | 5 | NHSO$_2$ | — | Pr |
| 1-2473 | 5 | NHSO$_2$ | — | CH$_2$Cl |
| 1-2474 | 5 | NHSO$_2$ | — | Ph |
| 1-2475 | 5 | NHSO$_2$ | — | 4-Me—Ph |
| 1-2476 | 5 | CO | NMe | Ph |
| 1-2477 | 5 | CO | NMe | 2-Me—PH |
| 1-2478 | 5 | CO | NMe | 4-Me—Ph |
| 1-2479 | 5 | CO | NMe | 2,4-diMe—Ph |
| 1-2480 | 5 | CO | NMe | 3,4-diMe—Ph |
| 1-2481 | 5 | CO | NMe | 2-(CF$_3$)Ph |
| 1-2482 | 5 | CO | NMe | 4-(CF$_3$)Ph |
| 1-2483 | 5 | CO | NMe | 2-MeOPh |
| 1-2484 | 5 | CO | NMe | 4-MeOPh |
| 1-2485 | 5 | CO | NMe | 2-EtOPh |
| 1-2486 | 5 | CO | NMe | 4-EtOPh |
| 1-2487 | 5 | CO | NMe | 2-HOPh |
| 1-2488 | 5 | CO | NMe | 4-HOPh |
| 1-2489 | 5 | CO | NMe | 2-(HOOC)Ph |
| 1-2490 | 5 | CO | NMe | 4-(HOOC)Ph |
| 1-2491 | 5 | CO | NMe | 2-(MeOOC)Ph |
| 1-2492 | 5 | CO | NMe | 4-(MeOOC)Ph |
| 1-2493 | 5 | CO | NMe | 2-(EtOOC)Ph |
| 1-2494 | 5 | CO | NMe | 4-(EtOOC)Ph |
| 1-2495 | 5 | CO | NMe | 2-(tBuOOC)Ph |
| 1-2496 | 5 | CO | NMe | 4-(tBuOOC)Ph |
| 1-2497 | 5 | CO | NMe | 2-Cl—Ph |
| 1-2498 | 5 | CO | NMe | 4-Cl—Ph |
| 1-2499 | 5 | CO | NMe | 2-Br—Ph |
| 1-2500 | 5 | CO | NMe | 4-Br—Ph |
| 1-2501 | 5 | CO | NMe | 2-I—Ph |
| 1-2502 | 5 | CO | NMe | 4-I—Ph |
| 1-2503 | 5 | CO | NMe | 2-NO$_2$—Ph |
| 1-2504 | 5 | CO | NMe | 4-NO$_2$—Ph |
| 1-2505 | 5 | CO | NMe | 2-NH$_2$—Ph |
| 1-2506 | 5 | CO | NMe | 4-NH$_2$—Ph |
| 1-2507 | 5 | CO | NMe | 2-(HO$_3$S)Ph |
| 1-2508 | 5 | CO | NMe | 4-(HO$_3$S)Ph |
| 1-2509 | 5 | CO | NMe | 2-(NH$_2$O$_2$S)Ph |
| 1-2510 | 5 | CO | NMe | 4-(NH$_2$O$_2$S)Ph |
| 1-2511 | 5 | CO | NMe | 2-CN—Ph |
| 1-2512 | 5 | CO | NMe | 4-CN—Ph |
| 1-2513 | 5 | CO | NMe | 2-(HOCH$_2$)Ph |
| 1-2514 | 5 | CO | NMe | 4-(HOCH$_2$)Ph |
| 1-2515 | 5 | CO | NMe | Me |
| 1-2516 | 5 | CO | NMe | Et |
| 1-2517 | 5 | CO | NMe | Pr |
| 1-2518 | 5 | CO | NMe | iPr |
| 1-2519 | 5 | CO | NMe | Bu |
| 1-2520 | 5 | CO | NMe | HOOCCH$_2$ |
| 1-2521 | 5 | CO | NMe | HOOC—(CH$_2$)$_2$ |
| 1-2522 | 5 | CO | NMe | MeCH(COOH) |
| 1-2523 | 5 | CO | NMe | HOOC—(CH$_2$)$_3$— |
| 1-2524 | 5 | CO | NMe | MeCH(COOMe) |
| 1-2525 | 5 | CO | NMe | 1-HOOC-iBu |
| 1-2526 | 5 | CO | NMe | 1-MeOOC-iBu |
| 1-2527 | 5 | CO | NMe | 1-HOOC-iPn |
| 1-2528 | 5 | CO | NMe | 1-MeOCC-iPn |
| 1-2529 | 5 | CO | NMe | 1-HOOC-2-Me—Bu |
| 1-2530 | 5 | CO | NMe | 1-MeOOC-2-Me—Bu |
| 1-2531 | 5 | CO | NMe | CH$_2$CH$_2$SO$_3$H |
| 1-2532 | 5 | CO | NMe | OH |
| 1-2533 | 5 | CO | NMe | MeO |
| 1-2534 | 5 | CO | NMe | EtO |
| 1-2535 | 5 | CO | NMe | PrO |

TABLE 1-continued

| Cpd. No. | k | A | B | R¹ |
|---|---|---|---|---|
| 1-2536 | 5 | CO | NMe | iPrO |
| 1-2537 | 5 | CO | NMe | BuO |
| 1-2538 | 5 | CO | NMe | iBuO |
| 1-2539 | 5 | CO | NMe | sBuO |
| 1-2540 | 5 | CO | NMe | tBuO |
| 1-2541 | 5 | CO | NMe | HxO |
| 1-2542 | 5 | CO | NMe | PhO |
| 1-2543 | 5 | CO | NMe | BzO |
| 1-2544 | 5 | CO | NMe | Z-1 |
| 1-2545 | 5 | CO | NMe | Z-2 |
| 1-2546 | 5 | CO | NMe | Z-3 |
| 1-2547 | 5 | CO | NMe | Z-4 |
| 1-2548 | 5 | CO | NMe | Z-5 |
| 1-2549 | 5 | CO | NMe | Z-6 |
| 1-2550 | 5 | CO | NMe | Z-7 |
| 1-2551 | 5 | CO | NMe | Z-8 |
| 1-2552 | 5 | CO | NMe | Z-9 |
| 1-2553 | 5 | CO | NMe | Z-10 |
| 1-2554 | 5 | CO | NMe | Z-11 |
| 1-2555 | 5 | CO | NMe | Z-12 |
| 1-2556 | 5 | CO | NMe | 3-Py |
| 1-2557 | 5 | CO | NMe | 4-Py |
| 1-2558 | 5 | CO | | Thiad |
| 1-2559 | 5 | CO | | NHThiad |
| 1-2560 | 5 | NHCO | | Thiad |
| 1-2561 | 5 | NHCO | | NHThiad |
| 1-2562 | 5 | CONHCO | | Thiad |
| 1-2563 | 5 | CONHCO | | NHThiad |
| 1-2564 | 5 | CONHSO₂ | | Thiad |
| 1-2565 | 5 | CONHSO₂ | | NHThiad |
| 1-2566 | 5 | NHCS | NH | H |
| 1-2567 | 5 | NHCS | NH | Me |
| 1-2568 | 5 | NHCS | NH | Et |
| 1-2569 | 5 | NHCS | NH | Ph |
| 1-2570 | 5 | NHCS | NH | HOOCCH₂ |
| 1-2571 | 5 | NHCS | NH | MeOOCCH₂ |
| 1-2572 | 5 | NHCS | NH | MeCH(COOH) |
| 1-2573 | 5 | NHCS | NH | HOOC—(CH₂)₂ |
| 1-2574 | 5 | NHCS | NH | MeCH(COOMe) |
| 1-2575 | 5 | CO | NH | HOOC—(CH₂)₃— |
| 1-2576 | 5 | NHCO | NH | HOOC—(CH₂)₃— |
| 1-2577 | 5 | NHCO | — | HOOC—(CH₂)₃— |
| 1-2578 | 5 | NHCS | NH | HOOC—(CH₂)₃— |
| 1-2579 | 5 | CO | NH | MeSO₂NHCOCH(Me) |
| 1-2580 | 5 | NHCO | NH | MeSO₂NHCOCH(Me) |
| 1-2581 | 5 | NHCO | — | MeSO₂NHCOCH(Me) |
| 1-2582 | 5 | NHCS | NH | MeSO₂NHCOCH(Me) |
| 1-2583 | 5 | — | NH | HOOCCH₂ |
| 1-2584 | 5 | — | NH | MeOOCCH₂ |
| 1-2585 | 5 | — | NH | MeCH(COOH) |
| 1-2586 | 5 | — | NH | HOOC—(CH₂)₂ |
| 1-2587 | 5 | — | NH | MeCH(COOMe) |
| 1-2588 | 5 | — | NH | HOOC—(CH₂)₃— |
| 1-2589 | 5 | NHCOCO | — | OH |
| 1-2590 | 5 | NHCOCO | — | MeO |
| 1-2591 | 5 | NHCOCO | — | EtO |
| 1-2592 | 5 | NHCOCO | — | PrO |
| 1-2593 | 5 | NHCOCO | — | iPrO |
| 1-2594 | 5 | NHCOCO | — | BuO |
| 1-2595 | 5 | NHCOCO | — | iBuO |
| 1-2596 | 5 | NHCOCO | — | sBuO |
| 1-2597 | 5 | NHCOCO | — | tBuO |
| 1-2598 | 5 | NHCOCO | — | HxO |
| 1-2599 | 5 | NHCOCO | — | PhO |
| 1-2600 | 5 | NHCOCO | — | BzO |
| 1-2601 | 0 | — | | 1,3-diox-IInd |
| 1-2602 | 1 | — | | 1,3-diox-IInd |
| 1-2603 | 2 | — | | 1,3-diox-IInd |
| 1-2604 | 3 | — | | 1,3-diox-IInd |
| 1-2605 | 4 | — | | 1,3-diox-IInd |
| 1-2606 | 5 | — | | 1,3-diox-IInd |
| 1-2607 | 6 | — | | 1,3-diox-IInd |
| 1-2608 | 7 | — | | 1,3-diox-IInd |
| 1-2609 | 8 | — | | 1,3-diox-IInd |
| 1-2610 | 9 | — | | 1,3-diox-IInd |
| 1-2611 | 10 | — | | 1,3-diox-IInd |

TABLE 1-continued

| Cpd. No. | k | A | B | R¹ |
|---|---|---|---|---|
| 1-2612 | 11 | — | | 1,3-diox-IInd |
| 1-2613 | 12 | — | | 1,3-diox-IInd |
| 1-2614 | 4 | NHCONHSO₂NHCO | NH | Z-4 |
| 1-2615 | 4 | NHCONHSO₂NHCO | NH | Pn |
| 1-2616 | 2 | O | — | H |
| 1-2617 | 4 | O | — | H |
| 1-2618 | 5 | O | — | H |
| 1-2619 | 5 | O | — | Ph |
| 1-2620 | 5 | O | — | 2-Py |
| 1-2621 | 5 | O | — | 3-Py |
| 1-2622 | 5 | O | — | 4-Py |
| 1-2623 | 5 | O | — | Z-1 |
| 1-2624 | 5 | O | — | Z-2 |
| 1-2625 | 5 | O | — | Z-3 |
| 1-2626 | 5 | O | — | Z-4 |
| 1-2627 | 5 | O | — | Z-5 |
| 1-2628 | 5 | O | — | Z-6 |
| 1-2629 | 5 | O | — | Z-7 |
| 1-2630 | 5 | O | — | Z-8 |
| 1-2631 | 5 | O | — | Z-9 |
| 1-2632 | 5 | O | — | Z-10 |
| 1-2633 | 5 | O | — | Z-11 |
| 1-2634 | 5 | O | — | Z-12 |
| 1-2635 | 4 | NHCO | — | 3-Py |
| 1-2636 | 5 | NHCO | — | 3-Py |
| 1-2637 | 4 | CO | NH | HOCH₂CH(CH₃)CH₂ |
| 1-2638 | 5 | CO | NH | HOCH₂CH(CH₃)CH₂ |
| 1-2639 | 4 | NHCO | NH | HOCH₂CH(CH₃)CH₂ |
| 1-2640 | 5 | NHCO | NH | HOCH₂CH(CH₃)CH₂ |
| 1-2641 | 4 | CO | NH | MeSO₂NHCOCH₂ |
| 1-2642 | 5 | CO | NH | MeSO₂NHCOCH₂ |
| 1-2643 | 4 | NHCO | NH | MeSO₂NHCOCH₂ |
| 1-2644 | 5 | NHCO | NH | MeSO₂NHCOCH₂ |
| 1-2645 | 4 | CO | NH | H₂NSO₂NHCOCH₂ |
| 1-2646 | 5 | CO | NH | H₂NSO₂NHCOCH₂ |
| 1-2647 | 4 | NHCO | NH | H₂NSO₂NHCOCH₂ |
| 1-2648 | 5 | NHCO | NH | H₂NSO₂NHCOCH₂ |
| 1-2649 | 4 | CO | NH | 1-(MeSO₂NHCO)—Et |
| 1-2650 | 5 | CO | NH | 1-(MeSO₂NHCO)—Et |
| 1-2651 | 4 | NHCO | NH | 1-(MeSO₂NHCO)—Et |
| 1-2652 | 5 | NHCO | NH | 1-(MeSO₂NHCO)—Et |
| 1-2653 | 4 | CO | NH | 1-(H₂NSO₂NHCO)—Et |
| 1-2654 | 5 | CO | NH | 1-(H₂NSO₂NHCO)—Et |
| 1-2655 | 4 | NHCO | NH | 1-(H₂NSO₂NHCO)—Et |
| 1-2656 | 5 | NHCO | NH | 1-(H₂NSO₂NHCO)—Et |
| 1-2657 | 4 | CO | NH | HOOC—(CH₂)₄ |
| 1-2658 | 5 | CO | NH | HOOC—(CH₂)₄ |
| 1-2659 | 4 | NHCO | NH | HOOC—(CH₂)₄ |
| 1-2660 | 5 | NHCO | NH | HOOC—(CH₂)₄ |
| 1-2661 | 4 | CO | NH | HO—(CH₂)₂ |
| 1-2662 | 5 | CO | NH | HO—(CH₂)₂ |
| 1-2663 | 4 | NHCO | NH | HO—(CH₂)₂ |
| 1-2664 | 5 | NHCO | NH | HO—(CH₂)₂ |
| 1-2665 | 4 | CO | NH | HO—CH₂—CH(CH₃) |
| 1-2666 | 5 | CO | NH | HO—CH₂—CH(CH₃) |
| 1-2667 | 4 | NHCO | NH | HO—CH₂—CH(CH₃) |
| 1-2668 | 5 | NHCO | NH | HO—CH₂—CH(CH₃) |
| 1-2669 | 4 | CO | NMe | HOOC—(CH₂)₃ |
| 1-2670 | 4 | NHCO | NMe | HOOC—(CH₂)₃ |
| 1-2671 | 5 | NHCO | NMe | HOOC—(CH₂)₃ |
| 1-2672 | 4 | CONMeSO₂ | — | Me |
| 1-2673 | 5 | CONMeSO₂ | — | Me |
| 1-2674 | 4 | CO | | 1-Indn |
| 1-2675 | 5 | CO | | 1-Indn |
| 1-2676 | 4 | NHCO | | 1-Indn |
| 1-2677 | 5 | NHCO | | 1-Indn |
| 1-2678 | 4 | CO | | 2-(HOOC)-1-Indn |
| 1-2679 | 5 | CO | | 2-(HOOC)-1-Indn |
| 1-2680 | 4 | NHCO | | 2-(HOOC)-1-Indn |
| 1-2681 | 5 | NHCO | | 2-(HOOC)-1-Indn |
| 1-2682 | 4 | — | | 3,4-diMe-2,5-diox-1-Imdd |
| 1-2683 | 5 | — | | 3,4-diMe-2,5-diox-1-Imdd |
| 1-2684 | 4 | CONHSO₂ | — | CF₃ |

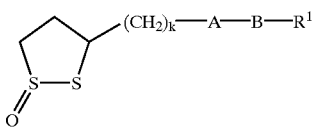

(I-2)

TABLE 2

| Cpd. No. | k | A | B | R¹ |
|---|---|---|---|---|
| 2-1 | 4 | CO | NH | H |
| 2-2 | 4 | CO | NH | Ph |
| 2-3 | 4 | CO | NH | 2-Me-Ph |
| 2-4 | 4 | CO | NH | 4-Me-Ph |
| 2-5 | 4 | CO | NH | 2,4-diMe-Ph |
| 2-6 | 4 | CO | NH | 3,4-diMe-Ph |
| 2-7 | 4 | CO | NH | 2-(CF$_3$)-Ph |
| 2-8 | 4 | CO | NH | 4-(CF$_3$)-Ph |
| 2-9 | 4 | CO | NH | 2-MeOPh |
| 2-10 | 4 | CO | NH | 4-MeOPh |
| 2-11 | 4 | CO | NH | 2-EtOPh |
| 2-12 | 4 | CO | NH | 4-EtOPh |
| 2-13 | 4 | CO | NH | 2-HOPh |
| 2-14 | 4 | CO | NH | 4-HOPh |
| 2-15 | 4 | CO | NH | 2-(HOOC)-Ph |
| 2-16 | 4 | CO | NH | 4-(HOOC)-Ph |
| 2-17 | 4 | CO | NH | 2-(MeOOC)-Ph |
| 2-18 | 4 | CO | NH | 4-(MeOOC)-Ph |
| 2-19 | 4 | CO | NH | 2-(EtOOC)-Ph |
| 2-20 | 4 | CO | NH | 4-(EtOOC)-Ph |
| 2-21 | 4 | CO | NH | 2-(tBuOOC)-Ph |
| 2-22 | 4 | CO | NH | 4-(tBuOOC)-Ph |
| 2-23 | 4 | CO | NH | 2-Cl-Ph |
| 2-24 | 4 | CO | NH | 4-Cl-Ph |
| 2-25 | 4 | CO | NH | 2-Br-Ph |
| 2-26 | 4 | CO | NH | 4-Br-Ph |
| 2-27 | 4 | CO | NH | 2-I-Ph |
| 2-28 | 4 | CO | NH | 4-I-Ph |
| 2-29 | 4 | CO | NH | 2-NO$_2$-Ph |
| 2-30 | 4 | CO | NH | 4-NO$_2$-Ph |
| 2-31 | 4 | CO | NH | 2-NH$_2$-Ph |
| 2-32 | 4 | CO | NH | 4-NH$_2$-Ph |
| 2-33 | 4 | CO | NH | 2-(HO$_3$S)-Ph |
| 2-34 | 4 | CO | NH | 4-(HO$_3$S)-Ph |
| 2-35 | 4 | CO | NH | 2-NH$_2$O$_2$S)-Ph |
| 2-36 | 4 | CO | NH | 4-(NH$_2$O$_2$S)-Ph |
| 2-37 | 4 | CO | NH | 2-CN-Ph |
| 2-38 | 4 | CO | NH | 4-CN-Ph |
| 2-39 | 4 | CO | NH | 2-(HOCH$_2$)-Ph |
| 2-40 | 4 | CO | NH | 4-(HOCH$_2$)-Ph |
| 2-41 | 4 | CO | NH | Me |
| 2-42 | 4 | CO | NH | Et |
| 2-43 | 4 | CO | NH | Pr |
| 2-44 | 4 | CO | NH | iPr |
| 2-45 | 4 | CO | NH | Bu |
| 2-46 | 4 | CO | NH | HOOCCH$_2$— |
| 2-47 | 4 | CO | NH | MeOOCCH$_2$— |
| 2-48 | 4 | CO | NH | MeCH(COOH)— |
| 2-49 | 4 | CO | NH | HOOC—(CH$_2$)$_2$— |
| 2-50 | 4 | CO | NH | MeCH(COOMe)— |
| 2-51 | 4 | CO | NH | 1-HOOC-iBu |
| 2-52 | 4 | CO | NH | 1-MeOOC-iBu |
| 2-53 | 4 | CO | NH | 1-HOOC-iPn |
| 2-54 | 4 | CO | NH | 1-MeOOC-iPn |
| 2-55 | 4 | CO | NH | 1-HOOC-2-Me-Bu |
| 2-56 | 4 | CO | NH | 1-MeOOC-2-Me-Bu |
| 2-57 | 4 | CO | NH | CH$_2$CH$_2$SO$_3$H |
| 2-58 | 4 | CO | NH | OH |
| 2-59 | 4 | CO | NH | MeO |
| 2-60 | 4 | CO | NH | EtO |
| 2-61 | 4 | CO | NH | Pro |
| 2-62 | 4 | CO | NH | iPrO |
| 2-63 | 4 | CO | NH | BuO |
| 2-64 | 4 | CO | NH | iBuO |
| 2-65 | 4 | CO | NH | sBuO |
| 2-66 | 4 | CO | NH | tBuO |
| 2-67 | 4 | CO | NH | HxO |
| 2-68 | 4 | CO | NH | PhO |
| 2-69 | 4 | CO | NH | BnO |
| 2-70 | 4 | CO | NH | Z-1 |
| 2-71 | 4 | CO | NH | Z-2 |
| 2-72 | 4 | CO | NH | Z-3 |
| 2-73 | 4 | CO | NH | Z-4 |
| 2-74 | 4 | CO | NH | Z-5 |
| 2-75 | 4 | CO | NH | Z-6 |
| 2-76 | 4 | CO | NH | Z-7 |
| 2-77 | 4 | CO | NH | Z-8 |
| 2-78 | 4 | CO | NH | Z-9 |
| 2-79 | 4 | CO | NH | Z-10 |
| 2-80 | 4 | CO | NH | Z-11 |
| 2-81 | 4 | CO | NH | Z-12 |
| 2-82 | 4 | CO | NH | 3-Py |
| 2-83 | 4 | CO | NH | 4-Py |
| 2-84 | 4 | CO | N(Ac) | H |
| 2-85 | 4 | CO | N(Ac) | Ph |
| 2-86 | 4 | CO | N(Ac) | 2-Me-Ph |
| 2-87 | 4 | CO | N(Ac) | 4-Me-Ph |
| 2-88 | 4 | CO | N(Ac) | 2,4-diMe-Ph |
| 2-89 | 4 | CO | N(Ac) | 3,4-diMe-Ph |
| 2-90 | 4 | CO | N(Ac) | 2-(CF$_3$)-Ph |
| 2-91 | 4 | CO | N(Ac) | 4-(CF$_3$)Ph |
| 2-92 | 4 | CO | N(Ac) | 2-MeOPh |
| 2-93 | 4 | CO | N(Ac) | 4-MeOPh |
| 2-94 | 4 | CO | N(Ac) | 2-EtOPh |
| 2-95 | 4 | CO | N(Ac) | 4-EtOPh |
| 2-96 | 4 | CO | N(Ac) | 2-HOPh |
| 2-97 | 4 | CO | N(Ac) | 4-HOPh |
| 2-98 | 4 | CO | N(Ac) | 2-(HOOC)Ph |
| 2-99 | 4 | CO | N(Ac) | 4-(HOOC)Ph |
| 2-100 | 4 | CO | N(Ac) | 2-(MeOOC)Ph |
| 2-101 | 4 | CO | N(Ac) | 4-(MeOOC)Ph |
| 2-102 | 4 | CO | N(Ac) | 2-(EtOOC)-Ph |
| 2-103 | 4 | CO | N(Ac) | 4-(EtOOC)-Ph |
| 2-104 | 4 | CO | N(Ac) | 2-(tBuOOC)Ph |
| 2-105 | 4 | CO | N(Ac) | 4-(tBuOOC)Ph |
| 2-106 | 4 | CO | N(Ac) | 2-Cl-Ph |
| 2-107 | 4 | CO | N(Ac) | 4-Cl-Ph |
| 2-108 | 4 | CO | N(Ac) | 2-Br-Ph |
| 2-109 | 4 | CO | N(Ac) | 4-Br-Ph |
| 2-110 | 4 | CO | N(Ac) | 2-I-Ph |
| 2-111 | 4 | CO | N(Ac) | 4-I-Ph |
| 2-112 | 4 | CO | N(Ac) | 2-NO$_2$-Ph |
| 2-113 | 4 | CO | N(Ac) | 4-NO$_2$-Ph |
| 2-114 | 4 | CO | N(Ac) | 2-NH$_2$-Ph |
| 2-115 | 4 | CO | N(Ac) | 4-NH$_2$-Ph |
| 2-116 | 4 | CO | N(Ac) | 2-(HO$_3$S)Ph |
| 2-117 | 4 | CO | N(Ac) | 4-(HO$_3$S)Ph |
| 2-118 | 4 | CO | N(Ac) | 2-(NH$_2$O$_2$S)Ph |
| 2-119 | 4 | CO | N(Ac) | 4-(NH$_2$O$_2$S)Ph |
| 2-120 | 4 | CO | N(Ac) | 2-CN-Ph |
| 2-121 | 4 | CO | N(Ac) | 4-CN-Ph |
| 2-122 | 4 | CO | N(Ac) | 2-(HOCH$_2$)Ph |
| 2-123 | 4 | CO | N(Ac) | 4-(HOCH$_2$)Ph |
| 2-124 | 4 | CO | N(Ac) | Me |
| 2-125 | 4 | CO | N(Ac) | Et |
| 2-126 | 4 | CO | N(Ac) | Pr |
| 2-127 | 4 | CO | N(Ac) | iPr |
| 2-128 | 4 | CO | N(Ac) | Bu |
| 2-129 | 4 | CO | N(Ac) | HOOCCH$_2$— |
| 2-130 | 4 | CO | N(Ac) | MeOOCCH$_2$— |
| 2-131 | 4 | CO | N(Ac) | MeCH(COOH) |
| 2-132 | 4 | CO | N(Ac) | HOOC—(CH$_2$)$_2$— |
| 2-133 | 4 | CO | N(Ac) | MeCH(COOMe) |
| 2-134 | 4 | CO | N(Ac) | 1-HOOC-iBu |
| 2-135 | 4 | CO | N(Ac) | 1-MeOOC-iBu |
| 2-136 | 4 | CO | N(Ac) | 1-HOOC-iPn |
| 2-137 | 4 | CO | N(Ac) | 1-MeOOC-iPn |
| 2-138 | 4 | CO | N(Ac) | 1-HOOC-2-Me-Bu |
| 2-139 | 4 | CO | N(Ac) | 1-MeOOC-2-Me-Bu |
| 2-140 | 4 | CO | N(Ac) | CH$_2$CH$_2$SO$_3$H |
| 2-141 | 4 | CO | N(Ac) | OH |

TABLE 2-continued

| Cpd. No. | k | A | B | R¹ |
|---|---|---|---|---|
| 2-142 | 4 | CO | N(Ac) | MeO |
| 2-143 | -4 | CO | N(Ac) | EtO |
| 2-144 | 4 | CO | N(Ac) | PrO |
| 2-145 | 4 | CO | N(Ac) | iPrO |
| 2-146 | 4 | CO | N(Ac) | BuO |
| 2-147 | 4 | CO | N(Ac) | iBuO |
| 2-148 | 4 | CO | N(Ac) | sBuO |
| 2-149 | 4 | CO | N(Ac) | tBuO |
| 2-150 | 4 | CO | N(Ac) | HxO |
| 2-151 | 4 | CO | N(Ac) | PhO |
| 2-152 | 4 | CO | N(Ac) | BnO |
| 2-153 | 4 | CO | N(Ac) | Z-1 |
| 2-154 | 4 | CO | N(Ac) | Z-2 |
| 2-155 | 4 | CO | N(Ac) | Z-3 |
| 2-156 | 4 | CO | N(Ac) | Z-4 |
| 2-157 | 4 | CO | N(Ac) | Z-5 |
| 2-158 | 4 | CO | N(Ac) | Z-6 |
| 2-159 | 4 | CO | N(Ac) | Z-7 |
| 2-160 | 4 | CO | N(Ac) | Z-8 |
| 2-161 | 4 | CO | N(Ac) | Z-9 |
| 2-162 | 4 | CO | N(Ac) | Z-10 |
| 2-163 | 4 | CO | N(Ac) | Z-11 |
| 2-164 | 4 | CO | N(Ac) | Z-12 |
| 2-165 | 4 | CO | N(Ac) | 3-Py |
| 2-166 | 4 | CO | N(Ac) | 4-Py |
| 2-167 | 4 | COO | — | H |
| 2-168 | 4 | COO | — | Ph |
| 2-169 | 4 | COO | — | 2-Me-Ph |
| 2-170 | 4 | COO | — | 4-Me-Ph |
| 2-171 | 4 | COO | — | 2,4-diMe-Ph |
| 2-172 | 4 | COO | — | 3,4-diMe-Ph |
| 2-173 | 4 | COO | — | 2-(CF₃)Ph |
| 2-174 | 4 | COO | — | 4-(CF₃)Ph |
| 2-175 | 4 | COO | — | 2-MeOPh |
| 2-176 | 4 | COO | — | 4-MeOPh |
| 2-177 | 4 | COO | — | 2-EtOPh |
| 2-178 | 4 | COO | — | 4-EtOPh |
| 2-179 | 4 | COO | — | 2-HOPh |
| 2-180 | 4 | COO | — | 4-HOPh |
| 2-181 | 4 | COO | — | 2-(HOOC)Ph |
| 2-182 | 4 | COO | — | 4-(HOOC)Ph |
| 2-183 | 4 | COO | — | 2-(MeOOC)Ph |
| 2-184 | 4 | COO | — | 4-(MeOOC)Ph |
| 2-185 | 4 | COO | — | 2-(EtOOC)Ph |
| 2-186 | 4 | COO | — | 4-(EtOOC)Ph |
| 2-187 | 4 | COO | — | 2-(tBuOOC)Ph |
| 2-188 | 4 | COO | — | 4-(tBuOOC)Ph |
| 2-189 | 4 | COO | — | 2-Cl-Ph |
| 2-190 | 4 | COO | — | 4-Cl-Ph |
| 2-191 | 4 | COO | — | 2-Br-Ph |
| 2-192 | 4 | COO | — | 4-Br-Ph |
| 2-193 | 4 | COO | — | 2-I-Ph |
| 2-194 | 4 | COO | — | 4-I-Ph |
| 2-195 | 4 | COO | — | 2-NO₂-Ph |
| 2-196 | 4 | COO | — | 4-NO₂-Ph |
| 2-197 | 4 | COO | — | 2-NH₂-Ph |
| 2-198 | 4 | COO | — | 4-NH₂-Ph |
| 2-199 | 4 | COO | — | 2-(HO₃S)Ph |
| 2-200 | 4 | COO | — | 4-(HO₃S)Ph |
| 2-201 | 4 | COO | — | 2-(NH₂O₂S)Ph |
| 2-202 | 4 | COO | — | 4-(NH₂O₂S)Ph |
| 2-203 | 4 | COO | — | 2-CN-Ph |
| 2-204 | 4 | COO | — | 4-CN-Ph |
| 2-205 | 4 | COO | — | 2-(HOCH₂)Ph |
| 2-206 | 4 | COO | — | 4-(HOCH₂)Ph |
| 2-207 | 4 | COO | — | Me |
| 2-208 | 4 | COO | — | Et |
| 2-209 | 4 | COO | — | Pr |
| 2-210 | 4 | COO | — | iPr |
| 2-211 | 4 | COO | — | Bu |
| 2-212 | 4 | COO | — | HOOCCH₂— |
| 2-213 | 4 | COO | — | HOOC—(CH₂)₂— |
| 2-214 | 4 | COO | — | MeCH(COOMe) |
| 2-215 | 4 | COO | — | 1-HOOC-iBu |
| 2-216 | 4 | COO | — | 1-HOOC-iPn |
| 2-217 | 4 | COO | — | Z-1 |
| 2-218 | 4 | COO | — | Z-2 |
| 2-219 | 4 | COO | — | Z-3 |
| 2-220 | 4 | COO | — | Z-4 |
| 2-221 | 4 | COO | — | Z-5 |
| 2-222 | 4 | COO | — | Z-6 |
| 2-223 | 4 | COO | — | Z-7 |
| 2-224 | 4 | COO | — | Z-8 |
| 2-225 | 4 | COO | — | Z-9 |
| 2-226 | 4 | COO | — | Z-10 |
| 2-227 | 4 | COO | — | Z-11 |
| 2-228 | 4 | COO | — | Z-12 |
| 2-229 | 4 | COO | — | 3-Py |
| 2-230 | 4 | COO | — | 4-Py |
| 2-231 | 4 | CONHCO | — | H |
| 2-232 | 4 | CONHCO | — | Ph |
| 2-233 | 4 | CONHCO | — | 2-Me-Ph |
| 2-234 | 4 | CONHCO | — | 4-Me-Ph |
| 2-235 | 4 | CONHCO | — | 2,4-diMe-Ph |
| 2-236 | 4 | CONHCO | — | 3,4-diMe-Ph |
| 2-237 | 4 | CONHCO | — | 2-(CF₃)Ph |
| 2-238 | 4 | CONHCO | — | 4-(CF₃)Ph |
| 2-239 | 4 | CONHCO | — | 2-MeOPh |
| 2-240 | 4 | CONHCO | — | 4-MeOPh |
| 2-241 | 4 | CONHCO | — | 2-EtOPh |
| 2-242 | 4 | CONHCO | — | 4-EtOPh |
| 2-243 | 4 | CONHCO | — | 2-HOPh |
| 2-244 | 4 | CONHCO | — | 4-HOPh |
| 2-245 | 4 | CONHCO | — | 2-(HOOC)Ph |
| 2-246 | 4 | CONHCO | — | 4-(HOOC)Ph |
| 2-247 | 4 | CONHCO | — | 2-(MeOOC)Ph |
| 2-248 | 4 | CONHCO | — | 4-(MeOOC)Ph |
| 2-249 | 4 | CONHCO | — | 2-(EtOOC)Ph |
| 2-250 | 4 | CONHCO | — | 4-(EtOOC)Ph |
| 2-251 | 4 | CONHCO | — | 2-(tBuOOC)Ph |
| 2-252 | 4 | CONHCO | — | 4-(tBuOOC)Ph |
| 2-253 | 4 | CONHCO | — | 2-Cl-Ph |
| 2-254 | 4 | CONHCO | — | 4-Cl-Ph |
| 2-255 | 4 | CONHCO | — | 2-Br-Ph |
| 2-256 | 4 | CONHCO | — | 4-Br-Ph |
| 2-257 | 4 | CONHCO | — | 2-I-Ph |
| 2-258 | 4 | CONHCO | — | 4-I-Ph |
| 2-259 | 4 | CONHCO | — | 2-NO₂-Ph |
| 2-260 | 4 | CONHCO | — | 4-NO₂-Ph |
| 2-261 | 4 | CONHCO | — | 2-NH₂-Ph |
| 2-262 | 4 | CONHCO | — | 4-NH₂-Ph |
| 2-263 | 4 | CONHCO | — | 2-(HO₃S)Ph |
| 2-264 | 4 | CONHCO | — | 4-(HO₃S)Ph |
| 2-265 | 4 | CONHCO | — | 2-(NH₂O₂S)Ph |
| 2-266 | 4 | CONHCO | — | 4-(NH₂O₂S)Ph |
| 2-267 | 4 | CONHCO | — | 2-CN-Ph |
| 2-268 | 4 | CONHCO | — | 4-CN-Ph |
| 2-269 | 4 | CONHCO | — | 2-(HOCH₂)Ph |
| 2-270 | 4 | CONHCO | — | 4-(HOCH₂)Ph |
| 2-271 | 4 | CONHCO | — | Me |
| 2-272 | 4 | CONHCO | — | Et |
| 2-273 | 4 | CONHCO | — | Pr |
| 2-274 | 4 | CONHCO | — | iPr |
| 2-275 | 4 | CONHCO | — | Bu |
| 2-276 | 4 | CONHCO | — | HOOCCH₂— |
| 2-277 | 4 | CONHCO | — | MeOOCCH₂— |
| 2-278 | 4 | CONHCO | — | MeCH(COOH) |
| 2-279 | 4 | CONHCO | — | HOOC—(CH₂)₂— |
| 2-280 | 4 | CONHCO | — | MeCH(COOMe) |
| 2-281 | 4 | CONHCO | — | 1-HOOC-iBu |
| 2-282 | 4 | CONHCO | — | 1-MeOOC-iBu |
| 2-283 | 4 | CONHCO | — | 1-HOOC-iPn |
| 2-284 | 4 | CONHCO | — | 1-MeOOC-iPn |
| 2-285 | 4 | CONHCO | — | 1-HOOC-2-Me-Bu |
| 2-286 | 4 | CONHCO | — | 1-MeOOC-2-Me-Bu |
| 2-287 | 4 | CONHCO | — | CH₂CH₂SO₃H |
| 2-288 | 4 | CONHCO | — | Z-1 |
| 2-289 | 4 | CONHCO | — | Z-2 |
| 2-290 | 4 | CONHCO | — | Z-3 |
| 2-291 | 4 | CONHCO | — | Z-4 |
| 2-292 | 4 | CONHCO | — | Z-5 |
| 2-293 | 4 | CONHCO | — | Z-6 |

TABLE 2-continued

| Cpd. No. | k | A | B | R¹ |
|---|---|---|---|---|
| 2-294 | 4 | CONHCO | — | Z-7 |
| 2-295 | 4 | CONHCO | — | Z-8 |
| 2-296 | 4 | CONHCO | — | Z-9 |
| 2-297 | 4 | CONHCO | — | Z-10 |
| 2-298 | 4 | CONHCO | — | Z-11 |
| 2-299 | 4 | CONHCO | — | Z-12 |
| 2-300 | 4 | CONHCO | — | 3-Py |
| 2-301 | 4 | CONHCO | — | 4-Py |
| 2-302 | 4 | CON(Ac)CO | — | H |
| 2-303 | 4 | CON(Ac)CO | — | Ph |
| 2-304 | 4 | CON(Ac)CO | — | 2-Me-Ph |
| 2-305 | 4 | CON(Ac)CO | — | 4-Me-Ph |
| 2-306 | 4 | CON(Ac)CO | — | 2,4-diMe-Ph |
| 2-307 | 4 | CON(Ac)CO | — | 3,4-diMe-Ph |
| 2-308 | 4 | CON(Ac)CO | — | 2-(CF$_3$)Ph |
| 2-309 | 4 | CON(Ac)CO | — | 4-(CF$_3$)Ph |
| 2-310 | 4 | CON(Ac)CO | — | 2-MeOPh |
| 2-311 | 4 | CON(Ac)CO | — | 4-MeOPh |
| 2-312 | 4 | CON(Ac)CO | — | 2-EtOPh |
| 2-313 | 4 | CON(Ac)CO | — | 4-EtOPh |
| 2-314 | 4 | CON(Ac)CO | — | 2-HOPh |
| 2-315 | 4 | CON(Ac)CO | — | 4-HOPh |
| 2-316 | 4 | CON(Ac)CO | — | 2-(HOOC)Ph |
| 2-317 | 4 | CON(Ac)CO | — | 4-(HOOC)Ph |
| 2-318 | 4 | CON(Ac)CO | — | 2-(MeOOC)Ph |
| 2-319 | 4 | CON(Ac)CO | — | 4-(MeOOC)Ph |
| 2-320 | 4 | CON(Ac)CO | — | 2-(EtOOC)Ph |
| 2-321 | 4 | CON(Ac)CO | — | 4-(EtOOC)Ph |
| 2-322 | 4 | CON(Ac)CO | — | 2-(tBuOOC)Ph |
| 2-323 | 4 | CON(Ac)CO | — | 4-(tBuOOC)Ph |
| 2-324 | 4 | CON(Ac)CO | — | 2-Cl-Ph |
| 2-325 | 4 | CON(Ac)CO | — | 4-Cl-Ph |
| 2-326 | 4 | CON(Ac)CO | — | 2-Br-Ph |
| 2-327 | 4 | CON(Ac)CO | — | 4-Br-Ph |
| 2-328 | 4 | CON(Ac)CO | — | 2-I-Ph |
| 2-329 | 4 | CON(Ac)CO | — | 4-I-Ph |
| 2-330 | 4 | CON(Ac)CO | — | 2-NO$_2$-Ph |
| 2-331 | 4 | CON(Ac)CO | — | 4-NO$_2$-Ph |
| 2-332 | 4 | CON(Ac)CO | — | 2-NH$_2$-Ph |
| 2-333 | 4 | CON(Ac)CO | — | 4-NH$_2$-Ph |
| 2-334 | 4 | CON(Ac)CO | — | 2-(HO$_3$S)Ph |
| 2-335 | 4 | CON(Ac)CO | — | 4-(HO$_3$S)Ph |
| 2-336 | 4 | CON(Ac)CO | — | 2-(NH$_2$O$_2$S)Ph |
| 2-337 | 4 | CON(Ac)CO | — | 4-(NH$_2$O$_2$S)Ph |
| 2-338 | 4 | CON(Ac)CO | — | 2-CN-Ph |
| 2-339 | 4 | CON(Ac)CO | — | 4-CN-Ph |
| 2-340 | 4 | CON(Ac)CO | — | 2-(HOCH$_2$)Ph |
| 2-341 | 4 | CON(Ac)CO | — | 4-(HOCH$_2$)Ph |
| 2-342 | 4 | CON(Ac)CO | — | Me |
| 2-343 | 4 | CON(Ac)CO | — | Et |
| 2-344 | 4 | CON(Ac)CO | — | Pr |
| 2-345 | 4 | CON(Ac)CO | — | iPr |
| 2-346 | 4 | CON(Ac)CO | — | Bu |
| 2-347 | 4 | CON(Ac)CO | — | HOOCCH$_2$— |
| 2-348 | 4 | CON(Ac)CO | — | MeOOCCH$_2$— |
| 2-349 | 4 | CON(Ac)CO | — | MeCH(COOH) |
| 2-350 | 4 | CON(Ac)CO | — | HOOC—(CH$_2$)$_2$— |
| 2-351 | 4 | CON(Ac)CO | — | MeCH(COOMe) |
| 2-352 | 4 | CON(Ac)CO | — | 1-HOOC-iBu |
| 2-353 | 4 | CON(Ac)CO | — | 1-MeOOC-iBu |
| 2-354 | 4 | CON(Ac)CO | — | 1-HOOC-iPn |
| 2-355 | 4 | CON(Ac)CO | — | l-MeOOC-iPn |
| 2-356 | 4 | CON(Ac)CO | — | 1-HOOC-2-Me-Bu |
| 2-357 | 4 | CON(Ac)CO | — | 1-MeOOC-2-Me-Bu |
| 2-358 | 4 | CON(Ac)CO | — | CH$_2$CH$_2$SO$_3$H |
| 2-359 | 4 | CON(Ac)CO | — | Z-1 |
| 2-360 | 4 | CON(Ac)CO | — | Z-2 |
| 2-361 | 4 | CON(Ac)CO | — | Z-3 |
| 2-362 | 4 | CON(Ac)CO | — | Z-4 |
| 2-363 | 4 | CON(Ac)CO | — | Z-5 |
| 2-364 | 4 | CON(Ac)CO | — | Z-6 |
| 2-365 | 4 | CON(Ac)CO | — | Z-7 |
| 2-366 | 4 | CON(Ac)CO | — | Z-8 |
| 2-367 | 4 | CON(Ac)CO | — | Z-9 |
| 2-368 | 4 | CON(Ac)CO | — | Z-10 |
| 2-369 | 4 | CON(Ac)CO | — | Z-11 |
| 2-370 | 4 | CON(Ac)CO | — | Z-12 |
| 2-371 | 4 | CON(Ac)CO | — | 3-Py |
| 2-372 | 4 | CON(Ac)CO | — | 4-Py |
| 2-373 | 4 | CONHCO | NH | H |
| 2-374 | 4 | CONHCO | NH | Ph |
| 2-375 | 4 | CONHCO | NH | 2-Me-Ph |
| 2-376 | 4 | CONHCO | NH | 4-Me-Ph |
| 2-377 | 4 | CONHCO | NH | 2,4-diMe-Ph |
| 2-378 | 4 | CONHCO | NH | 3,4-diMe-Ph |
| 2-379 | 4 | CONHCO | NH | 2-(CF$_3$)Ph |
| 2-380 | 4 | CONHCO | NH | 4-(CF$_3$)Ph |
| 2-381 | 4 | CONHCO | NH | 2-MeOPh |
| 2-382 | 4 | CONHCO | NH | 4-MeOPh |
| 2-383 | 4 | CONHCO | NH | 2-EtOPh |
| 2-384 | 4 | CONHCO | NH | 4-EtOPh |
| 2-385 | 4 | CONHCO | NH | 2-HOPh |
| 2-386 | 4 | CONHCO | NH | 4-HOPh |
| 2-387 | 4 | CONHCO | NH | 2-(HOOC)Ph |
| 2-388 | 4 | CONHCO | NH | 4-(HOOC)Ph |
| 2-389 | 4 | CONHCO | NH | 2-(MeOOC)Ph |
| 2-390 | 4 | CONHCO | NH | 4-(MeOOC)Ph |
| 2-391 | 4 | CONHCO | NH | 2-(EtOOC)Ph |
| 2-392 | 4 | CONHCO | NH | 4-(EtOOC)Ph |
| 2-393 | 4 | CONHCO | NH | 2-(tBuOOC)Ph |
| 2-394 | 4 | CONHCO | NH | 4-(tBuOOC)Ph |
| 2-395 | 4 | CONHCO | NH | 2-Cl-Ph |
| 2-396 | 4 | CONHCO | NH | 4-Cl-Ph |
| 2-397 | 4 | CONHCO | NH | 2-Br-Ph |
| 2-398 | 4 | CONHCO | NH | 4-Br-Ph |
| 2-399 | 4 | CONHCO | NH | 2-I-Ph |
| 2-400 | 4 | CONHCO | NH | 4-I-Ph |
| 2-401 | 4 | CONHCO | NH | 2-NO$_2$-Ph |
| 2-402 | 4 | CONHCO | NH | 4-NO$_2$-Ph |
| 2-403 | 4 | CONHCO | NH | 2-NH$_2$-Ph |
| 2-404 | 4 | CONHCO | NH | 4-NH$_2$-Ph |
| 2-405 | 4 | CONHCO | NH | 2-(HO$_3$S)Ph |
| 2-406 | 4 | CONHCO | NH | 4-(HO$_3$S)Ph |
| 2-407 | 4 | CONHCO | NH | 2-(NH$_2$O$_2$S)Ph |
| 2-408 | 4 | CONHCO | NH | 4-(NH$_2$O$_2$S)Ph |
| 2-409 | 4 | CONHCO | NH | 2-CN-Ph |
| 2-410 | 4 | CONHCO | NH | 4-CN-Ph |
| 2-411 | 4 | CONHCO | NH | 2-(HOCH$_2$)Ph |
| 2-412 | 4 | CONHCO | NH | 4-(HOCH$_2$)Ph |
| 2-413 | 4 | CONHCO | NH | Me |
| 2-414 | 4 | CONHCO | NH | Et |
| 2-415 | 4 | CONHCO | NH | Pr |
| 2-416 | 4 | CONHCO | NH | iPr |
| 2-417 | 4 | CONHCO | NH | Bu |
| 2-418 | 4 | CONHCO | NH | HOOCCH$_2$— |
| 2-419 | 4 | CONHCO | NH | MeOOCCH$_2$— |
| 2-420 | 4 | CONHCO | NH | MeCH(COOH) |
| 2-421 | 4 | CONHCO | NH | HOOC—(CH$_2$)$_2$— |
| 2-422 | 4 | CONHCO | NH | MeCH(COOMe) |
| 2-423 | 4 | CONHCO | NH | 1-HOOC-iBu |
| 2-424 | 4 | CONHCO | NH | 1-MeOOC-iBu |
| 2-425 | 4 | CONHCO | NH | 1-HOOC-iPn |
| 2-426 | 4 | CONHCO | NH | 1-MeOOC-iPn |
| 2-427 | 4 | CONHCO | NH | 1-HOOC-2-Me-Bu |
| 2-428 | 4 | CONHCO | NH | 1-MeOOC-2-Me-Bu |
| 2-429 | 4 | CONHCO | NH | CH$_2$CH$_2$SO$_3$H |
| 2-430 | 4 | CONHCO | NH | HO |
| 2-431 | 4 | CONHCO | NH | MeO |
| 2-432 | 4 | CONHCO | NH | EtO |
| 2-433 | 4 | CONHCO | NH | PrO |
| 2-434 | 4 | CONHCO | NH | iPrO |
| 2-435 | 4 | CONHCO | NH | BuO |
| 2-436 | 4 | CONHCO | NH | iBuO |
| 2-437 | 4 | CONHCO | NH | sBuO |
| 2-438 | 4 | CONHCO | NH | tBuO |
| 2-439 | 4 | CONHCO | NH | HxO |
| 2-440 | 7 | CONHCO | NH | PhO |
| 2-441 | 4 | CONHCO | NH | BnO |
| 2-442 | 4 | CONHCO | NH | Z-1 |
| 2-443 | 4 | CONHCO | NH | Z-2 |
| 2-444 | 4 | CONHCO | NH | Z-3 |
| 2-445 | 4 | CONHCO | NH | Z-4 |

TABLE 2-continued

| Cpd. No. | k | A | B | R¹ |
|---|---|---|---|---|
| 2-446 | 4 | CONHCO | NH | Z-5 |
| 2-447 | 4 | CONHCO | NH | Z-6 |
| 2-448 | 4 | CONHCO | NH | Z-7 |
| 2-449 | 4 | CONHCO | NH | Z-8 |
| 2-450 | 4 | CONHCO | NH | Z-9 |
| 2-451 | 4 | CONHCO | NH | Z-10 |
| 2-452 | 4 | CONHCO | NH | Z-11 |
| 2-453 | 4 | CONHCO | NH | Z-12 |
| 2-454 | 4 | CONHCO | NH | 3-Py |
| 2-455 | 4 | CONHCO | NH | 4-Py |
| 2-456 | 4 | $CONHSO_2$ | — | H |
| 2-457 | 4 | $CONHSO_2$ | — | Ph |
| 2-458 | 4 | $CONHSO_2$ | — | 2-Me-Ph |
| 2-459 | 4 | $CONHSO_2$ | — | 4-Me-Ph |
| 2-460 | 4 | $CONHSO_2$ | — | 2,4-diMe-Ph |
| 2-461 | 4 | $CONHSO_2$ | — | 3,4-diMe-Ph |
| 2-462 | 4 | $CONHSO_2$ | — | 2-$(CF_3)$Ph |
| 2-463 | 4 | $CONHSO_2$ | — | 4-$(CF_3)$Ph |
| 2-464 | 4 | $CONHSO_2$ | — | 2-MeOPh |
| 2-465 | 4 | $CONHSO_2$ | — | 4-MeOPh |
| 2-466 | 4 | $CONHSO_2$ | — | 2-EtOPh |
| 2-467 | 4 | $CONHSO_2$ | — | 4-EtOPh |
| 2-468 | 4 | $CONHSO_2$ | — | 2-HOPh |
| 2-469 | 4 | $CONHSO_2$ | — | 4-HOPh |
| 2-470 | 4 | $CONHSO_2$ | — | 2-(HOOC)Ph |
| 2-471 | 4 | $CONHSO_2$ | — | 4-(HOOC)Ph |
| 2-472 | 4 | $CONHSO_2$ | — | 2-(MeOOC)Ph |
| 2-473 | 4 | $CONHSO_2$ | — | 4-(MeOOC)Ph |
| 2-474 | 4 | $CONHSO_2$ | — | 2-(EtOOC)Ph |
| 2-475 | 4 | $CONHSO_2$ | — | 4-(EtOOC)Ph |
| 2-476 | 4 | $CONHSO_2$ | — | 2-(tBuOOC)Ph |
| 2-477 | 4 | $CONHSO_2$ | — | 4-(tBuOOC)Ph |
| 2-478 | 4 | $CONHSO_2$ | — | 2-Cl-Ph |
| 2-479 | 4 | $CONHSO_2$ | — | 4-Cl-Ph |
| 2-480 | 4 | $CONHSO_2$ | — | 2-Br-Ph |
| 2-481 | 4 | $CONHSO_2$ | — | 4-Br-Ph |
| 2-482 | 4 | $CONHSO_2$ | — | 2-I-Ph |
| 2-483 | 4 | $CONHSO_2$ | — | 4-I-Ph |
| 2-484 | 4 | $CONHSO_2$ | — | 2-$NO_2$-Ph |
| 2-485 | 4 | $CONHSO_2$ | — | 4-$NO_2$-Ph |
| 2-486 | 4 | $CONHSO_2$ | — | 2-$NH_2$-Ph |
| 2-487 | 4 | $CONHSO_2$ | — | 4-$NH_2$-Ph |
| 2-488 | 4 | $CONHSO_2$ | — | 2-$(HO_3S)$Ph |
| 2-489 | 4 | $CONHSO_2$ | — | 4-$(HO_3S)$Ph |
| 2-490 | 4 | $CONHSO_2$ | — | 2-$(NH_2O_2S)$Ph |
| 2-491 | 4 | $CONHSO_2$ | — | 4-$(NH_2O_2S)$Ph |
| 2-492 | 4 | $CONHSO_2$ | — | 2-CN-Ph |
| 2-493 | 4 | $CONHSO_2$ | — | 4-CN-Ph |
| 2-494 | 4 | $CONHSO_2$ | — | 2-$(HOCH_2)$Ph |
| 2-495 | 4 | $CONHSO_2$ | — | 4-$(HOCH_2)$Ph |
| 2-496 | 4 | $CONHSO_2$ | — | Me |
| 2-497 | 4 | $CONHSO_2$ | — | Et |
| 2-498 | 4 | $CONHSO_2$ | — | Pr |
| 2-499 | 4 | $CONHSO_2$ | — | iPr |
| 2-500 | 4 | $CONHSO_2$ | — | Bu |
| 2-501 | 4 | $CONHSO_2$ | — | $HOOCCH_2$— |
| 2-502 | 4 | $CONHSO_2$ | — | $MeOOCCH_2$— |
| 2-503 | 4 | $CONHSO_2$ | — | MeCH(COOH) |
| 2-504 | 4 | $CONHSO_2$ | — | HOOC—$(CH_2)_2$— |
| 2-505 | 4 | $CONHSO_2$ | — | MeCH(COOMe) |
| 2-506 | 4 | $CONHSO_2$ | — | 1-HOOC-iBu |
| 2-507 | 4 | $CONHSO_2$ | — | 1-MeOOC-iBu |
| 2-508 | 4 | $CONHSO_2$ | — | 1-HOOC-iPn |
| 2-509 | 4 | $CONHSO_2$ | — | 1-MeOOC-iPn |
| 2-510 | 4 | $CONHSO_2$ | — | 1-HOOC-2-Me-Bu |
| 2-511 | 4 | $CONHSO_2$ | — | 1-MeOOC-2-Me-Bu |
| 2-512 | 4 | $CONHSO_2$ | — | $CH_2CH_2SO_3H$ |
| 2-513 | 4 | $CONHSO_2$ | — | OH |
| 2-514 | 4 | $CONHSO_2$ | — | MeO |
| 2-515 | 4 | $CONHSO_2$ | — | EtO |
| 2-516 | 4 | $CONHSO_2$ | — | PrO |
| 2-517 | 4 | $CONHSO_2$ | — | iPrO |
| 2-518 | 4 | $CONHSO_2$ | — | BuO |
| 2-519 | 4 | $CONHSO_2$ | — | iBuO |
| 2-520 | 4 | $CONHSO_2$ | — | sBuO |
| 2-521 | 4 | $CONHSO_2$ | — | tBuO |
| 2-522 | 4 | $CONHSO_2$ | — | HxO |
| 2-523 | 4 | $CONHSO_2$ | — | PhO |
| 2-524 | 4 | $CONHSO_2$ | — | BnO |
| 2-525 | 4 | $CONHSO_2$ | — | Z-1 |
| 2-526 | 4 | $CONHSO_2$ | — | Z-2 |
| 2-527 | 4 | $CONHSO_2$ | — | Z-3 |
| 2-528 | 4 | $CONHSO_2$ | — | Z-4 |
| 2-529 | 4 | $CONHSO_2$ | — | Z-5 |
| 2-530 | 4 | $CONHSO_2$ | — | Z-6 |
| 2-531 | 4 | $CONHSO_2$ | — | Z-7 |
| 2-532 | 4 | $CONHSO_2$ | — | Z-8 |
| 2-533 | 4 | $CONHSO_2$ | — | Z-9 |
| 2-534 | 4 | $CONHSO_2$ | — | Z-10 |
| 2-535 | 4 | $CONHSO_2$ | — | Z-11 |
| 2-536 | 4 | $CONHSO_2$ | — | Z-12 |
| 2-537 | 4 | $CONHSO_2$ | — | 3-Py |
| 2-538 | 4 | $CONHSO_2$ | — | 4-Py |
| 2-539 | 4 | $CONHSO_2$ | NH | H |
| 2-540 | 4 | $CONHSO_2$ | NH | Ph |
| 2-541 | 4 | $CONHSO_2$ | NH | 2-Me-Ph |
| 2-542 | 4 | $CONHSO_2$ | NH | 4-Me-Ph |
| 2-543 | 4 | $CONHSO_2$ | NH | 2,4-diMe-Ph |
| 2-544 | 4 | $CONHSO_2$ | NH | 3,4-diMe-Ph |
| 2-545 | 4 | $CONHSO_2$ | NH | 2-$(CF_3)$Ph |
| 2-546 | 4 | $CONHSO_2$ | NH | 4-$(CF_3)$Ph |
| 2-547 | 4 | $CONHSO_2$ | NH | 2-MeOPh |
| 2-548 | 4 | $CONHSO_2$ | NH | 4-MeOPh |
| 2-549 | 4 | $CONHSO_2$ | NH | 2-EtOPh |
| 2-550 | 4 | $CONHSO_2$ | NH | 4-EtOPh |
| 2-551 | 4 | $CONHSO_2$ | NH | 2-HOPh |
| 2-552 | 4 | $CONHSO_2$ | NH | 4-HOPh |
| 2-553 | 4 | $CONHSO_2$ | NH | 2-(HOOC)Ph |
| 2-554 | 4 | $CONHSO_2$ | NH | 4-(HOOC)Ph |
| 2-555 | 4 | $CONHSO_2$ | NH | 2-(MeOOC)Ph |
| 2-556 | 4 | $CONHSO_2$ | NH | 4-(MeOOC)Ph |
| 2-557 | 4 | $CONHSO_2$ | NH | 2-(EtOOC)Ph |
| 2-558 | 4 | $CONHSO_2$ | NH | 4-(EtOOC)Ph |
| 2-559 | 4 | $CONHSO_2$ | NH | 2-(tBuOOC)Ph |
| 2-560 | 4 | $CONHSO_2$ | NH | 4-(tBuOOC)Ph |
| 2-561 | 4 | $CONHSO_2$ | NH | 2-Cl-Ph |
| 2-562 | 4 | $CONHSO_2$ | NH | 4-Cl-Ph |
| 2-563 | 4 | $CONHSO_2$ | NH | 2-Br-Ph |
| 2-564 | 4 | $CONHSO_2$ | NH | 4-Br-Ph |
| 2-565 | 4 | $CONHSO_2$ | NH | 2-I-Ph |
| 2-566 | 4 | $CONHSO_2$ | NH | 4-I-Ph |
| 2-567 | 4 | $CONHSO_2$ | NH | 2-$NO_2$-Ph |
| 2-568 | 4 | $CONHSO_2$ | NH | 4-$NO_2$-Ph |
| 2-569 | 4 | $CONHSO_2$ | NH | 2-$NH_2$-Ph |
| 2-570 | 4 | $CONHSO_2$ | NH | 4-$NH_2$-Ph |
| 2-571 | 4 | $CONHSO_2$ | NH | 2-$(HO_3S)$Ph |
| 2-572 | 4 | $CONHSO_2$ | NH | 4-$(HO_3S)$Ph |
| 2-573 | 4 | $CONHSO_2$ | NH | 2-$(NH_2O_2S)$Ph |
| 2-574 | 4 | $CONHSO_2$ | NH | 4-$(NH_2O_2S)$Ph |
| 2-575 | 4 | $CONHSO_2$ | NH | 2-CN-Ph |
| 2-576 | 4 | $CONHSO_2$ | NH | 4-CN-Ph |
| 2-577 | 4 | $CONHSO_2$ | NH | 2-$(HOCH_2)$Ph |
| 2-578 | 4 | $CONHSO_2$ | NH | 4-$(HOCH_2)$Ph |
| 2-579 | 4 | $CONHSO_2$ | NH | Me |
| 2-580 | 4 | $CONHSO_2$ | NH | Et |
| 2-581 | 4 | $CONHSO_2$ | NH | Pr |
| 2-582 | 4 | $CONHSO_2$ | NH | iPr |
| 2-583 | 4 | $CONHSO_2$ | NH | Bu |
| 2-584 | 4 | $CONHSO_2$ | NH | $HOOCCH_2$— |
| 2-585 | 4 | $CONHSO_2$ | NH | $MeOOCCH_2$— |
| 2-586 | 4 | $CONHSO_2$ | NH | MeCH(COOH) |
| 2-587 | 4 | $CONHSO_2$ | NH | HOOC—$(CH_2)_2$— |
| 2-588 | 4 | $CONHSO_2$ | NH | MeCH(COOMe) |
| 2-589 | 4 | $CONHSO_2$ | NH | 1-HOOC-iBu |
| 2-590 | 4 | $CONHSO_2$ | NH | 1-MeOOC-iBu |
| 2-591 | 4 | $CONHSO_2$ | NH | 1-HOOC-iPn |
| 2-592 | 4 | $CONHSO_2$ | NH | 1-MeOOC-iPn |
| 2-593 | 4 | $CONHSO_2$ | NH | 1-HOOC-2-Me-Bu |
| 2-594 | 4 | $CONHSO_2$ | NH | 1-MeOOC-2-Me-Bu |
| 2-595 | 4 | $CONHSO_2$ | NH | $CH_2CH_2SO_3H$ |
| 2-596 | 4 | $CONHSO_2$ | NH | OH |
| 2-597 | 4 | $CONHSO_2$ | NH | MeO |

TABLE 2-continued

| Cpd. No. | k | A | B | R¹ |
|---|---|---|---|---|
| 2-598 | 4 | CONHSO$_2$ | NH | EtO |
| 2-599 | 4 | CONHSO$_2$ | NH | PrO |
| 2-600 | 4 | CONHSO$_2$ | NH | iPrO |
| 2-601 | 4 | CONHSO$_2$ | NH | BuO |
| 2-602 | 4 | CONHSO$_2$ | NH | iBuO |
| 2-603 | 4 | CONHSO$_2$ | NH | sBuO |
| 2-604 | 4 | CONHSO$_2$ | NH | tBuO |
| 2-605 | 4 | CONHSO$_2$ | NH | HxO |
| 2-606 | 4 | CONHSO$_2$ | NH | PhO |
| 2-607 | 4 | CONHSO$_2$ | NH | BnO |
| 2-608 | 4 | CONHSO$_2$ | NH | Z-1 |
| 2-609 | 4 | CONHSO$_2$ | NH | Z-2 |
| 2-610 | 4 | CONHSO$_2$ | NH | Z-3 |
| 2-611 | 4 | CONHSO$_2$ | NH | Z-4 |
| 2-612 | 4 | CONHSO$_2$ | NH | Z-5 |
| 2-613 | 4 | CONHSO$_2$ | NH | Z-6 |
| 2-614 | 4 | CONHSO$_2$ | NH | Z-7 |
| 2-615 | 4 | CONHSO$_2$ | NH | Z-8 |
| 2-616 | 4 | CONHSO$_2$ | NH | Z-9 |
| 2-617 | 4 | CONHSO$_2$ | NH | Z-10 |
| 2-618 | 4 | CONHSO$_2$ | NH | Z-11 |
| 2-619 | 4 | CONHSO$_2$ | NH | Z-12 |
| 2-620 | 4 | CONHSO$_2$ | NH | 3-Py |
| 2-621 | 4 | CONHSO$_2$ | NH | 4-Py |
| 2-622 | 4 | NHCO | — | H |
| 2-623 | 4 | NHCO | — | Ph |
| 2-624 | 4 | NHCO | — | 2-Me-Ph |
| 2-625 | 4 | NHCO | — | 4-Me-Ph |
| 2-626 | 4 | NHCO | — | 2,4-diMe-Ph |
| 2-627 | 4 | NHCO | — | 3,4-diMe-Ph |
| 2-628 | 4 | NHCO | — | 2-(CF$_3$)Ph |
| 2-629 | 4 | NHCO | — | 4-(CF$_3$)Ph |
| 2-630 | 4 | NHCO | — | 2-MeOPh |
| 2-631 | 4 | NHCO | — | 4-MeOPh |
| 2-632 | 4 | NHCO | — | 2-EtOPh |
| 2-633 | 4 | NHCO | — | 4-EtOPh |
| 2-634 | 4 | NHCO | — | 2-HOPh |
| 2-635 | 4 | NHCO | — | 4-HOPh |
| 2-636 | 4 | NHCO | — | 2-(HOOC)Ph |
| 2-637 | 4 | NHCO | — | 4-(HOOC)Ph |
| 2-638 | 4 | NHCO | — | 2-(MeOOC)Ph |
| 2-639 | 4 | NHCO | — | 4-(MeOOC)Ph |
| 2-640 | 4 | NHCO | — | 2-(EtOOC)Ph |
| 2-641 | 4 | NHCO | — | 4-(EtOOC)Ph |
| 2-642 | 4 | NHCO | — | 2-(tBuOOC)Ph |
| 2-643 | 4 | NHCO | — | 4-(tBuOOC)Ph |
| 2-644 | 4 | NHCO | — | 2-Cl-Ph |
| 2-645 | 4 | NHCO | — | 4-Cl-Ph |
| 2-646 | 4 | NHCO | — | 2-Br-Ph |
| 2-647 | 4 | NHCO | — | 4-Br-Ph |
| 2-648 | 4 | NHCO | — | 2-I-Ph |
| 2-649 | 4 | NHCO | — | 4-I-Ph |
| 2-650 | 4 | NHCO | — | 2-NO$_2$-Ph |
| 2-651 | 4 | NHCO | — | 4-NO$_2$-Ph |
| 2-652 | 4 | NHCO | — | 2-NH$_2$-Ph |
| 2-653 | 4 | NHCO | — | 4-NH$_2$-Ph |
| 2-654 | 4 | NHCO | — | 2-(HO$_3$S)Ph |
| 2-655 | 4 | NHCO | — | 4-(HO$_3$S)Ph |
| 2-656 | 4 | NHCO | — | 2-(NH$_2$O$_2$S)Ph |
| 2-657 | 4 | NHCO | — | 4-(NH$_2$O$_2$S)Ph |
| 2-658 | 4 | NHCO | — | 2-CN-Ph |
| 2-659 | 4 | NHCO | — | 4-CN-Ph |
| 2-660 | 4 | NHCO | — | 2-(HOCH$_2$)Ph |
| 2-661 | 4 | NHCO | — | 4-(HOCH$_2$)Ph |
| 2-662 | 4 | NHCO | — | Me |
| 2-663 | 4 | NHCO | — | Et |
| 2-664 | 4 | NHCO | — | Pr |
| 2-665 | 4 | NHCO | — | iPr |
| 2-666 | 4 | NHCO | — | Bu |
| 2-667 | 4 | NHCO | — | HOOCCH$_2$— |
| 2-668 | 4 | NHCO | — | MeOOCCH$_2$— |
| 2-669 | 4 | NHCO | — | MeCH(COOH) |
| 2-670 | 4 | NHCO | — | HOOC—(CH$_2$)$_2$— |
| 2-671 | 4 | NHCO | — | MeCH(COOMe) |
| 2-672 | 4 | NHCO | — | 1-HOOC-iBu |
| 2-673 | 4 | NHCO | — | 1-HOOC-iPn |
| 2-674 | 4 | NHCO | — | 1-HOOC-2-Me-Bu |
| 2-675 | 4 | NHCO | — | CH$_2$CH$_2$SO$_3$H |
| 2-676 | 4 | NHCO | — | MeO |
| 2-677 | 4 | NHCO | — | EtO |
| 2-678 | 4 | NHCO | — | PrO |
| 2-679 | 4 | NHCO | — | Z-1 |
| 2-680 | 4 | NHCO | — | Z-2 |
| 2-681 | 4 | NHCO | — | Z-3 |
| 2-682 | 4 | NHCO | — | Z-4 |
| 2-683 | 4 | NHCO | — | Z-5 |
| 2-684 | 4 | NHCO | — | Z-6 |
| 2-685 | 4 | NHCO | — | Z-7 |
| 2-686 | 4 | NHCO | — | Z-8 |
| 2-687 | 4 | NHCO | — | Z-9 |
| 2-688 | 4 | NHCO | — | Z-10 |
| 2-689 | 4 | NHCO | — | Z-11 |
| 2-690 | 4 | NHCO | — | Z-12 |
| 2-691 | 4 | NHCO | — | 3-Py |
| 2-692 | 4 | NHCO | — | 4-Py |
| 2-693 | 4 | NHCO | NH | H |
| 2-694 | 4 | NHCO | NH | Ph |
| 2-695 | 4 | NHCO | NH | 2-Me-Ph |
| 2-696 | 4 | NHCO | NH | 4-Me-Ph |
| 2-697 | 4 | NHCO | NH | 2,4-diMe-Ph |
| 2-698 | 4 | NHCO | NH | 3,4-diMe-Ph |
| 2-699 | 4 | NHCO | NH | 2-(CF$_3$)Ph |
| 2-700 | 4 | NHCO | NH | 4-(CF$_3$)Ph |
| 2-701 | 4 | NHCO | NH | 2-MeOPh |
| 2-702 | 4 | NHCO | NH | 4-MeOPh |
| 2-703 | 4 | NHCO | NH | 2-EtOPh |
| 2-704 | 4 | NHCO | NH | 4-EtOPh |
| 2-705 | 4 | NHCO | NH | 2-HOPh |
| 2-706 | 4 | NHCO | NH | 4-HOPh |
| 2-707 | 4 | NHCO | NH | 2-(HOOC)Ph |
| 2-708 | 4 | NHCO | NH | 4-(HOOC)Ph |
| 2-709 | 4 | NHCO | NH | 2-(MeOOC)Ph |
| 2-710 | 4 | NHCO | NH | 4-(MeOOC)Ph |
| 2-711 | 4 | NHCO | NH | 2-(EtOOC)Ph |
| 2-712 | 4 | NHCO | NH | 4-(EtOOC)Ph |
| 2-713 | 4 | NHCO | NH | 2-(tBuOOC)Ph |
| 2-714 | 4 | NHCO | NH | 4-(tBuOOC)Ph |
| 2-715 | 4 | NHCO | NH | 2-Cl-Ph |
| 2-716 | 4 | NHCO | NH | 4-Cl-Ph |
| 2-717 | 4 | NHCO | NH | 2-Br-Ph |
| 2-718 | 4 | NHCO | NH | 4-Br-Ph |
| 2-719 | 4 | NHCO | NH | 2-I-Ph |
| 2-720 | 4 | NHCO | NH | 4-I-Ph |
| 2-721 | 4 | NHCO | NH | 2-NO$_2$-Ph |
| 2-722 | 4 | NHCO | NH | 4-NO$_2$-Ph |
| 2-723 | 4 | NHCO | NH | 2-NH$_2$-Ph |
| 2-724 | 4 | NHCO | NH | 4-NH$_2$-Ph |
| 2-725 | 4 | NHCO | NH | 2-(HO$_3$S)Ph |
| 2-726 | 4 | NHCO | NH | 4-(HO$_3$S)Ph |
| 2-727 | 4 | NHCO | NH | 2-(NH$_2$O$_2$S)Ph |
| 2-728 | 4 | NHCO | NH | 4-(NH$_2$O$_2$S)Ph |
| 2-729 | 4 | NHCO | NH | 2-CN-Ph |
| 2-730 | 4 | NHCO | NH | 4-CN-Ph |
| 2-731 | 4 | NHCO | NH | 2-(HOCH$_2$)Ph |
| 2-732 | 4 | NHCO | NH | 4-(HOCH$_2$)Ph |
| 2-733 | 4 | NHCO | NH | Me |
| 2-734 | 4 | NHCO | NH | Et |
| 2-735 | 4 | NHCO | NH | Pr |
| 2-736 | 4 | NHCO | NH | iPr |
| 2-737 | 4 | NHCO | NH | Bu |
| 2-738 | 4 | NHCO | NH | HOOCCH$_2$— |
| 2-739 | 4 | NHCO | NH | MeOOCCH$_2$— |
| 2-740 | 4 | NHCO | NH | MeCH(COOH) |
| 2-741 | 4 | NHCO | NH | HOOC—(CH$_2$)$_2$— |
| 2-742 | 4 | NHCO | NH | MeCH(COOMe) |
| 2-743 | 4 | NHCO | NH | 1-HOOC-iBu |
| 2-744 | 4 | NHCO | NH | 1-MeOOC-iBu |
| 2-745 | 4 | NHCO | NH | 1-HOOC-iPn |
| 2-746 | 4 | NHCO | NH | 1-MeOOC-iPn |
| 2-747 | 4 | NHCO | NH | 1-HOOC-2-Me-Bu |
| 2-748 | 4 | NHCO | NH | 1-MeOOC-2-Me-Bu |
| 2-749 | 4 | NHCO | NH | CH$_2$CH$_2$SO$_3$H |

TABLE 2-continued

| Cpd. No. | k | A | B | R¹ |
|---|---|---|---|---|
| 2-750 | 4 | NHCO | NH | OH |
| 2-751 | 4 | NHCO | NH | MeO |
| 2-752 | 4 | NHCO | NH | EtO |
| 2-753 | 4 | NHCO | NH | PrO |
| 2-754 | 4 | NHCO | NH | iPrO |
| 2-755 | 4 | NHCO | NH | BuO |
| 2-756 | 4 | NHCO | NH | iBuO |
| 2-757 | 4 | NHCO | NH | sBuO |
| 2-758 | 4 | NHCO | NH | tBuO |
| 2-759 | 4 | NHCO | NH | HxO |
| 2-760 | 4 | NHCO | NH | PhO |
| 2-761 | 4 | NHCO | NH | BnO |
| 2-762 | 4 | NHCO | NH | Z-1 |
| 2-763 | 4 | NHCO | NH | Z-2 |
| 2-764 | 4 | NHCO | NH | Z-3 |
| 2-765 | 4 | NHCO | NH | Z-4 |
| 2-766 | 4 | NHCO | NH | Z-5 |
| 2-767 | 4 | NHCO | NH | Z-6 |
| 2-768 | 4 | NHCO | NH | Z-7 |
| 2-769 | 4 | NHCO | NH | Z-8 |
| 2-770 | 4 | NHCO | NH | Z-9 |
| 2-771 | 4 | NHCO | NH | Z-10 |
| 2-772 | 4 | NHCO | NH | Z-11 |
| 2-773 | 4 | NHCO | NH | Z-12 |
| 2-774 | 4 | NHCO | NH | 3-Py |
| 2-775 | 4 | NHCO | NH | 4-Py |
| 2-776 | 4 | NHCO | NMe | Ph |
| 2-777 | 4 | NHCO | NMe | 2-Me-Ph |
| 2-778 | 4 | NHCO | NMe | 4-Me-Ph |
| 2-779 | 4 | NHCO | NMe | 2,4-diMe-Ph |
| 2-780 | 4 | NHCO | NMe | 3,4-diMe-Ph |
| 2-781 | 4 | NHCO | NMe | 2-(CF$_3$)Ph |
| 2-782 | 4 | NHCO | NMe | 4-(CF$_3$)Ph |
| 2-783 | 4 | NHCO | NMe | 2-MeOPh |
| 2-784 | 4 | NHCO | NMe | 4-MeOPh |
| 2-785 | 4 | NHCO | NMe | 2-EtOPh |
| 2-786 | 4 | NHCO | NMe | 4-EtOPh |
| 2-787 | 4 | NHCO | NMe | 2-HOPh |
| 2-788 | 4 | NHCO | NMe | 4-HOPh |
| 2-789 | 4 | NHCO | NMe | 2-(HOOC)Ph |
| 2-790 | 4 | NHCO | NMe | 4-(HOOC)Ph |
| 2-791 | 4 | NHCO | NMe | 2-(MeOOC)Ph |
| 2-792 | 4 | NHCO | NMe | 4-(MeOOC)Ph |
| 2-793 | 4 | NHCO | NMe | 2-(EtOOC)Ph |
| 2-794 | 4 | NHCO | NMe | 4-(EtOOC)Ph |
| 2-795 | 4 | NHCO | NMe | 2-(tBuOOC)Ph |
| 2-796 | 4 | NHCO | NMe | 4-(tBuOOC)Ph |
| 2-797 | 4 | NHCO | NMe | 2-Cl-Ph |
| 2-798 | 4 | NHCO | NMe | 4-Cl-Ph |
| 2-799 | 4 | NHCO | NMe | 2-Br-Ph |
| 2-800 | 4 | NHCO | NMe | 4-Br-Ph |
| 2-801 | 4 | NHCO | NMe | 2-I-Ph |
| 2-802 | 4 | NHCO | NMe | 4-I-Ph |
| 2-803 | 4 | NHCO | NMe | 2-NO$_2$-Ph |
| 2-804 | 4 | NHCO | NMe | 4-NO$_2$-Ph |
| 2-805 | 4 | NHCO | NMe | 2-NH$_2$-Ph |
| 2-806 | 4 | NHCO | NMe | 4-NH$_2$-Ph |
| 2-807 | 4 | NHCO | NMe | 2-(HO$_3$S)Ph |
| 2-808 | 4 | NHCO | NMe | 4-(HO$_3$S)Ph |
| 2-809 | 4 | NHCO | NMe | 2-(NH$_2$O$_2$S)Ph |
| 2-810 | 4 | NHCO | NMe | 4-(NH$_2$O$_2$S)Ph |
| 2-811 | 4 | NHCO | NMe | 2-CN-Ph |
| 2-812 | 4 | NHCO | NMe | 4-CN-Ph |
| 2-813 | 4 | NHCO | NMe | 2-(HOCH$_2$)Ph |
| 2-814 | 4 | NHCO | NMe | 4-(HOCH$_2$)Ph |
| 2-815 | 4 | NHCO | NMe | Me |
| 2-816 | 4 | NHCO | NMe | Et |
| 2-817 | 4 | NHCO | NMe | Pr |
| 2-818 | 4 | NHCO | NMe | iPr |
| 2-819 | 4 | NHCO | NMe | Bu |
| 2-820 | 4 | NHCO | NMe | HOOCCH$_2$— |
| 2-821 | 4 | NHCO | NMe | MeOOCCH$_2$— |
| 2-822 | 4 | NHCO | NMe | MeCH(COOH) |
| 2-823 | 4 | NHCO | NMe | HOOC—(CH$_2$)$_2$— |
| 2-824 | 4 | NHCO | NMe | MeCH(COOMe) |
| 2-825 | 4 | NHCO | NMe | 1-HOOC-iBu |
| 2-826 | 4 | NHCO | NMe | 1-MeOOC-iBu |
| 2-827 | 4 | NHCO | NMe | 1-HOOC-iPn |
| 2-828 | 4 | NHCO | NMe | 1-MeOOC-iPn |
| 2-829 | 4 | NHCO | NMe | 1-HOOC-2-Me-Bu |
| 2-830 | 4 | NHCO | NMe | 1-MeOOC-2-Me-Bu |
| 2-831 | 4 | NHCO | NMe | CH$_2$CH$_2$SO$_3$H |
| 2-832 | 4 | NHCO | NMe | OH |
| 2-833 | 4 | NHCO | NMe | MeO |
| 2-834 | 4 | NHCO | NMe | EtO |
| 2-835 | 4 | NHCO | NMe | PrO |
| 2-836 | 4 | NHCO | NMe | iPrO |
| 2-837 | 4 | NHCO | NMe | BuO |
| 2-838 | 4 | NHCO | NMe | iBuO |
| 2-839 | 4 | NHCO | NMe | sBuO |
| 2-840 | 4 | NHCO | NMe | tBuO |
| 2-841 | 4 | NHCO | NMe | HxO |
| 2-842 | 4 | NHCO | NMe | PhO |
| 2-843 | 4 | NHCO | NMe | BnO |
| 2-844 | 4 | NHCO | NMe | Z-1 |
| 2-845 | 4 | NHCO | NMe | Z-2 |
| 2-846 | 4 | NHCO | NMe | Z-3 |
| 2-847 | 4 | NHCO | NMe | Z-4 |
| 2-848 | 4 | NHCO | NMe | Z-5 |
| 2-849 | 4 | NHCO | NMe | Z-6 |
| 2-850 | 4 | NHCO | NMe | Z-7 |
| 2-851 | 4 | NHCO | NMe | Z-8 |
| 2-852 | 4 | NHCO | NMe | Z-9 |
| 2-853 | 4 | NHCO | NMe | Z-10 |
| 2-854 | 4 | NHCO | NMe | Z-11 |
| 2-855 | 4 | NHCO | NMe | Z-12 |
| 2-856 | 4 | NHCO | NMe | 3-Py |
| 2-857 | 4 | NHCO | NMe | 4-Py |
| 2-858 | 4 | NHCO | NHNH | H |
| 2-859 | 4 | NHCO | NHNH | Me |
| 2-860 | 4 | NHCO | NHNH | Et |
| 2-861 | 4 | NHCO | NHNH | Me |
| 2-862 | 4 | NHCO | NHNH | Et |
| 2-863 | 4 | NHCO | NHNH | Pr |
| 2-864 | 4 | NHCONHNHCO | NH | H |
| 2-865 | 4 | NHCONHNHCO | NH | Ph |
| 2-866 | 4 | NHCONHNHCO | NH | 2-Me-Ph |
| 2-867 | 4 | NHCONHNHCO | NH | 4-Me-Ph |
| 2-868 | 4 | NHCONHNHCO | NH | 2,4-diMe-Ph |
| 2-869 | 4 | NHCONHNHCO | NH | 3,4-diMe-Ph |
| 2-870 | 4 | NHCONHNHCO | NH | 2-(CF$_3$)Ph |
| 2-871 | 4 | NHCONHNHCO | NH | 4-(CF$_3$)Ph |
| 2-872 | 4 | NHCONHNHCO | NH | 2-MeOPh |
| 2-873 | 4 | NHCONHNHCO | NH | 4-MeOPh |
| 2-874 | 4 | NHCONHNHCO | NH | 2-EtOPh |
| 2-875 | 4 | NHCONHNHCO | NH | 4-EtOPh |
| 2-876 | 4 | NHCONHNHCO | NH | 2-HOPh |
| 2-877 | 4 | NHCONHNHCO | NH | 4-HOPh |
| 2-878 | 4 | NHCONHNHCO | NH | 2-(HOOC)Ph |
| 2-879 | 4 | NHCONHNHCO | NH | 4-(HOOC)Ph |
| 2-880 | 4 | NHCONHNHCO | NH | 2-(MeOOC)Ph |
| 2-881 | 4 | NHCONHNHCO | NH | 4-(MeOOC)Ph |
| 2-882 | 4 | NHCONHNHCO | NH | 2-(EtOOC)Ph |
| 2-883 | 4 | NHCONHNHCO | NH | 4-(EtOOC)Ph |
| 2-884 | 4 | NHCONHNHCO | NH | 2-(tBuOOC)Ph |
| 2-885 | 4 | NHCONHNHCO | NH | 4-(tBuOOC)Ph |
| 2-886 | 4 | NHCONHNHCO | NH | 2-Cl-Ph |
| 2-887 | 4 | NHCONHNHCO | NH | 4-Cl-Ph |
| 2-888 | 4 | NHCONHNHCO | NH | 2-Br-Ph |
| 2-889 | 4 | NHCONHNHCO | NH | 4-Br-Ph |
| 2-890 | 4 | NHCONHNHCO | NH | 2-I-Ph |
| 2-891 | 4 | NHCONHNHCO | NH | 4-I-Ph |
| 2-892 | 4 | NHCONHNHCO | NH | 2-NO$_2$-Ph |
| 2-893 | 4 | NHCONHNHCO | NH | 4-NO$_2$-Ph |
| 2-894 | 4 | NHCONHNHCO | NH | 2-NH$_2$-Ph |
| 2-895 | 4 | NHCONHNHCO | NH | 4-NH$_2$-Ph |
| 2-896 | 4 | NHCONHNHCO | NH | 2-(HO$_3$S)Ph |
| 2-897 | 4 | NHCONHNHCO | NH | 4-(HO$_3$S)Ph |
| 2-898 | 4 | NHCONHNHCO | NH | 2-(NH$_2$O$_2$S)Ph |
| 2-899 | 4 | NHCONHNHCO | NH | 4-(NH$_2$O$_2$S)Ph |
| 2-900 | 4 | NHCONHNHCO | NH | 2-CN-Ph |
| 2-901 | 4 | NHCONHNHCO | NH | 4-CN-Ph |

TABLE 2-continued

| Cpd. No. | k | A | B | R¹ |
|---|---|---|---|---|
| 2-902 | 4 | NHCONHNHCO | NH | 2-(HOCH₂)Ph |
| 2-903 | 4 | NHCONHNHCO | NH | 4-(HOCH₂)Ph |
| 2-904 | 4 | NHCONHNHCO | NH | Me |
| 2-905 | 4 | NHCONHNHCO | NH | Et |
| 2-906 | 4 | NHCONHNHCO | NH | Pr |
| 2-907 | 4 | NHCONHNHCO | NH | iPr |
| 2-908 | 4 | NHCONHNHCO | NH | Bu |
| 2-909 | 4 | NHCONHNHCO | NH | HOOCCH₂— |
| 2-910 | 4 | NHCONHNHCO | NH | MeOOCCH₂— |
| 2-911 | 4 | NHCONHNHCO | NH | MeCH(COOH) |
| 2-912 | 4 | NHCONHNHCO | NH | HOOC—(CH₂)₂— |
| 2-913 | 4 | NHCONHNHCO | NH | MeCH(COOMe) |
| 2-914 | 4 | NHCONHNHCO | NH | 1-HOOC-iBu |
| 2-915 | 4 | NHCONHNHCO | NH | 1-MeOOC-iBu |
| 2-916 | 4 | NHCONHNHCO | NH | 1-HOOC-iPn |
| 2-917 | 4 | NHCONHNHCO | NH | 1-MeOOC-iPn |
| 2-918 | 4 | NHCONHNHCO | NH | 1-HOOC-2-Me-Bu |
| 2-919 | 4 | NHCONHNHCO | NH | 1-MeOOC-2-Me-Bu |
| 2-920 | 4 | NHCONHNHCO | NH | CH₂CH₂SO₃H |
| 2-921 | 4 | NHCONHNHCO | NH | OH |
| 2-922 | 4 | NHCONHNHCO | NH | MeO |
| 2-923 | 4 | NHCONHNHCO | NH | EtO |
| 2-924 | 4 | NHCONHNHCO | NH | PrO |
| 2-925 | 4 | NHCONHNHCO | NH | iPrO |
| 2-926 | 4 | NHCONHNHCO | NH | BuO |
| 2-927 | 4 | NHCONHNHCO | NH | iBuO |
| 2-928 | 4 | NHCONHNHCO | NH | sBuO |
| 2-929 | 4 | NHCONHNHCO | NH | tBuO |
| 2-930 | 4 | NHCONHNHCO | NH | HxO |
| 2-931 | 4 | NHCONHNHCO | NH | PhO |
| 2-932 | 4 | NHCONHNHCO | NH | BnO |
| 2-933 | 4 | NHCONHNHCO | NH | Z-1 |
| 2-934 | 4 | NHCONHNHCO | NH | Z-2 |
| 2-935 | 4 | NHCONHNHCO | NH | Z-3 |
| 2-936 | 4 | NHCONHNHCO | NH | Z-4 |
| 2-937 | 4 | NHCONHNHCO | NH | Z-5 |
| 2-938 | 4 | NHCONHNHCO | NH | Z-6 |
| 2-939 | 4 | NHCONHNHCO | NH | Z-7 |
| 2-940 | 4 | NHCONHNHCO | NH | Z-8 |
| 2-941 | 4 | NHCONHNHCO | NH | Z-9 |
| 2-942 | 4 | NHCONHNHCO | NH | Z-10 |
| 2-943 | 4 | NHCONHNHCO | NH | Z-11 |
| 2-944 | 4 | NHCONHNHCO | NH | Z-12 |
| 2-945 | 4 | NHCONHNHCO | NH | 3-Py |
| 2-946 | 4 | NHCONHNHCO | NH | 4-Py |
| 2-947 | 4 | NHCONHCO | — | H |
| 2-948 | 4 | NHCONHCO | — | Ph |
| 2-949 | 4 | NHCONHCO | — | 2-Me-Ph |
| 2-950 | 4 | NHCONHCO | — | 4-Me-Ph |
| 2-951 | 4 | NHCONHCO | — | 2,4-diMe-Ph |
| 2-952 | 4 | NHCONHCO | — | 3,4-diMe-Ph |
| 2-953 | 4 | NHCONHCO | — | 2-(CF₃)Ph |
| 2-954 | 4 | NHCONHCO | — | 4-(CF₃)Ph |
| 2-955 | 4 | NHCONHCO | — | 2-MeOPh |
| 2-956 | 4 | NHCONHCO | — | 4-MeOPh |
| 2-957 | 4 | NHCONHCO | — | 2-EtOPh |
| 2-958 | 4 | NHCONHCO | — | 4-EtOPh |
| 2-959 | 4 | NHCONHCO | — | 2-HOPh |
| 2-960 | 4 | NHCONHCO | — | 4-HOPh |
| 2-961 | 4 | NHCONHCO | — | 2-(HOOC)Ph |
| 2-962 | 4 | NHCONHCO | — | 4-(HOOC)Ph |
| 2-963 | 4 | NHCONHCO | — | 2-(MeOOC)Ph |
| 2-964 | 4 | NHCONHCO | — | 4-(MeOOC)Ph |
| 2-965 | 4 | NHCONHCO | — | 2-(EtOOC)Ph |
| 2-966 | 4 | NHCONHCO | — | 4-(EtOOC)Ph |
| 2-967 | 4 | NHCONHCO | — | 2-(tBuOOC)Ph |
| 2-968 | 4 | NHCONHCO | — | 4-(tBuOOC)Ph |
| 2-969 | 4 | NHCONHCO | — | 2-Cl-Ph |
| 2-970 | 4 | NHCONHCO | — | 4-Cl-Ph |
| 2-971 | 4 | NHCONHCO | — | 2-Br-Ph |
| 2-972 | 4 | NHCONHCO | — | 4-Br-Ph |
| 2-973 | 4 | NHCONHCO | — | 2-I-Ph |
| 2-974 | 4 | NHCONHCO | — | 4-I-Ph |
| 2-975 | 4 | NHCONHCO | — | 2-NO₂-Ph |
| 2-976 | 4 | NHCONHCO | — | 4-NO₂-Ph |
| 2-977 | 4 | NHCONHCO | — | 2-NH₂-Ph |
| 2-978 | 4 | NHCONHCO | — | 4-NH₂-Ph |
| 2-979 | 4 | NHCONHCO | — | 2-(HO₃S)Ph |
| 2-980 | 4 | NHCONHCO | — | 4-(HO₃S)Ph |
| 2-981 | 4 | NHCONHCO | — | 2-(NH₂O₂S)Ph |
| 2-982 | 4 | NHCONHCO | — | 4-(NH₂O₂S)Ph |
| 2-983 | 4 | NHCONHCO | — | 2-CN-Ph |
| 2-984 | 4 | NHCONHCO | — | 4-CN-Ph |
| 2-985 | 4 | NHCONHCO | — | 2-(HOCH₂)Ph |
| 2-986 | 4 | NHCONHCO | — | 4-(HOCH₂)Ph |
| 2-987 | 4 | NHCONHCO | — | Me |
| 2-988 | 4 | NHCONHCO | — | Et |
| 2-989 | 4 | NHCONHCO | — | Pr |
| 2-990 | 4 | NHCONHCO | — | iPr |
| 2-991 | 4 | NHCONHCO | — | Bu |
| 2-992 | 4 | NHCONHCO | — | HOOCCH₂— |
| 2-993 | 4 | NHCONHCO | — | MeOOCCH₂— |
| 2-994 | 4 | NHCONHCO | — | MeCH(COOH) |
| 2-995 | 4 | NHCONHCO | — | HOOC—(CH₂)₂— |
| 2-996 | 4 | NHCONHCO | — | MeCH(COOMe) |
| 2-997 | 4 | NHCONHCO | — | 1-HOOC-iBu |
| 2-998 | 4 | NHCONHCO | — | 1-MeOOC-iBu |
| 2-999 | 4 | NHCONHCO | — | 1-HOOC-iPn |
| 2-1000 | 4 | NHCONHCO | — | 1-MeOOC-iPn |
| 2-1001 | 4 | NHCONHCO | — | 1-HOOC-2-Me-Bu |
| 2-1002 | 4 | NHCONHCO | — | 1-MeOOC-2-Me-Bu |
| 2-1003 | 4 | NHCONHCO | — | CH₂CH₂SO₃H |
| 2-1004 | 4 | NHCONHCO | — | MeO |
| 2-1005 | 4 | NHCONHCO | — | EtO |
| 2-1006 | 4 | NHCONHCO | — | PrO |
| 2-1007 | 4 | NHCONHCO | — | iPrO |
| 2-1008 | 4 | NHCONHCO | — | BuO |
| 2-1009 | 4 | NHCONHCO | — | iBuO |
| 2-1010 | 4 | NHCONHCO | — | sBuO |
| 2-1011 | 4 | NHCONHCO | — | tBuO |
| 2-1012 | 4 | NHCONHCO | — | HxO |
| 2-1013 | 4 | NHCONHCO | — | PhO |
| 2-1014 | 4 | NHCONHCO | — | BnO |
| 2-1015 | 4 | NHCONHCO | — | Z-1 |
| 2-1016 | 4 | NHCONHCO | — | Z-2 |
| 2-1017 | 4 | NHCONHCO | — | Z-3 |
| 2-1018 | 4 | NHCONHCO | — | Z-4 |
| 2-1019 | 4 | NHCONHCO | — | Z-5 |
| 2-1020 | 4 | NHCONHCO | — | Z-6 |
| 2-1021 | 4 | NHCONHCO | — | Z-7 |
| 2-1022 | 4 | NHCONHCO | — | Z-8 |
| 2-1023 | 4 | NHCONHCO | — | Z-9 |
| 2-1024 | 4 | NHCONHCO | — | Z-10 |
| 2-1025 | 4 | NHCONHCO | — | Z-11 |
| 2-1026 | 4 | NHCONHCO | — | Z-12 |
| 2-1027 | 4 | NHCONHCO | — | 3-Py |
| 2-1028 | 4 | NHCONHCO | — | 4-Py |
| 2-1029 | 4 | NHCONHSO₂ | — | H |
| 2-1030 | 4 | NHCONHSO₂ | — | Ph |
| 2-1031 | 4 | NHCONHSO₂ | — | 2-Me-Ph |
| 2-1032 | 4 | NHCONHSO₂ | — | 4-Me-Ph |
| 2-1033 | 4 | NHCONHSO₂ | — | 2,4-diMe-Ph |
| 2-1034 | 4 | NHCONHSO₂ | — | 3,4-diMe-Ph |
| 2-1035 | 4 | NHCONHSO₂ | — | 2-(CF₃)Ph |
| 2-1036 | 4 | NHCONHSO₂ | — | 4-(CF₃)Ph |
| 2-1037 | 4 | NHCONHSO₂ | — | 2-MeOPh |
| 2-1038 | 4 | NHCONHSO₂ | — | 4-MeOPh |
| 2-1039 | 4 | NHCONHSO₂ | — | 2-EtOPh |
| 2-1040 | 4 | NHCONHSO₂ | — | 4-EtOPh |
| 2-1041 | 4 | NHCONHSO₂ | — | 2-HOPh |
| 2-1042 | 4 | NHCONHSO₂ | — | 4-HOPh |
| 2-1043 | 4 | NHCONHSO₂ | — | 2-(HOOC)Ph |
| 2-1044 | 4 | NHCONHSO₂ | — | 4-(HOOC)Ph |
| 2-1045 | 4 | NHCONHSO₂ | — | 2-(MeOOC)Ph |
| 2-1046 | 4 | NHCONHSO₂ | — | 4-(MeOOC)Ph |
| 2-1047 | 4 | NHCONHSO₂ | — | 2-(EtOOC)Ph |
| 2-1048 | 4 | NHCONHSO₂ | — | 4-(EtOOC)Ph |
| 2-1049 | 4 | NHCONHSO₂ | — | 2-(tBuOOC)Ph |
| 2-1050 | 4 | NHCONHSO₂ | — | 4-(tBuOOC)Ph |
| 2-1051 | 4 | NHCONHSO₂ | — | 2-Cl-Ph |
| 2-1052 | 4 | NHCONHSO₂ | — | 4-Cl-Ph |
| 2-1053 | 4 | NHCONHSO₂ | — | 2-Br-Ph |

TABLE 2-continued

| Cpd. No. | k | A | B | R¹ |
|---|---|---|---|---|
| 2-1054 | 4 | NHCONHSO₂ | — | 4-Br-Ph |
| 2-1055 | 4 | NHCONHSO₂ | — | 2-I-Ph |
| 2-1056 | 4 | NHCONHSO₂ | — | 4-I-Ph |
| 2-1057 | 4 | NHCONHSO₂ | — | 2-NO₂-Ph |
| 2-1058 | 4 | NHCONHSO₂ | — | 4-NO₂-Ph |
| 2-1059 | 4 | NHCONHSO₂ | — | 2-NH₂-Ph |
| 2-1060 | 4 | NHCONHSO₂ | — | 4-NH₂-Ph |
| 2-1061 | 4 | NHCONHSO₂ | — | 2-(HO₃S)Ph |
| 2-1062 | 4 | NHCONHSO₂ | — | 4-(HO₃S)Ph |
| 2-1063 | 4 | NHCONHSO₂ | — | 2-(NH₂O₂S)Ph |
| 2-1064 | 4 | NHCONHSO₂ | — | 4-(NH₂O₂S)Ph |
| 2-1065 | 4 | NHCONHSO₂ | — | 2-CN-Ph |
| 2-1066 | 4 | NHCONHSO₂ | — | 4-CN-Ph |
| 2-1067 | 4 | NHCONHSO₂ | — | 2-(HOCH₂)Ph |
| 2-1068 | 4 | NHCONHSO₂ | — | 4-(HOCH₂)Ph |
| 2-1069 | 4 | NHCONHSO₂ | — | Me |
| 2-1070 | 4 | NHCONHSO₂ | — | Et |
| 2-1071 | 4 | NHCONHSO₂ | — | Pr |
| 2-1072 | 4 | NHCONHSO₂ | — | iPr |
| 2-1073 | 4 | NHCONHSO₂ | — | Bu |
| 2-1074 | 4 | NHCONHSO₂ | — | HOOCCH₂— |
| 2-1075 | 4 | NHCONHSO₂ | — | MeOOCCH₂— |
| 2-1076 | 4 | NHCONHSO₂ | — | MeCH(COOH) |
| 2-1077 | 4 | NHCONHSO₂ | — | HOOC—(CH₂)₂— |
| 2-1078 | 4 | NHCONHSO₂ | — | MeCH(COOMe) |
| 2-1079 | 4 | NHCONHSO₂ | — | 1-HOOC-iBu |
| 2-1080 | 4 | NHCONHSO₂ | — | 1-MeOOC-iBu |
| 2-1081 | 4 | NHCONHSO₂ | — | 1-HOOC-iPn |
| 2-1082 | 4 | NHCONHSO₂ | — | 1-MeOOC-iPn |
| 2-1083 | 4 | NHCONHSO₂ | — | 1-HOOC-2-Me-Bu |
| 2-1084 | 4 | NHCONHSO₂ | — | 1-MeOOC-2-Me-Bu |
| 2-1085 | 4 | NHCONHSO₂ | — | CH₂CH₂SO₃H |
| 2-1086 | 4 | NHCONHSO₂ | — | OH |
| 2-1087 | 4 | NHCONHSO₂ | — | MeO |
| 2-1088 | 4 | NHCONHSO₂ | — | EtO |
| 2-1089 | 4 | NHCONHSO₂ | — | PrO |
| 2-1090 | 4 | NHCONHSO₂ | — | iPrO |
| 2-1091 | 4 | NHCONHSO₂ | — | BuO |
| 2-1092 | 4 | NHCONHSO₂ | — | iBuO |
| 2-1093 | 4 | NHCONHSO₂ | — | sBuO |
| 2-1094 | 4 | NHCONHSO₂ | — | tBuO |
| 2-1095 | 4 | NHCONHSO₂ | — | HxO |
| 2-1096 | 4 | NHCONHSO₂ | — | PhO |
| 2-1097 | 4 | NHCONHSO₂ | — | BnO |
| 2-1098 | 4 | NHCONHSO₂ | — | Z-1 |
| 2-1099 | 4 | NHCONHSO₂ | — | Z-2 |
| 2-1100 | 4 | NHCONHSO₂ | — | Z-3 |
| 2-1101 | 4 | NHCONHSO₂ | — | Z-4 |
| 2-1102 | 4 | NHCONHSO₂ | — | Z-5 |
| 2-1103 | 4 | NHCONHSO₂ | — | Z-6 |
| 2-1104 | 4 | NHCONHSO₂ | — | Z-7 |
| 2-1105 | 4 | NHCONHSO₂ | — | Z-8 |
| 2-1106 | 4 | NHCONHSO₂ | — | Z-9 |
| 2-1107 | 4 | NHCONHSO₂ | — | Z-10 |
| 2-1108 | 4 | NHCONHSO₂ | — | Z-11 |
| 2-1109 | 4 | NHCONHSO₂ | — | Z-12 |
| 2-1110 | 4 | NHCONHSO₂ | — | 3-Py |
| 2-1111 | 4 | NHCONHSO₂ | — | 4-Py |
| 2-1112 | 4 | NHCONHSO₂ | NH | H |
| 2-1113 | 4 | NHCONHSO₂ | NH | Me |
| 2-1114 | 4 | NHCONHSO₂ | NH | Et |
| 2-1115 | 4 | NHCONHSO₂ | NH | Pr |
| 2-1116 | 4 | NHCONHSO₂ | NH | iPr |
| 2-1117 | 4 | NHCONHSO₂ | NH | Bu |
| 2-1118 | 4 | NHCONHSO₂ | NMe | Me |
| 2-1119 | 4 | NHCONHSO₂ | NMe | Et |
| 2-1120 | 4 | NHCONHSO₂ | NMe | Pr |
| 2-1121 | 4 | NHCONHSO₂ | NMe | iPr |
| 2-1122 | 4 | NHCONHSO₂ | NMe | Bu |
| 2-1123 | 4 | — | NH | H |
| 2-1124 | 4 | — | NH | Me |
| 2-1125 | 4 | — | NH | Et |
| 2-1126 | 4 | — | NH | Pr |
| 2-1127 | 4 | — | NH | iPr |
| 2-1128 | 4 | — | NH | Bu |
| 2-1129 | 4 | CO | | Pyr |
| 2-1130 | 4 | CO | | Pipri |
| 2-1131 | 4 | CO | | Pipra |
| 2-1132 | 4 | CO | | Mor |
| 2-1133 | 4 | CO | | Thmor |
| 2-1134 | 4 | CO | | NHPyr |
| 2-1135 | 4 | CO | | NHPipri |
| 2-1136 | 4 | CO | | NHPipra |
| 2-1137 | 4 | CO | | NHMor |
| 2-1138 | 4 | CO | | NHThmor |
| 2-1139 | 4 | NHCO | | Pyr |
| 2-1140 | 4 | NHCO | | Pipri |
| 2-1141 | 4 | NHCO | | Pipra |
| 2-1142 | 4 | NHCO | | Mor |
| 2-1143 | 4 | NHCO | | Thmor |
| 2-1144 | 4 | NHCO | | NHPyr |
| 2-1145 | 4 | NHCO | | NHPipri |
| 2-1146 | 4 | NHCO | | NHPipra |
| 2-1147 | 4 | NHCO | | NHMor |
| 2-1148 | 4 | NHCO | | NHThmor |
| 2-1149 | 4 | CONHCO | | Pyr |
| 2-1150 | 4 | CONHCO | | Pipri |
| 2-1151 | 4 | CONHCO | | Pipra |
| 2-1152 | 4 | CONHCO | | Mor |
| 2-1153 | 4 | CONHCO | | Thmor |
| 2-1154 | 4 | CONHCO | | NHPyr |
| 2-1155 | 4 | CONHCO | | NHPipri |
| 2-1156 | 4 | CONHCO | | NHPipra |
| 2-1157 | 4 | CONHCO | | NHMor |
| 2-1158 | 4 | CONHCO | | NHThmor |
| 2-1159 | 4 | CONHSO₂ | | Pyr |
| 2-1160 | 4 | CONHSO₂ | | Pipri |
| 2-1161 | 4 | CONHSO₂ | | Pipra |
| 2-1162 | 4 | CONHSO₂ | | Mor |
| 2-1163 | 4 | CONHSO₂ | | Thmor |
| 2-1164 | 4 | CONHSO₂ | | NHPyr |
| 2-1165 | 4 | CONHSO₂ | | NHPipri |
| 2-1166 | 4 | CONHSO₂ | | NHPipra |
| 2-1167 | 4 | CONHSO₂ | | NHMor |
| 2-1168 | 4 | CONHSO₂ | | NHThmor |
| 2-1169 | 4 | NHSO₂ | NH | Z-4 |
| 2-1170 | 4 | NHSO₂ | — | Me |
| 2-1171 | 4 | NHSO₂ | — | Et |
| 2-1172 | 4 | NHSO₂ | — | Pr |
| 2-1173 | 4 | NHSO₂ | — | CH₂—Cl |
| 2-1174 | 4 | NHSO₂ | — | Ph |
| 2-1175 | 4 | NHSO₂ | — | 4-Me-Ph |
| 2-1176 | 4 | CO | NMe | Ph |
| 2-1177 | 4 | CO | NMe | 2-Me-Ph |
| 2-1178 | 4 | CO | NMe | 4-Me-Ph |
| 2-1179 | 4 | CO | NMe | 2,4-diMe-Ph |
| 2-1180 | 4 | CO | NMe | 3,4-diMe-Ph |
| 2-1181 | 4 | CO | NMe | 2-(CF₃)Ph |
| 2-1182 | 4 | CO | NMe | 4-(CF₃)Ph |
| 2-1183 | 4 | CO | NMe | 2-MeOPh |
| 2-1184 | 4 | CO | NMe | 4-MeOPh |
| 2-1185 | 4 | CO | NMe | 2-EtOPh |
| 2-1186 | 4 | CO | NMe | 4-EtOPh |
| 2-1187 | 4 | CO | NMe | 2-HOPh |
| 2-1188 | 4 | CO | NMe | 4-HOPh |
| 2-1189 | 4 | CO | NMe | 2-(HOOC)Ph |
| 2-1190 | 4 | CO | NMe | 4-(HOOC)Ph |
| 2-1191 | 4 | CO | NMe | 2-(MeOOC)Ph |
| 2-1192 | 4 | CO | NMe | 4-(MeOOC)Ph |
| 2-1193 | 4 | CO | NMe | 2-(EtOOC)Ph |
| 2-1194 | 4 | CO | NMe | 4-(EtOOC)Ph |
| 2-1195 | 4 | CO | NMe | 2-(tBuOOC)Ph |
| 2-1196 | 4 | CO | NMe | 4-(tBuOOC)Ph |
| 2-1197 | 4 | CO | NMe | 2-Cl-Ph |
| 2-1198 | 4 | CO | NMe | 4-Cl-Ph |
| 2-1199 | 4 | CO | NMe | 2-Br-Ph |
| 2-1200 | 4 | CO | NMe | 4-Br-Ph |
| 2-1201 | 4 | CO | NMe | 2-I-Ph |
| 2-1202 | 4 | CO | NMe | 4-I-Ph |
| 2-1203 | 4 | CO | NMe | 2-NO₂-Ph |
| 2-1204 | 4 | CO | NMe | 4-NO₂-Ph |
| 2-1205 | 4 | CO | NMe | 2-NH₂-Ph |

TABLE 2-continued

| Cpd. No. | k | A | B | R¹ |
|---|---|---|---|---|
| 2-1206 | 4 | CO | NMe | 4-NH₂-Ph |
| 2-1207 | 4 | CO | NMe | 2-(HO₃S)Ph |
| 2-1208 | 4 | CO | NMe | 4-(HO₃S)Ph |
| 2-1209 | 4 | CO | NMe | 2-(NH₂O₂S)Ph |
| 2-1210 | 4 | CO | NMe | 4-(NH₂O₂S)Ph |
| 2-1211 | 4 | CO | NMe | 2-CN-Ph |
| 2-1212 | 4 | CO | NMe | 4-CN-Ph |
| 2-1213 | 4 | CO | NMe | 2-(HOCH₂)Ph |
| 2-1214 | 4 | CO | NMe | 4-(HOCH₂)Ph |
| 2-1215 | 4 | CO | NMe | Me |
| 2-1216 | 4 | CO | NMe | Et |
| 2-1217 | 4 | CO | NMe | Pr |
| 2-1218 | 4 | CO | NMe | iPr |
| 2-1219 | 4 | CO | NMe | Bu |
| 2-1220 | 4 | CO | NMe | HOOCCH₂— |
| 2-1221 | 4 | CO | NMe | MeOOCCH₂— |
| 2-1222 | 4 | CO | NMe | MeCH(COOH) |
| 2-1223 | 4 | CO | NMe | HOOC—(CH₂)₂— |
| 2-1224 | 4 | CO | NMe | MeCH(COOMe) |
| 2-1225 | 4 | CO | NMe | 1-HOOC-iBu |
| 2-1226 | 4 | CO | NMe | 1-MeOOC-iBu |
| 2-1227 | 4 | CO | NMe | 1-HOOC-iPn |
| 2-1228 | 4 | CO | NMe | 1-MeOOC-iPn |
| 2-1229 | 4 | CO | NMe | 1-HOOC-2-Me-Bu |
| 2-1230 | 4 | CO | NMe | 1-MeOOC-2-Me-Bu |
| 2-1231 | 4 | CO | NMe | CH₂CH₂SO₃H |
| 2-1232 | 4 | CO | NMe | OH |
| 2-1233 | 4 | CO | NMe | MeO |
| 2-1234 | 4 | CO | NMe | EtO |
| 2-1235 | 4 | CO | NMe | PrO |
| 2-1236 | 4 | CO | NMe | iPrO |
| 2-1237 | 4 | CO | NMe | BuO |
| 2-1238 | 4 | CO | NMe | iBuO |
| 2-1239 | 4 | CO | NMe | sBuO |
| 2-1240 | 4 | CO | NMe | tBuO |
| 2-1241 | 4 | CO | NMe | HxO |
| 2-1242 | 4 | CO | NMe | PhO |
| 2-1243 | 4 | CO | NMe | BnO |
| 2-1244 | 4 | CO | NMe | Z-1 |
| 2-1245 | 4 | CO | NMe | Z-2 |
| 2-1246 | 4 | CO | NMe | Z-3 |
| 2-1247 | 4 | CO | NMe | Z-4 |
| 2-1248 | 4 | CO | NMe | Z-5 |
| 2-1249 | 4 | CO | NMe | Z-6 |
| 2-1250 | 4 | CO | NMe | Z-7 |
| 2-1251 | 4 | CO | NMe | Z-8 |
| 2-1252 | 4 | CO | NMe | Z-9 |
| 2-1253 | 4 | CO | NMe | Z-10 |
| 2-1254 | 4 | CO | NMe | Z-11 |
| 2-1255 | 4 | CO | NMe | Z-12 |
| 2-1256 | 4 | CO | NMe | 3-Py |
| 2-1257 | 4 | CO | NMe | 4-Py |
| 2-1258 | 4 | CO | | Thiad |
| 2-1259 | 4 | CO | | NHThiad |
| 2-1260 | 4 | NHCO | | Thiad |
| 2-1261 | 4 | NHCO | | NHThiad |
| 2-1262 | 4 | CONHCO | | Thiad |
| 2-1263 | 4 | CONHCO | | NHThiad |
| 2-1264 | 4 | CONHSO₂ | | Thiad |
| 2-1265 | 4 | CONHSO₂ | | NHThiad |
| 2-1266 | 4 | NHCS | NH | H |
| 2-1267 | 4 | NHCS | NH | Me |
| 2-1268 | 4 | NHCS | NH | Et |
| 2-1269 | 4 | NHCS | NH | Ph |
| 2-1270 | 4 | NHCS | NH | HOOCCH₂— |
| 2-1271 | 4 | NHCS | NH | MeOOCCH₂— |
| 2-1272 | 4 | NHCS | NH | MeCH(COOH) |
| 2-1273 | 4 | NHCS | NH | HOOC—(CH₂)₂— |
| 2-1274 | 4 | NHCS | NH | MeCH(COOMe) |
| 2-1275 | 4 | CO | NH | HOOC—(CH₂)₃— |
| 2-1276 | 4 | NHCO | NH | HOOC—(CH₂)₃— |
| 2-1277 | 4 | NHCO | — | HOOC—(CH₂)₃— |
| 2-1278 | 4 | NHCS | NH | HOOC—(CH₂)₃— |
| 2-1279 | 4 | CO | NH | MeSO₂NHCOCH(Me) |
| 2-1280 | 4 | NHCO | NH | MeSO₂NHCOCH(Me) |
| 2-1281 | 4 | NHCO | — | MeSO₂NHCOCH(Me) |
| 2-1282 | 4 | NHCS | NH | MeSO₂NHCOCH(Me) |
| 2-1283 | 4 | — | NH | HOOCCH₂— |
| 2-1284 | 4 | — | NH | MeOOCCH₂— |
| 2-1285 | 4 | — | NH | MeCH(COOH) |
| 2-1286 | 4 | — | NH | HOOC—(CH₂)₂— |
| 2-1287 | 4 | — | NH | MeCH(COOMe) |
| 2-1288 | 4 | — | NH | HOOC—(CH₂)₃— |
| 2-1289 | 4 | NHCOCO | — | OH |
| 2-1290 | 4 | NHCOCO | — | MeO |
| 2-1291 | 4 | NHCOCO | — | EtO |
| 2-1292 | 4 | NHCOCO | — | PrO |
| 2-1293 | 4 | NHCOCO | — | iPrO |
| 2-1294 | 4 | NHCOCO | — | BuO |
| 2-1295 | 4 | NHCOCO | — | iBuO |
| 2-1296 | 4 | NHCOCO | — | sBuO |
| 2-1297 | 4 | NHCOCO | — | tBuO |
| 2-1298 | 4 | NHCOCO | — | HxO |
| 2-1299 | 4 | NHCOCO | — | PhO |
| 2-1300 | 4 | NHCOCO | — | BnO |
| 2-1301 | 5 | CO | NH | H |
| 2-1302 | 5 | CO | NH | Ph |
| 2-1303 | 5 | CO | NH | 2-Me-Ph |
| 2-1304 | 5 | CO | NH | 4-Me-Ph |
| 2-1305 | 5 | CO | NH | 2,4-diMe-Ph |
| 2-1306 | 5 | CO | NH | 3,4-diMe-Ph |
| 2-1307 | 5 | CO | NH | 2-(CF₃)Ph |
| 2-1308 | 5 | CO | NH | 4-(CF₃)Ph |
| 2-1309 | 5 | CO | NH | 2-MeOPh |
| 2-1310 | 5 | CO | NH | 4-MeOPh |
| 2-1311 | 5 | CO | NH | 2-EtOPh |
| 2-1312 | 5 | CO | NH | 4-EtOPh |
| 2-1313 | 5 | CO | NH | 2-HOPh |
| 2-1314 | 5 | CO | NH | 4-HOPh |
| 2-1315 | 5 | CO | NH | 2-(HOOC)Ph |
| 2-1316 | 5 | CO | NH | 4-(HOOC)Ph |
| 2-1317 | 5 | CO | NH | 2-(MeOOC)Ph |
| 2-1318 | 5 | CO | NH | 4-(MeOOC)Ph |
| 2-1319 | 5 | CO | NH | 2-(EtOOC)Ph |
| 2-1320 | 5 | CO | NH | 4-(EtOOC)Ph |
| 2-1321 | 5 | CO | NH | 2-(tBuOOC)Ph |
| 2-1322 | 5 | CO | NH | 4-(tBuOOC)Ph |
| 2-1323 | 5 | CO | NH | 2-Cl-Ph |
| 2-1324 | 5 | CO | NH | 4-Cl-Ph |
| 2-1325 | 5 | CO | NH | 2-Br-Ph |
| 2-1326 | 5 | CO | NH | 4-Br-Ph |
| 2-1327 | 5 | CO | NH | 2-I-Ph |
| 2-1328 | 5 | CO | NH | 4-I-Ph |
| 2-1329 | 5 | CO | NH | 2-NO₂-Ph |
| 2-1330 | 5 | CO | NH | 4-NO₂-Ph |
| 2-1331 | 5 | CO | NH | 2-NH₂-Ph |
| 2-1332 | 5 | CO | NH | 4-NH₂-Ph |
| 2-1333 | 5 | CO | NH | 2-(HO₃S)Ph |
| 2-1334 | 5 | CO | NH | 4-(HO₃S)Ph |
| 2-1335 | 5 | CO | NH | 2-(NH₂O₂S)Ph |
| 2-1336 | 5 | CO | NH | 4-(NH₂O₂S)Ph |
| 2-1337 | 5 | CO | NH | 2-CN-Ph |
| 2-1338 | 5 | CO | NH | 4-CN-Ph |
| 2-1339 | 5 | CO | NH | 2-(HOCH₂)Ph |
| 2-1340 | 5 | CO | NH | 4-(HOCH₂)Ph |
| 2-1341 | 5 | CO | NH | Me |
| 2-1342 | 5 | CO | NH | Et |
| 2-1343 | 5 | CO | NH | Pr |
| 2-1344 | 5 | CO | NH | iPr |
| 2-1345 | 5 | CO | NH | Bu |
| 2-1346 | 5 | CO | NH | HOOCCH₂— |
| 2-1347 | 5 | CO | NH | MeOOCCH₂— |
| 2-1348 | 5 | CO | NH | MeCH(COOH) |
| 2-1349 | 5 | CO | NH | HOOC—(CH₂)₂— |
| 2-1350 | 5 | CO | NH | MeCH(COOMe) |
| 2-1351 | 5 | CO | NH | 1-HOOC-iBu |
| 2-1352 | 5 | CO | NH | 1-MeOOC-iBu |
| 2-1353 | 5 | CO | NH | 1-HOOC-iPn |
| 2-1354 | 5 | CO | NH | 1-MeOOC-iPn |
| 2-1355 | 5 | CO | NH | 1-HOOC-2-Me-Bu |
| 2-1356 | 5 | CO | NH | 1-MeOOC-2-Me-Bu |
| 2-1357 | 5 | CO | NH | CH₂CH₂SO₂H |

TABLE 2-continued

| Cpd. No. | k | A | B | R¹ |
|---|---|---|---|---|
| 2-1358 | 5 | CO | NH | OH |
| 2-1359 | 5 | CO | NH | MeO |
| 2-1360 | 5 | CO | NH | EtO |
| 2-1361 | 5 | CO | NH | PrO |
| 2-1362 | 5 | CO | NH | iPrO |
| 2-1363 | 5 | CO | NH | BuO |
| 2-1364 | 5 | CO | NH | iBuO |
| 2-1365 | 5 | CO | NH | sBuO |
| 2-1366 | 5 | CO | NH | tBuO |
| 2-1367 | 5 | CO | NH | HxO |
| 2-1368 | 5 | CO | NH | PhO |
| 2-1369 | 5 | CO | NH | BnO |
| 2-1370 | 5 | CO | NH | Z-1 |
| 2-1371 | 5 | CO | NH | Z-2 |
| 2-1372 | 5 | CO | NH | Z-3 |
| 2-1373 | 5 | CO | NH | Z-4 |
| 2-1374 | 5 | CO | NH | Z-5 |
| 2-1375 | 5 | CO | NH | Z-6 |
| 2-1376 | 5 | CO | NH | Z-7 |
| 2-1377 | 5 | CO | NH | Z-8 |
| 2-1378 | 5 | CO | NH | Z-9 |
| 2-1379 | 5 | CO | NH | Z-10 |
| 2-1380 | 5 | CO | NH | Z-11 |
| 2-1381 | 5 | CO | NH | Z-12 |
| 2-1382 | 5 | CO | NH | 3-Py |
| 2-1383 | 5 | CO | NH | 4-Py |
| 2-1384 | 5 | CO | N(Ac) | H |
| 2-1385 | 5 | CO | N(Ac) | Ph |
| 2-1386 | 5 | CO | N(Ac) | 2-Me-Ph |
| 2-1387 | 5 | CO | N(Ac) | 4-Me-Ph |
| 2-1388 | 5 | CO | N(Ac) | 2,4-diMe-Ph |
| 2-1389 | 5 | CO | N(Ac) | 3,4-diMe-Ph |
| 2-1390 | 5 | CO | N(Ac) | 2-(CF₃)Ph |
| 2-1391 | 5 | CO | N(Ac) | 4-(CF₃)Ph |
| 2-1392 | 5 | CO | N(Ac) | 2-MeOPh |
| 2-1393 | 5 | CO | N(Ac) | 4-MeOPh |
| 2-1394 | 5 | CO | N(Ac) | 2-EtOPh |
| 2-1395 | 5 | CO | N(Ac) | 4-EtOPh |
| 2-1396 | 5 | CO | N(Ac) | 2-HOPh |
| 2-1397 | 5 | CO | N(Ac) | 4-HOPh |
| 2-1398 | 5 | CO | N(Ac) | 2-(HOOC)Ph |
| 2-1399 | 5 | CO | N(Ac) | 4-(HOOC)Ph |
| 2-1400 | 5 | CO | N(Ac) | 2-(MeOOC)Ph |
| 2-1401 | 5 | CO | N(Ac) | 4-(MeOOC)Ph |
| 2-1402 | 5 | CO | N(Ac) | 2-(EtOOC)Ph |
| 2-1403 | 5 | CO | N(Ac) | 4-(EtOOC)Ph |
| 2-1404 | 5 | CO | N(Ac) | 2-(tBuOOC)Ph |
| 2-1405 | 5 | CO | N(Ac) | 4-(tBuOOC)Ph |
| 2-1406 | 5 | CO | N(Ac) | 2-Cl-Ph |
| 2-1407 | 5 | CO | N(Ac) | 4-Cl-Ph |
| 2-1408 | 5 | CO | N(Ac) | 2-Br-Ph |
| 2-1409 | 5 | CO | N(Ac) | 4-Br-Ph |
| 2-1410 | 5 | CO | N(Ac) | 2-I-Ph |
| 2-1411 | 5 | CO | N(Ac) | 4-I-Ph |
| 2-1412 | 5 | CO | N(Ac) | 2-NO₂-Ph |
| 2-1413 | 5 | CO | N(Ac) | 4-NO₂-Ph |
| 2-1414 | 5 | CO | N(Ac) | 2-NH₂-Ph |
| 2-1415 | 5 | CO | N(Ac) | 4-NH₂-Ph |
| 2-1416 | 5 | CO | N(Ac) | 2-(HO₃S)Ph |
| 2-1417 | 5 | CO | N(Ac) | 4-(HO₃S)Ph |
| 2-1418 | 5 | CO | N(Ac) | 2-(NH₂O₂S)Ph |
| 2-1419 | 5 | CO | N(Ac) | 4-(NH₂O₂S)Ph |
| 2-1420 | 5 | CO | N(Ac) | 2-CN-Ph |
| 2-1421 | 5 | CO | N(Ac) | 4-CN-Ph |
| 2-1422 | 5 | CO | N(Ac) | 2-(HOCH₂)Ph |
| 2-1423 | 5 | CO | N(Ac) | 4-(HOCH₂)Ph |
| 2-1424 | 5 | CO | N(Ac) | Me |
| 2-1425 | 5 | CO | N(Ac) | Et |
| 2-1426 | 5 | CO | N(Ac) | Pr |
| 2-1427 | 5 | CO | N(Ac) | iPr |
| 2-1428 | 5 | CO | N(Ac) | Bu |
| 2-1429 | 5 | CO | N(Ac) | HOOCCH₂— |
| 2-1430 | 5 | CO | N(Ac) | MeOOCCH₂— |
| 2-1431 | 5 | CO | N(Ac) | MeCH(COOH) |
| 2-1432 | 5 | CO | N(Ac) | HOOC—(CH₂)₂— |
| 2-1433 | 5 | CO | N(Ac) | MeCH-(COOMe) |
| 2-1434 | 5 | CO | N(Ac) | 1-HOOC-iBu |
| 2-1435 | 5 | CO | N(Ac) | 1-MeOOC-iBu |
| 2-1436 | 5 | CO | N(Ac) | 1-HOOC-iPn |
| 2-1437 | 5 | CO | N(Ac) | 1-MeOOC-iPn |
| 2-1438 | 5 | CO | N(Ac) | 1-HOOC-2-Me-Bu |
| 2-1439 | 5 | CO | N(Ac) | 1-MeOOC-2-Me-Bu |
| 2-1440 | 5 | CO | N(Ac) | CH₂CH₂SO₃H |
| 2-1441 | 5 | CO | N(Ac) | OH |
| 2-1442 | 5 | CO | N(Ac) | MeO |
| 2-1443 | 5 | CO | N(Ac) | EtO |
| 2-1444 | 5 | CO | N(Ac) | PrO |
| 2-1445 | 5 | CO | N(Ac) | iPrO |
| 2-1446 | 5 | CO | N(Ac) | BuO |
| 2-1447 | 5 | CO | N(Ac) | iBuO |
| 2-1448 | 5 | CO | N(Ac) | sBuO |
| 2-1449 | 5 | CO | N(Ac) | tBuO |
| 2-1450 | 5 | CO | N(Ac) | HxO |
| 2-1451 | 5 | CO | N(Ac) | PhO |
| 2-1452 | 5 | CO | N(Ac) | BnO |
| 2-1453 | 5 | CO | N(Ac) | Z-1 |
| 2-1454 | 5 | CO | N(Ac) | Z-2 |
| 2-1455 | 5 | CO | N(Ac) | Z-3 |
| 2-1456 | 5 | CO | N(Ac) | Z-4 |
| 2-1457 | 5 | CO | N(Ac) | Z-5 |
| 2-1458 | 5 | CO | N(Ac) | Z-6 |
| 2-1459 | 5 | CO | N(Ac) | Z-7 |
| 2-1460 | 5 | CO | N(Ac) | Z-8 |
| 2-1461 | 5 | CO | N(Ac) | Z-9 |
| 2-1462 | 5 | CO | N(Ac) | Z-10 |
| 2-1463 | 5 | CO | N(Ac) | Z-11 |
| 2-1464 | 5 | CO | N(Ac) | Z-12 |
| 2-1465 | 5 | CO | N(Ac) | 3-Py |
| 2-1466 | 5 | CO | N(Ac) | 4-Py |
| 2-1467 | 5 | COO | — | H |
| 2-1468 | 5 | COO | — | Ph |
| 2-1469 | 5 | COO | — | 2-Me-Ph |
| 2-1470 | 5 | COO | — | 4-Me-Ph |
| 2-1471 | 5 | COO | — | 2,4-diMe-Ph |
| 2-1472 | 5 | COO | — | 3,4-diMe-Ph |
| 2-1473 | 5 | COO | — | 2-(CF₃)Ph |
| 2-1474 | 5 | COO | — | 4-(CF₃)Ph |
| 2-1475 | 5 | COO | — | 2-MeOPh |
| 2-1476 | 5 | COO | — | 4-MeOPh |
| 2-1477 | 5 | COO | — | 2-EtOPh |
| 2-1478 | 5 | COO | — | 4-EtOPh |
| 2-1479 | 5 | COO | — | 2-HOPh |
| 2-1480 | 5 | COO | — | 4-HOPh |
| 2-1481 | 5 | COO | — | 2-(HOOC)Ph |
| 2-1482 | 5 | COO | — | 4-(HOOC)Ph |
| 2-1483 | 5 | COO | — | 2-(MeOOC)Ph |
| 2-1484 | 5 | COO | — | 4-(MeOOC)Ph |
| 2-1485 | 5 | COO | — | 2-(EtOOC)Ph |
| 2-1486 | 5 | COO | — | 4-(EtOOC)Ph |
| 2-1487 | 5 | COO | — | 2-(tBuOOC)Ph |
| 2-1488 | 5 | COO | — | 4-(tBuOOC)Ph |
| 2-1489 | 5 | COO | — | 2-Cl-Ph |
| 2-1490 | 5 | COO | — | 4-Cl-Ph |
| 2-1491 | 5 | COO | — | 2-Br-Ph |
| 2-1492 | 5 | COO | — | 4-Br-Ph |
| 2-1493 | 5 | COO | — | 2-I-Ph |
| 2-1494 | 5 | COO | — | 4-I-Ph |
| 2-1495 | 5 | COO | — | 2-NO₂-Ph |
| 2-1496 | 5 | COO | — | 4-NO₂-Ph |
| 2-1497 | 5 | COO | — | 2-NH₂-Ph |
| 2-1498 | 5 | COO | — | 4-NH₂-Ph |
| 2-1499 | 5 | COO | — | 2-(HO₃S)Ph |
| 2-1500 | 5 | COO | — | 4-(HO₃S)Ph |
| 2-1501 | 5 | COO | — | 2-(NH₂O₂S)Ph |
| 2-1502 | 5 | COO | — | 4-(NH₂O₂S)Ph |
| 2-1503 | 5 | COO | — | 2-CN-Ph |
| 2-1504 | 5 | COO | — | 4-CN-Ph |
| 2-1505 | 5 | COO | — | 2-(HOCH₂)Ph |
| 2-1506 | 5 | COO | — | 4-(HOCH₂)Ph |
| 2-1507 | 5 | COO | — | Me |
| 2-1508 | 5 | COO | — | Et |
| 2-1509 | 5 | COO | — | Pr |

TABLE 2-continued

| Cpd. No. | k | A | B | R¹ |
|---|---|---|---|---|
| 2-1510 | 5 | COO | — | iPr |
| 2-1511 | 5 | COO | — | Bu |
| 2-1512 | 5 | COO | — | HOOCCH₂— |
| 2-1513 | 5 | COO | — | HOOC—(CH₂)₂— |
| 2-1514 | 5 | COO | — | MeCH(COOMe) |
| 2-1515 | 5 | COO | — | 1-HOOC-iBu |
| 2-1516 | 5 | COO | — | 1-HOOC-iPn |
| 2-1517 | 5 | COO | — | Z-1 |
| 2-1518 | 5 | COO | — | Z-2 |
| 2-1519 | 5 | COO | — | Z-3 |
| 2-1520 | 5 | COO | — | Z-4 |
| 2-1521 | 5 | COO | — | Z-5 |
| 2-1522 | 5 | COO | — | Z-6 |
| 2-1523 | 5 | COO | — | Z-7 |
| 2-1524 | 5 | COO | — | Z-8 |
| 2-1525 | 5 | COO | — | Z-9 |
| 2-1526 | 5 | COO | — | Z-10 |
| 2-1527 | 5 | COO | — | Z-11 |
| 2-1528 | 5 | COO | — | Z-12 |
| 2-1529 | 5 | COO | — | 3-Py |
| 2-1530 | 5 | COO | — | 4-Py |
| 2-1531 | 5 | CONHCO | — | H |
| 2-1532 | 5 | CONHCO | — | Ph |
| 2-1533 | 5 | CONHCO | — | 2-Me-Ph |
| 2-1534 | 5 | CONHCO | — | 4-Me-Ph |
| 2-1535 | 5 | CONHCO | — | 2,4-diMe-Ph |
| 2-1536 | 5 | CONHCO | — | 3,4-diMe-Ph |
| 2-1537 | 5 | CONHCO | — | 2-(CF₃)Ph |
| 2-1538 | 5 | CONHCO | — | 4-(CF₃)Ph |
| 2-1539 | 5 | CONHCO | — | 2-MeOPh |
| 2-1540 | 5 | CONHCO | — | 4-MeOPh |
| 2-1541 | 5 | CONHCO | — | 2-EtOPh |
| 2-1542 | 5 | CONHCO | — | 4-EtOPh |
| 2-1543 | 5 | CONHCO | — | 2-HOPh |
| 2-1544 | 5 | CONHCO | — | 4-HOPh |
| 2-1545 | 5 | CONHCO | — | 2-(HOOC)Ph |
| 2-1546 | 5 | CONHCO | — | 4-(HOOC)Ph |
| 2-1547 | 5 | CONHCO | — | 2-(MeOOC)Ph |
| 2-1548 | 5 | CONHCO | — | 4-(MeOOC)Ph |
| 2-1549 | 5 | CONHCO | — | 2-(EtOOC)Ph |
| 2-1550 | 5 | CONHCO | — | 4-(EtOOC)Ph |
| 2-1551 | 5 | CONHCO | — | 2-(tBuOOC)Ph |
| 2-1552 | 5 | CONHCO | — | 4-(tBuOOC)Ph |
| 2-1553 | 5 | CONHCO | — | 2-Cl-Ph |
| 2-1554 | 5 | CONHCO | — | 4-Cl-Ph |
| 2-1555 | 5 | CONHCO | — | 2-Br-Ph |
| 2-1556 | 5 | CONHCO | — | 4-Br-Ph |
| 2-1557 | 5 | CONHCO | — | 2-I-Ph |
| 2-1558 | 5 | CONHCO | — | 4-I-Ph |
| 2-1559 | 5 | CONHCO | — | 2-NO₂-Ph |
| 2-1560 | 5 | CONHCO | — | 4-NO₂-Ph |
| 2-1561 | 5 | CONHCO | — | 2-NH₂-Ph |
| 2-1562 | 5 | CONHCO | — | 4-NH₂-Ph |
| 2-1563 | 5 | CONHCO | — | 2-(HO₃S)Ph |
| 2-1564 | 5 | CONHCO | — | 4-(HO₃S)Ph |
| 2-1565 | 5 | CONHCO | — | 2-(NH₂O₂S)Ph |
| 2-1566 | 5 | CONHCO | — | 4-9NH₂O₂S)Ph |
| 2-1567 | 5 | CONHCO | — | 2-CN-Ph |
| 2-1568 | 5 | CONHCO | — | 4-CN-Ph |
| 2-1569 | 5 | CONHCO | — | 2-(HOCH₂)Ph |
| 2-1570 | 5 | CONHCO | — | 4-(HOCH₂)Ph |
| 2-1571 | 5 | CONHCO | — | Me |
| 2-1572 | 5 | CONHCO | — | Et |
| 2-1573 | 5 | CONHCO | — | Pr |
| 2-1574 | 5 | CONHCO | — | iPr |
| 2-1575 | 5 | CONHCO | — | Bu |
| 2-1576 | 5 | CONHCO | — | HOOCCH₂— |
| 2-1577 | 5 | CONHCO | — | MeOOCCH₂— |
| 2-1578 | 5 | CONHCO | — | MeCH(COOH) |
| 2-1579 | 5 | CONHCO | — | HOOC—(CH₂)₂— |
| 2-1580 | 5 | CONHCO | — | MeCH(COOMe) |
| 2-1581 | 5 | CONHCO | — | 1-HOOC-iBu |
| 2-1582 | 5 | CONHCO | — | 1-MeOOC-iBu |
| 2-1583 | 5 | CONHCO | — | 1-HOOC-iPn |
| 2-1584 | 5 | CONHCO | — | 1-MeOOC-iPn |
| 2-1585 | 5 | CONHCO | — | 1-HOOC-2-Me-Bu |
| 2-1586 | 5 | CONHCO | — | 1-MeOOC-2-Me-Bu |
| 2-1587 | 5 | CONHCO | — | CH₂CH₂SO₃H |
| 2-1588 | 5 | CONHCO | — | Z-1 |
| 2-1589 | 5 | CONHCO | — | Z-2 |
| 2-1590 | 5 | CONHCO | — | Z-3 |
| 2-1591 | 5 | CONHCO | — | Z-4 |
| 2-1592 | 5 | CONHCO | — | Z-5 |
| 2-1593 | 5 | CONHCO | — | Z-6 |
| 2-1594 | 5 | CONHCO | — | Z-7 |
| 2-1595 | 5 | CONHCO | — | Z-8 |
| 2-1596 | 5 | CONHCO | — | Z-9 |
| 2-1597 | 5 | CONHCO | — | Z-10 |
| 2-1598 | 5 | CONHCO | — | Z-11 |
| 2-1599 | 5 | CONHCO | — | Z-12 |
| 2-1600 | 5 | CONHCO | — | 3-Py |
| 2-1601 | 5 | CONHCO | — | 4-Py |
| 2-1602 | 5 | CON(Ac)CO | — | H |
| 2-1603 | 5 | CON(Ac)CO | — | Ph |
| 2-1604 | 5 | CON(Ac)CO | — | 2-Me-Ph |
| 2-1605 | 5 | CON(Ac)CO | — | 4-Me-Ph |
| 2-1606 | 5 | CON(Ac)CO | — | 2,4-diMe-Ph |
| 2-1607 | 5 | CON(Ac)CO | — | 3,4-diMe-Ph |
| 2-1608 | 5 | CON(Ac)CO | — | 2-(CF₃)Ph |
| 2-1609 | 5 | CON(Ac)CO | — | 4-(CF₃)Ph |
| 2-1610 | 5 | CON(Ac)CO | — | 2-MeOPh |
| 2-1611 | 5 | CON(Ac)CO | — | 4-MeOPh |
| 2-1612 | 5 | CON(Ac)CO | — | 2-EtOPh |
| 2-1613 | 5 | CON(Ac)CO | — | 4-EtOPh |
| 2-1614 | 5 | CON(Ac)CO | — | 2-HOPh |
| 2-1615 | 5 | CON(Ac)CO | — | 4-HOPh |
| 2-1616 | 5 | CON(Ac)CO | — | 2-(HOOC)Ph |
| 2-1617 | 5 | CON(Ac)CO | — | 4-(HOOC)Ph |
| 2-1618 | 5 | CON(Ac)CO | — | 2-(MeOOC)Ph |
| 2-1619 | 5 | CON(Ac)CO | — | 4-(MeOOC)Ph |
| 2-1620 | 5 | CON(Ac)CO | — | 2-(EtOOC)Ph |
| 2-1621 | 5 | CON(Ac)CO | — | 4-(EtOOC)Ph |
| 2-1622 | 5 | CON(Ac)CO | — | 2-(tBuOOC)Ph |
| 2-1623 | 5 | CON(Ac)CO | — | 4-(tBuOOC)Ph |
| 2-1624 | 5 | CON(Ac)CO | — | 2-Cl-Ph |
| 2-1625 | 5 | CON(Ac)CO | — | 4-Cl-Ph |
| 2-1626 | 5 | CON(Ac)CO | — | 2-Br-Ph |
| 2-1627 | 5 | CON(Ac)CO | — | 4-Br-Ph |
| 2-1628 | 5 | CON(Ac)CO | — | 2-I-Ph |
| 2-1629 | 5 | CON(Ac)CO | — | 4-I-Ph |
| 2-1630 | 5 | CON(Ac)CO | — | 2-NO₂-Ph |
| 2-1631 | 5 | CON(Ac)CO | — | 4-NO₂-Ph |
| 2-1632 | 5 | CON(Ac)CO | — | 2-NH₂-Ph |
| 2-1633 | 5 | CON(Ac)CO | — | 4-NH₂-Ph |
| 2-1634 | 5 | CON(Ac)CO | — | 2-(HO₃S)Ph |
| 2-1635 | 5 | CON(Ac)CO | — | 4-(HO₃S)Ph |
| 2-1636 | 5 | CON(Ac)CO | — | 2-(NH₂O₂S)Ph |
| 2-1637 | 5 | CON(Ac)CO | — | 4-(NH₂O₂S)Ph |
| 2-1638 | 5 | CON(Ac)CO | — | 2-CN-Ph |
| 2-1639 | 5 | CON(Ac)CO | — | 4-CN-Ph |
| 2-1640 | 5 | CON(Ac)CO | — | 2-(HOCH₂)Ph |
| 2-1641 | 5 | CON(Ac)CO | — | 4-(HOCH₂)Ph |
| 2-1642 | 5 | CON(Ac)CO | — | Me |
| 2-1643 | 5 | CON(Ac)CO | — | Et |
| 2-1644 | 5 | CON(Ac)CO | — | Pr |
| 2-1645 | 5 | CON(Ac)CO | — | iPr |
| 2-1646 | 5 | CON(Ac)CO | — | Bu |
| 2-1647 | 5 | CON(Ac)CO | — | HOOCCH₂— |
| 2-1648 | 5 | CON(Ac)CO | — | MeOOCCH₂— |
| 2-1649 | 5 | CON(Ac)CO | — | MeCH(COOH) |
| 2-1650 | 5 | CON(Ac)CO | — | HOOC—(CH₂)₂— |
| 2-1651 | 5 | CON(Ac)CO | — | MeCH(COOMe) |
| 2-1652 | 5 | CON(Ac)CO | — | 1-HOOC-iBu |
| 2-1653 | 5 | CON(Ac)CO | — | 1-MeOOC-iBu |
| 2-1654 | 5 | CON(Ac)CO | — | 1-HOOC-iPn |
| 2-1655 | 5 | CON(Ac)CO | — | 1-MeOOC-iPn |
| 2-1656 | 5 | CON(Ac)CO | — | 1-HOOC-2-Me-Bu |
| 2-1657 | 5 | CON(Ac)CO | — | 1-MeOOC-2-Me-Bu |
| 2-1658 | 5 | CON(Ac)CO | — | CH₂CH₂SO₃H |
| 2-1659 | 5 | CON(Ac)CO | — | Z-1 |
| 2-1660 | 5 | CON(Ac)CO | — | Z-2 |
| 2-1661 | 5 | CON(Ac)CO | — | Z-3 |

TABLE 2-continued

| Cpd. No. | k | A | B | R¹ |
|---|---|---|---|---|
| 2-1662 | 5 | CON(Ac)CO | — | Z-4 |
| 2-1663 | 5 | CON(Ac)CO | — | Z-5 |
| 2-1664 | 5 | CON(Ac)CO | — | Z-6 |
| 2-1665 | 5 | CON(Ac)CO | — | Z-7 |
| 2-1666 | 5 | CON(Ac)CO | — | Z-8 |
| 2-1667 | 5 | CON(Ac)CO | — | Z-9 |
| 2-1668 | 5 | CON(Ac)CO | — | Z-10 |
| 2-1669 | 5 | CON(Ac)CO | — | Z-11 |
| 2-1670 | 5 | CON(Ac)CO | — | Z-12 |
| 2-1671 | 5 | CON(Ac)CO | — | 3-Py |
| 2-1672 | 5 | CON(Ac)CO | — | 4-Py |
| 2-1673 | 5 | CONHCO | NH | H |
| 2-1674 | 5 | CONHCO | NH | Ph |
| 2-1675 | 5 | CONHCO | NH | 2-Me-Ph |
| 2-1676 | 5 | CONHCO | NH | 4-Me-Ph |
| 2-1677 | 5 | CONHCO | NH | 2,4-diMe-Ph |
| 2-1678 | 5 | CONHCO | NH | 3,4-diMe-Ph |
| 2-1679 | 5 | CONHCO | NH | 2-($CF_3$)Ph |
| 2-1680 | 5 | CONHCO | NH | 4-($CF_3$)Ph |
| 2-1681 | 5 | CONHCO | NH | 2-MeOPh |
| 2-1682 | 5 | CONHCO | NH | 4-MeOPh |
| 2-1683 | 5 | CONHCO | NH | 2-EtOPh |
| 2-1684 | 5 | CONHCO | NH | 4-EtOPh |
| 2-1685 | 5 | CONHCO | NH | 2-HOPh |
| 2-1686 | 5 | CONHCO | NH | 4-HOPh |
| 2-1687 | 5 | CONHCO | NH | 2-(HOOC)Ph |
| 2-1688 | 5 | CONHCO | NH | 4-(HOOC)Ph |
| 2-1689 | 5 | CONHCO | NH | 2-(MeOOC)Ph |
| 2-1690 | 5 | CONHCO | NH | 4-(MeOOC)Ph |
| 2-1691 | 5 | CONHCO | NH | 2-(EtOOC)Ph |
| 2-1692 | 5 | CONHCO | NH | 4-(EtOOC)Ph |
| 2-1693 | 5 | CONHCO | NH | 2-(tBuOOC)Ph |
| 2-1694 | 5 | CONHCO | NH | 4-(tBuOOC)Ph |
| 2-1695 | 5 | CONHCO | NH | 2-Cl-Ph |
| 2-1696 | 5 | CONHCO | NH | 4-Cl-Ph |
| 2-1697 | 5 | CONHCO | NH | 2-Br-Ph |
| 2-1698 | 5 | CONHCO | NH | 4-Br-Ph |
| 2-1699 | 5 | CONHCO | NH | 2-I-Ph |
| 2-1700 | 5 | CONHCO | NH | 4-I-Ph |
| 2-1701 | 5 | CONHCO | NH | 2-$NO_2$-Ph |
| 2-1702 | 5 | CONHCO | NH | 4-$NO_2$-Ph |
| 2-1703 | 5 | CONHCO | NH | 2-$NH_2$-Ph |
| 2-1704 | 5 | CONHCO | NH | 4-$NH_2$-Ph |
| 2-1705 | 5 | CONHCO | NH | 2-($HO_3$S)Ph |
| 2-1706 | 5 | CONHCO | NH | 4-($HO_3$S)Ph |
| 2-1707 | 5 | CONHCO | NH | 2-($NH_2O_2$S)Ph |
| 2-1708 | 5 | CONHCO | NH | 4-($NH_2O_2$S)Ph |
| 2-1709 | 5 | CONHCO | NH | 2-CN-Ph |
| 2-1710 | 5 | CONHCO | NH | 4-CN-Ph |
| 2-1711 | 5 | CONHCO | NH | 2-($HOCH_2$)Ph |
| 2-1712 | 5 | CONHCO | NH | 4-($HOCH_2$)Ph |
| 2-1713 | 5 | CONHCO | NH | Me |
| 2-1714 | 5 | CONHCO | NH | Et |
| 2-1715 | 5 | CONHCO | NH | Pr |
| 2-1716 | 5 | CONHCO | NH | iPr |
| 2-1717 | 5 | CONHCO | NH | Bu |
| 2-1718 | 5 | CONHCO | NH | HOOC$CH_2$— |
| 2-1719 | 5 | CONHCO | NH | MeOOC$CH_2$— |
| 2-1720 | 5 | CONHCO | NH | MeCH(COOH) |
| 2-1721 | 5 | CONHCO | NH | HOOC—($CH_2$)$_2$— |
| 2-1722 | 5 | CONHCO | NH | MeCH(COOMe) |
| 2-1723 | 5 | CONHCO | NH | 1-HOOC-iBu |
| 2-1724 | 5 | CONHCO | NH | 1-MeOOC-iBu |
| 2-1725 | 5 | CONHCO | NH | 1-HOOC-iPn |
| 2-1726 | 5 | CONHCO | NH | 1-MeOOC-iPn |
| 2-1727 | 5 | CONHCO | NH | 1-HOOC-2-Me-Bu |
| 2-1728 | 5 | CONHCO | NH | 1-MeOOC-2-Me-Bu |
| 2-1729 | 5 | CONHCO | NH | $CH_2CH_2SO_3$H |
| 2-1730 | 5 | CONHCO | NH | HO |
| 2-1731 | 5 | CONHCO | NH | MeO |
| 2-1732 | 5 | CONHCO | NH | EtO |
| 2-1733 | 5 | CONHCO | NH | PrO |
| 2-1734 | 5 | CONHCO | NH | iPrO |
| 2-1735 | 5 | CONHCO | NH | BuO |
| 2-1736 | 5 | CONHCO | NH | iBuO |
| 2-1737 | 5 | CONHCO | NH | sBuO |
| 2-1738 | 5 | CONHCO | NH | tBuO |
| 2-1739 | 5 | CONHCO | NH | HxO |
| 2-1740 | 5 | CONHCO | NH | PhO |
| 2-1741 | 5 | CONHCO | NH | BnO |
| 2-1742 | 5 | CONHCO | NH | Z-1 |
| 2-1743 | 5 | CONHCO | NH | Z-2 |
| 2-1744 | 5 | CONHCO | NH | Z-3 |
| 2-1745 | 5 | CONHCO | NH | Z-4 |
| 2-1746 | 5 | CONHCO | NH | Z-5 |
| 2-1747 | 5 | CONHCO | NH | Z-6 |
| 2-1748 | 5 | CONHCO | NH | Z-7 |
| 2-1749 | 5 | CONHCO | NH | Z-8 |
| 2-1750 | 5 | CONHCO | NH | Z-9 |
| 2-1751 | 5 | CONHCO | NH | Z-10 |
| 2-1752 | 5 | CONHCO | NH | Z-11 |
| 2-1753 | 5 | CONHCO | NH | Z-12 |
| 2-1754 | 5 | CONHCO | NH | 3-Py |
| 2-1755 | 5 | CONHCO | NH | 4-Py |
| 2-1756 | 5 | CONH$SO_2$ | — | H |
| 2-1757 | 5 | CONH$SO_2$ | — | Ph |
| 2-1758 | 5 | CONH$SO_2$ | — | 2-Me-Ph |
| 2-1759 | 5 | CONH$SO_2$ | — | 4-Me-Ph |
| 2-1760 | 5 | CONH$SO_2$ | — | 2,4-diMe-Ph |
| 2-1761 | 5 | CONH$SO_2$ | — | 3,4-diMe-Ph |
| 2-1762 | 5 | CONH$SO_2$ | — | 2-($CF_3$)Ph |
| 2-1763 | 5 | CONH$SO_2$ | — | 4-($CF_3$)Ph |
| 2-1764 | 5 | CONH$SO_2$ | — | 2-MeOPh |
| 2-1765 | 5 | CONH$SO_2$ | — | 4-MeOPh |
| 2-1766 | 5 | CONH$SO_2$ | — | 2-EtOPh |
| 2-1767 | 5 | CONH$SO_2$ | — | 4-EtOPh |
| 2-1768 | 5 | CONH$SO_2$ | — | 2-HOPh |
| 2-1769 | 5 | CONH$SO_2$ | — | 4-HOPh |
| 2-1770 | 5 | CONH$SO_2$ | — | 2-(HOOC)Ph |
| 2-1771 | 5 | CONH$SO_2$ | — | 4-(HOOC)Ph |
| 2-1772 | 5 | CONH$SO_2$ | — | 2-(MeOOC)Ph |
| 2-1773 | 5 | CONH$SO_2$ | — | 4-(MeOOC)Ph |
| 2-1774 | 5 | CONH$SO_2$ | — | 2-(EtOOC)Ph |
| 2-1775 | 5 | CONH$SO_2$ | — | 4-(EtOOC)Ph |
| 2-1776 | 5 | CONH$SO_2$ | — | 2-(tBuOOC)Ph |
| 2-1777 | 5 | CONH$SO_2$ | — | 4-(tBuOOC)Ph |
| 2-1778 | 5 | CONH$SO_2$ | — | 2-Cl-Ph |
| 2-1779 | 5 | CONH$SO_2$ | — | 4-Cl-Ph |
| 2-1780 | 5 | CONH$SO_2$ | — | 2-Br-Ph |
| 2-1781 | 5 | CONH$SO_2$ | — | 4-Br-Ph |
| 2-1782 | 5 | CONH$SO_2$ | — | 2-I-Ph |
| 2-1783 | 5 | CONH$SO_2$ | — | 4-I-Ph |
| 2-1784 | 5 | CONH$SO_2$ | — | 2-$NO_2$-Ph |
| 2-1785 | 5 | CONH$SO_2$ | — | 4-$NO_2$-Ph |
| 2-1786 | 5 | CONH$SO_2$ | — | 2-$NH_2$-Ph |
| 2-1787 | 5 | CONH$SO_2$ | — | 4-$NH_2$-Ph |
| 2-1788 | 5 | CONH$SO_2$ | — | 2-($HO_3$S)Ph |
| 2-1789 | 5 | CONH$SO_2$ | — | 4-($HO_3$S)Ph |
| 2-1790 | 5 | CONH$SO_2$ | — | 2-($NH_2$)$_2$S)Ph |
| 2-1791 | 5 | CONH$SO_2$ | — | 4-($NH_2$)$_2$S)Ph |
| 2-1792 | 5 | CONH$SO_2$ | — | 2-CN-Ph |
| 2-1793 | 5 | CONH$SO_2$ | — | 4-CN-Ph |
| 2-1794 | 5 | CONH$SO_2$ | — | 2-($HOCH_2$)Ph |
| 2-1795 | 5 | CONH$SO_2$ | — | 4-($HOCH_2$)Ph |
| 2-1796 | 5 | CONH$SO_2$ | — | Me |
| 2-1797 | 5 | CONH$SO_2$ | — | Et |
| 2-1798 | 5 | CONH$SO_2$ | — | Pr |
| 2-1799 | 5 | CONH$SO_2$ | — | iPr |
| 2-1800 | 5 | CONH$SO_2$ | — | Bu |
| 2-1801 | 5 | CONH$SO_2$ | — | HOOC$CH_2$— |
| 2-1802 | 5 | CONH$SO_2$ | — | MeOOC$CH_2$— |
| 2-1803 | 5 | CONH$SO_2$ | — | MeCH(COOH) |
| 2-1804 | 5 | CONH$SO_2$ | — | HOOC—($CH_2$)$_2$— |
| 2-1805 | 5 | CONH$SO_2$ | — | MeCH(COOMe) |
| 2-1806 | 5 | CONH$SO_2$ | — | 1-HOOC-iBu |
| 2-1807 | 5 | CONH$SO_2$ | — | 1-MeOOC-iBu |
| 2-1808 | 5 | CONH$SO_2$ | — | 1-HOOC-iPn |
| 2-1809 | 5 | CONH$SO_2$ | — | 1-MeOOC-iPn |
| 2-1810 | 5 | CONH$SO_2$ | — | 1-HOOC-2-Me-Bu |
| 2-1811 | 5 | CONH$SO_2$ | — | 1-MeOOC-2-Me-Bu |
| 2-1812 | 5 | CONH$SO_2$ | — | $CH_2CH_2SO_3$H |
| 2-1813 | 5 | CONH$SO_2$ | — | OH |

TABLE 2-continued

| Cpd. No. | k | A | B | R¹ |
|---|---|---|---|---|
| 2-1814 | 5 | CONHSO₂ | — | MeO |
| 2-1815 | 5 | CONHSO₂ | — | EtO |
| 2-1816 | 5 | CONHSO₂ | — | PrO |
| 2-1817 | 5 | CONHSO₂ | — | iPrO |
| 2-1818 | 5 | CONHSO₂ | — | BuO |
| 2-1819 | 5 | CONHSO₂ | — | iBuO |
| 2-1820 | 5 | CONHSO₂ | — | sBuO |
| 2-1821 | 5 | CONHSO₂ | — | tBuO |
| 2-1822 | 5 | CONHSO₂ | — | HxO |
| 2-1823 | 5 | CONHSO₂ | — | PhO |
| 2-1824 | 5 | CONHSO₂ | — | BnO |
| 2-1825 | 5 | CONHSO₂ | — | Z-1 |
| 2-1826 | 5 | CONHSO₂ | — | Z-2 |
| 2-1827 | 5 | CONHSO₂ | — | Z-3 |
| 2-1828 | 5 | CONHSO₂ | — | Z-4 |
| 2-1829 | 5 | CONHSO₂ | — | Z-5 |
| 2-1830 | 5 | CONHSO₂ | — | Z-6 |
| 2-1831 | 5 | CONHSO₂ | — | Z-7 |
| 2-1832 | 5 | CONHSO₂ | — | Z-8 |
| 2-1833 | 5 | CONHSO₂ | — | Z-9 |
| 2-1834 | 5 | CONHSO₂ | — | Z-10 |
| 2-1835 | 5 | CONHSO₂ | — | Z-11 |
| 2-1836 | 5 | CONHSO₂ | — | Z-12 |
| 2-1837 | 5 | CONHSO₂ | — | 3-Py |
| 2-1838 | 5 | CONHSO₂ | — | 4-Py |
| 2-1839 | 5 | CONHSO₂ | NH | H |
| 2-1840 | 5 | CONHSO₂ | NH | Ph |
| 2-1841 | 5 | CONHSO₂ | NH | 2-Me-Ph |
| 2-1842 | 5 | CONHSO₂ | NH | 4-Me-Ph |
| 2-1843 | 5 | CONHSO₂ | NH | 2,4-diMe-Ph |
| 2-1844 | 5 | CONHSO₂ | NH | 3,4-diMe-Ph |
| 2-1845 | 5 | CONHSO₂ | NH | 2-(CF₃)Ph |
| 2-1846 | 5 | CONHSO₂ | NH | 4-(CF₃)Ph |
| 2-1847 | 5 | CONHSO₂ | NH | 2-MeOPh |
| 2-1848 | 5 | CONHSO₂ | NH | 4-MeOPh |
| 2-1849 | 5 | CONHSO₂ | NH | 2-EtOPh |
| 2-1850 | 5 | CONHSO₂ | NH | 4-EtOPh |
| 2-1851 | 5 | CONHSO₂ | NH | 2-HOPh |
| 2-1852 | 5 | CONHSO₂ | NH | 4-HOPh |
| 2-1853 | 5 | CONHSO₂ | NH | 2-(HOOC)Ph |
| 2-1854 | 5 | CONHSO₂ | NH | 4-(HOOC)Ph |
| 2-1855 | 5 | CONHSO₂ | NH | 2-(MeOOC)Ph |
| 2-1856 | 5 | CONHSO₂ | NH | 4-(MeOOC)Ph |
| 2-1857 | 5 | CONHSO₂ | NH | 2-(EtOOC)Ph |
| 2-1858 | 5 | CONHSO₂ | NH | 4-(EtOOC)Ph |
| 2-1859 | 5 | CONHSO₂ | NH | 2-(tBuOOC)Ph |
| 2-1860 | 5 | CONHSO₂ | NH | 4-(tBuOOC)Ph |
| 2-1861 | 5 | CONHSO₂ | NH | 2-Cl-Ph |
| 2-1862 | 5 | CONHSO₂ | NH | 4-Cl-Ph |
| 2-1863 | 5 | CONHSO₂ | NH | 2-Br-Ph |
| 2-1864 | 5 | CONHSO₂ | NH | 4-Br-Ph |
| 2-1865 | 5 | CONHSO₂ | NH | 2-I-Ph |
| 2-1866 | 5 | CONHSO₂ | NH | 4-I-Ph |
| 2-1867 | 5 | CONHSO₂ | NH | 2-NO₂-Ph |
| 2-1868 | 5 | CONHSO₂ | NH | 4-NO₂-Ph |
| 2-1869 | 5 | CONHSO₂ | NH | 2-NH₂-Ph |
| 2-1870 | 5 | CONHSO₂ | NH | 4-NH₂-Ph |
| 2-1871 | 5 | CONHSO₂ | NH | 2-(HO₃S)Ph |
| 2-1872 | 5 | CONHSO₂ | NH | 4-(HO₃S)Ph |
| 2-1873 | 5 | CONHSO₂ | NH | 2-(NH₂O₂S)Ph |
| 2-1874 | 5 | CONHSO₂ | NH | 4-(NH₂O₂S)Ph |
| 2-1875 | 5 | CONHSO₂ | NH | 2-CN-Ph |
| 2-1876 | 5 | CONHSO₂ | NH | 4-CN-Ph |
| 2-1877 | 5 | CONHSO₂ | NH | 2-(HOCH₂)Ph |
| 2-1878 | 5 | CONHSO₂ | NH | 4-(HOCH₂)Ph |
| 2-1879 | 5 | CONHSO₂ | NH | Me |
| 2-1880 | 5 | CONHSO₂ | NH | Et |
| 2-1881 | 5 | CONHSO₂ | NH | Pr |
| 2-1882 | 5 | CONHSO₂ | NH | iPr |
| 2-1883 | 5 | CONHSO₂ | NH | Bu |
| 2-1884 | 5 | CONHSO₂ | NH | HOOCCH₂— |
| 2-1885 | 5 | CONHSO₂ | NH | MeOOCCH₂— |
| 2-1886 | 5 | CONHSO₂ | NH | MeCH(COOH) |
| 2-1887 | 5 | CONHSO₂ | NH | HOOC—(CH₂)₂— |
| 2-1888 | 5 | CONHSO₂ | NH | MeCH(COOMe) |
| 2-1889 | 5 | CONHSO₂ | NH | 1-HOOC-iBu |
| 2-1890 | 5 | CONHSO₂ | NH | 1-MeOOC-iBu |
| 2-1891 | 5 | CONHSO₂ | NH | 1-HOOC-iPn |
| 2-1892 | 5 | CONHSO₂ | NH | 1-MeOOC-iPn |
| 2-1893 | 5 | CONHSO₂ | NH | 1-HOOC-2-Me-Bu |
| 2-1894 | 5 | CONHSO₂ | NH | 1-MeOOC-2-Me-Bu |
| 2-1895 | 5 | CONHSO₂ | NH | CH₂CH₂SO₃H |
| 2-1896 | 5 | CONHSO₂ | NH | OH |
| 2-1897 | 5 | CONHSO₂ | NH | MeO |
| 2-1898 | 5 | CONHSO₂ | NH | EtO |
| 2-1899 | 5 | CONHSO₂ | NH | PrO |
| 2-1900 | 5 | CONHSO₂ | NH | iPrO |
| 2-1901 | 5 | CONHSO₂ | NH | BuO |
| 2-1902 | 5 | CONHSO₂ | NH | iBuO |
| 2-1903 | 5 | CONHSO₂ | NH | sBuO |
| 2-1904 | 5 | CONHSO₂ | NH | tBuO |
| 2-1905 | 5 | CONHSO₂ | NH | HxO |
| 2-1906 | 5 | CONHSO₂ | NH | PhO |
| 2-1907 | 5 | CONHSO₂ | NH | BnO |
| 2-1908 | 5 | CONHSO₂ | NH | Z-1 |
| 2-1909 | 5 | CONHSO₂ | NH | Z-2 |
| 2-1910 | 5 | CONHSO₂ | NH | Z-3 |
| 2-1911 | 5 | CONHSO₂ | NH | Z-4 |
| 2-1912 | 5 | CONHSO₂ | NH | Z-5 |
| 2-1913 | 5 | CONHSO₂ | NH | Z-6 |
| 2-1914 | 5 | CONHSO₂ | NH | Z-7 |
| 2-1915 | 5 | CONHSO₂ | NH | Z-8 |
| 2-1916 | 5 | CONHSO₂ | NH | Z-9 |
| 2-1917 | 5 | CONHSO₂ | NH | Z-10 |
| 2-1918 | 5 | CONHSO₂ | NH | Z-11 |
| 2-1919 | 5 | CONHSO₂ | NH | Z-12 |
| 2-1920 | 5 | CONHSO₂ | NH | 3-Py |
| 2-1921 | 5 | CONHSO₂ | NH | 4-Py |
| 2-1922 | 5 | NHCO | — | H |
| 2-1923 | 5 | NHCO | — | Ph |
| 2-1924 | 5 | NHCO | — | 2-Me-Ph |
| 2-1925 | 5 | NHCO | — | 4-Me-Ph |
| 2-1926 | 5 | NHCO | — | 2,4-diMe-Ph |
| 2-1927 | 5 | NHCO | — | 3,4-diMe-Ph |
| 2-1928 | 5 | NHCO | — | 2-(CF₃)Ph |
| 2-1929 | 5 | NHCO | — | 4-(CF₃)Ph |
| 2-1930 | 5 | NHCO | — | 2-MeOPh |
| 2-1931 | 5 | NHCO | — | 4-MeOPh |
| 2-1932 | 5 | NHCO | — | 2-EtOPh |
| 2-1933 | 5 | NHCO | — | 4-EtOPh |
| 2-1934 | 5 | NHCO | — | 2-HOPh |
| 2-1935 | 5 | NHCO | — | 4-HOPh |
| 2-1936 | 5 | NHCO | — | 2-(HOOC)Ph |
| 2-1937 | 5 | NHCO | — | 4-(HOOC)Ph |
| 2-1938 | 5 | NHCO | — | 2-(MeOOC)Ph |
| 2-1939 | 5 | NHCO | — | 4-(MeOOC)Ph |
| 2-1940 | 5 | NHCO | — | 2-(EtOOC)Ph |
| 2-1941 | 5 | NHCO | — | 4-(EtOOC)Ph |
| 2-1942 | 5 | NHCO | — | 2-(tBuOOC)Ph |
| 2-1943 | 5 | NHCO | — | 4-(tBuOOC)Ph |
| 2-1944 | 5 | NHCO | — | 2-Cl-Ph |
| 2-1945 | 5 | NHCO | — | 4-Cl-Ph |
| 2-1946 | 5 | NHCO | — | 2-Br-Ph |
| 2-1947 | 5 | NHCO | — | 4-Br-Ph |
| 2-1948 | 5 | NHCO | — | 2-I-Ph |
| 2-1949 | 5 | NHCO | — | 4-I-Ph |
| 2-1950 | 5 | NHCO | — | 2-NO₂-Ph |
| 2-1951 | 5 | NHCO | — | 4-NO₂-Ph |
| 2-1952 | 5 | NHCO | — | 2-NH₂-Ph |
| 2-1953 | 5 | NHCO | — | 4-NH₂-Ph |
| 2-1954 | 5 | NHCO | — | 2-(HO₃S)Ph |
| 2-1955 | 5 | NHCO | — | 4-(HO₃S)Ph |
| 2-1956 | 5 | NHCO | — | 2-(NH₂O₂S)Ph |
| 2-1957 | 5 | NHCO | — | 4-(NH₂O₂S)Ph |
| 2-1958 | 5 | NHCO | — | 2-CN-Ph |
| 2-1959 | 5 | NHCO | — | 4-CN-Ph |
| 2-1960 | 5 | NHCO | — | 2-(HOCH₂)Ph |
| 2-1961 | 5 | NHCO | — | 4-(HOCH₂)Ph |
| 2-1962 | 5 | NHCO | — | Me |
| 2-1963 | 5 | NHCO | — | Et |
| 2-1964 | 5 | NHCO | — | Pr |
| 2-1965 | 5 | NHCO | — | iPr |

TABLE 2-continued

| Cpd. No. | k | A | B | R¹ |
|---|---|---|---|---|
| 2-1966 | 5 | NHCO | — | Bu |
| 2-1967 | 5 | NHCO | — | HOOCCH$_2$— |
| 2-1968 | 5 | NHCO | — | MeOOCCH$_2$— |
| 2-1969 | 5 | NHCO | — | MeCH(COOH) |
| 2-1970 | 5 | NHCO | — | HOOC—(CH$_2$)$_2$— |
| 2-1971 | 5 | NHCO | — | MeCH(COOMe) |
| 2-1972 | 5 | NHCO | — | 1-HOOC-iBu |
| 2-1973 | 5 | NHCO | — | 1-HOOC-iPn |
| 2-1974 | 5 | NHCO | — | 1-HOOC-2-Me-Bu |
| 2-1975 | 5 | NHCO | — | CH$_2$CH$_2$SO$_3$H |
| 2-1976 | 5 | NHCO | — | MeO |
| 2-1977 | 5 | NHCO | — | EtO |
| 2-1978 | 5 | NHCO | — | PrO |
| 2-1979 | 5 | NHCO | — | Z-1 |
| 2-1980 | 5 | NHCO | — | Z-2 |
| 2-1981 | 5 | NHCO | — | Z-3 |
| 2-1982 | 5 | NHCO | — | Z-4 |
| 2-1983 | 5 | NHCO | — | Z-5 |
| 2-1984 | 5 | NHCO | — | Z-6 |
| 2-1985 | 5 | NHCO | — | Z-7 |
| 2-1986 | 5 | NHCO | — | Z-8 |
| 2-1987 | 5 | NHCO | — | Z-9 |
| 2-1988 | 5 | NHCO | — | Z-10 |
| 2-1989 | 5 | NHCO | — | Z-11 |
| 2-1990 | 5 | NHCO | — | Z-12 |
| 2-1991 | 5 | NHCO | — | 3-Py |
| 2-1992 | 5 | NHCO | — | 4-Py |
| 2-1993 | 5 | NHCO | NH | H |
| 2-1994 | 5 | NHCO | NH | Ph |
| 2-1995 | 5 | NHCO | NH | 2-Me-Ph |
| 2-1996 | 5 | NHCO | NH | 4-Me-Ph |
| 2-1997 | 5 | NHCO | NH | 2,4-diMe-Ph |
| 2-1998 | 5 | NHCO | NH | 3,4-diMe-Ph |
| 2-1999 | 5 | NHCO | NH | 2-(CF$_3$)Ph |
| 2-2000 | 5 | NHCO | NH | 4-(CF$_3$)Ph |
| 2-2001 | 5 | NHCO | NH | 2-Me-Ph |
| 2-2002 | 5 | NHCO | NH | 4-Me-Ph |
| 2-2003 | 5 | NHCO | NH | 2-EtOPh |
| 2-2004 | 5 | NHCO | NH | 4-EtOPh |
| 2-2005 | 5 | NHCO | NH | 2-HOPh |
| 2-2006 | 5 | NHCO | NH | 4-HOPh |
| 2-2007 | 5 | NHCO | NH | 2-(HOOC)Ph |
| 2-2008 | 5 | NHCO | NH | 4-(HOOC)Ph |
| 2-2009 | 5 | NHCO | NH | 2-(MeOOC)Ph |
| 2-2010 | 5 | NHCO | NH | 4-(MeOOC)Ph |
| 2-2011 | 5 | NHCO | NH | 2-(EtOOC)Ph |
| 2-2012 | 5 | NHCO | NH | 4-(EtOOC)Ph |
| 2-2013 | 5 | NHCO | NH | 2-(tBuOOC)Ph |
| 2-2014 | 5 | NHCO | NH | 4-(tBuOOC)Ph |
| 2-2015 | 5 | NHCO | NH | 2-Cl-Ph |
| 2-2016 | 5 | NHCO | NH | 4-Cl-Ph |
| 2-2017 | 5 | NHCO | NH | 2-Br-Ph |
| 2-2018 | 5 | NHCO | NH | 4-Br-Ph |
| 2-2019 | 5 | NHCO | NH | 2-I-Ph |
| 2-2020 | 5 | NHCO | NH | 4-I-Ph |
| 2-2021 | 5 | NHCO | NH | 2-NO$_2$-Ph |
| 2-2022 | 5 | NHCO | NH | 4-NO$_2$-Ph |
| 2-2023 | 5 | NHCO | NH | 2-NH$_2$-Ph |
| 2-2024 | 5 | NHCO | NH | 4-NH$_2$-Ph |
| 2-2025 | 5 | NHCO | NH | 2-(HO$_3$S)Ph |
| 2-2026 | 5 | NHCO | NH | 4-(HO$_3$S)Ph |
| 2-2027 | 5 | NHCO | NH | 2-(NH$_2$O$_2$S)Ph |
| 2-2028 | 5 | NHCO | NH | 4-(NH$_2$O$_2$S)Ph |
| 2-2029 | 5 | NHCO | NH | 2-CN-Ph |
| 2-2030 | 5 | NHCO | NH | 4-CN-Ph |
| 2-2031 | 5 | NHCO | NH | 2-(HOCH$_2$)Ph |
| 2-2032 | 5 | NHCO | NH | 4-(HOCH$_2$)Ph |
| 2-2033 | 5 | NHCO | NH | Me |
| 2-2034 | 5 | NHCO | NH | Et |
| 2-2035 | 5 | NHCO | NH | Pr |
| 2-2036 | 5 | NHCO | NH | iPr |
| 2-2037 | 5 | NHCO | NH | Bu |
| 2-2038 | 5 | NHCO | NH | HOOCCH$_2$— |
| 2-2039 | 5 | NHCO | NH | MeOOCCH$_2$— |
| 2-2040 | 5 | NHCO | NH | MeCH(COOH) |
| 2-2041 | 5 | NHCO | NH | HOOC—(CH$_2$)$_2$— |
| 2-2042 | 5 | NHCO | NH | MeCH(COOMe) |
| 2-2043 | 5 | NHCO | NH | 1-HOOC-iBu |
| 2-2044 | 5 | NHCO | NH | 1-MeOOC-iBu |
| 2-2045 | 5 | NHCO | NH | 1-HOOC-iPn |
| 2-2046 | 5 | NHCO | NH | 1-MeOOC-iPn |
| 2-2047 | 5 | NHCO | NH | 1-HOOC-2-Me-Bu |
| 2-2048 | 5 | NHCO | NH | 1-MeOOC-2-Me-Bu |
| 2-2049 | 5 | NHCO | NH | CH$_2$CH$_2$SO$_3$H |
| 2-2050 | 5 | NHCO | NH | OH |
| 2-2051 | 5 | NHCO | NH | MeO |
| 2-2052 | 5 | NHCO | NH | EtO |
| 2-2053 | 5 | NHCO | NH | PrO |
| 2-2054 | 5 | NHCO | NH | iPrO |
| 2-2055 | 5 | NHCO | NH | BuO |
| 2-2056 | 5 | NHCO | NH | iBuO |
| 2-2057 | 5 | NHCO | NH | sBuO |
| 2-2058 | 5 | NHCO | NH | tBuO |
| 2-2059 | 5 | NHCO | NH | HxO |
| 2-2060 | 5 | NHCO | NH | PhO |
| 2-2061 | 5 | NHCO | NH | BnO |
| 2-2062 | 5 | NHCO | NH | Z-1 |
| 2-2063 | 5 | NHCO | NH | Z-2 |
| 2-2064 | 5 | NHCO | NH | Z-3 |
| 2-2065 | 5 | NHCO | NH | Z-4 |
| 2-2066 | 5 | NHCO | NH | Z-5 |
| 2-2067 | 5 | NHCO | NH | Z-6 |
| 2-2068 | 5 | NHCO | NH | Z-7 |
| 2-2069 | 5 | NHCO | NH | Z-8 |
| 2-2070 | 5 | NHCO | NH | Z-9 |
| 2-2071 | 5 | NHCO | NH | Z-10 |
| 2-2072 | 5 | NHCO | NH | Z-11 |
| 2-2073 | 5 | NHCO | NH | Z-12 |
| 2-2074 | 5 | NHCO | NH | 3-Py |
| 2-2075 | 5 | NHCO | NH | 4-Py |
| 2-2076 | 5 | NHCO | NMe | Ph |
| 2-2077 | 5 | NHCO | NMe | 2-Me-Ph |
| 2-2078 | 5 | NHCO | NMe | 4-Me-Ph |
| 2-2079 | 5 | NHCO | NMe | 2,4-diMe-Ph |
| 2-2080 | 5 | NHCO | NMe | 3,4-diMe-Ph |
| 2-2081 | 5 | NHCO | NMe | 2-(CF$_3$)Ph |
| 2-2082 | 5 | NHCO | NMe | 4-(CF$_3$)Ph |
| 2-2083 | 5 | NHCO | NMe | 2-MeOPh |
| 2-2084 | 5 | NHCO | NMe | 4-MeOPh |
| 2-2085 | 5 | NHCO | NMe | 2-EtOPh |
| 2-2086 | 5 | NHCO | NMe | 4-EtOPh |
| 2-2087 | 5 | NHCO | NMe | 2-HOPh |
| 2-2088 | 5 | NHCO | NMe | 4-HOPh |
| 2-2089 | 5 | NHCO | NMe | 2-(HOOC)Ph |
| 2-2090 | 5 | NHCO | NMe | 4-(HOOC)Ph |
| 2-2091 | 5 | NHCO | NMe | 2-(MeOOC)Ph |
| 2-2092 | 5 | NHCO | NMe | 4-(MeOOC)Ph |
| 2-2093 | 5 | NHCO | NMe | 2-(EtOOC)Ph |
| 2-2094 | 5 | NHCO | NMe | 4-(EtOOC)Ph |
| 2-2095 | 5 | NHCO | NMe | 2-(tBuOOC)Ph |
| 2-2096 | 5 | NHCO | NMe | 4-(tBuOOC)Ph |
| 2-2097 | 5 | NHCO | NMe | 2-Cl-Ph |
| 2-2098 | 5 | NHCO | NMe | 4-Cl-Ph |
| 2-2099 | 5 | NHCO | NMe | 2-Br-Ph |
| 2-2100 | 5 | NHCO | NMe | 4-Br-Ph |
| 2-2101 | 5 | NHCO | NMe | 2-I-Ph |
| 2-2102 | 5 | NHCO | NMe | 4-I-Ph |
| 2-2103 | 5 | NHCO | NMe | 2-NO$_2$-Ph |
| 2-2104 | 5 | NHCO | NMe | 4-NO$_2$-Ph |
| 2-2105 | 5 | NHCO | NMe | 2-NH$_2$-Ph |
| 2-2106 | 5 | NHCO | NMe | 4-NH$_2$-Ph |
| 2-2107 | 5 | NHCO | NMe | 2-(HO$_3$S)Ph |
| 2-2108 | 5 | NHCO | NMe | 4-(HO$_3$S)Ph |
| 2-2109 | 5 | NHCO | NMe | 2-(NH$_2$O$_2$S)Ph |
| 2-2110 | 5 | NHCO | NMe | 4-(NH$_2$O$_2$S)Ph |
| 2-2111 | 5 | NHCO | NMe | 2-CN-Ph |
| 2-2112 | 5 | NHCO | NMe | 4-CN-Ph |
| 2-2113 | 5 | NHCO | NMe | 2-(HOCH$_2$)Ph |
| 2-2114 | 5 | NHCO | NMe | 4-(HOCH$_2$)Ph |
| 2-2115 | 5 | NHCO | NMe | Me |
| 2-2116 | 5 | NHCO | NMe | Et |
| 2-2117 | 5 | NHCO | NMe | Pr |

TABLE 2-continued

| Cpd. No. | k | A | B | R¹ |
|---|---|---|---|---|
| 2-2118 | 5 | NHCO | NMe | iPr |
| 2-2119 | 5 | NHCO | NMe | Bu |
| 2-2120 | 5 | NHCO | NMe | HOOCCH₂— |
| 2-2121 | 5 | NHCO | NMe | MeOOCCH₂— |
| 2-2122 | 5 | NHCO | NMe | MeCH(COOH) |
| 2-2123 | 5 | NHCO | NMe | HOOC—(CH₂)₂— |
| 2-2124 | 5 | NHCO | NMe | MeCH(COOMe) |
| 2-2125 | 5 | NHCO | NMe | 1-HOOC-iBu |
| 2-2126 | 5 | NHCO | NMe | 1-MeOOC-iBu |
| 2-2127 | 5 | NHCO | NMe | 1-HOOC-iPn |
| 2-2128 | 5 | NHCO | NMe | 1-MeOOC-iPn |
| 2-2129 | 5 | NHCO | NMe | 1-HOOC-2-Me-Bu |
| 2-2130 | 5 | NHCO | NMe | 1-MeOOC-2-Me-Bu |
| 2-2131 | 5 | NHCO | NMe | CH₂CH₂SO₃H |
| 2-2132 | 5 | NHCO | NMe | OH |
| 2-2133 | 5 | NHCO | NMe | MeO |
| 2-2134 | 5 | NHCO | NMe | EtO |
| 2-2135 | 5 | NHCO | NMe | PrO |
| 2-2136 | 5 | NHCO | NMe | iPrO |
| 2-2137 | 5 | NHCO | NMe | BuO |
| 2-2138 | 5 | NHCO | NMe | iBuO |
| 2-2139 | 5 | NHCO | NMe | sBuO |
| 2-2140 | 5 | NHCO | NMe | tBuO |
| 2-2141 | 5 | NHCO | NMe | HxO |
| 2-2142 | 5 | NHCO | NMe | PhO |
| 2-2143 | 5 | NHCO | NMe | BnO |
| 2-2144 | 5 | NHCO | NMe | Z-1 |
| 2-2145 | 5 | NHCO | NMe | Z-2 |
| 2-2146 | 5 | NHCO | NMe | Z-3 |
| 2-2147 | 5 | NHCO | NMe | Z-4 |
| 2-2148 | 5 | NHCO | NMe | Z-5 |
| 2-2149 | 5 | NHCO | NMe | Z-6 |
| 2-2150 | 5 | NHCO | NMe | Z-7 |
| 2-2151 | 5 | NHCO | NMe | Z-8 |
| 2-2152 | 5 | NHCO | NMe | Z-9 |
| 2-2153 | 5 | NHCO | NMe | Z-10 |
| 2-2154 | 5 | NHCO | NMe | Z-11 |
| 2-2155 | 5 | NHCO | NMe | Z-12 |
| 2-2156 | 5 | NHCO | NMe | 3-Py |
| 2-2157 | 5 | NHCO | NMe | 4-Py |
| 2-2158 | 5 | NHCO | NHNH | H |
| 2-2159 | 5 | NHCO | NHNH | Me |
| 2-2160 | 5 | NHCO | NHNH | Et |
| 2-2161 | 5 | NHCO | NHNME | Me |
| 2-2162 | 5 | NHCO | NHNME | Et |
| 2-2163 | 5 | NHCO | NHNME | Pr |
| 2-2164 | 5 | NHCONHNHCO | NH | H |
| 2-2165 | 5 | NHCONHNHCO | NH | Ph |
| 2-2166 | 5 | NHCONHNHCO | NH | 2-Me-Ph |
| 2-2167 | 5 | NHCONHNHCO | NH | 4-Me-Ph |
| 2-2168 | 5 | NHCONHNHCO | NH | 2,4-diMe-Ph |
| 2-2169 | 5 | NHCONHNHCO | NH | 3,4-diMe-Ph |
| 2-2170 | 5 | NHCONHNHCO | NH | 2-(CF₃)Ph |
| 2-2171 | 5 | NHCONHNHCO | NH | 4-(CF₃)Ph |
| 2-2172 | 5 | NHCONHNHCO | NH | 2-MeOPh |
| 2-2173 | 5 | NHCONHNHCO | NH | 4-MeOPh |
| 2-2174 | 5 | NHCONHNHCO | NH | 2-EtOPh |
| 2-2175 | 5 | NHCONHNHCO | NH | 4-EtOPh |
| 2-2176 | 5 | NHCONHNHCO | NH | 2-HOPh |
| 2-2177 | 5 | NHCONHNHCO | NH | 4-HOPh |
| 2-2178 | 5 | NHCONHNHCO | NH | 2-(HOOC)Ph |
| 2-2179 | 5 | NHCONHNHCO | NH | 4-(HOOC)Ph |
| 2-2180 | 5 | NHCONHNHCO | NH | 2-(MeOOC)Ph |
| 2-2181 | 5 | NHCONHNHCO | NH | 4-(MeOOC)Ph |
| 2-2182 | 5 | NHCONHNHCO | NH | 2-(EtOOC)Ph |
| 2-2183 | 5 | NHCONHNHCO | NH | 4-(EtOOC)Ph |
| 2-2184 | 5 | NHCONHNHCO | NH | 2-(tBuOOC)Ph |
| 2-2185 | 5 | NHCONHNHCO | NH | 4-(tBuOOC)Ph |
| 2-2186 | 5 | NHCONHNHCO | NH | 2-Cl-Ph |
| 2-2187 | 5 | NHCONHNHCO | NH | 4-Cl-Ph |
| 2-2188 | 5 | NHCONHNHCO | NH | 2-Br-Ph |
| 2-2189 | 5 | NHCONHNHCO | NH | 4-Br-Ph |
| 2-2190 | 5 | NHCONHNHCO | NH | 2-I-Ph |
| 2-2191 | 5 | NHCONHNHCO | NH | 4-I-Ph |
| 2-2192 | 5 | NHCONHNHCO | NH | 2-NO₂-Ph |
| 2-2193 | 5 | NHCONHNHCO | NH | 4-NO₂-Ph |
| 2-2194 | 5 | NHCONHNHCO | NH | 2-NH₂-Ph |
| 2-2195 | 5 | NHCONHNHCO | NH | 4-NH₂-Ph |
| 2-2196 | 5 | NHCONHNHCO | NH | 2-(HO₃S)Ph |
| 2-2197 | 5 | NHCONHNHCO | NH | 4-(HO₃S)Ph |
| 2-2198 | 5 | NHCONHNHCO | NH | 2-(NH₂O₂S)Ph |
| 2-2199 | 5 | NHCONHNHCO | NH | 4-(NH₂O₂S)Ph |
| 2-2200 | 5 | NHCONHNHCO | NH | 2-CN-Ph |
| 2-2201 | 5 | NHCONHNHCO | NH | 4-CN-Ph |
| 2-2202 | 5 | NHCONHNHCO | NH | 2-(HOCH₂)Ph |
| 2-2203 | 5 | NHCONHNHCO | NH | 4-(HOCH₂)Ph |
| 2-2204 | 5 | NHCONHNHCO | NH | Me |
| 2-2205 | 5 | NHCONHNHCO | NH | Et |
| 2-2206 | 5 | NHCONHNHCO | NH | Pr |
| 2-2207 | 5 | NHCONHNHCO | NH | iPr |
| 2-2208 | 5 | NHCONHNHCO | NH | Bu |
| 2-2209 | 5 | NHCONHNHCO | NH | HOOCCH₂— |
| 2-2210 | 5 | NHCONHNHCO | NH | MeOOCCH₂— |
| 2-2211 | 5 | NHCONHNHCO | NH | MeCH(COOH) |
| 2-2212 | 5 | NHCONHNHCO | NH | HOOC—(CH₂)₂— |
| 2-2213 | 5 | NHCONHNHCO | NH | MeCH(COOMe) |
| 2-2214 | 5 | NHCONHNHCO | NH | 1-HOOC-iBu |
| 2-2215 | 5 | NHCONHNHCO | NH | 1-MeOOC-iBu |
| 2-2216 | 5 | NHCONHNHCO | NH | 1-HOOC-iPn |
| 2-2217 | 5 | NHCONHNHCO | NH | 1-MeOOC-iPn |
| 2-2218 | 5 | NHCONHNHCO | NH | 1-HOOC-2-Me-Bu |
| 2-2219 | 5 | NHCONHNHCO | NH | 1-MeOOC-2-Me-Bu |
| 2-2220 | 5 | NHCONHNHCO | NH | CH₂CH₂SO₃H |
| 2-2221 | 5 | NHCONHNHCO | NH | OH |
| 2-2222 | 5 | NHCONHNHCO | NH | MeO |
| 2-2223 | 5 | NHCONHNHCO | NH | EtO |
| 2-2224 | 5 | NHCONHNHCO | NH | PrO |
| 2-2225 | 5 | NHCONHNHCO | NH | iPrO |
| 2-2226 | 5 | NHCONHNHCO | NH | BuO |
| 2-2227 | 5 | NHCONHNHCO | NH | iBuO |
| 2-2228 | 5 | NHCONHNHCO | NH | sBuO |
| 2-2229 | 5 | NHCONHNHCO | NH | tBuO |
| 2-2230 | 5 | NHCONHNHCO | NH | HxO |
| 2-2231 | 5 | NHCONHNHCO | NH | PhO |
| 2-2232 | 5 | NHCONHNHCO | NH | BnO |
| 2-2233 | 5 | NHCONHNHCO | NH | Z-1 |
| 2-2234 | 5 | NHCONHNHCO | NH | Z-2 |
| 2-2235 | 5 | NHCONHNHCO | NH | Z-3 |
| 2-2236 | 5 | NHCONHNHCO | NH | Z-4 |
| 2-2237 | 5 | NHCONHNHCO | NH | Z-5 |
| 2-2238 | 5 | NHCONHNHCO | NH | Z-6 |
| 2-2239 | 5 | NHCONHNHCO | NH | Z-7 |
| 2-2240 | 5 | NHCONHNHCO | NH | Z-8 |
| 2-2241 | 5 | NHCONHNHCO | NH | Z-9 |
| 2-2242 | 5 | NHCONHNHCO | NH | Z-10 |
| 2-2243 | 5 | NHCONHNHCO | NH | Z-11 |
| 2-2244 | 5 | NHCONHNHCO | NH | Z-12 |
| 2-2245 | 5 | NHCONHNHCO | NH | 3-Py |
| 2-2246 | 5 | NHCONHNHCO | NH | 4-Py |
| 2-2247 | 5 | NHCONHCO | — | H |
| 2-2248 | 5 | NHCONHCO | — | Ph |
| 2-2249 | 5 | NHCONHCO | — | 2-Me-Ph |
| 2-2250 | 5 | NHCONHCO | — | 4-Me-Ph |
| 2-2251 | 5 | NHCONHCO | — | 2,4-diMe-Ph |
| 2-2252 | 5 | NHCONHCO | — | 3,4-diMe-Ph |
| 2-2253 | 5 | NHCONHCO | — | 2-(CF₃)Ph |
| 2-2254 | 5 | NHCONHCO | — | 4-(CF₃)Ph |
| 2-2255 | 5 | NHCONHCO | — | 2-MeOPh |
| 2-2256 | 5 | NHCONHCO | — | 4-MeOPh |
| 2-2257 | 5 | NHCONHCO | — | 2-EtOPh |
| 2-2258 | 5 | NHCONHCO | — | 4-EtOPh |
| 2-2259 | 5 | NHCONHCO | — | 2-HOPh |
| 2-2260 | 5 | NHCONHCO | — | 4-HOPh |
| 2-2261 | 5 | NHCONHCO | — | 2-(HOOC)Ph |
| 2-2262 | 5 | NHCONHCO | — | 4-(HOOC)Ph |
| 2-2263 | 5 | NHCONHCO | — | 2-(MeOOC)Ph |
| 2-2264 | 5 | NHCONHCO | — | 4-(MeOOC)Ph |
| 2-2265 | 5 | NHCONHCO | — | 2-(EtOOC)Ph |
| 2-2266 | 5 | NHCONHCO | — | 4-(EtOOC)Ph |
| 2-2267 | 5 | NHCONHCO | — | 2-(tBuOOC)Ph |
| 2-2268 | 5 | NHCONHCO | — | 4-(tBuOOC)Ph |
| 2-2269 | 5 | NHCONHCO | — | 2-Cl-Ph |

TABLE 2-continued

| Cpd. No. | k | A | B | R¹ |
|---|---|---|---|---|
| 2-2270 | 5 | NHCONHCO | — | 4-Cl-Ph |
| 2-2271 | 5 | NHCONHCO | — | 2-Br-Ph |
| 2-2272 | 5 | NHCONHCO | — | 4-Br-Ph |
| 2-2273 | 5 | NHCONHCO | — | 2-I-Ph |
| 2-2274 | 5 | NHCONHCO | — | 4-I-Ph |
| 2-2275 | 5 | NHCONHCO | — | 2-NO$_2$-Ph |
| 2-2276 | 5 | NHCONHCO | — | 4-NO$_2$-Ph |
| 2-2277 | 5 | NHCONHCO | — | 2-NH$_2$-Ph |
| 2-2278 | 5 | NHCONHCO | — | 4-NH$_2$-Ph |
| 2-2279 | 5 | NHCONHCO | — | 2-(HO$_3$S)Ph |
| 2-2280 | 5 | NHCONHCO | — | 4-(HO$_3$S)Ph |
| 2-2281 | 5 | NHCONHCO | — | 2-(NH$_2$O$_2$S)Ph |
| 2-2282 | 5 | NHCONHCO | — | 4-(NH$_2$O$_2$S)Ph |
| 2-2283 | 5 | NHCONHCO | — | 2-CN-Ph |
| 2-2284 | 5 | NHCONHCO | — | 4-CN-Ph |
| 2-2285 | 5 | NHCONHCO | — | 2-(HOCH$_2$)Ph |
| 2-2286 | 5 | NHCONHCO | — | 4-(HOCH$_2$)Ph |
| 2-2287 | 5 | NHCONHCO | — | Me |
| 2-2288 | 5 | NHCONHCO | — | Et |
| 2-2289 | 5 | NHCONHCO | — | Pr |
| 2-2290 | 5 | NHCONHCO | — | iPr |
| 2-2291 | 5 | NHCONHCO | — | Bu |
| 2-2292 | 5 | NHCONHCO | — | HOOCCH$_2$— |
| 2-2293 | 5 | NHCONHCO | — | MeOOCCH$_2$— |
| 2-2294 | 5 | NHCONHCO | — | MeCH(COOH) |
| 2-2295 | 5 | NHCONHCO | — | HOOC—(CH$_2$)$_2$— |
| 2-2296 | 5 | NHCONHCO | — | MeCH(COOMe) |
| 2-2297 | 5 | NHCONHCO | — | 1-HOOC-iBu |
| 2-2298 | 5 | NHCONHCO | — | 1-MeOOC-iBu |
| 2-2299 | 5 | NHCONHCO | — | 1-HOOC-iPn |
| 2-2300 | 5 | NHCONHCO | — | 1-MeOOC-iPn |
| 2-2301 | 5 | NHCONHCO | — | 1-HOOC-2-Me-Bu |
| 2-2302 | 5 | NHCONHCO | — | 1-MeOOC-2-Me-Bu |
| 2-2303 | 5 | NHCONHCO | — | CH$_2$CH$_2$SO$_3$H |
| 2-2304 | 5 | NHCONHCO | — | MeO |
| 2-2305 | 5 | NHCONHCO | — | EtO |
| 2-2306 | 5 | NHCONHCO | — | PrO |
| 2-2307 | 5 | NHCONHCO | — | iPrO |
| 2-2308 | 5 | NHCONHCO | — | BuO |
| 2-2309 | 5 | NHCONHCO | — | iBuO |
| 2-2310 | 5 | NHCONHCO | — | sBuO |
| 2-2311 | 5 | NHCONHCO | — | tBuO |
| 2-2312 | 5 | NHCONHCO | — | HxO |
| 2-2313 | 5 | NHCONHCO | — | PhO |
| 2-2314 | 5 | NHCONHCO | — | BnO |
| 2-2315 | 5 | NHCONHCO | — | Z-1 |
| 2-2316 | 5 | NHCONHCO | — | Z-2 |
| 2-2317 | 5 | NHCONHCO | — | Z-3 |
| 2-2318 | 5 | NHCONHCO | — | Z-4 |
| 2-2319 | 5 | NHCONHCO | — | Z-5 |
| 2-2320 | 5 | NHCONHCO | — | Z-6 |
| 2-2321 | 5 | NHCONHCO | — | Z-7 |
| 2-2322 | 5 | NHCONHCO | — | Z-8 |
| 2-2323 | 5 | NHCONHCO | — | Z-9 |
| 2-2324 | 5 | NHCONHCO | — | Z-10 |
| 2-2325 | 5 | NHCONHCO | — | Z-11 |
| 2-2326 | 5 | NHCONHCO | — | Z-12 |
| 2-2327 | 5 | NHCONHCO | — | 3-Py |
| 2-2328 | 5 | NHCONHCO | — | 4-Py |
| 2-2329 | 5 | NHCONHSO$_2$ | — | H |
| 2-2330 | 5 | NHCONHSO$_2$ | — | Ph |
| 2-2331 | 5 | NHCONHSO$_2$ | — | 2-Me-Ph |
| 2-2332 | 5 | NHCONHSO$_2$ | — | 4-Me-Ph |
| 2-2333 | 5 | NHCONHSO$_2$ | — | 2,4-diMe-Ph |
| 2-2334 | 5 | NHCONHSO$_2$ | — | 3,4-diMe-Ph |
| 2-2335 | 5 | NHCONHSO$_2$ | — | 2-(CF$_3$)Ph |
| 2-2336 | 5 | NHCONHSO$_2$ | — | 4-(CF$_3$)Ph |
| 2-2337 | 5 | NHCONHSO$_2$ | — | 2-MeOPh |
| 2-2338 | 5 | NHCONHSO$_2$ | — | 4-MeOPh |
| 2-2339 | 5 | NHCONHSO$_2$ | — | 2-EtOPh |
| 2-2340 | 5 | NHCONHSO$_2$ | — | 4-EtOPh |
| 2-2341 | 5 | NHCONHSO$_2$ | — | 2-HOPh |
| 2-2342 | 5 | NHCONHSO$_2$ | — | 4-HOPh |
| 2-2343 | 5 | NHCONHSO$_2$ | — | 2-(HOOC)Ph |
| 2-2344 | 5 | NHCONHSO$_2$ | — | 4-(HOOC)Ph |
| 2-2345 | 5 | NHCONHSO$_2$ | — | 2-(MeOOC)Ph |
| 2-2346 | 5 | NHCONHSO$_2$ | — | 4-(MeOOC)Ph |
| 2-2347 | 5 | NHCONHSO$_2$ | — | 2-(EtOOC)Ph |
| 2-2348 | 5 | NHCONHSO$_2$ | — | 4-(EtOOC)Ph |
| 2-2349 | 5 | NHCONHSO$_2$ | — | 2-(tBuOOC)Ph |
| 2-2350 | 5 | NHCONHSO$_2$ | — | 4-(tBuOOC)Ph |
| 2-2351 | 5 | NHCONHSO$_2$ | — | 2-Cl-Ph |
| 2-2352 | 5 | NHCONHSO$_2$ | — | 4-Cl-Ph |
| 2-2353 | 5 | NHCONHSO$_2$ | — | 2-Br-Ph |
| 2-2354 | 5 | NHCONHSO$_2$ | — | 4-Br-Ph |
| 2-2355 | 5 | NHCONHSO$_2$ | — | 2-I-Ph |
| 2-2356 | 5 | NHCONHSO$_2$ | — | 4-I-Ph |
| 2-2357 | 5 | NHCONHSO$_2$ | — | 2-NO$_2$-Ph |
| 2-2358 | 5 | NHCONHSO$_2$ | — | 4-NO$_2$-Ph |
| 2-2359 | 5 | NHCONHSO$_2$ | — | 2-NH$_2$-Ph |
| 2-2360 | 5 | NHCONHSO$_2$ | — | 4-NH$_2$-Ph |
| 2-2361 | 5 | NHCONHSO$_2$ | — | 2-(HO$_3$S)Ph |
| 2-2362 | 5 | NHCONHSO$_2$ | — | 4-(HO$_3$S)Ph |
| 2-2363 | 5 | NHCONHSO$_2$ | — | 2-(NH$_2$O$_2$S)Ph |
| 2-2364 | 5 | NHCONHSO$_2$ | — | 4-(NH$_2$O$_2$S)Ph |
| 2-2365 | 5 | NHCONHSO$_2$ | — | 2-CN-Ph |
| 2-2366 | 5 | NHCONHSO$_2$ | — | 4-CN-Ph |
| 2-2367 | 5 | NHCONHSO$_2$ | — | 2-(HOCH$_2$)Ph |
| 2-2368 | 5 | NHCONHSO$_2$ | — | 4-(HOCH$_2$)Ph |
| 2-2369 | 5 | NHCONHSO$_2$ | — | Me |
| 2-2370 | 5 | NHCONHSO$_2$ | — | Et |
| 2-2371 | 5 | NHCONHSO$_2$ | — | Pr |
| 2-2372 | 5 | NHCONHSO$_2$ | — | iPr |
| 2-2373 | 5 | NHCONHSO$_2$ | — | Bu |
| 2-2374 | 5 | NHCONHSO$_2$ | — | HOOCCH$_2$ |
| 2-2375 | 5 | NHCONHSO$_2$ | — | MeOOCCH$_2$ |
| 2-2376 | 5 | NHCONHSO$_2$ | — | MeCH(COOH) |
| 2-2377 | 5 | NHCONHSO$_2$ | — | HOOC—(CH$_2$)$_2$ |
| 2-2378 | 5 | NHCONHSO$_2$ | — | MeCH(COOMe) |
| 2-2379 | 5 | NHCONHSO$_2$ | — | 1-HOOC-iBu |
| 2-2380 | 5 | NHCONHSO$_2$ | — | 1-MeOOC-iPn |
| 2-2381 | 5 | NHCONHSO$_2$ | — | 1-HOOC-iPn |
| 2-2382 | 5 | NHCONHSO$_2$ | — | 1-MeOOC-iPn |
| 2-2383 | 5 | NHCONHSO$_2$ | — | 1-HOOC-2-Me-Bu |
| 2-2384 | 5 | NHCONHSO$_2$ | — | 1-MeOOC-2-Me-Bu |
| 2-2385 | 5 | NHCONHSO$_2$ | — | CH$_2$CH$_2$SO$_3$H |
| 2-2386 | 5 | NHCONHSO$_2$ | — | OH |
| 2-2387 | 5 | NHCONHSO$_2$ | — | MeO |
| 2-2388 | 5 | NHCONHSO$_2$ | — | EtO |
| 2-2389 | 5 | NHCONHSO$_2$ | — | PrO |
| 2-2390 | 5 | NHCONHSO$_2$ | — | iPrO |
| 2-2391 | 5 | NHCONHSO$_2$ | — | BuO |
| 2-2392 | 5 | NHCONHSO$_2$ | — | iBuO |
| 2-2393 | 5 | NHCONHSO$_2$ | — | sBuO |
| 2-2394 | 5 | NHCONHSO$_2$ | — | tBuO |
| 2-2395 | 5 | NHCONHSO$_2$ | — | HxO |
| 2-2396 | 5 | NHCONHSO$_2$ | — | PhO |
| 2-2397 | 5 | NHCONHSO$_2$ | — | BnO |
| 2-2398 | 5 | NHCONHSO$_2$ | — | Z-1 |
| 2-2399 | 5 | NHCONHSO$_2$ | — | Z-2 |
| 2-2400 | 5 | NHCONHSO$_2$ | — | Z-3 |
| 2-2401 | 5 | NHCONHSO$_2$ | — | Z-4 |
| 2-2402 | 5 | NHCONHSO$_2$ | — | Z-5 |
| 2-2403 | 5 | NHCONHSO$_2$ | — | Z-6 |
| 2-2404 | 5 | NHCONHSO$_2$ | — | Z-7 |
| 2-2405 | 5 | NHCONHSO$_2$ | — | Z-8 |
| 2-2406 | 5 | NHCONHSO$_2$ | — | Z-9 |
| 2-2407 | 5 | NHCONHSO$_2$ | — | Z-10 |
| 2-2408 | 5 | NHCONHSO$_2$ | — | Z-11 |
| 2-2409 | 5 | NHCONHSO$_2$ | — | Z-12 |
| 2-2410 | 5 | NHCONHSO$_2$ | — | 3-Py |
| 2-2411 | 5 | NHCONHSO$_2$ | — | 4-Py |
| 2-2412 | 5 | NHCONHSO$_2$ | NH | H |
| 2-2413 | 5 | NHCONHSO$_2$ | NH | Me |
| 2-2414 | 5 | NHCONHSO$_2$ | NH | Et |
| 2-2415 | 5 | NHCONHSO$_2$ | NH | Pr |
| 2-2416 | 5 | NHCONHSO$_2$ | NH | iPr |
| 2-2417 | 5 | NHCONHSO$_2$ | NH | Bu |
| 2-2418 | 5 | NHCONHSO$_2$ | NMe | Me |
| 2-2419 | 5 | NHCONHSO$_2$ | NMe | Et |
| 2-2420 | 5 | NHCONHSO$_2$ | NMe | Pr |
| 2-2421 | 5 | NHCONHSO$_2$ | NMe | iPr |

TABLE 2-continued

| Cpd. No. | k | A | B | R¹ |
|---|---|---|---|---|
| 2-2422 | 5 | NHCONHSO$_2$ | NMe | Bu |
| 2-2423 | 5 | — | NH | H |
| 2-2424 | 5 | — | NH | Me |
| 2-2425 | 5 | — | NH | Et |
| 2-2426 | 5 | — | NH | Pr |
| 2-2427 | 5 | — | NH | iPr |
| 2-2428 | 5 | — | NH | Bu |
| 2-2429 | 5 | CO | | Pyr |
| 2-2430 | 5 | CO | | Pipri |
| 2-2431 | 5 | CO | | Pipra |
| 2-2432 | 5 | CO | | Mor |
| 2-2433 | 5 | CO | | Thmor |
| 2-2434 | 5 | CO | | NHPyr |
| 2-2435 | 5 | CO | | NHPipri |
| 2-2436 | 5 | CO | | NHPipra |
| 2-2437 | 5 | CO | | NHMor |
| 2-2438 | 5 | CO | | NHThmor |
| 2-2439 | 5 | NHCO | | Pyr |
| 2-2440 | 5 | NHCO | | Pipri |
| 2-2441 | 5 | NHCO | | Pipra |
| 2-2442 | 5 | NHCO | | Mor |
| 2-2443 | 5 | NHCO | | Thmor |
| 2-2444 | 5 | NHCO | | NHPyr |
| 2-2445 | 5 | NHCO | | NHPipri |
| 2-2446 | 5 | NHCO | | NHPipra |
| 2-2447 | 5 | NHCO | | NHMor |
| 2-2448 | 5 | NHCO | | NHThmor |
| 2-2449 | 5 | CONHCO | | Pyr |
| 2-2450 | 5 | CONHCO | | Pipri |
| 2-2451 | 5 | CONHCO | | Pipra |
| 2-2452 | 5 | CONHCO | | Mor |
| 2-2453 | 5 | CONHCO | | Thmor |
| 2-2454 | 5 | CONHCO | | NHPyr |
| 2-2455 | 5 | CONHCO | | NHPipri |
| 2-2456 | 5 | CONHCO | | NHPipra |
| 2-2457 | 5 | CONHCO | | NHMor |
| 2-2458 | 5 | CONHCO | | NHThmor |
| 2-2459 | 5 | CONHSO$_2$ | | Pyr |
| 2-2460 | 5 | CONHSO$_2$ | | Pipri |
| 2-2461 | 5 | CONHSO$_2$ | | Pipra |
| 2-2462 | 5 | CONHSO$_2$ | | Mor |
| 2-2463 | 5 | CONHSO$_2$ | | Thmor |
| 2-2464 | 5 | CONHSO$_2$ | | NHPyr |
| 2-2465 | 5 | CONHSO$_2$ | | NHPipri |
| 2-2466 | 5 | CONHSO$_2$ | | NHPipra |
| 2-2467 | 5 | CONHSO$_2$ | | NHMor |
| 2-2468 | 5 | CONHSO$_2$ | | NHThmor |
| 2-2469 | 5 | NHSO$_2$ | NH | Z-4 |
| 2-2470 | 5 | NHSO$_2$ | — | Me |
| 2-2471 | 5 | NHSO$_2$ | — | Et |
| 2-2472 | 5 | NHSO$_2$ | — | Pr |
| 2-2473 | 5 | NHSO$_2$ | — | CH$_2$—Cl |
| 2-2474 | 5 | NHSO$_2$ | — | Ph |
| 2-2475 | 5 | NHSO$_2$ | — | 4-Me-Ph |
| 2-2476 | 5 | CO | NMe | Ph |
| 2-2477 | 5 | CO | NMe | 2-Me-Ph |
| 2-2478 | 5 | CO | NMe | 4-Me-Ph |
| 2-2479 | 5 | CO | NMe | 2,4-diMe-Ph |
| 2-2480 | 5 | CO | NMe | 3,4-diMe-Ph |
| 2-2481 | 5 | CO | NMe | 2-(CF$_3$)Ph |
| 2-2482 | 5 | CO | NMe | 4-(CF$_3$)Ph |
| 2-2483 | 5 | CO | NMe | 2-MeOPh |
| 2-2484 | 5 | CO | NMe | 4-MeOPh |
| 2-2485 | 5 | CO | NMe | 2-EtOPh |
| 2-2486 | 5 | CO | NMe | 4-EtOPh |
| 2-2487 | 5 | CO | NMe | 2-HOPh |
| 2-2488 | 5 | CO | NMe | 4-HOPh |
| 2-2489 | 5 | CO | NMe | 2-(HOOC)Ph |
| 2-2490 | 5 | CO | NMe | 4-(HOOC)Ph |
| 2-2491 | 5 | CO | NMe | 2-(MeOOC)Ph |
| 2-2492 | 5 | CO | NMe | 4-(MeOOC)Ph |
| 2-2493 | 5 | CO | NMe | 2-(EtOOC)Ph |
| 2-2494 | 5 | CO | NMe | 4-(EtOOC)Ph |
| 2-2495 | 5 | CO | NMe | 2-(tBuOOC)Ph |
| 2-2496 | 5 | CO | NMe | 4-(tBuOOC)Ph |
| 2-2497 | 5 | CO | NMe | 2-Cl-Ph |
| 2-2498 | 5 | CO | NMe | 4-Cl-Ph |
| 2-2499 | 5 | CO | NMe | 2-Br-Ph |
| 2-2500 | 5 | CO | NMe | 4-Br-Ph |
| 2-2501 | 5 | CO | NMe | 2-I-Ph |
| 2-2502 | 5 | CO | NMe | 4-I-Ph |
| 2-2503 | 5 | CO | NMe | 2-NO$_2$-Ph |
| 2-2504 | 5 | CO | NMe | 4-NO$_2$-Ph |
| 2-2505 | 5 | CO | NMe | 2-NH$_2$-Ph |
| 2-2506 | 5 | CO | NMe | 4-NH$_2$-Ph |
| 2-2507 | 5 | CO | NMe | 2-(HO$_3$S)Ph |
| 2-2508 | 5 | CO | NMe | 4-(HO$_3$S)Ph |
| 2-2509 | 5 | CO | NMe | 2-(NH$_2$O$_2$S)Ph |
| 2-2510 | 5 | CO | NMe | 4-(NH$_2$O$_2$S)Ph |
| 2-2511 | 5 | CO | NMe | 2-CN-Ph |
| 2-2512 | 5 | CO | NMe | 4-CN-Ph |
| 2-2513 | 5 | CO | NMe | 2-(HOCH$_2$)Ph |
| 2-2514 | 5 | CO | NMe | 4-(HOCH$_2$)Ph |
| 2-2515 | 5 | CO | NMe | Me |
| 2-2516 | 5 | CO | NMe | Et |
| 2-2517 | 5 | CO | NMe | Pr |
| 2-2518 | 5 | CO | NMe | iPr |
| 2-2519 | 5 | CO | NMe | Bu |
| 2-2520 | 5 | CO | NMe | HOOCCH$_2$ |
| 2-2521 | 5 | CO | NMe | HOOC—(CH$_2$)$_2$ |
| 2-2522 | 5 | CO | NMe | MeCH(COOH) |
| 2-2523 | 5 | CO | NMe | HOOC—(CH$_2$)$_3$— |
| 2-2524 | 5 | CO | NMe | MeCH(COOMe) |
| 2-2525 | 5 | CO | NMe | 1-HOOC-iBu |
| 2-2526 | 5 | CO | NMe | 1-MeOOC-iBu |
| 2-2527 | 5 | CO | NMe | 1-HOOC-iPn |
| 2-2528 | 5 | CO | NMe | 1-MeOOC-iPn |
| 2-2529 | 5 | CO | NMe | 1-HOOC-2-Me-Bu |
| 2-2530 | 5 | CO | NMe | 1-MeOOC-2-Me-Bu |
| 2-2531 | 5 | CO | NMe | CH$_2$CH$_2$SO$_3$H |
| 2-2532 | 5 | CO | NMe | OH |
| 2-2533 | 5 | CO | NMe | MeO |
| 2-2534 | 5 | CO | NMe | EtO |
| 2-2535 | 5 | CO | NMe | PrO |
| 2-2536 | 5 | CO | NMe | iPrO |
| 2-2537 | 5 | CO | NMe | BuO |
| 2-2538 | 5 | CO | NMe | iBuO |
| 2-2539 | 5 | CO | NMe | sBuO |
| 2-2540 | 5 | CO | NMe | tBuO |
| 2-2541 | 5 | CO | NMe | HxO |
| 2-2542 | 5 | CO | NMe | PhO |
| 2-2543 | 5 | CO | NMe | BnO |
| 2-2544 | 5 | CO | NMe | Z-1 |
| 2-2545 | 5 | CO | NMe | Z-2 |
| 2-2546 | 5 | CO | NMe | Z-3 |
| 2-2547 | 5 | CO | NMe | Z-4 |
| 2-2548 | 5 | CO | NMe | Z-5 |
| 2-2549 | 5 | CO | NMe | Z-6 |
| 2-2550 | 5 | CO | NMe | Z-7 |
| 2-2551 | 5 | CO | NMe | Z-8 |
| 2-2552 | 5 | CO | NMe | Z-9 |
| 2-2553 | 5 | CO | NMe | Z-10 |
| 2-2554 | 5 | CO | NMe | Z-11 |
| 2-2555 | 5 | CO | NMe | Z-12 |
| 2-2556 | 5 | CO | NMe | 3-Py |
| 2-2557 | 5 | CO | NMe | 4-Py |
| 2-2558 | 5 | CO | | Thiad |
| 2-2559 | 5 | CO | | NHThiad |
| 2-2560 | 5 | NHCO | | Thiad |
| 2-2561 | 5 | NHCO | | NHThiad |
| 2-2562 | 5 | CONHCO | | Thiad |
| 2-2563 | 5 | CONHCO | | NHThiad |
| 2-2564 | 5 | CONHSO$_2$ | | Thiad |
| 2-2565 | 5 | CONHSO$_2$ | | NHThiad |
| 2-2566 | 5 | NHCS | NH | H |
| 2-2567 | 5 | NHCS | NH | Me |
| 2-2568 | 5 | NHCS | NH | Et |
| 2-2569 | 5 | NHCS | NH | Ph |
| 2-2570 | 5 | NHCS | NH | HOOCCH$_2$ |
| 2-2571 | 5 | NHCS | NH | MeOOCCH$_2$ |
| 2-2572 | 5 | NHCS | NH | MeCH(COOH) |
| 2-2573 | 5 | NHCS | NH | HOOC—(CH$_2$)$_2$ |

TABLE 2-continued

| Cpd. No. | k | A | B | R¹ |
|---|---|---|---|---|
| 2-2574 | 5 | NHCS | NH | MeCH(COOMe) |
| 2-2575 | 5 | CO | NH | HOOC—(CH$_2$)$_3$— |
| 2-2576 | 5 | NHCO | NH | HOOC—(CH$_2$)$_3$— |
| 2-2577 | 5 | NHCO | — | HOOC—(CH$_2$)$_3$— |
| 2-2578 | 5 | NHCS | NH | HOOC—(CH$_2$)$_3$— |
| 2-2579 | 5 | CO | NH | MeSO$_2$NHCOCH(Me) |
| 2-2580 | 5 | NHCO | NH | MeSO$_2$NHCOCH(Me) |
| 2-2581 | 5 | NHCO | — | MeSO$_2$NHCOCH(Me) |
| 2-2582 | 5 | NHCS | NH | MeSO$_2$NHCOCH(Me) |
| 2-2583 | 5 | — | NH | HOOCCH$_2$ |
| 2-2584 | 5 | — | NH | MeOOCCH$_2$ |
| 2-2585 | 5 | — | NH | MeCH(COOH) |
| 2-2586 | 5 | — | NH | HOOC—(CH$_2$)$_2$ |
| 2-2587 | 5 | — | NH | MeCH(COOMe) |
| 2-2588 | 5 | — | NH | HOOC—(CH$_2$)$_3$— |
| 2-2589 | 5 | NHCOCO | — | OH |
| 2-2590 | 5 | NHCOCO | — | MeO |
| 2-2591 | 5 | NHCOCO | — | EtO |
| 2-2592 | 5 | NHCOCO | — | PrO |
| 2-2593 | 5 | NHCOCO | — | iPrO |
| 2-2594 | 5 | NHCOCO | — | BuO |
| 2-2595 | 5 | NHCOCO | — | iBuO |
| 2-2596 | 5 | NHCOCO | — | sBuO |
| 2-2597 | 5 | NHCOCO | — | tBuO |
| 2-2598 | 5 | NHCOCO | — | HxO |
| 2-2599 | 5 | NHCOCO | — | PhO |
| 2-2600 | 5 | NHCOCO | — | BnO |
| 2-2601 | 0 | — | — | 1,3-diox-lInd |
| 2-2602 | 1 | — | — | 1,3-diox-lInd |
| 2-2603 | 2 | — | — | 1,3-diox-lInd |
| 2-2604 | 3 | — | — | 1,3-diox-lInd |
| 2-2605 | 4 | — | — | 1,3-diox-lInd |
| 2-2606 | 5 | — | — | 1,3-diox-lInd |
| 2-2607 | 6 | — | — | 1,3-diox-lInd |
| 2-2608 | 7 | — | — | 1,3-diox-lInd |
| 2-2609 | 8 | — | — | 1,3-diox-lInd |
| 2-2610 | 9 | — | — | 1,3-diox-lInd |
| 2-2611 | 10 | — | — | 1,3-diox-lInd |
| 2-2612 | 11 | — | — | 1,3-diox-lInd |
| 2-2613 | 12 | — | — | 1,3-diox-lInd |
| 2-2614 | 4 | NHCONHSO$_2$NHCO | NH | Z-4 |
| 2-2615 | 4 | NHCONHSO$_2$NHCO | NH | Pn |
| 2-2616 | 2 | O | — | H |
| 2-2617 | 4 | O | — | H |
| 2-2618 | 5 | O | — | H |
| 2-2619 | 5 | O | — | Ph |
| 2-2620 | 5 | O | — | 2-Py |
| 2-2621 | 5 | O | — | 3-Py |
| 2-2622 | 5 | O | — | 4-Py |
| 2-2623 | 5 | O | — | Z-1 |
| 2-2624 | 5 | O | — | Z-2 |
| 2-2625 | 5 | O | — | Z-3 |
| 2-2626 | 5 | O | — | Z-4 |
| 2-2627 | 5 | O | — | Z-5 |
| 2-2628 | 5 | O | — | Z-6 |
| 2-2629 | 5 | O | — | Z-7 |
| 2-2630 | 5 | O | — | Z-8 |
| 2-2631 | 5 | O | — | Z-9 |
| 2-2632 | 5 | O | — | Z-10 |
| 2-2633 | 5 | O | — | Z-11 |
| 2-2634 | 5 | O | — | Z-12 |
| 2-2635 | 4 | NHCO | — | 3-Py |
| 2-2636 | 5 | NHCO | — | 3-Py |
| 2-2637 | 4 | CO | NH | HOCH$_2$CH(CH$_3$)CH$_2$ |
| 2-2638 | 5 | CO | NH | HOCH$_2$CH(CH$_3$)CH$_2$ |
| 2-2639 | 4 | NHCO | NH | HOCH$_2$CH(CH$_3$)CH$_2$ |
| 2-2640 | 5 | NHCO | NH | HOCH$_2$CH(CH$_3$)CH$_2$ |
| 2-2641 | 4 | CO | NH | MeSO$_2$NHCOCH$_2$ |
| 2-2642 | 5 | CO | NH | MeSO$_2$NHCOCH$_2$ |
| 2-2643 | 4 | NHCO | NH | MeSO$_2$NHCOCH$_2$ |
| 2-2644 | 5 | NHCO | NH | MeSO$_2$NHCOCH$_2$ |
| 2-2645 | 4 | CO | NH | H$_2$NSO$_2$NHCOCH$_2$ |
| 2-2646 | 5 | CO | NH | H$_2$NSO$_2$NHCOCH$_2$ |
| 2-2647 | 4 | NHCO | NH | H$_2$NSO$_2$NHCOCH$_2$ |
| 2-2648 | 5 | CO | NH | H$_2$NSO$_2$NHCOCH$_2$ |
| 2-2649 | 4 | CO | NH | 1-(MeSO$_2$NHCO)-Et |
| 2-2650 | 5 | CO | NH | 1-(MeSO$_2$NHCO)-Et |
| 2-2651 | 4 | NHCO | NH | 1-(MeSO$_2$NHCO)-Et |
| 2-2652 | 5 | NHCO | NH | 1-(MeSO$_2$NHCO)-Et |
| 2-2653 | 4 | CO | NH | 1-(H$_2$NSO$_2$NHCO)-Et |
| 2-2654 | 5 | CO | NH | 1-(H$_2$NSO$_2$NHCO)-Et |
| 2-2655 | 4 | NHCO | NH | 1-(H$_2$NSO$_2$NHCO)-Et |
| 2-2656 | 5 | NHCO | NH | 1-(H$_2$NSO$_2$NHCO)-Et |
| 2-2657 | 4 | CO | NH | HOOC—(CH$_2$)$_4$ |
| 2-2658 | 5 | CO | NH | HOOC—(CH$_2$)$_4$ |
| 2-2659 | 4 | NHCO | NH | HOOC—(CH$_2$)$_4$ |
| 2-2660 | 5 | NHCO | NH | HOOC—(CH$_2$)$_4$ |
| 2-2661 | 4 | CO | NH | HO—(CH$_2$)$_2$ |
| 2-2662 | 5 | CO | NH | HO—(CH$_2$)$_2$ |
| 2-2663 | 4 | NHCO | NH | HO—(CH$_2$)$_2$ |
| 2-2664 | 5 | NHCO | NH | HO—(CH$_2$)$_2$ |
| 2-2665 | 4 | CO | NH | HO—CH$_2$—CH(CH$_3$) |
| 2-2666 | 5 | CO | NH | HO—CH$_2$—CH(CH$_3$) |
| 2-2667 | 4 | NHCO | NH | HO—CH$_2$—CH(CH$_3$) |
| 2-2668 | 5 | NHCO | NH | HO—CH$_2$—CH(CH$_3$) |
| 2-2669 | 4 | CO | NMe | HOOC—(CH$_2$)$_3$ |
| 2-2670 | 4 | NHCO | NMe | HOOC—(CH$_2$)$_3$ |
| 2-2671 | 5 | NHCO | NMe | HOOC—(CH$_2$)$_3$ |
| 2-2672 | 4 | CONMeSO$_2$ | — | Me |
| 2-2673 | 5 | CONMeSO$_2$ | — | Me |
| 2-2674 | 4 | CO | NH | 1-Indn |
| 2-2675 | 5 | CO | NH | 1-Indn |
| 2-2676 | 4 | NHCO | NH | 1-Indn |
| 2-2677 | 5 | NHCO | NH | 1-Indn |
| 2-2678 | 4 | CO | NH | 2-(HOOC)-1-Indn |
| 2-2679 | 5 | CO | NH | 2-(HOOC)-1-Indn |
| 2-2680 | 4 | NHCO | NH | 2-(HOOC)-1-Indn |
| 2-2681 | 5 | NHCO | NH | 2-(HOOC)-1-Indn |
| 2-2682 | 4 | — | — | 3,4-diMe-2,5-diox-1-Imdd |
| 2-2683 | 5 | — | — | 3,4-diMe-2,5-diox-1-Imdd |

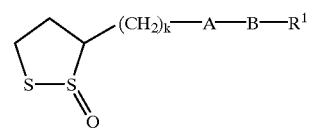

(I-3)

TABLE 3

| Cpd. No. | k | A | B | R¹ |
|---|---|---|---|---|
| 3-1 | 4 | CO | NH | H |
| 3-2 | 4 | CO | NH | Ph |
| 3-3 | 4 | CO | NH | 2-Me—Ph |
| 3-4 | 4 | CO | NH | 4-Me—Ph |
| 3-5 | 4 | CO | NH | 2,4-diMe—Ph |
| 3-6 | 4 | CO | NH | 3,4-diMe—Ph |
| 3-7 | 4 | CO | NH | 2-(CF$_3$)—Ph |
| 3-8 | 4 | CO | NH | 4-(CF$_3$)—Ph |
| 3-9 | 4 | CO | NH | 2-MeOPh |
| 3-10 | 4 | CO | NH | 4-MeOPh |
| 3-11 | 4 | CO | NH | 2-EtOPh |
| 3-12 | 4 | CO | NH | 4-EtOPh |
| 3-13 | 4 | CO | NH | 2-HOPh |
| 3-14 | 4 | CO | NH | 4-HOPh |
| 3-15 | 4 | CO | NH | 2-(HOOC)—Ph |
| 3-16 | 4 | CO | NH | 4-(HOOC)—Ph |
| 3-17 | 4 | CO | NH | 2-(MeOOC)—Ph |
| 3-18 | 4 | CO | NH | 4-(MeOOC)—Ph |
| 3-19 | 4 | CO | NH | 2-(EtOOC)—Ph |
| 3-20 | 4 | CO | NH | 4-(EtOOC)—Ph |
| 3-21 | 4 | CO | NH | 2-(tBuOOC)—Ph |
| 3-22 | 4 | CO | NH | 4-(tBuOOC)—Ph |
| 3-23 | 4 | CO | NH | 2-Cl—Ph |

TABLE 3-continued

| Cpd. No. | k | A | B | R¹ |
|---|---|---|---|---|
| 3-24 | 4 | CO | NH | 4-Cl—Ph |
| 3-25 | 4 | CO | NH | 2-Br—Ph |
| 3-26 | 4 | CO | NH | 4-Br—Ph |
| 3-27 | 4 | CO | NH | 2-I—Ph |
| 3-28 | 4 | CO | NH | 4-I—Ph |
| 3-29 | 4 | CO | NH | 2-NO$_2$—Ph |
| 3-30 | 4 | CO | NH | 4-NO$_2$—Ph |
| 3-31 | 4 | CO | NH | 2-NH$_2$—Ph |
| 3-32 | 4 | CO | NH | 4-NH$_2$—Ph |
| 3-33 | 4 | CO | NH | 2-(HO$_3$S)—Ph |
| 3-34 | 4 | CO | NH | 4-(HO$_3$S)—Ph |
| 3-35 | 4 | CO | NH | 2-(NH$_2$O$_2$S)—Ph |
| 3-36 | 4 | CO | NH | 4-(NH$_2$O$_2$S)—Ph |
| 3-37 | 4 | CO | NH | 2-CN—Ph |
| 3-38 | 4 | CO | NH | 4-CN—Ph |
| 3-39 | 4 | CO | NH | 2-(HOCH$_2$)—Ph |
| 3-40 | 4 | CO | NH | 4-(HOCH$_2$)—Ph |
| 3-41 | 4 | CO | NH | Me |
| 3-42 | 4 | CO | NH | Et |
| 3-43 | 4 | CO | NH | Pr |
| 3-44 | 4 | CO | NH | iPr |
| 3-45 | 4 | CO | NH | Bu |
| 3-46 | 4 | CO | NH | HOOCCH$_2$— |
| 3-47 | 4 | CO | NH | MeOOCCH$_2$— |
| 3-48 | 4 | CO | NH | MeCH(COOH)— |
| 3-49 | 4 | CO | NH | HOOC—(CH$_2$)$_2$— |
| 3-50 | 4 | CO | NH | MeCH(COOMe)- |
| 3-51 | 4 | CO | NH | 1-HOOC-iBu |
| 3-52 | 4 | CO | NH | 1-MeOOC-iBu |
| 3-53 | 4 | CO | NH | 1-HOOC-iPn |
| 3-54 | 4 | CO | NH | 1-MeOOC-iPn |
| 3-55 | 4 | CO | NH | 1-HOOC-2-Me—Bu |
| 3-56 | 4 | CO | NH | 1-MeOOC-2-Me—Bu |
| 3-57 | 4 | CO | NH | CH$_2$CH$_2$SO$_3$H |
| 3-58 | 4 | CO | NH | OH |
| 3-59 | 4 | CO | NH | MeO |
| 3-60 | 4 | CO | NH | EtO |
| 3-61 | 4 | CO | NH | Pro |
| 3-62 | 4 | CO | NH | iPro |
| 3-63 | 4 | CO | NH | BuO |
| 3-64 | 4 | CO | NH | iBuO |
| 3-65 | 4 | CO | NH | sBuO |
| 3-66 | 4 | CO | NH | tBuO |
| 3-67 | 4 | CO | NH | HxO |
| 3-68 | 4 | CO | NH | PhO |
| 3-69 | 4 | CO | NH | BnO |
| 3-70 | 4 | CO | NH | Z-1 |
| 3-71 | 4 | CO | NH | Z-2 |
| 3-72 | 4 | CO | NH | Z-3 |
| 3-73 | 4 | CO | NH | Z-4 |
| 3-74 | 4 | CO | NH | Z-5 |
| 3-75 | 4 | CO | NH | Z-6 |
| 3-76 | 4 | CO | NH | Z-7 |
| 3-77 | 4 | CO | NH | Z-8 |
| 3-78 | 4 | CO | NH | Z-9 |
| 3-79 | 4 | CO | NH | Z-10 |
| 3-80 | 4 | CO | NH | Z-11 |
| 3-81 | 4 | CO | NH | Z-12 |
| 3-82 | 4 | CO | NH | 3-Py |
| 3-83 | 4 | CO | NH | 4-Py |
| 3-84 | 4 | CO | N(Ac) | H |
| 3-85 | 4 | CO | N(Ac) | Ph |
| 3-86 | 4 | CO | N(Ac) | 2-Me—Ph |
| 3-87 | 4 | CO | N(Ac) | 4-Me—Ph |
| 3-88 | 4 | CO | N(Ac) | 2,4-diMe—Ph |
| 3-89 | 4 | CO | N(Ac) | 3,4-diMe—Ph |
| 3-90 | 4 | CO | N(Ac) | 2-(CF$_3$)Ph |
| 3-91 | 4 | CO | N(Ac) | 4-(CF$_3$)Ph |
| 3-92 | 4 | CO | N(Ac) | 2-MeOPh |
| 3-93 | 4 | CO | N(Ac) | 4-MeOPh |
| 3-94 | 4 | CO | N(Ac) | 2-EtOPh |
| 3-95 | 4 | CO | N(Ac) | 4-EtOPh |
| 3-96 | 4 | CO | N(Ac) | 2-HOPh |
| 3-97 | 4 | CO | N(Ac) | 4-HOPh |
| 3-98 | 4 | CO | N(Ac) | 2-(HOOC)Ph |
| 3-99 | 4 | CO | N(Ac) | 4-(HOOC)Ph |
| 3-100 | 4 | CO | N(Ac) | 2-(MeOOC)Ph |
| 3-101 | 4 | CO | N(Ac) | 4-(MeOOC)Ph |
| 3-102 | 4 | CO | N(Ac) | 2-(EtOOC)Ph |
| 3-103 | 4 | CO | N(Ac) | 4-(EtOOC)Ph |
| 3-104 | 4 | CO | N(Ac) | 2-(tBuOOC)Ph |
| 3-105 | 4 | CO | N(Ac) | 4-(tBuOOC)Ph |
| 3-106 | 4 | CO | N(Ac) | 2-Cl—Ph |
| 3-107 | 4 | CO | N(Ac) | 4-Cl—Ph |
| 3-108 | 4 | CO | N(Ac) | 2-Br—Ph |
| 3-109 | 4 | CO | N(Ac) | 4-Br—Ph |
| 3-110 | 4 | CO | N(Ac) | 2-I—Ph |
| 3-111 | 4 | CO | N(Ac) | 4-I—Ph |
| 3-112 | 4 | CO | N(Ac) | 2-NO$_2$—Ph |
| 3-113 | 4 | CO | N(Ac) | 4-NO$_2$—Ph |
| 3-114 | 4 | CO | N(Ac) | 2-NH$_2$—Ph |
| 3-115 | 4 | CO | N(Ac) | 4-NH$_2$—Ph |
| 3-116 | 4 | CO | N(Ac) | 2-(HO$_3$S)Ph |
| 3-117 | 4 | CO | N(Ac) | 4-(HO$_3$S)Ph |
| 3-118 | 4 | CO | N(Ac) | 2-(NH$_2$O$_2$S)Ph |
| 3-119 | 4 | CO | N(Ac) | 4-(NH$_2$O$_2$S)Ph |
| 3-120 | 4 | CO | N(Ac) | 2-CN—Ph |
| 3-121 | 4 | CO | N(Ac) | 4-CN—Ph |
| 3-122 | 4 | CO | N(Ac) | 2-(HOCH$_2$)Ph |
| 3-123 | 4 | CO | N(Ac) | 4-(HOCH$_2$)Ph |
| 3-124 | 4 | CO | N(Ac) | Me |
| 3-125 | 4 | CO | N(Ac) | Et |
| 3-126 | 4 | CO | N(Ac) | Pr |
| 3-127 | 4 | CO | N(Ac) | iPr |
| 3-128 | 4 | CO | N(Ac) | Bu |
| 3-129 | 4 | CO | N(Ac) | HOOCCH$_2$— |
| 3-130 | 4 | CO | N(Ac) | MeOOCCH$_2$— |
| 3-131 | 4 | CO | N(Ac) | MeCH(COOH) |
| 3-132 | 4 | CO | N(Ac) | HOOC—(CH$_2$)$_2$— |
| 3-133 | 4 | CO | N(Ac) | MeCH(COOMe) |
| 3-134 | 4 | CO | N(Ac) | 1-HOOC-iBu |
| 3-135 | 4 | CO | N(Ac) | 1-MeOOC-iBu |
| 3-136 | 4 | CO | N(Ac) | 1-HOOC-iPn |
| 3-137 | 4 | CO | N(Ac) | 1-MeOOC-iPn |
| 3-138 | 4 | CO | N(Ac) | 1-HOOC-2-Me—Bu |
| 3-139 | 4 | CO | N(Ac) | 1-MeOOC-2-Me—Bu |
| 3-140 | 4 | CO | N(Ac) | CH$_2$CH$_2$SO$_3$H |
| 3-141 | 4 | CO | N(Ac) | OH |
| 3-142 | 4 | CO | N(Ac) | MeO |
| 3-143 | 4 | CO | N(Ac) | EtO |
| 3-144 | 4 | CO | N(Ac) | PrO |
| 3-145 | 4 | CO | N(Ac) | iPrO |
| 3-146 | 4 | CO | N(Ac) | BuO |
| 3-147 | 4 | CO | N(Ac) | iBuO |
| 3-148 | 4 | CO | N(Ac) | sBuO |
| 3-149 | 4 | CO | N(Ac) | tBuO |
| 3-150 | 4 | CO | N(Ac) | HxO |
| 3-151 | 4 | CO | N(Ac) | PhO |
| 3-152 | 4 | CO | N(Ac) | BnO |
| 3-153 | 4 | CO | N(Ac) | Z-1 |
| 3-154 | 4 | CO | N(Ac) | Z-2 |
| 3-155 | 4 | CO | N(Ac) | Z-3 |
| 3-156 | 4 | CO | N(Ac) | Z-4 |
| 3-157 | 4 | CO | N(Ac) | Z-5 |
| 3-158 | 4 | CO | N(Ac) | Z-6 |
| 3-159 | 4 | CO | N(Ac) | Z-7 |
| 3-160 | 4 | CO | N(Ac) | Z-8 |
| 3-161 | 4 | CO | N(Ac) | Z-9 |
| 3-162 | 4 | CO | N(Ac) | Z-10 |
| 3-163 | 4 | CO | N(Ac) | Z-11 |
| 3-164 | 4 | CO | N(Ac) | Z-12 |
| 3-165 | 4 | CO | N(Ac) | 3-Py |
| 3-166 | 4 | CO | N(Ac) | 4-Py |
| 3-167 | 4 | COO | — | H |
| 3-168 | 4 | COO | — | Ph |
| 3-169 | 4 | COO | — | 2-Me—Ph |
| 3-170 | 4 | COO | — | 4-Me—Ph |
| 3-171 | 4 | COO | — | 2,4-diMe—Ph |
| 3-172 | 4 | COO | — | 3,4-diMe—Ph |
| 3-173 | 4 | COO | — | 2-(CF$_3$)Ph |
| 3-174 | 4 | COO | — | 4-(CF$_3$)Ph |
| 3-175 | 4 | COO | — | 2-MeOPh |

TABLE 3-continued

| Cpd. No. | k | A | B | R¹ |
|---|---|---|---|---|
| 3-176 | 4 | COO | — | 4-MeOPh |
| 3-177 | 4 | COO | — | 2-EtOPh |
| 3-178 | 4 | COO | — | 4-EtOPh |
| 3-179 | 4 | COO | — | 2-HOPh |
| 3-180 | 4 | COO | — | 4-HOPh |
| 3-181 | 4 | COO | — | 2-(HOOC)Ph |
| 3-182 | 4 | COO | — | 4-(HOOC)Ph |
| 3-183 | 4 | COO | — | 2-(MeOOC)Ph |
| 3-184 | 4 | COO | — | 4-(MeOOC)Ph |
| 3-185 | 4 | COO | — | 2-(EtOOC)Ph |
| 3-186 | 4 | COO | — | 4-(EtOOC)Ph |
| 3-187 | 4 | COO | — | 2-(tBuOOC)Ph |
| 3-188 | 4 | COO | — | 4-(tBuOOC)Ph |
| 3-189 | 4 | COO | — | 2-Cl—Ph |
| 3-190 | 4 | COO | — | 4-Cl—Ph |
| 3-191 | 4 | COO | — | 2-Br—Ph |
| 3-192 | 4 | COO | — | 4-Br—Ph |
| 3-193 | 4 | COO | — | 2-I—Ph |
| 3-194 | 4 | COO | — | 4-I—Ph |
| 3-195 | 4 | COO | — | 2-$NO_2$—Ph |
| 3-196 | 4 | COO | — | 4-$NO_2$—Ph |
| 3-197 | 4 | COO | — | 2-$NH_2$—Ph |
| 3-198 | 4 | COO | — | 4-$NH_2$—Ph |
| 3-199 | 4 | COO | — | 2-($HO_3S$)Ph |
| 3-200 | 4 | COO | — | 4-($HO_3S$)Ph |
| 3-201 | 4 | COO | — | 2-($NH_2O_2S$)Ph |
| 3-202 | 4 | COO | — | 4-($NH_2O_2S$)Ph |
| 3-203 | 4 | COO | — | 2-CN—Ph |
| 3-204 | 4 | COO | — | 4-CN—Ph |
| 3-205 | 4 | COO | — | 2-($HOCH_2$)Ph |
| 3-206 | 4 | COO | — | 4-($HOCH_2$)Ph |
| 3-207 | 4 | COO | — | Me |
| 3-208 | 4 | COO | — | Et |
| 3-209 | 4 | COO | — | Pr |
| 3-210 | 4 | COO | — | iPr |
| 3-211 | 4 | COO | — | Bu |
| 3-212 | 4 | COO | — | HOOC$CH_2$— |
| 3-213 | 4 | COO | — | HOOC—($CH_2$)$_2$— |
| 3-214 | 4 | COO | — | MeCH(COOMe) |
| 3-215 | 4 | COO | — | 1-HOOC-iBu |
| 3-216 | 4 | COO | — | 1-HOOC-iPn |
| 3-217 | 4 | COO | — | Z-1 |
| 3-218 | 4 | COO | — | Z-2 |
| 3-219 | 4 | COO | — | Z-3 |
| 3-220 | 4 | COO | — | Z-4 |
| 3-221 | 4 | COO | — | Z-5 |
| 3-222 | 4 | COO | — | Z-6 |
| 3-223 | 4 | COO | — | Z-7 |
| 3-224 | 4 | COO | — | Z-8 |
| 3-225 | 4 | COO | — | Z-9 |
| 3-226 | 4 | COO | — | Z-10 |
| 3-227 | 4 | COO | — | Z-11 |
| 3-228 | 4 | COO | — | Z-12 |
| 3-229 | 4 | COO | — | 3-Py |
| 3-230 | 4 | COO | — | 4-Py |
| 3-231 | 4 | CONHCO | — | H |
| 3-232 | 4 | CONHCO | — | Ph |
| 3-233 | 4 | CONHCO | — | 2-Me—Ph |
| 3-234 | 4 | CONHCO | — | 4-Me—Ph |
| 3-235 | 4 | CONHCO | — | 2,4-diMe—Ph |
| 3-236 | 4 | CONHCO | — | 3,4-diMe—Ph |
| 3-237 | 4 | CONHCO | — | 2-($CF_3$)Ph |
| 3-238 | 4 | CONHCO | — | 4-($CF_3$)Ph |
| 3-239 | 4 | CONHCO | — | 2-MeOPh |
| 3-240 | 4 | CONHCO | — | 4-MeOPh |
| 3-241 | 4 | CONHCO | — | 2-EtOPh |
| 3-242 | 4 | CONHCO | — | 4-EtOPh |
| 3-243 | 4 | CONHCO | — | 2-HOPh |
| 3-244 | 4 | CONHCO | — | 4-HOPh |
| 3-245 | 4 | CONHCO | — | 2-(HOOC)Ph |
| 3-246 | 4 | CONHCO | — | 4-(HOOC)Ph |
| 3-247 | 4 | CONHCO | — | 2-(MeOOC)Ph |
| 3-248 | 4 | CONHCO | — | 4-(MeOOC)Ph |
| 3-249 | 4 | CONHCO | — | 2-(EtOOC)Ph |
| 3-250 | 4 | CONHCO | — | 4-(EtOOC)Ph |
| 3-251 | 4 | CONHCO | — | 2-(tBuOOC)Ph |
| 3-252 | 4 | CONHCO | — | 4-(tBuOOC)Ph |
| 3-253 | 4 | CONHCO | — | 2-Cl—Ph |
| 3-254 | 4 | CONHCO | — | 4-Cl—Ph |
| 3-255 | 4 | CONHCO | — | 2-Br—Ph |
| 3-256 | 4 | CONHCO | — | 4-Br—Ph |
| 3-257 | 4 | CONHCO | — | 2-I—Ph |
| 3-258 | 4 | CONHCO | — | 4-I—Ph |
| 3-259 | 4 | CONHCO | — | 2-$NO_2$—Ph |
| 3-260 | 4 | CONHCO | — | 4-$NO_2$—Ph |
| 3-261 | 4 | CONHCO | — | 2-$NH_2$—Ph |
| 3-262 | 4 | CONHCO | — | 4-$NH_2$—Ph |
| 3-263 | 4 | CONHCO | — | 2-($HO_3S$)Ph |
| 3-264 | 4 | CONHCO | — | 4-($HO_3S$)Ph |
| 3-265 | 4 | CONHCO | — | 2-($NH_2O_2S$)Ph |
| 3-266 | 4 | CONHCO | — | 4-($NH_2O_2S$)Ph |
| 3-267 | 4 | CONHCO | — | 2-CN—Ph |
| 3-268 | 4 | CONHCO | — | 4-CN—Ph |
| 3-269 | 4 | CONHCO | — | 2-($HOCH_2$)Ph |
| 3-270 | 4 | CONHCO | — | 4-($HOCH_2$)Ph |
| 3-271 | 4 | CONHCO | — | Me |
| 3-272 | 4 | CONHCO | — | Et |
| 3-273 | 4 | CONHCO | — | Pr |
| 3-274 | 4 | CONHCO | — | iPr |
| 3-275 | 4 | CONHCO | — | Bu |
| 3-276 | 4 | CONHCO | — | HOOC$CH_2$— |
| 3-277 | 4 | CONHCO | — | MeOOC$CH_2$— |
| 3-278 | 4 | CONHCO | — | MeCH(COOH) |
| 3-279 | 4 | CONHCO | — | HOOC—($CH_2$)$_2$— |
| 3-280 | 4 | CONHCO | — | MeCH(COOMe) |
| 3-281 | 4 | CONHCO | — | 1-HOOC-iBu |
| 3-282 | 4 | CONHCO | — | 1-MeOOC-iBu |
| 3-283 | 4 | CONHCO | — | 1-HOOC-iPn |
| 3-284 | 4 | CONHCO | — | 1-MeOOC-iPn |
| 3-285 | 4 | CONHCO | — | 1-HOOC-2-Me—Bu |
| 3-286 | 4 | CONHCO | — | 1-MeOOC-2-Me—Bu |
| 3-287 | 4 | CONHCO | — | $CH_2CH_2SO_3H$ |
| 3-288 | 4 | CONHCO | — | Z-1 |
| 3-289 | 4 | CONHCO | — | Z-2 |
| 3-290 | 4 | CONHCO | — | Z-3 |
| 3-291 | 4 | CONHCO | — | Z-4 |
| 3-292 | 4 | CONHCO | — | Z-5 |
| 3-293 | 4 | CONHCO | — | Z-6 |
| 3-294 | 4 | CONHCO | — | Z-7 |
| 3-295 | 4 | CONHCO | — | Z-8 |
| 3-296 | 4 | CONHCO | — | Z-9 |
| 3-297 | 4 | CONHCO | — | Z-10 |
| 3-298 | 4 | CONHCO | — | Z-11 |
| 3-299 | 4 | CONHCO | — | Z-12 |
| 3-300 | 4 | CONHCO | — | 3-Py |
| 3-301 | 4 | CONHCO | — | 4-Py |
| 3-302 | 4 | CON(Ac)CO | — | H |
| 3-303 | 4 | CON(Ac)CO | — | Ph |
| 3-304 | 4 | CON(Ac)CO | — | 2-Me—Ph |
| 3-305 | 4 | CON(Ac)CO | — | 4-Me—Ph |
| 3-306 | 4 | CON(Ac)CO | — | 2,4-diMe—Ph |
| 3-307 | 4 | CON(Ac)CO | — | 3,4-diMe—Ph |
| 3-308 | 4 | CON(Ac)CO | — | 2-($CF_3$)Ph |
| 3-309 | 4 | CON(Ac)CO | — | 4-($CF_3$)Ph |
| 3-310 | 4 | CON(Ac)CO | — | 2-MeOPh |
| 3-311 | 4 | CON(Ac)CO | — | 4-MeOPh |
| 3-312 | 4 | CON(Ac)CO | — | 2-EtOPh |
| 3-313 | 4 | CON(Ac)CO | — | 4-EtOPh |
| 3-314 | 4 | CON(Ac)CO | — | 2-HOPh |
| 3-315 | 4 | CON(Ac)CO | — | 4-HOPh |
| 3-316 | 4 | CON(Ac)CO | — | 2-(HOOC)Ph |
| 3-317 | 4 | CON(Ac)CO | — | 4-(HOOC)Ph |
| 3-318 | 4 | CON(Ac)CO | — | 2-(MeOOC)Ph |
| 3-319 | 4 | CON(Ac)CO | — | 4-(MeOOC)Ph |
| 3-320 | 4 | CON(Ac)CO | — | 2-(EtOOC)Ph |
| 3-321 | 4 | CON(Ac)CO | — | 4-(EtOOC)Ph |
| 3-322 | 4 | CON(Ac)CO | — | 2-(tBuOOC)Ph |
| 3-323 | 4 | CON(Ac)CO | — | 4-(tBuOOC)Ph |
| 3-324 | 4 | CON(Ac)CO | — | 2-Cl—Ph |
| 3-325 | 4 | CON(Ac)CO | — | 4-Cl—Ph |
| 3-326 | 4 | CON(Ac)CO | — | 2-Br—Ph |
| 3-327 | 4 | CON(Ac)CO | — | 4-Br—Ph |

TABLE 3-continued

| Cpd. No. | k | A | B | R¹ |
|---|---|---|---|---|
| 3-328 | 4 | CON(Ac)CO | — | 2-I—Ph |
| 3-329 | 4 | CON(Ac)CO | — | 4-I—Ph |
| 3-330 | 4 | CON(Ac)CO | — | 2-NO$_2$—Ph |
| 3-331 | 4 | CON(Ac)CO | — | 4-NO$_2$—Ph |
| 3-332 | 4 | CON(Ac)CO | — | 2-NH$_2$—Ph |
| 3-333 | 4 | CON(Ac)CO | — | 4-NH$_2$—Ph |
| 3-334 | 4 | CON(Ac)CO | — | 2-(HO$_3$S)Ph |
| 3-335 | 4 | CON(Ac)CO | — | 4-(HO$_3$S)Ph |
| 3-336 | 4 | CON(Ac)CO | — | 2-(NH$_2$O$_2$S)Ph |
| 3-337 | 4 | CON(Ac)CO | — | 4-(NH$_2$O$_2$S)Ph |
| 3-338 | 4 | CON(Ac)CO | — | 2-CN—Ph |
| 3-339 | 4 | CON(Ac)CO | — | 4-CN—Ph |
| 3-340 | 4 | CON(Ac)CO | — | 2-(HOCH$_2$)Ph |
| 3-341 | 4 | CON(Ac)CO | — | 4-(HOCH$_2$)Ph |
| 3-342 | 4 | CON(Ac)CO | — | Me |
| 3-343 | 4 | CON(Ac)CO | — | Et |
| 3-344 | 4 | CON(Ac)CO | — | Pr |
| 3-345 | 4 | CON(Ac)CO | — | iPr |
| 3-346 | 4 | CON(Ac)CO | — | Bu |
| 3-347 | 4 | CON(Ac)CO | — | HOOCCH$_2$— |
| 3-348 | 4 | CON(Ac)CO | — | MeOOCCH$_2$— |
| 3-349 | 4 | CON(Ac)CO | — | MeCH(COOH) |
| 3-350 | 4 | CON(Ac)CO | — | HOOC—(CH$_2$)$_2$— |
| 3-351 | 4 | CON(Ac)CO | — | MeCH(COOMe) |
| 3-352 | 4 | CON(Ac)CO | — | 1-HOOC-iBu |
| 3-353 | 4 | CON(Ac)CO | — | 1-MeOOC-iBu |
| 3-354 | 4 | CON(Ac)CO | — | 1-HOOC-iPn |
| 3-355 | 4 | CON(Ac)CO | — | 1-MeOOC-iPn |
| 3-356 | 4 | CON(Ac)CO | — | 1-HOOC-2-Me—Bu |
| 3-357 | 4 | CON(Ac)CO | — | 1-MeOOC-2-Me—Bu |
| 3-358 | 4 | CON(Ac)CO | — | CH$_2$CH$_2$SO$_3$H |
| 3-359 | 4 | CON(Ac)CO | — | Z-1 |
| 3-360 | 4 | CON(Ac)CO | — | Z-2 |
| 3-361 | 4 | CON(Ac)CO | — | Z-3 |
| 3-362 | 4 | CON(Ac)CO | — | Z-4 |
| 3-363 | 4 | CON(Ac)CO | — | Z-5 |
| 3-364 | 4 | CON(Ac)CO | — | Z-6 |
| 3-365 | 4 | CON(Ac)CO | — | Z-7 |
| 3-366 | 4 | CON(Ac)CO | — | Z-8 |
| 3-367 | 4 | CON(Ac)CO | — | Z-9 |
| 3-368 | 4 | CON(Ac)CO | — | Z-10 |
| 3-369 | 4 | CON(Ac)CO | — | Z-11 |
| 3-370 | 4 | CON(Ac)CO | — | Z-12 |
| 3-371 | 4 | CON(Ac)CO | — | 3-Py |
| 3-372 | 4 | CON(Ac)CO | — | 4-Py |
| 3-373 | 4 | CONHCO | NH | H |
| 3-374 | 4 | CONHCO | NH | Ph |
| 3-375 | 4 | CONHCO | NH | 2-Me—Ph |
| 3-376 | 4 | CONHCO | NH | 4-Me—Ph |
| 3-377 | 4 | CONHCO | NH | 2,4-diMe—Ph |
| 3-378 | 4 | CONHCO | NH | 3,4-diMe—Ph |
| 3-379 | 4 | CONHCO | NH | 2-(CF$_3$)Ph |
| 3-380 | 4 | CONHCO | NH | 4-(CF$_3$)Ph |
| 3-381 | 4 | CONHCO | NH | 2-MeOPh |
| 3-382 | 4 | CONHCO | NH | 4-MeOPh |
| 3-383 | 4 | CONHCO | NH | 2-EtOPh |
| 3-384 | 4 | CONHCO | NH | 4-EtOPh |
| 3-385 | 4 | CONHCO | NH | 2-HOPh |
| 3-386 | 4 | CONHCO | NH | 4-HOPh |
| 3-387 | 4 | CONHCO | NH | 2-(HOOC)Ph |
| 3-388 | 4 | CONHCO | NH | 4-(HOOC)Ph |
| 3-389 | 4 | CONHCO | NH | 2-(MeOOC)Ph |
| 3-390 | 4 | CONHCO | NH | 4-(MeOOC)Ph |
| 3-391 | 4 | CONHCO | NH | 2-(EtOOC)Ph |
| 3-392 | 4 | CONHCO | NH | 4-(EtOOC)Ph |
| 3-393 | 4 | CONHCO | NH | 2-(tBuOOC)Ph |
| 3-394 | 4 | CONHCO | NH | 4-(tBuOOC)Ph |
| 3-395 | 4 | CONHCO | NH | 2-Cl—Ph |
| 3-396 | 4 | CONHCO | NH | 4-Cl—Ph |
| 3-397 | 4 | CONHCO | NH | 2-Br—Ph |
| 3-398 | 4 | CONHCO | NH | 4-Br—Ph |
| 3-399 | 4 | CONHCO | NH | 2-I—Ph |
| 3-400 | 4 | CONHCO | NH | 4-I—Ph |
| 3-401 | 4 | CONHCO | NH | 2-NO$_2$—Ph |
| 3-402 | 4 | CONHCO | NH | 4-NO$_2$—Ph |
| 3-403 | 4 | CONHCO | NH | 2-NH$_2$—Ph |
| 3-404 | 4 | CONHCO | NH | 4-NH$_2$—Ph |
| 3-405 | 4 | CONHCO | NH | 2-(HO$_3$S)Ph |
| 3-406 | 4 | CONHCO | NH | 4-(HO$_3$S)Ph |
| 3-407 | 4 | CONHCO | NH | 2-(NH$_2$O$_2$S)Ph |
| 3-408 | 4 | CONHCO | NH | 4-(NH$_2$O$_2$S)Ph |
| 3-409 | 4 | CONHCO | NH | 2-CN—Ph |
| 3-410 | 4 | CONHCO | NH | 4-CN—Ph |
| 3-411 | 4 | CONHCO | NH | 2-(HOCH$_2$)Ph |
| 3-412 | 4 | CONHCO | NH | 4-(HOCH$_2$)Ph |
| 3-413 | 4 | CONHCO | NH | Me |
| 3-414 | 4 | CONHCO | NH | Et |
| 3-415 | 4 | CONHCO | NH | Pr |
| 3-416 | 4 | CONHCO | NH | iPr |
| 3-417 | 4 | CONHCO | NH | Bu |
| 3-418 | 4 | CONHCO | NH | HOOCCH$_2$— |
| 3-419 | 4 | CONHCO | NH | MeOOCCH$_2$— |
| 3-420 | 4 | CONHCO | NH | MeCH(COOH) |
| 3-421 | 4 | CONHCO | NH | HOOC—(CH$_2$)$_2$— |
| 3-422 | 4 | CONHCO | NH | MeCH(COOMe) |
| 3-423 | 4 | CONHCO | NH | 1-HOOC-iBu |
| 3-424 | 4 | CONHCO | NH | 1-MeOOC-iBu |
| 3-425 | 4 | CONHCO | NH | 1-HOOC-iPn |
| 3-426 | 4 | CONHCO | NH | 1-MeOOC-iPn |
| 3-427 | 4 | CONHCO | NH | 1-HOOC-2-Me—Bu |
| 3-428 | 4 | CONHCO | NH | 1-MeOOC-2-Me—Bu |
| 3-429 | 4 | CONHCO | NH | CH$_2$CH$_2$SO$_3$H |
| 3-430 | 4 | CONHCO | NH | HO |
| 3-431 | 4 | CONHCO | NH | MeO |
| 3-432 | 4 | CONHCO | NH | EtO |
| 3-433 | 4 | CONHCO | NH | PrO |
| 3-434 | 4 | CONHCO | NH | iPrO |
| 3-435 | 4 | CONHCO | NH | BuO |
| 3-436 | 4 | CONHCO | NH | iBuO |
| 3-437 | 4 | CONHCO | NH | sBuO |
| 3-438 | 4 | CONHCO | NH | tBuO |
| 3-439 | 4 | CONHCO | NH | HxO |
| 3-440 | 4 | CONHCO | NH | PhO |
| 3-441 | 4 | CONHCO | NH | BnO |
| 3-442 | 4 | CONHCO | NH | Z-1 |
| 3-443 | 4 | CONHCO | NH | Z-2 |
| 3-444 | 4 | CONHCO | NH | Z-3 |
| 3-445 | 4 | CONHCO | NH | Z-4 |
| 3-446 | 4 | CONHCO | NH | Z-5 |
| 3-447 | 4 | CONHCO | NH | Z-6 |
| 3-448 | 4 | CONHCO | NH | Z-7 |
| 3-449 | 4 | CONHCO | NH | Z-8 |
| 3-450 | 4 | CONHCO | NH | Z-9 |
| 3-451 | 4 | CONHCO | NH | Z-10 |
| 3-452 | 4 | CONHCO | NH | Z-11 |
| 3-453 | 4 | CONHCO | NH | Z-12 |
| 3-454 | 4 | CONHCO | NH | 3-Py |
| 3-455 | 4 | CONHCO | NH | 4-Py |
| 3-456 | 4 | CONHSO$_2$ | — | H |
| 3-457 | 4 | CONHSO$_2$ | — | Ph |
| 3-458 | 4 | CONHSO$_2$ | — | 2-Me—Ph |
| 3-459 | 4 | CONHSO$_2$ | — | 4-Me—Ph |
| 3-460 | 4 | CONHSO$_2$ | — | 2,4-diMe—Ph |
| 3-461 | 4 | CONHSO$_2$ | — | 3,4-diMe—Ph |
| 3-462 | 4 | CONHSO$_2$ | — | 2-(CF$_3$)Ph |
| 3-463 | 4 | CONHSO$_2$ | — | 4-(CF$_3$)Ph |
| 3-464 | 4 | CONHSO$_2$ | — | 2-MeOPh |
| 3-465 | 4 | CONHSO$_2$ | — | 4-MeOPh |
| 3-466 | 4 | CONHSO$_2$ | — | 2-EtOPh |
| 3-467 | 4 | CONHSO$_2$ | — | 4-EtOPh |
| 3-468 | 4 | CONHSO$_2$ | — | 2-HOPh |
| 3-469 | 4 | CONHSO$_2$ | — | 4-HOPh |
| 3-470 | 4 | CONHSO$_2$ | — | 2-(HOOC)Ph |
| 3-471 | 4 | CONHSO$_2$ | — | 4-(HOOC)Ph |
| 3-472 | 4 | CONHSO$_2$ | — | 2-(MeOOC)Ph |
| 3-473 | 4 | CONHSO$_2$ | — | 4-(MeOOC)Ph |
| 3-474 | 4 | CONHSO$_2$ | — | 2-(EtOOC)Ph |
| 3-475 | 4 | CONHSO$_2$ | — | 4-(EtOOC)Ph |
| 3-476 | 4 | CONHSO$_2$ | — | 2-(tBuOOC)Ph |
| 3-477 | 4 | CONHSO$_2$ | — | 4-(tBuOOC)Ph |
| 3-478 | 4 | CONHSO$_2$ | — | 2-Cl—Ph |
| 3-479 | 4 | CONHSO$_2$ | — | 4-Cl—Ph |

TABLE 3-continued

| Cpd. No. | k | A | B | R¹ |
|---|---|---|---|---|
| 3-480 | 4 | CONHSO$_2$ | — | 2-Br—Ph |
| 3-481 | 4 | CONHSO$_2$ | — | 4-Br—Ph |
| 3-482 | 4 | CONHSO$_2$ | — | 2-I—Ph |
| 3-483 | 4 | CONHSO$_2$ | — | 4-I—Ph |
| 3-484 | 4 | CONHSO$_2$ | — | 2-NO$_2$—Ph |
| 3-485 | 4 | CONHSO$_2$ | — | 4-NO$_2$—Ph |
| 3-486 | 4 | CONHSO$_2$ | — | 2-NH$_2$—Ph |
| 3-487 | 4 | CONHSO$_2$ | — | 4-NH$_2$—Ph |
| 3-488 | 4 | CONHSO$_2$ | — | 2-(HO$_3$S)Ph |
| 3-489 | 4 | CONHSO$_2$ | — | 4-(HO$_3$S)Ph |
| 3-490 | 4 | CONHSO$_2$ | — | 2-(NH$_2$O$_2$S)Ph |
| 3-491 | 4 | CONHSO$_2$ | — | 4-(NH$_2$O$_2$S)Ph |
| 3-492 | 4 | CONHSO$_2$ | — | 2-CN—Ph |
| 3-493 | 4 | CONHSO$_2$ | — | 4-CN—Ph |
| 3-494 | 4 | CONHSO$_2$ | — | 2-(HOCH$_2$)Ph |
| 3-495 | 4 | CONHSO$_2$ | — | 4-(HOCH$_2$)Ph |
| 3-496 | 4 | CONHSO$_2$ | — | Me |
| 3-497 | 4 | CONHSO$_2$ | — | Et |
| 3-498 | 4 | CONHSO$_2$ | — | Pr |
| 3-499 | 4 | CONHSO$_2$ | — | iPr |
| 3-500 | 4 | CONHSO$_2$ | — | Bu |
| 3-501 | 4 | CONHSO$_2$ | — | HOOCCH$_2$— |
| 3-502 | 4 | CONHSO$_2$ | — | MeOOCCH$_2$— |
| 3-503 | 4 | CONHSO$_2$ | — | MeCH(COOH) |
| 3-504 | 4 | CONHSO$_2$ | — | HOOC-(CH$_2$)$_2$— |
| 3-505 | 4 | CONHSO$_2$ | — | MeCH(COOMe) |
| 3-506 | 4 | CONHSO$_2$ | — | 1-HOOC-iBu |
| 3-507 | 4 | CONHSO$_2$ | — | 1-MeOOC-iBu |
| 3-508 | 4 | CONHSO$_2$ | — | 1-HOOC-iPn |
| 3-509 | 4 | CONHSO$_2$ | — | 1-MeOOC-iPn |
| 3-510 | 4 | CONHSO$_2$ | — | 1-HOOC-2-Me—Bu |
| 3-511 | 4 | CONHSO$_2$ | — | 1-MeOOC-2-Me—Bu |
| 3-512 | 4 | CONHSO$_2$ | — | CH$_2$CH$_2$SO$_3$H |
| 3-513 | 4 | CONHSO$_2$ | — | OH |
| 3-514 | 4 | CONHSO$_2$ | — | MeO |
| 3-515 | 4 | CONHSO$_2$ | — | EtO |
| 3-516 | 4 | CONHSO$_2$ | — | Pro |
| 3-517 | 4 | CONHSO$_2$ | — | iPrO |
| 3-518 | 4 | CONHSO$_2$ | — | BuO |
| 3-519 | 4 | CONHSO$_2$ | — | iBuO |
| 3-520 | 4 | CONHSO$_2$ | — | sBuO |
| 3-521 | 4 | CONHSO$_2$ | — | tBuO |
| 3-522 | 4 | CONHSO$_2$ | — | HxO |
| 3-523 | 4 | CONHSO$_2$ | — | PhO |
| 3-524 | 4 | CONHSO$_2$ | — | BnO |
| 3-525 | 4 | CONHSO$_2$ | — | Z-1 |
| 3-526 | 4 | CONHSO$_2$ | — | Z-2 |
| 3-527 | 4 | CONHSO$_2$ | — | Z-3 |
| 3-528 | 4 | CONHSO$_2$ | — | Z-4 |
| 3-529 | 4 | CONHSO$_2$ | — | Z-5 |
| 3-530 | 4 | CONHSO$_2$ | — | Z-6 |
| 3-531 | 4 | CONHSO$_2$ | — | Z-7 |
| 3-532 | 4 | CONHSO$_2$ | — | Z-8 |
| 3-533 | 4 | CONHSO$_2$ | — | Z-9 |
| 3-534 | 4 | CONHSO$_2$ | — | Z-10 |
| 3-535 | 4 | CONHSO$_2$ | — | Z-11 |
| 3-536 | 4 | CONHSO$_2$ | — | Z-12 |
| 3-537 | 4 | CONHSO$_2$ | — | 3-Py |
| 3-538 | 4 | CONHSO$_2$ | — | 4-Py |
| 3-539 | 4 | CONHSO$_2$ | NH | H |
| 3-540 | 4 | CONHSO$_2$ | NH | Ph |
| 3-541 | 4 | CONHSO$_2$ | NH | 2-Me—Ph |
| 3-542 | 4 | CONHSO$_2$ | NH | 4-Me—Ph |
| 3-543 | 4 | CONHSO$_2$ | NH | 2,4-diMe—Ph |
| 3-544 | 4 | CONHSO$_2$ | NH | 3,4-diMe—Ph |
| 3-545 | 4 | CONHSO$_2$ | NH | 2-(CF$_3$)Ph |
| 3-546 | 4 | CONHSO$_2$ | NH | 4-(CF$_3$)Ph |
| 3-547 | 4 | CONHSO$_2$ | NH | 2-MeOPh |
| 3-548 | 4 | CONHSO$_2$ | NH | 4-MeOPh |
| 3-549 | 4 | CONHSO$_2$ | NH | 2-EtOPh |
| 3-550 | 4 | CONHSO$_2$ | NH | 4-EtOPh |
| 3-551 | 4 | CONHSO$_2$ | NH | 2-HOPh |
| 3-552 | 4 | CONHSO$_2$ | NH | 4-HOPh |
| 3-553 | 4 | CONHSO$_2$ | NH | 2-(HOOC)Ph |
| 3-554 | 4 | CONHSO$_2$ | NH | 4-(HOOC)Ph |
| 3-555 | 4 | CONHSO$_2$ | NH | 2-(MeOOC)Ph |
| 3-556 | 4 | CONHSO$_2$ | NH | 4-(MeOOC)Ph |
| 3-557 | 4 | CONHSO$_2$ | NH | 2-(EtOOC)Ph |
| 3-558 | 4 | CONHSO$_2$ | NH | 4-(EtOOC)Ph |
| 3-559 | 4 | CONHSO$_2$ | NH | 2-(tBuOOC)Ph |
| 3-560 | 4 | CONHSO$_2$ | NH | 4-(tBuOOC)Ph |
| 3-561 | 4 | CONHSO$_2$ | NH | 2-Cl—Ph |
| 3-562 | 4 | CONHSO$_2$ | NH | 4-Cl—Ph |
| 3-563 | 4 | CONHSO$_2$ | NH | 2-Br—Ph |
| 3-564 | 4 | CONHSO$_2$ | NH | 4-Br—Ph |
| 3-565 | 4 | CONHSO$_2$ | NH | 2-I—Ph |
| 3-566 | 4 | CONHSO$_2$ | NH | 4-I—Ph |
| 3-567 | 4 | CONHSO$_2$ | NH | 2-NO$_2$—Ph |
| 3-568 | 4 | CONHSO$_2$ | NH | 4-NO$_2$—Ph |
| 3-569 | 4 | CONHSO$_2$ | NH | 2-NH$_2$—Ph |
| 3-570 | 4 | CONHSO$_2$ | NH | 4-NH$_2$—Ph |
| 3-571 | 4 | CONHSO$_2$ | NH | 2-(HO$_3$S)Ph |
| 3-572 | 4 | CONHSO$_2$ | NH | 4-(HO$_3$S)Ph |
| 3-573 | 4 | CONHSO$_2$ | NH | 2-(NH$_2$O$_2$S)Ph |
| 3-574 | 4 | CONHSO$_2$ | NH | 4-(NH$_2$O$_2$S)Ph |
| 3-575 | 4 | CONHSO$_2$ | NH | 2-CN—Ph |
| 3-576 | 4 | CONHSO$_2$ | NH | 4-CN—Ph |
| 3-577 | 4 | CONHSO$_2$ | NH | 2-(HOCH$_2$)Ph |
| 3-578 | 4 | CONHSO$_2$ | NH | 4-(HOCH$_2$)Ph |
| 3-579 | 4 | CONHSO$_2$ | NH | Me |
| 3-580 | 4 | CONHSO$_2$ | NH | Et |
| 3-581 | 4 | CONHSO$_2$ | NH | Pr |
| 3-582 | 4 | CONHSO$_2$ | NH | iPr |
| 3-583 | 4 | CONHSO$_2$ | NH | Bu |
| 3-584 | 4 | CONHSO$_2$ | NH | HOOCCH$_2$— |
| 3-585 | 4 | CONHSO$_2$ | NH | MeOOCCH$_2$— |
| 3-586 | 4 | CONHSO$_2$ | NH | MeCH(COOH) |
| 3-587 | 4 | CONHSO$_2$ | NH | HOOC—(CH$_2$)$_2$— |
| 3-588 | 4 | CONHSO$_2$ | NH | MeCH(COOMe) |
| 3-589 | 4 | CONHSO$_2$ | NH | 1-HOOC-iBu |
| 3-590 | 4 | CONHSO$_2$ | NH | 1-MeOOC-iBu |
| 3-591 | 4 | CONHSO$_2$ | NH | 1-HOOC-iPn |
| 3-592 | 4 | CONHSO$_2$ | NH | 1-MeOOC-iPn |
| 3-593 | 4 | CONHSO$_2$ | NH | 1-HOOC-2-Me—Bu |
| 3-594 | 4 | CONHSO$_2$ | NH | 1-MeOOC-2-Me—Bu |
| 3-595 | 4 | CONHSO$_2$ | NH | CH$_2$CH$_2$SO$_3$H |
| 3-596 | 4 | CONHSO$_2$ | NH | OH |
| 3-597 | 4 | CONHSO$_2$ | NH | MeO |
| 3-598 | 4 | CONHSO$_2$ | NH | EtO |
| 3-599 | 4 | CONHSO$_2$ | NH | PrO |
| 3-600 | 4 | CONHSO$_2$ | NH | iPro |
| 3-601 | 4 | CONHSO$_2$ | NH | BuO |
| 3-602 | 4 | CONHSO$_2$ | NH | iBuO |
| 3-603 | 4 | CONHSO$_2$ | NH | sBuO |
| 3-604 | 4 | CONHSO$_2$ | NH | tBuO |
| 3-605 | 4 | CONHSO$_2$ | NH | HxO |
| 3-606 | 4 | CONHSO$_2$ | NH | PhO |
| 3-607 | 4 | CONHSO$_2$ | NH | BnO |
| 3-608 | 4 | CONHSO$_2$ | NH | Z-1 |
| 3-609 | 4 | CONHSO$_2$ | NH | Z-2 |
| 3-610 | 4 | CONHSO$_2$ | NH | Z-3 |
| 3-611 | 4 | CONHSO$_2$ | NH | Z-4 |
| 3-612 | 4 | CONHSO$_2$ | NH | Z-5 |
| 3-613 | 4 | CONHSO$_2$ | NH | Z-6 |
| 3-614 | 4 | CONHSO$_2$ | NH | Z-7 |
| 3-615 | 4 | CONHSO$_2$ | NH | Z-8 |
| 3-616 | 4 | CONHSO$_2$ | NH | Z-9 |
| 3-617 | 4 | CONHSO$_2$ | NH | Z-10 |
| 3-618 | 4 | CONHSO$_2$ | NH | Z-11 |
| 3-619 | 4 | CONHSO$_2$ | NH | Z-12 |
| 3-620 | 4 | CONHSO$_2$ | NH | 3-Py |
| 3-621 | 4 | CONHSO$_2$ | NH | 4-Py |
| 3-622 | 4 | NHCO | — | H |
| 3-623 | 4 | NHCO | — | Ph |
| 3-624 | 4 | NHCO | — | 2-Me—Ph |
| 3-625 | 4 | NHCO | — | 4-Me—Ph |
| 3-626 | 4 | NHCO | — | 2,4-diMe—Ph |
| 3-627 | 4 | NHCO | — | 3,4-diMe—Ph |
| 3-628 | 4 | NHCO | — | 2-(CF$_3$)Ph |
| 3-629 | 4 | NHCO | — | 4-(CF$_3$)Ph |
| 3-630 | 4 | NHCO | — | 2-MeOPh |
| 3-631 | 4 | NHCO | — | 4-MeOPh |

TABLE 3-continued

| Cpd. No. | k | A | B | R$^1$ |
|---|---|---|---|---|
| 3-632 | 4 | NHCO | — | 2-EtOPh |
| 3-633 | 4 | NHCO | — | 4-EtOPh |
| 3-634 | 4 | NHCO | — | 2-HOPh |
| 3-635 | 4 | NHCO | — | 4-HOPh |
| 3-636 | 4 | NHCO | — | 2-(HOOC)Ph |
| 3-637 | 4 | NHCO | — | 4-(HOOC)Ph |
| 3-638 | 4 | NHCO | — | 2-(MeOOC)Ph |
| 3-639 | 4 | NHCO | — | 4-(MeOOC)Ph |
| 3-640 | 4 | NHCO | — | 2-(EtOOC)Ph |
| 3-641 | 4 | NHCO | — | 4-(EtOOC)Ph |
| 3-642 | 4 | NHCO | — | 2-(tBuOOC)Ph |
| 3-643 | 4 | NHCO | — | 4-(tBuOOC)Ph |
| 3-644 | 4 | NHCO | — | 2-Cl—Ph |
| 3-645 | 4 | NHCO | — | 4-Cl—Ph |
| 3-646 | 4 | NHCO | — | 2-Br—Ph |
| 3-647 | 4 | NHCO | — | 4-Br—Ph |
| 3-648 | 4 | NHCO | — | 2-I—Ph |
| 3-649 | 4 | NHCO | — | 4-I—Ph |
| 3-650 | 4 | NHCO | — | 2-NO$_2$—Ph |
| 3-651 | 4 | NHCO | — | 4-NO$_2$—Ph |
| 3-652 | 4 | NHCO | — | 2-NH$_2$—Ph |
| 3-653 | 4 | NHCO | — | 4-NH$_2$—Ph |
| 3-654 | 4 | NHCO | — | 2-(HO$_3$S)Ph |
| 3-655 | 4 | NHCO | — | 4-(HO$_3$S)Ph |
| 3-656 | 4 | NHCO | — | 2-(NH$_2$O$_2$S)Ph |
| 3-657 | 4 | NHCO | — | 4-(NH$_2$O$_2$S)Ph |
| 3-658 | 4 | NHCO | — | 2-CN—Ph |
| 3-659 | 4 | NHCO | — | 4-CN—Ph |
| 3-660 | 4 | NHCO | — | 2-(HOCH$_2$)Ph |
| 3-661 | 4 | NHCO | — | 4-(HOCH$_2$)Ph |
| 3-662 | 4 | NHCO | — | Me |
| 3-663 | 4 | NHCO | — | Et |
| 3-664 | 4 | NHCO | — | Pr |
| 3-665 | 4 | NHCO | — | iPr |
| 3-666 | 4 | NHCO | — | Bu |
| 3-667 | 4 | NHCO | — | HOOCCH$_2$— |
| 3-668 | 4 | NHCO | — | MeOOCCH$_2$— |
| 3-669 | 4 | NHCO | — | MeCH(COOH) |
| 3-670 | 4 | NHCO | — | HOOC—(CH$_2$)$_2$— |
| 3-671 | 4 | NHCO | — | MeCH(COOMe) |
| 3-672 | 4 | NHCO | — | 1-HOOC-iBu |
| 3-673 | 4 | NHCO | — | 1-HOOC-iPn |
| 3-674 | 4 | NHCO | — | 1-HOOC-2-Me-Bu |
| 3-675 | 4 | NHCO | — | CH$_2$CH$_2$SO$_3$H |
| 3-676 | 4 | NHCO | — | MeO |
| 3-677 | 4 | NHCO | — | EtO |
| 3-678 | 4 | NHCO | — | PrO |
| 3-679 | 4 | NHCO | — | Z-1 |
| 3-680 | 4 | NHCO | — | Z-2 |
| 3-681 | 4 | NHCO | — | Z-3 |
| 3-682 | 4 | NHCO | — | Z-4 |
| 3-683 | 4 | NHCO | — | Z-5 |
| 3-684 | 4 | NHCO | — | Z-6 |
| 3-685 | 4 | NHCO | — | Z-7 |
| 3-686 | 4 | NHCO | — | Z-8 |
| 3-687 | 4 | NHCO | — | Z-9 |
| 3-688 | 4 | NHCO | — | Z-10 |
| 3-689 | 4 | NHCO | — | Z-11 |
| 3-690 | 4 | NHCO | — | Z-12 |
| 3-691 | 4 | NHCO | — | 3-Py |
| 3-692 | 4 | NHCO | — | 4-Py |
| 3-693 | 4 | NHCO | NH | H |
| 3-694 | 4 | NHCO | NH | Ph |
| 3-695 | 4 | NHCO | NH | 2-Me—Ph |
| 3-696 | 4 | NHCO | NH | 4-Me—Ph |
| 3-697 | 4 | NHCO | NH | 2,4-diMe—Ph |
| 3-698 | 4 | NHCO | NH | 3,4-diMe—Ph |
| 3-699 | 4 | NHCO | NH | 2-(CF$_3$)Ph |
| 3-700 | 4 | NHCO | NH | 4-(CF$_3$)Ph |
| 3-701 | 4 | NHCO | NH | 2-MeOPh |
| 3-702 | 4 | NHCO | NH | 4-MeOPh |
| 3-703 | 4 | NHCO | NH | 2-EtOPh |
| 3-704 | 4 | NHCO | NH | 4-EtOPh |
| 3-705 | 4 | NHCO | NH | 2-HOPh |
| 3-706 | 4 | NHCO | NH | 4-HOPh |
| 3-707 | 4 | NHCO | NH | 2-(HOOC)Ph |
| 3-708 | 4 | NHCO | NH | 4-(HOOC)Ph |
| 3-709 | 4 | NHCO | NH | 2-(MeOOC)Ph |
| 3-710 | 4 | NHCO | NH | 4-(MeOOC)Ph |
| 3-711 | 4 | NHCO | NH | 2-(EtOOC)Ph |
| 3-712 | 4 | NHCO | NH | 4-(EtOOC)Ph |
| 3-713 | 4 | NHCO | NH | 2-(tBuOOC)Ph |
| 3-714 | 4 | NHCO | NH | 4-(tBuOOC)Ph |
| 3-715 | 4 | NHCO | NH | 2-Cl—Ph |
| 3-716 | 4 | NHCO | NH | 4-Cl—Ph |
| 3-717 | 4 | NHCO | NH | 2-Br—Ph |
| 3-718 | 4 | NHCO | NH | 4-Br—Ph |
| 3-719 | 4 | NHCO | NH | 2-I—Ph |
| 3-720 | 4 | NHCO | NH | 4-I—Ph |
| 3-721 | 4 | NHCO | NH | 2-NO$_2$—Ph |
| 3-722 | 4 | NHCO | NH | 4-NO$_2$—Ph |
| 3-723 | 4 | NHCO | NH | 2-NH$_2$—Ph |
| 3-724 | 4 | NHCO | NH | 4-NH$_2$—Ph |
| 3-725 | 4 | NHCO | NH | 2-(HO$_3$S)Ph |
| 3-726 | 4 | NHCO | NH | 4-(HO$_3$S)Ph |
| 3-727 | 4 | NHCO | NH | 2-(NH$_2$O$_2$S)Ph |
| 3-728 | 4 | NHCO | NH | 4-(NH$_2$O$_2$S)Ph |
| 3-729 | 4 | NHCO | NH | 2-CN—Ph |
| 3-730 | 4 | NHCO | NH | 4-CN—Ph |
| 3-731 | 4 | NHCO | NH | 2-(HOCH$_2$)Ph |
| 3-732 | 4 | NHCO | NH | 4-(HOCH$_2$)Ph |
| 3-733 | 4 | NHCO | NH | Me |
| 3-734 | 4 | NHCO | NH | Et |
| 3-735 | 4 | NHCO | NH | Pr |
| 3-736 | 4 | NHCO | NH | iPr |
| 3-737 | 4 | NHCO | NH | Bu |
| 3-738 | 4 | NHCO | NH | HOOCCH$_2$— |
| 3-739 | 4 | NHCO | NH | MeOOCCH$_2$— |
| 3-740 | 4 | NHCO | NH | MeCH(COOH) |
| 3-741 | 4 | NHCO | NH | HOOC—(CH$_2$)$_2$— |
| 3-742 | 4 | NHCO | NH | MeCH(COOMe) |
| 3-743 | 4 | NHCO | NH | 1-HOOC-iBu |
| 3-744 | 4 | NHCO | NH | 1-MeOOC-iBu |
| 3-745 | 4 | NHCO | NH | 1-HOOC-iPn |
| 3-746 | 4 | NHCO | NH | 1-MeOOC-iPn |
| 3-747 | 4 | NHCO | NH | 1-HOOC-2-Me—Bu |
| 3-748 | 4 | NHCO | NH | 1-MeOOC-2-Me—Bu |
| 3-749 | 4 | NHCO | NH | CH$_2$CH$_2$SO$_3$H |
| 3-750 | 4 | NHCO | NH | OH |
| 3-751 | 4 | NHCO | NH | MeO |
| 3-752 | 4 | NHCO | NH | EtO |
| 3-753 | 4 | NHCO | NH | PrO |
| 3-754 | 4 | NHCO | NH | iPro |
| 3-755 | 4 | NHCO | NH | BuO |
| 3-756 | 4 | NHCO | NH | iBuO |
| 3-757 | 4 | NHCO | NH | sBuO |
| 3-758 | 4 | NHCO | NH | tBuO |
| 3-759 | 4 | NHCO | NH | HxO |
| 3-760 | 4 | NHCO | NH | PhO |
| 3-761 | 4 | NHCO | NH | BnO |
| 3-762 | 4 | NHCO | NH | Z-1 |
| 3-763 | 4 | NHCO | NH | Z-2 |
| 3-764 | 4 | NHCO | NH | Z-3 |
| 3-765 | 4 | NHCO | NH | Z-4 |
| 3-766 | 4 | NHCO | NH | Z-5 |
| 3-767 | 4 | NHCO | NH | Z-6 |
| 3-768 | 4 | NHCO | NH | Z-7 |
| 3-769 | 4 | NHCO | NH | Z-8 |
| 3-770 | 4 | NHCO | NH | Z-9 |
| 3-771 | 4 | NHCO | NH | Z-10 |
| 3-772 | 4 | NHCO | NH | Z-11 |
| 3-773 | 4 | NHCO | NH | Z-12 |
| 3-774 | 4 | NHCO | NH | 3-Py |
| 3-775 | 4 | NHCO | NH | 4-Py |
| 3-776 | 4 | NHCO | NMe | Ph |
| 3-777 | 4 | NHCO | NMe | 2-Me—Ph |
| 3-778 | 4 | NHCO | NMe | 4-Me—Ph |
| 3-779 | 4 | NHCO | NMe | 2,4-diMe—Ph |
| 3-780 | 4 | NHCO | NMe | 3,4-diMe—Ph |
| 3-781 | 4 | NHCO | NMe | 2-(CF$_3$)Ph |
| 3-782 | 4 | NHCO | NMe | 4-(CF$_3$)Ph |
| 3-783 | 4 | NHCO | NMe | 2-MeOPh |

TABLE 3-continued

| Cpd. No. | k | A | B | R¹ |
|---|---|---|---|---|
| 3-784 | 4 | NHCO | NMe | 4-MeOPh |
| 3-785 | 4 | NHCO | NMe | 2-EtOPh |
| 3-786 | 4 | NHCO | NMe | 4-EtOPh |
| 3-787 | 4 | NHCO | NMe | 2-HOPh |
| 3-788 | 4 | NHCO | NMe | 4-HOPh |
| 3-789 | 4 | NHCO | NMe | 2-(HOOC)Ph |
| 3-790 | 4 | NHCO | NMe | 4-(HOOC)Ph |
| 3-791 | 4 | NHCO | NMe | 2-(MeOOC)Ph |
| 3-792 | 4 | NHCO | NMe | 4-(MeOOC)Ph |
| 3-793 | 4 | NHCO | NMe | 2-(EtOOC)Ph |
| 3-794 | 4 | NHCO | NMe | 4-(EtOOC)Ph |
| 3-795 | 4 | NHCO | NMe | 2-(tBuOOC)Ph |
| 3-796 | 4 | NHCO | NMe | 4-(tBuOOC)Ph |
| 3-797 | 4 | NHCO | NMe | 2-Cl—Ph |
| 3-798 | 4 | NHCO | NMe | 4-Cl—Ph |
| 3-799 | 4 | NHCO | NMe | 2-Br—Ph |
| 3-800 | 4 | NHCO | NMe | 4-Br—Ph |
| 3-801 | 4 | NHCO | NMe | 2-I—Ph |
| 3-802 | 4 | NHCO | NMe | 4-I—Ph |
| 3-803 | 4 | NHCO | NMe | 2-NO₂—Ph |
| 3-804 | 4 | NHCO | NMe | 4-NO₂—Ph |
| 3-805 | 4 | NHCO | NMe | 2-NH₂—Ph |
| 3-806 | 4 | NHCO | NMe | 4-NH₂—Ph |
| 3-807 | 4 | NHCO | NMe | 2-(HO₃S)Ph |
| 3-808 | 4 | NHCO | NMe | 4-(HO₃S)Ph |
| 3-809 | 4 | NHCO | NMe | 2-(NH₂O₂S)Ph |
| 3-810 | 4 | NHCO | NMe | 4-(NH₂O₂S)Ph |
| 3-811 | 4 | NHCO | NMe | 2-CN—Ph |
| 3-812 | 4 | NHCO | NMe | 4-CN—Ph |
| 3-813 | 4 | NHCO | NMe | 2-(HOCH₂)Ph |
| 3-814 | 4 | NHCO | NMe | 4-(HOCH₂)Ph |
| 3-815 | 4 | NHCO | NMe | Me |
| 3-816 | 4 | NHCO | NMe | Et |
| 3-817 | 4 | NHCO | NMe | Pr |
| 3-818 | 4 | NHCO | NMe | iPr |
| 3-819 | 4 | NHCO | NMe | Bu |
| 3-820 | 4 | NHCO | NMe | HOOCCH₂— |
| 3-821 | 4 | NHCO | NMe | MeOOCCH₂— |
| 3-822 | 4 | NHCO | NMe | MeCH(COOH) |
| 3-823 | 4 | NHCO | NMe | HOOC—(CH₂)₂— |
| 3-824 | 4 | NHCO | NMe | MeCH(COOMe) |
| 3-825 | 4 | NHCO | NMe | 1-HOOC-iBu |
| 3-826 | 4 | NHCO | NMe | 1-MeOOC-iBu |
| 3-827 | 4 | NHCO | NMe | 1-HOOC-iPn |
| 3-828 | 4 | NHCO | NMe | 1-MeOOC-iPn |
| 3-829 | 4 | NHCO | NMe | 1-HOOC-2-Me—Bu |
| 3-830 | 4 | NHCO | NMe | 1-MeOOC-2-Me—Bu |
| 3-831 | 4 | NHCO | NMe | CH₂CH₂SO₃H |
| 3-832 | 4 | NHCO | NMe | OH |
| 3-833 | 4 | NHCO | NMe | MeO |
| 3-834 | 4 | NHCO | NMe | EtO |
| 3-835 | 4 | NHCO | NMe | PrO |
| 3-836 | 4 | NHCO | NMe | iPrO |
| 3-837 | 4 | NHCO | NMe | BuO |
| 3-838 | 4 | NHCO | NMe | iBuO |
| 3-839 | 4 | NHCO | NMe | sBuO |
| 3-840 | 4 | NHCO | NMe | tBuO |
| 3-841 | 4 | NHCO | NMe | HxO |
| 3-842 | 4 | NHCO | NMe | PhO |
| 3-843 | 4 | NHCO | NMe | BnO |
| 3-844 | 4 | NHCO | NMe | Z-1 |
| 3-845 | 4 | NHCO | NMe | Z-2 |
| 3-846 | 4 | NHCO | NMe | Z-3 |
| 3-847 | 4 | NHCO | NMe | Z-4 |
| 3-848 | 4 | NHCO | NMe | Z-5 |
| 3-849 | 4 | NHCO | NMe | Z-6 |
| 3-850 | 4 | NHCO | NMe | Z-7 |
| 3-851 | 4 | NHCO | NMe | Z-8 |
| 3-852 | 4 | NHCO | NMe | Z-9 |
| 3-853 | 4 | NHCO | NMe | Z-10 |
| 3-854 | 4 | NHCO | NMe | Z-11 |
| 3-855 | 4 | NHCO | NMe | Z-12 |
| 3-856 | 4 | NHCO | NMe | 3-Py |
| 3-857 | 4 | NHCO | NMe | 4-Py |
| 3-858 | 4 | NHCO | NHNH | H |
| 3-859 | 4 | NHCO | NHNH | Me |
| 3-860 | 4 | NHCO | NHNH | Et |
| 3-861 | 4 | NHCO | NHNMe | Me |
| 3-862 | 4 | NHCO | NHNMe | Et |
| 3-863 | 4 | NHCO | NHNMe | Pr |
| 3-864 | 4 | NHCONHNHCO | NH | H |
| 3-865 | 4 | NHCONHNHCO | NH | Ph |
| 3-866 | 4 | NHCONHNHCO | NH | 2-Me—Ph |
| 3-867 | 4 | NHCONHNHCO | NH | 4-Me—Ph |
| 3-868 | 4 | NHCONHNHCO | NH | 2,4-diMe—Ph |
| 3-869 | 4 | NHCONHNHCO | NH | 3,4-diMe—Ph |
| 3-870 | 4 | NHCONHNHCO | NH | 2-(CF₃)Ph |
| 3-871 | 4 | NHCONHNHCO | NH | 4-(CF₃)Ph |
| 3-872 | 4 | NHCONHNHCO | NH | 2-MeOPh |
| 3-873 | 4 | NHCONHNHCO | NH | 4-MeOPh |
| 3-874 | 4 | NHCONHNHCO | NH | 2-EtOPh |
| 3-875 | 4 | NHCONHNHCO | NH | 4-EtOPh |
| 3-876 | 4 | NHCONHNHCO | NH | 2-HOPh |
| 3-877 | 4 | NHCONHNHCO | NH | 4-HOPh |
| 3-878 | 4 | NHCONHNHCO | NH | 2-(HOOC)Ph |
| 3-879 | 4 | NHCONHNHCO | NH | 4-(HOOC)Ph |
| 3-880 | 4 | NHCONHNHCO | NH | 2-(MeOOC)Ph |
| 3-881 | 4 | NHCONHNHCO | NH | 4-(MeOOC)Ph |
| 3-882 | 4 | NHCONHNHCO | NH | 2-(EtOOC)Ph |
| 3-883 | 4 | NHCONHNHCO | NH | 4-(EtOOC)Ph |
| 3-884 | 4 | NHCONHNHCO | NH | 2-(tBuOOC)Ph |
| 3-885 | 4 | NHCONHNHCO | NH | 4-(tBuOOC)Ph |
| 3-886 | 4 | NHCONHNHCO | NH | 2-Cl—Ph |
| 3-887 | 4 | NHCONHNHCO | NH | 4-Cl—Ph |
| 3-888 | 4 | NHCONHNHCO | NH | 2-Br—Ph |
| 3-889 | 4 | NHCONHNHCO | NH | 4-Br—Ph |
| 3-890 | 4 | NHCONHNHCO | NH | 2-I—Ph |
| 3-891 | 4 | NHCONHNHCO | NH | 4-I—Ph |
| 3-892 | 4 | NHCONHNHCO | NH | 2-NO₂—Ph |
| 3-893 | 4 | NHCONHNHCO | NH | 4-NO₂—Ph |
| 3-894 | 4 | NHCONHNHCO | NH | 2-NH₂—Ph |
| 3-895 | 4 | NHCONHNHCO | NH | 4-NH₂—Ph |
| 3-896 | 4 | NHCONHNHCO | NH | 2-(HO₃S)Ph |
| 3-897 | 4 | NHCONHNHCO | NH | 4-(HO₃S)Ph |
| 3-898 | 4 | NHCONHNHCO | NH | 2-(NH₂O₂S)Ph |
| 3-899 | 4 | NHCONHNHCO | NH | 4-(NH₂O₂S)Ph |
| 3-900 | 4 | NHCONHNHCO | NH | 2-CN—Ph |
| 3-901 | 4 | NHCONHNHCO | NH | 4-CN—Ph |
| 3-902 | 4 | NHCONHNHCO | NH | 2-(HOCH₂)Ph |
| 3-903 | 4 | NHCONHNHCO | NH | 4-(HOCH₂)Ph |
| 3-904 | 4 | NHCONHNHCO | NH | Me |
| 3-905 | 4 | NHCONHNHCO | NH | Et |
| 3-906 | 4 | NHCONHNHCO | NH | Pr |
| 3-907 | 4 | NHCONHNHCO | NH | iPr |
| 3-908 | 4 | NHCONHNHCO | NH | Bu |
| 3-909 | 4 | NHCONHNHCO | NH | HOOCCH₂— |
| 3-910 | 4 | NHCONHNHCO | NH | MeOOCCH₂— |
| 3-911 | 4 | NHCONHNHCO | NH | MeCH(COOH) |
| 3-912 | 4 | NHCONHNHCO | NH | HOOC—(CH₂)₂— |
| 3-913 | 4 | NHCONHNHCO | NH | MeCH(COOMe) |
| 3-914 | 4 | NHCONHNHCO | NH | 1-HOOC-iBu |
| 3-915 | 4 | NHCONHNHCO | NH | 1-MeOOC-iBu |
| 3-916 | 4 | NHCONHNHCO | NH | 1-HOOC-iPn |
| 3-917 | 4 | NHCONHNHCO | NH | 1-MeOOC-iPn |
| 3-918 | 4 | NHCONHNHCO | NH | 1-HOOC-2-Me—Bu |
| 3-919 | 4 | NHCONHNHCO | NH | 1-MeOOC-2-Me—Bu |
| 3-920 | 4 | NHCONHNHCO | NH | CH₂CH₂SO₃H |
| 3-921 | 4 | NHCONHNHCO | NH | OH |
| 3-922 | 4 | NHCONHNHCO | NH | MeO |
| 3-923 | 4 | NHCONHNHCO | NH | EtO |
| 3-924 | 4 | NHCONHNHCO | NH | PrO |
| 3-925 | 4 | NHCONHNHCO | NH | iPrO |
| 3-926 | 4 | NHCONHNHCO | NH | BuO |
| 3-927 | 4 | NHCONHNHCO | NH | iBuO |
| 3-928 | 4 | NHCONHNHCO | NH | sBuO |
| 3-929 | 4 | NHCONHNHCO | NH | tBuO |
| 3-930 | 4 | NHCONHNHCO | NH | HxO |
| 3-931 | 4 | NHCONHNHCO | NH | PhO |
| 3-932 | 4 | NHCONHNHCO | NH | BnO |
| 3-933 | 4 | NHCONHNHCO | NH | Z-1 |
| 3-934 | 4 | NHCONHNHCO | NH | Z-2 |
| 3-935 | 4 | NHCONHNHCO | NH | Z-3 |

TABLE 3-continued

| Cpd. No. | k | A | B | R¹ |
|---|---|---|---|---|
| 3-936 | 4 | NHCONHNHCO | NH | Z-4 |
| 3-937 | 4 | NHCONHNHCO | NH | Z-5 |
| 3-938 | 4 | NHCONHNHCO | NH | Z-6 |
| 3-939 | 4 | NHCONHNHCO | NH | Z-7 |
| 3-940 | 4 | NHCONHNHCO | NH | Z-8 |
| 3-941 | 4 | NHCONHNHCO | NH | Z-9 |
| 3-942 | 4 | NHCONHNHCO | NH | Z-10 |
| 3-943 | 4 | NHCONHNHCO | NH | Z-11 |
| 3-944 | 4 | NHCONHNHCO | NH | Z-12 |
| 3-945 | 4 | NHCONHNHCO | NH | 3-Py |
| 3-946 | 4 | NHCONHNHCO | NH | 4-Py |
| 3-947 | 4 | NHCONHCO | — | H |
| 3-948 | 4 | NHCONHCO | — | Ph |
| 3-949 | 4 | NHCONHCO | — | 2-Me—Ph |
| 3-950 | 4 | NHCONHCO | — | 4-Me—Ph |
| 3-951 | 4 | NHCONHCO | — | 2,4-diMe—Ph |
| 3-952 | 4 | NHCONHCO | — | 3,4-diMe—Ph |
| 3-953 | 4 | NHCONHCO | — | 2-(CF$_3$)Ph |
| 3-954 | 4 | NHCONHCO | — | 4-(CF$_3$)Ph |
| 3-955 | 4 | NHCONHCO | — | 2-MeOPh |
| 3-956 | 4 | NHCONHCO | — | 4-MeOPh |
| 3-957 | 4 | NHCONHCO | — | 2-EtOPh |
| 3-958 | 4 | NHCONHCO | — | 4-EtOPh |
| 3-959 | 4 | NHCONHCO | — | 2-HOPh |
| 3-960 | 4 | NHCONHCO | — | 4-HOPh |
| 3-961 | 4 | NHCONHCO | — | 2-(HOOC)Ph |
| 3-962 | 4 | NHCONHCO | — | 4-(HOOC)Ph |
| 3-963 | 4 | NHCONHCO | — | 2-(MeOOC)Ph |
| 3-964 | 4 | NHCONHCO | — | 4-(MeOOC)Ph |
| 3-965 | 4 | NHCONHCO | — | 2-(EtOOC)Ph |
| 3-966 | 4 | NHCONHCO | — | 4-(EtOOC)Ph |
| 3-967 | 4 | NHCONHCO | — | 2-(tBuOOC)Ph |
| 3-968 | 4 | NHCONHCO | — | 4-(tBuOOC)Ph |
| 3-969 | 4 | NHCONHCO | — | 2-Cl—Ph |
| 3-970 | 4 | NHCONHCO | — | 4-Cl—Ph |
| 4-971 | 4 | NHCONHCO | — | 2-Br—Ph |
| 3-972 | 4 | NHCONHCO | — | 4-Br—Ph |
| 3-973 | 4 | NHCONHCO | — | 2-I—Ph |
| 3-974 | 4 | NHCONHCO | — | 4-I—Ph |
| 3-975 | 4 | NHCONHCO | — | 2-NO$_2$—Ph |
| 3-976 | 4 | NHCONHCO | — | 4-NO$_2$—Ph |
| 3-977 | 4 | NHCONHCO | — | 2-NH$_2$—Ph |
| 3-978 | 4 | NHCONHCO | — | 4-NH$_2$—Ph |
| 3-979 | 4 | NHCONHCO | — | 2-(HO$_3$S)Ph |
| 3-980 | 4 | NHCONHCO | — | 4-(HO$_3$S)Ph |
| 3-981 | 4 | NHCONHCO | — | 2-(NH$_2$O$_2$S)Ph |
| 3-982 | 4 | NHCONHCO | — | 4-(NH$_2$O$_2$S)Ph |
| 3-983 | 4 | NHCONHCO | — | 2-CN—Ph |
| 3-984 | 4 | NHCONHCO | — | 4-CN—Ph |
| 3-985 | 4 | NHCONHCO | — | 2-(HOCH$_2$)Ph |
| 3-986 | 4 | NHCONHCO | — | 4-(HOCH$_2$)Ph |
| 3-987 | 4 | NHCONHCO | — | Me |
| 3-988 | 4 | NHCONHCO | — | Et |
| 3-989 | 4 | NHCONHCO | — | Pr |
| 3-990 | 4 | NHCONHCO | — | iPr |
| 3-991 | 4 | NHCONHCO | — | Bu |
| 3-992 | 4 | NHCONHCO | — | HOOCCH$_2$— |
| 3-993 | 4 | NHCONHCO | — | MeOOCCH$_2$— |
| 3-994 | 4 | NHCONHCO | — | MeCH(COOH) |
| 3-995 | 4 | NHCONHCO | — | HOOC—(CH$_2$)$_2$— |
| 3-996 | 4 | NHCONHCO | — | MeCH(COOMe) |
| 3-997 | 4 | NHCONHCO | — | 1-HOOC-iBu |
| 3-998 | 4 | NHCONHCO | — | 1-MeOOC-iBu |
| 3-999 | 4 | NHCONHCO | — | 1-HOOC-iPn |
| 3-1000 | 4 | NHCONHCO | — | 1-MeOOC-iPn |
| 3-1001 | 4 | NHCONHCO | — | 1-HOOC-2-Me—Bu |
| 3-1002 | 4 | NHCONHCO | — | 1-MeOOC-2-Me—Bu |
| 3-1003 | 4 | NHCONHCO | — | CH$_2$CH$_2$SO$_3$H |
| 3-1004 | 4 | NHCONHCO | — | MeO |
| 3-1005 | 4 | NHCONHCO | — | EtO |
| 3-1006 | 4 | NHCONHCO | — | PrO |
| 3-1007 | 4 | NHCONHCO | — | iPrO |
| 3-1008 | 4 | NHCONHCO | — | BuO |
| 3-1009 | 4 | NHCONHCO | — | iBuO |
| 3-1010 | 4 | NHCONHCO | — | sBuO |
| 3-1011 | 4 | NHCONHCO | — | tBuO |
| 3-1012 | 4 | NHCONHCO | — | HxO |
| 3-1013 | 4 | NHCONHCO | — | PhO |
| 3-1014 | 4 | NHCONHCO | — | BnO |
| 3-1015 | 4 | NHCONHCO | — | Z-1 |
| 3-1016 | 4 | NHCONHCO | — | Z-2 |
| 3-1017 | 4 | NHCONHCO | — | Z-3 |
| 3-1018 | 4 | NHCONHCO | — | Z-4 |
| 3-1019 | 4 | NHCONHCO | — | Z-5 |
| 3-1020 | 4 | NHCONHCO | — | Z-6 |
| 3-1021 | 4 | NHCONHCO | — | Z-7 |
| 3-1022 | 4 | NHCONHCO | — | Z-8 |
| 3-1023 | 4 | NHCONHCO | — | Z-9 |
| 3-1024 | 4 | NHCONHCO | — | Z-10 |
| 3-1025 | 4 | NHCONHCO | — | Z-11 |
| 3-1026 | 4 | NHCONHCO | — | Z-12 |
| 3-1027 | 4 | NHCONHCO | — | 3-Py |
| 3-1028 | 4 | NHCONHCO | — | 4-Py |
| 3-1029 | 4 | NHCONHSO$_2$ | — | H |
| 3-1030 | 4 | NHCONHSO$_2$ | — | Ph |
| 3-1031 | 4 | NHCONHSO$_2$ | — | 2-Me—Ph |
| 3-1032 | 4 | NHCONHSO$_2$ | — | 4-Me—Ph |
| 3-1033 | 4 | NHCONHSO$_2$ | — | 2,4-diMe—Ph |
| 3-1034 | 4 | NHCONHSO$_2$ | — | 3,4-diMe—Ph |
| 3-1035 | 4 | NHCONHSO$_2$ | — | 2-(CF$_3$)Ph |
| 3-1036 | 4 | NHCONHSO$_2$ | — | 4-(CF$_3$)Ph |
| 3-1037 | 4 | NHCONHSO$_2$ | — | 2-MeOPh |
| 3-1038 | 4 | NHCONHSO$_2$ | — | 4-MeOPh |
| 3-1039 | 4 | NHCONHSO$_2$ | — | 2-EtOPh |
| 3-1040 | 4 | NHCONHSO$_2$ | — | 4-EtOPh |
| 3-1041 | 4 | NHCONHSO$_2$ | — | 2-HOPh |
| 3-1042 | 4 | NHCONHSO$_2$ | — | 4-HOPh |
| 3-1043 | 4 | NHCONHSO$_2$ | — | 2-(HOOC)Ph |
| 3-1044 | 4 | NHCONHSO$_2$ | — | 4-(HOOC)Ph |
| 3-1045 | 4 | NHCONHSO$_2$ | — | 2-(MeOOC)Ph |
| 3-1046 | 4 | NHCONHSO$_2$ | — | 4-(MeOOC)Ph |
| 3-1047 | 4 | NHCONHSO$_2$ | — | 2-(EtOOC)Ph |
| 3-1048 | 4 | NHCONHSO$_2$ | — | 4-(EtOOC)Ph |
| 3-1049 | 4 | NHCONHSO$_2$ | — | 2-(tBuOOC)Ph |
| 3-1050 | 4 | NHCONHSO$_2$ | — | 4-(tBuOOC)Ph |
| 3-1051 | 4 | NHCONHSO$_2$ | — | 2-Cl—Ph |
| 3-1052 | 4 | NHCONHSO$_2$ | — | 4-Cl—Ph |
| 3-1053 | 4 | NHCONHSO$_2$ | — | 2-Br—Ph |
| 3-1054 | 4 | NHCONHSO$_2$ | — | 4-Br—Ph |
| 3-1055 | 4 | NHCONHSO$_2$ | — | 2-I—Ph |
| 3-1056 | 4 | NHCONHSO$_2$ | — | 4-I—Ph |
| 3-1057 | 4 | NHCONSHO$_2$ | — | 2-NO$_2$—Ph |
| 3-1058 | 4 | NHCONHSO$_2$ | — | 4-NO$_2$—Ph |
| 3-1059 | 4 | NHCONHSO$_2$ | — | 2-NH$_2$—Ph |
| 3-1060 | 4 | NHCONHSO$_2$ | — | 4-NH$_2$—Ph |
| 3-1061 | 4 | NHCONHSO$_2$ | — | 2-(HO$_3$S)Ph |
| 3-1062 | 4 | NHCONHSO$_2$ | — | 4-(HO$_3$S)Ph |
| 3-1063 | 4 | NHCONHSO$_2$ | — | 2-(NH$_2$O$_2$S)Ph |
| 3-1064 | 4 | NHCONHSO$_2$ | — | 4-(NH$_2$O$_2$S)Ph |
| 3-1065 | 4 | NHCONHSO$_2$ | — | 2-CN—Ph |
| 3-1066 | 4 | NHCONHSO$_2$ | — | 4-CN—Ph |
| 3-1067 | 4 | NHCONHSO$_2$ | — | 2-(HOCH$_2$)Ph |
| 3-1068 | 4 | NHCONHSO$_2$ | — | 4-(HOCH$_2$)Ph |
| 3-1069 | 4 | NHCONHSO$_2$ | — | Me |
| 3-1070 | 4 | NHCONHSO$_2$ | — | Et |
| 3-1071 | 4 | NHCONHSO$_2$ | — | Pr |
| 3-1072 | 4 | NHCONHSO$_2$ | — | iPr |
| 3-1073 | 4 | NHCONHSO$_2$ | — | Bu |
| 3-1074 | 4 | NHCONHSO$_2$ | — | HOOCCH$_2$— |
| 3-1075 | 4 | NHCONHSO$_2$ | — | MeOOCCH$_2$— |
| 3-1076 | 4 | NHCONHSO$_2$ | — | MeCH(COOH) |
| 3-1077 | 4 | NHCONHSO$_2$ | — | HOOC—(CH$_2$)$_2$— |
| 3-1078 | 4 | NHCONHSO$_2$ | — | MeCH(COOMe) |
| 3-1079 | 4 | NHCONHSO$_2$ | — | 1-HOOC-iBu |
| 3-1080 | 4 | NHCONHSO$_2$ | — | 1-MeOOC-iBu |
| 3-1081 | 4 | NHCONHSO$_2$ | — | 1-HOOC-iPn |
| 3-1082 | 4 | NHCONHSO$_2$ | — | 1-MeOOC-iPn |
| 3-1083 | 4 | NHCONHSO$_2$ | — | 1-HOOC-2-Me—Bu |
| 3-1084 | 4 | NHCONHSO$_2$ | — | 1-MeOOC-2-Me—Bu |
| 3-1085 | 4 | NHCONHSO$_2$ | — | CH$_2$CH$_2$SO$_3$H |
| 3-1086 | 4 | NHCONHSO$_2$ | — | OH |
| 3-1087 | 4 | NHCONHSO$_2$ | — | MeO |

TABLE 3-continued

| Cpd. No. | k | A | B | R¹ |
|---|---|---|---|---|
| 3-1088 | 4 | NHCONHSO$_2$ | — | EtO |
| 3-1089 | 4 | NHCONHSO$_2$ | — | PrO |
| 3-1090 | 4 | NHCONHSO$_2$ | — | iPrO |
| 3-1091 | 4 | NHCONHSO$_2$ | — | BuO |
| 3-1092 | 4 | NHCONHSO$_2$ | — | iBuO |
| 3-1093 | 4 | NHCONHSO$_2$ | — | sBuO |
| 3-1094 | 4 | NHCONHSO$_2$ | — | tBuO |
| 3-1095 | 4 | NHCONHSO$_2$ | — | HxO |
| 3-1096 | 4 | NHCONHSO$_2$ | — | PhO |
| 3-1097 | 4 | NHCONHSO$_2$ | — | BnO |
| 3-1098 | 4 | NHCONHSO$_2$ | — | Z-1 |
| 3-1099 | 4 | NHCONHSO$_2$ | — | Z-2 |
| 3-1100 | 4 | NHCONHSO$_2$ | — | Z-3 |
| 3-1101 | 4 | NHCONHSO$_2$ | — | Z-4 |
| 3-1102 | 4 | NHCONHSO$_2$ | — | Z-5 |
| 3-1103 | 4 | NHCONHSO$_2$ | — | Z-6 |
| 3-1104 | 4 | NHCONHSO$_2$ | — | Z-7 |
| 3-1105 | 4 | NHCONHSO$_2$ | — | Z-8 |
| 3-1106 | 4 | NHCONHSO$_2$ | — | Z-9 |
| 3-1107 | 4 | NHCONHSO$_2$ | — | Z-10 |
| 3-1108 | 4 | NHCONHSO$_2$ | — | Z-11 |
| 3-1109 | 4 | NHCONHSO$_2$ | — | Z-12 |
| 3-1110 | 4 | NHCONHSO$_2$ | — | 3-Py |
| 3-1111 | 4 | NHCONHSO$_2$ | — | 4-Py |
| 3-1112 | 4 | NHCONHSO$_2$ | NH | H |
| 3-1113 | 4 | NHCONHSO$_2$ | NH | Me |
| 3-1114 | 4 | NHCONHSO$_2$ | NH | Et |
| 3-1115 | 4 | NHCONHSO$_2$ | NH | Pr |
| 3-1116 | 4 | NHCONHSO$_2$ | NH | iPr |
| 3-1117 | 4 | NHCONHSO$_2$ | NH | Bu |
| 3-1118 | 4 | NHCONHSO$_2$ | NMe | Me |
| 3-1119 | 4 | NHCONHSO$_2$ | NMe | Et |
| 3-1120 | 4 | NHCONHSO$_2$ | NMe | Pr |
| 3-1121 | 4 | NHCONHSO$_2$ | NMe | iPr |
| 3-1122 | 4 | NHCONHSO$_2$ | NMe | Bu |
| 3-1123 | 4 | — | NH | H |
| 3-1124 | 4 | — | NH | Me |
| 3-1125 | 4 | — | NH | Et |
| 3-1126 | 4 | — | NH | Pr |
| 3-1127 | 4 | — | NH | iPr |
| 3-1128 | 4 | — | NH | Bu |
| 3-1129 | 4 | CO | Pyr | |
| 3-1130 | 4 | CO | Pipri | |
| 3-1131 | 4 | CO | Pipra | |
| 3-1132 | 4 | CO | Mor | |
| 3-1133 | 4 | CO | Thmor | |
| 3-1134 | 4 | CO | NHPyr | |
| 3-1135 | 4 | CO | NHPipri | |
| 3-1136 | 4 | CO | NHPipra | |
| 3-1137 | 4 | CO | NHMor | |
| 3-1138 | 4 | CO | NHThmor | |
| 3-1139 | 4 | NHCO | Pyr | |
| 3-1140 | 4 | NHCO | Pipri | |
| 3-1141 | 4 | NHCO | Pipra | |
| 3-1142 | 4 | NHCO | Mor | |
| 3-1143 | 4 | NHCO | Thmor | |
| 3-1144 | 4 | NHCO | NHPyr | |
| 3-1145 | 4 | NHCO | NHPipri | |
| 3-1146 | 4 | NHCO | NHPipra | |
| 3-1147 | 4 | NHCO | NHMor | |
| 3-1148 | 4 | NHCO | NHThmor | |
| 3-1149 | 4 | CONHCO | Pyr | |
| 3-1150 | 4 | CONHCO | Pipri | |
| 3-1151 | 4 | CONHCO | Pipra | |
| 3-1152 | 4 | CONHCO | Mor | |
| 3-1153 | 4 | CONHCO | Thmor | |
| 3-1154 | 4 | CONHCO | NHPyr | |
| 3-1155 | 4 | CONHCO | NHPipri | |
| 3-1156 | 4 | CONHCO | NHPipra | |
| 3-1157 | 4 | CONHCO | NHMor | |
| 3-1158 | 4 | CONHCO | NHThmor | |
| 3-1159 | 4 | CONHSO$_2$ | Pyr | |
| 3-1160 | 4 | CONHSO$_2$ | Pipri | |
| 3-1161 | 4 | CONHSO$_2$ | Pipra | |
| 3-1162 | 4 | CONHSO$_2$ | Mor | |
| 3-1163 | 4 | CONHSO$_2$ | Thmor | |
| 3-1164 | 4 | CONHSO$_2$ | NHPyr | |
| 3-1165 | 4 | CONHSO$_2$ | NHPipri | |
| 3-1166 | 4 | CONHSO$_2$ | NHPipra | |
| 3-1167 | 4 | CONHSO$_2$ | NHMor | |
| 3-1168 | 4 | CONHSO$_2$ | NHThmor | |
| 3-1169 | 4 | NHSO$_2$ | NH | Z-4 |
| 3-1170 | 4 | NHSO$_2$ | — | Me |
| 3-1171 | 4 | NHSO$_2$ | — | Et |
| 3-1172 | 4 | NHSO$_2$ | — | Pr |
| 3-1173 | 4 | NHSO$_2$ | — | CH$_2$—Cl |
| 3-1174 | 4 | NHSO$_2$ | — | Ph |
| 3-1175 | 4 | NHSO$_2$ | — | 4-Me—Ph |
| 3-1176 | 4 | CO | NMe | Ph |
| 3-1177 | 4 | CO | NMe | 2-Me—Ph |
| 3-1178 | 4 | CO | NMe | 4-Me—Ph |
| 3-1179 | 4 | CO | NMe | 2,4-diMe—Ph |
| 3-1180 | 4 | CO | NMe | 3,4-diMe—Ph |
| 3-1181 | 4 | CO | NMe | 2-(CF$_3$)Ph |
| 3-1182 | 4 | CO | NMe | 4-(CF$_3$)Ph |
| 3-1183 | 4 | CO | NMe | 2-MeOPh |
| 3-1184 | 4 | CO | NMe | 4-MeOPh |
| 3-1185 | 4 | CO | NMe | 2-EtOPh |
| 3-1186 | 4 | CO | NMe | 4-EtOPh |
| 3-1187 | 4 | CO | NMe | 2-HOPh |
| 3-1188 | 4 | CO | NMe | 4-HOPh |
| 3-1189 | 4 | CO | NMe | 2-(HOOC)Ph |
| 3-1190 | 4 | CO | NMe | 4-(HOOC)Ph |
| 3-1191 | 4 | CO | NMe | 2-(MeOOC)Ph |
| 3-1192 | 4 | CO | NMe | 4-(MeOOC)Ph |
| 3-1193 | 4 | CO | NMe | 2-(EtOOC)Ph |
| 3-1194 | 4 | CO | NMe | 4-(EtOOC)Ph |
| 3-1195 | 4 | CO | NMe | 2-(tBuOOC)Ph |
| 3-1196 | 4 | CO | NMe | 4-(tBuOOC)Ph |
| 3-1197 | 4 | CO | NMe | 2-Cl—Ph |
| 3-1198 | 4 | CO | NMe | 4-Cl—Ph |
| 3-1199 | 4 | CO | NMe | 2-Br—Ph |
| 3-1200 | 4 | CO | NMe | 4-Br—Ph |
| 3-1201 | 4 | CO | NMe | 2-I—Ph |
| 3-1202 | 4 | CO | NMe | 4-I—Ph |
| 3-1203 | 4 | CO | NMe | 2-NO$_2$—Ph |
| 3-1204 | 4 | CO | NMe | 4-NO$_2$—Ph |
| 3-1205 | 4 | CO | NMe | 2-NH$_2$—Ph |
| 3-1206 | 4 | CO | NMe | 4-NH$_2$—Ph |
| 3-1207 | 4 | CO | NMe | 2-(HO$_3$S)Ph |
| 3-1208 | 4 | CO | NMe | 4-(HO$_3$S)Ph |
| 3-1209 | 4 | CO | NMe | 2-(NH$_2$O$_2$S)Ph |
| 3-1210 | 4 | CO | NMe | 4-(NH$_2$O$_2$S)Ph |
| 3-1211 | 4 | CO | NMe | 2-CN—Ph |
| 3-1212 | 4 | CO | NMe | 4-CN—Ph |
| 3-1213 | 4 | CO | NMe | 2-(HOCH$_2$)Ph |
| 3-1214 | 4 | CO | NMe | 4-(HOCH$_2$)Ph |
| 3-1215 | 4 | CO | NMe | Me |
| 3-1216 | 4 | CO | NMe | Et |
| 3-1217 | 4 | CO | NMe | Pr |
| 3-1218 | 4 | CO | NMe | iPr |
| 3-1219 | 4 | CO | NMe | Bu |
| 3-1220 | 4 | CO | NMe | HOOCCH$_2$— |
| 3-1221 | 4 | CO | NMe | MeOOCCH$_2$— |
| 3-1222 | 4 | CO | NMe | MeCH(COOH) |
| 3-1223 | 4 | CO | NMe | HOOC—(CH$_2$)$_2$— |
| 3-1224 | 4 | CO | NMe | MeCH(COOMe) |
| 3-1225 | 4 | CO | NMe | 1-HOOC-iBu |
| 3-1226 | 4 | CO | NMe | 1-MeOOC-iBu |
| 3-1227 | 4 | CO | NMe | 1-HOOC-iPn |
| 3-1228 | 4 | CO | NMe | 1-MeOOC-iPn |
| 3-1229 | 4 | CO | NMe | 1-HOOC-2-Me—Bu |
| 3-1230 | 4 | CO | NMe | 1-MeOOC-2-Me—Bu |
| 3-1231 | 4 | CO | NMe | CH$_2$CH$_2$SO$_3$H |
| 3-1232 | 4 | CO | NMe | OH |
| 3-1233 | 4 | CO | NMe | MeO |
| 3-1234 | 4 | CO | NMe | EtO |
| 3-1235 | 4 | CO | NMe | PrO |
| 3-1236 | 4 | CO | NMe | iPrO |
| 3-1237 | 4 | CO | NMe | BuO |
| 3-1238 | 4 | CO | NMe | iBuO |
| 3-1239 | 4 | CO | NMe | sBuO |

TABLE 3-continued

| Cpd. No. | k | A | B | R¹ |
|---|---|---|---|---|
| 3-1240 | 4 | CO | NMe | tBuO |
| 3-1241 | 4 | CO | NMe | HxO |
| 3-1242 | 4 | CO | NMe | PhO |
| 3-1243 | 4 | CO | NMe | BnO |
| 3-1244 | 4 | CO | NMe | Z-1 |
| 3-1245 | 4 | CO | NMe | Z-2 |
| 3-1246 | 4 | CO | NMe | Z-3 |
| 3-1247 | 4 | CO | NMe | Z-4 |
| 3-1248 | 4 | CO | NMe | Z-5 |
| 3-1249 | 4 | CO | NMe | Z-6 |
| 3-1250 | 4 | CO | NMe | Z-7 |
| 3-1251 | 4 | CO | NMe | Z-8 |
| 3-1252 | 4 | CO | NMe | Z-9 |
| 3-1253 | 4 | CO | NMe | Z-10 |
| 3-1254 | 4 | CO | NMe | Z-11 |
| 3-1255 | 4 | CO | NMe | Z-12 |
| 3-1256 | 4 | CO | NMe | 3-Py |
| 3-1257 | 4 | CO | NMe | 4-Py |
| 3-1258 | 4 | CO | Thiad | |
| 3-1259 | 4 | CO | NHThiad | |
| 3-1260 | 4 | NHCO | Thiad | |
| 3-1261 | 4 | NHCO | NHThiad | |
| 3-1262 | 4 | CONHCO | Thiad | |
| 3-1263 | 4 | CONHCO | NHThiad | |
| 3-1264 | 4 | CONHSO₂ | Thiad | |
| 3-1265 | 4 | CONHSO₂ | NHThiad | |
| 3-1266 | 4 | NHCS | NH | H |
| 3-1267 | 4 | NHCS | NH | Me |
| 3-1268 | 4 | NHCS | NH | Et |
| 3-1269 | 4 | NHCS | NH | Ph |
| 3-1270 | 4 | NHCS | NH | HOOCCH₂— |
| 3-1271 | 4 | NHCS | NH | MeOOCCH₂— |
| 3-1272 | 4 | NHCS | NH | MeCH(COOH) |
| 3-1273 | 4 | NHCS | NH | HOOC—(CH₂)₂— |
| 3-1274 | 4 | NHCS | NH | MeCH(COOMe) |
| 3-1275 | 4 | CO | NH | HOOC—(CH₂)₃— |
| 3-1276 | 4 | NHCO | NH | HOOC—(CH₂)₃— |
| 3-1277 | 4 | NHCO | — | HOOC—(CH₂)₃— |
| 3-1278 | 4 | NHCS | NH | HOOC—(CH₂)₃— |
| 3-1279 | 4 | CO | NH | MeSO₂NHCOCH(Me) |
| 3-1280 | 4 | NHCO | NH | MeSO₂NHCOCH(Me) |
| 3-1281 | 4 | NHCO | — | MeSO₂NHCOCH(Me) |
| 3-1282 | 4 | NHCS | NH | MeSO₂NHCOCH(Me) |
| 3-1283 | 4 | — | NH | HOOCCH₂— |
| 3-1284 | 4 | — | NH | MeOOCCH₂— |
| 3-1285 | 4 | — | NH | MeCH(COOH) |
| 3-1286 | 4 | — | NH | HOOC—(CH₂)₂— |
| 3-1287 | 4 | — | NH | MeCH(COOMe) |
| 3-1288 | 4 | — | NH | HOOC—(CH₂)₃— |
| 3-1289 | 4 | NHCOCO | — | OH |
| 3-1290 | 4 | NHCOCO | — | MeO |
| 3-1291 | 4 | NHCOCO | — | EtO |
| 3-1292 | 4 | NHCOCO | — | PrO |
| 3-1293 | 4 | NHCOCO | — | iPrO |
| 3-1294 | 4 | NHCOCO | — | BuO |
| 3-1295 | 4 | NHCOCO | — | iBuO |
| 3-1296 | 4 | NHCOCO | — | sBuO |
| 3-1297 | 4 | NHCOCO | — | tBuO |
| 3-1298 | 4 | NHCOCO | — | HxO |
| 3-1299 | 4 | NHCOCO | — | PhO |
| 3-1300 | 4 | NHCOCO | — | BnO |
| 3-1301 | 5 | CO | NH | H |
| 3-1302 | 5 | CO | NH | Ph |
| 3-1303 | 5 | CO | NH | 2-Me—Ph |
| 3-1304 | 5 | CO | NH | 4-Me—Ph |
| 3-1305 | 5 | CO | NH | 2,4-diMe—Ph |
| 3-1306 | 5 | CO | NH | 3,4-diMe—Ph |
| 3-1307 | 5 | CO | NH | 2-(CF₃)Ph |
| 3-1308 | 5 | CO | NH | 4-(CF₃)Ph |
| 3-1309 | 5 | CO | NH | 2-MeOPh |
| 3-1310 | 5 | CO | NH | 4-MeOPh |
| 3-1311 | 5 | CO | NH | 2-EtOPh |
| 3-1312 | 5 | CO | NH | 4-EtOPh |
| 3-1313 | 5 | CO | NH | 2-HOPh |
| 3-1314 | 5 | CO | NH | 4-HOPh |
| 3-1315 | 5 | CO | NH | 2-(HOOC)Ph |
| 3-1316 | 5 | CO | NH | 4-(HOOC)Ph |
| 3-1317 | 5 | CO | NH | 2-(MeOOC)Ph |
| 3-1318 | 5 | CO | NH | 4-(MeOOC)Ph |
| 3-1319 | 5 | CO | NH | 2-(EtOOC)Ph |
| 3-1320 | 5 | CO | NH | 4-(EtOOC)Ph |
| 3-1321 | 5 | CO | NH | 2-(tBuOOC)Ph |
| 3-1322 | 5 | CO | NH | 4-(tBuOOC)Ph |
| 3-1323 | 5 | CO | NH | 2-Cl—Ph |
| 3-1324 | 5 | CO | NH | 4-Cl—Ph |
| 3-1325 | 5 | CO | NH | 2-Br—Ph |
| 3-1326 | 5 | CO | NH | 4-Br—Ph |
| 3-1327 | 5 | CO | NH | 2-I—Ph |
| 3-1328 | 5 | CO | NH | 4-I—Ph |
| 3-1329 | 5 | CO | NH | 2-NO₂—Ph |
| 3-1330 | 5 | CO | NH | 4-NO₂—Ph |
| 3-1331 | 5 | CO | NH | 2-NH₂—Ph |
| 3-1332 | 5 | CO | NH | 4-NH₂—Ph |
| 3-1333 | 5 | CO | NH | 2-(HO₃S)Ph |
| 3-1334 | 5 | CO | NH | 4-(HO₃S)Ph |
| 3-1335 | 5 | CO | NH | 2-(NH₂O₂S)Ph |
| 3-1336 | 5 | CO | NH | 4-(NH₂O₂S)Ph |
| 3-1337 | 5 | CO | NH | 2-CN—Ph |
| 3-1338 | 5 | CO | NH | 4-CN—Ph |
| 3-1339 | 5 | CO | NH | 2-(HOCH₂)Ph |
| 3-1340 | 5 | CO | NH | 4-(HOCH₂)Ph |
| 3-1341 | 5 | CO | NH | Me |
| 3-1342 | 5 | CO | NH | Et |
| 3-1343 | 5 | CO | NH | Pr |
| 3-1344 | 5 | CO | NH | iPr |
| 3-1345 | 5 | CO | NH | Bu |
| 3-1346 | 5 | CO | NH | HOOCCH₂— |
| 3-1347 | 5 | CO | NH | MeOOCCH₂— |
| 3-1348 | 5 | CO | NH | MeCH(COOH) |
| 3-1349 | 5 | CO | NH | HOOC—(CH₂)₂— |
| 3-1350 | 5 | CO | NH | MeCH(COOMe) |
| 3-1351 | 5 | CO | NH | 1-HOOC-iBu |
| 3-1352 | 5 | CO | NH | 1-MeOOC-iBu |
| 3-1353 | 5 | CO | NH | 1-HOOC-iPn |
| 3-1354 | 5 | CO | NH | 1-MeOOC-iPn |
| 3-1355 | 5 | CO | NH | 1-HOOC-2-Me—Bu |
| 3-1356 | 5 | CO | NH | 1-MeOOC-2-Me—Bu |
| 3-1357 | 5 | CO | NH | CH₂CH₂SO₃H |
| 3-1358 | 5 | CO | NH | OH |
| 3-1359 | 5 | CO | NH | MeO |
| 3-1360 | 5 | CO | NH | EtO |
| 3-1361 | 5 | CO | NH | PrO |
| 3-1362 | 5 | CO | NH | iPrO |
| 3-1363 | 5 | CO | NH | BuO |
| 3-1364 | 5 | CO | NH | iBuO |
| 3-1365 | 5 | CO | NH | sBuO |
| 3-1366 | 5 | CO | NH | tBuO |
| 3-1367 | 5 | CO | NH | HxO |
| 3-1368 | 5 | CO | NH | PhO |
| 3-1369 | 5 | CO | NH | BnO |
| 3-1370 | 5 | CO | NH | Z-1 |
| 3-1371 | 5 | CO | NH | Z-2 |
| 3-1372 | 5 | CO | NH | Z-3 |
| 3-1373 | 5 | CO | NH | Z-4 |
| 3-1374 | 5 | CO | NH | Z-6 |
| 3-1375 | 5 | CO | NH | Z-7 |
| 3-1376 | 5 | CO | NH | Z-8 |
| 3-1377 | 5 | CO | NH | Z-9 |
| 3-1378 | 5 | CO | NH | Z-10 |
| 3-1379 | 5 | CO | NH | Z-11 |
| 3-1380 | 5 | CO | NH | Z-12 |
| 3-1381 | 5 | CO | NH | 3-Py |
| 3-1382 | 5 | CO | NH | 4-Py |
| 3-1383 | 5 | CO | N(Ac) | H |
| 3-1384 | 5 | CO | N(Ac) | Ph |
| 3-1385 | 5 | CO | N(Ac) | 2-Me—Ph |
| 3-1386 | 5 | CO | N(Ac) | 4-Me—Ph |
| 3-1387 | 5 | CO | N(Ac) | 2,4-diMe—Ph |
| 3-1388 | 5 | CO | N(Ac) | 3,4-diMe—Ph |
| 3-1389 | 5 | CO | N(Ac) | 2-(CF₃)Ph |
| 3-1390 | 5 | CO | N(Ac) | 4-(CF₃)Ph |
| 3-1391 | 5 | CO | N(Ac) | 2-MeOPh |

TABLE 3-continued

| Cpd. No. | k | A | B | R¹ |
|---|---|---|---|---|
| 3-1393 | 5 | CO | N(Ac) | 4-MeOPh |
| 3-1394 | 5 | CO | N(Ac) | 2-EtOPh |
| 3-1395 | 5 | CO | N(Ac) | 4-EtOPh |
| 3-1396 | 5 | CO | N(Ac) | 2-HOPh |
| 3-1397 | 5 | CO | N(Ac) | 4-HOPh |
| 3-1398 | 5 | CO | N(Ac) | 2-(HOOC)Ph |
| 3-1399 | 5 | CO | N(Ac) | 4-(HOOC)Ph |
| 3-1400 | 5 | CO | N(Ac) | 2-(MeOOC)Ph |
| 3-1401 | 5 | CO | N(Ac) | 4-(MeOOC)Ph |
| 3-1402 | 5 | CO | N(Ac) | 2-(EtOOC)Ph |
| 3-1403 | 5 | CO | N(Ac) | 4-(EtOOC)Ph |
| 3-1404 | 5 | CO | N(Ac) | 2-(tBuOOC)Ph |
| 3-1405 | 5 | CO | N(Ac) | 4-(tBuOOC)Ph |
| 3-1406 | 5 | CO | N(Ac) | 2-Cl—Ph |
| 3-1407 | 5 | CO | N(Ac) | 4-Cl—Ph |
| 3-1408 | 5 | CO | N(Ac) | 2-Br—Ph |
| 3-1409 | 5 | CO | N(Ac) | 4-Br—Ph |
| 3-1410 | 5 | CO | N(Ac) | 2-I—Ph |
| 3-1411 | 5 | CO | N(Ac) | 4-I—Ph |
| 3-1412 | 5 | CO | N(Ac) | 2-NO$_2$—Ph |
| 3-1413 | 5 | CO | N(Ac) | 4-NO$_2$—Ph |
| 3-1414 | 5 | CO | N(Ac) | 2-NH$_2$—Ph |
| 3-1415 | 5 | CO | N(Ac) | 4-NH$_2$—Ph |
| 3-1416 | 5 | CO | N(Ac) | 2-(HO$_3$S)Ph |
| 3-1417 | 5 | CO | N(Ac) | 4-(HO$_3$S)Ph |
| 3-1419 | 5 | CO | N(Ac) | 2-(NH$_2$O$_2$S)Ph |
| 3-1420 | 5 | CO | N(Ac) | 2-CN—Ph |
| 3-1421 | 5 | CO | N(Ac) | 4-CN—Ph |
| 3-1422 | 5 | CO | N(Ac) | 2-(HOCH$_2$)Ph |
| 3-1423 | 5 | CO | N(Ac) | 4-(HOCH$_2$)Ph |
| 3-1424 | 5 | CO | N(Ac) | Me |
| 3-1425 | 5 | CO | N(Ac) | Et |
| 3-1426 | 5 | CO | N(Ac) | Pr |
| 3-1427 | 5 | CO | N(Ac) | iPr |
| 3-1428 | 5 | CO | N(Ac) | Bu |
| 3-1429 | 5 | CO | N(Ac) | HOOCCH$_2$— |
| 3-1430 | 5 | CO | N(Ac) | MeOOCCH$_2$— |
| 3-1431 | 5 | CO | N(Ac) | MeCH(COOH) |
| 3-1432 | 5 | CO | N(Ac) | HOOC—(CH$_2$)$_2$— |
| 3-1433 | 5 | CO | N(Ac) | MeCH(COOMe) |
| 3-1434 | 5 | CO | N(Ac) | 1-HOOC-iBu |
| 3-1435 | 5 | CO | N(Ac) | 1-MeOOC-iBu |
| 3-1436 | 5 | CO | N(Ac) | 1-HOOC-iPn |
| 3-1437 | 5 | CO | N(Ac) | 1-MeOOC-iPn |
| 3-1438 | 5 | CO | N(Ac) | 1-HOOC-2-Me—Bu |
| 3-1439 | 5 | CO | N(Ac) | 1-MeOOC-2-Me—Bu |
| 3-1440 | 5 | CO | N(Ac) | CH$_2$CH$_2$SO$_3$H |
| 3-1441 | 5 | CO | N(Ac) | OH |
| 3-1442 | 5 | CO | N(Ac) | MeO |
| 3-1443 | 5 | CO | N(Ac) | EtO |
| 3-1444 | 5 | CO | N(Ac) | PrO |
| 3-1445 | 5 | CO | N(Ac) | iPrO |
| 3-1446 | 5 | CO | N(Ac) | BuO |
| 3-1447 | 5 | CO | N(Ac) | iBuO |
| 3-1448 | 5 | CO | N(Ac) | sBuO |
| 3-1449 | 5 | CO | N(Ac) | tBuO |
| 3-1450 | 5 | CO | N(Ac) | HxO |
| 3-1451 | 5 | CO | N(Ac) | PhO |
| 3-1452 | 5 | CO | N(Ac) | BnO |
| 3-1453 | 5 | CO | N(Ac) | Z-1 |
| 3-1454 | 5 | CO | N(Ac) | Z-2 |
| 3-1455 | 5 | CO | N(Ac) | Z-3 |
| 3-1456 | 5 | CO | N(Ac) | Z-4 |
| 3-1457 | 5 | CO | N(Ac) | Z-5 |
| 3-1458 | 5 | CO | N(Ac) | Z-6 |
| 3-1459 | 5 | CO | N(Ac) | Z-7 |
| 3-1460 | 5 | CO | N(Ac) | Z-8 |
| 3-1461 | 5 | CO | N(Ac) | Z-9 |
| 3-1462 | 5 | CO | N(Ac) | Z-10 |
| 3-1463 | 5 | CO | N(Ac) | Z-11 |
| 3-1464 | 5 | CO | N(Ac) | Z-12 |
| 3-1465 | 5 | CO | N(Ac) | 3-Py |
| 3-1466 | 5 | CO | N(Ac) | 4-Py |
| 3-1467 | 5 | COO | — | H |
| 3-1468 | 5 | COO | — | Ph |
| 3-1469 | 5 | COO | — | 2-Me—Ph |
| 3-1470 | 5 | COO | — | 4-Me—Ph |
| 3-1471 | 5 | COO | — | 2,4-diMe—Ph |
| 3-1472 | 5 | COO | — | 3,4-diMe—Ph |
| 3-1473 | 5 | COO | — | 2-(CF$_3$)Ph |
| 3-1474 | 5 | COO | — | 4-(CF$_3$)Ph |
| 3-1475 | 5 | COO | — | 2-MeOPh |
| 3-1476 | 5 | COO | — | 4-MeOPh |
| 3-1477 | 5 | COO | — | 2-EtOPh |
| 3-1478 | 5 | COO | — | 4-EtOPh |
| 3-1479 | 5 | COO | — | 2-HOPh |
| 3-1480 | 5 | COO | — | 4-HOPh |
| 3-1481 | 5 | COO | — | 2-(HOOC)Ph |
| 3-1482 | 5 | COO | — | 4-(HOOC)Ph |
| 3-1483 | 5 | COO | — | 2-(MeOOC)Ph |
| 3-1484 | 5 | COO | — | 4-(MeOOC)Ph |
| 3-1485 | 5 | COO | — | 2-(EtOOC)Ph |
| 3-1486 | 5 | COO | — | 4-(EtOOC)Ph |
| 3-1487 | 5 | COO | — | 2-(tBuOOC)Ph |
| 3-1488 | 5 | COO | — | 4-(tBuOOC)Ph |
| 3-1489 | 5 | COO | — | 2-Cl—Ph |
| 3-1490 | 5 | COO | — | 4-Cl—Ph |
| 3-1491 | 5 | COO | — | 2-Br—Ph |
| 3-1492 | 5 | COO | — | 4-Br—Ph |
| 3-1493 | 5 | COO | — | 2-I—Ph |
| 3-1494 | 5 | COO | — | 4-I—Ph |
| 3-1495 | 5 | COO | — | 2-NO$_2$—Ph |
| 3-1496 | 5 | COO | — | 4-NO$_2$—Ph |
| 3-1497 | 5 | COO | — | 2-NH$_2$—Ph |
| 3-1498 | 5 | COO | — | 4-NH$_2$—Ph |
| 3-1499 | 5 | COO | — | 2-(HO$_3$S)Ph |
| 3-1500 | 5 | COO | — | 4-(HO$_3$S)Ph |
| 3-1501 | 5 | COO | — | 2-(NH$_2$O$_2$S)Ph |
| 3-1502 | 5 | COO | — | 4-(NH$_2$O$_2$S)Ph |
| 3-1503 | 5 | COO | — | 2-CN—Ph |
| 3-1504 | 5 | COO | — | 4-CN—Ph |
| 3-1505 | 5 | COO | — | 2-(HOCH$_2$)Ph |
| 3-1506 | 5 | COO | — | 4-(HOCH$_2$)Ph |
| 3-1507 | 5 | COO | — | Me |
| 3-1508 | 5 | COO | — | Et |
| 3-1509 | 5 | COO | — | Pr |
| 3-1510 | 5 | COO | — | iPr |
| 3-1511 | 5 | COO | — | Bu |
| 3-1512 | 5 | COO | — | HOOCCH$_2$— |
| 3-1513 | 5 | COO | — | HOOC—(CH$_2$)$_2$— |
| 3-1514 | 5 | COO | — | MeCH(COOMe) |
| 3-1515 | 5 | COO | — | 1-HOOC-iBu |
| 3-1516 | 5 | COO | — | 1-HOOC-iPn |
| 3-1517 | 5 | COO | — | Z-1 |
| 3-1518 | 5 | COO | — | Z-2 |
| 3-1519 | 5 | COO | — | Z-3 |
| 3-1520 | 5 | COO | — | Z-4 |
| 3-1521 | 5 | COO | — | Z-5 |
| 3-1522 | 5 | COO | — | Z-6 |
| 3-1523 | 5 | COO | — | Z-7 |
| 3-1524 | 5 | COO | — | Z-8 |
| 3-1525 | 5 | COO | — | Z-9 |
| 3-1526 | 5 | COO | — | Z-10 |
| 3-1527 | 5 | COO | — | Z-11 |
| 3-1528 | 5 | COO | — | Z-12 |
| 3-1529 | 5 | COO | — | 3-Py |
| 3-1530 | 5 | COO | — | 4-Py |
| 3-1531 | 5 | CONHCO | — | H |
| 3-1532 | 5 | CONHCO | — | Ph |
| 3-1533 | 5 | CONHCO | — | 2-Me—Ph |
| 3-1534 | 5 | CONHCO | — | 4-Me—Ph |
| 3-1535 | 5 | CONHCO | — | 2,4-diMe—Ph |
| 3-1536 | 5 | CONHCO | — | 3,4-diMe—Ph |
| 3-1537 | 5 | CONHCO | — | 2-(CF$_3$)Ph |
| 3-1538 | 5 | CONHCO | — | 4-(CF$_3$)Ph |
| 3-1539 | 5 | CONHCO | — | 2-MeOPh |
| 3-1540 | 5 | CONHCO | — | 4-MeOPh |
| 3-1541 | 5 | CONHCO | — | 2-EtOPh |
| 3-1542 | 5 | CONHCO | — | 4-EtOPh |
| 3-1543 | 5 | CONHCO | — | 2-HOPh |
| 3-1544 | 5 | CONHCO | — | 4-HOPh |
| 3-1545 | 5 | CONHCO | — | 2-(HOOC)Ph |

TABLE 3-continued

| Cpd. No. | k | A | B | R¹ |
|---|---|---|---|---|
| 3-1546 | 5 | CONHCO | — | 4-(HOOC)Ph |
| 3-1547 | 5 | CONHCO | — | 2-(MeOOC)Ph |
| 3-1548 | 5 | CONHCO | — | 4-(MeOOC)Ph |
| 3-1549 | 5 | CONHCO | — | 2-(EtOOC)Ph |
| 3-1550 | 5 | CONHCO | — | 4-(EtOOC)Ph |
| 3-1551 | 5 | CONHCO | — | 2-(tBuOOC)Ph |
| 3-1552 | 5 | CONHCO | — | 4-(tBuOOC)Ph |
| 3-1553 | 5 | CONHCO | — | 2-Cl—Ph |
| 3-1554 | 5 | CONHCO | — | 4-Cl—Ph |
| 3-1555 | 5 | CONHCO | — | 2-Br—Ph |
| 3-1556 | 5 | CONHCO | — | 4-Br—Ph |
| 3-1557 | 5 | CONHCO | — | 2-I—Ph |
| 3-1558 | 5 | CONHCO | — | 4-I—Ph |
| 3-1559 | 5 | CONHCO | — | 2-NO$_2$—Ph |
| 3-1560 | 5 | CONHCO | — | 4-NO$_2$—Ph |
| 3-1561 | 5 | CONHCO | — | 2-NH$_2$—Ph |
| 3-1562 | 5 | CONHCO | — | 4-NH$_2$—Ph |
| 3-1563 | 5 | CONHCO | — | 2-(HO$_3$S)Ph |
| 3-1564 | 5 | CONHCO | — | 4-(HO$_3$S)Ph |
| 3-1565 | 5 | CONHCO | — | 2-(NH$_2$O$_2$S)Ph |
| 3-1566 | 5 | CONHCO | — | 4-(NH$_2$O$_2$S)Ph |
| 3-1567 | 5 | CONHCO | — | 2-CN—Ph |
| 3-1568 | 5 | CONHCO | — | 4-CN—Ph |
| 3-1569 | 5 | CONHCO | — | 2-(HOCH$_2$)Ph |
| 3-1570 | 5 | CONHCO | — | 4-(HOCH$_2$)Ph |
| 3-1571 | 5 | CONHCO | — | Me |
| 3-1572 | 5 | CONHCO | — | Et |
| 3-1573 | 5 | CONHCO | — | Pr |
| 3-1574 | 5 | CONCHO | — | iPr |
| 3-1575 | 5 | CONHCO | — | Bu |
| 3-1576 | 5 | CONHCO | — | HOOCCH$_2$— |
| 3-1577 | 5 | CONHCO | — | MeOOCCH$_2$— |
| 3-1578 | 5 | CONHCO | — | MeCH(COOH) |
| 3-1579 | 5 | CONHCO | — | HOOC—(CH$_2$)$_2$— |
| 3-1580 | 5 | CONHCO | — | MeCH(COOMe) |
| 3-1581 | 5 | CONHCO | — | 1-HOOC-iBu |
| 3-1582 | 5 | CONHCO | — | 1-MeOOC-iBu |
| 3-1583 | 5 | CONHCO | — | 1-HOOC-iPn |
| 3-1584 | 5 | CONHCO | — | 1-MeOOC-iPn |
| 3-1585 | 5 | CONHCO | — | 1-HOOC-2-Me—Bu |
| 3-1586 | 5 | CONHCO | — | 1-MeOOC-2-Me—Bu |
| 3-1587 | 5 | CONHCO | — | CH$_2$CH$_2$SO$_3$H |
| 3-1588 | 5 | CONHCO | — | Z-1 |
| 3-1589 | 5 | CONHCO | — | Z-2 |
| 3-1590 | 5 | CONHCO | — | Z-3 |
| 3-1591 | 5 | CONHCO | — | Z-4 |
| 3-1592 | 5 | CONHCO | — | Z-5 |
| 3-1593 | 5 | CONHCO | — | Z-6 |
| 3-1594 | 5 | CONHCO | — | Z-7 |
| 3-1595 | 5 | CONHCO | — | Z-8 |
| 3-1596 | 5 | CONHCO | — | Z-9 |
| 3-1597 | 5 | CONHCO | — | Z-10 |
| 3-1598 | 5 | CONHCO | — | Z-11 |
| 3-1599 | 5 | CONHCO | — | Z-12 |
| 3-1600 | 5 | CONHCO | — | 3-Py |
| 3-1601 | 5 | CONHCO | — | 4-Py |
| 3-1602 | 5 | CON(Ac)CO | — | H |
| 3-1603 | 5 | CON(Ac)CO | — | Ph |
| 3-1604 | 5 | CON(Ac)CO | — | 2-Me—Ph |
| 3-1605 | 5 | CON(Ac)CO | — | 4-Me—Ph |
| 3-1606 | 5 | CON(Ac)CO | — | 2,4-diMe—Ph |
| 3-1607 | 5 | CON(Ac)CO | — | 3,4-diMe—Ph |
| 3-1608 | 5 | CON(Ac)CO | — | 2-(CF$_3$)Ph |
| 3-1609 | 5 | CON(Ac)CO | — | 4-(CF$_3$)Ph |
| 3-1610 | 5 | CON(Ac)CO | — | 2-MeOPh |
| 3-1611 | 5 | CON(Ac)CO | — | 4-EtOPh |
| 3-1612 | 5 | CON(Ac)CO | — | 2-EtOPh |
| 3-1613 | 5 | CON(Ac)CO | — | 4-EtOPh |
| 3-1614 | 5 | CON(Ac)CO | — | 2-HOPh |
| 3-1615 | 5 | CON(Ac)CO | — | 4-HOPh |
| 3-1616 | 5 | CON(Ac)CO | — | 2-(HOOC)Ph |
| 3-1617 | 5 | CON(Ac)CO | — | 4-(HOOC)Ph |
| 3-1618 | 5 | CON(Ac)CO | — | 2-(MeOOC)Ph |
| 3-1619 | 5 | CON(Ac)CO | — | 4-(MeOOC)Ph |
| 3-1620 | 5 | CON(Ac)CO | — | 2-(EtOOC)Ph |
| 3-1621 | 5 | CON(Ac)CO | — | 4-(EtOOC)Ph |
| 3-1622 | 5 | CON(Ac)CO | — | 2-(tBuOOC)Ph |
| 3-1623 | 5 | CON(Ac)CO | — | 4-(tBuOOC)Ph |
| 3-1624 | 5 | CON(Ac)CO | — | 2-Cl—Ph |
| 3-1625 | 5 | CON(Ac)CO | — | 4-Cl—Ph |
| 3-1626 | 5 | CON(Ac)CO | — | 2-Br—Ph |
| 3-1627 | 5 | CON(Ac)CO | — | 4-Br—Ph |
| 3-1628 | 5 | CON(Ac)CO | — | 2-I—Ph |
| 3-1629 | 5 | CON(Ac)CO | — | 4-I—Ph |
| 3-1630 | 5 | CON(Ac)CO | — | 2-NO$_2$—Ph |
| 3-1631 | 5 | CON(Ac)CO | — | 4-NO$_2$—Ph |
| 3-1632 | 5 | CON(Ac)CO | — | 2-NH$_2$—Ph |
| 3-1633 | 5 | CON(Ac)CO | — | 4-NH$_2$—Ph |
| 3-1634 | 5 | CON(Ac)CO | — | 2-(HO$_3$S)Ph |
| 3-1635 | 5 | CON(Ac)CO | — | 4-(HO$_3$S)Ph |
| 3-1636 | 5 | CON(Ac)CO | — | 2-(NH$_2$O$_2$S)Ph |
| 3-1637 | 5 | CON(Ac)CO | — | 4-(NH$_2$O$_2$S)Ph |
| 3-1638 | 5 | CON(Ac)CO | — | 2-CN—Ph |
| 3-1639 | 5 | CON(Ac)CO | — | 4-CN—Ph |
| 3-1640 | 5 | CON(Ac)CO | — | 2-(HOCH$_2$)Ph |
| 3-1641 | 5 | CON(Ac)CO | — | 4-(HOCH$_2$)Ph |
| 3-1642 | 5 | CON(Ac)CO | — | Me |
| 3-1643 | 5 | CON(Ac)CO | — | Et |
| 3-1644 | 5 | CON(Ac)CO | — | Pr |
| 3-1645 | 5 | CON(Ac)CO | — | iPr |
| 3-1646 | 5 | CON(Ac)CO | — | Bu |
| 3-1647 | 5 | CON(Ac)CO | — | HOOCCH$_2$— |
| 3-1648 | 5 | CON(Ac)CO | — | MeOOCCH$_2$— |
| 3-1649 | 5 | CON(Ac)CO | — | MeCH(COOH) |
| 3-1650 | 5 | CON(Ac)CO | — | HOOC—(CH$_2$)$_2$— |
| 3-1651 | 5 | CON(Ac)CO | — | MeCH(COOMe) |
| 3-1652 | 5 | CON(Ac)CO | — | 1-HOOC-iBu |
| 3-1653 | 5 | CON(Ac)CO | — | 1-MeOOC-iBu |
| 3-1654 | 5 | CON(Ac)CO | — | 1-HOOC-iPn |
| 3-1655 | 5 | CON(Ac)CO | — | 1-MeOOC-iPn |
| 3-1656 | 5 | CON(Ac)CO | — | 1-HOOC-2-Me—Bu |
| 3-1657 | 5 | CON(Ac)CO | — | 1-MeOOC-2-Me—Bu |
| 3-1658 | 5 | CON(ac)CO | — | CH$_2$CH$_2$SO$_3$H |
| 3-1659 | 5 | CON(Ac)CO | — | Z-1 |
| 3-1660 | 5 | CON(Ac)CO | — | Z-2 |
| 3-1661 | 5 | CON(Ac)CO | — | Z-3 |
| 3-1662 | 5 | CON(Ac)CO | — | Z-4 |
| 3-1663 | 5 | CON(Ac)CO | — | Z-5 |
| 3-1664 | 5 | CON(Ac)CO | — | Z-6 |
| 3-1665 | 5 | CON(Ac)CO | — | Z-7 |
| 3-1666 | 5 | CON(Ac)CO | — | Z-8 |
| 3-1667 | 5 | CON(Ac)CO | — | Z-9 |
| 3-1668 | 5 | CON(Ac)CO | — | Z-10 |
| 3-1669 | 5 | CON(Ac)CO | — | Z-11 |
| 3-1670 | 5 | CON(Ac)CO | — | Z-12 |
| 3-1671 | 5 | CON(Ac)CO | — | 3-Py |
| 3-1672 | 5 | CON(Ac)CO | — | 4-Py |
| 3-1673 | 5 | CONHCO | NH | H |
| 3-1674 | 5 | CONHCO | NH | Ph |
| 3-1675 | 5 | CONHCO | NH | 2-Me—Ph |
| 3-1676 | 5 | CONHCO | NH | 4-Me—Ph |
| 3-1677 | 5 | CONHCO | NH | 2,4-diMe—Ph |
| 3-1678 | 5 | CONHCO | NH | 3,4-diMe—Ph |
| 3-1679 | 5 | CONHCO | NH | 2-(CF$_3$)Ph |
| 3-1680 | 5 | CONHCO | NH | 4-(CF$_3$)Ph |
| 3-1681 | 5 | CONHCO | NH | 2-MeOPh |
| 3-1682 | 5 | CONHCO | NH | 4-MeOPh |
| 3-1683 | 5 | CONHCO | NH | 2-EtOPh |
| 3-1684 | 5 | CONHCO | NH | 4-EtOPh |
| 3-1685 | 5 | CONHCO | NH | 2-HOPh |
| 3-1686 | 5 | CONHCO | NH | 4-HOPh |
| 3-1687 | 5 | CONHCO | NH | 2-(HOOC)Ph |
| 3-1688 | 5 | CONHCO | MH | 4-(HOOC)Ph |
| 3-1689 | 5 | CONHCO | nH | 2-(MeOOC)Ph |
| 3-1690 | 5 | CONHCO | NH | 4-(MeOOC)Ph |
| 3-1691 | 5 | CONHCO | NH | 2-(EtOOC)Ph |
| 3-1692 | 5 | CONHCO | NH | 4-(EtOOC)Ph |
| 3-1693 | 5 | CONHCO | NH | 2-(tBuOOC)Ph |
| 3-1694 | 5 | CONHCO | NH | 4-(tBuOOC)Ph |
| 3-1695 | 5 | CONHCO | NH | 2-Cl—Ph |
| 3-1696 | 5 | CONHCO | NH | 4-Cl—Ph |
| 3-1697 | 5 | CONHCO | NH | 2-Br—Ph |

TABLE 3-continued

| Cpd. No. | k | A | B | R¹ |
|---|---|---|---|---|
| 3-1698 | 5 | CONHCO | NH | 4-Br—Ph |
| 3-1699 | 5 | CONHCO | NH | 2-I—Ph |
| 3-1700 | 5 | CONHCO | NH | 4-I—Ph |
| 3-1701 | 5 | CONHCO | NH | 2-NO$_2$—Ph |
| 3-1702 | 5 | CONHCO | NH | 4-NO$_2$—Ph |
| 3-1703 | 5 | CONHCO | NH | 2-NH$_2$—Ph |
| 3-1704 | 5 | CONHCO | NH | 4-NH$_2$—Ph |
| 3-1705 | 5 | CONHCO | NH | 2-(HO$_3$S)Ph |
| 3-1706 | 5 | CONHCO | NH | 4-(HO$_3$S)Ph |
| 3-1707 | 5 | CONHCO | NH | 2-(NH$_2$O$_2$S)Ph |
| 3-1708 | 5 | CONHCO | NH | 4-(NH$_2$O$_2$S)Ph |
| 3-1709 | 5 | CONHCO | NH | 2-CN—Ph |
| 3-1710 | 5 | CONHCO | NH | 4-CN—Ph |
| 3-1711 | 5 | CONHCO | NH | 2-(HOCH$_2$)Ph |
| 3-1712 | 5 | CONHCO | NH | 4-(HOCH$_2$)Ph |
| 3-1713 | 5 | CONHCO | NH | Me |
| 3-1714 | 5 | CONHCO | NH | Et |
| 3-1715 | 5 | CONHCO | NH | Pr |
| 3-1716 | 5 | CONHCO | NH | iPr |
| 3-1717 | 5 | CONHCO | NH | Bu |
| 3-1718 | 5 | CONHCO | NH | HOOCCH$_2$— |
| 3-1719 | 5 | CONHCO | NH | MeOOCCH$_2$— |
| 3-1720 | 5 | CONHCO | NH | MeCH(COOH) |
| 3-1721 | 5 | CONHCO | NH | HOOC—(CH$_2$)$_2$— |
| 3-1722 | 5 | CONHCO | NH | MeCH(COOMe) |
| 3-1723 | 5 | CONHCO | NH | 1-HOOC-iBu |
| 3-1724 | 5 | CONHCO | NH | 1-MeOOC-iBu |
| 3-1725 | 5 | CONHCO | NH | 1-HOOC-iPn |
| 3-1726 | 5 | CONHCO | NH | 1-MeOOC-iPn |
| 3-1727 | 5 | CONHCO | NH | 1-HOOC-2-Me—Bu |
| 3-1728 | 5 | CONHOCO | NH | 1-MeOOC-2-Me—Bu |
| 3-1729 | 5 | CONHCO | NH | CH$_2$CH$_2$SO$_3$H |
| 3-1730 | 5 | CONHCO | NH | HO |
| 3-1731 | 5 | CONHCO | NH | MeO |
| 3-1732 | 5 | CONHCO | NH | EtO |
| 3-1733 | 5 | CONHCO | NH | Pro |
| 3-1734 | 5 | CONHCO | NH | iPrO |
| 3-1735 | 5 | CONHCO | NH | BuO |
| 3-1736 | 5 | CONHOC | NH | iBuO |
| 3-1737 | 5 | CONHCO | NH | sBuO |
| 3-1738 | 5 | CONHCO | NH | tBuO |
| 3-1739 | 5 | CONHOC | NH | HxO |
| 3-1740 | 5 | CONHCO | NH | PhO |
| 3-1741 | 5 | CONHCO | NH | BnO |
| 3-1742 | 5 | CONHCO | NH | Z-1 |
| 3-1744 | 5 | CONHCO | NH | Z-3 |
| 3-1745 | 5 | CONHCO | NH | Z-4 |
| 3-1748 | 5 | CONHCO | NH | Z-5 |
| 3-1747 | 5 | CONHCO | NH | Z-6 |
| 3-1748 | 5 | CONHCO | NH | Z-7 |
| 3-1749 | 5 | CONHCO | NH | Z-8 |
| 3-1750 | 5 | CONHCO | NH | Z-9 |
| 3-1751 | 5 | CONHCO | NH | Z-10 |
| 3-1752 | 5 | CONHCO | NH | Z-11 |
| 3-1753 | 5 | CONHCO | NH | Z-12 |
| 3-1754 | 5 | CONHCO | NH | 3-Py |
| 3-1755 | 5 | CONHCO | NH | 4-Py |
| 3-1756 | 5 | CONHSO$_2$ | — | H |
| 3-1757 | 5 | CONHSO$_2$ | — | Ph |
| 3-1758 | 5 | CONHSO$_2$ | — | 2-Me—Ph |
| 3-1759 | 5 | CONHSO$_2$ | — | 4-Me—Ph |
| 3-1760 | 5 | CONHSO$_2$ | — | 2,4-diMe—Ph |
| 3-1761 | 5 | CONHSO$_2$ | — | 3,4-diMe—Ph |
| 3-1762 | 5 | CONHSO$_2$ | — | 2-(CF$_3$)Ph |
| 3-1763 | 5 | CONHSO$_2$ | — | 4-(CF$_3$)Ph |
| 3-1764 | 5 | CONHSO$_2$ | — | 2-MeOPh |
| 3-1765 | 5 | CONHSO$_2$ | — | 4-MeOPh |
| 3-1766 | 5 | CONHSO$_2$ | — | 2-EtOPh |
| 3-1767 | 5 | CONHSO$_2$ | — | 4-EtOPh |
| 3-1768 | 5 | CONHSO$_2$ | — | 2-HOPh |
| 3-1769 | 5 | CONHSO$_2$ | — | 4-HOPh |
| 3-1770 | 5 | CONHSO$_2$ | — | 2-(HOOC)Ph |
| 3-1771 | 5 | CONHSO$_2$ | — | 4-(HOOC)Ph |
| 3-1772 | 5 | CONHSO$_2$ | — | 2-(MeOOC)Ph |
| 3-1773 | 5 | CONHSO$_2$ | — | 4-(MeOOC)Ph |
| 3-1774 | 5 | CONHSO$_2$ | — | 2-(EtOOC)Ph |
| 3-1775 | 5 | CONHSO$_2$ | — | 4-(EtOOC)Ph |
| 3-1776 | 5 | CONHSO$_2$ | — | 2-(tBuOOC)Ph |
| 3-1777 | 5 | CONHSO$_2$ | — | 4-(tBuOOC)Ph |
| 3-1778 | 5 | CONHSO$_2$ | — | 2-Cl—Ph |
| 3-1779 | 5 | CONHSO$_2$ | — | 4-Cl—Ph |
| 3-1780 | 5 | CONHSO$_2$ | — | 2-Br—Ph |
| 3-1781 | 5 | CONHSO$_2$ | — | 4-Br—Ph |
| 3-1782 | 5 | CONHSO$_2$ | — | 2-I—Ph |
| 3-1783 | 5 | CONHSO$_2$ | — | 4-I—Ph |
| 3-1784 | 5 | CONHSO$_2$ | — | 2-NO$_2$—Ph |
| 3-1785 | 5 | CONHSO$_2$ | — | 4-NO$_2$—Ph |
| 3-1786 | 5 | CONHSO$_2$ | — | 2-NH$_2$—Ph |
| 3-1787 | 5 | CONHSO$_2$ | — | 4-NH$_2$—Ph |
| 3-1788 | 5 | CONHSO$_2$ | — | 2-(HO$_3$S)Ph |
| 3-1789 | 5 | CONHSO$_2$ | — | 4-(HO$_3$S)Ph |
| 3-1790 | 5 | CONHSO$_2$ | — | 2-(NH$_2$O$_2$S)Ph |
| 3-1791 | 5 | CONHSO$_2$ | — | 4-(NH$_2$O$_2$S)Ph |
| 3-1792 | 5 | CONHSO$_2$ | — | 2-CN—Ph |
| 3-1793 | 5 | CONHSO$_2$ | — | 4-CN—Ph |
| 3-1794 | 5 | CONHSO$_2$ | — | 2-(HOCH$_2$)Ph |
| 3-1795 | 5 | CONHSO$_2$ | — | 4-(HOCH$_2$)Ph |
| 3-1796 | 5 | CONHSO$_2$ | — | Me |
| 3-1797 | 5 | CONHSO$_2$ | — | Et |
| 3-1798 | 5 | CONHSO$_2$ | — | Pr |
| 3-1799 | 5 | CONHSO$_2$ | — | iPr |
| 3-1800 | 5 | CONHSO$_2$ | — | Bu |
| 3-1801 | 5 | CONHSO$_2$ | — | HOOCCH$_2$— |
| 3-1802 | 5 | CONHSO$_2$ | — | MeOOCCH$_2$— |
| 3-1803 | 5 | CONHSO$_2$ | — | MeCH(COOH) |
| 3-1804 | 5 | CONHSO$_2$ | — | HOOC—(CH$_2$)$_2$— |
| 3-1805 | 5 | CONHSO$_2$ | — | MeCH(COOMe) |
| 3-1806 | 5 | CONHSO$_2$ | — | 1-HOOC-iBu |
| 3-1807 | 5 | CONHSO$_2$ | — | 1-MeOOC-iBu |
| 3-1808 | 5 | CONHSO$_2$ | — | 1-HOOC-iPn |
| 3-1809 | 5 | CONHSO$_2$ | — | 1-MeOOC-iPn |
| 3-1810 | 5 | CONHSO$_2$ | — | 1-HOOC-2-Me—Bu |
| 3-1811 | 5 | CONHSO$_2$ | — | 1-MeOOC-2-Me—Bu |
| 3-1812 | 5 | CONHSO$_2$ | — | CH$_2$CH$_2$SO$_3$H |
| 3-1813 | 5 | CONHSO$_2$ | — | OH |
| 3-1814 | 5 | CONHSO$_2$ | — | MeO |
| 3-1815 | 5 | CONHSO$_2$ | — | EtO |
| 3-1816 | 5 | CONHSO$_2$ | — | PrO |
| 3-1817 | 5 | CONHSO$_2$ | — | iPrO |
| 3-1818 | 5 | CONHSO$_2$ | — | BuO |
| 3-1819 | 5 | CONHSO$_2$ | — | iBuO |
| 3-1820 | 5 | CONHSO$_2$ | — | sBuO |
| 3-1821 | 5 | CONHSO$_2$ | — | tBuO |
| 3-1822 | 5 | CONHSO$_2$ | — | HxO |
| 3-1823 | 5 | CONHSO$_2$ | — | PhO |
| 3-1824 | 5 | CONHSO$_2$ | — | BnO |
| 3-1825 | 5 | CONHSO$_2$ | — | Z-1 |
| 3-1826 | 5 | CONHSO$_2$ | — | Z-2 |
| 3-1827 | 5 | CONHSO$_2$ | — | Z-3 |
| 3-1828 | 5 | CONHSO$_2$ | — | Z-4 |
| 3-1829 | 5 | CONHSO$_2$ | — | Z-5 |
| 3-1830 | 5 | CONHSO$_2$ | — | Z-6 |
| 3-1831 | 5 | CONHSO$_2$ | — | Z-7 |
| 3-1832 | 5 | CONHSO$_2$ | — | Z-8 |
| 3-1833 | 5 | CONHSO$_2$ | — | Z-9 |
| 3-1834 | 5 | CONHSO$_2$ | — | Z-10 |
| 3-1835 | 5 | CONHSO$_2$ | — | Z-11 |
| 3-1836 | 5 | CONHSO$_2$ | — | Z-12 |
| 3-1837 | 5 | CONHSO$_2$ | — | 3-Py |
| 3-1838 | 5 | CONHSO$_2$ | — | 4-Py |
| 3-1839 | 5 | CONHSO$_2$ | NH | H |
| 3-1840 | 5 | CONHSO$_2$ | NH | Ph |
| 3-1841 | 5 | CONHSO$_2$ | NH | 2-Me—Ph |
| 3-1842 | 5 | CONHSO$_2$ | NH | 4-Me—Ph |
| 3-1843 | 5 | CONHSO$_2$ | NH | 2,4-diMe—Ph |
| 3-1844 | 5 | CONHSO$_2$ | NH | 3,4-diMe—Ph |
| 3-1845 | 5 | CONHSO$_2$ | NH | 2-(CF$_3$)Ph |
| 3-1846 | 5 | CONHSO$_2$ | NH | 4-(CF$_3$)Ph |
| 3-1847 | 5 | CONHSO$_2$ | NH | 2-MeOPh |
| 3-1848 | 5 | CONHSO$_2$ | NH | 4-MeOPh |
| 3-1849 | 5 | CONHSO$_2$ | NH | 2-EtOPh |
| 3-1850 | 5 | CONHSO$_2$ | NH | 4-EtOPh |

TABLE 3-continued

| Cpd. No. | k | A | B | R¹ |
|---|---|---|---|---|
| 3-1851 | 5 | CONHSO₂ | NH | 2-HOPh |
| 3-1852 | 5 | CONHSO₂ | NH | 4-HOPh |
| 3-1853 | 5 | CONHSO₂ | NH | 2-(HOOC)Ph |
| 3-1854 | 5 | CONHSO₂ | NH | 4-(HOOC)Ph |
| 3-1855 | 5 | CONHSO₂ | NH | 2-(MeOOC)Ph |
| 3-1856 | 5 | CONHSO₂ | NH | 4-(MeOOC)Ph |
| 3-1857 | 5 | CONHSO₂ | NH | 2-(EtOOC)Ph |
| 3-1858 | 5 | CONHSO₂ | NH | 4-(EtOOC)Ph |
| 3-1859 | 5 | CONHSO₂ | NH | 2-(tBuOOC)Ph |
| 3-1860 | 5 | CONHSO₂ | NH | 4-(tBuOOC)Ph |
| 3-1861 | 5 | CONHSO₂ | NH | 2-Cl—Ph |
| 3-1862 | 5 | CONHSO₂ | NH | 4-Cl—Ph |
| 3-1863 | 5 | CONHSO₂ | NH | 2-Br—Ph |
| 3-1864 | 5 | CONHSO₂ | NH | 4-Br—Ph |
| 3-1865 | 5 | CONHSO₂ | NH | 2-I—Ph |
| 3-1866 | 5 | CONHSO₂ | NH | 4-I—Ph |
| 3-1867 | 5 | CONHSO₂ | NH | 2-NO₂—Ph |
| 3-1868 | 5 | CONHSO₂ | NH | 4-NO₂—Ph |
| 3-1869 | 5 | CONHSO₂ | NH | 2-NH₂—Ph |
| 3-1870 | 5 | CONHSO₂ | NH | 4-NH₂—Ph |
| 3-1871 | 5 | CONHSO₂ | NH | 2-(HO₃S)Ph |
| 3-1872 | 5 | CONHSO₂ | NH | 4-(HO₃S)Ph |
| 3-1873 | 5 | CONHSO₂ | NH | 2-(NH₂O₂S)Ph |
| 3-1874 | 5 | CONHSO₂ | NH | 4-(NH₂O₂S)Ph |
| 3-1875 | 5 | CONHSO₂ | NH | 2-CN—Ph |
| 3-1876 | 5 | CONHSO₂ | NH | 4-CN—Ph |
| 3-1877 | 5 | CONHSO₂ | NH | 2-(HOCH₂)Ph |
| 3-1878 | 5 | CONHSO₂ | NH | 4-(HOCH₂)Ph |
| 3-1879 | 5 | CONHSO₂ | NH | Me |
| 3-1880 | 5 | CONHSO₂ | NH | Et |
| 3-1881 | 5 | CONHSO₂ | NH | Pr |
| 3-1882 | 5 | CONHSO₂ | NH | iPr |
| 3-1883 | 5 | CONHSO₂ | NH | Bu |
| 3-1884 | 5 | CONHSO₂ | NH | HOOCCH₂— |
| 3-1885 | 5 | CONHSO₂ | NH | MeOOCCH₂— |
| 3-1886 | 5 | CONHSO₂ | NH | MeCH(COOH) |
| 3-1887 | 5 | CONHSO₂ | NH | HOOC—(CH₂)₂— |
| 3-1888 | 5 | CONHSO₂ | NH | MeCH(COOMe) |
| 3-1889 | 5 | CONHSO₂ | NH | 1-HOOC-iBu |
| 3-1890 | 5 | CONHSO₂ | NH | 1-MeOOC-iBu |
| 3-1891 | 5 | CONHSO₂ | NH | 1-HOOC-iPn |
| 3-1892 | 5 | CONHSO₂ | NH | 1-MeOOC-iPn |
| 3-1893 | 5 | CONHSO₂ | NH | 1-HOOC-2-Me—Bu |
| 3-1894 | 5 | CONHSO₂ | NH | 1-MeOOC-2-Me—Bu |
| 3-1895 | 5 | CONHSO₂ | NH | CH₂CH₂SO₃H |
| 3-1896 | 5 | CONHSO₂ | NH | OH |
| 3-1897 | 5 | CONHSO₂ | NH | MeO |
| 3-1898 | 5 | CONHSO₂ | NH | EtO |
| 3-1899 | 5 | CONHSO₂ | NH | PrO |
| 3-1900 | 5 | CONHSO₂ | NH | iPrO |
| 3-1901 | 5 | CONHSO₂ | NH | BuO |
| 3-1902 | 5 | CONHSO₂ | NH | iBuO |
| 3-1903 | 5 | CONHSO₂ | NH | sBuO |
| 3-1904 | 5 | CONHSO₂ | NH | tBuO |
| 3-1905 | 5 | CONHSO₂ | NH | HxO |
| 3-1906 | 5 | CONHSO₂ | NH | PhO |
| 3-1907 | 5 | CONHSO₂ | NH | BnO |
| 3-1908 | 5 | CONHSO₂ | NH | Z-1 |
| 3-1909 | 5 | CONHSO₂ | NH | Z-2 |
| 3-1910 | 5 | CONHSO₂ | NH | Z-3 |
| 3-1911 | 5 | CONHSO₂ | NH | Z-4 |
| 3-1912 | 5 | CONHSO₂ | NH | Z-5 |
| 3-1913 | 5 | CONHSO₂ | NH | Z-6 |
| 3-1914 | 5 | CONHSO₂ | NH | Z-7 |
| 3-1915 | 5 | CONHSO₂ | NH | Z-8 |
| 3-1916 | 5 | CONHSO₂ | NH | Z-9 |
| 3-1917 | 5 | CONHSO₂ | NH | Z-10 |
| 3-1918 | 5 | CONHSO₂ | NH | Z-11 |
| 3-1919 | 5 | CONHSO₂ | NH | Z-12 |
| 3-1920 | 5 | CONHSO₂ | NH | 3-Py |
| 3-1921 | 5 | CONHSO₂ | NH | 4-Py |
| 3-1922 | 5 | NHCO | — | H |
| 3-1923 | 5 | NHCO | — | Ph |
| 3-1924 | 5 | NHCO | — | 2-Me—Ph |
| 3-1925 | 5 | NHCO | — | 4-Me—Ph |
| 3-1926 | 5 | NHCO | — | 2,4-diMe—Ph |
| 3-1927 | 5 | NHCO | — | 3,4-diMe—Ph |
| 3-1928 | 5 | NHCO | — | 2-(CF₃)Ph |
| 3-1929 | 5 | NHOC | — | 4-(CF₃)Ph |
| 3-1930 | 5 | NHOC | — | 2-MeOPh |
| 3-1931 | 5 | NHCO | — | 4-MeOPh |
| 3-1932 | 5 | NHCO | — | 2-EtOPh |
| 3-1933 | 5 | NHCO | — | 4-EtOPh |
| 3-1934 | 5 | NHCO | — | 2-HOPh |
| 3-1935 | 5 | NHCO | — | 4-HOPh |
| 3-1936 | 5 | NHCO | — | 2-(HOOC)Ph |
| 3-1937 | 5 | NHCO | — | 4-(HOOC)Ph |
| 3-1938 | 5 | NHCO | — | 2-(MeOOC)Ph |
| 3-1939 | 5 | NHCO | — | 4-(MeOOC)Ph |
| 3-1940 | 5 | NHCO | — | 2-(EtOOC)Ph |
| 3-1941 | 5 | NHCO | — | 4-(EtOOC)Ph |
| 3-1942 | 5 | NHCO | — | 2-(tBuOOC)Ph |
| 3-1943 | 5 | NHCO | — | 4-(tBuOOC)Ph |
| 3-1944 | 5 | NHCO | — | 2-Cl—Ph |
| 3-1945 | 5 | NHCO | — | 4-Cl—Ph |
| 3-1946 | 5 | NHCO | — | 2-Br—Ph |
| 3-1947 | 5 | NHCO | — | 4-Br—Ph |
| 3-1948 | 5 | NHCO | — | 2-I—Ph |
| 3-1949 | 5 | NHCO | — | 4-I—Ph |
| 3-1950 | 5 | NHCO | — | 2-NO₂—Ph |
| 3-1951 | 5 | NHCO | — | 4-NO₂—Ph |
| 3-1952 | 5 | NHCO | — | 2-NH₂—Ph |
| 3-1953 | 5 | NHCO | — | 4-NH₂—Ph |
| 3-1954 | 5 | NHCO | — | 2-(HO₃S)Ph |
| 3-1955 | 5 | NHCO | — | 4-(HO₃S)Ph |
| 3-1956 | 5 | NHCO | — | 2-(NH₂O₂S)Ph |
| 3-1957 | 5 | NHCO | — | 4-(NH₂O₂S)Ph |
| 3-1958 | 5 | NHCO | — | 2-CN—Ph |
| 3-1959 | 5 | NHCO | — | 4-CN—Ph |
| 3-1960 | 5 | NHCO | — | 2-(HOCH₂)Ph |
| 3-1961 | 5 | NHCO | — | 4-(HOCH₂)Ph |
| 3-1962 | 5 | NHCO | — | Me |
| 3-1963 | 5 | NHCO | — | Et |
| 3-1964 | 5 | NHCO | — | Pr |
| 3-1965 | 5 | NHCO | — | iPr |
| 3-1966 | 5 | NHCO | — | Bu |
| 3-1967 | 5 | NHCO | — | HOOCCH₂— |
| 3-1968 | 5 | NHCO | — | MeOOCCH₂— |
| 3-1969 | 5 | NHCO | — | MeCH(COOH) |
| 3-1970 | 5 | NHCO | — | HOOC—(CH₂)₂— |
| 3-1971 | 5 | NHCO | — | MeCH(COOMe) |
| 3-1972 | 5 | NHCO | — | 1-HOOC-iBu |
| 3-1973 | 5 | NHCO | — | 1-HOOC-iPn |
| 3-1974 | 5 | NHCO | — | 1-HOOC-2-Me—Bu |
| 3-1975 | 5 | NHCO | — | CH₂CH₂SO₃OH |
| 3-1976 | 5 | NHCO | — | MeO |
| 3-1977 | 5 | NHCO | — | EtO |
| 3-1978 | 5 | NHCO | — | PrO |
| 3-1979 | 5 | NHCO | — | Z-1 |
| 3-1980 | 5 | NHCO | — | Z-2 |
| 3-1981 | 5 | NHCO | — | Z-3 |
| 3-1982 | 5 | NHCO | — | Z-4 |
| 3-1983 | 5 | NHCO | — | Z-5 |
| 3-1984 | 5 | NHCO | — | Z-6 |
| 3-1985 | 5 | NHCO | — | Z-7 |
| 3-1986 | 5 | NHCO | — | Z-8 |
| 3-1987 | 5 | NHCO | — | Z-9 |
| 3-1988 | 5 | NHCO | — | Z-10 |
| 3-1989 | 5 | NHCO | — | Z-11 |
| 3-1990 | 5 | NHCO | — | Z-12 |
| 3-1991 | 5 | NHCO | — | 3-Py |
| 3-1992 | 5 | NHCO | — | 4-Py |
| 3-1993 | 5 | NHCO | NH | H |
| 3-1994 | 5 | NHCO | NH | Ph |
| 3-1995 | 5 | NHCO | NH | 2-Me—Ph |
| 3-1996 | 5 | NHCO | NH | 4-Me—Ph |
| 3-1997 | 5 | NHCO | NH | 2,4-diMe—Ph |
| 3-1998 | 5 | NHCO | NH | 3,4-diMe—Ph |
| 3-1999 | 5 | NHCO | NH | 2-(CF₃)Ph |
| 3-2000 | 5 | NHCO | NH | 4-(CF₃)Ph |
| 3-2001 | 5 | NHCO | NH | 2-MeOPh |
| 3-2002 | 5 | NHCO | NH | 4-MeOPh |

TABLE 3-continued

| Cpd. No. | k | A | B | R¹ |
|---|---|---|---|---|
| 3-2003 | 5 | NHCO | NH | 2-EtOPh |
| 3-2004 | 5 | NHCO | NH | 4-EtOPh |
| 3-2005 | 5 | NHCO | NH | 2-HOPh |
| 3-2006 | 5 | NHCO | NH | 4-HOPh |
| 3-2007 | 5 | NHCO | NH | 2-(HOOC)Ph |
| 3-2008 | 5 | NHCO | NH | 4-(HOOC)Ph |
| 3-2009 | 5 | NHCO | NH | 2-(MeOOC)Ph |
| 3-2010 | 5 | NHCO | NH | 4-(MeOOC)Ph |
| 3-2011 | 5 | NHCO | NH | 2-(EtOOC)Ph |
| 3-2012 | 5 | NHCO | NH | 4-(EtOOC)Ph |
| 3-2013 | 5 | NHCO | NH | 2-(tBuOOC)Ph |
| 3-2014 | 5 | NHCO | NH | 4-(tBuOOC)Ph |
| 3-2015 | 5 | NHCO | NH | 2-Cl—Ph |
| 3-2016 | 5 | NHCO | NH | 4-Cl—Ph |
| 3-2018 | 5 | NHCO | NH | 4-Br—Ph |
| 3-2019 | 5 | NHCO | NH | 2-I—Ph |
| 3-2020 | 5 | NHCO | NH | 4-I—Ph |
| 3-2021 | 5 | NHCO | NH | 2-NO₂—Ph |
| 3-2022 | 5 | NHCO | NH | 4-NO₂—Ph |
| 3-2023 | 5 | NHCO | NH | 2-NH₂—Ph |
| 3-2024 | 5 | NHCO | NH | 4-NH₂—Ph |
| 3-2025 | 5 | NHCO | NH | 2-(HO₃S)Ph |
| 3-2026 | 5 | NHCO | NH | 4-(HO₃S)Ph |
| 3-2027 | 5 | NHCO | NH | 2-(NH₂O₂S)Ph |
| 3-2028 | 5 | NHCO | NH | 4-(NH₂O₂S)Ph |
| 3-2029 | 5 | NHCO | NH | 2-CN—Ph |
| 3-2030 | 5 | NHCO | NH | 4-CN—Ph |
| 3-2031 | 5 | NHCO | NH | 2-(HOCH₂)Ph |
| 3-2032 | 5 | NHOC | NH | 4-(HOCH₂)Ph |
| 3-2033 | 5 | NHCO | NH | Me |
| 3-2034 | 5 | NHCO | NH | Et |
| 3-2035 | 5 | NHCO | NH | Pr |
| 3-2036 | 5 | NHCO | NH | iPr |
| 3-2037 | 5 | NHCO | NH | Bu |
| 3-2038 | 5 | NHCO | NH | HOOCCH₂— |
| 3-2039 | 5 | NHCO | NH | MeOOCCH₂— |
| 3-2040 | 5 | NHCO | NH | MeCH(COOH) |
| 3-2041 | 5 | NHCO | NH | HOOC—(CH₂)₂— |
| 3-2042 | 5 | NHCO | NH | MeCH(COOMe) |
| 3-2043 | 5 | NHCO | NH | 1-HOOC-iBu |
| 3-2044 | 5 | NHCO | NH | 1-MeOOC-iBu |
| 3-2045 | 5 | NHCO | NH | 1-HOOC-iPn |
| 3-2046 | 5 | NHCO | NH | 1-MeOOC-iPn |
| 3-2047 | 5 | NHOC | NH | 1-HOOC-2-Me—Bu |
| 3-2048 | 5 | NHCO | NH | 1-MeOOC-2-Me—Bu |
| 3-2049 | 5 | NHCO | NH | CH₂CH₂SO₃H |
| 3-2050 | 5 | NHCO | NH | OH |
| 3-2051 | 5 | NHCO | NH | MeO |
| 3-2052 | 5 | NHOC | NH | EtO |
| 3-2053 | 5 | NHOC | NH | PrO |
| 3-2054 | 5 | NHCO | NH | iPrO |
| 3-2055 | 5 | NHCO | NH | BuO |
| 3-2056 | 5 | NHCO | NH | iBuO |
| 3-2057 | 5 | NHCO | NH | sBuO |
| 3-2058 | 5 | NHCO | NH | tBuO |
| 3-2059 | 5 | NHCO | NH | HxO |
| 3-2060 | 5 | NHCO | NH | PhO |
| 3-2061 | 5 | NHCO | NH | BnO |
| 3-2062 | 5 | NHCO | NH | Z-1 |
| 3-2063 | 5 | NHCO | NH | Z-2 |
| 3-2064 | 5 | NHCO | NH | Z-3 |
| 3-2065 | 5 | NHCO | NH | Z-4 |
| 3-2066 | 5 | NHCO | NH | Z-5 |
| 3-2067 | 5 | NHCO | NH | Z-6 |
| 3-2068 | 5 | NHCO | NH | Z-7 |
| 3-2069 | 5 | NHCO | NH | Z-8 |
| 3-2070 | 5 | NHCO | NH | Z-9 |
| 3-2071 | 5 | NHCO | NH | Z-10 |
| 3-2072 | 5 | NHCO | NH | Z-11 |
| 3-2073 | 5 | NHCO | NH | Z-12 |
| 3-2074 | 5 | NHCO | NH | 3-Py |
| 3-2075 | 5 | NHCO | NH | 4-Py |
| 3-2076 | 5 | NHCO | NMe | Ph |
| 3-2077 | 5 | NHCO | NMe | 2-Me—Ph |
| 3-2078 | 5 | NHCO | NMe | 4-Me—Ph |
| 3-2079 | 5 | NHCO | NMe | 2,4-diMe—Ph |
| 3-2080 | 5 | NHCO | NMe | 3,4-diMe—Ph |
| 3-2081 | 5 | NHCO | NMe | 2-(CF₃)Ph |
| 3-2082 | 5 | NHCO | NMe | 4-(CF₃)Ph |
| 3-2083 | 5 | NHCO | NMe | 2-MeOPh |
| 3-2084 | 5 | NHCO | NMe | 4-MeOPh |
| 3-2085 | 5 | NHCO | NMe | 2-EtOPh |
| 3-2086 | 5 | NHCO | NMe | 4-EtOPh |
| 3-2087 | 5 | NHCO | NMe | 2-HOPh |
| 3-2088 | 5 | NHCO | NMe | 4-HOPh |
| 3-2089 | 5 | NHOC | NMe | 2-(HOOC)Ph |
| 3-2090 | 5 | NHCO | NMe | 4-(HOOC)Ph |
| 3-2091 | 5 | NHCO | NMe | 2-(MeOOC)Ph |
| 3-2092 | 5 | NHCO | NMe | 4-(MeOOC)Ph |
| 3-2093 | 5 | NHCO | NMe | 2-(EtOOC)Ph |
| 3-2095 | 5 | NHCO | NMe | 2-(tBuOOC)Ph |
| 3-2096 | 5 | NHCO | NMe | 4-(tBuOOC)Ph |
| 3-2097 | 5 | NHCO | NMe | 2-Cl—Ph |
| 3-2098 | 5 | NHCO | NMe | 4-Cl—Ph |
| 3-2100 | 5 | NHCO | NMe | 4-Br—Ph |
| 3-2101 | 5 | NHOC | NMe | 2-I—Ph |
| 3-2102 | 5 | NHCO | NMe | 4-I—Ph |
| 3-2103 | 5 | NHCO | NMe | 2-NO₂—Ph |
| 3-2104 | 5 | NHCO | NMe | 4-NO₂—Ph |
| 3-2105 | 5 | NHCO | NMe | 2-NH₂—Ph |
| 3-2106 | 5 | NHCO | NMe | 4-NH₂—Ph |
| 3-2107 | 5 | NHCO | NMe | 2-(HO₃S)Ph |
| 3-2108 | 5 | NHCO | NMe | 4-(HO₃S)Ph |
| 3-2109 | 5 | NHCO | NMe | 2-(NH₂O₂S)Ph |
| 3-2110 | 5 | NHCO | NMe | 4-(NH₂O₂S)Ph |
| 3-2111 | 5 | NHCO | NMe | 2-CN—Ph |
| 3-2112 | 5 | NHCO | NMe | 4-CN—Ph |
| 3-2113 | 5 | NHCO | NMe | 2-(HOCH₂)Ph |
| 3-2114 | 5 | NHCO | NMe | 4-(HOCH₂)Ph |
| 3-2115 | 5 | NHCO | NMe | Me |
| 3-2116 | 5 | NHCO | NMe | Et |
| 3-2117 | 5 | NHCO | NMe | Pr |
| 3-2118 | 5 | NHCO | NMe | iPr |
| 3-2119 | 5 | NHCO | NMe | Bu |
| 3-2120 | 5 | NHCO | NMe | HOOCCH₂— |
| 3-2121 | 5 | NHCO | NMe | MeOOCCH₂— |
| 3-2122 | 5 | NHCO | NMe | MeCH(COOH) |
| 3-2123 | 5 | NHCO | NMe | HOOC—(CH₂)₂— |
| 3-2124 | 5 | NHCO | NMe | MeCH(COOMe) |
| 3-2125 | 5 | NHCO | NMe | 1-HOOC-iBu |
| 3-2126 | 5 | NHCO | NMe | 1-MeOOC-iBu |
| 3-2127 | 5 | NHCO | NMe | 1-HOOC-iPn |
| 3-2128 | 5 | NHCO | NMe | 1-MeOOC-iPn |
| 3-2129 | 5 | NHCO | NMe | 1-HOOC-2-Me—Bu |
| 3-2130 | 5 | NHCO | NMe | 1-MeOOC-2-Me—Bu |
| 3-2131 | 5 | NHCO | NMe | CH₂CH₂SO₃H |
| 3-2132 | 5 | NHCO | NMe | OH |
| 3-2133 | 5 | NHCO | NMe | MeO |
| 3-2134 | 5 | NHCO | NMe | EtO |
| 3-2135 | 5 | NHCO | NMe | PrO |
| 3-2136 | 5 | NHCO | NMe | iPrO |
| 3-2137 | 5 | NHCO | NMe | BuO |
| 3-2138 | 5 | NHCO | NMe | iBuO |
| 3-2139 | 5 | NHCO | NMe | sBuO |
| 3-2140 | 5 | NHCO | NMe | tBuO |
| 3-2141 | 5 | NHCO | NMe | HxO |
| 3-2142 | 5 | NHCO | NMe | PhO |
| 3-2143 | 5 | NHCO | NMe | BnO |
| 3-2144 | 5 | NHCO | NMe | Z-1 |
| 3-2145 | 5 | NHCO | NMe | Z-2 |
| 3-2146 | 5 | NHCO | NMe | Z-3 |
| 3-2147 | 5 | NHCO | NMe | Z-4 |
| 3-2148 | 5 | NHCO | NMe | Z-5 |
| 3-2149 | 5 | NHCO | NMe | Z-6 |
| 3-2150 | 5 | NHCO | NMe | Z-7 |
| 3-2151 | 5 | NHCO | NMe | Z-8 |
| 3-2152 | 5 | NHCO | NMe | Z-9 |
| 3-2153 | 5 | NHCO | NMe | Z-10 |
| 3-2154 | 5 | NHCO | NMe | Z-11 |
| 3-2155 | 5 | NHCO | NMe | Z-12 |
| 3-2156 | 5 | NHCO | NMe | 3-Py |
| 3-2157 | 5 | NHCO | NMe | 4-Py |

TABLE 3-continued

| Cpd. No. | k | A | B | R¹ |
|---|---|---|---|---|
| 3-2158 | 5 | NHCO | NHNH | H |
| 3-2159 | 5 | NHCO | NHNH | Me |
| 3-2160 | 5 | NHCO | NHNH | Et |
| 3-2161 | 5 | NHCO | NHNMe | Me |
| 3-2162 | 5 | NHCO | NHNMe | Et |
| 3-2163 | 5 | NHCO | NHNMe | Pr |
| 3-2164 | 5 | NHCONHNHCO | NH | H |
| 3-2165 | 5 | NHCONHNHCO | NH | Ph |
| 3-2166 | 5 | NHCONHNHCO | NH | 2-Me—Ph |
| 3-2167 | 5 | NHCONHNHCO | NH | 4-Me—Ph |
| 3-2168 | 5 | NHCONHNHCO | NH | 2,4-diMe—Ph |
| 3-2169 | 5 | NHCONHNHCO | NH | 3,4-diMe—Ph |
| 3-2170 | 5 | NHCONHNHCO | NH | 2-($CF_3$)Ph |
| 3-2171 | 5 | NHCONHNHCO | NH | 4-($CF_3$)Ph |
| 3-2172 | 5 | NHCONHNHCO | NH | 2-MeOPh |
| 3-2173 | 5 | NHCONHNHCO | NH | 4-MeOPh |
| 3-2174 | 5 | NHCONHNHCO | NH | 2-EtOPh |
| 3-2175 | 5 | NHCONHNHCO | NH | 4-EtOPh |
| 3-2176 | 5 | NHCONHNHCO | NH | 2-HOPh |
| 3-2177 | 5 | NHCONHNHCO | NH | 4-HOPh |
| 3-2178 | 5 | NHCONHNHCO | NH | 2-(HOOC)Ph |
| 3-2179 | 5 | NHCONHNHCO | NH | 4-(HOOC)Ph |
| 3-2180 | 5 | NHCONHNHCO | NH | 2-(MeOOC)Ph |
| 3-2181 | 5 | NHCONHNHCO | NH | 4-(MeOOC)Ph |
| 3-2182 | 5 | NHCONHNHCO | NH | 2-(EtOOC)Ph |
| 3-2183 | 5 | NHCONHNHCO | NH | 4-(EtOOC)Ph |
| 3-2184 | 5 | NHCONHNHCO | NH | 2-(tBuOOC)Ph |
| 3-2185 | 5 | NHCONHNHCO | NH | 4-(tBuOOC)Ph |
| 3-2186 | 5 | NHCONHNHCO | NH | 2-Cl—Ph |
| 3-2187 | 5 | NHCONHNHCO | NH | 4-Cl—Ph |
| 3-2188 | 5 | NHCONHNHCO | NH | 2-Br—Ph |
| 3-2189 | 5 | NHCONHNHCO | NH | 4-Br—Ph |
| 3-2190 | 5 | NHCONHNHCO | NH | 2-I—Ph |
| 3-2191 | 5 | NHCONHNHCO | NH | 4-I—Ph |
| 3-2192 | 5 | NHCONHNHCO | NH | 2-$NO_2$—Ph |
| 3-2193 | 5 | NHCONHNHCO | NH | 4-$NO_2$—Ph |
| 3-2194 | 5 | NHCONHNHCO | NH | 2-$NH_2$—Ph |
| 3-2195 | 5 | NHCONHNHCO | NH | 4-$NH_2$—Ph |
| 3-2196 | 5 | NHCONHNHCO | NH | 2-($HO_3S$)Ph |
| 3-2197 | 5 | NHCONHNHCO | NH | 4-($HO_3S$)Ph |
| 3-2198 | 5 | NHCONHNHCO | NH | 2-($NH_2O_2S$)Ph |
| 3-2199 | 5 | NHCONHNHCO | NH | 4-($NH_2O_2S$)Ph |
| 3-2200 | 5 | NHCONHNHCO | NH | 2-CN—Ph |
| 3-2201 | 5 | NHCONHNHCO | NH | 4-CN—Ph |
| 3-2202 | 5 | NHCONHNHCO | NH | 2-($HOCH_2$)Ph |
| 3-2203 | 5 | NHCONHNHCO | NH | 4-($HOCH_2$)Ph |
| 3-2204 | 5 | NHCONHNHCO | NH | Me |
| 3-2205 | 5 | NHCONHNHCO | NH | Et |
| 3-2206 | 5 | NHCONHNHCO | NH | Pr |
| 3-2207 | 5 | NHCONHNHCO | NH | iPr |
| 3-2208 | 5 | NHCONHNHCO | NH | Bu |
| 3-2209 | 5 | NHCONHNHCO | NH | HOOC$CH_2$— |
| 3-2210 | 5 | NHCONHNHCO | NH | MeOOC$CH_2$— |
| 3-2211 | 5 | NHCONHNHCO | NH | MeCH(COOH) |
| 3-2212 | 5 | NHCONHNHCO | NH | HOOC—$(CH_2)_2$— |
| 3-2213 | 5 | NHCONHNHCO | NH | MeCH(COOMe) |
| 3-2214 | 5 | NHCONHNHCO | NH | 1-HOOC-iBu |
| 3-2215 | 5 | NHCONHNHCO | NH | 1-MeOOC-iBu |
| 3-2216 | 5 | NHCONHNHCO | NH | 1-HOOC-iPn |
| 3-2217 | 5 | NHCONHNHCO | NH | 1-MeOOC-iPn |
| 3-2218 | 5 | NHCONHNHCO | NH | 1-HOOC-2-Me—Bu |
| 3-2219 | 5 | NHCONHNHCO | NH | 1-MeOOC-2-Me—Bu |
| 3-2220 | 5 | NHCONHNHCO | NH | $CH_2CH_2SO_3H$ |
| 3-2221 | 5 | NHCONHNHCO | NH | OH |
| 3-2222 | 5 | NHCONHNHCO | NH | MeO |
| 3-2223 | 5 | NHCONHNHCO | NH | EtO |
| 3-2224 | 5 | NHCONHNHCO | NH | PrO |
| 3-2225 | 5 | NHCONHNHCO | NH | iPrO |
| 3-2226 | 5 | NHCONHNHCO | NH | BuO |
| 3-2227 | 5 | NHCONHNHCO | NH | iBuO |
| 3-2228 | 5 | NHCONHNHCO | NH | sBuO |
| 3-2229 | 5 | NHCONHNHCO | NH | tBuO |
| 3-2230 | 5 | NHCONHNHCO | NH | Hxo |
| 3-2231 | 5 | NHCONHNHCO | NH | PhO |
| 3-2232 | 5 | NHCONHNHCO | NH | BnO |
| 3-2233 | 5 | NHCONHNHCO | NH | Z-1 |
| 3-2234 | 5 | NHCONHNHCO | NH | Z-2 |
| 3-2235 | 5 | NHCONHNHCO | NH | Z-3 |
| 3-2236 | 5 | NHCONHNHCO | NH | Z-4 |
| 3-2237 | 5 | NHCONHNHCO | NH | Z-5 |
| 3-2238 | 5 | NHCONHNHCO | NH | Z-6 |
| 3-2239 | 5 | NHCONHNHCO | NH | Z-7 |
| 3-2240 | 5 | NHCONHNHCO | NH | Z-8 |
| 3-2241 | 5 | NHCONHNHCO | NH | Z-9 |
| 3-2242 | 5 | NHCONHNHCO | NH | Z-10 |
| 3-2243 | 5 | NHCONHNHCO | NH | Z-11 |
| 3-2244 | 5 | NHCONHNHCO | NH | Z-12 |
| 3-2245 | 5 | NHCONHNHCO | NH | 3-Py |
| 3-2246 | 5 | NHCONHNHCO | NH | 4-Py |
| 3-2247 | 5 | NHCONHCO | — | H |
| 3-2248 | 5 | NHCONHCO | — | Ph |
| 3-2249 | 5 | NHCONHCO | — | 2-Me—Ph |
| 3-2250 | 5 | NHCONHCO | — | 4-Me—Ph |
| 3-2251 | 5 | NHCONHCO | — | 2,4-diMe—Ph |
| 3-2252 | 5 | NHCONHCO | — | 3,4-diMe—Ph |
| 3-2253 | 5 | NHCONHCO | — | 2-($CF_3$)Ph |
| 3-2254 | 5 | NHCONHCO | — | 4-($CF_3$)Ph |
| 3-2255 | 5 | NHCONHCO | — | 2-MeOPh |
| 3-2256 | 5 | NHCONHCO | — | 4-MeOPh |
| 3-2257 | 5 | NHCONHCO | — | 2-EtOPh |
| 3-2258 | 5 | NHCONHCO | — | 4-EtOPh |
| 3-2259 | 5 | NHCONHCO | — | 2-HOPh |
| 3-2260 | 5 | NHCONHCO | — | 4-HOPh |
| 3-2261 | 5 | NHCONHCO | — | 2-(HOOC)Ph |
| 3-2262 | 5 | NHCONHCO | — | 4-(HOOC)Ph |
| 3-2263 | 5 | NHCONHCO | — | 2-(MeOOC)Ph |
| 3-2264 | 5 | NHCONHCO | — | 4-(MeOOC)Ph |
| 3-2265 | 5 | NHCONHCO | — | 2-(EtOOC)Ph |
| 3-2266 | 5 | NHCONHCO | — | 4-(EtOOC)Ph |
| 3-2267 | 5 | NHCONHCO | — | 2-(tBuOOC)Ph |
| 3-2268 | 5 | NHCONHCO | — | 4-(tBuOOC)Ph |
| 3-2269 | 5 | NHCONHCO | — | 2-Cl—Ph |
| 3-2270 | 5 | NHCONHCO | — | 4-Cl—Ph |
| 3-2271 | 5 | NHCONHCO | — | 2-Br—Ph |
| 3-2272 | 5 | NHCONHCO | — | 4-Br—Ph |
| 3-2273 | 5 | NHCONHCO | — | 2-I—Ph |
| 3-2274 | 5 | NHCONHCO | — | 4-I—Ph |
| 3-2275 | 5 | NHCONHCO | — | 2-$NO_2$—Ph |
| 3-2276 | 5 | NHCONHCO | — | 4-$NO_2$—Ph |
| 3-2277 | 5 | NHCONHCO | — | 2-$NH_2$—Ph |
| 3-2278 | 5 | NHCONHCO | — | 4-$NH_2$—Ph |
| 3-2279 | 5 | NHCONHCO | — | 2-($HO_3S$)Ph |
| 3-2280 | 5 | NHCONHCO | — | 4-($HO_3S$)Ph |
| 3-2281 | 5 | NHCONHCO | — | 2-($NH_2O_2S$)Ph |
| 3-2282 | 5 | NHCONHCO | — | 4-($NH_2O_2S$)Ph |
| 3-2283 | 5 | NHCONHCO | — | 2-CN—Ph |
| 3-2284 | 5 | NHCONHCO | — | 4-CN—Ph |
| 3-2285 | 5 | NHCONHCO | — | 2-($HOCH_2$)Ph |
| 3-2286 | 5 | NHCONHCO | — | 4-($HOCH_2$)Ph |
| 3-2287 | 5 | NHCONHCO | — | Me |
| 3-2288 | 5 | NHCONHCO | — | Et |
| 3-2289 | 5 | NHCONHCO | — | Pr |
| 3-2290 | 5 | NHCONHCO | — | iPr |
| 3-2291 | 5 | NHCONHCO | — | Bu |
| 3-2292 | 5 | NHCONHCO | — | HOOC$CH_2$— |
| 3-2293 | 5 | NHCONHCO | — | MeOOC$CH_2$— |
| 3-2294 | 5 | NHCONHCO | — | MeCH(COOH) |
| 3-2295 | 5 | NHCONHCO | — | HOOC—$(CH_2)_2$— |
| 3-2296 | 5 | NHCONHCO | — | MeCH(COOMe) |
| 3-2297 | 5 | NHCONHCO | — | 1-HOOC-iBu |
| 3-2298 | 5 | NHCONHCO | — | 1-MeOOC-iBu |
| 3-2299 | 5 | NHCONHCO | — | 1-HOOC-iPn |
| 3-2300 | 5 | NHCONHCO | — | 1-MeOOC-iPn |
| 3-2301 | 5 | NHCONHCO | — | 1-HOOC-2-Me—Bu |
| 3-2302 | 5 | NHCONHCO | — | 1-MeOOC-2-Me—Bu |
| 3-2303 | 5 | NHCONHCO | — | $CH_2CH_2SO_3H$ |
| 3-2304 | 5 | NHCONHCO | — | MeO |
| 3-2305 | 5 | NHCONHCO | — | EtO |
| 3-2306 | 5 | NHCONHCO | — | PrO |
| 3-2307 | 5 | NHCONHCO | — | iPrO |
| 3-2308 | 5 | NHCONHCO | — | BuO |
| 3-2309 | 5 | NHCONHCO | — | iBuO |

TABLE 3-continued

| Cpd. No. | k | A | B | R¹ |
|---|---|---|---|---|
| 3-2310 | 5 | NHCONHCO | — | sBuO |
| 3-2311 | 5 | NHCONHCO | — | tBuO |
| 3-2312 | 5 | NHCONHCO | — | HxO |
| 3-2313 | 5 | NHCONHCO | — | PhO |
| 3-2314 | 5 | NHCONHCO | — | BnO |
| 3-2315 | 5 | NHCONHCO | — | Z-1 |
| 3-2316 | 5 | NHCONHCO | — | Z-2 |
| 3-2317 | 5 | NHCONHCO | — | Z-3 |
| 3-2318 | 5 | NHCONHCO | — | Z-4 |
| 3-2319 | 5 | NHCONHCO | — | Z-5 |
| 3-2320 | 5 | NHCONHCO | — | Z-6 |
| 3-2321 | 5 | NHCONHCO | — | Z-7 |
| 3-2322 | 5 | NHCONHCO | — | Z-8 |
| 3-2323 | 5 | NHCONHCO | — | Z-9 |
| 3-2324 | 5 | NHCONHCO | — | Z-10 |
| 3-2325 | 5 | NHCONHCO | — | Z-11 |
| 3-2326 | 5 | NHCONHCO | — | Z-12 |
| 3-2327 | 5 | NHCONHCO | — | 3-Py |
| 3-2328 | 5 | NHCONHCO | — | 4-Py |
| 3-2329 | 5 | NHCONHSO$_2$ | — | H |
| 3-2330 | 5 | NHCONHSO$_2$ | — | Ph |
| 3-2331 | 5 | NHCONHSO$_2$ | — | 2-Me—Ph |
| 3-2332 | 5 | NHCONHSO$_2$ | — | 4-Me—Ph |
| 3-2333 | 5 | NHCONHSO$_2$ | — | 2,4-diMe—Ph |
| 3-2334 | 5 | NHCONHSO$_2$ | — | 3,4-diMe—Ph |
| 3-2335 | 5 | NHCONHSO$_2$ | — | 2-(CF$_3$)Ph |
| 3-2336 | 5 | NHCONHSO$_2$ | — | 4-(CF$_3$)Ph |
| 3-2337 | 5 | NHCONHSO$_2$ | — | 2-MeOPh |
| 3-2338 | 5 | NHCONHSO$_2$ | — | 4-MeOPh |
| 3-2339 | 5 | NHCONHSO$_2$ | — | 2-EtOPh |
| 3-2340 | 5 | NHCONHSO$_2$ | — | 4-EtOPh |
| 3-2341 | 5 | NHCONHSO$_2$ | — | 2-HOPh |
| 3-2342 | 5 | NHCONHSO$_2$ | — | 4-HOPh |
| 3-2343 | 5 | NHCONHSO$_2$ | — | 2-(HOOC)Ph |
| 3-2344 | 5 | NHCONHSO$_2$ | — | 4-(HOOC)Ph |
| 3-2345 | 5 | NHCONHSO$_2$ | — | 2-(MeOOC)Ph |
| 3-2346 | 5 | NHCONHSO$_2$ | — | 4-(MeOOC)Ph |
| 3-2347 | 5 | NHCONHSO$_2$ | — | 2-(EtOOC)Ph |
| 3-2348 | 5 | NHCONHSO$_2$ | — | 4-(EtOOC)Ph |
| 3-2349 | 5 | NHCONHSO$_2$ | — | 2-(tBuOOC)Ph |
| 3-2350 | 5 | NHCONHSO$_2$ | — | 4-(tBuOOC)Ph |
| 3-2351 | 5 | NHCONHSO$_2$ | — | 2-Cl—Ph |
| 3-2352 | 5 | NHCONHSO$_2$ | — | 4-Cl—Ph |
| 3-2353 | 5 | NHCONHSO$_2$ | — | 2-Br—Ph |
| 3-2354 | 5 | NHCONHSO$_2$ | — | 4-Br—Ph |
| 3-2355 | 5 | NHCONHSO$_2$ | — | 2-I—Ph |
| 3-2356 | 5 | NHCONHSO$_2$ | — | 4-I—Ph |
| 3-2357 | 5 | NHCONHSO$_2$ | — | 2-NO$_2$—Ph |
| 3-2358 | 5 | NHCONHSO$_2$ | — | 4-NO$_2$—Ph |
| 3-2359 | 5 | NHCONHSO$_2$ | — | 2-NH$_2$—Ph |
| 3-2360 | 5 | NHCONHSO$_2$ | — | 4-NH$_2$—Ph |
| 3-2361 | 5 | NHCONHSO$_2$ | — | 2-(HO$_3$S)Ph |
| 3-2362 | 5 | NHCONHSO$_2$ | — | 4-(HO$_3$S)Ph |
| 3-2363 | 5 | NHCONHSO$_2$ | — | 2-(NH$_2$O$_2$S)Ph |
| 3-2364 | 5 | NHCONHSO$_2$ | — | 4-(NH$_2$O$_2$S)Ph |
| 3-2365 | 5 | NHCONHSO$_2$ | — | 2-CN—Ph |
| 3-2366 | 5 | NHCONHSO$_2$ | — | 4-CN—Ph |
| 3-2367 | 5 | NHCONHSO$_2$ | — | 2-(HOCH$_2$)Ph |
| 3-2368 | 5 | NHCONHSO$_2$ | — | 4-(HOCH$_2$)Ph |
| 3-2369 | 5 | NHCONHSO$_2$ | — | Me |
| 3-2370 | 5 | NHCONHSO$_2$ | — | Et |
| 3-2371 | 5 | NHCONHSO$_2$ | — | Pr |
| 3-2372 | 5 | NHCONHSO$_2$ | — | iPr |
| 3-2373 | 5 | NHCONHSO$_2$ | — | Bu |
| 3-2374 | 5 | NHCONHSO$_2$ | — | HOOCCH$_2$ |
| 3-2375 | 5 | NHCONHSO$_2$ | — | MeOOCCH$_2$ |
| 3-2376 | 5 | NHCONHSO$_2$ | — | MeCH(COOH) |
| 3-2377 | 5 | NHCONHSO$_2$ | — | HOOC—(CH$_2$)$_2$ |
| 3-2378 | 5 | NHCONHSO$_2$ | — | MeCH(COOMe) |
| 3-2379 | 5 | NHCONHSO$_2$ | — | 1-HOOC-iBu |
| 3-2380 | 5 | NHCONHSO$_2$ | — | 1-MeOOC-iBu |
| 3-2381 | 5 | NHCONHSO$_2$ | — | 1-HOOC-iPn |
| 3-2382 | 5 | NHCONHSO$_2$ | — | 1-MeOOC-iPn |
| 3-2383 | 5 | NHCONHSO$_2$ | — | 1-HOOC-2-Me—Bu |
| 3-2384 | 5 | NHCONHSO$_2$ | — | 1-MeOOC-2-Me—Bu |
| 3-2385 | 5 | NHCONHSO$_2$ | — | CH$_2$CH$_2$SO$_3$H |
| 3-2386 | 5 | NHCONHSO$_2$ | — | OH |
| 3-2387 | 5 | NHCONHSO$_2$ | — | MeO |
| 3-2388 | 5 | NHCONHSO$_2$ | — | EtO |
| 3-2389 | 5 | NHCONHSO$_2$ | — | Pro |
| 3-2390 | 5 | NHCONHSO$_2$ | — | iPrO |
| 3-2391 | 5 | NHCONHSO$_2$ | — | BuO |
| 3-2392 | 5 | NHCONHSO$_2$ | — | iBuO |
| 3-2393 | 5 | NHCONHSO$_2$ | — | sBuO |
| 3-2394 | 5 | NHCONHSO$_2$ | — | tBuO |
| 3-2395 | 5 | NHCONHSO$_2$ | — | HxO |
| 3-2396 | 5 | NHCONHSO$_2$ | — | PhO |
| 3-2397 | 5 | NHCONHSO$_2$ | — | Bno |
| 3-2398 | 5 | NHCONHSO$_2$ | — | Z-1 |
| 3-2399 | 5 | NHCONHSO$_2$ | — | Z-2 |
| 3-2400 | 5 | NHCONHSO$_2$ | — | Z-3 |
| 3-2401 | 5 | NHCONHSO$_2$ | — | Z-4 |
| 3-2402 | 5 | NHCONHSO$_2$ | — | Z-5 |
| 3-2403 | 5 | NHCONHSO$_2$ | — | Z-6 |
| 3-2404 | 5 | NHCONHSO$_2$ | — | Z-7 |
| 3-2405 | 5 | NHCONHSO$_2$ | — | Z-8 |
| 3-2406 | 5 | NHCONHSO$_2$ | — | Z-9 |
| 3-2407 | 5 | NHCONHSO$_2$ | — | Z-10 |
| 3-2408 | 5 | NHCONHSO$_2$ | — | Z-11 |
| 3-2409 | 5 | NHCONHSO$_2$ | — | Z-12 |
| 3-2410 | 5 | NHCONHSO$_2$ | — | 3-Py |
| 3-2411 | 5 | NHCONHSO$_2$ | — | 4-Py |
| 3-2412 | 5 | NHCONHSO$_2$ | NH | H |
| 3-2413 | 5 | NHCONHSO$_2$ | NH | Me |
| 3-2414 | 5 | NHCONHSO$_2$ | NH | Et |
| 3-2415 | 5 | NHCONHSO$_2$ | NH | Pr |
| 3-2416 | 5 | NHCONHSO$_2$ | NH | iPr |
| 3-2417 | 5 | NHCONHSO$_2$ | NH | Bu |
| 3-2418 | 5 | NHCONHSO$_2$ | NMe | Me |
| 3-2419 | 5 | NHCONHSO$_2$ | NMe | Et |
| 3-2420 | 5 | NHCONHSO$_2$ | NMe | Pr |
| 3-2421 | 5 | NHCONHSO$_2$ | NMe | iPr |
| 3-2422 | 5 | NHCONHSO$_2$ | NMe | Bu |
| 3-2423 | 5 | — | NH | H |
| 3-2424 | 5 | — | NH | Me |
| 3-2425 | 5 | — | NH | Et |
| 3-2426 | 5 | — | NH | Pr |
| 3-2427 | 5 | — | NH | iPr |
| 3-2428 | 5 | — | NH | Bu |
| 3-2429 | 5 | CO | | Pyr |
| 3-2430 | 5 | CO | | Pipri |
| 3-2431 | 5 | CO | | Pipra |
| 3-2432 | 5 | CO | | Mor |
| 3-2433 | 5 | CO | | Thmor |
| 3-2434 | 5 | CO | | NHPyr |
| 3-2435 | 5 | CO | | NHPipri |
| 3-2436 | 5 | CO | | NHPipra |
| 3-2437 | 5 | CO | | NHMor |
| 3-2438 | 5 | CO | | NHThmor |
| 3-2439 | 5 | NHCO | | Pyr |
| 3-2440 | 5 | NHCO | | Pipri |
| 3-2441 | 5 | NHCO | | Pipra |
| 3-2442 | 5 | NHCO | | Mor |
| 3-2443 | 5 | NHCO | | Thmor |
| 3-2444 | 5 | NHCO | | NHPyr |
| 3-2445 | 5 | NHCO | | NHPipri |
| 3-2446 | 5 | NHCO | | NHPipra |
| 3-2447 | 5 | NHCO | | NHMor |
| 3-2448 | 5 | NHCO | | NHThmor |
| 3-2449 | 5 | CONHCO | | Pyr |
| 3-2450 | 5 | CONHCO | | Pipri |
| 3-2451 | 5 | CONHCO | | Pipra |
| 3-2452 | 5 | CONHCO | | Mor |
| 3-2453 | 5 | CONHCO | | Thmor |
| 3-2454 | 5 | CONHCO | | NHPyr |
| 3-2455 | 5 | CONHCO | | NHPipri |
| 3-2456 | 5 | CONHCO | | NHPipra |
| 3-2457 | 5 | CONHCO | | NHMor |
| 3-2458 | 5 | CONHCO | | NHThmor |
| 3-2459 | 5 | CONHSO$_2$ | | Pyr |
| 3-2460 | 5 | CONHSO$_2$ | | Pipri |
| 3-2461 | 5 | CONHSO$_2$ | | Pipra |

TABLE 3-continued

| Cpd. No. | k | A | B | R¹ |
|---|---|---|---|---|
| 3-2462 | 5 | CONHSO₂ | Mor | |
| 3-2463 | 5 | CONHSO₂ | Thmor | |
| 3-2464 | 5 | CONHSO₂ | NHPyr | |
| 3-2465 | 5 | CONHSO₂ | NHPipri | |
| 3-2466 | 5 | CONHSO₂ | NHPipra | |
| 3-2467 | 5 | CONHSO₂ | NHMor | |
| 3-2468 | 5 | CONHSO₂ | NHThmor | |
| 3-2469 | 5 | NHSO₂ | NH | Z-4 |
| 3-2470 | 5 | NHSO₂ | — | Me |
| 3-2471 | 5 | NHSO₂ | — | Et |
| 3-2472 | 5 | NHSO₂ | — | Pr |
| 3-2473 | 5 | NHSO₂ | — | CH₂—Cl |
| 3-2474 | 5 | NHSO₂ | — | Ph |
| 3-2475 | 5 | NHSO₂ | — | 4-Me—Ph |
| 3-2476 | 5 | CO | NMe | Ph |
| 3-2477 | 5 | CO | NMe | 2-Me—Ph |
| 3-2478 | 5 | CO | NMe | 4-Me—Ph |
| 3-2479 | 5 | CO | NMe | 2,4-diMe—Ph |
| 3-2480 | 5 | CO | NMe | 3,4-diMe—Ph |
| 3-2481 | 5 | CO | NMe | 2-(CF₃)Ph |
| 3-2482 | 5 | CO | NMe | 4-(CF₃)Ph |
| 3-2483 | 5 | CO | NMe | 2-MeOPh |
| 3-2484 | 5 | CO | NMe | 4-MeOPh |
| 3-2485 | 5 | CO | NMe | 2-EtOPh |
| 3-2486 | 5 | CO | NMe | 4-EtOPh |
| 3-2487 | 5 | CO | NMe | 2-HOPh |
| 3-2488 | 5 | CO | NMe | 4-HOPh |
| 3-2489 | 5 | CO | NMe | 2-(HOOC)Ph |
| 3-2490 | 5 | CO | NMe | 4-(HOOC)Ph |
| 3-2491 | 5 | CO | NMe | 2-(MeOOC)Ph |
| 3-2492 | 5 | CO | NMe | 4-(MeOOC)Ph |
| 3-2493 | 5 | CO | NMe | 2-(EtOOC)Ph |
| 3-2494 | 5 | CO | NMe | 4-(EtOOC)Ph |
| 3-2495 | 5 | CO | NMe | 2-(tBuOOC)Ph |
| 3-2496 | 5 | CO | NMe | 4-(tBuOOC)Ph |
| 3-2497 | 5 | CO | NMe | 2-Cl—Ph |
| 3-2498 | 5 | CO | NMe | 4-Cl—Ph |
| 3-2499 | 5 | CO | NMe | 2-Br—Ph |
| 3-2500 | 5 | CO | NMe | 4-Br—Ph |
| 3-2501 | 5 | CO | NMe | 2-I—Ph |
| 3-2502 | 5 | CO | NMe | 4-I—Ph |
| 3-2503 | 5 | CO | NMe | 2-NO₂—Ph |
| 3-2504 | 5 | CO | NMe | 4-NO₂—Ph |
| 3-2505 | 5 | CO | NMe | 2-NH₂—Ph |
| 3-2506 | 5 | CO | NMe | 4-NH₂—Ph |
| 3-2507 | 5 | CO | NMe | 2-(HO₃S)Ph |
| 3-2508 | 5 | CO | NMe | 4-(HO₃S)Ph |
| 3-2509 | 5 | CO | NMe | 2-(NH₂O₂S)Ph |
| 3-2510 | 5 | CO | NMe | 4-(NH₂O₂S)Ph |
| 3-2511 | 5 | CO | NMe | 2-CN—Ph |
| 3-2512 | 5 | CO | NMe | 4-CN—Ph |
| 3-2513 | 5 | CO | NMe | 2-(HOCH₂)Ph |
| 3-2514 | 5 | CO | NMe | 4-(HOCH₂)Ph |
| 3-2515 | 5 | CO | NMe | Me |
| 3-2516 | 5 | CO | NMe | Et |
| 3-2517 | 5 | CO | NMe | Pr |
| 3-2518 | 5 | CO | NMe | iPr |
| 3-2519 | 5 | CO | NMe | Bu |
| 3-2520 | 5 | CO | NMe | HOOCCH₂ |
| 3-2521 | 5 | CO | NMe | HOOC—(CH₂)₂ |
| 3-2522 | 5 | CO | NMe | MeCH(COOH) |
| 3-2523 | 5 | CO | NMe | HOOC—(CH₂)₃— |
| 3-2524 | 5 | CO | NMe | MeCH(COOMe) |
| 3-2525 | 5 | CO | NMe | 1-HOOC-iBu |
| 3-2526 | 5 | CO | NMe | 1-MeOOC-iBu |
| 3-2527 | 5 | CO | NMe | 1-HOOC-iPn |
| 3-2528 | 5 | CO | NMe | 1-MeOOC-iPn |
| 3-2529 | 5 | CO | Nme | 1-HOOC-2-Me—Bu |
| 3-2530 | 5 | CO | NMe | 1-MeOOC-2-Me—Bu |
| 3-2531 | 5 | CO | NMe | CH₂CH₂SO₃H |
| 3-2532 | 5 | CO | NMe | OH |
| 3-2533 | 5 | CO | NMe | MeO |
| 3-2534 | 5 | CO | NMe | EtO |
| 3-2535 | 5 | CO | NMe | Pro |
| 3-2536 | 5 | CO | NMe | iPrO |
| 3-2537 | 5 | CO | NMe | BuO |
| 3-2538 | 5 | CO | NMe | iBuO |
| 3-2539 | 5 | CO | NMe | sBuO |
| 3-2540 | 5 | CO | NMe | tBuO |
| 3-2541 | 5 | CO | NMe | HxO |
| 3-2542 | 5 | CO | NMe | PhO |
| 3-2543 | 5 | CO | NMe | BnO |
| 3-2544 | 5 | CO | NMe | Z-1 |
| 3-2545 | 5 | CO | NMe | Z-2 |
| 3-2546 | 5 | CO | NMe | Z-3 |
| 3-2547 | 5 | CO | NMe | Z-4 |
| 3-2548 | 5 | CO | NMe | Z-5 |
| 3-2549 | 5 | CO | NMe | Z-6 |
| 3-2550 | 5 | CO | NMe | Z-7 |
| 3-2551 | 5 | CO | NMe | Z-8 |
| 3-2552 | 5 | CO | NMe | Z-9 |
| 3-2553 | 5 | CO | NMe | Z-10 |
| 3-2554 | 5 | CO | NMe | Z-11 |
| 3-2555 | 5 | CO | NMe | Z-12 |
| 3-2556 | 5 | CO | NMe | 3-Py |
| 3-2557 | 5 | CO | NMe | 4-Py |
| 3-2558 | 5 | CO | Thiad | |
| 3-2559 | 5 | CO | NHThiad | |
| 3-2560 | 5 | NHCO | Thiad | |
| 3-2561 | 5 | NHCO | NHThiad | |
| 3-2562 | 5 | CONHCO | Thiad | |
| 3-2563 | 5 | CONHCO | NHThiad | |
| 3-2564 | 5 | CONHSO₂ | Thiad | |
| 3-2565 | 5 | CONHSO₂ | NHThiad | |
| 3-2566 | 5 | NHCS | NH | H |
| 3-2567 | 5 | NHCS | NH | Me |
| 3-2568 | 5 | NHCS | NH | Et |
| 3-2569 | 5 | NHCS | NH | Ph |
| 3-2570 | 5 | NHCS | NH | HOOCCH₂ |
| 3-2571 | 5 | NHCS | NH | MeOOCCH₂ |
| 3-2572 | 5 | NHCS | NH | MeCH(COOH) |
| 3-2573 | 5 | NHC S | NH | HOOC—(CH₂)₂ |
| 3-2574 | 5 | NHCS | NH | MeCH(COOMe) |
| 3-2575 | 5 | CO | NH | HOOC—(CH₂)₃— |
| 3-2576 | 5 | NHCO | NH | HOOC—(CH₂)₃— |
| 3-2577 | 5 | NHCO | — | HOOC—(CH₂)₃— |
| 3-2578 | 5 | NHCS | NH | MeCH(COOH) |
| 3-2579 | 5 | CO | NH | MeSO₂NHCOCH(Me) |
| 3-2580 | 5 | NHCO | NH | MeSO₂NHCOCH(Me) |
| 3-2581 | 5 | NHCO | — | MeSO₂NHCOCH(Me) |
| 3-2582 | 5 | NHCS | NH | MeSO₂NHCOCH(Me) |
| 3-2583 | 5 | — | NH | HOOCCH₂ |
| 3-2584 | 5 | — | NH | MeOOCCH₂ |
| 3-2585 | 5 | — | NH | MeCH(COOH) |
| 3-2586 | 5 | — | NH | HOOC—(CH₂)₂ |
| 3-2587 | 5 | — | NH | MeCH(COOMe) |
| 3-2588 | 5 | — | NH | HOOC—(CH₂)₃— |
| 3-2589 | 5 | NHCOCO | — | OH |
| 3-2590 | 5 | NHCOCO | — | MeO |
| 3-2591 | 5 | NHCOCO | — | Eto |
| 3-2592 | 5 | NHCOCO | — | PrO |
| 3-2593 | 5 | NHCOCO | — | iPrO |
| 3-2594 | 5 | NHCOCO | — | BuO |
| 3-2595 | 5 | NHCOCO | — | iBuO |
| 3-2596 | 5 | NHCOCO | — | sBuO |
| 3-2597 | 5 | NHCOCO | — | sBuO |
| 3-2598 | 5 | NHCOCO | — | HxO |
| 3-2599 | 5 | NHCOCO | — | PhO |
| 3-2600 | 5 | NHCOCO | — | BnO |
| 3-2601 | 0 | — | | 1,3-diox-IInd |
| 3-2602 | 1 | — | | 1,3-diox-IInd |
| 3-2603 | 2 | — | | 1,3-diox-IInd |
| 3-2604 | 3 | — | | 1,3-diox-IInd |
| 3-2605 | 4 | — | | 1,3-diox-IInd |
| 3-2606 | 5 | — | | 1,3-diox-IInd |
| 3-2607 | 6 | — | | 1,3-diox-IInd |
| 3-2608 | 7 | — | | 1,3-diox-IInd |
| 3-2609 | 8 | — | | 1,3-diox-IInd |
| 3-2610 | 9 | — | | 1,3-diox-IInd |
| 3-2611 | 10 | — | | 1,3-diox-IInd |
| 3-2612 | 11 | — | | 1,3-diox-IInd |
| 3-2613 | 12 | — | | 1,3-diox-IInd |

TABLE 3-continued

| Cpd. No. | k | A | B | R¹ |
|---|---|---|---|---|
| 3-2614 | 4 | NHCONHSO₂NHCO | NH | Z-4 |
| 3-2615 | 4 | NHCONHSO₂NHCO | NH | Pn |
| 3-2616 | 2 | O | — | H |
| 3-2617 | 4 | O | — | H |
| 3-2618 | 5 | O | — | H |
| 3-2619 | 5 | O | — | Ph |
| 3-2620 | 5 | O | — | 2-Py |
| 3-2621 | 5 | O | — | 3-Py |
| 3-2622 | 5 | O | — | 4-Py |
| 3-2623 | 5 | O | — | Z-1 |
| 3-2624 | 5 | O | — | Z-2 |
| 3-2625 | 5 | O | — | Z-3 |
| 3-2626 | 5 | O | — | Z-4 |
| 3-2627 | 5 | O | — | Z-5 |
| 3-2628 | 5 | O | — | Z-6 |
| 3-2629 | 5 | O | — | Z-7 |
| 3-2630 | 5 | O | — | Z-8 |
| 3-2631 | 5 | O | — | Z-9 |
| 3-2632 | 5 | O | — | Z-10 |
| 3-2633 | 5 | O | — | Z-11 |
| 3-2634 | 5 | O | — | Z-12 |
| 3-2635 | 4 | NHCO | — | 3-Py |
| 3-2636 | 5 | NHCO | — | 3-Py |
| 3-2637 | 4 | CO | NH | HOCH₂CH(CH₃)CH₂ |
| 3-2638 | 5 | CO | NH | HOCH₂CH(CH₃)CH₂ |
| 3-2639 | 4 | NHCO | NH | HOCH₂CH(CH₃)CH₂ |
| 3-2640 | 5 | NHCO | NH | HOCH₂CH(CH₃)CH₂ |
| 3-2641 | 4 | CO | NH | MeSO₂NHCOCH₂ |
| 3-2642 | 5 | CO | NH | MeSO₂NHCOCH₂ |
| 3-2643 | 4 | NHCO | NH | MeSO₂NHCOCH₂ |
| 3-2644 | 5 | NHCO | NH | MeSO₂NHCOCH₂ |
| 3-2645 | 4 | CO | NH | H₂NSO₂NHCOCH₂ |
| 3-2646 | 5 | CO | NH | H₂NSO₂NHCOCH₂ |
| 3-2647 | 4 | NHCO | NH | H₂NSO₂NHCOCH₂ |
| 3-2648 | 5 | NHCO | NH | H₂NSO₂NHCOCH₂ |
| 3-2649 | 4 | CO | NH | 1-(MeSO₂NHCO)-Et |
| 3-2650 | 5 | CO | NH | 1-(MeSO₂NHCO)-Et |
| 3-2651 | 4 | NHCO | NH | 1-(meSO₂NHCO)-Et |
| 3-2652 | 5 | NHCO | NH | 1-(MeSO₂NHCO)-Et |
| 3-2653 | 4 | CO | NH | 1-(H₂NSO₂NHCO)-Et |
| 3-2654 | 5 | CO | NH | 1-(H₂NSO₂NHCO)-Et |
| 3-2655 | 4 | NHCO | NH | 1-(H₂NSO₂NHCO)-Et |
| 3-2656 | 5 | NHCO | NH | 1-(H₂NSO₂NHCO)-Et |
| 3-2657 | 4 | CO | NH | HOOC—(CH₂)₄ |
| 3-2658 | 5 | CO | NH | HOOC—(CH₂)₄ |
| 3-2659 | 4 | NHCO | NH | HOOC—(CH₂)₄ |
| 3-2660 | 5 | NHCO | NH | HOOC—(CH₂)₄ |
| 3-2661 | 4 | CO | NH | HO—(CH₂)₂ |
| 3-2662 | 5 | CO | NH | HO—(CH₂)₂ |
| 3-2663 | 4 | NHCO | NH | HO—(CH₂)₂ |
| 3-2664 | 5 | NHCO | NH | HO—(CH₂)₂ |
| 3-2665 | 4 | CO | NH | HO—CH₂—CH(CH₃) |
| 3-2666 | 5 | CO | NH | HO—CH₂—CH(CH₃) |
| 3-2667 | 4 | NHCO | NH | HO—CH₂—CH(CH₃) |
| 3-2668 | 5 | NHCO | NH | HO—CH₂—CH(CH₃) |
| 3-2669 | 4 | CO | NMe | HOOC—(CH₂)₃ |
| 3-2670 | 4 | NHCO | NMe | HOOC—(CH₂)₃ |
| 3-2671 | 5 | NHCO | NMe | HOOC—(CH₂)₃ |
| 3-2672 | 4 | CONMeSO₂ | — | Me |
| 3-2673 | 5 | CONMeSO₂ | — | Me |
| 3-2674 | 4 | CO | 1-Indn | |
| 3-2675 | 5 | CO | 1-Indn | |
| 3-2676 | 4 | NHCO | 1-Indn | |
| 3-2677 | 5 | NHCO | 1-Indn | |
| 3-2678 | 4 | CO | 2-(HOOC)-1-Indn | |
| 3-2679 | 5 | CO | 2-(HOOC)-1-Indn | |
| 3-2680 | 4 | NHCO | 2-(HOOC)-1-Indn | |
| 3-2681 | 5 | NHCO | 2-(HOOC)-1-Indn | |
| 3-2682 | 4 | — | 2,4-diMe-2,5-diox-1-Imdd | |
| 3-2683 | 5 | — | 3,4-diMe-2,5-diox-1-Imdd | |

Of the above compounds, preferred compounds are Compounds No.: 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-257, 1-258, 1-259, 1-260, 1-261, 1-262, 1-263, 1-264, 1-265, 1-266, 1-267, 1-268, 1-269, 1-270, 1-271, 1-272, 1-273, 1-274, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 1-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, 1-396, 1-397, 1-398, 1-399, 1-400, 1-401, 1-402, 1-403, 1-404, 1-405, 1-406, 1-407, 1-408, 1-409, 1-410, 1-411, 1-412, 1-413, 1-414, 1-415, 1-416, 1-417, 1-418, 1-419, 1-420, 1-421, 1-422, 1-423, 1-424, 1-425, 1-426, 1-427, 1-428, 1-429, 1-430, 1-431, 1-432, 1-433, 1-434, 1-435, 1-436, 1-437, 1-438, 1-439, 1-440, 1-441, 1-442, 1-443, 1-444, 1-445, 1-446, 1-447, 1-448, 1-449, 1-450, 1-451, 1-452, 1-453, 1-454, 1-455, 1-456, 1-457, 1-458, 1-459, 1-460, 1-461, 1-462, 1-463, 1-464, 1-465, 1-466, 1-467, 1-468, 1-469, 1-470, 1-471, 1-472, 1-473, 1-474, 1-475, 1-476, 1-477, 1-478, 1-479, 1-480, 1-481, 1-482, 1-483, 1-484, 1-485, 1-486, 1-487, 1-488, 1-489, 1-490, 1-491, 1-492, 1-493, 1-494, 1-495, 1-496, 1-497, 1-498, 1-499, 1-500, 1-501, 1-502, 1-503, 1-504, 1-505, 1-506, 1-507, 1-508, 1-509, 1-510, 1-511, 1-512, 1-513, 1-514, 1-515, 1-516, 1-517, 1-518, 1-519, 1-520, 1-521, 1-522, 1-523, 1-524, 1-525, 1-526, 1-527, 1-528, 1-529, 1-530, 1-531, 1-532, 1-533, 1-534, 1-535, 1-536, 1-537, 1-538, 1-539, 1-540, 1-541, 1-542, 1-543, 1-544, 1-545, 1-546, 1-547, 1-548, 1-549, 1-550, 1-551, 1-552, 1-553, 1-554, 1-555, 1-556, 1-557, 1-558, 1-559, 1-560, 1-561, 1-562, 1-563, 1-564, 1-565, 1-566, 1-567, 1-568, 1-569, 1-570, 1-571, 1-572, 1-573, 1-574, 1-575, 1-576, 1-577, 1-578, 1-579, 1-580, 1-581, 1-582, 1-583, 1-584, 1-585, 1-586, 1-587, 1-588, 1-589, 1-590, 1-591, 1-592, 1-593, 1-594, 1-595, 1-596, 1-597, 1-598, 1-599, 1-600, 1-601, 1-602, 1-603, 1-604, 1-605, 1-606, 1-607, 1-608, 1-609, 1-610, 1-611, 1-612, 1-613, 1-614, 1-615, 1-616, 1-617, 1-618, 1-619, 1-620, 1-621, 1-676, 1-677, 1-678, 1-679, 1-680, 1-681, 1-682, 1-683, 1-684, 1-685, 1-686, 1-687, 1-688, 1-689, 1-690, 1-691, 1-692, 1-693, 1-694, 1-695, 1-696, 1-697, 1-698, 1-699, 1-700, 1-701, 1-702, 1-703, 1-704, 1-705, 1-706, 1-707, 1-708, 1-709, 1-710, 1-711, 1-712, 1-713, 1-714, 1-715, 1-716, 1-717, 1-718, 1-719, 1-720, 1-721, 1-722, 1-723, 1-724, 1-725, 1-726, 1-727, 1-728, 1-729, 1-730, 1-731, 1-732, 1-733, 1-734, 1-735, 1-736, 1-737, 1-738, 1-739, 1-740, 1-741, 1-742, 1-743, 1-744, 1-745, 1-746, 1-747, 1-748, 1-749, 1-750, 1-751, 1-752, 1-753, 1-754, 1-755, 1-756, 1-757, 1-758, 1-759, 1-760, 1-761, 1-762, 1-763, 1-764, 1-765, 1-766, 1-767, 1-768, 1-769, 1-770, 1-771, 1-772, 1-773, 1-774, 1-775, 1-776, 1-777, 1-778, 1-779, 1-780, 1-781, 1-782, 1-783, 1-784, 1-785, 1-786, 1-787, 1-788, 1-789, 1-790, 1-791, 1-792, 1-793, 1-794, 1-795, 1-796, 1-797, 1-798, 1-799, 1-800, 1-801, 1-802, 1-803, 1-804, 1-805, 1-806, 1-807, 1-808, 1-809, 1-810, 1-811, 1-812, 1-813, 1-814, 1-815, 1-816, 1-817, 1-818, 1-819, 1-820, 1-821, 1-822, 1-823, 1-824, 1-825, 1-826, 1-827, 1-828, 1-829, 1-830, 1-831, 1-832, 1-833, 1-834, 1-835, 1-836, 1-837, 1-838, 1-839, 1-840, 1-841, 1-842, 1-843, 1-844, 1-845, 1-846, 1-847, 1-848, 1-849, 1-850, 1-851, 1-852, 1-853, 1-854, 1-855, 1-856, 1-857, 1-858, 1-859, 1-860, 1-861, 1-862, 1-863, 1-1112, 1-1113, 1-1114, 1-1115, 1-1116, 1-1117, 1-1118, 1-1119, 1-1120, 1-1121, 1-1122, 1-1123, 1-1124, 1-1125, 1-1126, 1-1127, 1-1128, 1-1129, 1-1130, 1-1131, 1-1132, 1-1133, 1-1134, 1-1135, 1-1136, 1-1137, 1-1138, 1-1139, 1-1140, 1-1141, 1-1142, 1-1143, 1-1144, 1-1145, 1-1146, 1-1147, 1-1148, 1-1149, 1-1150, 1-1151, 1-1152, 1-1153, 1-1154, 1-1155, 1-1156, 1-1157, 1-1158, 1-1159, 1-1160, 1-1161, 1-1162, 1-1163, 1-1164, 1-1165, 1-1166, 1-1167, 1-1168, 1-1169, 1-1224, 1-1258, 1-1259, 1-1260, 1-1261, 1-1262, 1-1263, 1-1264, 1-1265, 1-1266, 1-1267, 1-1268, 1-1269, 1-1270, 1-1271, 1-1272, 1-1273, 1-1274, 1-1275, 1-1276, 1-1277, 1-1278, 1-1279, 1-1280, 1-1281, 1-1282, 1-1283, 1-1284, 1-1285, 1-1286, 1-1287, 1-1288, 1-1289, 1-1290, 1-1291, 1-1292, 1-1293, 1-1294, 1-1295, 1-1296, 1-1297, 1-1298, 1-1299, 1-1300, 1-1301, 1-1302, 1-1303, 1-1304, 1-1305, 1-1306, 1-1307, 1-1308, 1-1309, 1-1310, 1-1311, 1-1312, 1-1313, 1-1314, 1-1315, 1-1316, 1-1317, 1-1318, 1-1319, 1-1320, 1-1321, 1-1322, 1-1323, 1-1324, 1-1325, 1-1326, 1-1327, 1-1328, 1-1329, 1-1330, 1-1331, 1-1332, 1-1333, 1-1334, 1-1335, 1-1336, 1-1337, 1-1338, 1-1339, 1-1340, 1-1341, 1-1342, 1-1343, 1-1344, 1-1345, 1-1346, 1-1347, 1-1348, 1-1349, 1-1350, 1-1351, 1-1352, 1-1353, 1-1354, 1-1355, 1-1356, 1-1357, 1-1358, 1-1359, 1-1360, 1-1361, 1-1362, 1-1363, 1-1364, 1-1365, 1-1366, 1-1367, 1-1368, 1-1369, 1-1370, 1-1371, 1-1372, 1-1373, 1-1374, 1-1375, 1-1376, 1-1377, 1-1378, 1-1379, 1-1380, 1-1381, 1-1382, 1-1383, 1-1532, 1-1533, 1-1534, 1-1535, 1-1536, 1-1537, 1-1538, 1-1539, 1-1540, 1-1541, 1-1542, 1-1543, 1-1544, 1-1545, 1-1546, 1-1547, 1-1548, 1-1549, 1-1550, 1-1551, 1-1552, 1-1553, 1-1554, 1-1555, 1-1556, 1-1557, 1-1558, 1-1559, 1-1560, 1-1561, 1-1562, 1-1563, 1-1564, 1-1565, 1-1566, 1-1567, 1-1568, 1-1569, 1-1570, 1-1571, 1-1572, 1-1573, 1-1574, 1-1575, 1-1576, 1-1577, 1-1578, 1-1579, 1-1580, 1-1581, 1-1582, 1-1583, 1-1584, 1-1585, 1-1586, 1-1587, 1-1588, 1-1589, 1-1590, 1-1591, 1-1592, 1-1593, 1-1594, 1-1595, 1-1596, 1-1597, 1-1598, 1-1599, 1-1600, 1-1601, 1-1602, 1-1603, 1-1604, 1-1605, 1-1606, 1-1607, 1-1608, 1-1609, 1-1610, 1-1611, 1-1612, 1-1613, 1-1614, 1-1615, 1-1616, 1-1617, 1-1618, 1-1619, 1-1620, 1-1621, 1-1622, 1-1623, 1-1624, 1-1625, 1-1626, 1-1627, 1-1628, 1-1629, 1-1630, 1-1631, 1-1632, 1-1633, 1-1634, 1-1635, 1-1636, 1-1637, 1-1638, 1-1639, 1-1640, 1-1641, 1-1642, 1-1643, 1-1644, 1-1645, 1-1646, 1-1647, 1-1648, 1-1649, 1-1650, 1-1651, 1-1652, 1-1653, 1-1654, 1-1655, 1-1656, 1-1657, 1-1658, 1-1659, 1-1660, 1-1661, 1-1662, 1-1663, 1-1664, 1-1665, 1-1666, 1-1667, 1-1668, 1-1669, 1-1670, 1-1671, 1-1672, 1-1673, 1-1674, 1-1675, 1-1676, 1-1677, 1-1678, 1-1679, 1-1680, 1-1681, 1-1682, 1-1683, 1-1684, 1-1685, 1-1686, 1-1687, 1-1688, 1-1689, 1-1690, 1-1691, 1-1692, 1-1693, 1-1694, 1-1695, 1-1696, 1-1697, 1-1698, 1-1699, 1-1700, 1-1701, 1-1702, 1-1703, 1-1704, 1-1705, 1-1706, 1-1707, 1-1708, 1-1709, 1-1710, 1-1711, 1-1712, 1-1713, 1-1714, 1-1715, 1-1716, 1-1717, 1-1718, 1-1719, 1-1720, 1-1721, 1-1722, 1-1723, 1-1724, 1-1725, 1-1726, 1-1727, 1-1728, 1-1729, 1-1730, 1-1731, 1-1732, 1-1733, 1-1734, 1-1735, 1-1736, 1-1737, 1-1738, 1-1739, 1-1740, 1-1741, 1-1742, 1-1743, 1-1744, 1-1745, 1-1746, 1-1747, 1-1748, 1-1749, 1-1750, 1-1751, 1-1752, 1-1753, 1-1754, 1-1755, 1-1756, 1-1757, 1-1758, 1-1759, 1-1760, 1-1761, 1-1762, 1-1763, 1-1764, 1-1765, 1-1766, 1-1767, 1-1768, 1-1769, 1-1770, 1-1771, 1-1772, 1-1773, 1-1774, 1-1775, 1-1776, 1-1777, 1-1778, 1-1779, 1-1780, 1-1781, 1-1782, 1-1783, 1-1784, 1-1785, 1-1786, 1-1787, 1-1788, 1-1789, 1-1790, 1-1791, 1-1792, 1-1793, 1-1794, 1-1795, 1-1796, 1-1797, 1-1798, 1-1799, 1-1800, 1-1801, 1-1802, 1-1803, 1-1804, 1-1805, 1-1806, 1-1807, 1-1808, 1-1809, 1-1810, 1-1811, 1-1812, 1-1813, 1-1814, 1-1815, 1-1816, 1-1817, 1-1818, 1-1819, 1-1820, 1-1821, 1-1822, 1-1823, 1-1824, 1-1825, 1-1826, 1-1827, 1-1828, 1-1829, 1-1830, 1-1831, 1-1832, 1-1833, 1-1834, 1-1835, 1-1836, 1-1837, 1-1838, 1-1839, 1-1840, 1-1841, 1-1842, 1-1843, 1-1844, 1-1845, 1-1846, 1-1847, 1-1848, 1-1849, 1-1850, 1-1851, 1-1852, 1-1853, 1-1854, 1-1855, 1-1856, 1-1857, 1-1858, 1-1859, 1-1860, 1-1861, 1-1862, 1-1863, 1-1864, 1-1865, 1-1866, 1-1867, 1-1868, 1-1869, 1-1870, 1-1871, 1-1872, 1-1873, 1-1874, 1-1875, 1-1876, 1-1877, 1-1878, 1-1879, 1-1880, 1-1881, 1-1882, 1-1883, 1-1884, 1-1885, 1-1886, 1-1887, 1-1888, 1-1889, 1-1890, 1-1891, 1-1892, 1-1893, 1-1894, 1-1895, 1-1896, 1-1897, 1-1898, 1-1899, 1-1900, 1-1901, 1-1902, 1-1903, 1-1904, 1-1905, 1-1906, 1-1907, 1-1908, 1-1909, 1-1910, 1-1911, 1-1912, 1-1913, 1-1914, 1-1915, 1-1916, 1-1917, 1-1918, 1-1919, 1-1920, 1-1921, 1-1962, 1-1963, 1-1964, 1-1965, 1-1966, 1-1967, 1-1968, 1-1969, 1-1970, 1-1971, 1-1972, 1-1973, 1-1974, 1-1975, 1-1976, 1-1977, 1-1978, 1-1979, 1-1980, 1-1981, 1-1982, 1-1983, 1-1984, 1-1985, 1-1986, 1-1987, 1-1988, 1-1989, 1-1990, 1-1991, 1-1992, 1-1993, 1-1994, 1-1995, 1-1996, 1-1997, 1-1998, 1-1999, 1-2000, 1-2001, 1-2002, 1-2003, 1-2004, 1-2005, 1-2006, 1-2007, 1-2008, 1-2009, 1-2010, 1-2011, 1-2012, 1-2013, 1-2014, 1-2015, 1-2016, 1-2017, 1-2018, 1-2019, 1-2020, 1-2021, 1-2022, 1-2023, 1-2024, 1-2025, 1-2026, 1-2027, 1-2028, 1-2029, 1-2030, 1-2031, 1-2032, 1-2033, 1-2034, 1-2035, 1-2036, 1-2037, 1-2038, 1-2039, 1-2040, 1-2041, 1-2042, 1-2043, 1-2044, 1-2045, 1-2046, 1-2047, 1-2048, 1-2049, 1-2050, 1-2051, 1-2052, 1-2053, 1-2054, 1-2055, 1-2056, 1-2057, 1-2058, 1-2059, 1-2060, 1-2061, 1-2062, 1-2063, 1-2064, 1-2065, 1-2066, 1-2067, 1-2068, 1-2069, 1-2070, 1-2071, 1-2072, 1-2073, 1-2074, 1-2075, 1-2076, 1-2077, 1-2078, 1-2079, 1-2080, 1-2081, 1-2082, 1-2083, 1-2084, 1-2085, 1-2086, 1-2087, 1-2088, 1-2089, 1-2090, 1-2091, 1-2092, 1-2093, 1-2094, 1-2095, 1-2096, 1-2097, 1-2098, 1-2099, 1-2100, 1-2101, 1-2102, 1-2103, 1-2104, 1-2105, 1-2106, 1-2107, 1-2108, 1-2109, 1-2110, 1-2111, 1-2112, 1-2113, 1-2114, 1-2115, 1-2116, 1-2117, 1-2118, 1-2119, 1-2120, 1-2121, 1-2122, 1-2123, 1-2124, 1-2125, 1-2126, 1-2127, 1-2128, 1-2129, 1-2130, 1-2131, 1-2132, 1-2133, 1-2134, 1-2135, 1-2136, 1-2137, 1-2138, 1-2139, 1-2140, 1-2141, 1-2142, 1-2143, 1-2144, 1-2145, 1-2146, 1-2147, 1-2147, 1-2149, 1-2150, 1-2151, 1-2152, 1-2153, 1-2154, 1-2155, 1-2156, 1-2157, 1-2158, 1-2159, 1-2160, 1-2161, 1-2162, 1-2163, 1-2429, 1-2430, 1-2431, 1-2432, 1-2433, 1-2434, 1-2435, 1-2436, 1-2437, 1-2438, 1-2439, 1-2440, 1-2441, 1-2442, 1-2443, 1-2444, 1-2445, 1-2446, 1-2447, 1-2448, 1-2449, 1-2450, 1-2451, 1-2452, 1-2453, 1-2454, 1-2455, 1-2456, 1-2457, 1-2458, 1-2459, 1-2460, 1-2461, 1-2462, 1-2463, 1-2464, 1-2465, 1-2466, 1-2467, 1-2468, 1-2469, 1-2470, 1-2471, 1-2472, 1-2473, 1-2474, 1-2475, 1-2476, 1-2477, 1-2478, 1-2479, 1-2480, 1-2481, 1-2482, 1-2483, 1-2484, 1-2485, 1-2486, 1-2487, 1-2488, 1-2489, 1-2490, 1-2491, 1-2492, 1-2493, 1-2494, 1-2495, 1-2496, 1-2497, 1-2498, 1-2499, 1-2500, 1-2501, 1-2502, 1-2503, 1-2504, 1-2505, 1-2506, 1-2507, 1-2508, 1-2509, 1-2510, 1-2511, 1-2512, 1-2513, 1-2514, 1-2515, 1-2516, 1-2517, 1-2518, 1-2519, 1-2520, 1-2521, 1-2522, 1-2523, 1-2524, 1-2525, 1-2526, 1-2527, 1-2528, 1-2529, 1-2530, 1-2531, 1-2532, 1-2533, 1-2534, 1-2535, 1-2536, 1-2537, 1-2538, 1-2539, 1-2540, 1-2541, 1-2542, 1-2543, 1-2544, 1-2545, 1-2546, 1-2547, 1-2548, 1-2549, 1-2550, 1-2551, 1-2552, 1-2553, 1-2554, 1-2555, 1-2556, 1-2557, 1-2558, 1-2559, 1-2560, 1-2561, 1-2562, 1-2563, 1-2564, 1-2565, 1-2566, 1-2567, 1-2568, 1-2569, 1-2570, 1-2571, 1-2572, 1-2573, 1-2574, 1-2575, 1-2576, 1-2577, 1-2578, 1-2579, 1-2580, 1-2581, 1-2582, 1-2583, 1-2584, 1-2585, 1-2586, 1-2587, 1-2588, 1-2589, 1-2590, 1-2591, 1-2592, 1-2593, 1-2594, 1-2595, 1-2596, 1-2597, 1-2598, 1-2599, 1-2600, 1-2601, 1-2602, 1-2603, 1-2604, 1-2605, 1-2606, 1-2607, 1-2608, 1-2609, 1-2610, 1-2611, 1-2612, 1-2613, 1-2614, 1-2657, 1-2665, 1-2667, 1-2669, 2-1, 2-2, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-78, 2-79, 2-80, 2-81, 2-82, 2-83, 2-232, 2-233, 2-234, 2-235, 2-236, 2-237, 2-238, 2-239, 2-240, 2-241, 2-242, 2-243, 2-244, 2-245, 2-246, 2-247, 2-248, 2-249, 2-250, 2-251, 2-252, 2-253, 2-254, 2-255, 2-256, 2-257, 2-258, 2-259, 2-260, 2-261, 2-262, 2-263, 2-264, 2-265, 2-266, 2-267, 2-268, 2-269, 2-270, 2-271, 2-272, 2-273, 2-274, 2-275, 2-276, 2-277, 2-278, 2-279, 2-280, 2-281, 2-282, 2-283, 2-284, 2-285, 2-286, 2-287, 2-288, 2-289, 2-290, 2-291, 2-292, 2-293, 2-294, 2-295, 2-286, 2-297, 2-298, 2-299, 2-300, 2-301, 2-302, 2-303, 2-304, 2-305, 2-306, 2-307, 2-308, 2-309, 2-310, 2-311, 2-312, 2-313, 2-314, 2-315, 2-316, 2-317, 2-318, 2-319, 2-320, 2-321, 2-322, 2-323, 2-324, 2-325, 2-326, 2-327, 2-328, 2-329, 2-330, 2-331, 2-332, 2-333, 2-334, 2-335, 2-336, 2-337, 2-338, 2-339, 2-340, 2-341, 2-342, 2-343, 2-344, 2-345, 2-346, 2-347, 2-348, 2-349, 2-350, 2-351, 2-352, 2-353, 2-354, 2-355, 2-356, 2-357, 2-358, 2-359, 2-360, 2-361, 2-362, 2-363, 2-364, 2-365, 2-366, 2-367, 2-368, 2-369, 2-370, 2-371, 2-372, 2-373, 2-374, 2-375, 2-376, 2-377, 2-378, 2-379, 2-380, 2-381, 2-382, 2-383, 2-384, 2-385, 2-386, 2-387, 2-388, 2-389, 2-390, 2-391, 2-392, 2-393, 2-394, 2-395, 2-396, 2-397, 2-398, 2-399, 2-400, 2-401, 2-402, 2-403, 2-404, 2-405, 2-406, 2-407, 2-408, 2-409, 2-410, 2-411, 2-412, 2-413, 2-414, 2-415, 2-416, 2-417, 2-418, 2-419, 2-420, 2-421, 2-422, 2-423, 2-424, 2-425, 2-426, 2-427, 2-428, 2-429, 2-430, 2-431, 2-432, 2-433, 2-434, 2-435, 2-436, 2-437, 2-438, 2-439, 2-440, 2-441, 2-442, 2-443, 2-444, 2-445, 2-446, 2-447, 2-448, 2-449, 2-450, 2-451, 2-452, 2-453, 2-454, 2-455, 2-456, 2-457, 2-458, 2-459, 2-460, 2-461, 2-462, 2-463, 2-464, 2-465, 2-466, 2-467, 2-468, 2-469, 2-470, 2-471, 2-472, 2-473, 2-474, 2-475, 2-476, 2-477, 2-478, 2-479, 2-480, 2-481, 2-482, 2-483, 2-484, 2-485, 2-486, 2-487, 2-488, 2-489, 2-490, 2-491, 2-492, 2-493, 2-494, 2-495, 2-496, 2-497, 2-498, 2-499, 2-500, 2-501, 2-502, 2-503, 2-504, 2-505, 2-506, 2-507, 2-508, 2-509, 2-510, 2-511, 2-512, 2-513, 2-514, 2-515, 2-516, 2-517, 2-518, 2-519, 2-520, 2-521, 2-522, 2-523, 2-524, 2-525, 2-526, 2-527, 2-528, 2-529, 2-530, 2-531, 2-532, 2-533, 2-534, 2-535, 2-536, 2-537, 2-538, 2-539, 2-540, 2-541, 2-542, 2-543, 2-544, 2-545, 2-546, 2-547, 2-548, 2-549, 2-550, 2-551, 2-552, 2-553, 2-554, 2-555, 2-556, 2-557, 2-558, 2-559, 2-560, 2-561, 2-562, 2-563, 2-564, 2-565, 2-566, 2-567, 2-568, 2-569, 2-570, 2-571, 2-572, 2-573, 2-574, 2-575, 2-576, 2-577, 2-578, 2-579, 2-580, 2-581, 2-582, 2-583, 2-584, 2-585, 2-586, 2-587, 2-588, 2-589, 2-590, 2-591, 2-592, 2-593, 2-594, 2-595, 2-596, 2-597, 2-598, 2-599, 2-600, 2-601, 2-602, 2-603, 2-604, 2-605, 2-606, 2-607, 2-608, 2-609, 2-610, 2-611, 2-612, 2-613, 2-614, 2-615, 2-616, 2-617, 2-618, 2-619, 2-620, 2-621, 2-676, 2-677, 2-678, 2-679, 2-680, 2-681, 2-682, 2-683, 2-684, 2-685, 2-686, 2-687, 2-688, 2-689, 2-690, 2-691, 2-692, 2-693, 2-694, 2-695, 2-696, 2-697, 2-698, 2-699, 2-700, 2-701, 2-702, 2-703, 2-704, 2-705, 2-706, 2-707, 2-708, 2-709, 2-710, 2-711, 2-712, 2-713, 2-714, 2-715, 2-716, 2-717, 2-718, 2-719, 2-720, 2-721, 2-722, 2-723, 2-724, 2-725, 2-726, 2-727, 2-728, 2-729, 2-730, 2-731, 2-732, 2-733, 2-734, 2-735, 2-736, 2-737, 2-738, 2-739, 2-740, 2-741, 2-742, 2-743, 2-744, 2-745, 2-746, 2-747, 2-748, 2-749, 2-750, 2-751, 2-752, 2-753, 2-754, 2-755, 2-756, 2-757, 2-758, 2-759, 2-760, 2-761, 2-762, 2-763, 2-764, 2-765, 2-766, 2-767, 2-768, 2-769, 2-770, 2-771, 2-772, 2-773, 2-774, 2-775, 2-776, 2-777, 2-778, 2-779, 2-780, 2-781, 2-782, 2-783, 2-784, 2-785, 2-786, 2-787, 2-788, 2-789, 2-790, 2-791, 2-792, 2-793, 2-794, 2-795, 2-796, 2-797, 2-798, 2-799, 2-800, 2-801, 2-802, 2-803, 2-804, 2-805, 2-806, 2-807, 2-808, 2-809, 2-810, 2-811, 2-812, 2-813, 2-814, 2-815, 2-816, 2-817, 2-818, 2-819, 2-820, 2-821, 2-822, 2-823, 2-824, 2-825, 2-826, 2-827, 2-828, 2-829, 2-830, 2-831, 2-832, 2-833, 2-834, 2-835, 2-836, 2-837, 2-838, 2-839, 2-840, 2-841, 2-842, 2-843, 2-844, 2-845, 2-846, 2-847, 2-848, 2-849, 2-850, 2-851, 2-852, 2-853, 2-854, 2-855, 2-856, 2-857, 2-858, 2-859, 2-860, 2-861, 2-862, 2-863, 2-1112, 2-1113, 2-1114, 2-1115, 2-1116, 2-1117, 2-1118, 2-1119, 2-1120, 2-1121, 2-1122, 2-1123, 2-1124, 2-1125, 2-1126, 2-1127, 2-1128, 2-1129, 2-1130, 2-1131, 2-1132, 2-1133, 2-1134, 2-1135, 2-1136, 2-1137, 2-1138, 2-1139, 2-1140, 2-1141, 2-1142, 2-1143, 2-1144, 2-1145, 2-1146, 2-1147, 2-1148, 2-1149, 2-1150, 2-1151, 2-1152, 2-1153, 2-1154, 2-1155, 2-1156, 2-1157, 2-1158, 2-1159, 2-1160, 2-1161, 2-1162, 2-1163, 2-1164, 2-1165, 2-1166, 2-1167, 2-1168, 2-1169, 2-1224, 2-1258, 2-1259, 2-1260, 2-1261, 2-1262, 2-1263, 2-1264, 2-1265, 2-1266, 2-1267, 2-1268, 2-1269, 2-1270, 2-1271, 2-1272, 2-1273, 2-1274, 2-1275, 2-1276, 2-1277, 2-1278, 2-1279, 2-1280, 2-1281, 2-1282, 2-1283, 2-1284, 2-1285, 2-1286, 2-1287, 2-1288, 2-1289, 2-1290, 2-1291, 2-1292, 2-1293, 2-1294, 2-1295, 2-1296, 2-1297, 2-1298, 2-1299, 2-1300, 2-1301, 2-1302, 2-1303, 2-1304, 2-1305, 2-1306, 2-1307, 2-1308, 2-1309, 2-1310, 2-1311, 2-1312, 2-1313, 2-1314, 2-1315, 2-1316, 2-1317, 2-1318, 2-1319, 2-1320, 2-1321, 2-1322, 2-1323, 2-1324, 2-1325, 2-1326, 2-1327, 2-1328, 2-1329, 2-1330, 2-1331, 2-1332, 2-1333, 2-1334, 2-1335, 2-1336, 2-1337, 2-1138, 2-1139, 2-1140, 2-1341, 2-1342, 2-1343, 2-1344, 2-1345, 2-1346, 2-1347, 2-1348, 2-1349, 2-1350, 2-1351, 2-1352, 2-1353, 2-1354, 2-1355, 2-1356, 2-1357, 2-1358, 2-1359, 2-1360, 2-1361, 2-1362, 2-1363, 2-1364, 2-1365, 2-1366, 2-1367, 2-1368, 2-1369, 2-1370, 2-1371, 2-1372, 2-1373, 2-1374, 2-1375, 2-1376, 2-1377, 2-1378, 2-1379, 2-1380, 2-1381, 2-1382, 2-1383, 2-1532, 2-1533, 2-1534, 2-1535, 2-1536, 2-1537, 2-1538, 2-1539, 2-1540, 2-1541, 2-1542, 2-1543, 2-1544, 2-1545, 2-1546, 2-1547, 2-1548, 2-1549, 2-1550, 2-1551, 2-1552, 2-1553, 2-1554, 2-1555, 2-1556, 2-1557, 2-1558, 2-1559, 2-1560, 2-1561, 2-1562, 2-1563, 2-1564, 2-1565, 2-1566, 2-1567, 2-1568, 2-1569, 2-1570, 2-1571, 2-1572, 2-1573, 2-1574, 2-1575, 2-1576, 2-1577, 2-1578, 2-1579, 2-1580, 2-1581, 2-1582, 2-1583, 2-1584, 2-1585, 2-1586, 2-1587, 2-1588, 2-1589, 2-1590, 2-1591, 2-1592, 2-1593, 2-1594, 2-1595, 2-1596, 2-1597, 2-1598, 2-1599, 2-1600, 2-1601, 2-1602, 2-1603, 2-1604, 2-1605, 2-1606, 2-1607, 2-1608, 2-1609, 2-1610, 2-1611, 2-1612, 2-1613, 2-1614, 2-1615, 2-1616, 2-1617, 2-1618, 2-1619, 2-1620, 2-1621, 2-1622, 2-1623, 2-1624, 2-1625, 2-1626, 2-1627,
2-1628, 2-1629, 2-1630, 2-1631, 2-1632, 2-1633, 2-1634,
2-1635, 2-1636, 2-1637, 2-1638, 2-1639, 2-1640, 2-1641,
2-1642, 2-1643, 2-1644, 2-1645, 2-1646, 2-1647, 2-1648,
2-1649, 2-1650, 2-1651, 2-1652, 2-1653, 2-1654, 2-1655,
2-1656, 2-1657, 2-1658, 2-1569, 2-1660, 2-1661, 2-1662,
2-1663, 2-1664, 2-1665, 2-1666, 2-1667, 2-1668, 2-1669,
2-1670, 2-1671, 2-1672, 2-1673, 2-1674, 2-1675, 2-1676,
2-1677, 2-1678, 2-1679, 2-1680, 2-1681, 2-1682, 2-1683,
2-1684, 2-1685, 2-1686, 2-1687, 2-1688, 2-1689, 2-1690,
2-1691, 2-1692, 2-1693, 2-1694, 2-1695, 2-1696, 2-1697,
2-1698, 2-1699, 2-1700, 2-1701, 2-1702, 2-1703, 2-1704,
2-1705, 2-1706, 2-1707, 2-1708, 2-1709, 2-1710, 2-1711,
2-1712, 2-1713, 2-1714, 2-1715, 2-1716, 2-1717, 2-1718,
2-1719, 2-1720, 2-1721, 2-1722, 2-1723, 2-1724, 2-1725,
2-1726, 2-1727, 2-1728, 2-1729, 2-1730, 2-1731, 2-1732,
2-1733, 2-1734, 2-1735, 2-1736, 2-1737, 2-1738, 2-1739,
2-1740, 2-1741, 2-1742, 2-1743, 2-1744, 2-1745, 2-1746,
2-1747, 2-1748, 2-1749, 2-1750, 2-1751, 2-1752, 2-1753,
2-1754, 2-1755, 2-1756, 2-1757, 2-1758, 2-1759, 2-1760,
2-1761, 2-1762, 2-1763, 2-1764, 2-1765, 2-1766, 2-1767,
2-1768, 2-1769, 2-1770, 2-1771, 2-1772, 2-1773, 2-1774,
2-1775, 2-1776, 2-1777, 2-1778, 2-1779, 2-1780, 2-1781,
2-1782, 2-1783, 2-1784, 2-1785, 2-1786, 2-1787, 2-1788,
2-1789, 2-1790, 2-1791, 2-1792, 2-1793, 2-1794, 2-1795,
2-1796, 2-1797, 2-1798, 2-1799, 2-1800, 2-1801, 2-1802,
2-1803, 2-1804, 2-1805, 2-1806, 2-1807, 2-1808, 2-1809,
2-1810, 2-1811, 2-1812, 2-1813, 2-1814, 2-1815, 2-1816,
2-1817, 2-1818, 2-1819, 2-1820, 2-1821, 2-1822, 2-1823,
2-1824, 2-1825, 2-1826, 2-1827, 2-1828, 2-1829, 2-1830,
2-1831, 2-1832, 2-1833, 2-1834, 2-1835, 2-1836, 2-1837,
2-1838, 2-1839, 2-1840, 2-1841, 2-1842, 2-1843, 2-1844,
2-1845, 2-1846, 2-1847, 2-1848, 2-1849, 2-1850, 2-1851,
2-1852, 2-1853, 2-1854, 2-1855, 2-1856, 2-1857, 2-1858,
2-1859, 2-1860, 2-1861, 2-1862, 2-1863, 2-1864, 2-1865,
2-1866, 2-1867, 2-1868, 2-1869, 2-1870, 2-1871, 2-1872,
2-1873, 2-1874, 2-1875, 2-1876, 2-1877, 2-1878, 2-1879,
2-1880, 2-1881, 2-1882, 2-1883, 2-1884, 2-1885, 2-1886,
2-1887, 2-1888, 2-1889, 2-1890, 2-1891, 2-1892, 2-1893,
2-1894, 2-1895, 2-1896, 2-1897, 2-1898, 2-1899, 2-1900,
2-1901, 2-1902, 2-1903, 2-1904, 2-1905, 2-1906, 2-1907,
2-1908, 2-1909, 2-1910, 2-1911, 2-1912, 2-1913, 2-1914,
2-1915, 2-1916, 2-1917, 2-1918, 2-1919, 2-1920, 2-1921,
2-1962, 2-1963, 2-1964, 2-1965, 2-1966, 2-1967, 2-1968,
2-1969, 2-1970, 2-1971, 2-1972, 2-1973, 2-1974, 2-1975,
2-1976, 2-1977, 2-1978, 2-1979, 2-1980, 2-1981, 2-1982,
2-1983, 2-1984, 2-1985, 2-1986, 2-1987, 2-1988, 2-1989,
2-1990, 2-1991, 2-1992, 2-1993, 2-1994, 2-1995, 2-1996,
2-1997, 2-1998, 2-1999, 2-2000, 2-2001, 2-2002, 2-2003,
2-2004, 2-2005, 2-2006, 2-2007, 2-2008, 2-2009, 2-2010,
2-2011, 2-2012, 2-2013, 2-2014, 2-2015, 2-2016, 2-2017,
2-2018, 2-2019, 2-2020, 2-2021, 2-2022, 2-2023, 2-2024,
2-2025, 2-2026, 2-2027, 2-2028, 2-2029, 2-2030, 2-2031,
2-2032, 2-2033, 2-2034, 2-2035, 2-2036, 2-2037, 2-2038,
2-2039, 2-2040, 2-2041, 2-2042, 2-2043, 2-2044, 2-2045,
2-2046, 2-2047, 2-2048, 2-2049, 2-2050, 2-2051, 2-2052,
2-2053, 2-2054, 2-2055, 2-2056, 2-2057, 2-2058, 2-2059,
2-2060, 2-2061, 2-2062, 2-2063, 2-2064, 2-2065, 2-2066,
2-2067, 2-2068, 2-2069, 2-2070, 2-2071, 2-2072, 2-2073,
2-2074, 2-2075, 2-2076, 2-2077, 2-2078, 2-2079, 2-2080,
2-2081, 2-2082, 2-2083, 2-2084, 2-2085, 2-2086, 2-2087,
2-2088, 2-2089, 2-2090, 2-2091, 2-2092, 2-2093, 2-2094,
2-2095, 2-2096, 2-2097, 2-2098, 2-2099, 2-2100, 2-2101,
2-2102, 2-2103, 2-2104, 2-2105, 2-2106, 2-2107, 2-2108,
2-2109, 2-2110, 2-2111, 2-2112, 2-2113, 2-2114, 2-2115,
2-2116, 2-2117, 2-2118, 2-2119, 2-2120, 2-2121, 2-2122,
2-2123, 2-2124, 2-2125, 2-2126, 2-2127, 2-2128, 2-2129,
2-2130, 2-2131, 2-2132, 2-2133, 2-2134, 2-2135, 2-2136,
2-2137, 2-2138, 2-2139, 2-2140, 2-2141, 2-2142, 2-2143,
2-2144, 2-2145, 2-2146, 2-2147, 2-2148, 2-2149, 2-2150,
2-2151, 2-2152, 2-2153, 2-2154, 2-2155, 2-2156, 2-2157,
2-2158, 2-2159, 2-2160, 2-2161, 2-2162, 2-2163, 2-2429,
2-2430, 2-2431, 2-2432, 2-2433, 2-2434, 2-2435, 2-2436,
2-2437, 2-2438, 2-2439, 2-2440, 2-2441, 2-2442, 2-2443,
2-2444, 2-2445, 2-2446, 2-2447, 2-2448, 2-2449, 2-2450,
2-2451, 2-2452, 2-2453, 2-2454, 2-2455, 2-2456, 2-2457,
2-2458, 2-2459, 2-2460, 2-2461, 2-2462, 2-2463, 2-2464,
2-2465, 2-2466, 2-2467, 2-2468, 2-2469, 2-2470, 2-2471,
2-2472, 2-2473, 2-2474, 2-2475, 2-2476, 2-2477, 2-2478,
2-2479, 2-2480, 2-2481, 2-2482, 2-2483, 2-2484, 2-2485,
2-2486, 2-2487, 2-2488, 2-2489, 2-2490, 2-2491, 2-2492,
2-2493, 2-2494, 2-2495, 2-2496, 2-2497, 2-2498, 2-2499,
2-2500, 2-2501, 2-2501, 2-2503, 2-2504, 2-2505, 2-2506,
2-2507, 2-2508, 2-2509, 2-2510, 2-2511, 2-2512, 2-2513,
2-2514, 2-2515, 2-2516, 2-2517, 2-2518, 2-2519, 2-2520,
2-2521, 2-2522, 2-2523, 2-2524, 2-2525, 2-2526, 2-2527,
2-2528, 2-2529, 2-2530, 2-2531, 2-2532, 2-2533, 2-2534,
2-2535, 2-2536, 2-2537, 2-2538, 2-2539, 2-2540, 2-2541,
2-2542, 2-2543, 2-2544, 2-2545, 2-2546, 2-2547, 2-2548,
2-2549, 2-2550, 2-2551, 2-2552, 2-2553, 2-2554, 2-2555,
2-2556, 2-2557, 2-2558, 2-2559, 2-2560, 2-2561, 2-2562,
2-2563, 2-2564, 2-2565, 2-2566, 2-2567, 2-2568, 2-2569,
2-2570, 2-2571, 2-2572, 2-2573, 2-2574, 2-2575, 2-2576,
2-2577, 2-2578, 2-2579, 2-2580, 2-2581, 2-2582, 2-2583,
2-2584, 2-2585, 2-2586, 2-2587, 2-2588, 2-2589, 2-2590,
2-2591, 2-2592, 2-2593, 2-2594, 2-2595, 2-2596, 2-2597,
2-2598, 2-2599, 2-2600, 2-2601, 2-2602, 2-2603, 2-2604,
2-2605, 2-2606, 2-2607, 2-2608, 2-2609, 2-2610, 2-2611,
2-2612, 2-2613, 2-2614, 2-2657, 2-2665, 2-2667, 2-2669,
3-1, 3-2, 3-3, 3-4, 3-5, 3-6, 3-7, 3-8, 3-9, 3-10, 3-11, 3-12,
3-13, 3-14, 3-15, 3-16, 3-17, 3-18, 3-19, 3-20, 3-21, 3-22,
3-23, 3-24, 3-25, 3-26, 3-27, 3-28, 3-29, 3-30, 3-31, 3-32,
3-33, 3-34, 3-35, 3-36, 3-37, 3-38, 3-39, 3-40, 3-41, 3-42,
3-43, 3-44, 3-45, 3-46, 3-47, 3-48, 3-49, 3-50, 3-51, 3-52,
3-53, 3-54, 3-55, 3-56, 3-57, 3-58, 3-59, 3-60, 3-61, 3-62,
3-63, 3-64, 3-65, 3-66, 3-67, 3-68, 3-69, 3-70, 3-71, 3-72,
3-73, 3-74, 3-75, 3-76, 3-77, 3-78, 3-79, 3-80, 3-81, 3-82,
3-83, 3-232, 3-233, 3-234, 3-235, 3-236, 3-237, 3-238,
3-239, 3-240, 3-241, 3-242, 3-243, 3-244, 3-245, 3-246,
3-247, 3-248, 3-249, 3-250, 3-251, 3-252, 3-253, 3-254,
3-255, 3-256, 3-257, 3-258, 3-259, 3-260, 3-261, 3-262,
3-263, 3-264, 3-265, 3-266, 3-267, 3-268, 3-269, 3-270,
3-271, 3-272, 3-273, 3-274, 3-275, 3-276, 3-277, 3-277,
3-279, 3-280, 3-281, 3-282, 3-283, 3-284, 3-285, 3-286,
3-287, 3-288, 3-289, 3-290, 3-291, 3-292, 3-293, 3-294,
3-295, 3-296, 3-297, 3-298, 3-299, 3-300, 3-301, 3-302,
3-303, 3-304, 3-305, 3-306, 3-307, 3-308, 3-309, 3-310,
3-311, 3-312, 3-313, 3-314, 3-315, 3-316, 3-317, 3-318,
3-319, 3-320, 3-321, 3-322, 3-323, 3-324, 3-325, 3-326,
3-327, 3-328, 3-329, 3-330, 3-331, 3-332, 3-333, 3-334,
3-335, 3-336, 3-337, 3-338, 3-339, 3-340, 3-341, 3-342,
3-343, 3-344, 3-345, 3-346, 3-347, 3-348, 3-349, 3-350,
3-351, 3-352, 3-353, 3-354, 3-355, 3-356, 3-357, 3-358,
3-359, 3-360, 3-361, 3-362, 3-363, 3-364, 3-365, 3-366,
3-367, 3-368, 3-369, 3-370, 3-371, 3-372, 3-373, 3-374,
3-375, 3-376, 3-377, 3-378, 3-379, 3-380, 3-381, 3-382,
3-383, 3-384, 3-385, 3-386, 3-387, 3-388, 3-389, 3-390,
3-391, 3-392, 3-393, 3-394, 3-395, 3-396, 3-397, 3-398,
3-399, 3-400, 3-401, 3-402, 3-403, 3-404, 3-405, 3-406,
3-407, 3-408, 3-409, 3-410, 3-411, 3-412, 3-413, 3-414,
3-415, 3-416, 3-417, 3-418, 3-419, 3-420, 3-421, 3-422,
3-423, 3-424, 3-425, 3-426, 3-427, 3-428, 3-429, 3-430,
3-431, 3-432, 3-433, 3-434, 3-435, 3-436, 3-437, 3-438,
3-439, 3-440, 3-441, 3-442, 3-443, 3-444, 3-445, 3-446, 3-447, 3-448, 3-449, 3-450, 3-451, 3-452, 3-453, 3-454, 3-455, 3-456, 3-457, 3-458, 3-459, 3-460, 3-461, 3-462, 3-463, 3-464, 3-465, 3-466, 3-467, 3-468, 3-469, 3-470, 3-471, 3-472, 3-473, 3-474, 3-475, 3-476, 3-477, 3-478, 3-479, 3-480, 3-481, 3-482, 3-483, 3-484, 3-485, 3-486, 3-487, 3-488, 3-489, 3-490, 3-491, 3-492, 3-493, 3-494, 3-495, 3-496, 3-497, 3-498, 3-499, 3-500, 3-501, 3-502, 3-503, 3-504, 3-505, 3-506, 3-507, 3-508, 3-509, 3-510, 3-511, 3-512, 3-513, 3-514, 3-515, 3-516, 3-517, 3-518, 3-519, 3-520, 3-521, 3-522, 3-523, 3-524, 3-525, 3-526, 3-527, 3-528, 3-529, 3-530, 3-531, 3-532, 3-533, 3-534, 3-535, 3-536, 3-537, 3-538, 3-539, 3-540, 3-541, 3-542, 3-543, 3-544, 3-545, 3-546, 3-547, 3-548, 3-549, 3-550, 3-551, 3-552, 3-553, 3-554, 3-555, 3-556, 3-557, 3-558, 3-559, 3-560, 3-561, 3-562, 3-563, 3-564, 3-565, 3-566, 3-567, 3-568, 3-569, 3-570, 3-571, 3-572, 3-573, 3-574, 3-575, 3-576, 3-577, 3-578, 3-579, 3-580, 3-581, 3-582, 3-583, 3-584, 3-585, 3-586, 3-587, 3-588, 3-589, 3-590, 3-591, 3-592, 3-593, 3-594, 3-595, 3-596, 3-597, 3-598, 3-599, 3-600, 3-601, 3-602, 3-603, 3-604, 3-605, 3-606, 3-607, 3-608, 3-609, 3-610, 3-611, 3-612, 3-613, 3-614, 3-615, 3-616, 3-617, 3-618, 3-619, 3-620, 3-621, 3-676, 3-677, 3-678, 3-679, 3-680, 3-681, 3-682, 3-683, 3-684, 3-685, 3-686, 3-687, 3-688, 3-689, 3-690, 3-691, 3-692, 3-693, 3-694, 3-695, 3-696, 3-697, 3-698, 3-699, 3-700, 3-701, 3-702, 3-703, 3-704, 3-705, 3-706, 3-707, 3-708, 3-709, 3-710, 3-711, 3-712, 3-713, 3-714, 3-715, 3-716, 3-717, 3-718, 3-719, 3-720, 3-721, 3-722, 3-723, 3-724, 3-725, 3-726, 3-727, 3-728, 3-729, 3-730, 3-731, 3-732, 3-733, 3-734, 3-735, 3-736, 3-737, 3-738, 3-739, 3-740, 3-741, 3-742, 3-743, 3-744, 3-745, 3-746, 3-747, 3-748, 3-749, 3-750, 3-751, 3-752, 3-753, 3-754, 3-755, 3-756, 3-757, 3-758, 3-759, 3-760, 3-761, 3-762, 3-763, 3-764, 3-765, 3-766, 3-767, 3-768, 3-769, 3-770, 3-771, 3-772, 3-773, 3-774, 3-775, 3-776, 3-777, 3-778, 3-779, 3-780, 3-781, 3-782, 3-783, 3-784, 3-785, 3-786, 3-787, 3-788, 3-789, 3-790, 3-791, 3-792, 3-793, 3-794, 3-795, 3-796, 3-797, 3-798, 3-799, 3-800, 3-801, 3-802, 3-803, 3-804, 3-805, 3-806, 3-807, 3-808, 3-809, 3-810, 3-811, 3-812, 3-813, 3-814, 3-815, 3-816, 3-817, 3-818, 3-819, 3-820, 3-821, 3-822, 3-823, 3-824, 3-825, 3-826, 3-827, 3-828, 3-829, 3-830, 3-831, 3-832, 3-833, 3-834, 3-835, 3-836, 3-837, 3-838, 3-839, 3-840, 3-841, 3-842, 3-843, 3-844, 3-845, 3-846, 3-847, 3-848, 3-849, 3-850, 3-851, 3-852, 3-853, 3-854, 3-855, 3-856, 3-857, 3-858, 3-859, 3-860, 3-861, 3-862, 3-863, 3-1112, 3-1113, 3-1114, 3-1115, 3-1116, 3-1117, 3-1118, 3-1119, 3-1120, 3-1121, 3-1122, 3-1123, 3-1124, 3-1125, 3-1126, 3-1127, 3-1128, 3-1129, 3-1130, 3-1131, 3-1132, 3-1133, 3-1134, 3-1135, 3-1136, 3-1137, 3-1138, 3-1139, 3-1140, 3-1141, 3-1142, 3-1143, 3-1144, 3-1145, 3-1146, 3-1147, 3-1148, 3-1149, 3-1150, 3-1151, 3-1152, 3-1153, 3-1154, 3-1155, 3-1156, 3-1157, 3-1158, 3-1159, 3-1160, 3-1161, 3-1162, 3-1163, 3-1164, 3-1165, 3-1166, 3-1167, 3-1168, 3-1169, 3-1224, 3-1258, 3-1259, 3-1260, 3-1261, 3-1262, 3-1263, 3-1264, 3-1265, 3-1266, 3-1267, 3-1268, 3-1269, 3-1270, 3-1271, 3-1272, 3-1273, 3-1274, 3-1275, 3-1276, 3-1277, 3-1278, 3-1279, 3-1280, 3-1281, 3-1282, 3-1283, 3-1284, 3-1285, 3-1286, 3-1287, 3-1288, 3-1289, 3-1290, 3-1291, 2-1292, 3-1293, 3-1294, 3-1295, 3-1296, 3-1297, 3-1298, 3-1299, 3-1300, 3-1301, 3-1302, 3-1303, 3-1304, 3-1305, 3-1306 3-1307, 3-1308, 3-1309, 3-1310, 3-1311, 3-1312, 3-1313, 3-1314, 3-1315, 3-1316, 3-1317, 3-1318, 3-1319, 3-1320, 3-1321, 3-1322, 3-1323, 3-1324, 3-1325, 3-1326, 3-1327, 3-1328, 3-1329, 3-1330, 3-1331, 3-1332, 3-1333, 3-1334, 3-1335, 3-1336, 3-1337, 3-1338, 3-1339, 3-1340, 3-1341, 3-1342, 3-1343, 3-1344, 3-1345, 3-1346, 3-1347, 3-1348, 3-1349, 3-1350, 3-1351, 3-1352, 3-1353, 3-1354, 3-1355, 3-1356, 3-1357, 3-1358, 3-1359, 3-1360, 3-1361, 3-1362, 3-1363, 3-1364, 3-1365, 3-1366, 3-1367, 3-1368, 3-1369, 3-1370, 3-1371, 3-1372, 3-1373, 3-1374, 3-1375, 3-1376, 3-1377, 3-1378, 3-1379, 3-1380, 3-1381, 3-1382, 3-1383, 3-1532, 3-1533, 3-1534, 3-1535, 3-1536, 3-1537, 3-1538, 3-1539, 3-1540, 3-1541, 3-1542, 3-1543, 3-1544, 3-1545, 3-1546, 3-1547, 3-1548, 3-1549, 3-1550, 3-1551, 3-1552, 3-1553, 3-1554, 3-1555, 3-1556, 3-1557, 3-1558, 3-1559, 3-1560, 3-1561, 3-1562, 3-1563, 3-1564, 3-1565, 3-1566, 3-1567, 3-1568, 3-1569, 3-1570, 3-1571, 3-1572, 3-1573, 3-1574, 3-1575, 3-1576, 3-1577, 3-1578, 3-1579, 3-1580, 3-1581, 3-1582, 3-1583, 3-1584, 3-1585, 3-1586, 3-1587, 3-1588, 3-1589, 3-1590, 3-1591, 3-1592, 3-1593, 3-1594, 3-1595, 3-1596, 3-1597, 3-1598, 3-1600, 3-1601, 3-1601, 3-1602, 3-1603, 3-1604, 3-1605, 3-1606, 3-1607, 3-1608, 3-1609, 3-1610, 3-1611, 3-1612, 3-1613, 3-1614 3-1615, 3-1616, 3-1617, 3-1618, 3-1619, 3-1620, 3-1621, 3-1622, 3-1623, 3-1624, 3-1625, 3-1626, 3-1627, 3-1628, 3-1629, 3-1630, 3-1631, 3-1632, 3-1633, 3-1634, 3-1635, 3-1636, 3-1637, 3-1638, 3-1639, 3-1640, 3-1641, 3-1642, 3-1643, 3-1644, 3-1645, 3-1646, 3-1647, 3-1648, 3-1649, 3-1650, 3-1651, 3-1652, 3-1653, 3-1654, 3-1655, 3-1656, 3-1657, 3-1658, 3-1659, 3-1660, 3-1661, 3-1662, 3-1663, 3-1664, 3-1665, 3-1666, 3-1667, 3-1668, 3-1669, 3-1670, 3-1671, 3-1672, 3-1673, 3-1674, 3-1675, 3-1676, 3-1677, 3-1678, 3-1679, 3-1680, 3-1681, 3-1682, 3-1683, 3-1684, 3-1685, 3-1686, 3-1687, 3-1688, 3-1689, 3-1690, 3-1691, 3-1692, 3-1693, 3-1694, 3-1695, 3-1696, 3-1697, 3-1698, 3-1699, 3-1700, 3-1701, 3-1702, 3-1703, 3-1704, 3-1705, 3-1706, 3-1707, 3-1708, 3-1709, 3-1710, 3-1711, 3-1712, 3-1713, 3-1714, 3-1715, 3-1716, 3-1717, 3-1718, 3-1719, 3-1720, 3-1721, 3-1722, 3-1723, 3-1724, 3-1725, 3-1726, 3-1727, 3-1728, 3-1729, 3-1730, 3-1731, 3-1732, 3-1733, 3-1734, 3-1735, 3-1736, 3-1737, 3-1738, 3-1739, 3-1740, 3-1741, 3-1742, 3-1743, 3-1744, 3-1745, 3-1746, 3-1747, 3-1748, 3-1749, 3-1750, 3-1751, 3-1752, 3-1753, 3-1754, 3-1755, 3-1756, 3-1757, 3-1758, 3-1759, 3-1760, 3-1761, 3-1762, 3-1763, 3-1764, 3-1765, 3-1766, 3-1767, 3-1768, 3-1769, 3-1770, 3-1771, 3-1772, 3-1773, 3-1774, 3-1775, 3-1776, 3-1777, 3-1778, 3-1779, 3-1780, 3-1781, 3-1782, 3-1783, 3-1784, 3-1785, 3-1786, 3-1787, 3-1788, 3-1789, 3-1790, 3-1791, 3-1792, 3-1793, 3-1794, 3-1795, 3-1796, 3-1797, 3-1798, 3-1799, 3-1800, 3-1801, 3-1802, 3-1803, 3-1804, 3-1805, 3-1806, 3-1807, 3-1808, 3-1809, 3-1810, 3-1811, 3-1812, 3-1813, 3-1814, 3-1815, 3-1816, 3-1817, 3-1818, 3-1819, 3-1820, 3-1821, 3-1822, 3-1823, 3-1824, 3-1825, 3-1826, 3-1827, 3-1828, 3-1829, 3-1830, 3-1831, 3-1832, 3-1833, 3-1834, 3-1835, 3-1836, 3-1837, 3-1838, 3-1839, 3-1840, 3-1841, 3-1842, 3-1843, 3-1844, 3-1845, 3-1846, 3-1847, 3-1848, 3-1849, 3-1850, 3-1851, 3-1852, 3-1853, 3-1854, 3-1855, 3-1856, 3-1857, 3-1858, 3-1859, 3-1860, 3-1861, 3-1862, 3-1863, 3-1864, 3-1865, 3-1866, 3-1867, 3-1868, 3-1869, 3-1870, 3-1871, 3-1872, 3-1873, 3-1874, 3-1875, 3-1876, 3-1877, 3-1878, 3-1879, 3-1880, 3-1881, 3-1882, 3-1883, 3-1884, 3-1885, 3-1886, 3-1887, 3-1888, 3-1889, 3-1890, 3-1891, 3-1892, 3-1893, 3-1894, 3-1895, 3-1896, 3-1897, 3-1898, 3-1899, 3-1900, 3-1901, 3-1902, 3-1903, 3-1904, 3-1905, 3-1906, 3-1907, 3-1908, 3-1909, 3-1910, 3-1911, 3-1912, 3-1913, 3-1914, 3-1915, 3-1916, 3-1917, 3-1918, 3-1919, 3-1920, 3-1921, 3-1962, 3-1963, 3-1964, 3-1965, 3-1966, 3-1967, 3-1968, 3-1969, 3-1970, 3-1971, 3-1972, 3-1973, 3-1974, 3-1975, 3-1976, 3-1977, 3-1978, 3-1979, 3-1980, 3-1981, 3-1982, 3-1983, 3-1984, 3-1985, 3-1986, 3-1987, 3-1988, 3-1989, 3-1990, 3-1991, 3-1992, 3-1993, 3-1994, 3-1995, 3-1996, 3-1997, 3-1998, 3-1999, 3-2000, 3-2001, 3-2002, 3-2003, 3-2004, 3-2005, 3-2006, 3-2007, 3-2008, 3-2009, 3-2010, 3-2011, 3-2012, 3-2013, 3-2014, 3-2015, 3-2016, 3-2017, 3-2018, 3-2019, 3-2020, 3-2021, 3-2022, 3-2023, 3-2024, 3-2025, 3-2026, 3-2027, 3-2028, 3-2029, 3-2030, 3-2031, 3-2032, 3-2033, 3-2034, 3-2035, 3-2036, 3-2037, 3-2038, 3-2039, 3-2040, 3-2041, 3-2042, 3-2043, 3-2044, 3-2045, 3-2046, 3-2047, 3-2048, 3-2049, 3-2050, 3-2051, 3-2052, 3-2053, 3-2054, 3-2055, 3-2056, 3-2057, 3-2058, 3-2059, 3-2060, 3-2061, 3-2062, 3-2063, 3-2064, 3-2065, 3-2066, 3-2067, 3-2068, 3-2069, 3-2070, 3-2071, 3-2072, 3-2073, 3-2074, 3-2075, 3-2076, 3-2077, 3-2078, 3-2079, 3-2080, 3-2081, 3-2082, 3-2083, 3-2084, 3-2085, 3-2086, 3-2087, 3-2088, 3-2089, 3-2090, 3-2091, 3-2092, 3-2093, 3-2094, 3-2095, 3-2096, 3-2097, 3-2098, 3-2099, 3-2100, 3-2101, 3-2102, 3-2103, 3-2104, 3-2105, 3-2106, 3-2107, 3-2108, 3-2109, 3-2110, 3-2111, 3-2112, 3-2113, 3-2114, 3-2115, 3-2116, 3-2117, 3-2118, 3-2119, 3-2120, 3-2121, 3-2122, 3-2123, 3-2124, 3-2125, 3-2126, 3-2127, 3-2128, 3-2129, 3-2130, 3-2131, 3-2132, 3-2133, 3-2134, 3-2135, 3-2136, 3-2137, 3-2138, 3-2139, 3-2140, 3-2141, 3-2142, 3-2143, 3-2144, 3-2145, 3-2146, 3-2147, 3-2148, 3-2149, 3-2150, 3-2151, 3-2152, 3-2153, 3-2154, 3-2155, 3-2156, 3-2157, 3-2158, 3-2159, 3-2160, 3-2161, 3-2162, 3-2163, 3-2429, 3-2430, 3-2431, 3-2432, 3-2433, 3-2434, 3-2435, 3-2436, 3-2437, 3-2438, 3-2439, 3-2440, 3-2441, 3-2442, 3-2443, 3-2444, 3-2445, 3-2446, 3-2447, 3-2448, 3-2449, 3-2450, 3-2451, 3-2452, 3-2453, 3-2454, 3-2455, 3-2456, 3-2457, 3-2458, 3-2459, 3-2460, 3-2461, 3-2462, 3-2463, 3-2464, 3-2465, 3-2466, 3-2467, 3-2468, 3-2469, 3-2470, 3-2471, 3-2472, 3-2473, 3-2474, 3-2475, 3-2476, 3-2477, 3-2478, 3-2479, 3-2480, 3-2481, 3-2482, 3-2483, 3-2484, 3-2485, 3-2486, 3-2487, 3-2488, 3-2489, 3-2490, 3-2491, 3-2492, 3-2493, 3-2494, 3-2495, 3-2496, 3-2497, 3-2498, 3-2499, 3-2500, 3-2501, 3-2502, 3-2503, 3-2504, 3-2505, 3-2506, 3-2507, 3-2508, 3-2509, 3-2510, 3-2511, 3-2512, 3-2513, 3-2514, 3-2515, 3-2516, 3-2517, 3-2518, 3-2519, 3-2520, 3-2521, 3-2522, 3-2523, 3-2524, 3-2525, 3-2526, 3-2527, 3-2528, 3-2529, 3-2530, 3-2531, 3-2532, 3-2533, 3-2534, 3-2535, 3-2536, 3-2537, 3-2538, 3-2539, 3-2540, 3-2541, 3-2542, 3-2543, 3-2544, 3-2545, 3-2546, 3-2547, 3-2548, 3-2549, 3-2550, 3-2551, 3-2552, 3-2553, 3-2554, 3-2555, 3-2556, 3-2557, 3-2558, 3-2559, 3-2560, 3-2561, 3-2562, 3-2563, 3-2564, 3-2565, 3-2566, 3-2567, 3-2568, 3-2569, 3-2570, 3-2571, 3-2572, 3-2573, 3-2574, 3-2575, 3-2576, 3-2577, 3-2578, 3-2579, 3-2580, 3-2581, 3-2582, 3-2583, 3-2584, 3-2585, 3-2586, 3-2587, 3-2588, 3-2589, 3-2590, 3-2591, 3-2592, 3-2593, 3-2594, 3-2595, 3-2596, 3-2597, 3-2598, 3-2599, 3-2600, 3-2601, 3-2602, 3-2603, 3-2604, 3-2605, 3-2606, 3-2607, 3-2608, 3-2609, 3-2610, 3-2611, 3-2612, 3-2613, 3-2614, 3-2657, 3-2665, 3-2667, and 3-2669.

The following compounds are more preferred, that is Compounds No.: 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-271, 1-272, 1-273, 1-274, 1-275, 1-276, 1-277, 1-278, 1-279, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-309, 1-310, 1-311, 1-312, 1-313, 3-314, 1-315, 1-316, 1-317, 1-318, 1-319, 1-320, 1-321, 1-322, 1-323, 1-324, 1-325, 1-326, 1-327, 1-328, 1-329, 1-330, 1-331, 1-332, 1-333, 1-334, 1-335, 1-336, 1-337, 1-338, 1-339, 1-340, 1-341, 1-342, 1-343, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-367, 1-368, 1-369, 1-370, 1-371, 1-372, 1-373, 1-374, 1-375, 1-376, 1-377, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, 1-396, 1-397, 1-398, 1-399, 1-400, 1-401, 1-402, 1-403, 1-404, 1-405, 1-406, 1-407, 1-408, 1-409, 1-410, 1-411, 1-412, 1-413, 1-414, 1-415, 1-416, 1-417, 1-418, 1-419, 1-420, 1-421, 1-422, 1-423, 1-424, 1-425, 1-426, 1-427, 1-428, 1-429, 1-430, 1-431, 1-432, 1-433, 1-434, 1-435, 1-436, 1-437, 1-438, 1-439, 1-440, 1-441, 1-442, 1-443, 1-444, 1-445, 1-446, 1-447, 1-448, 1-449, 1-450, 1-451, 1-452, 1-453, 1-454, 1-455, 1-456, 1-457, 1-458, 1-459, 1-460, 1-461, 1-462, 1-463, 1-464, 1-465, 1-466, 1-467, 1-468, 1-469, 1-470, 1-471, 1-472, 1-473, 1-474, 1-475, 1-476, 1-477, 1-478, 1-479, 1-480, 1-481, 1-482, 1-483, 1-484, 1-485, 1-486, 1-487, 1-488, 1-489, 1-490, 1-491, 1-492, 1-493, 1-494, 1-495, 1-496, 1-497, 1-498, 1-499, 1-500, 1-501, 1-502, 1-503, 1-504, 1-505, 1-506, 1-507, 1-508, 1-509, 1-510, 1-511, 1-512, 1-513, 1-514, 1-515, 1-516, 1-517, 1-518, 1-519, 1-520, 1-521, 1-522, 1-523, 1-524, 1-525, 1-526, 1-527, 1-528, 1-529, 1-530, 1-531, 1-532, 1-533, 1-534, 1-535, 1-536, 1-537, 1-538, 1-539, 1-676, 1-677, 1-678, 1-679, 1-680, 1-681, 1-682, 1-683, 1-684, 1-685, 1-686, 1-687, 1-688, 1-689, 1-690, 1-691, 1-692, 1-693, 1-694, 1-695, 1-696, 1-697, 1-698, 1-699, 1-700, 1-701, 1-702, 1-703, 1-704, 1-705, 1-706, 1-707, 1-708, 1-709, 1-710, 1-711, 1-712, 1-713, 1-714, 1-715, 1-716, 1-717, 1-718, 1-719, 1-720, 1-721, 1-722, 1-723, 1-724, 1-725, 1-726, 1-727, 1-728, 1-729, 1-730, 1-731, 1-732, 1-733, 1-734, 1-735, 1-736, 1-737, 1-738, 1-739, 1-740, 1-741, 1-742, 1-743, 1-744, 1-745, 1-746, 1-747, 1-748, 1-749, 1-750, 1-751, 1-752, 1-753, 1-754, 1-755, 1-756, 1-757, 1-758, 1-759, 1-760, 1-761, 1-762, 1-763, 1-764, 1-765, 1-766, 1-767, 1-768, 1-769, 1-770, 1-771, 1-772, 1-773, 1-774, 1-775, 1-776, 1-777, 1-778, 1-779, 1-780, 1-781, 1-782, 1-783, 1-784, 1-785, 1-786, 1-787, 1-788, 1-789, 1-790, 1-791, 1-792, 1-793, 1-794, 1-795, 1-796, 1-797, 1-798, 1-799, 1-800, 1-801, 1-802, 1-803, 1-804, 1-805, 1-806, 1-807, 1-808, 1-809, 1-810, 1-811, 1-812, 1-813, 1-814, 1-815, 1-816, 1-817, 1-818, 1-819, 1-820, 1-821, 1-822, 1-823, 1-824, 1-825, 1-826, 1-827, 1-828, 1-829, 1-830, 1-831, 1-832, 1-833, 1-834, 1-835, 1-836, 1-837, 1-838, 1-839, 1-840, 1-841, 1-842, 1-843, 1-844, 1-845, 1-846, 1-847, 1-848, 1-849, 1-850, 1-851, 1-852, 1-853, 1-854, 1-855, 1-856, 1-857, 1-858, 1-859, 1-860, 1-861, 1-862, 1-863, 1-1112, 1-1113, 1-1114, 1-1115, 1-1116, 1-1117, 1-1118, 1-1119, 1-1120, 1-1121, 1-1122, 1-1123, 1-1124, 1-1125, 1-1126, 1-1127, 1-1128, 1-1129, 1-1130, 1-1131, 1-1132, 1-1133, 1-1134, 1-1135, 1-1136, 1-1137, 1-1138, 1-1139, 1-1140, 1-1141, 1-1142, 1-1143, 1-1144, 1-1145, 1-1146, 1-1147, 1-1148, 1-1224, 1-1258, 1-1259, 1-1260, 1-1261, 1-1262, 1-1263, 1-1264, 1-1265, 1-1266, 1-1267, 1-1268, 1-1269, 1-1270, 1-1271, 1-1272, 1-1273, 1-1274, 1-1275, 1-1276, 1-1277, 1-1278, 1-1279, 1-1280, 1-1962, 1-1963, 1-1964, 1-1965, 1-1966, 1-1967, 1-1968, 1-1969, 1-1970, 1-1971, 1-1972, 1-1973, 1-1974, 1-1975, 1-1976, 1-1977, 1-1978, 1-1979, 1-1980, 1-1981, 1-1982, 1-1983, 1-1984, 1-1985, 1-1986, 1-1987, 1-1988, 1-1989, 1-1990, 1-1991, 1-1992, 1-1993, 1-2470, 1-2471, 1-2472, 1-2473, 1-2474, 1-2475, 1-2476, 1-2477, 1-2478, 1-2479, 1-2480, 1-2481, 1-2482, 1-2483, 1-2484, 1-2485, 1-2486, 1-2487, 1-2488, 1-2489, 1-2490, 1-2491, 1-2492, 1-2493, 1-2494, 1-2495, 1-2496, 1-2497, 1-2498, 1-2499, 1-2500, 1-2501, 1-2502, 1-2503, 1-2504, 1-2505, 1-2506, 1-2507, 1-2508, 1-2509, 1-2510, 1-2511, 1-2512, 1-2513, 1-2514, 1-2515, 1-2516, 1-2517, 1-2518, 1-2519, 1-2520, 1-2521, 1-2522, 1-2523, 1-2524, 1-2525, 1-2526, 1-2527, 1-2528, 1-2529, 1-2530, 1-2531, 1-2532, 1-2533, 1-2534, 1-2535, 1-2536, 1-2537, 1-2538, 1-2539, 1-2540, 1-2541, 1-2542, 1-2543, 1-2544, 1-2545, 1-2546, 1-2547, 1-2548, 1-2549, 1-2550, 1-2551, 1-2552, 1-2553, 1-2554, 1-2555, 1-2556, 1-2557, 1-2558, 1-2559, 1-2660, 1-2661, 1-2662, 1-2663, 1-2664, 1-2565, 1-2566, 1-2567, 1-2568, 1-2569, 1-2570, 1-2571, 1-2572, 1-2573, 1-2574, 1-2575, 1-2576, 1-2577, 1-2578, 1-2579, 1-2580, 1-2581, 1-2582, 1-2583, 1-2584, 1-2585, 1-2586, 1-2587, 1-2588, 1-2589, 1-2590, 1-2591, 1-2592, 1-2593, 1-2594, 1-2595, 1-2596, 1-2597, 1-2598, 1-2599, 1-2600, 1-2601, 1-2602, 1-2603, 1-2604, 1-2605, 1-2606, 1-2607, 1-2608, 1-2609, 1-2610, 1-2611, 1-2612, 1-2613, 1-2614, 1-2657, 1-2665, 1-2667 and 1-2669.

The following compounds are still more preferred, that is Compounds No.: 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-271, 1-272, 1-273, 1-274, 1-275, 1-276, 1-277, 1-278, 1-279, 1-280, 1-281, 1-282, 1-283, 1-284, 1-285, 1-286, 1-457, 1-458, 1-459, 1-460, 1-461, 1-462, 1-463, 1-464, 1-465, 1-466, 1-467, 1-468, 1-469, 1-470, 1-471, 1-472, 1-473, 1-474, 1-475, 1-476, 1-477, 1-478, 1-479, 1-480, 1-481, 1-482, 1-483, 1-484, 1-485, 1-486, 1-487, 1-488, 1-489, 1-490, 1-491, 1-492, 1-493, 1-494, 1-495, 1-496, 1-497, 1-498, 1-499, 1-500, 1-501, 1-502, 1-503, 1-504, 1-505, 1-506, 1-507, 1-508, 1-509, 1-510, 1-511, 1-512, 1-513, 1-514, 1-515, 1-516, 1-517, 1-518, 1-519, 1-520, 1-521, 1-522, 1-523, 1-524, 1-525, 1-526, 1-527, 1-528, 1-529, 1-530, 1-531, 1-532, 1-533, 1-534, 1-535, 1-536, 1-537, 1-538, 1-539, 1-733, 1-734, 1-735, 1-736, 1-737, 1-738, 1-739, 1-740, 1-741, 1-742, 1-743, 1-744, 1-745, 1-746, 1-747, 1-748, 1-749, 1-750, 1-815, 1-816, 1-817, 1-818, 1-819, 1-820, 1-821, 1-822, 1-824, 1-824, 1-825, 1-826, 1-827, 1-828, 1-829, 1-830, 1-831, 1-832, 1-833, 1-834, 1-835, 1-836, 1-837, 1-838, 1-839, 1-840, 1-841, 1-842, 1-843, 1-844, 1-845, 1-846, 1-847, 1-848, 1-849, 1-850, 1-851, 1-852, 1-853, 1-854, 1-855, 1-856, 1-857, 1-858, 1-859, 1-860, 1-861, 1-862, 1-863, 1-1129, 1-1130, 1-1131, 1-1132, 1-1133, 1-1134, 1-1135, 1-1136, 1-1137, 1-1138, 1-1139, 1-1140, 1-1141, 1-1142, 1-1143, 1-1144, 1-1145, 1-1146, 1-1147, 1-1148, 1-1224, 1-1258, 1-1259, 1-1260, 1-1261, 1-1262, 1-1263, 1-1264, 1-1265, 1-1266, 1-1267, 1-1268, 1-1269, 1-1270, 1-1271, 1-1272, 1-1273, 1-1274, 1-1275, 1-1276, 1-1277, 1-1278, 1-1279, 1-1280, 1-1962, 1-1963, 1-1964, 1-1965, 1-1966, 1-1967, 1-1968, 1-1969, 1-1970, 1-1971, 1-1972, 1-1973, 1-1974, 1-1975, 1-1976, 1-1977, 1-1978, 1-1979, 1-1980, 1-1981, 1-1982, 1-1983, 1-1984, 1-1985, 1-1986, 1-1987, 1-1988, 1-1989, 1-1990, 1-1991, 1-1992, 1-1993, 1-2470, 1-2471, 1-2472, 1-2473, 1-2474, 1-2475, 1-2476, 1-2477, 1-2478, 1-2479, 1-2480, 1-2481, 1-2482, 1-2483, 1-2484, 1-2485, 1-2486, 1-2487, 1-2488, 1-2489, 1-2490, 1-2491, 1-2492, 1-2493, 1-2494, 1-2495, 1-2496, 1-2497, 1-2498, 1-2499, 1-2500, 1-2501, 1-2502, 1-2503, 1-2504, 1-2505, 1-2506, 1-2507, 1-2508, 1-2509, 1-2510, 1-2511, 1-2512, 1-2513, 1-2514, 1-2515, 1-2516, 1-2517, 1-2518, 1-2519, 1-2520, 1-2521, 1-2522, 1-2523, 1-2524, 1-2525, 1-2526, 1-2527, 1-2528, 1-2529, 1-2530, 1-2531, 1-2532, 1-2533, 1-2534, 1-2535, 1-2536, 1-2537, 1-2538, 1-2539, 1-2540, 1-2541, 1-2542, 1-2543, 1-2544, 1-2545, 1-2546, 1-2547, 1-2548, 1-2549, 1-2550, 1-2551, 1-2552, 1-2553, 1-2554, 1-2555, 1-2556, 1-2557, 1-2558, 1-2559, 1-2560, 1-2561, 1-2562, 1-2563, 1-2564, 1-2565, 1-2566, 1-2567, 1-2568, 1-2569, 1-2570, 1-2571, 1-2572, 1-2573, 1-2574, 1-2575, 1-2576, 1-2577, 1-2578, 1-2657, 1-2665, 1-2667 and 1-2669.

The following compounds are even more preferred, that is Compounds No.:

1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-271, 1-272, 1-273, 1-274, 1-275, 1-276, 1-277, 1-278, 1-279, 1-280, 1-281, 1-282, 1-283, 1-284, 1-285, 1-286, 1-457, 1-458, 1-459, 1-460, 1-461, 1-462, 1-463, 1-464, 1-465, 1-466, 1-467, 1-468, 1-469, 1-470, 1-471, 1-472, 1-473, 1-474, 1-475, 1-476, 1-477, 1-478, 1-479, 1-480, 1-481, 1-482, 1-483, 1-484, 1-485, 1-486, 1-487, 1-488, 1-489, 1-490, 1-491, 1-492, 1-493, 1-494, 1-495, 1-496, 1-497, 1-498, 1-499, 1-500, 1-501, 1-502, 1-503, 1-504, 1-505, 1-506, 1-507, 1-508, 1-509, 1-510, 1-511, 1-512, 1-513, 1-514, 1-515, 1-516, 1-517, 1-518, 1-519, 1-520, 1-521, 1-522, 1-523, 1-524, 1-525, 1-526, 1-527, 1-528, 1-529, 1-530, 1-531, 1-532, 1-533, 1-534, 1-535, 1-536, 1-537, 1-538, 1-539, 1-733, 1-734, 1-735, 1-736, 1-737, 1-738, 1-739, 1-740, 1-741, 1-742, 1-743, 1-744, 1-745, 1-746, 1-747, 1-748, 1-749, 1-750, 1-815, 1-820, 1-861, 1-1134, 1-1135, 1-1136, 1-1137, 1-1138, 1-1139, 1-1140, 1-1141, 1-1142, 1-1143, 1-1144, 1-1145, 1-1146, 1-1147, 1-1148, 1-1224, 1-1258, 1-1259, 1-1260, 1-1261, 1-1262, 1-1263, 1-1264, 1-1265, 1-1266, 1-1267, 1-1268, 1-1269, 1-1270, 1-1271, 1-1272, 1-1273, 1-1274, 1-1275, 1-1276, 1-1277, 1-1278, 1-1279, 1-1280, 1-1963, 1-1993, 1-2470, 1-2520, 1-2566, 1-2567, 1-2568, 1-2569, 1-2570, 1-2571, 1-1272, 1-2573, 1-2574, 1-2575, 1-2576, 1-2577, 1-2578, 1-2657, 1-2665, 1-2667 and 1-2669.

The following compounds are further preferred, that is Compounds No.: 1-46, 1-47, 1-48, 1-49, 1-50, 1-71, 1-271, 1-496, 1-539, 1-733, 1-739, 1-740, 1-741, 1-742, 1-815, 1-820, 1-861, 1-1135, 1-1145, 1-1224, 1-1258, 1-1260, 1-1275, 1-1276, 1-1280, 1-1963, 1-1993, 1-2470, 1-2520, 1-2567, 1-2665, 1-2667 and 1-2669.

The following compounds are particularly preferred, that is Compounds No.: 1-49, 1-271, 1-496, 1-539, 1-733, 1-738, 1-739, 1-740, 1-741, 1-742, 1-820, 1-861, 1-1135, 1-1224, 1-1258, 1-1260, 1-1275, 1-1963, 1-2470, 1-2520, 1-2567, 1-2657, 1-2665, 1-2667, and 1-2669.

The most preferred compounds are

N-[5-(1,2-Dithiolan-3-yl)pentanoyl]methanesulfonamide (Compound No. 1-496);

Methyl 3-[4-(1,2-dithiolan-3-yl)butyl]ureidoacetate (Compounds No. 1-739);

2(S)-{3-[4-[1,2-Dithiolan-3-yl)butyl]ureido}propionic acid (Compound No. 1-740);

Methyl 2(S)-{3-[4-(1,2-dithiolan-3-yl)butyl [ureido}propionate (Compound No. 1-742);

Ethyl 3-[4-(1,2-dithiolan-3-yl)butyl]-1- methylureidoacetate (Compound No. 1-820 ethyl ester); and N-[5-(1,2-Dithiolan-3-yl)pentyl]methanesulfonamide (Compound No. 1-2470);

and pharmaceutically acceptable salts thereof.

The compounds of the present invention may be prepared by a variety of methods well known for the preparation of compounds of this general type. For example, they may be prepared by the following Methods A to G.

Method A

In this Method, a compound of formula (II) is reacted with a compound of formula (III), to give a compound of formula (Ia), which is a compound of formula (I) in which the meanings of A and B are somewhat restricted.

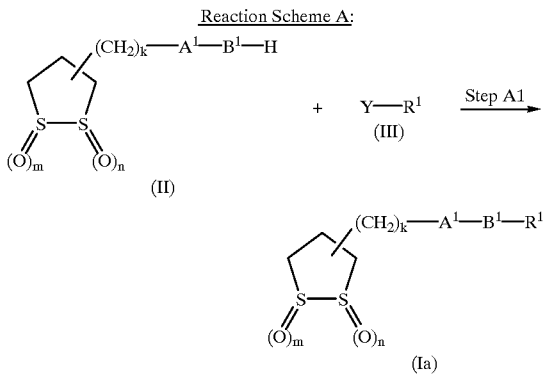

Reaction Scheme A:

In the above formulae:

$R^1$, k, m and n are as defined above;

$A^1$ represents any of the groups defined above for A, other than the groups of formula —CO—O— and —N($R^2$)O—[wherein $R^2$ is as defined above];

$B^1$ represents a group of formula —N($R^5$)— or —N($R^5$)N($R^6$)—[wherein $R^5$ and $R^6$ are as defined above]; and Y represents a group to be eliminated.

There is no particular restriction on the group to be eliminated, provided that it can be eliminated as a nucleophilic residue, and examples of such groups are well known to thos skilled in the art. Specific examples of such groups include:

halogen atoms, such as the chlorine, bromine and iodine atoms trihalomethyl groups, such as the trichloromethyl group;

lower alkanesulfonyloxy groups, such as the methanesulfonyloxy and ethanesulfonyloxy groups;

lower haloalkanesulfonyloxy groups, such as the trifluoromethanesulfonyloxy and pentafluoroethanesulfonyloxy groups; and arylsulfonyloxy groups, such as the benzenesulfonyloxy, p-toluenesulfonyloxy and p-nitrobenzenesulfonyloxy groups.

Of these, a halogen atom or an alkanesulfonyl group is preferred.

Step A1

In this Step, a dithiolan derivative of formula (Ia) is prepared by reacting a compound of formula (II) with a compound of formula (III) in a solvent in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include:

aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and disthylene glycol dimethyl ether; ketones, such as acetone, methyl ethyl ketone, methyl isobutyl ketone, isophorone and cyclohexanone; nitriles, such as acetonitrile, propionitrile and isobutyronitrile, amides, such a formamide, dimethylformamide, N,N-dimethylacetamide, N-methyl-2-pyrrolidone, N-methylpyrrolidinone and hexamethyl-phosphoric triamide; sulfoxides, such as dimethyl sulfoxide; and sulfones, such as sulfolane. Of these, we prefer the ketones, ethers and amides, more preferably acetone, tetrahydrofuran, dimethylformamide and N,N-dimethylacetamide.

There is likewise no particular restriction on the nature of the bases used, and any base commonly used in reactions of this type may equally be used here. Examples of such bases include: inorganic bases, such as alkali metal carbonates (for example sodium carbonate, potassium carbonate, lithium carbonate or cesium carbonate), alkali metal hydrogencarbonates (for example sodium hydrogencarbonate, potassium hydrogencarbonate or lithium hydrogencarbonate), alkali matals hydrides (for example lithium hydride, sodium hydride or potassium hydride), alkali metal or alkaline earth metal hydroxides (for example sodium hydroxide, potassium hydroxide, barium hydroxide or lithium hydroxide) and alkali metal fluorides (for example sodium fluoride or potassium fluoride); and alkali metal alkoxides (for example sodium sodium ethoxide, potassium methoxide, potassium ethoxide, potassium t-butoxide or lithium methoxide. Of these, the alkali metal carbonates, alkali metal hydrides and alkali metal alkoxides are preferred, and potassium carbonate, sodium, hydride and potassium t-butoxide are most preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 12 hours, will usually suffice.

Method B

This demonstrates the preparation of a compound of formula (Ib), that is a compound of formula (I) in which A represents an oxygen atom, or a group of formula —N($R^2$)CO—, —N($R^2$)$SO_2$—, —ON($R^2$)CO—, —ON($R^2$)$SO_2$—, —N($R^2$)N($R^3$)CO—, —($R^2$)N($R^3$)$SO_2$—, —N($R^2$)CON($R^3$)N($R^4$)CO—, —N($R^2$)CON($R^3$)CO— or —N($R^2$)CON($R^3$)$SO_2$—[wherein $R^2$, $R^3$ and $R^4$ are as defined above].

Reaction Scheme B:

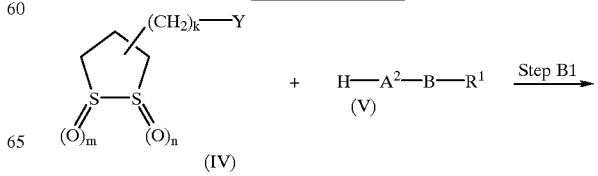

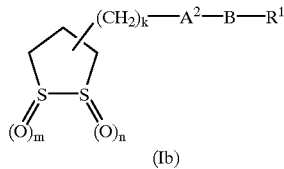
(Ib)

In the above formulae:

B, $R^1$, Y, k, m and n are as defined above; and $A^2$ represents an oxygen atom, or a group of formula —$N(R^2)CO$—, —$N(R^2)SO_2$—, —$ON(R^2)CO$—, —$ON(R^2)SO_2$—, —$N(R^2)N(R^3)CO$—, —$(R^2)N(R^3)SO_2$—, —$N(R^2)CON(R^3)N(R^4)CO$—, —$N(R^2)CON(R^3)CO$— or —$N(R^2)CON(R^3)SO_2$—[wherein $R^2$, $R^3$ and $R^4$ are as defined above].

Step B1

In this Step, a dithiolan derivative of formula (Ib) is prepared by reacting a compound of formula (IV) with a compound of formula (V) in a solvent in the presence of a base. The reaction is essentially the same as that described above in Step A1, and may be carried out using the same solvents, bases and reaction conditions.

Method C

This demonstrates the preparation of a compound of formula (Ic), that is a compound of formula (I) in which A represents a group of formula —$N(R^2)CO$—, —$N(R^2)SO_2$—, —$CON(R^2)N(R^3)CO$—, —$CON(R^2)CO$—, —$CON(R^2)SO_2$—, —O—CO—, —$ON(R^2)CO$—, —$ON(R^2)SO_2$—, —O—$CON(R^2)N(R^3)CO$—, —O—$CON(R^2)CO$—, —O—$CON(R^2)SO_2$—, —CO—$CON(R^2)N(R^3)CO$—, —CO—$CON(R^2)CO$—, —CO—$CON(R^2)SO_2$—, —$N(R^2)CO$—CO—, —$N(R^2)N(R^3)CO$—, —$N(R^2)N(R^3)SO_2$—, —$N(R^2)CON(R^3)N(R^4)CO$—, —$N(R^2)CON(R^3)CO$— or —$N(R^2)CON(R^3)SO_2$—[wherein $R^2$, $R^3$ and $R^4$ are as defined above], and B represents a single bond.

Reaction Scheme C:

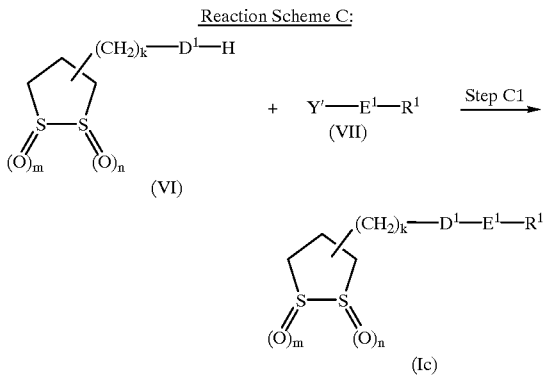

In the above formulae:

$R^1$, k, m and n are as defined above, $D^1$ represents an oxygen atom, or a group of formula —$N(R^2)$—, —$CON(R^2)$—, —$ON(R^2)$—, —O—$CON(R^2)$—, —$N(R^2)N(R^3)$— or —$N(R^2)CON(R^3)$— [wherein $R^2$ and $R^3$ are as defined above], $E^1$ represents a carbonyl group, a sulfonyl group or a group of formula —COCO—, and Y' represents a group to be eliminated, as in the definition of Y; however, the imidazolyl group, or an active ester residue, including acyloxy groups, such as the acetoxy group, or alkoxyacyloxy groups, such as the methoxyacetoxy group, are preferred.

Step C1

In this Step, a dithiolan derivative of formula (Ic) is prepared by acylating or sulfonylating a compound of formula (VI) with a compound of formula (VII) in a solvent in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile, propionitrile and isobutyronitrile; and amides, such as formamide, dimethylformamide, N,N-dimethylacetamide, N-methyl-2-pyrrolidone, N-methylpyrrolidinone and hexamethylphosphoric triamide. Of these, the aromatic hydrocarbons, halogentated hydrocarbons, ethers and amides are preferred, and halogenated hydrocarbons, ethers and amides are more preferred.

There is likewise no particular restriction on the nature of the bases used, and any base commonly used in reactions of this type may equally be used here. Examples of such based include: organic bases, such as N-methylmorpholine, triethylamine, tripropylamine, tributylamine, diisopropylethylamine, N-methyldicyclohexylamine, N-methylpiperidine, pyridine, 4-pyrrolidinopyridine, picoline, 4-(N,N-dimethylamino)pyridine, pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), of these, triethylamine and diisopropylethylamine are preferred.

The reaction can take place over a wide range of temperatures, and the precise reaction temperature is not critical to the invention. The preferred reaction temperature will depend upon such factors as the nature of the solvent, and the starting material or reagent used. However, in general, we fine it convenient to carry out the reaction at a temperature of from −20° C. to 100° C., more preferably from 0° C. to 80° C. The time required for the reaction may also vary widely, depending on many factors, notably the reaction temperature and the nature of the reagents and solvent employed. However, provided that the reaction is effected under the preferred conditions outlined above, a period of from 5 minutes to 2 days, more preferably from 20 minutes to 1 day, will usually suffice.

As an alternative, where the compound of formula (VI) is reacted with a compound of formula (VII) in which $E^1$ represents a carbonyl group, the reaction may also be accomplished using a compound of formula HOOC—$R^1$ (wherein $R^1$ is as defined above) by reacting the compound of formula (VI) with the compound of formula (VII) using a condensing agent in a solvent in the presence or absence of a base.

There is no particular restriction on the nature of the condensing agents used, and any condensing agent commonly used in reactions of this type may equally be used here. Examples of such condensing agents include:

(1) a combination of a phosphoric acid ester, such as diethyl cyanophosphate or diphenylphosphoryl azide, and the base described below;
(2) a carbodiimide, such as 1,3-dicyclohexylcarbodiimide, 1,3-diisopropylcarbodiimide or 1-ethyl-3-(3-dimethylaminopropyl)carbodiimide; a combination of one or more of the above carbodiimides and the base described below; a combination of one or more of the above carbodiimides and an N-hydroxy compound, such as N-hydroxysuccinimide, 1-hydroxybenzotriazole or N-hydroxy-5-norbornene-2,3-dicarboxyimide;
(3) a combination of a disulfide, such as 2,2'-dipyridyl disulfide or 2,2'-dibenzothiazolyl disulfide, and a phosphine, such as triphenylphosphine or tributylphosphine;
(4) a carbonate, such as N,N'-disuccinimidyl carbonate, di-2-pyridyl carbonate or S,S'-bis(1-phenyl-1H-tetrozol-5-yl)dithiocarbonate;
(5) a phosphinic chloride, such as N,N'-bis(2-oxo-3-oxazolidinyl)phosphinic chloride;
(6) an oxalate, such as N,N'-disuccinimidyl oxalate, N,N'-diphthalimide oxalate, N,N'-bis(5-norbornene-2,3-dicarboxyimidyl)oxalate, 1,1'-bis(benzotrialzolyl) oxalate, 1,1'-bis(6-chlorobenzotriazolyl) oxalate or 1,1'-bis(6-trifluoromethylbenzotriazolyl) oxalate;
(7) a combination of one or more of the above phosphines and an azodicarboxylic acid ester, such as diethyl azodicarboxylate, or an azodicarboxylic amide, such as 1,1'-(azodicarbonyl)dipiperidine; a combination of one or more of the above phosphines and the base described below;
(8) an N-lower alkyl-5-arylisoxazolium-3'-sulfonate, such as N-ethyl-5-phenylisoxazolium-3'-sulfonate;
(9) a diheteroaryldiselenide, such as di-2-pyridyl diselenide;
(10) an arylsulfonyltriazolide, such as p-nitrobenzenesulfonyltriazolide;
(11) a 2-halo-1-lower alkylpyridinium halide, such as 2-chloro-1-methylpyridinium iodide;
(12) an imidazole, such as 1,1'-oxalydiimidazole or N,N'-carbonyldiimidazole;
(13) a 3-lower alkyl-2-halobenzothiazolium fluoroborate such as 3-ethyl-2-chloro-benzothiazolium fluoroborate;
(14) a 3-lower alkyl-benzothiazole-2-serone, such as 3-methyl-benzothiazole-2-serone;
(15) a phosphate, such as phenyldichlorophosphate or polyphosphate ester;
(16) a halosulfonyl isocyanate, such as chlorosulfonyl isocyanate;
(17) a halosilane, such as trimethylsilyl chloride or triethylsilyl chloride;
(18) a combination of a lower alkanesulfonyl halide, such as methanesulfonyl chloride and the base described below;
(19) an N,N,N',N'-tetra lower alkylhaloformamidium chloride, such as N,N',N'-tetramethylchloroformamidium chloride; and
(20) a combination of a lower alkyloxycarbonyl halide, such as ethyl chlorocarbonate and the base described below;
preferably the above (1), (2), (7), (12) and (20).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyrontrile; and amides, such as formamide, dimethylformamide, N,N-dimethylacetamide, N-methyl-2-pyrrolidone, N-methylpyrrolidinone and hexamethylphosphoric triamide.

There is likewise no particular restriction on the nature of the bases used, and any base commonly used in reactions of this type may equally be used here. Examples of such bases include: organic bases, such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, quinoline, N,N-dimethylaniline and N,N-diethylaniline.

If desired, 4-(N,N-dimethylamino)pyridine and 4-pyrrolidinopyridine can be combined with other bases and used in a catalytic amount. Also, in order to carry out the reaction more effectively, a dehydrating agent such as a molecular sieve, a quaternary ammonium salt (for example benzyltriethylammonium chloride or tetrabutylammonium chloride), a crown ether, such as dibenzo-18-crown-6, or an acid trapping agent, such as 3,4-dihydro-2H-pyrido[1,2-1] pyrimidin-2-one, can be added to the reaction mixture.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Method D

This demonstrates the preparation of a compound of formula (Id), that is a compound of formula (I) in which A represents a carbonyl group, or a group of formula —CON($R^2$)N($R^3$)CO—, —CON($R^2$)CO—, —CON($R^2$)SO$_2$—, —CO—O—, —CO—CON($R^2$)N($R^3$)CO—, —CO—CON($R^2$)CO— or —CO—CON($R^2$)SO$_2$—[wherein $R^2$ and $R^3$ are as defined above].

Reaction Scheme D:

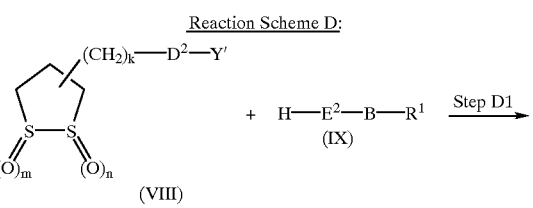

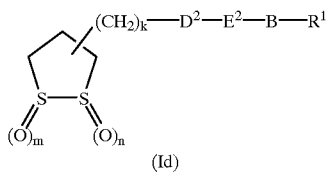

In the above formulae:

B, $R^1$, Y', k, m and n are as defined above, $D^2$ represents a carbonyl group or a group of formula —CO—CO—, and $E^2$ represents an oxygen atom, or a group of formula —N($R^2$)N($R^3$)CO—, —N($R^2$)CO— or —N($R^2$)$SO_2$— [wherein $R^2$ and $R^3$ are as defined above].

Step D1

In this Step, a dithiolan derivative of formula (Id) is prepared by acylating a compound of formula (IX) with a compound of formula (VIII) in a solvent in the presence of a base. The reaction is essentially the same as that described above in Step C1, and may be carried out using the same solvents, bases and reaction conditions.

Alternatively, the dithiolan derivative of formula (Id) can be prepared by reacting a compound of formula (VIII') with the compound of formula (IX) using a condensing agent in a solvent in the presence or absence of a base.

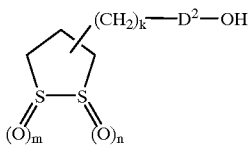

(VIII')

(wherein $D^2$, k, m and n are as defined above.)

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyrontrile; and amides, such as formamide, dimethylformamide, N,N-dimethylacetamide, N-methyl-2-pyrrolidone, N-methylpyrrolidinone and hexamethylphosphoric triamide.

There is likewise no particular restriction on the nature of the bases used, and any base commonly used in reactions of this type may equally be used here. Examples of such bases include: organic bases, such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, quinoline, N,N-dimethylaniline and N,N-diethylaniline.

If desired, 4-(N,N-dimethylamino)pyridine and 4-pyrrolidinopyridine can be combined with other bases and used in a catalytic amount. Also, in order to carry out the reaction more effectively, a dehydrating agent such as a molecular sieve, a quaternary ammonium salt (for example benzyltriethylammonium chloride or tetrabtylammonium chloride), a crown ether, such as dibenzo-18-crown-6, or an acid trapping agent, such as 3,4-dihydro-2H-pyrido[1,2-1] pyrimidin-2-one, can be added to the reaction mixture.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Method E

This demonstrates the preparation of a compound of formula (Ie), that is a compound of formula (I) in which:

A represents a group of formula —N($R^2$)CO—[wherein $R^2$ represents a hydrogen atom], and B represents a group of formula —N($R^5$)— or —N($R^5$)N($R^6$)—[wherein $R^5$ and $R^6$ are as defined above].

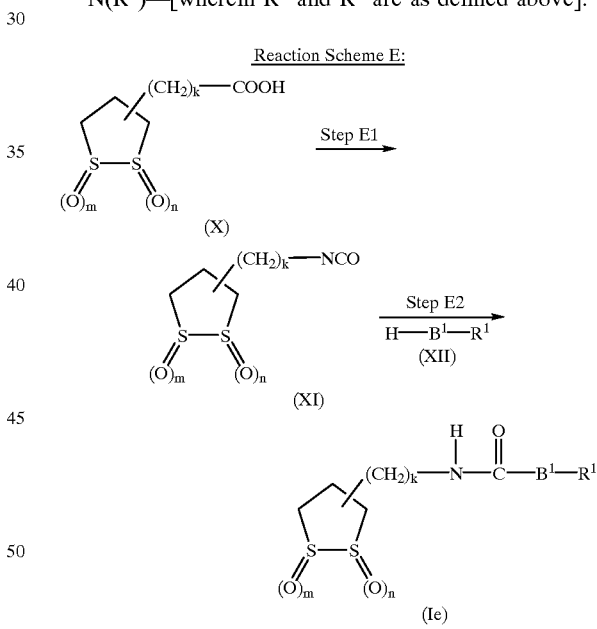

In the above formulae: $B^1$, $R^1$, k, m and n are as defined above.

Step E1

In this Step, an isocyanic acid ester of formula (XI) is prepared by azidating the carboxy group of a compound of formula (X) in a solvent in the presence or absence of a catalyst to obtain an acid azide compound and then heating it.

The azidation reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride and chloroform; ethers, such as diethyl ether, tetrahydrofuran, dioxane and dimethoxyethane; nitriles, such as acetonitrile; and amides, such as formamide, dimethylformamide, N,N-dimethylacetamide, N-methyl-2-pyrrolidone, N-methylpyrrolidinone and hexamethylphosphoric triamide. Of these, we prefer the aromatic hydrocarbons, the halogenated hydrocarbons and the ethers.

There is likewise no particular restriction on the nature of the azidation agents used, an any azidation agent commonly used in reactions of this type may equally be used here. Examples of such azidation agents include: diarylphosphoryl azide derivatives, such as diphenylphosphoryl azide; trialkylsilyl azides, such as trimethylsilyl azide or triethylsilyl azide; and alkali metal salt azides, such as sodium azide, potassium azide or lithium azide. Of these, we prefer the diarylphosphoryl azide derivatives.

There is likewise no particular restriction on the nature of the catalysts used, and any catalyst commonly used in reactions of this type may equally be used here. Examples of such catalysts include: Lewis acids, such as trialkylsilyl triflates (e.g. trimethylsilyl triflate and triethysilyl triflate), trifluoroborane etherate, aluminum chloride and zinc chloride; and organic bases, such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di-t-butyl-4-methylpyridine, quinoline, N,N-dimethylaniline and N,N-diethylaniline.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 20° C. to 180° C., more preferably from 50° C. to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 8 hours, will usually suffice.

Step E2

In this Step, a dithiolan derivative of formula (Ie) is prepared by reacting an isocyanic acid ester (XI) with a compound of formula (XII) in a solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile, propionitrile and isobutyronitrile; and amides, such as formamide, dimethylformamide, N,N-dimethylacetamide, N-methyl-2-pyrrolidone, N-methylpyrrolidinone and hexamethylphosphoric triamide; sulfoxides, such as dimethyl sulfoxide; and sulfones, such as sulfolane. Of these, we prefer the aromatic hydrocarbons, halogenated hydrocarbons, ethers, nitriles and amides, more preferably the aromatic hydrocarbons, halogentated hydrocarbons, ethers, nitriles and amides.

The reaction can take place over a wide range of temperatures, and the precise reaction temperature is not critical to the invention. The preferred reaction temperature will depend upon such factors as the nature of the solvent, and the starting material or reagent used. However, in general, we fine it convenient to carry out the reaction at a temperature of from −20° C. to 100° C., more preferably from 0° C. to 80° C. The time required for the reaction may also vary widely, depending on many factors, notably the reaction temperature and the nature of the reagents and solvent employed. However, provided that the reaction is effected under the preferred conditions outlined above, a period of from 5 minutes to 2 days, more preferably from 20 minutes to 1 day, will usually suffice.

Alternatively, the compound of formula (I) in which A represents a group of formula —N($R^2$)CON($R^3$)N($R^4$)CO—, —N($R^2$)CON($R^3$)CO— or —N($R^2$)CON($R^3$)SO$_2$—[wherein $R^2$ represents a hydrogen atom, and $R^3$ and $R^4$ are as defined above]can be prepared by reacting the above isocyanic acid ester of formula (XI) with a compound of formula: H—$D^3$—B—$R^1${wherein B and $R^1$ are as defined above, and $D^3$ represents a group of formula —N($R^3$)N($R^4$)CO—, —N($R^3$)CO— or —N($R^3$)SO$_2$—[wherein $R^3$ and $R^4$ are as defined above]}, following the same procedure as described above.

A compound of formula (I) in which A represents a group of formula —N($R^2$)CO— (wherein $R^2$ represents a hydrogen atom), B represents a single bond, and $R^1$ represents a group O$R^7$ (wherein $R^7$ is as defined above) can be prepared by reacting the above isocyanic acid ester of formula (XI) with a compound of formula: HO$R^7$ (wherein $R^7$ is as defined above), following the same procedure as described above.

A hydrogen atom of an amino, amide or imide group can be replaced by another group by reacting a compound of formula (I) in which $R^2$, $R^3$, $R^4$, $R^5$ and/or $R^6$ represent a hydrogen atom with a compound of formula: Y—$R^8$ (in which Y is as defined above and $R^8$ represents a group other than a hydrogen atom in the definition of $R^2$, $R^3$, $R^4$ and $R^6$) according to the above Method A, or by alkylation using a combination of an alcohol and a carbodiimide, such as dicyclohexylcarbodiimide. For example, after the dithiolan derivative of the present invention is synthesized according to the above Method E, a hydrogen atom of an amide group in the compound can be replaced by another group by these processes.

Method F

This demonstrates the preparation of a compound of formula (If), that is a compound of formula (I) in which:

A represents a group of formula —O—CO—, —N($R^2$)CO—, —N($R^2$)CS—, —CON($R^2$)CO—, —CON($R^2$)CS—, —ON($R^2$)CO—, —O—CON($R^2$)CO—, —N($R^2$)N($R^3$)CO— or —N($R^2$)CON($R^3$)CO—[wherein $R^2$ and $R^3$ are as defined above], B represents a single bond or a group of formula —N($R^{5'}$)—[wherein $R^{5'}$ represents the groups other than hydrogen in the definition of $R^{5-}$], and $R^1$ represents a group as defined above other than hydrogen.

Reaction Scheme F:

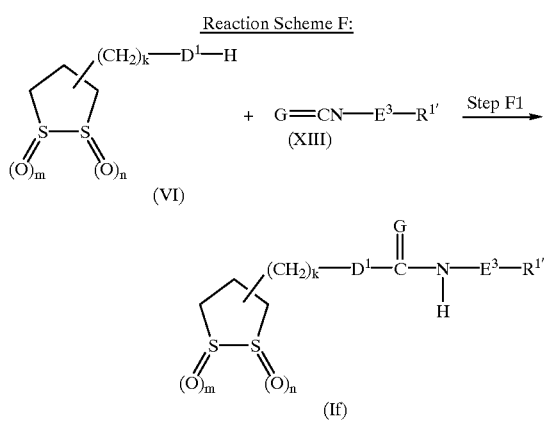

In the above formulae:

$D^1$, k, m and n are as defined above, $E^3$ represents a single bond or a group of formula —$N(R^{5'})$—[wherein $R^{5'}$ is as defined above], G represents an oxygen atom or a sulfur atom, and $R^{1'}$ represents a group as defined above for $R^1$ other than hydrogen.

Step F1

In this Step, a dithiolan derivative of formula (If) is prepared by reacting an isocyanic acid ester or an isothiocyanic acid ester of formula (XIII) with a compound of formula (VI). The reaction is essentially the same as that described above in Step E2, and may be carried out using the same solvents, bases and reaction conditions.

The compound of formula (If) wherein $E^3$ represents a single bond and $R^{1'}$ represents a hydrogen atom can also be prepared by carrying out the reaction using a compound of formula G=CN—$R^9$[wherein G is as defined above and $R^9$ represents a silyl group, such as a tri-lower alkylsilyl group, e.g. trimenthylsilyl, triethylsilyl, isopropyldimethylsilyl, t-butyldimenthylsilyl, methyldiisopropylsilyl, methyldi-t-butylsilyl or triisopropylsilyl, or a tri-lower alkylsilyl group substituted with 1 or 2 aryl groups, such as a diphenylmethylsilyl, diphenylbutylsilyl, diphenylisopropylsilyl or phenyldiisopropylsilyl group]instead of the isocyanic acid ester or the isothiocyanic acid ester of formula (XIII).

Where the dithiolan ring is subjected to ring-opening in the course of carrying out the reactions described in Methods A to F to produce a dithiol compound, a dithiolan derivative can be obtained by oxidizing the ring-opening compound to form a disulfide bond. The oxidation reaction is usually carried out using an oxidizing agent in the presence of a solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Preferred solvents include water-containing organic solvents. Such organic solvent include: ketones, such as acetone; halogenated hydrocarbons, such as methylene chloride, chloroform or carbon tetrachloride; nitriles, such as acetonitrile; ethers, such as diethyl ether, tetrahydrofuran and dioxane; amides, such as dimethylformamide, dimethylacetamide or hexamethylphosphoric triamide; sulfoxides, such as dimethyl sulfoxide; and alcohols, such as methanol or ethanol.

There is likewise no particular restriction on the nature of the oxidizing agents used, and any oxidizing agent commonly used in reactions of this type may equally be used here provided it can form a disulfide bond. Examples of such oxidizing agents include ferric chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

Method G

This illustrates the preparation of a compound of formula (I) in which at least one of m and n is 1 or 2, that is a compound of formula (Ig) from a compound of formula in which m and n are both zero, that is a compound of formula (Ig').

Reaction Scheme G:

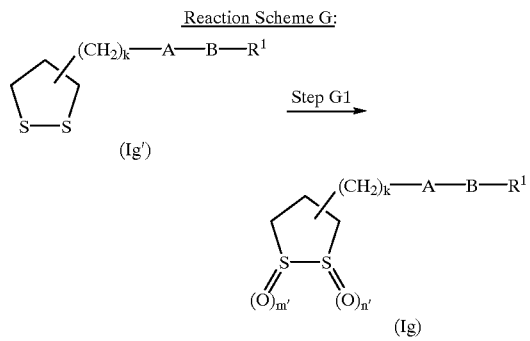

In the above formulae:

A, B, $R^1$ and k are as defined above; and m' and n' are as defined above for m and n provided that at least one is not 0.

Step G1

In this Step, a dithiolan derivative of formula (Ig) is prepared by oxidizing a compound of formula (Ig') [a compound of formula (I) wherein n and m are 0].

There is no particular restriction on the nature of the oxidizing agents used, and any oxidizing agent commonly used in reactions of this type may equally be used here, provided that it is capable of oxidising a sulfide to a sulfoxide or a sulfone. Examples of such oxidizing agents include: hydroperoxides, such as hydrogen peroxide, t-butyl hydroperoxide or pentyl hydroperoxide; dialkyl peroxides, such as di-t-butyl peroxide; peracids, such as perbenzoic acid, m-chloroperbenzoic acid or peracetic acid; peracid esters, such as methyl perbenzoate; and diacyl peroxides, such as benzoyl peroxide. Of these, we particularly prefer hydrogen peroxide, m-chloroperbenzoic acid and t-butyl hydroperoxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent.

Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile, propionitrile and isobutyronitrile; and amides, such as formamide, dimethylformamide, N,N-dimethylacetamide, N-methyl-2-pyrrolidone, N-methylpyrrolidinone and hexamethylphosphoric triamide; sulfoxides, such as dimethyl sulfoxide; sulfones, such as sulfolane; alcohols, such as methanol and ethanol; esters, such as ethyl formate, ethyl acetate, propyl acetate, butyl acetate and diethyl carbonate; and water. Of these, we prefer the aromatic hydrocarbons, halogenated hydrocarbons, ketones, amides, alcohols and water, more preferably the halogenated hydrocarbons, ketones, amides, alcohols and water.

The reaction can take place over a wide range of temperatures and the precise reaction temperature is not critical to the invention. The preferred reaction temperature will depend upon such factors as the nature of the solvent, and the starting material or reagent used. However, in general, we find it convenient to carry out the reaction at a temperature of from −50 to 100° C., more preferably from −20 to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 2 days, more preferably from 30 minutes to 12 hours, will usually suffice.

After completion of each of the above reactions, the desired compound may be recovered from the reaction mixture by conventional methods.

For example, the desired compound may be obtained by: suitably neutralising the reaction mixture; removing insolubles by filtration if insolubles exist; adding a water-immiscible organic solvent, such as ethyl acetate to the reaction mixture; washing with water or another suitable solvent; separating the organic layer containing the desired compound; drying it over a drying agent, such as anhydrous sodium sulfate or anhydrous magnesium sulfate; and removing the solvent, e.g. by evaporation.

The compound thus obtained can be separated and purified, if necessary, by appropriately combining conventional methods, for example, recrystallization, reprecipitation or other methods commonly used in the separation and purification of organic compounds, for example, adsorption column chromatography using a carrier such as silica gel, alumina or magnesium-silica gel type Florisil; a method using a synthesized adsorbent such as partition column chromatography using a carrier such as Sephadex LH-20 (™, manufactured by Pharmacia Co, Ltd.), Amberlite XAD-11 (™, manufactured by Rohm and Haas Co. Ltd.) and Diaion HP-20 (™, manufactured by Mitsubishi Kasei Corporation), a method using an ion exchange chromatogram, or normal phase or reverse phase column chromatography using silica gel or alkylated silica gel (preferably high performance liquid chromatography), and eluting with a suitable eluent.

The starting materials in Methods A to G are known compounds or are compounds synthesized from known compound by conventional methods. For example, the amino derivative of formula (Ih), which is a starting material in Method A, Method C and Method F can be prepared by the following Method H.

Method H

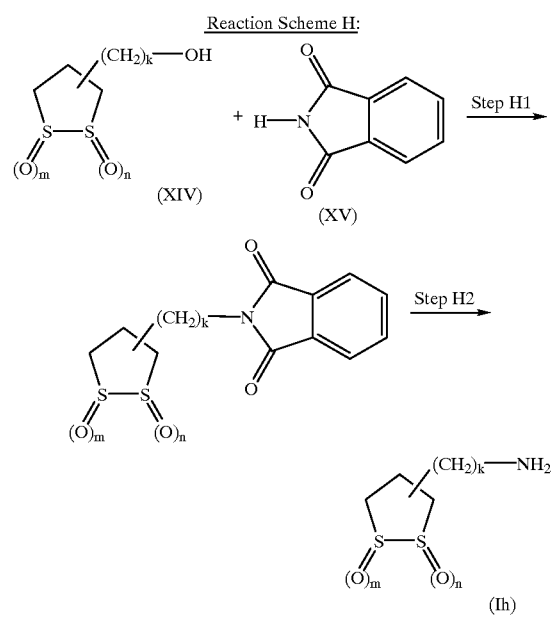

In the above formulae: k, m, and n are as defined above.

Step H1

In this Step, a phthalimide derivative of formula (XVI) is prepared by carrying out a Mitsunobu reaction between a compound of formula (XIV) and phthalimide of formula (XV).

There is no particular restriction on the nature of the reagents used in the Mitsunobu reaction, and any reagent commonly used in reactions of this type may equally be used here. Examples of such reagents include: a combination of an azo compound, such as a di-lower alkyl azodicarboxylate (for example dimethyl azodicarboxylate, diethyl azodicarboxylate or diisopropyl azodicarboxylate) or an azodicarboxamide [such as 1,1'-(axodicarbonyl)dipiperidine] and a phosphine, such as a triarylphosphine (for example triphenylphosphine) or a tri-lower alkyl phosphine (for example tributylphosphine), more particularly a combination of a di-lower alkyl azodicarboxylate and a triarylphosphine, most preferably a combination of dimethyl azodicarboxylate and triphenylphosphine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, N,N-dimethylacetamide, N-methyl-2- pyrrolidone, N-methylpyrrolidinone and hexamethylphosphoric triamide; and sulfoxides, such as dimethyl sulfoxide and sulfolane. Of these, we prefer the aromatic hydrocarbons and ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 100° C., more preferably from 0 to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 12 hours, will usually suffice.

Step H2

In this Step, an amino derivative of formula (Ih) is prepared by reacting the phthalimide derivative of formula (XVI) with butylamine or hydrazine in a solvent. For example it may be accomplished by reacting the phthalimide derivative of formula (XVI) with butylamine in methanol at room temperature for 6 hours.

Since the dithiolan derivatives have the effect of increasing the activity of glutathione reductase, a composition which increases the activity of glutathione reductase, containing those compounds or pharmaceutically acceptable salts thereof can be used for the prevention or treatment of diseases resulting from oxidative stress. Examples of diseases resulting from oxidative stress are disease or pathologic states including damage caused by alcohol abuse, exposure to xenobiotic agents or radiation; intracellular oxidative states caused by hepatic diseases; intoxication from drugs and chemical agents (e.g. carcinostats including platinum chelate, antibiotics, antiparasitics, paraquat, carbon tetrachloride and halothane); intoxication from heavy metals; disorders of the nervous system including brain and neurone degenerative disorders (e.g. cerebral ischemia, cerebral ictus, hypoglycemia, epileptic attacks, amyotrophic lateral schlerosis, Alzheimer's disease, Parkinson's disease and Huntington's chorea); diseases related to an altered functionality of the immune system, in particular tumour immunotherapy; infertility, in particular male infertility; coronary heart disease, ophthalmologic disorders such as cataract, retinopathy of prematurity and siderosis; pulmonary diseases such as idiopathic pulmonary fibrosis, adult respiratory distress syndrome, emphysema, asthma, bronchopulmonary dysplasia and interstitial pulmonary fibrosis; chronic renal failure; gastric ulcer; canceration and metastases of cancer including colorectal cancer; diabetes; hepatocyte necrosis and apoptosis including ethanol-induced hepatopathy; viral diseases including influenza, hepatitis B and HIV; abnormalities of blood or blood vessels such as Fanconi's anemia, septicemia, enhanced permeability through blood vessels and leukocyte adherence; various malformations such as Down's syndrome, Duchenne muscular dystrophy, Becker dystrophy, Dubin-Johnson-Spring syndrome and favism; and inflammatory diseases such as nephritis, pancreatitis, dermatitis, fatigue and rheumatism. In particular, the dithiolan derivatives and pharmaceutically acceptable salts thereof of the present invention are useful for the prevention or treatment of diseases or pathologic states such as damage caused by radiation, intracellular oxidative states caused by hepatic diseases, intoxication (i.e. side effects) from carcinostats including platinum chelate, disorders of the nervous system, cataract, diabetes, hepatocyte necrosis and apoptosis, viral diseases, and inflammatory diseases.

Among the above-described diseases resulting from oxidative stress, there are some diseases where the effects are irreversible, once they have occurred. A therapeutic agent for such a disease means a medicament which prevents or delays the progress of the disease.

The dithiolan derivatives of formula (I) or pharmaceutically acceptable salts thereof of the present invention can be used together with a medicament which is known as a preventive agent or therapeutic agent for a disease listed above as the diseases resulting from oxidative stress and may show a synergistic effect.

Cyanamide, disulfiram, adenine and cysteine are known as medicaments for treating the damage caused by alcohol abuse, exposure to xenobiotic agents or radiation; aminoethylsulfonic acid, protoporphyrin disodium and diisopropylamine dichloroacetate are known as medicaments for treating intracellular oxidative states caused by hepatic diseases; gluthathione, dimercaprol, and calcium disodium edetate are known as medicaments for treating intoxication from drugs and chemical agents (e.g. carcinostats including platinum chelate, antibiotics, antiparasitics, paraquat, carbon tetrachloride and halothane) or for treating intoxication from heavy metals; phenobarbital, phenytoin, bromocriptine mesylate, sulpiride, sodium valproate, haloperidol, levodopa-carbidopa, idebenone and aniracetam are known as medicaments for treating disorders of the nervous system including brain and neurone degenerative disorders (e.g. cerebral ischemia, cerebral ictus, hypoglycemia, epileptic attacks, amyotrophic lateral sclerosis, Alzeimer's disease, Parkinson's disease and Huntington's chorea); cyclophosphamide, interferon-α and interferon-β are known as medicaments for treating diseases related to an altered functionality of the immune system, in particular tumour immunotherapy; sildenafil is known as a medicament for treating infertility, in particular male infertility; digitoxin and digoxin are known as medicaments for treating coronary heart disease; pirenoxine is known as a medicament for treating ophtalmologic disorders such as cataract, retinopathy of prematurity and siderosis; theophylline, ketotifen fumarate, epinastine hydrochloride, pranlukast and suplatast tosylate are known as medicaments for treating pulmonary diseases such as idiopathic pulmonary fibrosis, adult respiratory distress syndrome, emphysema, asthma, bronchopulmonary dysplasia and interstitial pulmonary fibrosis; furosemide, etacrynic acid and bumetanide are known as medicaments for treating chronic renal failure; teprenone, rebamipide, ecabet sodium, plaunotol, famotidine, ranitidine hydrochloride and lansoprazole are known as medicaments for treating gastric ulcer; BB-2516 and AG3340 are known to be useful against canceration and metastases of cancer including colorectal cancer, epalrestat, voglibose, acarbose, insulin, glibenclamide and troglitazone are known as medicaments for treating diabetes; aminoethylsulfonic acid, protoporphyrin disodium and diisopropylamine dichloroacetate are known as medicaments for treating hepatocyte necrosis and apoptosis including ethanol-induced hepatopathy; acyclovir, zidovudine, interferon-α, interferon-β and interferon-γ are known as medicaments for treating viral diseases including influenza, hepatitis B and HIV; erythropoietin derivatives are known as medicaments for treating abnormalities of the blood or blood vessels such as Fanconi's anemia, septicemia, enhanced permeability through blood vessels and leukocyte adherence; fenipentol, camostat mesylate, indomethacin, loxoprofen sodium and diclofenac sodium are known as medicaments for treating inflammatory diseases such as nephritis, pancreatitis, dermatitis, fatigue and rheumatism.

The compounds of the present invention can be administered in any conventional pharmaceutical formulation, the nature of which will depend on the patient and the intended route of administration. For example for oral administration, suitable formulations include tablets, capsules, granules, powders or syrups. For parenteral administration suitable formulations include injections or suppositories. These formulations can be prepared by well-known methods using additives such as excipients, lubricants, binders, disintegrating agents, stabilizers, corrigents and diluents.

Examples of suitable excipients include organic excipients, for example: sugar derivatives such as lactose, sucrose, glucose, mannitol or sorbitol; starch derivatives such as corn starch, potato starch, α-starch, dextrin or carboxymethyl starch; cellulose derivatives such as crystalline cellulose, low substituted hydroxypropylcellulose, hydroxypropylmethylcellulose, carboxymethylcellulose, carboxymethylcellulose calcium or internally bridged carboxymethylcellulose sodium; gum arabic; dextran; and Pullulan; inorganic excipients including silicate derivatives such as light silicic acid anhydride, synthetic aluminum silicate or magnesium meta-silica acid aluminate; phosphates such as calcium phosphate; carbonates such as calcium carbonate; and sulfates such as calcium sulfate.

Examples of suitable lubricants include stearic acid, metal stearates such as calcium stearate or magnesium; talc; colloidal silica; waxes such as beeswax or spermaceti; boric acid; adipic acid; sulfates such as sodium sulfate; glycol; fumaric acid; sodium benzoate; DL-leucine; sodium salts of fatty acids; lauryl sulfates such as sodium lauryl sulfate or magnesium lauryl sulfate; silicates such as silicic acid anhydride or silicic acid hydrate; and the foregoing starch derivatives.

Examples of suitable binders include polyvinylpyrrolidone, Macrogol, and similar compounds to the excipients described above.

Examples of suitable disintegrating agents include similar compounds to the excipients described above; and chemically modified starches or celluloses such as crosscarmelose sodium, sodium carboxymethylstarch or bridged polyvinylpyrrolidone.

Examples of suitable stabilisers include paraoxybenzoates such as methylparaben or propylparaben; alcohols such as chlorobutanol, benzyl alcohol or phenylethyl alcohol; benzalkonium chloride; phenols such as phenol or cresol; thimerosal; dehydroacetic acid; and sorbic acid.

Examples of suitable corrigents include sweeteners, vinegar or perfumes such as those conventionally used.

Moreover, since the dithiolan derivative or the pharmaceutically acceptable salt thereof of the present invention is less stimulating for the eyes, it can be topically administered to the eyes. Suitable formulations for the topical administration to the eyes include solutions, suspensions, gels, ointments and solid inserting agents.

The formulation of these compositions for topical administration may contain the dithiolan derivative or the pharmaceutically acceptable salt thereof at a level of from 0.001% (preferably 0.01%) as a lower limit to 10% (preferably 5%) as an upper limit.

The pharmaceutical formulation containing an active compound can, if desired, be mixed with a non-toxic inorganic or organic carrier for pharmaceuticals.

Typical pharmaceutically acceptable carriers include water, a mixture of water and a water-miscible solvent such as a lower alkanol or aralkanol, a vegetable oil, polyalkylene glycol, a jelly using a petroleum as a base material, ethylcellulose, ethyl oleate, carboxymethylcellulose, polyvinylpyrrolidone, isopropyl myristate and other acceptable carriers which can be preferably used. The formulation may contain non-toxic auxiliary substances such as an emulsifier, a preservative, a wetting agent and an excipient, for example, polyethylene glycol 200, 300, 400 and 600, carbowax 1000, 1500, 4000, 6000 and 10000, ρ-hydoxybenzoic acid esters such as methyl ρ-hydroxybenzoate or propyl ρ-hydroxybenzoate, a quaternary ammonium compound (for example, benzetonium chloride or benzalkonium chloride) which are known as compounds having anti-fungal properties at low temperatures and are non-toxic when used, an anti-fungal agent such as a phenyl mercury salt, a buffering component such as thimerosal, methyl- and propylparaben, benzyl alcohol, phenylethanol, sodium chloride, sodium borate and sodium acetate, a gluconic acid buffering agent and sorbitan monolaurate, triethanolamine, polyoxyethylenesorbitan monopalmitate, sodium dioctyl sulfosuccinate, monothioglycerol, thiosorbitol and ethylenediaminetetraacetic acid.

Ophthalmological excipients can be used as a desired support medium for the compounds of the present invention and examples include the usual phosphoric acid buffering excipients (for example, a sodium phosphate buffer or a potassium phosphate buffer), isotonic boric acid excipients, isotonic sodium chloride excipients and isotonic sodium borate excipients.

As a further alternative, the pharmaceutical formulation may have the form of a solid insert which remains almost intact after the formulation has been administered, or it may also be formulated as a disintegrating insert which dissolves in the tear fluid or is disintegrated by other methods.

The dose of the dithiolan derivative of formula (I) or the pharmaceutically acceptable salt thereof of the present invention will vary, depending upon the condition and age of the patient and the form and route of administration. However, for example, in the case of oral administration, for an adult human patient, it is desirable to administer from 0.1 mg (preferably 1 mg) as a lower limit to 10000 mg (preferably 5000 mg) as an upper limit per day. In the case of intravenous administration, it is desirable to administer from 0.01 mg (preferably 0.1 mg) as a lower limit to 5000 mg (preferably 2000 mg) as an upper limit per day. In the case of topical administration to the eyes, it is desirable to administer from 0.001 mg (preferably 0.01 mg) as a lower limit to 500 mg (preferably 200 mg) as an upper limit per day. All of the above may be administered as a single dose or in divided doses. The dose and dosage regime will depend on the condition of the patient.

Pharmaceutical preparations of the present invention are illustrated by the following non-limiting Formulation Examples.

FORMULATION EXAMPLE 1

Powder 5 g of N-[5-(1,2-dithiolan-3-yl)pentanoyl]methanesulfonamide (the compound of Example 2 hereafter), 895 g of lactose and 100 g or corn starch are mixed by means of a blender to obtain a powder.

FORMULATION EXAMPLE 2

Granules 5 g of N-[5-(1,2-dithiolan-3-yl)pentanoyl]sulfamide (the compound of Example 7 hereafter), 865 g of lactose and 100 g of low substituted hydroxypropylcellulose are mixed. 300 g of a 10% w/v aqueous solution of hydoxypropyl cellulose are then added to the mixture, and then the resulting mixture is kneaded. The mixture is then granulated using an extruding granulator, after which it is dried to obtain a granule formulation.

FORMULATION EXAMPLE 3

Capsules 5 g of N-[4-(1,2-dithiolan-3-yl)butyl-N'-methylurea (the compound of Example 8 hereafter), 115 g of lactose, 58 g of corn starch and 2 g of magnesium stearate are mixed using a V-type mixer. 180 mg of the mixture are then encapsulated in a No. 3 capsule to obtain a capsule formulation.

FORMULATION EXAMPLE 4

Tablet 5 g of (R)-N-[5-(1,2-dithiolan-3-yl) pentanoyl] methanesulfonamide (the compound of Example 40 hereafter), 90 g of lactose, 34 g of corn starch, 20 g of crystalline cellulose and 1 g of magnesium stearate are mixed by means of a blender. The mixture is then pelletised by means of a tablet making machine to obtain tablets.

FORMULATION EXAMPLE 5

Eye drops

The following components are mixed:

| | |
|---|---|
| (R)-N-[5-(1,2-dithiolan-3-yl)pentanoyl]methane-sulfonamide (the Compound of Example 40) | 0.2 g |
| Disodium phosphate | 0.716 g |
| Sodium phosphate | 0.728 g |
| Sodium chloride | 0.400 g |
| Methyl p-hydroxybenzoate | 0.026 g |
| Propyl p-hydroxybenzoate | 0.014 g |
| Sterilised purified water | q.s. |
| Sodium hydroxide | q.s. |
| Total | 100 ml |

The pH of the mixture is adjusted to 7.0 and eye drops are prepared by a conventional method.

FORMULATION EXAMPLE 6

Eye drops

The following components are mixed:

| | |
|---|---|
| (R)-N-[5-(1,2-dithiolan-3-yl)pentanoyl]methane-sulfonamide (the Compound of Example 40) | 0.2 g |
| Disodium phosphate | 0.716 g |
| Sodium phosphate | 0.728 g |
| Sodium chloride | 0.400 g |
| Methyl p-hydroxybenzoate | 0.026 g |
| Propyl p-hydroxybenzoate | 0.014 g |
| Sterilised purified water | q.s. |
| Ascorbic acid | q.s. |
| Sodium hydroxide | q.s. |
| Total | 100 ml |

The pH of the mixture is adjusted to 7.0 and eye drops are prepared by a conventional method.

BIOLOGICAL ACTIVITY

The biological activity of the compounds of the present invention is illustrated by the following Test Examples.

TEST EXAMPLE 1

Measurement of Glutathione Reductase Activity (a) Lens Tissue Culture

The test animals were 6 to 8 week old male SD rats (supplier: Nippon SLC). The animals were sacrificed by suffocation by inhalation of carbon dioxide. Both eyeballs of each test animal were then excised. An incision was made in the sclera on the back of the eyeballs, and then the vitreous body and iris-ciliary body were removed, followed by removal of the lens.

Each lens obtained in this manner was cultured by immersing it in 3 ml of the culture solution described below in a 6-well tissue culture plate (FALCON). Culturing was performed for 72 hours in a $CO_2$ incubator maintained at 37° C. and 100% humidity in the presence of 5% $CO_2$ (in air).

Medium 199 (Gibco) containing penicillin (20 units/ml) and streptomycin (20 µg/ml) was used as the control culture solution.

The test culture solution contained the test compound added to the above-mentioned culture solution. The cultured lenses were placed in frozen storage until the time of the test.

(b) Measurement of Glutathione Reductase Activity

After homogenising each frozen rat lens in 2 ml of distilled water, the resulting homogenate was separated by centrifugation (10,000 g, 20 minutes) after which the resulting supernatant was used as the enzyme sample.

400 µl of enzyme sample were added to 0.6 ml of phosphate buffer containing 1 mM oxidized glutathione (GSSG) and 100 µM NADPH. After the mixture had reacted at 25° C. for 6 minutes, the absorbance of the reaction mixture (at 340 nm: i.e. $OD_{340\ nm}$) was measured. The difference ($\Delta OD_{340\ nm}$) between the $OD_{340\ nm}$ value before reaction and the $OD_{340\ nm}$ value after completion of the reaction was used as an indicator of glutathione reductase activity.

The results for the compound of Example 2 are shown in the following Table 4.

TABLE 4

| Concentration of the compound of Example 2 (µM) | $\Delta OD_{340\ nm}$/min/g protein |
|---|---|
| 0 | 3.10 ± 0.11 |
| 10 | 3.24 ± 0.10 |
| 30 | 3.20 ± 0.09 |
| 100 | 3.59 ± 0.05 (p < 0.05) |
| 300 | 3.70 ± 0.08 (p < 0.05) |
| 1000 | 4.16 ± 0.18 (p < 0.05) |

The dithiolan derivatives of the present invention exhibited excellent glutathione reductase activity enhancing effects.

TEST EXAMPLE 2

Anti-cataract Test

The test animals were 6 week old male SD rats (supplier: Nippon SLC). The animals were sacrificed by suffocation by inhalation of carbon dioxide. Both eyeballs of each test animal were then excised. The excised lenses were cultured at 37° C. for 24 hours in Medium 199 (Gibco) containing 0.05 mg/ml of the test compound and 5 mM hydrogen peroxide. For the control test, excised lenses were cultured at 37° C. for 24 hours in normal culture liquid (Medium 199, Gibco) or Medium 199 (Gibco) containing 5 mM hydrogen peroxide.

After culturing for 24 hours, the lenses were washed with physiological saline. Surface moisture was removed by placing the lenses on a piece of filter paper, and then the lenses were placed on a slide glass after which lens turbidity was scored under stereomicroscope from "−" (turbidity degree of the lens cultured in a normal culture medium) to "++++" (turbidity degree of the lens cultured in a medium containing hydrogen peroxide). The results are shown in Table 5.

TABLE 5

| Compound of Example No. | Rat Lens turbidity in 5 mM $H_2O_2$, 24 hours |
|---|---|
| 1 | ++ |
| 2 | ++ |
| 7 | + |
| 8 | ++ |
| 21 | ++ |
| 43 | ++ |
| 45 | ++ |
| 46 | + |
| 50 | + |
| 52 | + |
| 55 | + |
| 56 | ++ |
| 57 | + |
| 59 | + |
| 61 | + |
| 63 | ++ |
| 70 | ++ |
| 74 | ++ |
| 79 | ++ |
| 80 | ++ |
| 86 | ++ |
| 103 | ++ |
| 106 | ++ |
| 109 | + |
| 118 | ++ |
| 123 | ++ |
| lipoic acid | +++ |
| normal lens | − |
| without drug | +++ |

As can be seen from the above results, the compounds of the present invention substantially improve the opacity of the lens.

EXAMPLES

The present invention is further illustrated by reference to the following non-limiting Examples.

EXAMPLE 1

N-Acetyl-α-thioctamide (Compound No. 1-271)

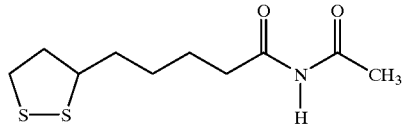

A mixture of 0.76 g of D,L-α-thioctamide, 1.5 g of acetic anhydride and 10 ml of pyridine was heated under reflux for 20 hours. The pyridine was then removed from the reaction mixture by distillation under reduced pressure, and water was added to the residue, which was then extracted with ethyl acetate. The extraction solution was washed twice with water and dried over anhydrous magnesium sulfate. 0.76 g of the crude product obtained by evaporating the solvent under reduced pressure was purified by silica gel column chromatography, using a 2:1 by volume mixture of hexane and ethyl acetate as eluent, to obtain 0.45 g of 3-(4-cyanobutyl)-1,2-dithiolan having [an Rf value of 0.84 (silica gel thin layer chromatography, using a 1:1 by volume mixture of hexane and ethyl acetate as the developing solvent)] as a first component and 0.17 g of the title compound, melting at 67° C. to 69° C. as a second component.

EXAMPLE 2

N-[5-(1,2-Dithiolan-3-yl)pentanoyl]methanesulfonamide (Compound No. 1-496)

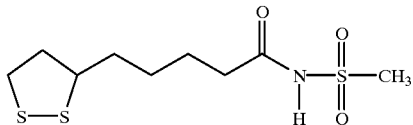

(a) 0.88 g of sodium hydride (as a 55% by weight dispersion in mineral oil) was washed with hexane, and 20 ml of dimethylformamide and 1.96 g of methanesulfonamide were added to the dispersion at room temperature. The resulting mixture was subjected to ultrasonic treatment for three hours and then left to stand at room temperature overnight, to give reaction mixture (A).

Separately, 2.06 g of D,L-α-lipoic acid were dissolved in 20 ml of dimethylformamide, and 1.63 g of N,N'-carbonyldiimidazole were added to the solution, whilst ice-cooling. The resulting mixture was then left to stand at room temperature overnight. At the end of this time, the reaction mixture was added dropwise to the above reaction mixture (A) at room temperature, and the mixture was stirred for 7 hours. The reaction mixture was then heated at 130° C. for 3 hours, after which it was left to cool, and then poured into ice-water. Diluted aqueous hydrochloric acid was added to the mixture to adjust the pH to 5, and the mixture was extracted with ethyl acetate. The extraction solution was washed three times with a saturated aqueous solution of sodium chloride and then dried over anhydrous magnesium sulfate. The solvent was then removed by distillation under reduced pressure, and the resulting residue was purified by silica gel column chromatography, using a 4:1 by volume mixture of ethyl acetate and hexane and then ethyl acetate alone as the eluent, to obtain 0.12 g of the title compound, melting at 87° C. to 88° C.

(b) 25.0 g of D,L-α-lipoic acid were dissolved in 500 ml of anhydrous dimethylformamide, and 21.57 g of N,N'-carbonyldiimidazole were added to the solution, whilst ice-cooling, after which the resulting mixture was stirred at room temperature for 2 hours and 30 minutes. 12.65 g of methanesulfonamide and 5.80 g of sodium hydride (as a 55% w/w dispersion in mineral oil) were then added, whilst ice-cooling, to the reaction mixture, and the mixture was stirred at room temperature for 4 hours and then left to stand at room temperature overnight. At the end of this time, the solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using 1:1,2:1 and 3:1 by volume mixtures of ethyl acetate and hexane as eluent, to obtain 19.85 g of the title compound, melting at 85° C. to 88° C.

EXAMPLE 3

N-[5-(1-Oxo-1,2-dithiolan-3-yl)pentanoyl] methanesulfonamide (Compound No. 2-496)

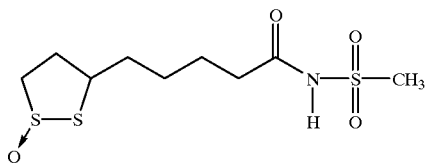

500 mg of N-[5-(1,2-dithiolan-3-yl)pentanoyl] methanesulfonamide (prepared as described in Example 2) were dissolved in 10 ml of acetone, and 0.44 ml of a 31% w/v aqueous solution of hydrogen peroxide was added to the solution, whilst ice-cooling. The mixture was stirred and then left to stand at room temperature overnight. At the end of this time, a further 0.2 ml of a 31% w/v aqueous solution of hydrogen peroxide was added to the reaction mixture, and then the mixture was stirred at room temperature for 30 minutes, and then stirred on an oil bath at 50° C. for 1 hour. The mixture was then left to stand at room temperature for 3 days, after which it was stirred on an oil bath at 50° C. for 10 hours; it was then left to stand at room temperature overnight. The solvent was then removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by reverse phase preparative silica gel column chromatography, using 1:3 and 2:3 by volume mixtures of acetonitrile and water as the eluent. The solvent was evaporated from the eluted fraction thus obtained under reduced pressure, and the fraction was lyophilised, to obtain 0.15 g of the title compound (diastereomer mixture) as a colorless oil having an Rf value of 0.43 (silica gel thin layer chromatography, using a 10:1 by volume mixture of ethyl acetate and methanol as the developing solvent).

EXAMPLE 4

N-[5-(1,2-Dithiolan-3-yl)pentanoyl] methanesulfonamide sodium salt (Compound No. 1-496. sodium salt)

750 mg of N-[5-(1,2-dithiolan-3-yl)pentanoyl] methanesulfonamide (prepared as described in Example 2) were dissolved in 15 ml of ethyl acetate, and 482 mg of sodium 2-ethylhexoate was added to the mixture at room temperature. The mixture was stirred for 2 hours, after which it was left to stand for 2 days at room temperature. The crystals which precipitated from the reaction mixture were collected by filtration, to obtain 550 mg of the title compound, melting at 202° C. to 204° C.

EXAMPLE 5

Ethyl 5-(1-oxo-1,2-dithiolan-3-yl)pentanoate and ethyl 5-(2-oxo-1,2-dithiolan-3-yl)pentanoate (Compound No. 2-208 and Compound No. 3-208)

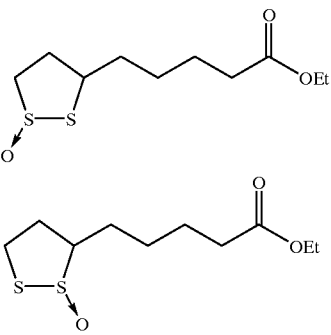

1.00 g of D,L-α-lipoic acid was dissolved in 20 ml of acetone, and 0.58 g of a 31% w/v aqueous solution of hydrogen peroxide was added to the solution on a dry ice-acetone bath. The mixture was stirred for 2 hours, and it was then left to stand at room temperature overnight. At the end of this time, the solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate, and then the solvent was removed by evaporation under reduced pressure. 16 ml of anhydrous ethanol and 4 ml of a 4 N solution of hydrogen chloride in ethyl acetate were added to the residue thus obtained, and the mixture was stirred for 2 hours. The solvent was then removed from the reaction mixture by evaporation under reduced pressure, and the residue thus obtained was purified by silica gel column chromatography, using 1:2, 2:1 and 3:1 by volume mixtures of ethyl acetate and hexane as eluent, to obtain 0.26 g of ethyl 5-(2-oxo-1,2-dithiolan-3-yl)pentanoate having an Rf value of 0.41 (silica gel thin layer chromatography; using a 2:1 by volume mixture of ethyl acetate and hexane as the developing solvent) and 0.67 g of ethyl 5-(1-oxo-1,2-dithiolan-3-yl) pentanoate having an Rf value of 0.29 (silica gel thin layer chromatography; using a 2:1 by volume mixture of ethyl acetate and hexane as the developing solvent).

EXAMPLE 6

N-[4-(1,2-Dithiolan-3-yl)butyl]-N',N'-dimethylurea (Compound No. 1-815)

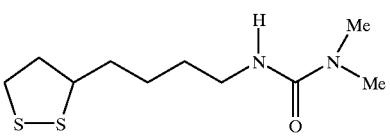

1.00 g of D,L-α-lipoic acid was dissolved in 20 ml of toluene, and 2.00 ml of triethylamine and 1.25 ml of diphenylphosphoryl azide were added to the resulting solution at room temperature, and then the mixture was stirred on an oil bath at 80° C. for 2 hours. 0.47 g of dimethylamine hydrochloride was then added to the reaction mixture, and the mixture was stirred at room temperature for 4 hours. At the end of this time, the solvent was removed from the reaction mixture by evaporation under reduced pressure, and 20 ml of anhydrous tetrahydrofuran and 0.52 ml of a 50% v/v aqueous solution of dimethylamine were added to the residue thus obtained; the mixture was then left to stand at room temperature overnight. The solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using ethyl acetate and then a 9:1 by volume mixture of ethyl acetate and methanol as eluent. The solvent was evaporated from the fraction including the title compound under reduced pressure, and the residue thus obtained was dissolved in dioxane. The solution was lyophilised, to obtain 832 mg of the title compound, melting at 52° C. to 53° C.

EXAMPLE 7

N-[5-(1,2-Dithiolan-3-yl)pentanoyl]sulfamide (Compound No. 1-539)

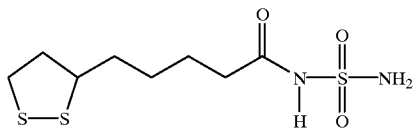

50 mg of D,L-α-lipoic acid were dissolved in 10 ml of anhydrous dimethylformamide, and 421 mg of N,N'-carbonyldiimidazole were added to the solution, whilst ice-cooling, and then the mixture was stirred at room temperature for 3 hours. 461 mg of sulfamide and 113 mg of sodium hydride (as a 55% w/w dispersion in mineral oil) were then added to the reaction mixture, whilst ice-cooling, and the mixture was stirred for 4 hours and then left to stand at room temperature overnight. At the end of this time, the solvent was removed from the reaction mixture by evaporation under reduced pressure, and water and 2 N aqueous hydrochloric acid were added to the residue thus obtained to adjust the pH to 5 to 6, after which it was extracted with ethyl acetate. The extraction solution was washed with a saturated aqueous solution of sodium chloride and dried over anhydrous sodium sulfate, and then the solvent was removed by evaporation under reduced pressure. The residue thus 2:1 by volume mixture of ethyl acetate and hexane as the eluent, and the resulting fraction was then recrystallized from a 1:2 by volume mixture of ethanol, diisopropyl ether and hexane, to obtain 119 mg of the title compound, melting at 141° C. to 142° C.

EXAMPLE 8

N-[4-(1,2-Dithiolan-3-yl)butyl-N'-methylurea (Compound No. 1-733)

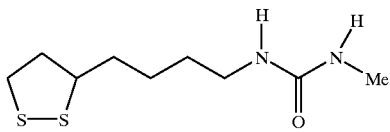

1.00 g of D,L-α-lipoic acid was dissolved in 20 ml of toluene, and 2.00 ml of triethylamine and 1.25 ml of diphenylphosphoryl azide were added to the resulting solution at room temperature, after which the resulting mixture was stirred on an oil bath at 80° C. for 3 hours. The solvent was then removed from the reaction mixture by evaporation under reduced pressure, and 20 ml of tetrahydrofuran and 0.45 ml of a 40% v/v aqueous solution of methylamine were added to the residue thus obtained, whilst ice-cooling, and the mixture was stirred at room temperature for 3 hours and then left to stand at room temperature overnight. The solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using ethyl acetate and then 20:1 and 10:1 by volume mixtures of ethyl acetate and methanol as the eluent, to obtain 425 mg of the title compound, melting at 89° C. to 90° C.

EXAMPLE 9

N-[4-(1,2-Dithiolan-3-yl)butyl]urea (Compound No. 1-693)

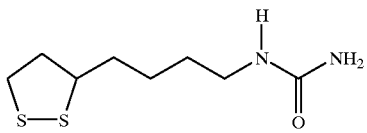

1.00 g of D,L-α-lipoic acid was dissolved in 20 ml of toluene, and 0.80 ml of triethylamine and 1.25 ml of diphenylphosphoryl azide were added to the solution at room temperature, after which the resulting mixture was stirred on an oil bath at 80° C. for 4 hours. The solvent was then removed from the reaction mixture by evaporation under reduced pressure, and 20 ml of tetrahydrofuran and 0.49 ml of 28% w/v aqueous ammonia were added to the residue thus obtained. The mixture was then stirred at room temperature for 4 hours, after which it was left to stand overnight. The solvent was then removed from the reaction mixture by evaporation under reduced pressure, and water and 2 N aqueous hydrochloric acid were added to the mixture to adjust the pH to 2, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using 10:1, 4:1 and 3:1 by volume mixtures of ethyl acetate and methanol as eluent, to obtain 340 mg of the title compound, melting at 110° C. to 113° C.

EXAMPLE 10

N-[5-(1,2-Dithiolan-3-yl)pentanoyl] benzenesulfonamide (Compound No. 1-457)

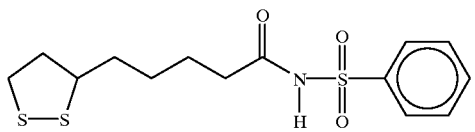

1.00 g of D,L-α-lipoic acid was dissolved in 20 ml of anhydrous dimethylformamide, and 0.86 g of N,N'-carbonyldiimidazole was added to the solution, whilst ice-cooling. The mixture was then stirred at room temperature for 2 hours and 30 minutes. 0.83 g of benzenesulfonamide and 0.23 g of sodium hydride (as a 55% w/w dispersion in mineral oil) were added to the reaction mixture, whilst ice-cooling, and the mixture was stirred for 2 hours. The solvent was then removed from the reaction mixture by evaporation under reduced pressure, and water and 2 N aqueous hydrochloric acid were added to the residue thus obtained to adjust the pH to 2, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using 1:2, 1:1 and 2:1 by volume mixtures of ethyl acetate and hexane as eluent, and then by reverse phase preparative silica gel column chromatography, using 3:7, 1:1 and 7:3 by volume mixtures of acetonitrile and water as eluent. The solvent was evaporated under reduced pressure from the fraction containing the title compound, and the residue thus obtained was dissolved in dioxane. The resulting solution was lyophilised, to obtain 0.61 g of the title compound having an Rf value of 0.51 (silica gel thin layer chromatography; using a 2:1 by volume mixture of ethyl acetate and hexane as the developing solvent).

EXAMPLE 11

N-[5-(1,2-Dithiolan-3-yl)pentanoyl] benzenesulfonamide sodium salt (Compound No. 1-457. sodium salt)

492 mg of N-[5-(1,2-dithiolan-3-yl)pentanoyl] benzenesulfonamide (prepared as described in Example 10) were dissolved in a mixture of 8 ml of ethyl acetate and 1 ml of tetrahydrofuran, and 283 mg of sodium 2-ethylhexoate were added to the mixture at room temperature. The resulting mixture was stirred for 1 hour and 30 minutes, after which it was left to stand for 2 days. The crystals which precipitated from the reaction mixture were collected by filtration to obtain 349 mg of the title compound, melting at 213° C. to 215° C.

EXAMPLE 12

$N^\alpha$-[5-(1,2-Dithiolan-3-yl)pentanoyl]-$N^{im}$-t-butoxycarbonylhistidine methyl ester (Compound No. 1-70)

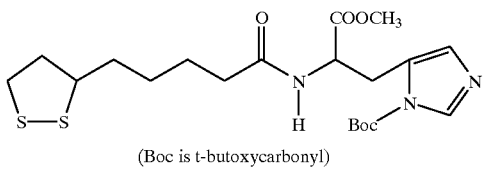

(Boc is t-butoxycarbonyl)

500 mg of D,L-α-lipoic acid were dissolved in 10 ml of anhydrous dimethylformamide, and 422 mg of N,N'-carbonyldiimidazole were added to the solution, whilst ice-cooling. The mixture was then stirred at room temperature for 2 hours. At the end of this time, 629 mg of L-histidine methyl ester dihydrochloride salt and 0.70 ml of triethylamine were added to the reaction mixture, whilst ice-cooling, and the mixture was stirred for 1 hour whilst ice-cooling, and then stirred at room temperature for a further 1 hour. The solvent was then removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using ethyl acetate and then 20:1, 10:1 and 5:1 by volume mixtures of ethyl acetate and methanol as eluent. The solvent was evaporated from the fraction containing the product under reduced pressure, and then 5 ml of ethyl acetate were added to the residue thus obtained. 0.55 ml of di-t-butyl dicarbonate, 0.33 ml of triethylamine and a catalytic amount of N,N-dimethylaminopyridine were added to the resulting solution, and the mixture was stirred for 1 hour. The reaction mixture was then purified by silica gel column chromatography, using a 2:1 by volume mixture of ethyl acetate and hexane and then ethyl acetate alone as eluent. The solvent was evaporated from the fraction containing the title compound under reduced pressure and the residue thus obtained was dissolved in dioxane. The solution was lyophilised, to obtain 844 mg of the title compound having an Rf value of 0.41 (silica gel thin layer chromatography; using ethyl acetate as the developing solvent).

EXAMPLE 13

$N^\alpha$-[5-(1,2-Dithiolan-3-yl)pentanoyl] histidine (Compound No. 1-71)

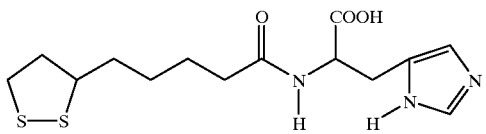

764 mg of $N^\alpha$-[5-(1,2-dithiolan-3-yl)pentanoyl]-$N^{im}$-t-butoxycarbonylhistidine methyl ester (prepared as described in Example 12) were dissolved in 5 ml of methanol, and 5.1 ml of a 1 N aqueous solution of sodium hydroxide were added to the solution at room temperature, after which the resulting mixture was stirred for 2 hours and 30 minutes. 2.60 ml of 2 N aqueous hydrochloric acid were then added to the mixture, and the resulting mixture was stirred and then left to stand overnight. The solvent was removed from the reaction mixture by evaporation under reduced pressure and the residue thus obtained was purified by reverse phase preparative silica gel column chromatography, using a 3:7 by volume mixture of acetonitrile and water as eluent, to obtain 0.51 g of a mixture of the title compound (77%), melting at 122° C. to 126° C., and sodium chloride (23%).

EXAMPLE 14

5-[5-(1,2-Dithiolan-3-yl)pentanoylamino]-1,2,4-dithiazole-3-thione (Compound No. 1-72)

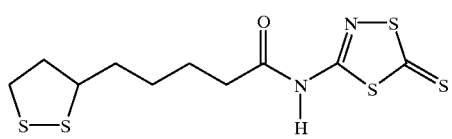

500 mg of D,L-α-lipoic acid were dissolved in 10 ml of anhydrous dimethylformamide, and 428 mg of N,N'-carbonyldiimidazole were added to the solution, whilst ice-cooling. The mixture was then stirred at room temperature for 3 hours, after which 391 mg of 3-amino-1,2,4-dithiazole-5-thione were added to the reaction mixture, whilst ice-cooling, and the mixture was stirred for 1 hour and 30 minutes. It was then left to stand at room temperature overnight. The solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using 1:2, 1:1 and 2:1 by volume mixtures of ethyl acetate and hexane as eluent, and then recrystallized from a mixture of ethyl acetate and hexane, to obtain 372 mg of the title compound, melting at 158° C. to 161° C.

EXAMPLE 15

4-(1,2-Dithiolan-3-yl)butylamine diphenylphosphate (Compound No. 1-1123 diphenylphosphate)

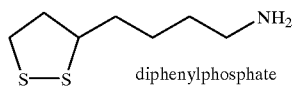

1.00 g of D,L-α-lipoic acid was dissolved in 20 ml of toluene, and 2.00 ml of triethylamine and 1.25 ml of diphenylphosphoryl azide were added to the solution at room temperature, after which the resulting mixture was stirred on an oil bath at 80° C. for 2 hours and 30 minutes. The solvent was then removed from the reaction mixture by evaporation under reduced pressure, and 20 ml of tetrahydrofuran and 1.21 ml of a 40% w/v aqueous solution of O-methylhydroxylamine hydrochloride were added to the residue thus obtained, whilst ice-cooling. 2 ml of methanol were then added to the mixture, after which the mixture was stirred at room temperature for 6 hours and then left to stand overnight. The solvent was then removed from the reaction mixture by evaporation under reduced pressure, and water and 2 N aqueous hydrochloric acid were added to the residue thus obtained to adjust the pH to 2, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using ethyl acetate and then a 3:1 by volume mixture of ethyl acetate and methanol as eluent, followed by reverse phase preparative silica gel column chromatography (using 1:4 and 1:1 by volume mixtures of acetonitrile and water as the eluent). The solvent was then removed from the fraction containing the title compound by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. Ethyl acetate was added to the residue thus obtained to recrystallise it, giving 116 mg of the title compound, melting at 100° C. to 103° C.

EXAMPLE 16

N,N'-Bis[4-(1,2-dithiolan-3-yl)butyl]urea (Compound No. 1-765)

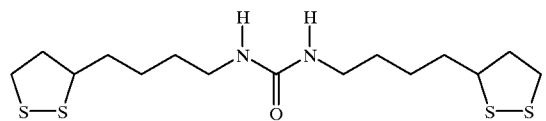

3.0 g of D,L-α-lipoic acid were dissolved in 60 ml of toluene, and 2.40 ml of triethylamine and 3.70 ml of diphenylphosphoryl azide were added to the resulting solution at room temperature, after which the resulting mixture was stirred on an oil bath at 80° C. for 2 hours. The solvent was then removed from the reaction mixture by evaporation under reduced pressure, and 60 ml of t-butanol were added at room temperature to the residue thus obtained. The mixture was then stirred and then left to stand for 5 days. At the end of this time, the solvent was removed from the reaction mixture by evaporation under reduced pressure, and the residue thus obtained was purified by silica gel column chromatography, using 1:5 and 1:3 by volume mixtures of ethyl acetate and hexane as eluent. The solvent was then removed by evaporation under reduced pressure, and 5 ml of dioxane were added to the resulting residue. The solvent was then removed by evaporation under reduced pressure. 5 ml of 2 N aqueous hydrochloric acid and 10 ml of methanol were added to the residue thus obtained, and the mixture was stirred on an oil bath at 60° C. for 2 hours. The solvent was then removed from the reaction mixture by evaporation under reduced pressure. Water was added to the residue and the mixture was neutralized with triethylamine, after which it was extracted with ethyl acetate. The extraction solution was washed with a saturated aqueous solution of sodium chloride and dried over anhydrous sodium sulfate. Ethyl acetate was removed from the extraction solution by evaporation under reduced pressure, and the residue was recrystallized from ethyl acetate, to obtain 260 mg of a crude product.

160 mg of this crude product were purified by reverse phase preparative silica gel column chromatography, using

EXAMPLE 17

5-(1,2-Dithiolan-3-yl)pentanohydroxamic acid
(Compound No. 1-58)

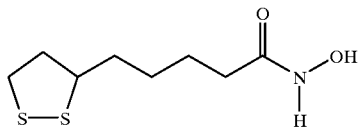

500 mg of D,L-α-lipoic acid were dissolved in 10 ml of anhydrous dimethylformamide, and 428 mg of N,N'-carbonyldiimidazole were added to the solution, whilst ice-cooling, and then the mixture was stirred at room temperature for 2 hours and 30 minutes. 0.67 ml of triethylamine and 334 mg of hydroxylamine hydrochloride were then added to the reaction mixture, whilst ice-cooling, and the mixture was stirred at room temperature for 2 hours and then left to stand overnight. At the end of this time, the solvent was removed from the reaction mixture by evaporation under reduced pressure, and water and 2 N aqueous hydrochloric acid were added to the residue thus obtained to adjust the pH to 6 to 7, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using a 4:1 by volume mixture of ethyl acetate and hexane, followed by a 20:1 by volume mixture of ethyl acetate and methanol, as eluent, and then by reverse phase preparative silica gel column chromatography, using 3:7 and 1:1 by volume mixtures of acetonitrile and water as eluent. The product thus obtained was lyophilised, to obtain 0.38 g of the title compound, melting at 63° C. to 64° C.

Then it was extracted with a 2:3, 1:1, 3:2 and 7:3 by volume mixtures of acetonitrile and water as the eluent. The solvent was then evaporated from the fraction containing the title compound under reduced pressure, to obtain 87 mg of the title compound, melting at 115° C. to 116° C.

EXAMPLE 18

N-[4-(1,2-Dithiolan-3-yl)butyl-N'-[1-methoxycarbonyl-2-(4-methoxybenzylthio)ethyl]urea (Compound No. 1-766)

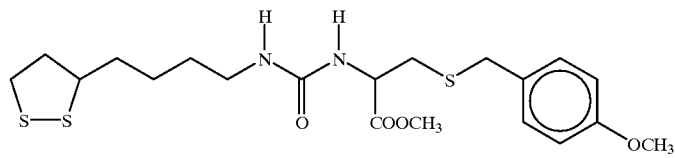

300 mg of D,L-α-lipoic acid were dissolved in 6 ml of toluene, and 0.24 ml of triethylamine and 0.37 ml of diphenylphosphoryl azide were added to the solution at room temperature. The mixture was then stirred on an oil bath at 80° C. for 2 hours. At the end of this time, a solution of 434 mg of S-(4-methoxybenzyl)-L-cysteine methyl ester in 3 ml of anhydrous tetrahydrofuran was added to the reaction mixture, whilst ice-cooling, and the mixture was stirred at room temperature for 3 hours and then left to stand overnight. The solvent was then removed from the reaction mixture by evaporation under reduced pressure, and the mixture was recrystallized from ethyl acetate, to obtain 434 mg of the title compound, melting at 105° C. to 107° C.

EXAMPLE 19

Hydrazine-N,N'-dicarboxylic acid bis[4-(1,2-dithiolan-3-yl)butylamide] (Compound No. 1-936)

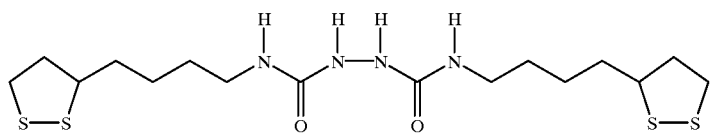

1.00 g of D,L-α-lipoic acid was dissolved in 20 ml of toluene, and 2.00 ml or triethylamine and 1.25 ml of diphenylphosphoryl azide were added to the resulting solution. The mixture was then stirred on an oil bath at 70° C. for 2 hours. 0.19 ml of anhydrous hydrazine was then added to the reaction mixture, whilst ice-cooling, and the mixture was stirred at room temperature for 2 hours. The solvent was then removed from the reaction mixture by evaporation under reduced pressure, and the residue thus obtained was washed with water and with ethyl acetate. The insolubles were then collected by filtration. The insolubles thus obtained were washed with a 5:2:1 by volume mixture of methanol, tetrahydrofuran and dimethylformamide, to obtain 401 mg of the title compound, melting at 205° C. to 207° C.

EXAMPLE 20

N-[5-(1,2-Dithiolan-3-yl)pentanoyl] ethanesulfonamide (Compound No. 1-497)

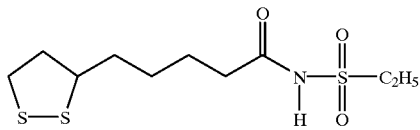

500 mg of D,L-α-lipoic acid were dissolved in 10 ml of anhydrous dimethylformamide, and 428 mg of N,N'-carbonyldiimidazole were added to the solution, whilst ice-cooling. The mixture was then stirred at room temperature for 1 hour. At the end of this time, a solution of 284 mg of ethanesulfonamide in 3 ml of dimethylformamide and 113 mg of sodium hydride (as a 55% w/w dispersion in mineral oil) were added to the reaction mixture, whilst ice-cooling, and the mixture was stirred at room temperature for 1 hour and then left to stand for 3 days. The solvent was then removed from the reaction mixture by evaporation under reduced pressure, and water and 2 N aqueous hydrochloric acid were added to the residue thus obtained to adjust the pH to 2, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using 1:1 and 2:1 by volume mixtures of ethyl acetate and hexane as eluent, followed by reverse phase preparative silica gel column chromatography, using 3:7, 2:3 and 1:1 by volume mixtures of acetonitrile and water as eluent. The solvent was then removed from the eluted fraction thus obtained by evaporation under reduced pressure, and the residue thus obtained was dissolved in dioxane. The solution was lyophilised, to obtain 30 mg of the title compound, melting at 98° C. to 100° C.

EXAMPLE 21

1,1-Dimethyl-4-[4-(1,2-dithiolan-3-yl)butyl] semicarbazide (Compound No. 1-861)

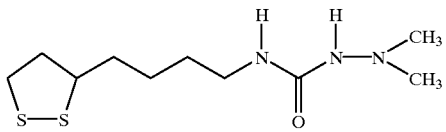

1.00 g of D,L-α-lipoic acid was dissolved in 10 ml of toluene, and 0.80 ml of triethylamine and 1.25 ml of diphenylphosphoryl azide were added to the resulting solution, after which the resulting mixture was stirred on an oil bath at 80° C. for 1 hour. 0.55 ml of 1,1-dimethylhydrazine was then added to the mixture, whilst ice-cooling, and the mixture was stirred at room temperature for 1 hour and then left to stand overnight. At the end of this time, the solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using a 3:1 by volume mixture of ethyl acetate and hexane and then a 10:1 by volume mixture of ethyl acetate and methanol as eluent, followed by reverse phase preparative silica gel column chromatography, using 7:13 and 2:3 by volume mixtures of acetonitrile and water as eluent. The eluted fraction thus obtained was lyophilised, to obtain 0.99 g of the title compound, melting at 60° C. to 61° C.

EXAMPLE 22

Morpholine-4- carboxylic acid 4-(1,2 -dithoilan-3-yl)butylamide (Compound No. 1-1142)

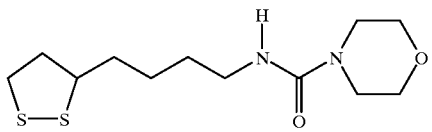

500 mg of D,L-α-lipoic acid were dissolved in 10 ml of toluene, and 0.36 ml of triethylamine and 0.56 ml of diphenylphosphoryl azide were added to the resulting solution, after which the resulting mixture was stirred on an oil bath at 80° C. for 1 hour and 30 minutes. 0.23 ml of morpholine was then added to the mixture, whilst ice-cooling, and the mixture was stirred at room temperature for 2 hours and then left to stand overnight. The solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromaatography, using ethyl acetate and then a 10:1 by volume mixture of ethyl acetate and methanol as eluent, followed by reverse phase preparative silica gel column chromatography, using 3:7 and 2:3 by volume mixtures of acetonitrile and water as eluent. The solvent was evaporated from the eluted fraction thus obtained under reduced pressure, and water was added to the residue, after which it was extracted with ethyl acetate. The extraction solution was washed with a saturated aqueous solution of sodium chloride and dried over anhydrous sodium sulfate, and then the solvent was removed by evaporation under reduced pressure, The residue thus obtained was dissolved in dioxane, and the solution was lyophilised, to obtain 0.51 g of the title compound, melting at 74° C. to 77° C.

EXAMPLE 23

N-Hydroxy-N'-[4-(1,2-dithiolan-3-yl)butyl]urea (Compound No. 1-750)

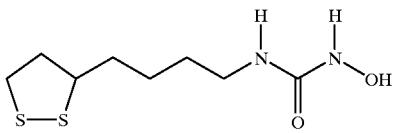

500 mg of D,L-α-lipoic acid were dissolved in 10 ml of toluene, and 0.69 ml of triethylamine and 0.56 ml of diphenylphosphoryl azide were added to the resulting solution, after which the resulting mixture was stirred on an oil bath at 80° C. for 2 hours. The solvent was then removed from the removed from the reaction mixture by evaporation under reduced pressure, and 10 ml of anhydrous tetrahydrofuran and 181 mg of hydroxylamine hydrochloride were added to the residue thus obtained on a bath containing ice and an aqueous solution of sodium chloride. The mixture was stirred for 2 hours at the bath temperature, and then stirred at room temperature for 3 hours, after which it was left to stand for 3 days. The solvent was then removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure, The residue thus obtained was subjected to silica gel column chromatography, eluted first with a 2:1 by volume mixture of ethyl acetate and hexane, then with ethyl acetate alone, and finally with a 10:1 by volume mixture of ethyl acetate and methanol. The solvent was removed from the eluted fraction thus obtained by evaporation under reduced pressure, and the precipitated powder was washed with a mixture of dimethylformamide, tetrahydrofuran, methanol and ethyl acetate and subjected to reverse phase preparative silica gel column chromatography, using 3:7 and 1:1 by volume mixtures of acetonitrile and water as eluent. The eluted fraction thus obtained was concentrated by evaporation under reduced pressure, and the crystals which precipitated were collected by filtration, to obtain 85 mg of the title compound, melting at 100° C. to 101° C.

EXAMPLE 24

2-[5-(1,2-Dithiolan-3-yl)pentanoylamino]ethanesulfonic acid imidazole salt (Compound No. 1-57 imidazole salt)

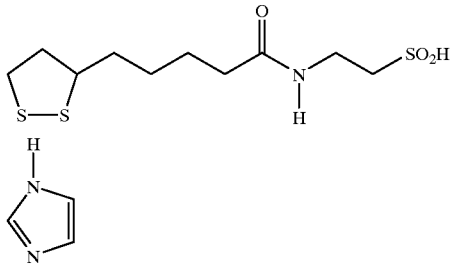

500 mg of D,L-α-lipoic acid were dissolved in 10 ml of anhydrous dimethylformamide, and 428 mg of N,N'-carbonyldiimidazole were added to the resulting solution, whilst ice-cooling, and then the mixture was stirred at room temperature for 4 hours. At the end of this time, 0.50 ml of triethylamine and 450 mg of 2-aminoethanesulfonic acid were added to the reaction mixture, whilst ice-cooling, and the mixture was stirred at room temperature of 4 hours and 30 minutes and then left to stand of 2 days. After this time, the reaction mixture was stirred on an oil bath at 50° C. for 6 hours and then stirred on an oil bath at 70° C. for 1 hour. It was then left to stand at room temperature overnight. The reaction mixture was then stirred on an oil bath at 70° C. for 2 hours and the solvent was removed from the reaction mixture by evaporation under reduced pressure, The residue thus obtained was washed with ethyl acetate and subjected to reverse phase preparative silica gel column chromatography, using a 1:9 by volume mixture of acetonitrile and water as eluent. The eluted fraction thus obtained was lyophilised, to obtain 268 mg of the title compound, melting at 96° C. to 99° C.

EXAMPLE 25

$N^\beta$-[5-(1,2-Dithiolan-3-yl)pentanoyl]histamine (Compound No. 1-75)

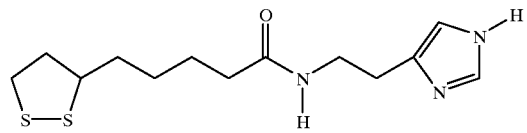

500 mg of D,L-α-lipoic acid were dissolved in 10 ml of anhydrous dimethylformamide, and 422 mg of N,N'-carbonyldiimidazole were added to the resulting solution, whilst ice-cooling. The mixture was then stirred at room temperature for 2 hours and 30 minutes. 0.73 ml of triethylamine and 479 mg of histamine dihydrochloride were then added to the reaction mixture at room temperature, and the mixture was stirred for 4 hours and 30 minutes. At the end of this time, the solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure. The residue thus obtained was purified by silica gel column chromatography, using 1:0, 5:1 and 3:1 by volume mixtures of ethyl acetate and ethanol as eluent. It was then recrystallized from a 1:2 by volume mixture of ethyl acetate and diisopropyl ether, to obtain 270 mg of the title compound, melting at 108° C. to 110° C.

EXAMPLE 26

N,N'-Bis[4-(1,2-dithiolan-3-yl)butylcarbamoyl] sulfamide (Compound No. 1-2614)

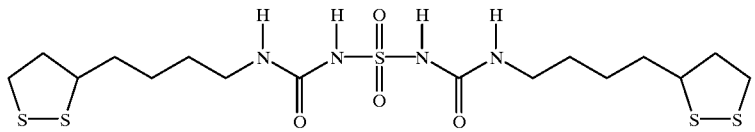

500 mg of D,L-α-lipoic acid were dissolved in 10 ml of toluene, and then 0.36 ml of triethylamine and 0.56 ml of diphenylphosphoryl azide were added to the mixture, after which the resulting mixture was stirred on an oil bath at 80° C. for 2 hours. The solvent was then removed from the reaction mixture by evaporation under reduced pressure, and 6 ml of anhydrous dimethylformamide were added to the residue thus obtained, to give a dimethylformamide solution.

Separately, 113 mg of sodium hydride (as a 55% w/w dispersion in mineral oil) were dispersed in 4 ml of dimethylformamide, and 252 mg of sulfamide were added to the suspension, whilst ice-cooling, after which the resulting mixture was stirred at room temperature for 2 hours. The above dimethylformamide solution was then added to the reaction mixture on a bath containing ice and an aqueous solution of sodium chloride, and the mixture was stirred at the same temperature of 1 hour and 30 minutes. The reaction mixture was then stirred at room temperature of 4 hours, after which it was left to stand at room temperature overnight. The solvent was the removed from the reaction mixture by evaporation under reduced pressure, and water was added to the residue thus obtained, after which it was neutralized by the addition of 2 N aqueous hydrochloric acid. The crystals which precipitated were washed with ethyl acetate, with water and with ethanol, to obtain 223 mg of the title compound, melting at 153° C. to 156° C.

EXAMPLE 27

$N^\beta,N^{im}$-Bis[4-(1,2-dithiolan-3-yl)butylcarbamoyl] histamine

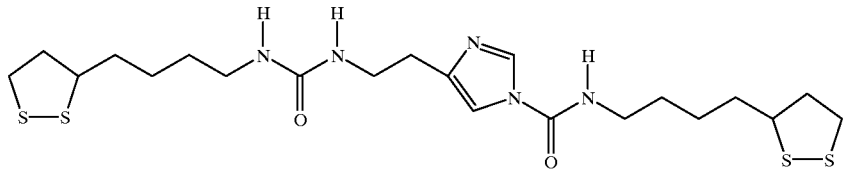

500 mg of D,L-α-lipoic acid were dissolved in 10 ml of toluene, and then 0.36 ml of triethylamine and 0.56 ml of diphenylphosphoryl azide were added to the solution, after which the resulting mixture was stirred on an oil bath at 80° C. for 1 hour and 30 minutes. The solvent was then removed form the reaction mixture by evaporation under reduced pressure, and 5 ml of anhydrous tetrahydrofuran were added to the residue thus obtained, to give a tetrahydrofuran solution.

Separately, 479 mg of histamine dihydrochloride were dissolved in 2 ml of anhydrous dimethylformamide, and then 0.72 ml of triethylamine was added to the solution, after which the resulting mixture was stirred at room temperature for 1 hour and 30 minutes. 5 ml of anhydrous tetrahydrofuran were then added to the reaction mixture, and then the above anhydrous tetrahydrofuran solution was added thereto, whilst ice-cooling. The mixture was stirred at room temperature for 3 hours and then left to stand overnight. At the end of this time, the solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate, and then the solvent was removed by evaporation under reduced pressure, The residue thus obtained was subjected to silica gel column chromatography, using 1:0, 5:1 and 3:1 by volume mixtures of methanol as the eluent, after which ti was subjected to reverse phase preparative silica gel column chromatography, using 1:4, 3:7, 2:3 and 1:1 by volume mixtures of acetonitrile and water as eluent. The solvent was evaporated under reduced pressure from the fraction containing the title compound, and water was added to the residue thus obtained, after which it was extracted with ethyl acetate. The extraction solution was washed with a saturated aqueous solution of sodium chloride and dried over anhydrous sodium sulfate. The solvent was removed form the extraction solution by evaporation under reduced pressure, and the residue thus obtained was dissolved in dioxane and lyophilised, to obtain 52 mg of the title compound, melting at 115° C. to 117° C.

EXAMPLE 28

N-[4-(1,2-Dithiolan-3-yl)butyl]-N'-methanesulfonylurea (Compound No. 1-1069)

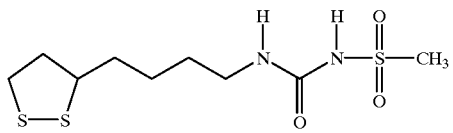

500 mg of D,L-α-lipoic acid were dissolved in 10 ml of toluene, and then 0.36 ml of triethylamine and 0.56 ml of diphenylphosphoryl azide were added to the solution, after which the resulting mixture was stirred on an oil bath at 80° C. for 2 hours. The solvent was removed from the reaction mixture by evaporation under reduced pressure, and 5 ml of anhydrous dimethylformamide were added to the residue thus obtained, to give a dimethylformamide solution.

Separately, 247 mg of methanesulfonamide were dissolved in 5 ml of anhydrous dimethylformamide, and then 113 mg of sodium hydride (as a 55% w/w dispersion in mineral oil) were added to the solution, after which the resulting mixture was stirred at room temperature for 2 hours. The above anhydrous dimethylformamide solution was then added to the reaction mixture, whilst ice-cooling, and the mixture was stirred at room temperature for 3 hours and then left to stand at room temperature of 3 days. The solvent was removed from the reaction mixture by evaporation under reduced pressure. Water was added to the residue thus obtained, and the mixture was neutralized by the addition of 2 N aqueous hydrochloric acid, after which it was extracted with ethyl acetate. The extraction solution was washed with a saturated aqueous solution of sodium chloride and dried over anhydrous sodium sulfate. The solvent was removed from the extraction solution by evaporation under reduced pressure. The residue thus obtained was purified by silica gel column chromatography, using ethyl acetate as eluent, and the active fraction was then recrystallized from ethyl acetate, to obtain 302 mg of the title compound, melting at 125° C. to 127° C.

EXAMPLE 29

4-[4-(1,2-Dithoilan-3-yl)butyl]simicarbazide diphenylphosphate (Compound No. 1-858 diphenylphosphate)

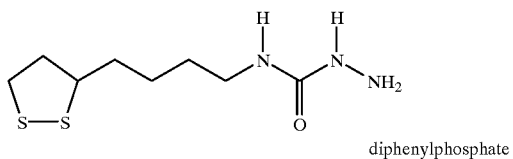

500 mg of D,L-α-lipoic acid were dissolved in 10 ml of toluene, and then 0.36 ml of triethylamine and 0.56 ml of diphenylphosphoryl azide were added to the solution, after which the resulting mixture was stirred on an oil bath at 80° C. for 1 hour and 30 minutes. The solvent was removed from the reaction mixture by evaporation under reduced pressure, and 3.5 ml of anhydrous tetrahydrofuran were added to the residue thus obtained, The solution was added to 0.75 mg of hydrazine and then 2 ml of anhydrous dimethylformamide were added thereto. The mixture was stirred at room temperature for 5 hours and then left to stand overnight. At the end of this time, the solvent was removed from the reaction mixture by evaporation under reduced pressure, and a saturated aqueous solution of sodium chloride was added to the residue thus obtained, after which it was extracted with ethyl acetate. The extraction solution was washed with a saturated aqueous solution of sodium chloride and dried over anhydrous sodium sulfate. The solvent was removed from the extraction solution by evaporation under reduced pressure. The residue thus obtained was purified by silica gel column chromatography, using 1:0, 10:1 and 5:1 by volume mixtures of ethyl acetate and methanol as eluent, after which it was recrystallized form a 1:1 by volume mixture of ethyl acetate and diisopropyl ether, to obtain 125 mg of the title compound, melting at 134° C. to 139° C.

EXAMPLE 30

N-[4-(1,2-Dithiolan-3-yl)butyl]-N'-aminosulfonylurea (Compound No. 1-1112)

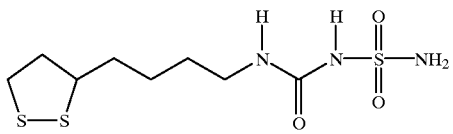

500 mg of D,L-α-lipoic acid were dissolved on 10 ml of toluene, and then 0.36 ml of triethylamine and 0.56 ml of diphenylphosphoryl azide were added to the solution, after which the resulting mixture was stirred on an oil bath at 70° C. for 2 hours. The solvent was then removed from the reaction mixture by evaporation under reduced pressure, and 5 ml of anhydrous dimethylformamide were added to the residue thus obtained, to give a dimethylformamide solution.

Separately, 1.15 g of sulfamide were dissolved in 10 ml of anhydrous dimethylformamide, and then 524 mg of sodium hydride (as a 55% w/w dispersion in mineral oil) were added to the solution, whilst ice-cooling, after which the resulting mixture was stirred at room temperature for 1 hour and 30 minutes. The above dimethylformamide solution was then added to the reaction mixture, whilst ice-cooling, and the mixture was stirred at room temperature for 4 hours and then left to stand for 2 days. At the end of this time, the solvent was removed from the reaction mixture by evaporation under reduced pressure, and water was added to the residue thus obtained. The mixture was neutralized by the addition of 2 N aqueous hydrochloric acid, after which it was extracted with ethyl acetate. The extraction solution was washed with a saturated aqueous solution of sodium chloride and dried over anhydrous sodium sulfate. The solvent was removed from the extraction solution by evaporation under reduced pressure, The residue thus obtained was purified by silica gel column chromatography, using 1:1, 2:1 and 4:1 by volume mixtures of ethyl acetate and hexane as eluent. It was then recrystallized from ethanol, to obtain 126 mg of the title compound, melting at 123° C. to 125° C.

EXAMPLE 31

Methyl N-[4-(1,2-Dithiolan-3-yl)butyl]carbamate
(Compound No. 1-676)

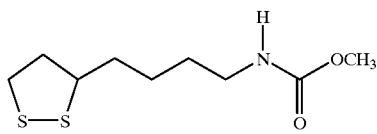

500 mg of D,L-α-lipoic acid were dissolved in 10 ml of toluene, and then 0.36 ml of triethylamine and 0.56 ml of diphenylphosphoryl azide were added to the solution, after which the resulting mixture was stirred on an oil bath at 80° C. for 1 hour. The solvent was then removed from the reaction mixture by evaporation under reduced pressure, and 10 ml of anhydrous methanol were added to the residue thus obtained. The mixture was stirred at room temperature of 6 hours and then left to stand overnight. At the end of this time, the solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate. The solvent was removed from the extraction solution by evaporation under reduced pressure. The residue thus obtained was purified by silica gel column chromatography, using 1:4 and 1:2 by volume mixtures of ethyl acetate and hexane as eluent, after which it was subject to reverse phase column chromatography, using 1:4, 3:7, 2:3 and 1:1 by volume mixtures of acetonitrile and water as eluent. The solvent was evaporated under reduced pressure from the fraction containing the title compound, and water was added to the residue thus obtained, after which it was extracted with ethyl acetate. The extraction solution was washed with a saturated aqueous solution of sodium chloride and dried over anhydrous sodium sulfate. The solvent was removed from the extraction solution by evaporation under reduced pressure, and the residue was dissolved in dioxane and lyophilised, to obtain 324 mg of the title compound, melting at 31° C. to 32° C.

EXAMPLE 32

N-[2-(5-Methoxy-1H-indol-3-yl)ethyl]lipoamide
(Compound No. 1-80)

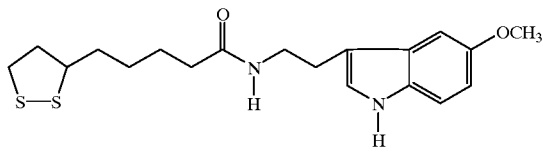

500 mg of D,L-α-lipoic acid were dissolved in 10 ml of anhydrous dimethylformamide, and 422 mg of N,N'-carbonyldiimidazole were added to the solution, whilst ice-cooling. The mixture was then stirred at room temperature of 3 hours and 30 minutes. At the end of this time, 495 mg of 5-methoxytryptamine were added to the reaction mixture, whilst ice-cooling, and the mixture was stirred at room temperature for 3 hours and then left to stand at room temperature overnight. The solvent was removed from the reaction mixture by evaporation under reduced pressure, and water was added to the residue thus obtained. The residue was extracted with ethyl acetate and then dried over anhydrous sodium sulfate. The solvent was removed form the extraction solution by evaporation under reduced pressure. The residue thus obtained was purified by silica gel column chromatography, using 2:1, 4:1 and 1:0 by volume mixtures of ethyl acetate and hexane as eluent, to obtain 515 mg of the title compound as a yellow oil having an Rf value of 0.26 (silica gel thin layer chromatography; using a 2:1 by volume mixture of ethyl acetate and hexane as the developing solvent).

EXAMPLE 33

N-[4-(1,2-Dithiolan-3-yl)butyl]-N'-[2-(5-methoxy-1H-indol-3-yl)ethyl]urea (Compound No. 1-772)

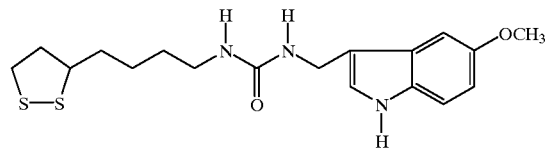

500 mg of D,L-α-lipoic acid were dissolved in 10 ml of toluene, and then 0.36 ml of triethylamine and 0.56 ml of diphenylphosphoryl azide were added to the solution, after which the resulting mixture was stirred on an oil bath at 80° C. for 1 hour The solvent was then removed from the reaction mixture by evaporation under reduced pressure, and 5 ml of anhydrous tetrahydrofuran were added to the residue thus obtained, to give a tetrahydrofuran solution.

Separately, 1.37 mg of 5-methoxytryptamine were dissolved in a mixture of 10 ml of anhydrous tetrahydrofuran and 4 ml of anhydrous dimethylformamide, and the resulting solution was added to the above anhydrous tetrahydrofuran solution. whilst ice-cooling. The mixture was stirred, whilst ice-cooling, for 1 hour and then at room temperature for 4 hours, after which it was left to stand at room temperature overnight. The solvent was then removed from the reaction mixture by evaporation under reduced pressure, and a saturated aqueous solution of sodium chloride was added to the residue thus obtained, after which it was extracted with ethyl acetate. The extraction solution was washed with a saturated aqueous solution of sodium chloride and then dried over anhydrous sodium sulfate. The solvent was removed from the extraction solution by evaporation under reduced pressure. The residue thus obtained was purified by silica gel column chromatography, using 3:1 and 1:0 by volume mixtures of ethyl acetate and hexane and then a 10:1 by volume mixture of ethyl acetate and methanol as eluent, after which it was recrystallized from ethyl acetate, to obtain 674 mg of the title compound, melting at 100° C. to 101° C.

EXAMPLE 34

N-[4-(1,2-Dithiolan-3-yl)butyl]pyrrolidine-1-carboxamide (Compound No. 1-1139)

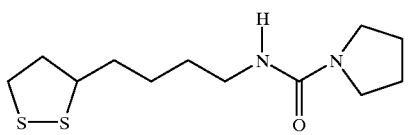

500 mg of D,L-α- lipoic acid were dissolved in 10 ml of anhydrous toluene, and then 0.56 ml of diphenylphosphoryl azide was added to the solution, after which the resulting mixture was stirred on an oil bath at 80° C. for 1 hour and 30 minutes. 0.22 ml of pyrrolidine was then added to the reaction mixture, whilst ice-cooling, and the mixture was stirred at room temperature for 1 hour and then let to stand at room temperature overnight. At the end of this time, the solvent was removed from the reaction mixture by evaporation under reduced pressure, and water was added to the residue thus obtained, after which it was extracted with ethyl acetate. The extraction solution was washed with a saturated aqueous solution of sodium chloride and then dried over anhydrous sodium sulfate. The solvent was removed from the extraction solution by evaporation under reduced pressure. The residue thus obtained was purified by silica gel column chromatography, using 1:0 and 10:1 by volume mixtures of ethyl acetate and methanol as eluent, after which it was recrystallized form a 1:1:1 by volume mixture of ethyl acetate, methanol and acetonitrile, to obtain 231 mg of the title compound, melting at 91° C. to 93° C.

EXAMPLE 35

1-[5-(1,2-Dithiolan-3-yl)pentanoyl]pyrrolidine
(Compound No. 1-1129)

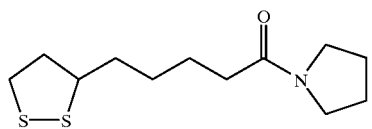

500 mg of D,L-α-lipoic acid were dissolved in 10 ml of anhydrous dimethylformamide, and then 422 mg of N,N'-carbonyldiimidazole were added to the solution. The resulting mixture was then stirred at room temperature for 1 hour and 30 minutes. 0.22 ml of pyrrolidine was added to the reaction mixture, whilst ice-cooling, and the mixture was stirred at room temperature for 2 hours. At the end of this time, the solvent was removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate. The solvent was removed from the extraction solution by evaporation under reduced pressure. The residue thus obtained was purified by silica gel column chromatography, using 2:1, 3:1 and 1:0 by volume mixtures of ethyl acetate and hexane as eluent, after which it was dissolved in dioxane and lyophilised, to obtain 364 mg of the title compound as a yellow oil having an Rf value of 0.15 (silica gel thin layer chromatography, using ethyl acetate as the developing solvent).

EXAMPLE 36

N-[4-(1,2-Dithiolan-3yl)butyl]piperidine-1-carboxamide (Compound No. 1-1140)

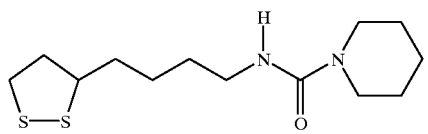

500 mg of D,L-α-lipoic acid were dissolved in 10 ml of anhydrous toluene, and then 0.36 ml of triethylamine and 0.56 of diphenylphosphoryl azide were added to the solution, after which the resulting mixture was stirred on an oil bath at 80° C. for 1 hour. 0.26 ml of piperidine was then added to the reaction mixture, whilst ice-cooling, and the mixture was left to stand at room temperature overnight. At the end of this time, the solvent was removed from the reaction mixture by evaporation under reduced pressure, and water was added to the residue thus obtained, after which it was extracted with ethyl acetate. The extraction solution was washed with a saturated aqueous solution of sodium chloride and then dried over anhydrous sodium sulfate. The solvent was then removed from the extraction solution by evaporation under reduced pressure, The residue thus obtained was purified by silica gel column chromatography, using 2:1, 4:1 and 1:0 by volume mixtures of ethyl acetate and hexane as eluent. It was then recrystallized from a 1:1 by volume mixture of ethyl acetate and methanol, to obtain 252 mg of the title compound, melting at 90° C. to 91° C.

EXAMPLE 37

1-[5-(1,2-Dithiolan-3-yl)pentanoyl]piperidine
(Compound No. 1-1130)

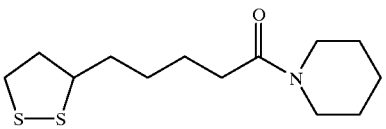

500 mg of D,L-α-lipoic acid were dissolved in 10 ml of anhydrous dimethylformamide, and then 422 mg of N,N'-carbonyldiimidazole were added to the solution. The mixture was then stirred at room temperature for 3 hours. At the end of this time, 0.26 ml of piperidine was added to the reaction mixture, and the mixture was stirred at room temperature for 4 hours and then left to stand overnight. The solvent was then removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate. The solvent was removed from the extraction solution by evaporation under reduced pressure. The residue thus obtained was purified by silica gel column chromatography, using 3:2 and 3:1 by volume mixtures of ethyl acetate and hexane as eluent. It was then dissolved in dioxane and lyophilised, to obtain 381 mg of the title compound as a yellow oil having an Rf value of 0.30 (silica gel thin layer chromatography, using a 3:2by volume mixture of ethyl acetate and hexane as the developing solvent).

EXAMPLE 38

N-[4-(1,2-Dithiolan-3-yl)butyl]thiomorpholine-4-carboxamide (Compound No. 1-1143)

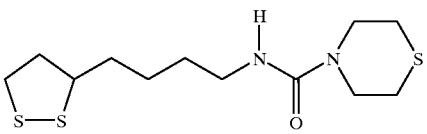

500 mg of D,L-α-lipoic acid was dissolved in 10 ml of anhydrous toluene, and then 0.36 ml of triethylamine and 0.56 of diphenylphosphoryl azide were added to the solution after which the resulting mixture was stirred on an oil bath at 80° C. for 1 hour. 0.25 ml of thiomorpholine was then added to the reaction mixture at room temperature, and the mixture was stirred for 5 hours and then left to stand for 2 days. At the end of this time, the solvent was removed from the reaction mixture by evaporation under reduced pressure, and water was added to the residue thus obtained, after which it was extracted with ethyl acetate. The extraction solution was washed with a saturated aqueous solution of sodium chloride and then dried over anhydrous sodium sulfate. The solvent was removed from the extraction solution by evaporation under reduced pressure, The residue thus obtained was purified by silica gel column chromatography, using 3:2, 3:1 and 1:0 by volume mixtures of ethyl acetate and hexane as eluent. It was then dissolved in dioxane and lyophilised, to obtain 583 mg of the title compound, melting at 80° C. to 81° C.

EXAMPLE 39

(S)-N-[5-(1,2-Dithiolan-3-yl)pentanoyl] methanesulfonamide (Compound No. 1-496)

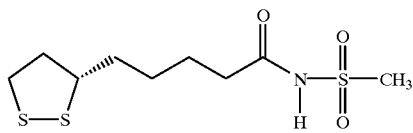

300 mg of (S)-α-lipoic acid were dissolved in 6 ml of anhydrous dimethylformamide, and 276 mg of N,N'-carbonyldiimidazole and 1 ml of anhydrous dimethylformamide were added to the solution, whilst ice-cooling. The mixture was then stirred at room temperature for 1 hour and 30 minutes. At the end of this time, 162 mg of methanesulfonamide and 74 mg of sodium hydride (as a 55% w/w dispersion in mineral oil) were added to the reaction mixture, whilst ice-cooling, and the mixture was stirred at room temperature for 1 hour and then left to stand for 2 days. The solvent was then removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate. The solvent was then removed from the extraction solution by evaporation under reduced pressure. The residue thus obtained was purified by silica gel column chromatography, using 1:1 and 3:1 by volume mixtures of ethyl acetate and hexane as eluent. It was then recrystallized form a 1:2 by volume mixture of ethyl acetate and hexane, to obtain 154 mg of the title compound, melting at 91° C. to 92° C.

EXAMPLE 40

(R)-N-[5-(1,2-Dithiolan-3-yl)pentanoyl] methanesulfonamide (Compound No. 1-496)

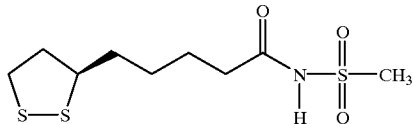

110 mg of (R)-α-lipoic acid were dissolved in 2 ml of anhydrous dimethylformamide, and 97 mg of N,N'-carbonyldiimidazole were added to the solution, whilst ice-cooling. The mixture was then stirred at room temperature for 4 hours. At the end of this time, 57 mg of methanesulfonamide and 26 mg of sodium hydride (as a 55% w/w dispersion in mineral oil) were added to the reaction mixture, whilst ice-cooling, and the mixture was stirred at room temperature for 5 hours and then left to stand overnight. The solvent was then removed from the reaction mixture by evaporation under reduced pressure, and water was added to the residue this obtained. The resulting mixture was neutralized by the addition of 2 N aqueous hydrochloric acid, after which it was extracted with ethyl acetate. The extraction solution was washed with a saturated aqueous solution of sodium chloride and then dried over anhydrous sodium sulfate. The solvent was removed from the extraction solution by evaporation under reduced pressure. The residue thus obtained was purified by silica gel column chromatography, using 1:1 and 3:1 by volume mixtures of ethyl acetate and hexane as eluent, after which it was dissolved in dioxane and lyophilised, to obtain 68 mg of the title compound, melting at 71° C. to 73° C.

EXAMPLE 41

4-[5-(1,2-Dithiolan-3-yl)pentanoyl]thiomorpholine (Compound No. 1-1133)

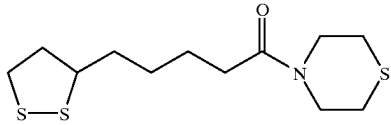

500 mg of D,L-α-lipoic acid were dissolved in 10 ml of anhydrous dimethylformamide, and then 422 mg of N,N'-carbonyldiimidazole were added to the solution. The mixture was then stirred at room temperature for 1 hour and 30 minutes, after which it was left to stand overnight. At the end of this time, 0.25 ml of thiomorpholine was added to the reaction mixture, and the mixture was stirred at room temperature for 5 hours and then left to stand overnight. The solvent was then removed from the reaction mixture by evaporation under reduced pressure, and water was added to the residue thus obtained, after which it was extracted with ethyl acetate. The extraction solution was washed with a saturated aqueous solution of sodium chloride and dried over anhydrous sodium sulfate. The solvent was then removed from the extraction solution by evaporation under reduced pressure. The residue thus obtained was purified by silica gel column chromatography, using 1:1 and 2:1 by volume mixtures of ethyl acetate and hexane as eluent. It was then dissolved in dioxane and lyophilised, to obtain 385 mg of the title compound as a yellow amorphous substance, melting at 31° C. to 32° C.

EXAMPLE 42

N-[4-(1,2-Dithiolan-3-yl)butyl]1-piperazinylcarboxamide (Compound No. 1-1141)

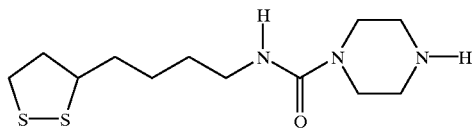

500 mg of D,L-α-lipoic acid were dissolved in 10 ml of anhydrous toluene, and then 0.36 ml of triethylamine and 0.56 ml of diphenylphosphoryl azide were added to the solution, after which the resulting mixture was stirred on an oil bath at 80° C. for 2 hours. A solution of 1.03 g of piperazine in 10 ml of anhydrous dimethylformamide was then added to the reaction mixture, whilst ice-cooling, and the mixture was stirred at room temperature for 3 hours and 30 minutes and then let to stand overnight. At the end of this time, the solvent was removed from the reaction mixture by evaporation under reduced pressure, and water was added to the residue thus obtained, after which it was neutralised by the addition of 2 N aqueous hydrochloric acid. The crystals which precipitated were collected by filtration and washed with water and ethyl acetate, to obtain 107 mg of the title compound melting at 175° C. to 177° C.

EXAMPLE 43

3-[5-(1,2-Dithiolan-3-yl)pentanoyl]thiazolidine (Compound No. 1-1258)

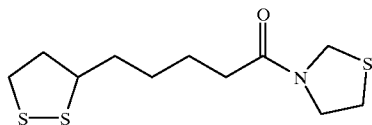

422 mg of n,N'-carbonyldiimidazole were added to a solution of 500 mg of D,L-α-lipoic acid in 10 ml of anhydrous dimethylformamide. The resulting mixture was stirred at room temperature for 1 hour and 30 minutes. 0.20 ml of thiazolidine was then added dropwise to the reaction mixture, and then the mixture was stirred at room temperature for 4 hours. The reaction mixture was allowed to stand overnight at room temperature and then the solvent was removed by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure, The residue was subjected to silica gel column chromatography, using 1:1, 3:1 and 1:0 by volume mixtures of ethyl acetate and hexane as eluent, followed by reverse phase preparative silica gel column chromatography, using a 2:3 by volume mixture of acetonitrile and water as eluent. Acetonitrile was removed from the eluate thus obtained by distillation under reduced pressure, and the residue was extracted with ethyl acetate. The extract was washed with a saturated aqueous solution of sodium chloride and then dried over anhydrous sodium sulfate. Ethyl acetate was removed from the extract by distillation under reduced pressure, and the resulting residue was dissolved in dioxane. The resulting solution was lyophilised, to give 317 mg of the title compound as a pale yellow amorphous substance, melting at 40 to 41° C.

EXAMPLE 44

N-[4-(1,2-Dithiolan-3-yl)butyl]-N'-(1piperidyl)urea (Compound No. 1-1145)

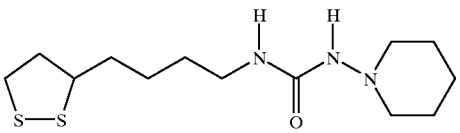

0.36 ml of triethylamine and 0.56 ml of diphenylphosphoryl azide were added to a solution of 500 mg of D,L-α-lipoic acid in 10 ml of anhydrous toluene. The resulting mixture was stirred on an oil bath at 80° C. for 1 hour and 30 minutes. 0.28 ml of 1-aminopiperidine was then added dropwise to the reaction mixture, whilst ice-cooling, and then the mixture was stirred at room temperature for 5 hours. The reaction mixture was then allowed to stand overnight at room temperature. The solvent was removed from the reaction mixture by distillation under reduced pressure. Water was added to the residue, after which it was extracted with ethyl acetate. The extract was washed with a saturated aqueous solution of sodium chloride and dried over anhydrous sodium sulfate. Ethyl acetate was removed from the extract by distillation under reduced pressure, and the residue was subjected to silica gel column chromatography, using 1:0 and 5:1 by volume mixtures of ethyl acetate and ethanol as eluent. The solvent was removed from the eluate by distillation under reduced pressure. The pressure was dissolved in dioxane, after which it was lyophilised, to give 593 mg of the title compound as a yellow amorphous substance, melting at 67 to 69° C.

EXAMPLE 45

N-(1-Piperidyl)-5-(1,2-dithiolan-3-yl)pentanamide (Compound No. 1-1135)

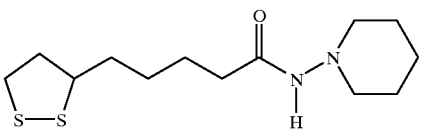

The reaction was effected as described in Example 43, but using 500 mg of D,L-α-lipoic acid, 10 of anhydrous dimethylformamide, 422 mg of N,N'-carbonyldiimidazole and 0.28 ml of 1-aminopiperidine. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromatography, using 2:1 and 1:0 by volume mixtures of ethyl acetate and hexane as eluent, after which it was recrystallised from ethyl acetate, to give 298 mg of the title compound as a yellow needle-like crystals, melting at 108 to 109° C.

EXAMPLE 46

Methyl 3-[4-(1,2-dithiolan-3-yl)butyl]ureidoacetate
(Compound No. 1-739)

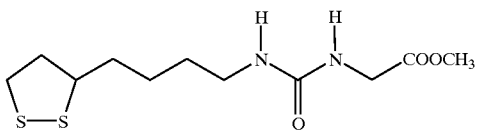

0.73 ml of triethylamine and 0.56 ml of diphenylphosphoryl azide were added to a solution of 500 mg of D,L-α-lipoic acid in 10 ml of anhydrous toluene. The resulting mixture was stirred on an oil bath at 80° C. for 1 hour and 30 minutes. The solvent was then removed from the reaction mixture by distillation under reduced pressure. 10 ml of anhydrous dimethylformamide were then added to the residue, after which 301 mg of L-glycine methyl ester hydrochloride were added, whilst ice-cooling. The resulting mixture was then stirred at room temperature for one hour. At the end of this time, the reaction mixture was allowed to stand overnight at room temperature, after which the solvent was removed by distillation under reduced pressure. Water was added to the residue, which was then extracted with ethyl acetate. The extract was washed with a saturated aqueous solution of sodium chloride and then dried over anhydrous sodium sulfate. Ethyl acetate was removed from the extract by distillation under reduced pressure, and the residue was subjected to silica gel column chromatography, using 2:1 and 1:0 by volume mixtures of ethyl acetate and hexane as eluent, followed by reverse phase preparative silica gel column chromatography, using 3:17, 3:7 and 3:2 by volume mixtures of acetontrile and water as eluent. Acetonitrile was removed from the eluate so obtained by distillation under reduced pressure, and the residue was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 336 mg of the title compound as a pale yellow amorphous substance, melting at 62 to 64° C.

EXAMPLE 47

Methyl [5-(1,2-dithiolan-3-yl)pentanoylamino]
acetate (Compound No. 1–47)

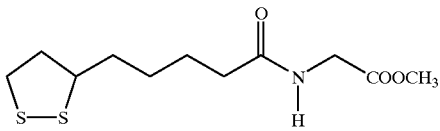

422 mg of N,N'-carbonyldimidazole were added to a solution of 500 mg of D,L-α-lipoic acid in 10 ml of anhydrous dimethylformamide. The resulting mixture was stirred at room temperature for 2 hours, after which 0.36 ml of triethylamine was added dropwise to the reaction mixture. 301 mg of glycine methyl ester hydrochloride were then added to the reaction mixture, and then the mixture was stirred at room temperature for 1 hour. The reaction mixture was allowed to stand at room temperature for two days, and then the solvent was removed by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromatography, using 3:1 and 1:0 by volume mixtures of ethyl acetate and hexane as eluent, followed by reverse phase preparative silica gel column chromatography, using 1:4, 3:7 and 1:1 by volume mixtures of acetonitrile and water as eluent. Acetonitrile was removed from the eluate thus obtained by distillation under reduced pressure, and the residue was extracted with ethyl acetate. The extract was washed with a saturated aqueous solution of sodium chloride and then dried over anhydrous sodium sulfate. Ethyl acetate was removed from the extract by distillation under reduced pressure and the residue was dissolved in dioxane, after which it was lyophilised, to give 320 mg of the title compound as a yellow oil having an Rf value of 0.26 (silica gel thin layer chromatography; using a 3:1 by volume mixture of ethyl acetate and hexane as the developing solvent).

EXAMPLE 48

{3-[4-(1,2-Dithiolan-3-yl)butyl]ureido}acetic acid
(Compound No. 1-738)

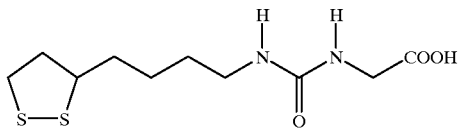

2.1 ml of a 1N aqueous solution of sodium hydroxide were added dropwise to a solution of 218 mg of methyl {3-[4-(1,2-dithiolan-3-yl)butyl]ureido}acetate (prepared as described in Example 46) in 4 ml of methanol, and then the mixture was stirred at room temperature for 5 hours. The reaction mixture was then allowed to stand overnight at room temperature, after which the solvent was removed from the reaction mixture by distillation under reduced pressure. Water was added to the residue. The resulting mixture was neutralized by the addition of 2N aqueous hydrochloric acid, after which it was extracted with ethyl acetate. The extract was washed with a saturated aqueous solution of sodium chloride and then dried over anhydrous sodium sulfate. Ethyl acetate was removed from the extract to distillation under reduced pressure. The residue was recrystallized from a 3:1 by volume mixture of ethyl acetate and hexane, to give 64 mg of the title compound as a pale yellow powder, melting at 95 to 96° C.

EXAMPLE 49

[4-(1,2-Dithiolan-3-yl)pentanoylamino]acetic acid
(Compound No. 1-46)

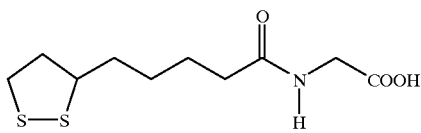

0.28 g of methyl 5-(1,2-dithiolan-3-yl) pentanoylaminoacetate (prepared as described in Example 47) was dissolved in a mixture of 2 ml of methanol and 2 ml of tetrahydrofuran. 2.0 ml of a 1N aqueous solution of sodium hydroxide were added dropwise to the resulting solution, and then the mixture was stirred at room temperature for 2 hours. The reaction mixture was then allowed to stand overnight at room temperature, after which the solvent was removed from the reaction mixture by distillation under reduced pressure. Water was added to the residue. The resulting mixture was neutralized by the addition of 2N aqueous hydrochloric acid, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 156 mg of the title compound as a yellow oil having an Rf value of 0.12 (silica gel thin layer chromatography; using a 5:1 by volume mixture of ethyl acetate and methanol as the developing solvent).

EXAMPLE 50

Methyl 2(S)-{3-[4-(1,2-dithiolan-3-yl)butyl] ureido}propionate Compound No. 1-742)

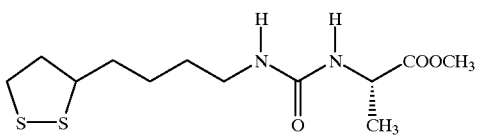

The reaction was effected as described in Example 46, but using 500 mg of D,L-α-lipoic acid, 10 ml of anhydrous toluene, 0.73 ml of triethylamine, 0.56 ml of diphenylphosphoryl azide, 10 ml of anhydrous dimethylformamide and 335 mg of L-alanine methyl ester hydrochloride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure and the residue was subjected to silica gel column chromatography, using 2:1 and 1:0 by volume mixtures of ethyl acetate and hexane as eluent. Ethyl acetate was removed from the eluate by distillation under reduced pressure, and the residue was recrystallized from a 1:1:1 by volume mixture of ethyl acetate, diisopropyl ether and hexane, to give 142 mg of the title compound as yellow crystals, melting at 90 to 92° C.

EXAMPLE 51

Methyl 2(S)-[5-(1,2-dithiolan-3-yl)pentanoylamino] propionate Compound No. 1-50)

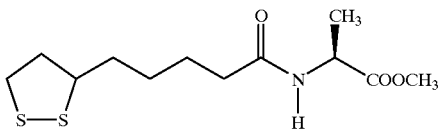

The reaction was effected as described in Example 47, but using 500 mg of D,L-α-lipoic acid, 10 ml of anhydrous dimethylformamide, 422 mg of N,N'-carbonyldiimidazole, 0.36 ml of triethylamine and 335 mg of L-alanine methyl ester hydrochloride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromatography, using a 2:1 by volume mixture of ethyl acetate and hexane as eluent, followed by reverse phase preparative silica gel column chromatography, using by volume 3:7 and 1:1 mixtures of acetonitrile and water as eluent. Acetonitrile was removed from the eluate so obtained by distillation under reduced pressure, and the residue was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 271 mg of the title compound as a pale yellow amorphous substance, melting at 48 to 49° C.

EXAMPLE 52

2(S)-{3-[4-(1,2-Dithiolan-3yl)butyl] ureido}propionic acid Compound No. 1-740)

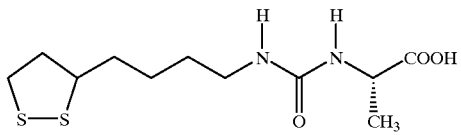

The reaction was effected as described in Example 46, but using 1.00 g of D,L-α-lipoic acid, 20 ml of anhydrous toluene, 1.47 ml of triethylamine, 1.14 ml of diphenylphosphoryl azide, 740 mg of L-alanine methyl ester hydrochloride and 20 ml of anhydrous dimethylformamide. The solvent was removed from the reaction mixture by distillation under reduced pressure. Water was added to the residue, after which it was extracted with ethyl acetate. The extract was washed with a saturated aqueous solution of sodium chloride and dried over anhydrous sodium sulfate. Ethyl acetate was removed from the extract by distillation under reduced pressure. The residue was subjected to silica gel column chromatography, using 2:1 and 1:0 by volume mixtures of ethyl acetate and hexane as eluent, after which it was recrystallised from ethyl acetate, to give 0.80 g of yellow crystals.

The resulting crystals were dissolved in a mixture of 10 of methanol and 3 ml of tetrahydrofuran, and then 16.8 ml of a 1N aqueous solution of sodium hydroxide were added dropwise thereto. The resulting mixture was stirred at room temperature for 6 hours and 30 minutes. The solvent was then removed from the reaction mixture by distillation under reduced pressure. Water was added to the residue. The resulting mixture was neutralized by the addition of 2N aqueous hydrochloric acid, after which it was extracted with ethyl acetate. The extract was washed with a saturated aqueous solution of sodium chloride and then dried over anhydrous sodium sulfate. Ethyl acetate was removed from the extract by distillation under reduced pressure and the residue was recrystallized from ethyl acetate, to give 141 mg of the title compound as pale yellow crystals, melting at 128 to 130° C.

EXAMPLE 53

2(S)-[1,2-dithiolan-3-yl)pentanoylamino]propionic acid (Compound No. 1-48)

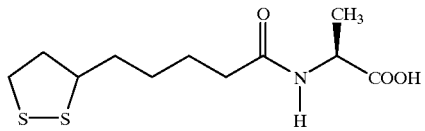

The reaction was effected as described in Example 49, but using (153 mg of methyl 2(S)-[5-(1,2-dithiolan-3-yl) pentanoylamino]propionate (prepared as described in Example 51), 3 ml of methanol and 1.3 ml of a 1N aqueous solution of sodium hydroxide. The solvent was removed from the reaction mixture by distillation under reduced pressure. Water was added to the residue. The resulting mixture was neutralized by the addition of 2N aqueous hydrochloric acid, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 90 mg of the title compound as a yellow oil having an Rf value of 0.18 (silica gel thin layer chromatography; using ethyl acetate as the developing solvent).

EXAMPLE 54

Methyl 3-{3-[4-(1,2-dithiolan-3-yl)butyl]ureido}propionate (Compound No. 1-741 methyl ester)

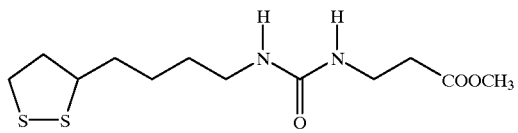

The reaction was effected as described in Example 46, but using 500 mg of D,L-α-lipoic acid, 10 ml of anhydrous toluene, 0.74 ml of triethylamine, 0.56 ml of diphenylphosphoryl azide, 335 mg of α-alanine methyl ester hydrochloride and 10 ml of anhydrous dimethylformamide. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure and the residue was subjected to silica gel column chromatography, using 3:1 and 1:0 by volume mixtures of ethyl acetate and hexane as eluent, after which it was recrystallised from a 1:2 by volume mixture of ethyl acetate and hexane, to give 213 mg of the title compound as yellow crystals, melting at 67 to 69° C.

EXAMPLE 55

Methyl 3-[5-(1,2-dithiolan-3-yl)pentanoylamino] propionate (Compound No. 1–49 methyl ester)

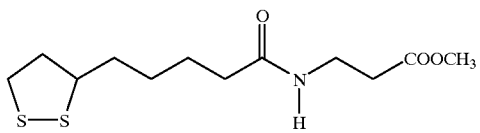

The reaction was effected as described in Example 47, but using 500 mg of D,L-α-lipoic acid, 10 ml of anhydrous dimethylformamide, 422 mg of N,N'-carbonyldiimidazole, 0.36 ml of triethylamine and 335 mg of β-alanine methyl ester hydrochloride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromatography, using 2:1 and 1:0 by volume mixtures of ethyl acetate and hexane as eluent, after which it was recrystallized from a 1:2 by volume mixture of ethyl acetate and hexane, to give 333 mg of the title compound as a yellow plate-like crystals, melting at 54 to 55° C.

EXAMPLE 56

3-{3-(4-(1,2-Dithiolan-3-yl)butyl]ureido}propionic acid (Compound No. 1-741)

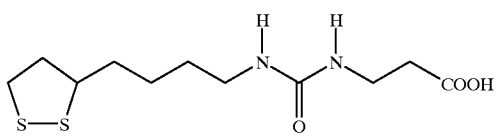

The reaction was effected as described in Example 48, but using 115 mg of methyl 3-{3-[4-(1,2-dithiolan-3-yl)butyl]ureido}propionate (prepared as described in Example 54), 3 ml of methanol, 2 ml of tetrahydrofuran and 1.40 ml of a 1N aqueous solution of sodium hydroxide. The solvent was removed from the reaction mixture by distillation under reduced pressure. Water was added to the residue. The resulting mixture was neutralized by the addition of 2N aqueous hydrochloric acid, after which it was extracted with ethyl acetate. The extract was washed with a saturated aqueous solution of sodium chloride and then dried over anhydrous sodium sulfate. Ethyl acetate was removed from the extract by distillation under reduced pressure and the crystals so precipitated were collected by filtration, to give 70 mg of the title compound as a yellow powder, melting at 108 to 110° C.

EXAMPLE 57

3-[5-(1,2-Dithiolan-3-yl)pentanoylamino]propionic acid (Compound No. 1–49)

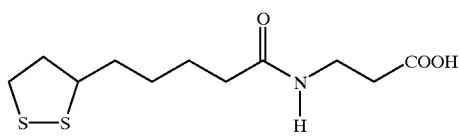

The reaction was effected as described in Example 49, but using 213 mg of methyl 3-[5-(1,2-dithiolan-3-yl)pentanoylamino]propionate (prepared as described in Example 55), 4 ml of methanol and 1.80 ml of a 1N aqueous solution of sodium hydroxide. The solvent was removed from the reaction mixture by distillation under reduced pressure. Water was added to the residue. The resulting mixture was neutralized by the addition of 2N aqueous hydrochloric acid, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 0.11 g of the title compound as a pale yellow amorphous substance, melting at 74 to 76° C.

EXAMPLE 58

2-[5-(1,2-Dithiolan-3-yl)pentyl]isoindole-1,3-dione (Compound No. 1-2606)

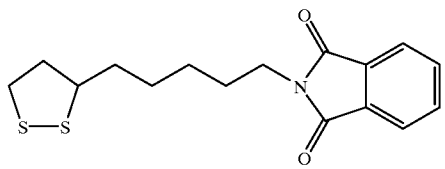

3.25 ml of dimethyl azodicarboxylate were added dropwise to a solution of 5.77 g of triphenylphosphine in 20 ml of tetrahydrofuran, whilst ice-cooling, and then the mixture was stirred at room temperature for 30 minutes. 3.24 g of phthalimide were then added to the reaction mixture, after which a mixture of 20 mmol of 5-(1,2-dithiolan-3-yl)pentanol (prepared as described in Preparation 1) in 30 ml of toluene and 10 ml of tetrahydrofuran was added dropwise, and the mixture was stirred at room temperature for one hour. The reaction mixture was allowed to stand overnight at room temperature, after which 1.57 g of triphenylphosphine and 0.89 ml of dimethyl azodicarboxylate were added. The resulting mixture was stirred at room temperature for 7 hours and 30 minutes. 0.88 g of phthalimide, 1.57 g of triphenylphosphine and 0.89 ml of dimethyl azodicarboxylate were then added to the reaction mixture. The reaction mixture was allowed to stand at room temperature for 4 days. At the end of this time, the solvent was removed from the reaction mixture by distillation under reduced pressure, and the residue was subjected to silica gel column chromatography, using 1:6 and 1:4 by volume mixtures of ethyl acetate and hexane as eluent. The solvent was removed from the eluate by distillation under reduced pressure, and 30 ml of toluene were added to the residue. 1 ml of the resulting mixture was weighed, and the solvent was removed from it by distillation under reduced pressure, to give 165 mg of the title compound as an orange oil having an Rf value of 0.35 (silica gel thin layer chromatography; using a 1:4 by volume mixture of ethyl acetate and hexane as the developing solvent).

EXAMPLE 59

N-[5-(1,2-Dithiolan-3-yl)pentyl] methanesulfonamide (Compound No. 1-2470)

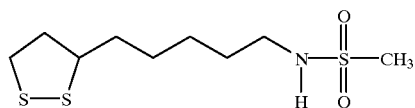

1 ml of butylamine was added to a solution of 0.24 g of 2-[5-(1,2-dithiolan-3-yl)pentyl]isoindole-1,3-dione in 1 ml of methanol. The resulting mixture was stirred at room temperature for 6 hours. The reaction mixture was then allowed to stand overnight at room temperature. At the end of this time, the solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. 2 ml of tetrahydrofuran were added to the residue, and then 0.22 ml of triethylamine and 0.12 ml of methanesulfonyl chloride were added dropwise thereto, whist ice-cooling. The mixture was then stirred at room temperature for 3 hours. At the end of this time, the solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure, and the residue was subjected to silica gel column chromatography, using 1:1 and 2:1 by volume mixtures of ethyl acetate and hexane as eluent, followed by reverse phase preparative silica gel column chromatography, using a 1:1 by volume mixture of acetontrile and water as eluent. Acetonitrile was removed from the eluate so obtained by distillation under reduced pressure, and the residue was extracted with ethyl acetate. The extract was washed with a saturated aqueous solution of sodium chloride and then dried over anhydrous sodium sulfate. Ethyl acetate was removed from the extract by distillation under reduced pressure, and the residue was dissolved in dioxane, after which it was lyophilised, to give 100 mg of the title compound as a pale yellow amorphous substance, melting at 43 to 46° C.

EXAMPLE 60

N-[5-(1,2-Dithiolan-3-yl)pentyl]acetamide
(Compound No. 1-1962)

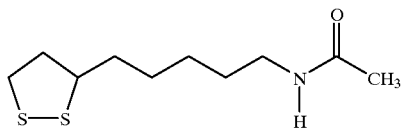

1 ml of butylamine was added to a mixture of 1.3 mmol of 2-[5-(1,2-dithiolan-3-yl)pentyl]isoindole-1,3-dione, 9 ml of toluene and 2 ml of methanol. The resulting mixture was stirred at room temperature for 3 hours, after which the reaction mixture was allowed to stand at room temperature for 2 days. 1 ml of butylamine was then added to the reaction mixture. The resulting mixture was stirred at room temperature for 3 hours. The solvent was then removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. 5 ml of anhydrous tetrahydrofuran were then added to the residue. 0.28 ml of triethylamine and 0.14 ml of acetyl chloride were then added to dropwise to the resulting mixture, whilst ice-cooling, and then the mixture was stirred at room temperature for 1 hour and 30 minutes. At the end of this time, the solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromotagraphy, using 1:0 and 10:1 by volume mixtures of ethyl acetate and methanol as eluent. The solvent was removed from the eluate by distillation under reduced pressure. The residue was dissolved in dioxane, after which it was lyophilised, to give 161 mg of the title compound as yellow crystals, melting at 28 to 33° C.

EXAMPLE 61

N-[5-(1,2-Dithiolan-3-yl)pentyl]propionamide
(Compound No. 1-1963)

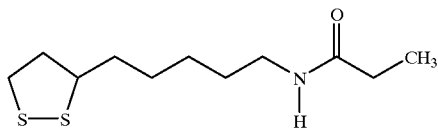

2 ml of methanol and 2 ml of butylamine were added to a solution of 1.6 mmol of 2-[5(1,2-dithiolan-3-yl)pentyl]isoindole-1,3-dione in 3 ml of toluene. The resulting mixture was stirred at room temperature for 6 hours. The reaction mixture was then allowed to stand overnight at room temperature. At the end of this time, the solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. 5 ml of pyridine were then added to the residue. 0.31 ml of propionic anhydride was added dropwise to the resulting mixture, and then the mixture was stirred at room temperature for 2 hours and 30 minutes. The solvent was removed from the reaction mixture by distillation under reduced pressure. Water was added to the residue after which it was extracted with ethyl acetate. The extract was washed with a saturated aqueous solution of sodium chloride and then dried over anhydrous sodium sulfate. Ethyl acetate was removed from the extract by distillation under reduced pressure. The residue was thereafter subjected to silica gel column chromatography, using 2:1, 3:1 and 1:0 by volume mixtures of ethyl acetate and hexane as eluent, followed by reverse phase preparative silica gel column chromatography, using 1:4, 3:7, 2:3 and 1:1 by volume mixtures of acetonitrile and water as eluent. Acetonitrile was removed from the eluate so obtained by distillation under reduced pressure, and the residue was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 125 mg of the title compound as a yellow oil having an Rf value of 0.45 (silica gel thin layer chromatography; using ethyl acetate as the developing solvent).

EXAMPLE 62

[5-(1,2-Dithiolan-3-yl)pentyl]urea (Compound No. 1-1993)

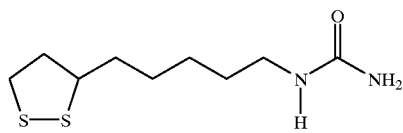

2 ml of methanol and 2 ml of butylamine were added to a solution of 1:6 mmol of 2-[5-(1,2-dithiolan-3-yl)pentyl] isoindole-1,3-dione in 3 ml of toluene. The resulting mixture was stirred at room temperature for 5 hours and 30 minutes. The reaction mixture was then allowed to stand overnight at room temperature. At the end of this time, the solvent was removed from the reaction mixture by distillation under reduced pressure. Water was added to the resulting residue, after which it was extracted with ethyl acetate. The extract was washed with a saturated aqueous solution of sodium chloride and then dried over anhydrous sodium sulfate. Ethyl acetate was removed from the extract by distillation under reduced pressure. 5 ml of tetrahydrofuran were added to the residue. 0.32 ml of trimethylsilyl isocyanate was then added dropwise to the resulting mixture, whilst ice-cooling, and then the mixture was stirred at room temperature for 3 hours and 30 minutes. At the end of this time, the solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure and the residue was subjected to silica gel column chromatography, using 1:0 and 5:1 by volume mixtures of ethyl acetate and methanol as eluent. The solvent was removed from the eluate by distillation under reduced pressure. The residue was recrystallized from ethyl acetate, to give 80 mg of the title compound as yellow crystals, melting at 74 to 78° C.

EXAMPLE 63

1-[5-(1,2-Dithiolan-3-yl)pentyl]-3-methylthiourea (Compound No. 1-2567)

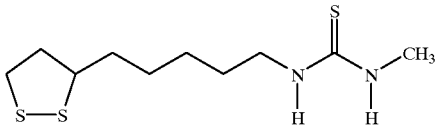

The reaction was effected as described in Example 62, but using a solution of 1.5 mmol of 2-[5-(1,2-dithiolan-3yl) pentyl]isoindole-1,3-dione in 3 ml of toluene, 2 ml of methanol, 2 ml of butylamine, 5 ml of anhydrous tetrahydrofuran and 0.12 ml of methyl isothiocyanate. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromatography, using 1:0 and 20:1 by volume mixtures of ethyl acetate and methanol as eluent, followed by reverse phase preparative silica gel column chromatography, using 3:7 and 1:1 by volume mixtures of acetonitrile and water as eluent. Acetonitrile was removed from the eluate so obtained by distillation under reduced pressure. The residue was thereafter extracted with ethyl acetate. The extract was washed with a saturated aqueous solution of sodium chloride and then dried over anhydrous sodium sulfate. Ethyl acetate was removed from the extract by distillation under reduced pressure. The residue was recrystallized from a 1:1 by volume mixture of ethyl acetate and hexane, to give 183 mg of the title composed as yellow crystals, melting at 64 to 65° C.

EXAMPLE 64

Ethyl [5-(1,2-dithiolan-3-yl)pentyl]carbamate (Compound No. 1-1977)

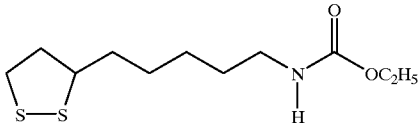

2 ml of methanol and 2 ml of butylamine were added to a solution of 1.6 mmol of 2-[5-(1,2-dithiolan-3-yl)pentyl] isoindole-1,3-dione in 3 ml of toluene. The resulting mixture was stirred at room temperature for 7 hours. At the end of this time, the reaction mixture was allowed to stand overnight at room temperature. The solvent was then removed from the reaction mixture by distillation under reduced pressure. Water was added to the resulting residue, after which it was extracted with ethyl acetate. The extract was washed with a saturated aqueous solution of sodium chloride and then dried over anhydrous sodium sulfate. Ethyl acetate was removed from the extract by distillation under reduced pressure. 2 ml of anhydrous tetrahydrofuran were added to the residue, and then 0.33 ml of triethylamine and 0.23 ml of ethyl chloroformate were added dropwise, whilst ice-cooling. The resulting mixture was stirred at room temperature for 2 hours. The solvent was then removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure, and the residue was subjected to silica gel column chromatography, using 1:3 and 1:2 by volume mixtures of ethyl acetate and hexane as eluent, followed by reverse phase preparative silica gel column chromatography, using a 1:1 by volume mixture of acetonitrile and water as eluent. Acetonitrile was removed from the eluate so obtained by distillation under reduced pressure, and the residue was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 75 mg of the title compound as a red oil having an Rf value of 0.46 (silica gel thin layer chromatography; using a 1:2 by volume mixture of ethyl acetate and hexane as the developing solvent).

EXAMPLE 65

Methyl N-[5-(1,2-dithiolan-3-yl)pentyl]oxalamidate (Compound No. 1-2590)

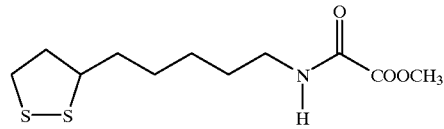

2 ml of methanol and 2 ml of butylamine were added to a solution of 1.5 mmol of 2-[5-(1,2-dithiolan-3-yl)pentyl] isoindole1,3-dione in 3 ml of toluene. The resulting mixture was stirred at room temperature for one hour. The reaction mixture was then allowed to stand overnight at room temperature. At the end of this time, the solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. 4 ml of anhydrous tetrahydrofuran were added to the residue, and then 0.32 ml of triethylamine and 0.21 ml of methyloxalyl acid chloride were added dropwise, whist ice-cooling. The resulting mixture was stirred at room temperature for 2 hours. At the end of this time, the solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure and the residue was subjected to reverse phase preparative silica gel column chromatography, using a 2:3 by volume mixture of acetonitrile and water as eluent. Acetonitrile was removed from the eluate so obtained by distillation under reduced pressure. The residue was thereafter extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 154 mg of the title compound as a pale yellow amorphous substance, melting at 42 to 43° C.

EXAMPLE 66

N-[5-(1,2-Dithiolan-3-yl)pentyl]succinamic acid
(Compound No. 1-1970)

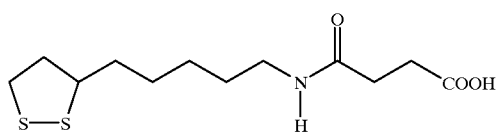

The reaction was effected as described in Example 61, but using a solution of 1.5 mmol of 2-[5-(1,2-dithiolan-3-yl) pentyl]isoindole-1,3-dione in 3 ml of toluene, 2 ml of methanol, 2 ml of butylamine, 4 ml of pyridine and 230 mg of succinic anhydride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure and the residue was subjected to reverse phase preparative silica gel column chromatography, using 2:3, 1:1 and 3:2 by volume mixtures of acetonitrile and water as eluent. Acetonitrile was removed from the eluate so obtained by distillation under reduced pressure. The residue was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 166 mg of the title compound as a pale yellow amorphous substance, melting at 74° C.

EXAMPLE 67

4-[5-(1,2-Dithiolan-3-yl)pentylcarbamoyl]butanoic acid (Compound No. 1-2577)

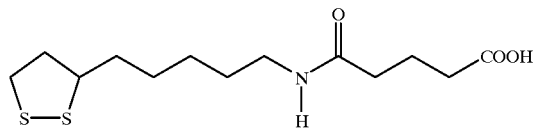

The reaction was effected as described in Example 61, but using a solution of 1.5 mmol of 2-[5-(1,2-dithiolan-3-yl) pentyl]isoindole-1,3-dione in 3 ml of toluene, 2 ml of methanol, 2 ml of butylamine, 4 ml of pyridine and 262 mg of glutaryl anhydride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure and the residue was subjected to reverse phase preparative silica gel column chromatography, using a 2:3 by volume mixture of acetonitrile and water as eluent. Acetonitrile was removed from the eluate so obtained by distillation under reduced pressure. The residue was then extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 132 mg of the title compound as a pale yellow amorphous substance, melting at 60 to 62° C.

EXAMPLE 68

Methyl [5-(1,2-dithiolan-3-yl)pentylamino]acetate
(Compound No. 1-2584)

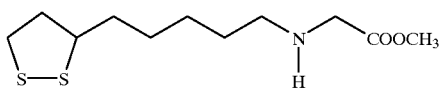

2 ml of methanol and 2 ml of butylamine were added to a solution of 1.6 mmol of 2-[5-(1,2-dithiolan-3-yl)pentyl] isoindole-1,3-dione in 3 ml of toluene. The resulting mixture was allowed to stand overnight at room temperature. The solvent was then removed from the reaction mixture by distillation under reduced pressure. Water was added to the resulting residue, after which it was extracted with ethyl acetate. The extract was washed with a saturated aqueous solution of sodium chloride and then dried over anhydrous sodium sulfate. Ethyl acetate was removed from the extract by distillation under reduced pressure. 4 ml of anhydrous tetrahydrofuran were added to the residue, and then 0.33 ml of triethylamine and 0.17 ml of methyl bromoacetate were added dropwise, whilst ice-cooling. The resulting mixture was stirred for one hour, whilst ice-cooling and then for 5 hours at room temperature. The reaction mixture was then allowes to stand at room temperature for 2 days. At the end of this time, the solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure, and the residue was subjected to silica gel column chromatography, using 1:0 and 20:1 by volume mixtures of ethyl acetate and methanol as eluent. The solvent was removed from the eluate so obtained by distillation under reduced pressure. The residue was dissolved in dioxane, after which it was lyophilised, to give 195 mg of the title compound as a yellow oil having an Rf value of 0.55 (silica gel thin layer chromatography; using a 4:1 by volume mixture of ethyl acetate and methanol as the developing solvent.

EXAMPLE 69

Methyl 3-[5-(1,2-dithiolan-3-yl)pentylamino]propionate (Compound No. 1-2586 methyl ester)

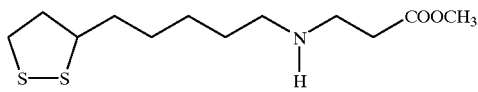

The reaction was effected as described in Example 68, but using a solution of 1.5 mmol of 2-[5-(1,2-dithiolan-3-yl)pentyl]isoindole-1,3-dione, 2 ml of methanol, 2 ml of butylamine, 4 ml of anhydrous tetrahydrofuran, 0.24 ml of triethylamine and 0.19 ml of methyl bromopropionate. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromatography, using 1:0, 20:1 and 4:1 by volume mixtures of ethyl acetate and methanol as eluent. The solvent was removed from the eluate so obtained by distillation under reduced pressure. The residue was dissolved in dioxane, after which it was lyophilised, to give 161 mg of the title compound as a yellow oil having an Rf value of 0.21 (silica gel thin layer chromatography, using a 4:1 by volume mixture of ethyl acetate and methanol as the developing solvent).

EXAMPLE 70

Methyl 2(R)-{3-[4-(1,2-dithiolan-3-yl)butyl]ureido}propionate (Compound No. 1-742)

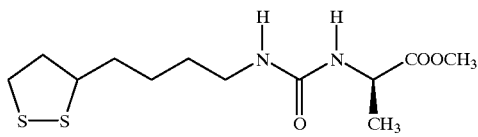

The reaction was effected as described in Example 46, but using 0.51 g of D,L-α-lipoic acid, 10 ml of anhydrous toluene, 0.75 ml of triethylamine, 0.59 ml of diphenylphosphoryl azide, 10 ml of anhydrous dimethylformamide and 0.34 g of D-alanine methyl ester hydrochloride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromatography, using 1:1 and 1:0 by volume mixtures of ethyl acetate and hexane as eluent. The solvent was removed from the eluate so obtained by distillation under reduced pressure. The residue was dissolved in dioxane, after which it was lyophilised, to give 0.27 g of the title compound as a yellow powder melting at 72 to 82° C.

EXAMPLE 71

2(R)-{3-[4-(1,2-Dithiolan-3-yl)butyl]ureido}propionic acid (Compound No. 1-740)

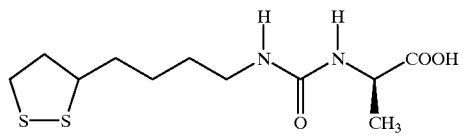

The reaction was effected as described in Example 48, but using 1.74 g of methyl 2(R)-{3-[4-(1,2-dithiolan-3-yl)butyl]ureido}propionate (prepared as described in Example 70), 30 ml of methanol, 22 ml of tetrahydrofuran and 17.0 ml of a 1N aqueous solution of sodium hydroxide. The solvent was removed from the reaction mixture by distillation under reduced pressure. Water was added to the residue. After neutralisation with 2N aqueous hydrochloric acid, the mixture was extracted with ethyl acetate. The extract was washed with a saturated aqueous solution of sodium chloride and then dried over anhydrous sodium sulfate. Ethyl acetate was removed from the extract by distillation under reduced pressure. The residue was recrystallized from ethyl acetate, to give 0.56 g of the title compound as yellow crystals, melting at 131 to 134° C.

EXAMPLE 72

N-(2-{3-[4-(1,2-Dithiolan-3-yl)butyl]ureido}propionyl)methanesulfonamide (Compound No. 1-1280)

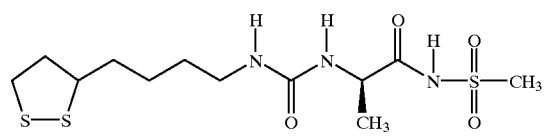

(a) 127 mg of N,N'-carbonyldimidazole were added to a solution of 208 mg of 2(R)-{3-[4-(1,2-dithiolan-3-yl)butyl]ureido}propionic acid (prepared as described in Example 71) in 2 ml of anhydrous dimethylformamide, and then the mixture was stirred at room temperature for 3 hours and 10 minutes.

(b) Meanwhile, 34 mg of sodium hydride (as a 55% w/w dispersion in mineral oil) were washed with hexane, and then 3 ml of anhydrous dimethylformamide were added. 74 mg of methanesulfonamide were added to the resulting mixture, whilst ice-cooling, and then the mixture was stirred at room temperature for 3 hours and 45 minutes. At the end of this time, the solution prepared as described in step (a) above was added dropwise to the reaction mixture, and the resulting mixture was stirred at room temperature for 4 hours. The reaction mixture was then allowed to stand overnight at room temperature. The solvent was then removed from the reaction mixture by distillation under reduced pressure. Water was added to the residue. After neutralisation with 2 N aqueous hydrochloric acid, the resulting mixture was extracted with ethyl acetate. The extract was washed with a saturated aqueous solution of sodium chloride and then dried over anhydrous sodium sulfate. Ethyl acetate was removed from the extract by distillation under reduced pressure. The residue was recrystallized from methanol, to give 77 mg of the title compound as a pale yellow powder, melting at 140 to 150° C.

EXAMPLE 73

Methyl 4-[5-(1,2-dithiolan-3-yl)pentanoylamino]butanoate (Compound No. 1-1275 methyl ester)

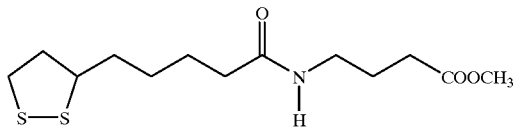

(a) 0.86 g of N,N'-carbonyldimidazole was added to a solution of 1.00 g of D,L-α-lipoic acid in 20 ml of anhydrous dimethylformamide, whilst ice-cooling. The resulting mixture was stirred at room temperature for 1 hour and 25 minutes.

(b) Meanwhile, 0.23 g of sodium hydride (as a 55% w/w dispersion in mineral oil) was washed with hexane, after which 20 ml of anhydrous dimethylformamide were added. 0.82 of methyl 4-aminobutanoate hydrochloride was then added, whilst ice-cooling, and then the resulting mixture was stirred at room temperature for 1 hour and 45 minutes. The solution prepared as described in step (a) above was then added dropwise to the reaction mixture, whilst ice-cooling, and then the mixture was stirred at room temperature for 1 hour and 30 minutes. The reaction mixture was allowed to stand overnight at room temperature, after which the solvent was removed from the reaction mixture by distillation under reduced pressure. Water was added to the residue. After neutralisation with 2N aqueous hydrochloric acid, the resulting mixture was extracted with ethyl acetate. The extract was washed with a saturated aqueous solution of sodium chloride and then dried over anhydrous sodium sulfate. Ethyl acetate was removed from the extract by distillation under reduced pressure, and the residue was subjected to silica gel column chromatography, using 1:1 and 1:0 by volume mixtures of ethyl acetate and hexane as eluent. The ethyl acetate was removed from the eluate so obtained by distillation under reduced pressure. The residue was dissolved in dioxane, after which it was lyophilised, to give 0.83 g of the title compound as a yellow powder, melting at 30 to 32° C.

EXAMPLE 74

4-[5-(1,2-Dithiolan-3-yl)pentanoylamino]butanoic acid (Compound No. 1-1275)

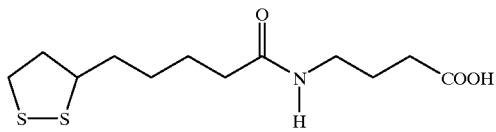

The reaction was effected as described in Example 49, but using 0.65 g of methyl 4-[5-(1,2-dithiolan-3yl)pentanoylamino]butanoate (prepared as described in Example 73), 13 ml of methanol and a 1N aqueous solution of sodium hydroxide. The solvent was removed from the reaction mixture by distillation under reduced pressure. Water was added to the residue. After neutralisation with 2N aqeous hydrochloric acid, the resulting mixture was extracted with ethyl acetate. The extract was washed with a saturated aqueous solution of sodium chloride and then dried over anhydrous sodium sulfate. Ethyl acetate was removed from the extract by distillation under reduced pressure. The residue was recrystallized from ethyl acetate, to give 0.28 g of the title compound as yellow crystals, melting at 56 to 58° C.

EXAMPLE 75

Methyl 4-{3-[4-(1,2-dithiolan-3-yl)buty]ureido}butanoate (Compound No. 1-1276 methyl ester)

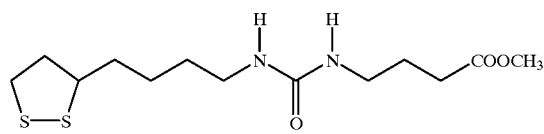

The reaction was effected as described in Example 46, but using 1.00 g of D,L-α-lipoic acid, 20 ml of anhydrous toluene, 1.48 ml of triethylamine, 1.15 ml of diphenylphosphoryl azide and 0.74 g of methyl 4-aminobutanoate hydrochloride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was subjected to silica gel column chromatography, using ethyl acetate as eluent. The ethyl acetate was removed from the eluate so obtained by distillation under reduced pressure, to give 1.18 g of the title compound as yellow crystals, melting at 63 to 70° C.

EXAMPLE 76

N-[5-(1,2-Dithiolan-3-yl)pentyl]oxalamic acid (Compound No. 1-2589)

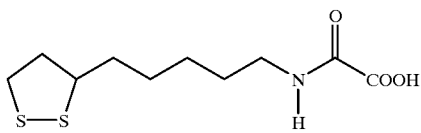

The reaction was effected as described in Example 49, but using 92 mg of methyl N-[5-(1,2-dithiolan-3-yl)pentyl]oxcalamidate (prepared as described in Example 65), 4 ml of methanol, 1 ml of tetrahydrofuran and 0.6 ml of a 1N aqueous solution of sodium hydroxide. The solvent was removed from the reaction mixture by distillation under reduced pressure. Water was added to the residue. The resulting mixture was neutralized by the addition of 2N aqueous hydrochloric acid, after which it was extracted with ethyl acetate. The extract was washed with a saturated aqueous solution of sodium chloride and then dried over anhydrous sodium sulfate. Ethyl acetate was removed from the extract by distillation under reduced pressure. The residue was dissolved in dioxane, after which it was lyophilised, to give 64 mg of the title compound as a pale yellow amorphous substrate, melting at 75 to 79° C.

EXAMPLE 77

Methyl N-[5-(1,2-dithiolan-3-yl)pentyl] succinamidate (Compound No. 1-1970 methyl ester)

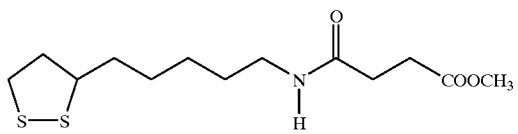

0.25 ml of a hexane solution containing 2.0 M of (trimethylsilyl)diazomethane was added dropwise to a mixture of 89 mg of N-[5-(1,2-dithiolan-3-yl)pentyl]-succinamic acid, 1 ml of methanol and 1.5 ml of toluene, and then the mixture was stirred at room temperature for 30 minutes. At the end of this time, the solvent was removed from the reaction mixture by distillation under reduced pressure. The resulting residue was subjected to silica gel column chromatography, using 1:1 and 1:0 by volume mixtures of ethyl acetate and hexane as eluent. Ethyl acetate and hexane were removed from the eluate so obtained by distillation under reduced pressure. The resulting residue was dissolved in dioxane, after which it was lyophilised, to give 77 mg of the title compound as a pale yellow amorphous substance, melting at 46 to 48° C.

EXAMPLE 78

Methyl 4-[5-(1,2-dithiolan-3-yl)pentylcarbamoyl] butanoate (Compound No. 1-2577 methyl ester)

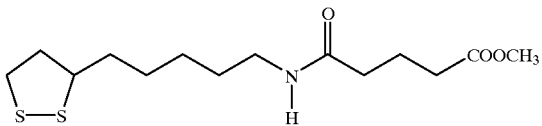

The reaction was effected as described in Example 77, but using 68 mg of 4-[5-(1,2-dithiolan-3-yl)pentylcarbamoyl] butanoic acid (prepared as described in Example 67), 1 ml of methanol, 1 ml of toluene and 0.40 ml of a hexane solution containing 2.0M of (trimethylsilyl)diazomethane. The solvent was then removed from the reaction mixture by distillation under reduced pressure. The residue was subjected to silica gel column chromatography, using 3:1 and 1:0 by volume mixtures of ethyl acetate and hexane as eluent. The solvent was removed from the eluate so obtained by distillation under reduced pressure. The residue was dissolved in dioxane, after which it was lyophilised, to give 62 mg of the title compound as a pale yellow amorphous substrate, melting at 69 to 71° C.

EXAMPLE 79

Ethyl {N-[5-(1,2-dithiolan-3-yl)pentanoyl]-N-methylamino}acetate (Compound No. 1-2520 ethyl ester)

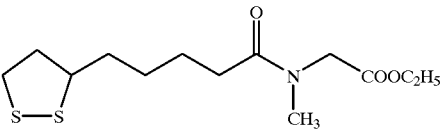

The reaction was effected as described in Example 47, but using 500 mg of D,L-α-lipoic acid, 10 ml of anhydrous dimethylformamide, 422 mg of N,N'-carbonyldiimidazole, 0.36 ml of triethylamine and 399 mg of sarcosine ethyl ester hydrochloride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure, and the residue was subjected to silica gel column chromatography, using a 2:1 by volume mixture of ethyl acetate and hexane as eluent. The solvent was removed from the eluate by distillation under reduced pressure. The residue was dissolved in dioxane, after which it was lyophilised, to give 558 mg of the title compound as a yellow oil having an Rf value of 0.39 (silica gel thin layer chromatography; using a 2:1 by volume mixture of ethyl acetate and hexane as the developing solvent).

EXAMPLE 80

Methyl 4-{N-[5-(1,2-dithiolan-3-yl)pentanoyl]-N-methylamino}butanoate (Compound No. 1-2669 methyl ester)

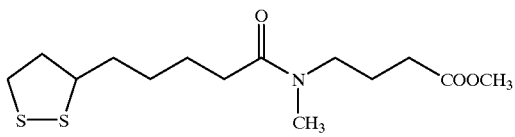

The reaction was effected as described in Example 47, but using 500 mg of D,L-α-lipoic acid, 10 ml of anhydrous dimethylformamide, 422 mg of N,N'-carbonyldiimidazole, 0.36 ml of triethylamine and 486 mg of methyl 4-(methylamino)butanoate hydrochloride. The solvent was removed from the reaction mixture by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure, and the residue was subjected to silica gel column chromatography, using 2:1 and 4:1 by volume mixtures of ethyl acetate and hexane as eluent, followed by reverse phase preparative silica gel column chromatography, using 2:3 and 9:11 by volume mixtures of acetonitrile and water as eluent. Acetonitrile was removed from the eluate so obtained by distillation under reduced pressure, and the residue was extracted with ethyl acetate. The extract was washed with a saturated aqueous solution of sodium chloride and then dried over anhydrous sodium sulfate. Ethyl acetate was removed from the extract by distillation under reduced pressure. The residue was then dissolved in dioxane, after which it was lyophilised, to give 229 mg of the title compound as a yellow oil having an Rf value of 0.37 (silica gel thin layer chromatography; using a 4:1 by volume mixture of ethyl acetate and hexane developing solvent).

EXAMPLE 81

2-[4-(1,2-Dioxothiazolidin-5-ylmethyl) phenoxymethyl]-2,5,7,8-tetramethylchroman-6-yl 5-(1,2-dithiolan-3-yl)pentanoate

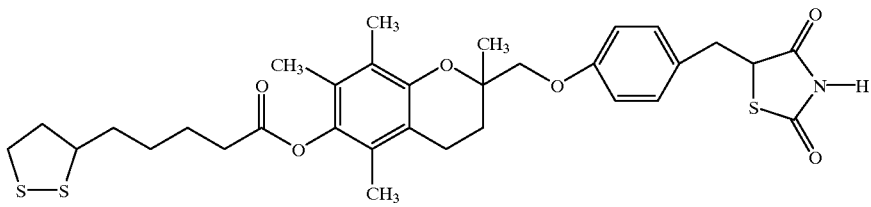

0.36 ml of triethylamine and then 0.25 ml of ethyl chloroformate were added dropwise to 10 ml of solution of 500 mg of D,L-α-lipoic acid in anhydrous dimethylformamide, whilst ice-cooling, and the mixture was stirred at room temperature for 2 hours. At the end of this time, 1.06 g of 5-[4-(2,5,7,8-tetramethylchroman-2-ylmethoxy)benzyl]thiazolidine-2,4-dione were added to the reaction solution, whilst ice-cooling, and the mixture was stirred at room temperature for 5 hours, after which it was left to stand at room temperature overnight. The mixture was then stirred on an oil bath at 50° C. for 1 hour, and then the solvent was removed from the reaction mixture by evaporation under reduced pressure. Water was added to the residue, and the mixture was extracted with ethyl acetate. The extraction solution was washed with a standard aqueous solution of sodium chloride and dried over anhydrous sodium sulfate. The ethyl acetate was removed from the extraction solution by evaporation under reduced pressure, and the residue was subjected to silica gel column chromatography, using a 3:2 by volume mixture of ethyl acetate and hexane as the eluent. The residue was then subjected to reverse phase preparative silica gel column chromatography, using 3:1 and 4:1 by volume mixtures of acetonitrile and water as eluent. The acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 0.57 g of the title compound as a yellow oil having an Rf value of 0.42 (silica gel thin layer chromatography; using a 1:2 by volume mixture of ethyl acetate and hexane as developing solvent).

EXAMPLE 82

2-(3,4-Dibenzyloxy-5-oxo-2,5-dihydrofuran-2-yl)-2-hydroxyethyl 5-(1,2-dithiolan-3-yl)pentanoate

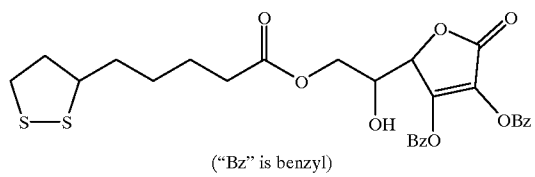

("Bz" is benzyl)

276 mg of N,N'-carbonyldiimidazole were added, whilst ice-cooling, to 6 ml of a solution of 300 mg of D,L-α-lipoic acid in anhydrous dimethylformamide and the mixture was stirred at room temperature for 1 hour and 30 minutes. At the end of this time, 0.24 ml of triethylamine and 536 mg of 2,3-O-dibenzylascorbic acid were added, whilst ice-cooling, to the reaction solution, and the mixture was stirred at room temperature for 1 hour, after which the reaction mixture was left to stand at room temperature for 2 days. The solvent was then removed from the reaction mixture by evaporation under reduced pressure. Water was added to the residue, and the mixture was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 1:3 and 1:1 by volume mixtures of ethyl acetate and hexane as the eluent. The residue was then subjected to reverse phase preparative silica gel column chromatography, using 11:9, 3:2 and 13:7 by volume mixtures of acetonitrile and water as eluent, and the acetonitrile was removed form the solution by evaporation. under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 321 mg of the title compound as a yellow oil having an Rf value of 0.34 (silica gel thin layer chromatography; using a 1:2 by volume mixture of ethyl acetate and hexane as developing solvent).

EXAMPLE 83

5-(1,2-Dithiolan-3-yl)-1-(imidazol-1-yl)pentan-1-one

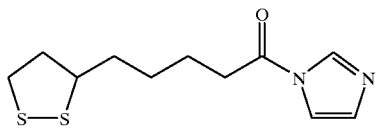

0.86 g of N,N'-carbonyldiimidazole was added, whilst ice-cooling, to 20 ml of a solution of 1.00 g of D,L-α-lipoic acid in anhydrous dimethylformamide, and the mixture was stirred at room temperature for 1 hour. At the end of this time, 311 mg of chloromethanesulfonamide and 104 mg of sodium hydride (as a 55% w/w dispersion in mineral oil) were added, whilst ice-cooling, to the reaction solution, and the mixture was stirred at room temperature for 1 hour. The reaction mixture was then left to stand at room temperature overnight, after which the solvent was removed from the reaction mixture by evaporation under reduced pressure. Water was added to the residue and the mixture was neutralized by the addition of 2N aqueous hydrochloric acid, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 2:1, 4:1 and 1:0 by volume mixtures of ethyl acetate and hexane as the eluent. The residue was then subjected to reverse phase preparative silica gel column chromatography, using 2:3 and 1:1 by volume mixtures of acetonitrile and water as eluent, and the acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 245 mg of the title compound as a pale yellow amorphous substance, melting at 37 to 39° C.

EXAMPLE 84 t-Butyl 4-[5-(1,2-dithiolan-3-yl)pentanoyl] piperazine-1-carboxylate (Compound No. 1-1131 t-butoxycarbonyl derivative)

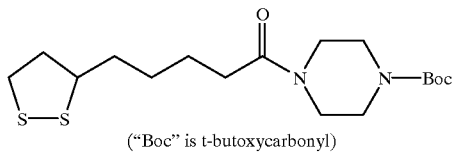

("Boc" is t-butoxycarbonyl)

The reaction was carried out as described in Example 43, but using 500 mg of D,L-α-lipoic acid, 10 ml of anhydrous dimethylformamide, 442 mg of N,N'-carbonyldiimidazole and 484 mg of N-t-butoxycarbonylpiperazine. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 2:1 and 1:0 by volume mixtures of ethyl acetate and hexane as the eluent. The residue was dissolved in dioxane and then lyophilised, to obtain 520 mg of the title compound as a pale yellow amorphous substance, melting at 70 to 71° C.

EXAMPLE 85

5-(1,2-Dithiolan-3-yl)-1-(piperazin-1-one hydrochloride (Compound No. 1-1131 hydrochloride)

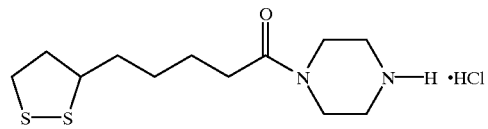

3 ml of a 4N solution of hydrogen chloride in ethyl acetate were added dropwise to 5 ml of a solution of 260 mg of t-butyl 4-[5-(1,2-dithiolan-3-yl)pentanoyl]-piperazine-1-carboxylate (prepared as described in Example 84) in ethyl acetate, and the mixture was stirred at room temperature for 3 hours. The crystals which precipitated were then collected by filtration, to obtain 217 mg of the title compound as a pale yellow powder, melting at 84 to 86° C.

EXAMPLE 86

Thiazolidine-3-carboxylic acid [4-(1,2-dithiolan-3yl)butyl]amide (Compound No. 1-1260)

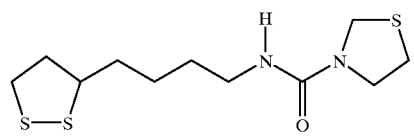

The reaction was carried out as described in Example 44, but using 500 mg of D,L-α-lipoic acid, 10 ml of anhydrous toluene, 0.36 ml of triethylamine, 0.56 ml of diphenylphosphoryl azide and 0.20 ml of thiazolidine. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel. column chromatography using 2:1 and 1:0 by volume mixtures of ethyl acetate and hexane as the eluent. The solvent was removed from the eluate by evaporation under reduced pressure, and the residue was recrystallized from a 1:1 by volume mixture of ethyl acetate and hexane, to obtain 386 mg of the title compound as yellow crystals, melting at 76 to 77° C.

EXAMPLE 87

5-(1,2-Dithiolan-3-yl)pentanoic acid (1-methyl-2-nitroxyethyl)amide (Compound No. 1-2665 nitrate)

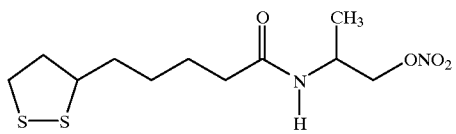

The reaction was carried out as described in Example 47, but using 300 mg of D,L-α-lipoic acid, 9 ml of anhydrous dimethylformamide, 259 mg of N,N'-carbonyldiimidazole, 0.22 ml of triethylamine and 251 mg of 1-methyl-2-nitroxyethylamine hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 3:2 and 2:1 by volume mixtures of ethyl acetate and hexane as the element. The residue was then subjected to reverse phase preparative silica gel column chromatography, using 3:7, and 2:3 and 7:3 by volume mixtures of acetonitrile and water as eluent, and the acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in a dioxane and then lyophilised, to obtain 119 mg of the title compound as a yellow oil having an Rf value of 0.39 (silica gel thin layer chromatography; using a 2:1 by volume mixture of ethyl acetate and hexane as developing solvent).

EXAMPLE 88

1-[4-(1,2-Dithiolan-3-yl)butyl]-3-(2-nitroxyethyl)urea (Compound No. 1-2661 nitrate)

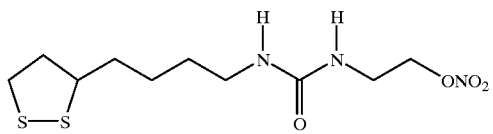

The reaction was carried out as described in Example 46, but using 500 mg of D,L-α-lipoic acid, 10 ml of anhydrous toluene, 0.72 ml of triethylamine, 0.56 ml of diphenylphosphoryl azide, 10 ml of anhydrous dimethylformamide and 342 mg of 2-nitroxyethylamine hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 2:1 and 1:0 by volume mixtures of ethyl acetate and hexane as the eluent. The solvent was removed from the eluate by evaporation under reduced pressure, and the residue was recrystallized from a 1:2 by volume mixture of ethyl acetate and hexane, to obtain 58 mg of the title compound as a pale yellow powder having an Rf value of 0.31 (silica gel thin layer chromatography; using a 2:1 by volume mixture of ethyl acetate and hexane as developing solvent).

EXAMPLE 89

3-(1,2-Dithiolan-3-yl)propionic acid

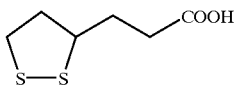

1.3 ml of 2N aqueous hydrochloric acid were added to a solution of 500 mg of 4,6-dithioxyhexanoic acid in 5 ml of a 1N aqueous solution of sodium hydroxide. 5 drops of a 1% w/v aqueous solution of ferric chloride were then added dropwise to the reaction solution, and the resulting mixture was stirred at room temperature for 1 hour while air was blown through the mixture. Water was then added to the reaction solution, which was then washed with ethyl acetate. The aqueous layer was neutralized by the addition of 2N aqueous hydrochloric acid and then extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 388 mg of the title compound as a yellow oil having an Rf value of 0.59 (silica gel thin layer chromatography; using a 2:1 by volume of ethyl acetate and hexane as developing solvent).

EXAMPLE 90

2-[5-(1,2-Dithiolan-3-yl)pentanoylamino]acetamide (Compound No. 1-46 amide)

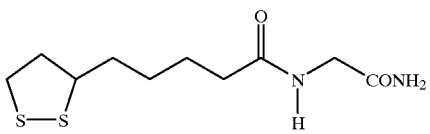

The reaction was carried out as described in Example 47, but using 500 mg of D,L-α-lipoic acid, 10 ml of anhydrous dimethylformamide, 422 mg of N,N'-carbonyldiimidazole, 0.36 ml of triethylamine and 265 mg of glycinamide. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the crystals which precipitated were collected by filtration, to obtain 330 mg of the title compound as yellow crystals, melting at 105 to 108° C.

EXAMPLE 91

2-{3-[4-(1,2-Dithiolan-3-yl)butyl]ureido}acetamide
(Compound No. 1-738 amide)

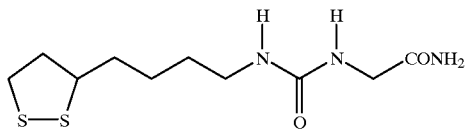

The reaction was carried out as described in Example 46, but using 500 mg of D,L-α-lipoic acid, 10 ml of anhydrous toluene, 0.56 ml of triethylamine, 0.72 ml of diphenylphosphoryl azide, 10 ml of anhydrous dimethylformamide and 265 mg of glycinamide hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was recrystallized from ethyl acetate, to obtain 149 mg of the title compound as yellow powder, melting at 141 to 143° C.

EXAMPLE 92

1-(Indolin-1-yl)-5-(1,2-dithiolan-3-yl)pentan-1-one
(Compound No. 1-2674)

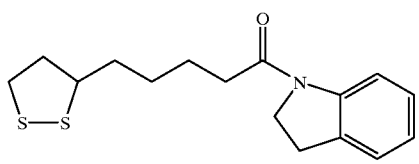

The reaction was carried out as described in Example 43, but using 1.00 g of D,L-α-lipoic acid, 30 ml of anhydrous dimethylformamide, 0.86 g of N,N'-carbonyldiimidazole, 0.73 ml of triethylamine and 1.13 g of methyl indoline-2-carboxylate hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 1:4 and 1:2 by volume mixtures of ethyl acetate and hexane as the eluent. The residue was then subjected to reverse phase preparative silica gel column chromatography, using a 3:2 by volume mixture of acetonitrile and water as eluent, and the acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 0.84 g of the title compound as a pale yellow powder, melting at 65 to 66° C.

EXAMPLE 93

Methyl 1-[4-(1,2-dithiolan-3-yl)butylcarbamoyl]
indoline-2-carboxylate (Compound No. 1-2676
methyl ester)

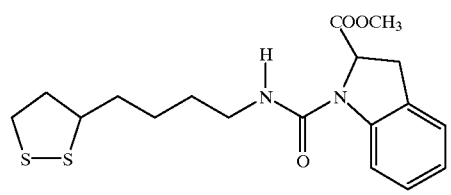

The reaction was carried out as described in Example 44, but using 1.00 g of D,L-α-lipoic acid, 25 ml of anhydrous toluene, 0.73 ml of triethylamine, 1.14 ml of diphenylphosphoryl azide and 0.94 g of methyl indoline-2-carboxylate. The reaction solution was washed with water, and the toluene layer was separated and washed with a saturated aqueous solution of sodium chloride and dried over anhydrous sodium sulfate. The toluene was removed from the extraction solution by evaporation under reduced pressure, and the residue was subjected to silica gel column chromatography, using 1:2, 1:1 and 2:1 by volume mixtures of ethyl acetate and hexane as the eluent. The solvent was removed from ethyl acetate, to obtain 485 mg of the title compound as yellow crystals, melting at 86 to 89° C.

EXAMPLE 94

1-[4-(1,2-Dithiolan-3-yl)butylcarbamoyl]indoline-2-
carboxylic acid (Compound No. 1-2676)

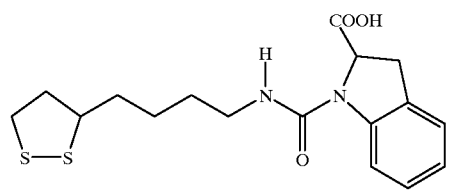

The reaction was carried out as described in Example 48, but using 200 mg of methyl 1-[4-(1,2-dithiolan-3-yl) butylcarbamoyl]indoline-2-carboxylate (prepared as described in Example 93), 4 ml of methanol, 2 ml of tetrahydrofuran and 1.0 ml of a 1N aqueous solution of sodium hydroxide. The solvent was removed from the reaction mixture by evaporation under reduced pressure, and water was added to the residue. The mixture was neutralized by the addition of 2N aqueous hydrochloride acid and extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 98 mg of the title compound as a pale yellow amorphous substance having an Rf value of 0.12 (silica gel thin layer chromatography, using a 2:1 by volume mixture of ethyl acetate and hexane as developing solvent).

EXAMPLE 95

Methyl 3-[3-(1,2-dithiolan-3-yl)propionylamino]propionate

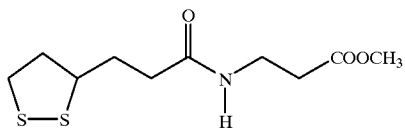

5 ml of anhydrous tetrahydrofuran were added to 6 ml of a mixture of 2.5 mmol of 3-(1,2-dithiolan-3-yl)propionic acid in a mixture of ethyl acetate and dimethylformamide. 0.6 ml of triethylamine, 349 mg of β-alanine methyl ester hydrochloride and 0.38 ml of diethyl cyanophosphate were added to the reaction solution, whilst ice-cooling, and the resulting mixture was stirred, whilst ice-cooling for 1 hour. At the end of this time, the reaction mixture was stirred at room temperature for 30 minutes, and then the solvent was removed from the reaction mixture by evaporation under reduced pressure. Water was added to the residue, and the mixture was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 2:1,3:1 and 1:0 by volume mixtures of ethyl acetate and hexane as the eluent. The residue was then subjected to reverse phase preparative silica gel column chromatography, using a 2:3 by volume mixture of acetonitrile and water as a eluent, and the acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyoiphilised, to obtain 229 mg of the title compound as a yellow oil having an Rf value of 0.24 (silica gel thin layer chromatography; using a 3:1 by volume mixture of ethyl acetate and hexane as developing solvent).

EXAMPLE 96

1,2-Dithiolane-4-carboxylic acid

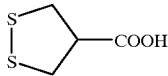

40 ml of 5N aqueous hydrochloric acid were added to 20 ml of a solution of 3.60 g of methyl (1,3-diacetylthio)propyl-2-carboxylic in methanol, and the mixture was heated under reflux for 5 hours and 30 minutes. At the end of this time, the reaction mixture was left to stand at room temperature overnight, and then the solvent was removed from the reaction mixture by evaporation under reduced pressure. Water was added to the residue, and the mixture was extracted with ethyl acetate. The extraction solution was washed with a dilute aqueous solution of sodium hydrogencarbonate, and then with a saturated aqueous solution of sodium chloride, after which it was dried over anhydrous sodiumسulfate. The ethyl acetate was removed from the extraction solution by evaporation under reduced pressure, and 150 ml of a saturated aqueous solution of sodium hydrogencarbonate and a catalytic amount of ferric chloride 6 hydrate were added to the residue, and then the mixture was stirred at room temperature for 8 hours. The reaction mixture was then left to stand at room temperature overnight, after which the solvent was removed from the reaction mixture by evaporation under reduced pressure. Water was added to the residue, and the resulting mixture was washed with ethyl acetate. The pH of the aqueous layer was adjusted to a value of 2 by the addition of aqueous hydrochloric acid, and the mixture was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 0.25 g of the title compound as yellow crystals having an Rf value of 0.56 (silica gel thin layer chromatography; using a 5:1 by volume mixture of ethyl acetate and methanol as developing solvent).

EXAMPLE 97

Methyl 1,2-dithiolan-4-ylcarbonylaminoacetate

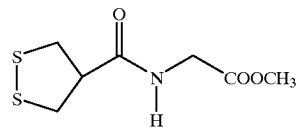

5 ml of anhydrous tetrahydrofuran, 1.01 ml of triethylamine and 398 mg of glycine methyl ester hydrochloride were added to 5 ml of a solution of 3.3 mmol of 1,2-dithiolane-4-carboxylic acid (prepared as described in Example 96) in anhydrous dimethylformamide, and 0.55 ml of diethyl cyanophosphate was then added to the resulting mixture, whilst the ice-cooling, after which the mixture was stirred at room temperature for 5 hours. At the end of this time, the reaction mixture was left to stand at room temperature overnight, after which the solvent was removed from the reaction mixture by evaporation under reduced pressure. Water was added to the residue, and the mixture was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using a 2:1 by volume mixture of ethyl acetate and hexane as the eluent. The solvent was then removed from the eluate solution by evaporation under reduced pressure, and the residue was recrystallized from a 1:2 by volume mixture of ethyl acetate and hexane, to obtain 54 mg of the title compound as pale yellow crystals, melting at 73 to 75° C.

EXAMPLE 98

Methyl 3-(1,2-dithiolan-4-ylcarbonyl)
aminopropionate

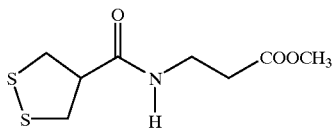

The reaction was carried out as described in Example 97, but using 5 ml of a solution of 3.3 mmol of 1,2-dithiolane-4-carboxylic acid (prepared as described in Example 96) in anhydrous dimethylformamide, 5 ml of anhydrous tetrahydrofuran, 1.01 ml of triethylamine, 502 mg of β-alanine methyl ester hydrochloride and 0.55 ml of diethyl cyanophosphate. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using a 2:1 by volume mixture of ethyl acetate and hexane as the eluent. The solvent was removed from the eluate solution by evaporation under reduced pressure, and the residue was recrystallized from a 2:1 by volume mixture of ethyl acetate and hexane, to obtain 73 mg of the title compound as pale yellow crystals having an Rf value of 0.41 (silica gel thin layer chromatography; using a 2:1 by volume mixture of ethyl acetate and hexane as developing solvent).

EXAMPLE 99

C-Chloro-N-[5-(1,2-dithiolan-3-yl)pentyl]
methanesulfonamide (Compound No. 1-2473)

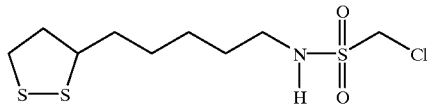

The reaction was carried out as described in Example 60, but using 3 ml of a solution of 1.6 mmol of 2-[5-(1,2-dithiolan-3-yl)pentyl]isoindoline-1,3-dione (prepared as described in Example 58) in toluene, 2 ml of methanol, 2 ml of butylamine, 5 ml of anhydrous tetrahydrofuran, 0.33 ml of triethylamine and 0.21 ml of chloromethanesulfonyl chloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 2:5 and 2:3 by volume mixtures of ethyl acetate and hexane as the eluent. The ethyl acetate was removed from the eluate solution by evaporation under reduced pressure, and the residue was dissolved in dioxane and then lyophilised, to obtain 42 mg of the title compound as a brown oil having an Rf value of 0.29 (silica gel thin layer chromatography; using a 2:5 by volume mixture of ethyl acetate and hexane as developing solvent).

EXAMPLE 100

N-[5-(1,2-Dithiolan-3-yl)pentyl]benzamide
(Compound No. 1-1923)

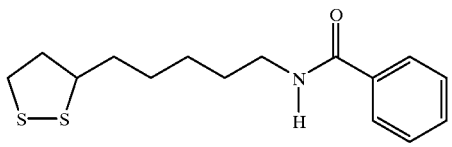

2 ml of methanol and 2 ml of butylamine were added to 3 ml of a solution of 1.6 mmol of 2-[5-(1,2-dithiolan-3-yl)pentyl]isoindoline-1,3-dione (prepared as described in Example 58) in toluene, and the mixture was stirred at room temperature for 1 hour. The reaction mixture was then left to stand at room temperature for 2 days, after which the solvent was removed from the reaction mixture by evaporation under reduced pressure. Water was added to the residue, and the mixture was extracted with ethyl acetate. The extraction solution was washed with saturated aqueous solution of sodium chloride and dried over anhydrous sodium sulfate. The ethyl acetate was removed from the extraction solution by evaporation under reduced pressure, and 5 ml of anhydrous tetrahydrofuran, 0.33 ml of triethylamine and 0.28 ml of benxoyl chloride were added to the residue. The mixture was then stirred at room temperature for 6 hours. At the end of this time, the solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 1:8, 1:4 and 1:2 by volume mixtures of ethyl acetate and hexane as the eluent. The residue was then subjected to reverse phase preparative silica gel column chromatography, using 2:3 and 1:1 by volume mixtures of acetonitrile and water was eluent, and the acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 56 mg of the title compound as a yellow amorphous substance, melting at 58 to 59° C.

EXAMPLE 101

N-[5-(1,2-Dithiolan-3-yl)pentyl]nicotinamide
(Compound No. 1-1991)

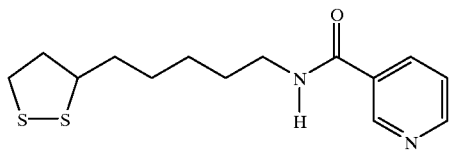

The reaction was carried out as described in Example 100, but using 3 ml of a solution of 1.6 mmol of 2-[5-(1,2-dithiolan-3-yl)pentyl]isoindoline-1,3-dione (prepared as described in Example 58) in toluene, 2 ml of methanol, 2 ml of butylamine, 5 ml of anhydrous tetrahydrofuran, 0.33 ml of triethylamine and 427 mg of nicotinoyl chloride hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 3:1 and 1:0 by volume mixtures of ethyl acetate and hexane and a 20:1 by volume mixture of ethyl acetate and methanol as the eluent. The solvent was removed from the eluate by evaporation under reduced pressure, and the residue was dissolved in dioxane and then lyophilised, to obtain 156 mg of the title compound as a yellow amorphous substance, melting at 41 to 44° C.

EXAMPLE 102

N-Butyl-N'-[5-(1,2-dithiolan-3-yl)pentyl]
phthalamide (Compound No. 1-1936 N-butylamide)

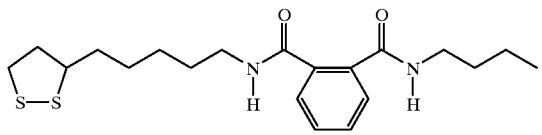

(a) 4 ml of methanol and 4 ml of butylamine were added to 6 ml of a solution of 3.0 mmol of 2-[5-(1,2-dithiolan-3-yl)pentyl]isoindoline-1,3-dione (prepared as described in Example 58) in toluene, and the mixture was stirred at room temperature for 1 hour. The reaction mixture was then left to stand at room temperature overnight, after which the solvent was removed from the reaction mixture by evaporation under reduced pressure. Water was added to the residue, and the mixture was extracted with ethyl acetate. The extraction solution was washed with a saturated aqueous solution of sodium chloride and dried over anhydrous sodium sulfate, and then the ethyl acetate was removed from the extraction solution by evaporation under reduced pressure, to give a residue.

(b) 584 mg of N,N'-carbonyldiimidazole were added to 5 ml of a solution of 770 mg of N-t-butoxycarbonylthiazolidine in anhydrous dimethylformamide, and the mixture was stirred at room temperature for 3 hours. A solution of three residue prepared as described in step (a) above in 3 ml of anhydrous dimethylformamide was then added to the reaction mixture, whilst ice-cooling, and the resulting mixture was stirred at room temperature for 5 hours and 30 minutes. The solvent was then removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to reverse phase preparative silica gel column chromatography, using a 1:1 by volume mixture of acetonitrile and water as eluent. The acetonitrile was removed from the solution by evaporation under reduced pressure, and the precipitated insolubles were collected by filtration, to obtain 118 mg of the title compound as a white powder having an Rf value of 0.44 (silica gel thin layer chromatography; using a 1:1 by volume mixture of ethyl acetate and hexane as developing solvent).

EXAMPLE 103

N-[4-(1,2-Dithiolan-3-yl)butyl]-N'-(2-hydroxy-1-methylethyl)urea (Compound No. 1-2667)

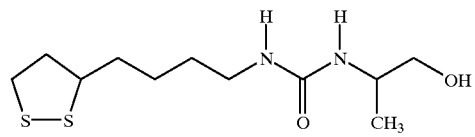

The reaction was carried out as described in Example 46, but using 1.00 g of D,L-α-lipoic acid, 25 ml of anhydrous toluene, 0.74 ml of triethylamine, 1.15 ml of diphenylphosphoryl azide and 0.39 ml of D,L-alaninol. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 40:1 and 20:1 by volume mixtures of ethyl acetate and ethanol as the eluent. The solvent was removed from the eluate by evaporation under reduced pressure, and the residue was recrystallized from methanol to obtain 0.63 g of the title compound as yellow crystals, melting at 87 to 89° C.

EXAMPLE 104

6-(1,2-Dithiolan-3-yl)hexanoic acid (Compound No. 1-1467)

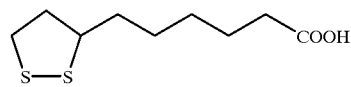

30 ml of water and 60 ml of aqueous hydrochloric acid were added to 7.16 g of 6-(2-oxo-1,3-dithian-4-yl) hexanenitrile, and the mixture was heated under reflux for 5 hours. The reaction mixture was then left to stand at room temperature overnight, after which it was heated under reflux for 2 hours and 30 minutes. The solvent was then removed from the reaction mixture by evaporation under reduced pressure, and water was added to the residue, which was then extracted with ethyl acetate. The extraction solution was washed with a saturated aqueous solution of sodium chloride and dried over anhydrous sodium sulfate. The ethyl acetate was removed from the extraction solution by evaporation under reduced pressure, and 150 ml of 1N aqueous solution of sodium hydroxide, 40 ml of 2N aqueous hydrochloric acid and 10 drops of a 1% w/v aqueous solution of ferric chloride were added to the residue. The mixture was then stirred at room temperature for 2 hours and 30 minutes while air was blown through it. The solvent was removed from the reaction mixture by evaporation under reduced pressure, and water was added to the residue, after which it was washed with ethyl acetate. The aqueous layer was neutralized by the addition of 2N aqueous hydrochloric acid, and ethyl acetate was added to the solution. The aqueous layer (a) and ethyl acetate layer were then separated from the mixture.

The ethyl acetate layer was washed with a saturated aqueous solution of sodium chloride and dried over anhydrous sodium sulfate. The ethyl acetate was removed from the extraction solution by evaporation under reduced pressure, and the residue was subjected to silica gel column chromatography, using a 1:1 by volume mixture of ethyl acetate and hexane as the eluent. The solvent was removed from the eluate by evaporation under reduced pressure, and the residue was dissolved in 40 ml of toluene.

The ethyl acetate was evaporated from the ethyl acetate layer liberated from the above aqueous layer (a), and 90 ml of a 1 N aqueous solution of sodium hydroxide, 17 ml of 2 N aqueous hydrochloric acid and 5 drops of a 1% w/v aqueous solution of ferric chloride were added to the residue, and then the mixture was stirred at room temperature for 1 hour while air was blown through the mixture. The reaction mixture was left to stand at room temperature overnight, and the solvent was removed from the reaction mixture by evaporation under reduced pressure. Water was added to the residue, and the mixture was washed with ethyl acetate. The aqueous layer was neutralized by the addition of 2 N aqueous hydrochloric acid and extracted with ethyl acetate. The extraction solution was washed with a saturated aqueous solution of sodium chloride and dried over anhydrous sodium sulfate. The extraction solution was combined with the above-mentioned toluene solution, and the solvent was removed from the solution by evaporation under reduced pressure. The residue was subjected to reverse phase preparation silica gel column chromatography, using 2:3, 1:1 and 3:2 by volume mixtures of acetonitrile and water as eluent, and acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in 50 ml of toluene. The toluene was evaporated from 2 ml of the resulting toluene solution, and the residue was dissolved in dioxane and then lyophilised, to obtain 69 mg of the title compound as a yellow oil having an Rf value of 0.39 (silica gel thin layer chromatography; using a 1:1 by volume mixture of ethyl acetate and hexane as developing solvent).

EXAMPLE 105

Methyl 6-(1,2-dithiolan-3-yl)hexanoylaminoacetate (Compound No. 1-1347)

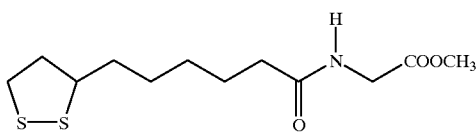

The reaction was carried out as described in Example 47, but using 5 ml of a solution of 1.6 mmol of 6-(1,2-dithiolan-3-yl)hexanoic acid (prepared as described in Example 104) in toluene, 7 ml of anhydrous dimethylformamide, 373 mg of N,N'-carbonyldiimidazole, 0.25 ml of triethylamine and 199 mg of glycine methyl ester hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 2:1 and 3:1 by volume mixtures of ethyl acetate and hexane as the eluent. The residue was then subjected to reverse phase preparative silica gel column chromatography, using 2:3 and 1:1 by volume mixtures of acetonitrile and water as eluent, and the acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 61 mg of the title compound as a pale yellow amorphous substance having an Rf value of 0.28 (silica gel thin layer chromatography; using 2:1 by volume mixture of ethyl acetate and hexane as developing solvent).

EXAMPLE 106

Methyl 2(S)-{N-[5-(1,2-dithiolan-3-yl)pentanoly]-N-methylamino}propionate (Compound No. 1-1224)

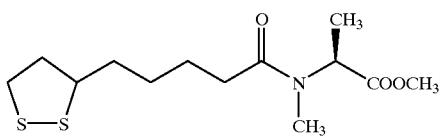

The reaction was carried out as described in Example 47, but using 500 mg of D,L-α-lipoic acid, 13 ml of anhydrous dimethylformamide, 422 mg of N,N'-carbonyldiimidazole, 0.36 ml of triethylamine and 399 mg of N-methyl-L-alanine methyl ester hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried out anhydrous sodium sulfate. The ethyl acetate was removed from the extraction solution by evaporation under reduced pressure, and the residue was subjected to silica gel column chromatography, using 3:1 and 1:0 by volume mixtures of ethyl acetate and hexane as the eluent. The solvent was evaporated from the eluate, and the residue was dissolved in dioxane and then lyophilised, to obtain 374 mg of the title compound as a yellow oil having an Rf value of 0.29 (silica gel thin layer chromatography; using ethyl acetate as developing solvent).

EXAMPLE 107

N-[6-(1,2-Dithiolan-3-yl)hexanoly] methanesulfonamide (Compound No. 1-1796)

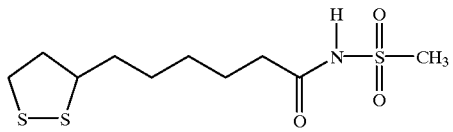

6 ml of anhydrous dimethylformamide and 276 mg of N,N'-carbonyldiimidazole were added to 10 ml of a solution of 1.5 mmol of 6-(1,2-dithiolan-3-yl)hexanoic acid (prepared as described in Example 104) in toluene, and the mixture was stirred at room temperature for 4 hours and 30 minutes. 162 mg of methanesulfanamide and 74 mg of sodium hydride (as a 55% w/w dispersion in mineral oil) were then added to the reaction solution, and the mixture was stirred at room temperature for 1 hour. The reaction mixture was then left to stand at room temperature overnight, and the solvent was removed from the reaction mixture by evaporation under reduced pressure. Water was added to the residue, and the mixture was washed with ethyl acetate and neutralized by the addition of 2 N aqueous hydrochloric acid, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using a 2:1 by volume mixture of ethyl acetate and hexane as the eluent). The solvent was evaporated from the eluate, and the residue was again subjected to silica gel column chromatography, using 2:3 and 3:2 by volume mixtures of ethyl acetate and hexane as the eluent. The solvent was removed from the eluate by evaporation under reduced pressure, and the residue was dissolved in dioxane and then lyophilised, to obtain 98 mg of the title compound as a yellow oil having an Rf value of 0.37 (silica gel thin layer chromatography; using a 3:2 by volume mixture of ethyl acetate and hexane as developing solvent).

EXAMPLE 108

Methyl 3-[5-(1,2-dithiolan-3-yl)pentyl]ureidoacetate (Compound No. 1-2039)

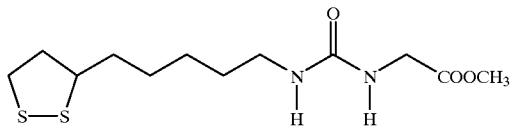

The reaction was carried out as described in Example 46, but using 10 ml of a solution of 1.5 mmol of 6-(1,2-dithiolan-3-yl)hexanoic acid (prepared as described in Example 104) in toluene, 6 ml of anhydrous toluene, 0.42 ml of triethylamine, 0.39 ml of diphenylphosphoryl azide, 6 ml of anhydrous dimethylformamide and 254 mg of glycine methyl ester hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 1:4 and 3:2 by volume mixtures of ethyl acetate and hexane as the eluent. The solvent was removed from the eluate by evaporation under reduced pressure, and the residue was dissolved in dioxane and then lyophilised, to obtain 16 mg of the title compound as yellow crystals having an Rf value of 0.62 (silica gel thin layer chromatography; using a 2:3 by volume mixture of ethyl acetate and hexane as developing solvent).

EXAMPLE 109

Ethyl 3-[4-(1,2-dithiolan-3-yl)butyl]-1-methylureidoacetate (Compound No. 1-820 Ethyl Ester)

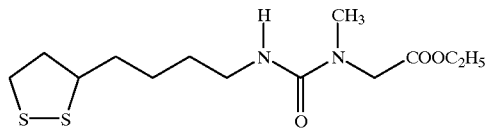

The reaction was carried out as described in Example 46, but using 500 mg of D,L-α-lipoic acid, 10 ml of anhydrous toluene, 0.73 ml of triethylamine, 0.56 ml of diphenylphosphoryl azide, 10 ml of anhydrous tetrahydrofuran and 399 mg of sarcosine ethyl ester hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 2:1 and 1:0 by volume mixtures of ethyl acetate and hexane as the eluent. The residue was then subjected to reverse phase preparative silica gel column chromatography, using 7:13, 2:3 and 1:1 by volume mixtures of acetonitrile and water as eluent, and acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 194 mg of the title compound as a pale yellow amorphous substance having an Rf value of 0.43 (silica gel thin layer chromatography, using ethyl acetate as developing solvent).

EXAMPLE 110

3-[4-(1,2-Dithiolan-3-yl)butyl]-1,5(S)-dimethylimidazolidine-2,4-dione (Compound No. 1-2682)

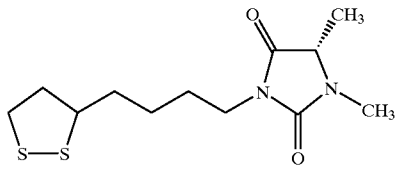

The reaction was carried out as described in Example 46, but using 500 mg of D,L-α-lipoic acid, 10 ml of anhydrous toluene, 0.73 ml of triethylamine, 0.56 ml of diphenylphosphoryl azide, 5 ml of anhydrous tetrahydrofuran, 5 ml of anhydrous dimethylformamide and 399 mg of N-methyl-L-alanine methyl ester hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 3:2 and 1:1 by volume mixtures of ethyl acetate and hexane as the eluent. The residue was then subjected to reverse phase preparative silica gel column chromatography, using 2:3 and 1:1 by volume mixtures of acetonitrile and water as eluent, and the acetonitrile was removed from the solution by evaporation under reduced pressure, after which the residue was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 283 mg of the title compound as a yellow oil having an Rf value 0.29 (silica gel thin layer chromatography, using a 3:2 by volume mixture of ethyl acetate and hexane as developing solvent).

EXAMPLE 111

Methyl 4-{3-[4-(1,2-dithiolan-3-yl)butyl]-1-methylureido}butanoate (Compound No. 1-2670 Methyl Ester)

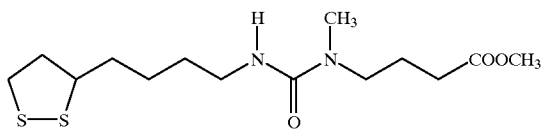

The reaction was carried out as described in Example 46, but using 500 mg of D,L-α-lipoic acid, 10 ml of anhydrous toluene, 0.73 ml of triethylamine, 0.56 ml of diphenylphosphoryl azide, 5 ml of anhydrous dimethylformamide and 477 mg of methyl 4-(methylamino)butanoate hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 1:0 and 20:1 by volume mixtures of ethyl acetate and methanol as the eluent. The solvent was removed from the eluate by evaporation under reduced pressure, and the residue was dissolved in dioxane and then lyophilised, to obtain 589 mg of the title compound as a pale yellow amorphous substance having an Rf value of 0.47 (silica gel thin layer chromatography, using a 20:1 by volume mixture of ethyl acetate and methanol as the developing solvent).

EXAMPLE 112

N-[6-(1,2-Dithiolan-3-yl)hexanoyl]sulfamide (Compound No. 1-1839)

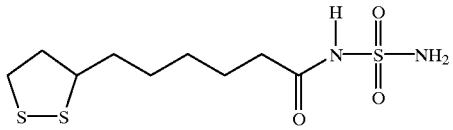

The reaction was carried out as described in Example 107, but using 5 ml of a solution of 1.6 mmol of 6(1,2-dithiolan-3-yl)hexanoic acid (prepared as described in Example 104) in toluene, 7 ml of anhydrous dimethylformamide, 308 mg of N,N'-carbonyldiimidazole, 365 mg of sulfamide and 83 mg of sodium hydride (as a 55% w/w dispersion in mineral oil). The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 3:2 and 2:1 by volume mixtures of ethyl acetate and hexane as the eluent. The solvent was removed from the eluate by evaporation under reduced pressure, and the residue was recrystallized from a 1:2 by volume mixture of ethyl acetate and hexane, to obtain 92 mg of the title compound as pale yellow crystals, melting at 130 to 132° C.

EXAMPLE 113

N-{3-[4-(1,2-Dithiolan-3-yl)butyl]ureidoacetyl}methanesulfonamide (Compound No. 1-2643)

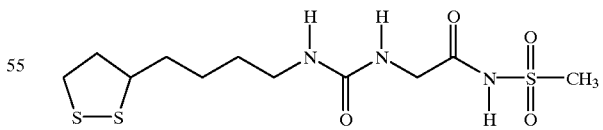

The reaction was carried out as described in Example 73, but using 201 mg of methyl 3-[4-(1,2-dithiolan-3-yl)butyl]ureidoacetate (prepared as described in Example 46), 4 ml of anhydrous dimethylformamide, 129 mg of N,N'-carbonyldiimidazole. 76 mg of methanesulfanomide and 35 mg of sodium hydride (as a 55% w/w dispersion in mineral oil). The solvent was removed from the reaction mixture by evaporation under reduced pressure, and water was added to

EXAMPLE 114

N-{3-[4-(1,2-Dithiolan-3-yl)butyl]
ureidoacetyl}sulfamide (Compound No. 1-2647)

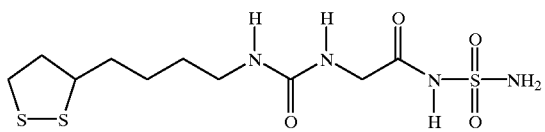

The reaction was carried out as described in Example 73, but using 0.20 g of 3-[4-(1,2-dithiolan-3-yl)butyl] ureidoacetic acid (prepared as described in Example 48), 4 ml of anhydrous dimethylformamide, 0.13 g of N,N'-carbonyldiimidazole, 0.15 g of sulfamide and 0.04 g of sodium hydride (as a 55% w/w dispersion in mineral oil). The solvent was removed from the reaction mixture by evaporation under reduced pressure, and water was added to the residue. The mixture was neutralized by the addition of 2 N aqueous hydrochloric acid, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was recrystallized from a mixture of methanol and ethyl acetate, to obtain 76 mg of the title compound as yellow crystals, melting at 143 to 145° C.

EXAMPLE 115

N-(2(R)-{3-[4-(1,2-Dithiolan-3-yl)butyl]
ureido}propionyl)sulfamide (Compound No. 1-2655)

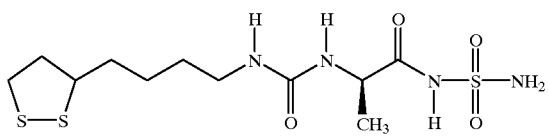

The reaction was carried out as described in Example 73, but using 0.21 g of 2(R)-{3-[4-(1,2-dithiolan-3-yl)butyl]ureido}propionic acid (prepared as described in Example 71), 5 ml of anhydrous dimethylformamide, 0.13 g of N,N'-carbonyldiimidazole, 0.15 g of sulfamide and 0.04 g of sodium hydride (as a 55% w/w dispersion in mineral oil). The solvent was removed from the reaction mixture by evaporation under reduced pressure, and water was added to the residue. The mixture was neutralized by the addition of 2 N aqueous hydrochloric acid, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was recrystallized from ethyl acetate, to obtain 114 mg of the title compound as a pale yellow powder, melting at 156 to 157° C.

EXAMPLE 116

N-(2(S)-{3-[4-(1,2-Dithiolan-3-yl)butyl]
ureido}propionyl)methanesulfanamide (Compound No. 1-2655)

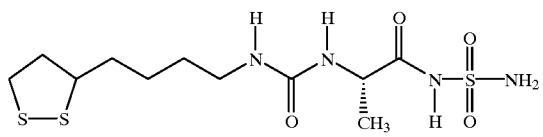

The reaction was carried out as described in Example 73, but using 0.13 g of 2(S)-{3-[4-(1,2-dithiolan-3-yl)butyl]ureido}propionic acid (prepared as described in Example 52), 4 ml of anhydrous dimethylformamide, 0.08 g of N,N'-carbonyldiimidazole, 0.05 g of methanesulfanomide and 0.02 g of sodium hydride (as a 55% w/w dispersion in mineral oil). The solvent was removed from the reaction mixture by evaporation under reduced pressure, and water was added to the residue. The mixture was neutralized by the addition of 2 N aqueous hydrochloric acid, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was recrystallized from ethyl acetate, to obtain 80 mg of the title compound as a white powder, melting at 142 to 147° C.

EXAMPLE 117

4-{3-[4-(1,2-Dithiolan-3-yl)butyl]ureido}butanoic Acid (Compound No. 1-1276)

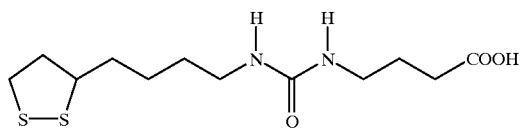

The reaction was carried out as described in Example 48, but using 0.65 g of methyl 4-{3-[4-(1,2-dithiolan-3-yl)butyl] ureido}butanoate (prepared as described in Example 75), 13 ml of methanol and 7.10 ml of a 1 N aqueous solution of sodium hydroxide. The solvent was removed from the reaction mixture by evaporation under reduced pressure, and water was added to the residue. The mixture was neutralized by the addition of 2 N aqueous hydrochloric acid, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was recrystallized from ethyl acetate, to obtain 0.46 g of the title compound as a pale yellow powder, melting at 94 to 99° C.

EXAMPLE 118

Methyl-5-[5-(1,2-dithiolan-3-yl)pentanoylamino]pentanoate (Compound No. 1-2657 Methyl Ester)

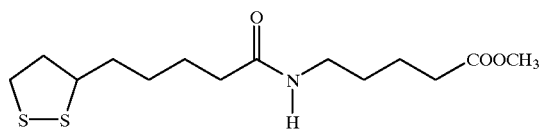

The reaction was carried out as described in Example 47, but using 1.00 g of D,L-α-lipoic acid, 40 ml of anhydrous dimethylformamide, 0.86 g of N,N'-carbonyldiimidazole, 0.74 ml of triethylamine and 0.89 g of methyl 5-aminopentanoate hydrochloride. The solvent was removed form the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 2:1 and 1:0 by volume mixtures of ethyl acetate and hexane as the eluent. It was then recrystallized from ethyl acetate, to obtain 1.10 g of the title compound as pale yellow crystals, melting at 60 to 62° C.

EXAMPLE 119

Methyl 5-{3-[4-(1,2-dithiolan-3-yl)butyl]ureido}pentanoate (Compound No. 1-2659 Methyl Ester)

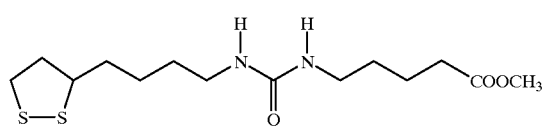

The reaction was carried out as described in Example 46, but using 1.00 g of D,L-α-lipoic acid, 20 ml of anhydrous toluene, 1.48 ml of triethylamine, 1.15 ml of diphenylphosphoryl azide and 0.81 g of methyl 5-aminopentanoate hydrochloride. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using a 2:1 by volume mixture of ethyl acetate and hexane, followed by a 9:1 by volume mixture of ethyl acetate and ethanol, as the eluent, to obtain 1.27 g of the title compound as a pale yellow powder, melting at 90 to 92° C.

EXAMPLE 120

5-[5-(1,2-Dithiolan-3-yl)pentanoylamino]pentanoic Acid (Compound No. 1-2657)

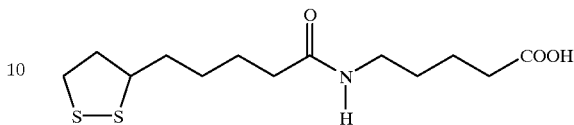

The reaction was carried out as described in Example 49, but using 0.65 g of methyl 5-[5-(1,2-dithiolan-3-yl)pentanoylamino]pentanoate (prepared as described in Example 118), 13 ml of methanol and 5.09 ml of a 1 N aqueous solution of sodium hydroxide. The solvent was removed from the reaction mixture by evaporation under reduced pressure, and water was added to the residue. The mixture was neutralized by the addition of 2 N aqueous hydrochloric acid, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was recrystallized from ethyl acetate, to obtain 0.33 g of the title compound as pale yellowish green crystals, melting at 98 to 100° C.

EXAMPLE 121

5-{3-[4-(1,2-Dithiolan-3-yl)butyl]ureido}pentanoic Acid (Compound No. 1-2659)

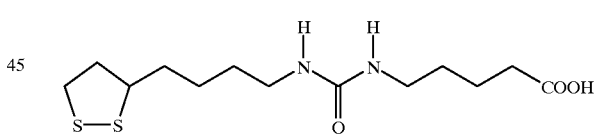

The reaction was carried out as described in Example 48, but using 0.30 g of methyl 5-{3-[4-(1,2-dithiolan-3-yl)butyl]ureido}pentanoate (prepared as described in Example 119), 10 ml of methanol and 3.14 ml of a 1 N aqueous solution of sodium hydroxide. The solvent was removed from the reaction mixture by evaporation under reduced pressure, and water was added to the residue. The mixture was neutralized by the addition of 2 N aqueous hydrochloric acid, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was recrystallized from ethyl acetate, to obtain 0.23 g of the title compound as pale yellow crystals, melting at 125 to 132° C.

EXAMPLE 122

5-(1,2-Dithiolan-3yl)-N-(2-hydroxyethyl) pentanamide (Compound No. 1-2661)

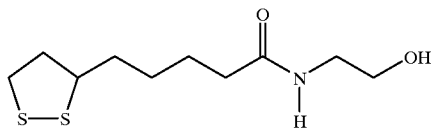

0.86 g of N,N'-carbonyldiimidazole was added to 20 ml of a solution of 1.00 g of D,L-α-lipoic acid in anhydrous dimethylformamide, and the mixture was stirred at room temperature for 1 hour and 20 minutes. 0.32 ml of 2-aminoethanol was then added to the reaction solution, and the resulting mixture was stirred at room temperature for 4 hours and 10 minutes. The solvent was then removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using a 19:1 by volume mixture of ethyl acetate and ethanol as the eluent. The solvent was removed from the eluate by evaporation under reduced pressure, and the residue was dissolved in dioxane and then lyophilised, to obtain 0.71 g of the title compound as a yellow amorphous substance having an Rf value of 0.38 (silica gel thin layer chromatography, using a 19:1 by volume mixture of ethyl acetate and ethanol as developing solvent).

EXAMPLE 123

5-(1,2-Dithiolan-3-yl)-N-(2-hydroxy-1-methylethyl) pentanamide (Compound No. 1-2665)

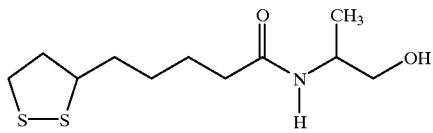

The reaction was carried out as described in Example 122, but using 1.00 g of D,L-α-lipoic acid, 20 ml of anhydrous dimethylformamide, 0.86 g of N,N'-carbonyldiimidazole and 0.42 ml of D,L-alaninol. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using ethyl acetate as the eluent. The solvent was removed from the eluate by evaporation under reduced pressure, and the residue was dissolved in dioxane and lyophilised, to obtain 0.39 g of the title compound as a yellow amorphous substance, melting at 52 to 56° C.

EXAMPLE 124

N-[4-(1,2-Dithiolan-3-yl)butyl]-N'-(2-hydroxyethyl) urea (Compound No. 1-2663)

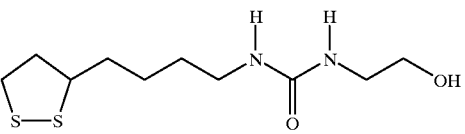

The reaction was carried out as described in Example 46, but using 1.00 g of D,L-α-lipoic acid, 20 ml of anhydrous toluene, 0.74 ml of triethylamine, 1.15 ml of diphenylphosphoryl azide and 0.29 ml of 2-hydroxy-1-ethylamine. The solvent was removed from the reaction mixture by evaporation under reduced pressure, and water was added to the residue, after which it was extracted with ethyl acetate. The extraction solution was washed with a saturated aqueous solution of sodium chloride and dried over anhydrous sodium sulfate. The ethyl acetate was removed from the extraction solution by evaporation under reduced pressure, and the residue was subjected to silica gel column chromatography, using 39:1 and 19:1 by volume mixtures of ethyl acetate and ethanol as the eluent. The solvent was removed from the eluate by evaporation under reduced pressure, and the residue was recrystallized from methanol to obtain 352 mg of the title compound as yellow crystals, melting at 50 to 65° C.

EXAMPLE 125

N-[5-(1,2-Dithiolan-3-yl)pentanoyl]-N-methylmethanesulfonamide (Compound No. 1-2672)

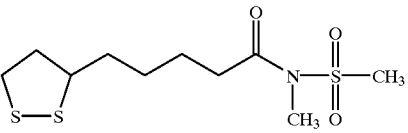

40 mg of copper chloride were added to 20 ml of a solution of 1.36 g of dicyclohexylcarbodiimide in anhydrous methanol, and the mixture was left to stand at room temperature for one and one half hours. The solvent was then removed from the mixture by distillation under reduced pressure. 20 ml of anhydrous dimethylformamide and 1.00 g of N-[5-(1,2-dithiolan-3-yl)pentanoyl] methanesulfonamide (prepared as described in Example 2) were then added to the residue, and the mixture was stirred at 70° C. on an oil bath for an hour. The mixture was then left to stand at room temperature overnight, after which it was stirred at 70° C. on an oil bath for 1 hour, and the solvent was removed from the reaction mixture by evaporation under reduced pressure. Water was added to the residue, and the mixture was extracted with ethyl acetate. Insoluble material in the extract was removed by filtration, and the filtrate was washed with a saturated aqueous solution of sodium chloride and dried over anhydrous sodium sulfate. The ethyl acetate was removed from the solution by evaporation under reduced pressure, and the residue was subjected to silica gel column chromatography, using 2:3 and 1:1 by volume mixtures of ethyl acetate and hexane as the eluent. The solvent was removed from the eluate by evaporation under reduced pressure, and the residue was subjected to reverse phase preparative silica gel column chromatography, using 1:1 and 3:2 by volume mixtures of acetonitrile and water as eluent. The acetonitrile was then removed from the solution by evaporation under reduced pressure, after the residue was extracted with ethyl acetate. The extracted solution was washed with a saturated aqueous solution of sodium chloride and dried over anhydrous sodium sulfate. The ethyl acetate was removed from the extraction solution by evaporation under reduced pressure, and the residue was dissolved in dioxane and then lyophilised, to obtain 660 mg of the title compound as a pale yellow amorphous substance having an Rf value of 0.27 (silica gel thin layer chromatography, using a 2:3 by volume mixture of ethyl acetate and hexane as developing solvent).

EXAMPLE 126

Allyl N-[4-(1,2-dithiolan-3-yl)butyl]carbamate

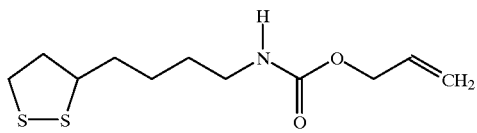

The reaction was carried out as described in Example 31, but using 1.00 g of D,L-α-lipoic acid, 10 ml of anhydrous toluene, 0.73 ml of triethylamine, 1.14 ml of diphenylphosphoryl azide and 2 ml of allyl alcohol. The reaction mixture was washed with water, the water layer was washed with ethyl acetate, and the ethyl acetate washings were combined with the above-mentioned toluene solution. The extract was washed with a saturated aqueous solution of sodium chloride and dried over anhydrous sodium sulfate. The solvent was removed from the extract by evaporation under reduced pressure, and the residue was subjected to silica gel column chromatography, using 1:4 and 1:2 by volume mixtures of ethyl acetate and hexane as the eluent. The solvent was removed from the eluate by evaporation under reduced pressure, and the residue was dissolved in dioxane and then lyophilised, to obtain 944 mg of the title compound as an oily yellow substance having an Rf value of 0.49 (silica gel thin layer chromatography, using a 1:2 by volume mixture of ethyl acetate and hexane as developing solvent).

PREPARATION 1

5(1,2-Dithiolan-3-yl)pentanol

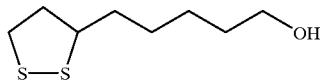

44 ml of a hexane solution containing 2.0 M of (trimethylsilyl)diazomethane was added dropwise, whilst ice-cooling, to a mixture of 15.00 g of D,L-α-lipoic acid in 15 ml of methanol and 150 ml of toluene, and then the mixture was stirred at room temperature for one hour. 11 ml of a hexane solution containing 2.0 M of (trimethylsilyl) diazomethane were then added dropwise to the reaction mixture. The resulting mixture was stirred at room temperature for 2 hour. The reaction mixture was then allowed to stand at room temperature for 2 days. The solvent was then removed by distillation under reduced pressure from the reaction mixture, to give ethyl 5-(1,2-dithiolan-3-yl) pentanoate as a yellow oil.

A solution of ethyl 5-(1,2-dithiolan-3-yl)pentanoate in 40 ml of anhydrous tetrahydrofuran was added dropwise, whilst cooling with ice and sodium chloride, to a suspension of 3.34 g of lithium aluminum hydride in 150 ml of anhydrous tetrahydrofuran. The resulting mixture was stirred at room temperature for 3 hours and 30 minutes. Sodium sulfate decahydrate was then added, whilst cooling with ice and sodium chloride, to the reaction mixture, and then the mixture was stirred at room temperature for 3 hours. The reaction mixture was allowed to stand overnight at room temperature, and then insoluble matter was filtered off using a Celite (trade mark) filter aid. The solvent was removed from the filtrate by distillation under reduced pressure. 50 ml of methanol, 25 ml of a 1 N aqueous solution of sodium hydroxide and 10 ml of 2 N aqueous hydrochloric acid were then added to the residue. Air was then blown into the resulting mixture. Five drops of a 1% aqueous solution of ferric chloride were added dropwise to the reaction mixture, and then the mixture was stirred at room temperature for one hour. The reaction mixture was allowed to stand overnight at room temperature, and then the solvent was removed by distillation under reduced pressure. Water was added to the residue, after which it was extracted with ethyl acetate. The extract was washed with a saturated aqueous solution of sodium chloride and then dried over anhydrous sodium sulfate. Ethyl acetate was removed from the extract by distillation under reduced pressure, and the residue was subjected to silica gel column chromatography, using 1:2 and 1:1 by volume mixtures of ethyl acetate and hexane as eluent. The solvent was removed from the resulting eluate by distillation under reduced pressure, and 30 ml of toluene were added to the residue. 1 ml was taken from the resulting solution, and the solvent was removed by distillation under reduced pressure, to give 0.13 g of the title compound as a yellow oil having an Rf value of 0.39 (silica gel thin layer chromatography; using a 1:1 by volume mixture of ethyl acetate and hexane as the eluent).

We claim:

1. A compound of formula (I):

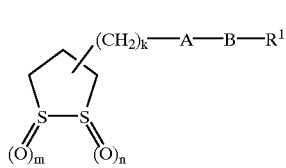

wherein
one of m and n represents 0, and the other represents 0, 1 or 2;
k represents 0 or an integer of from 1 to 12;
$R^1$ represents:
a hydrogen atom;
a substituent α selected from the group consisting of an unsubstituted aryl, an unsubstituted heterocyclic group, an aryl group substituted by 1 to 3 substituents β and a heterocyclic group substituted with 1 to 3 substituents β, wherein said substituents β are selected from the group consisting of an unsubstitued lower alkyl group, a halogenated lower alkyl group, a lower alkoxy group, a lower alkylthio group, a hydroxy group, a carboxy group, a carbamoyl group of which the nitrogen atom thereof is unsubstituted or substituted, a lower alkoxycarbonyl group, a halogen atom, a nitro group, an amine residue, a sulfo group, a sulfamoyl group, a cyano group and a hydroxy-substituted lower alkyl group;

an alkyl group having from 1 to 12 carbon atoms which is unsubstituted or is substituted from 1 to 3 substituents selected from the group consisting of said substituent α and a substituent γ selected from the group consisting of a lower alkoxy group, a lower alkylthio group, a hydroxy group, a nitrooxy group, a carboxy group, a lower alkoxycarbonyl group, a halogen atom, a sulfo group, a sulfamoyl group, an amine residue, and a carbamoyl group of which the nitrogen atom thereof is unsubstituted or substituted, or said unsubstituted or substituted alkyl group in which the carbon chain thereof is interrupted by an oxygen atom, a sulfur atom or both an oxygen atom and a sulfur atom;

a group of the formula —OR$^7$, wherein R$^7$ represents a lower alkyl group, a lower alkenyl group, an unsubstituted aralyl group, an arakyl group of which the aryl moiety thereof is substituted with 1 to 3 groups selected from the group consisting of said substituents β or a group selected from the group consisting of said substituents α; or a hydroxy group;

A represents —CON(R$^2$)SO$_2$—, wherein R$^2$ represents a hydrogen atom, an alkyl group having from 1 to 12 carbon atoms, an unsubstituted aralkyl group, an acyl group, an aralkyl group of which the aryl moiety thereof is substituted with from 1 to 3 groups selected from the group consisting of said substituents β, or R$^2$ is a group selected from the group consisting of said substitutents α; and B represents a single bond;

or a pharmaceutically acceptable salt thereof.

2. A compound of claim 1, represented by the formula (I'):

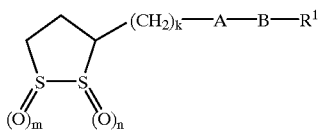

or a pharmaceutically acceptable salt thereof.

3. A compound of claim 1, wherein one of m and n is 0, and the other is 0 or 1.

4. A compound of claim 1, wherein k is 0 or an integer of from 1 to 8.

5. A compound of claim 1, wherein R$^1$ represents a heterocyclic group, an alkyl group having from 1 to 12 carbon atoms which is unsubstituted or is substituted by from 1 to 3 substitutents selected from the group consisting of said substituents α and said substituents γ or R$^1$ is said unsubstituted or unsubstituted alkyl group in which the carbon chain thereof is interrupted by an oxygen atom, a sulfur atom or both an oxygen atom and a sulfur atom.

6. A compound of claim 1, wherein R$^1$ represents a hydroxy group or an alkoxy group having from 1 to 5 carbon atoms.

7. A compound of claim 1, wherein R$^2$ represents a hydrogen atom, an alkyl group having from 1 to 12 carbon atoms or a benzyl group.

8. A compound of claim 2, wherein one of m and n is 0, and the other is 0 or 1.

9. A compound of claim 2, wherein k is 0 or an integer of from 1 to 8.

10. A compound of claim 2, wherein R$^1$ represents a heterocyclic group, an alkyl group having from 1 to 12 carbon atoms which is unsubstituted or is substituted by from 1 to 3 substituents selected from the group consisting of said substitutents α and said substitutents γ or R$^1$ is said unsubstituted or substituted alkyl group in which the carbon chain thereof is interrupted by an oxygen atom, a sulfur atom or both an oxygen atom and a sulfur atom.

11. A compound of claim 2, wherein R$^1$ represents a hydroxy group or an alkoxy group having from 1 to 5 carbon atoms.

12. A compound of claim 2, wherein R$^2$ represents a hydrogen atom, an alkyl group having from 1 to 12 carbon atoms or a benzyl group.

13. A compound of claim 1, wherein:

one or m and n is 0, and the other is 0 is 1;

k is 0 or an integer of from 1 to 8;

R$^1$ represents a heterocyclic group, a hydroxy group, an alkoxy group having from 1 to 5 carbon atoms, an alkyl group having from 1 to 12 carbon atoms which is unsubstituted or is substituted by from 1 to 3 substituents selected from the group consisting of said substitutents α and said substitutents γ or R$^1$ is said unsubstituted or substituted alkyl group in which the carbon chain thereof is interrupted by an oxygen atom, a sulfur atom or both an oxygen atom and a sulfur atom, or R$^1$ is a group of the formula —OR$^7$ wherein R$^7$ is a hydrogen atom or an alkyl group having 1 to 5 carbon atoms; and R$^2$ represents a hydrogen atom, an alkyl group having from 1 to 12 carbon atoms or a benzyl group.

14. A compound of claim 13, wherein said compound of formula (I) has the formula (I'):

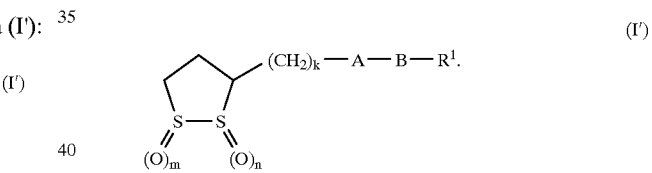

15. A compound of claim 1, wherein both of m and n are 0.

16. A compound of claim 1, wherein k is an integer of from 2 to 6.

17. A compound of claim 1, wherein R$^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group, an alkoxy group having from 1 to 5 carbon atoms or a hydroxy group.

18. A compound of claim 1, wherein R$^2$ represents a hydrogen atom or an alkyl group having from 1 to 12 carbon atoms.

19. A compound of claim 2, wherein both of m and n are 0.

20. A compound of claim 2, wherein k is an integer of from 2 to 6.

21. A compound of claim 2, wherein R$^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group, an alkoxy group having from 1 to 5 carbon atoms or a hydroxy group.

22. A compound of claim 2, wherein $R^2$ represents a hydrogen atom or an alkyl group having from 1 to 12 carbon atoms.

23. A compound of claim 1, wherein:

both of m and n are 0;

k is an integer of from 2 to 6; and $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group, an alkoxy group having from 1 to 5 carbon atoms or a hydroxy group $R^2$ represents a hydrogen atom or an alkyl group having from 1 to 12 carbon atoms.

24. A compound of claim 23, wherein said compound of formula (I) has the formula (I'):

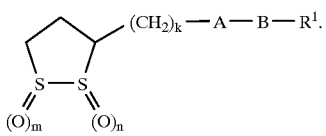

25. A compound of claim 1, wherein k is 4 or 5.

26. A compound of claim 1, wherein $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group or an alkoxy group having from 1 to 5 carbon atoms.

27. A compound of claim 1, wherein k is 4 or 5.

28. A compound of claim 2, wherein $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group or an alkoxy group having from 1 to 5 carbon atoms.

29. A compound of claim 1, wherein:

both of m and n are 0;

k is 4 or 5; and $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group or an alkoxy group having from 1 to 5 carbon atoms.

30. A compound of claim 29, wherein said compound of formula (I) has the formula (I'):

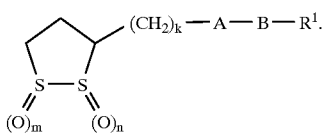

31. A compound of claim 1, selected from the group consisting of N-[5-(1,2-dithiolan-3-yl)pentanoyl]methanesulfonamide or a pharmaceutically acceptable salt thereof.

32. A method of enhancing the activity of glutathione reductase in a mammal, comprising administering to said mammal an effective amount of an active compound of the formula (I) according to claim 1, or a pharmaceutically acceptable salt thereof.

33. A method of claim 32, wherein said active compound is N-[5-(1,2-dithiolan-3-yl)pentanoyl]methanesulfonamide or a pharmaceutically acceptable salt thereof.

34. A method for the treatment or prevention of cataracts in a mammal comprising administering to said mammal an effective amount of an active compound of the formula (I) according to claim 1, or a pharmaceutically acceptable salt thereof.

35. A method of claim 34, wherein said active compound is N-[5-(1,2-dithiolan-3-yl)pentanoyl]methanesulfonamide or a pharmaceutically acceptable salt thereof.

36. A method of claim 32, wherein:

one of m and n is 0, and the other is 0 or 1;

k is 0 or an integer of from 1 to 8;

$R^1$ represents a hydroxy group, an alkoxy group having from 1 to 5 carbon atoms, a heterocyclic group, an alkyl group having from 1 to 12 carbon atoms which is unsubstituted or is substituted by from 1 to 3 substitutents selected from the group consisting of said substitutents α and said substitutents γ or $R^1$ is said unsubstituted or substituted alkyl group in which the carbon chain thereof is interrupted by an oxygen atom, a sulfur atom or both an oxygen atom and a sulfur atom; and $R^2$ represents a hydrogen atom, an alkyl group having from 1 to 12 carbon atoms or a benzyl group.

37. A method of claim 36, wherein said compound of formula (I) has the formula (I'):

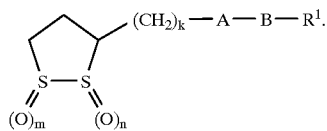

38. A method of claim 32, wherein:

both of m and n are 0;

k is an integer of from 2 to 6; and $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group, an alkoxy group having from 1 to 5 carbon atoms or a hydroxy group;

$R^2$ represents a hydrogen atom or an alkyl group having from 1 to 12 carbon atoms.

39. A method of claim 38, wherein said compound of formula (I) has the formula (I'):

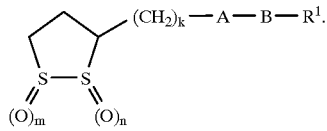

40. A method of claim 32, wherein:

both of m and n are 0;

k is 4 or 5; and $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group or an alkoxy group having from 1 to 5 carbon atoms.

41. A method of claim 40, wherein said compound of formula (I) has the formula (I'):

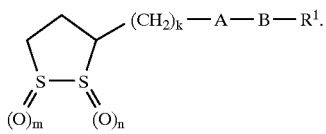

(I')

42. A method of claim 34, wherein:

one or m and n is 0, and the other is 0 or 1;

k is 0 or an integer of from 1 to 8; and $R^1$ represents a hydroxy group, an alkoxy group having from 1 to 5 carbon atoms, a heterocyclic group, an alkyl group having from 1 to 12 carbon atoms which is unsubstituted or is substituted by from 1 to 3 substituents selected from the group consisting of said substituents α and said substituents γ or $R^1$ is said unsubstituted or substituted alkyl group in which the carbon chain thereof is interrupted by an oxygen atom, a sulfur atom or both an oxygen atom and a sulfur atom.

43. A method of claim 42, wherein said compound of formula (I) has the formula (I'):

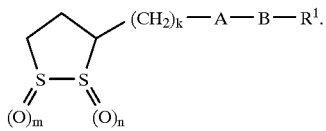

(I')

44. A method of claim 34, wherein:

both of m and n are 0;

k is an integer of from 2 to 6; and $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group, an alkoxy group having from 1 to 5 carbon atoms or a hydroxy group.

45. A method of claim 44, wherein said compound of formula (I) has the formula (I'):

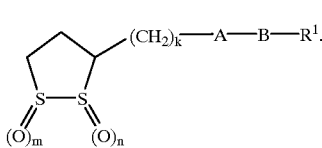

(I')

46. A method of claim 34, wherein:

both m and n are 0;

k is 4 or 5; and $R^1$ represents an alkyl group having from 1 to 5 carbon atoms, an alkoxycarbonylalkyl group having from 3 to 8 carbon atoms, a carboxyalkyl group having from 2 to 7 carbon atoms, a hydroxyalkyl group having from 2 to 5 carbon atoms, a heterocyclic group or an alkoxy group having from 1 to 5 carbon atoms.

47. A method of claim 46, wherein said compound of formula (I) has the formula (I'):

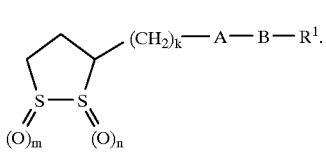

(I')

* * * * *